US012623047B2

(12) United States Patent
Poltorak

(10) Patent No.: US 12,623,047 B2
(45) Date of Patent: May 12, 2026

(54) DEVICE, METHOD, AND APP FOR FACILITATING SLEEP

(71) Applicant: Neuroenhancement Lab, LLC, Pomona, NY (US)

(72) Inventor: Alexander Poltorak, Pomona, NY (US)

(73) Assignee: NeuroLight, Inc., Pomona, NY (US)

( * ) Notice: Subject to any disclaimer, the term of this patent is extended or adjusted under 35 U.S.C. 154(b) by 53 days.

(21) Appl. No.: 18/380,403

(22) Filed: Oct. 16, 2023

(65) Prior Publication Data

US 2024/0066262 A1 Feb. 29, 2024

Related U.S. Application Data

(63) Continuation of application No. 16/883,541, filed on May 26, 2020, now Pat. No. 11,786,694.

(Continued)

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0044* (2013.01);
(Continued)

(58) Field of Classification Search
CPC .......... A61M 21/02; A61M 2021/0027; A61M 2021/0044; A61M 2205/3553; A61M 2205/507; A61M 2230/10; A61M 2021/0016; A61M 2021/0022; A61M 2021/0055; A61M 2021/0072; A61M 21/00; A61M 2021/0077; A61M 2205/3303; A61M 2205/332; A61M 2205/3375; A61M 2205/3592; A61M 2205/8206; A61M 2209/088; A61M 2230/04; A61M 2230/18; A61M 2230/205; A61M 2230/50; A61M 2205/3317; A61M 2205/505; A61M 2205/52; A61M 2230/06; A61M 2230/42; A61M 2230/60;
(Continued)

(56) References Cited

U.S. PATENT DOCUMENTS 3,565,059 A 2/1971 Hauser
3,735,753 A 5/1973 Pisarski
(Continued)

FOREIGN PATENT DOCUMENTS

CN 102458242 A 5/2012
CN 104605844 A 5/2015
(Continued)

*Primary Examiner* — Sunita Reddy
(74) *Attorney, Agent, or Firm* — Hoffberg & Associates; Steven M Hoffberg

(57) ABSTRACT

A device, system, and method for facilitating a sleep cycle in a subject, comprising selecting a waveform from a plurality of waveforms derived from brainwaves of at least one sleeping donor, wherein said waveform corresponds to at least one specific stage of sleep; and stimulating the subject with at least one stimulus, wherein said at least one stimulus is at least one of an auditory stimulus and a visual stimulus modulated with the selected waveform to entrain the brain of the subject with the selected waveform to facilitate sleep in the subject.

20 Claims, 14 Drawing Sheets

Related U.S. Application Data

(60) Provisional application No. 62/862,656, filed on Jun. 17, 2019, provisional application No. 62/852,877, filed on May 24, 2019.

(52) U.S. Cl.
CPC .............. *A61M 2205/3553* (2013.01); *A61M 2205/507* (2013.01); *A61M 2230/10* (2013.01)

(58) Field of Classification Search
CPC .......... A61M 2230/63; A61M 2230/65; A61B 5/165; A61B 5/245; A61B 5/7267; A61B 5/02055; A61B 2505/09; A61B 5/374; A61B 5/7278; A61B 5/7262; A61B 5/4812; A61N 1/0456; A61N 1/36025; A61N 1/36078; A61N 2/006; A61N 2/02; A61N 5/0618; A61N 5/0622; A61N 2005/0626; A61N 2005/0648; A61N 2005/0651; G16H 20/30; G16H 40/63; G16H 50/20; G16H 50/70; G06F 2203/011
USPC ..................................................... 600/26–28
See application file for complete search history.

(56) References Cited

U.S. PATENT DOCUMENTS

| | | | |
|---|---|---|---|
| 3,951,134 A | 4/1976 | Malech | |
| 3,957,036 A | 5/1976 | Normann | |
| 4,375,219 A | 3/1983 | Schmid | |
| 4,407,299 A | 10/1983 | Culver | |
| 4,408,616 A | 10/1983 | Duffy et al. | |
| 4,421,122 A | 12/1983 | Duffy | |
| 4,437,064 A | 3/1984 | Overton, Jr. et al. | |
| 4,493,327 A | 1/1985 | Bergelson et al. | |
| 4,550,736 A | 11/1985 | Broughton et al. | |
| 4,557,270 A | 12/1985 | John | |
| 4,561,448 A | 12/1985 | Buchas | |
| 4,579,125 A | 4/1986 | Strobl et al. | |
| 4,583,190 A | 4/1986 | Salb | |
| 4,585,011 A | 4/1986 | Broughton et al. | |
| 4,591,787 A | 5/1986 | Hoenig | |
| 4,595,017 A | 6/1986 | Semenov et al. | |
| 4,610,259 A | 9/1986 | Cohen et al. | |
| 4,613,817 A | 9/1986 | Hoenig | |
| 4,618,230 A | 10/1986 | Ens et al. | |
| 4,626,090 A | 12/1986 | Charlier et al. | |
| 4,638,807 A | 1/1987 | Ryder | |
| 4,649,482 A | 3/1987 | Raviv et al. | |
| 4,678,640 A | 7/1987 | Hamano et al. | |
| 4,689,559 A | 8/1987 | Hastings et al. | |
| 4,693,000 A | 9/1987 | Hoenig | |
| 4,700,135 A | 10/1987 | Hoenig | |
| 4,705,049 A | 11/1987 | John | |
| 4,733,180 A | 3/1988 | Hoenig et al. | |
| 4,736,307 A | 4/1988 | Salb | |
| 4,736,751 A | 4/1988 | Gevins et al. | |
| 4,744,029 A | 5/1988 | Raviv et al. | |
| 4,749,946 A | 6/1988 | Hoenig | |
| 4,753,246 A | 6/1988 | Freeman | |
| 4,761,611 A | 8/1988 | Hoenig | |
| 4,776,345 A | 10/1988 | Cohen et al. | |
| 4,792,145 A | 12/1988 | Eisenberg et al. | |
| 4,794,533 A | 12/1988 | Cohen | |
| 4,801,882 A | 1/1989 | Daalmans | |
| 4,815,839 A | 3/1989 | Waldorf | |
| 4,818,095 A | 4/1989 | Takeuchi | |
| 4,836,219 A | 6/1989 | Hobson et al. | |
| 4,838,681 A | 6/1989 | Pavlidis | |
| 4,846,190 A | 7/1989 | John | |
| 4,862,359 A | 8/1989 | Trivedi et al. | |
| 4,863,259 A | 9/1989 | Schneider et al. | |
| 4,883,067 A | 11/1989 | Knispel et al. | |
| 4,889,422 A | 12/1989 | Pavlidis | |
| 4,907,597 A | 3/1990 | Chamoun | |
| 4,913,152 A | 4/1990 | Ko et al. | |
| 4,924,875 A | 5/1990 | Chamoun | |
| 4,934,378 A | 6/1990 | Perry, Jr. | |
| 4,937,525 A | 6/1990 | Daalmans | |
| 4,940,058 A | 7/1990 | Taff et al. | |
| 4,947,480 A | 8/1990 | Lewis | |
| 4,949,725 A | 8/1990 | Raviv et al. | |
| 4,951,674 A | 8/1990 | Zanakis et al. | |
| 4,967,038 A | 10/1990 | Gevins et al. | |
| 4,972,492 A | 11/1990 | Tanaka et al. | |
| 4,974,602 A | 12/1990 | Abraham-Fuchs et al. | |
| 4,982,157 A | 1/1991 | Seifert | |
| 4,983,912 A | 1/1991 | Roehrlein et al. | |
| 4,988,183 A | 1/1991 | Kasahara et al. | |
| 4,993,825 A | 2/1991 | Abe et al. | |
| 4,996,479 A | 2/1991 | Hoenig | |
| 5,002,385 A | 3/1991 | Kasahara et al. | |
| 5,008,622 A | 4/1991 | Overton, Jr. et al. | |
| 5,010,891 A | 4/1991 | Chamoun | |
| 5,012,190 A | 4/1991 | Dossel | |
| 5,020,538 A | 6/1991 | Morgan et al. | |
| 5,020,540 A | 6/1991 | Chamoun | |
| 5,027,817 A | 7/1991 | John | |
| 5,029,082 A | 7/1991 | Shen et al. | |
| 5,059,814 A | 10/1991 | Mead et al. | |
| 5,061,680 A | 10/1991 | Paulson et al. | |
| 5,070,399 A | 12/1991 | Martel | |
| 5,070,883 A | 12/1991 | Kasahara | |
| 5,083,571 A | 1/1992 | Prichep | |
| 5,092,341 A | 3/1992 | Kelen | |
| 5,092,835 A | 3/1992 | Schurig et al. | |
| 5,094,521 A | 3/1992 | Jolson et al. | |
| 5,095,270 A | 3/1992 | Ludeke | |
| 5,105,354 A | 4/1992 | Nishimura | |
| 5,109,862 A | 5/1992 | Kelen et al. | |
| 5,118,606 A | 6/1992 | Lynch et al. | |
| 5,126,315 A | 6/1992 | Nishino et al. | |
| RE34,015 E | 8/1992 | Duffy | |
| 5,136,687 A | 8/1992 | Edelman et al. | |
| 5,137,345 A | 8/1992 | Waldorf et al. | |
| 5,158,932 A | 10/1992 | Hinshaw et al. | |
| 5,159,703 A | 10/1992 | Lowery | |
| 5,159,928 A | 11/1992 | Keppel | |
| 5,166,614 A | 11/1992 | Yokosawa et al. | |
| 5,187,327 A | 2/1993 | Ohta et al. | |
| 5,198,977 A | 3/1993 | Salb | |
| 5,204,703 A | 4/1993 | Hutchinson et al. | |
| 5,213,338 A | 5/1993 | Brotz | |
| 5,218,530 A | 6/1993 | Jastrzebski et al. | |
| 5,224,203 A | 6/1993 | Skeirik | |
| 5,230,344 A | 7/1993 | Ozdamar et al. | |
| 5,230,346 A | 7/1993 | Leuchter et al. | |
| 5,233,517 A | 8/1993 | Jindra | |
| 5,241,967 A | 9/1993 | Yasushi et al. | |
| 5,243,281 A | 9/1993 | Ahonen et al. | |
| 5,243,517 A | 9/1993 | Schmidt et al. | |
| 5,263,488 A | 11/1993 | Van Veen et al. | |
| 5,265,611 A | 11/1993 | Hoenig et al. | |
| 5,269,315 A | 12/1993 | Leuchter et al. | |
| 5,269,325 A | 12/1993 | Robinson et al. | |
| 5,273,037 A | 12/1993 | Itil et al. | |
| 5,273,038 A | 12/1993 | Beavin | |
| 5,280,791 A | 1/1994 | Lavie | |
| 5,282,474 A | 2/1994 | Valdes Sosa et al. | |
| 5,283,523 A | 2/1994 | Uhl et al. | |
| 5,287,859 A | 2/1994 | John | |
| 5,291,888 A | 3/1994 | Tucker | |
| 5,293,187 A | 3/1994 | Knapp et al. | |
| 5,303,705 A | 4/1994 | Nenov | |
| 5,306,228 A | 4/1994 | Rubins | |
| 5,307,807 A | 5/1994 | Valdes Sosa et al. | |
| 5,309,095 A | 5/1994 | Ahonen et al. | |
| 5,309,917 A | 5/1994 | Wang et al. | |
| 5,309,923 A | 5/1994 | Leuchter et al. | |
| 5,311,129 A | 5/1994 | Ludwig et al. | |
| 5,313,952 A | 5/1994 | Hoch | |
| 5,320,109 A | 6/1994 | Chamoun et al. | |

(56)                    References Cited

U.S. PATENT DOCUMENTS

| | | | |
|---|---|---|---|
| 5,323,777 A | 6/1994 | Ahonen et al. |
| 5,325,862 A | 7/1994 | Lewis et al. |
| 5,326,745 A | 7/1994 | Nishino et al. |
| 5,331,970 A | 7/1994 | Gevins et al. |
| 5,339,811 A | 8/1994 | Ohta et al. |
| 5,339,826 A | 8/1994 | Schmidt et al. |
| 5,356,368 A * | 10/1994 | Monroe ............... A61M 21/00 |
| | | 600/545 |
| 5,360,971 A | 11/1994 | Kaufman et al. |
| 5,377,100 A | 12/1994 | Pope et al. |
| 5,406,956 A | 4/1995 | Farwell |
| 5,406,957 A | 4/1995 | Tansey |
| 5,409,445 A | 4/1995 | Rubins |
| 5,417,211 A | 5/1995 | Abraham-Fuchs et al. |
| 5,418,512 A | 5/1995 | Ohta et al. |
| 5,422,689 A | 6/1995 | Knapp et al. |
| 5,442,289 A | 8/1995 | Dilorio et al. |
| 5,443,073 A | 8/1995 | Wang et al. |
| 5,447,154 A | 9/1995 | Cinquin et al. |
| 5,447,166 A | 9/1995 | Gevins |
| 5,458,117 A | 10/1995 | Chamoun et al. |
| 5,458,142 A | 10/1995 | Farmer et al. |
| 5,461,699 A | 10/1995 | Arbabi et al. |
| 5,469,057 A | 11/1995 | Robinson |
| 5,474,082 A | 12/1995 | Junker |
| 5,476,438 A | 12/1995 | Edrich et al. |
| 5,479,934 A | 1/1996 | Imran |
| 5,491,492 A | 2/1996 | Knapp et al. |
| 5,496,798 A | 3/1996 | Sakai et al. |
| 5,503,149 A | 4/1996 | Beavin |
| 5,513,649 A | 5/1996 | Gevins et al. |
| 5,515,301 A | 5/1996 | Corby, Jr. et al. |
| 5,517,021 A | 5/1996 | Kaufman et al. |
| 5,522,863 A | 6/1996 | Spano et al. |
| 5,546,943 A | 8/1996 | Gould |
| 5,552,375 A | 9/1996 | Nishino et al. |
| 5,555,889 A | 9/1996 | Karagueuzian et al. |
| 5,568,816 A | 10/1996 | Gevins et al. |
| 5,570,698 A | 11/1996 | Liang et al. |
| 5,574,473 A | 11/1996 | Sekiguchi |
| 5,579,241 A | 11/1996 | Corby, Jr. et al. |
| 5,594,849 A | 1/1997 | Kuc et al. |
| 5,600,243 A | 2/1997 | Colclough |
| 5,601,081 A | 2/1997 | Tomita et al. |
| 5,611,350 A | 3/1997 | John |
| 5,617,856 A | 4/1997 | Tamura et al. |
| 5,619,995 A | 4/1997 | Lobodzinski |
| 5,621,424 A | 4/1997 | Shimada et al. |
| 5,622,168 A | 4/1997 | Keusch et al. |
| 5,626,145 A | 5/1997 | Clapp et al. |
| 5,632,272 A | 5/1997 | Diab et al. |
| 5,640,493 A | 6/1997 | Skeirik |
| 5,643,325 A | 7/1997 | Karagueuzian et al. |
| 5,649,061 A | 7/1997 | Smyth |
| 5,656,937 A | 8/1997 | Cantor |
| 5,662,109 A | 9/1997 | Hutson |
| 5,671,740 A | 9/1997 | Tomita et al. |
| 5,678,561 A | 10/1997 | Karagueuzian et al. |
| 5,682,889 A | 11/1997 | Tomita et al. |
| 5,685,313 A | 11/1997 | Mayevsky |
| 5,692,517 A | 12/1997 | Junker |
| 5,694,939 A | 12/1997 | Cowings |
| 5,699,808 A | 12/1997 | John |
| 5,701,909 A | 12/1997 | Amir et al. |
| 5,706,402 A | 1/1998 | Bell |
| 5,706,811 A | 1/1998 | Takeda et al. |
| 5,707,652 A | 1/1998 | Lewy et al. |
| 5,715,821 A | 2/1998 | Faupel |
| 5,719,561 A | 2/1998 | Gonzales |
| 5,720,619 A | 2/1998 | Fisslinger |
| 5,722,418 A | 3/1998 | Bro |
| 5,724,987 A | 3/1998 | Gevins et al. |
| 5,726,916 A | 3/1998 | Smyth |
| 5,729,046 A | 3/1998 | Nishino et al. |
| 5,730,146 A | 3/1998 | Itil et al. |
| 5,736,543 A | 4/1998 | Rogers et al. |
| 5,737,485 A | 4/1998 | Flanagan et al. |
| 5,740,812 A | 4/1998 | Cowan |
| 5,743,854 A | 4/1998 | Dobson et al. |
| 5,743,860 A | 4/1998 | Hively et al. |
| 5,747,492 A | 5/1998 | Lynch et al. |
| 5,752,514 A | 5/1998 | Okamura et al. |
| 5,752,521 A | 5/1998 | Dardik |
| 5,752,911 A | 5/1998 | Canedo et al. |
| 5,755,227 A | 5/1998 | Tomita et al. |
| 5,755,739 A | 5/1998 | Sun et al. |
| 5,761,332 A | 6/1998 | Wischmann et al. |
| 5,762,611 A | 6/1998 | Lewis et al. |
| 5,767,043 A | 6/1998 | Cantor et al. |
| 5,771,261 A | 6/1998 | Anbar |
| 5,771,893 A | 6/1998 | Kassai et al. |
| 5,771,894 A | 6/1998 | Richards et al. |
| 5,771,897 A | 6/1998 | Zufrin |
| 5,791,342 A | 8/1998 | Woodard |
| 5,794,623 A | 8/1998 | Forbes |
| 5,795,304 A | 8/1998 | Sun et al. |
| 5,797,840 A | 8/1998 | Akselrod et al. |
| 5,797,853 A | 8/1998 | Musha et al. |
| 5,810,737 A | 9/1998 | Dardik |
| 5,813,993 A | 9/1998 | Kaplan et al. |
| 5,815,413 A | 9/1998 | Hively et al. |
| 5,816,247 A | 10/1998 | Maynard |
| 5,823,190 A | 10/1998 | Voipio |
| 5,827,195 A | 10/1998 | Lander |
| 5,840,040 A | 11/1998 | Altschuler et al. |
| 5,842,986 A | 12/1998 | Avrin et al. |
| 5,845,639 A | 12/1998 | Hochman et al. |
| 5,846,189 A | 12/1998 | Pincus |
| 5,846,208 A | 12/1998 | Pichlmayr et al. |
| 5,851,193 A | 12/1998 | Arikka et al. |
| 5,853,005 A | 12/1998 | Scanlon |
| 5,857,978 A | 1/1999 | Hively et al. |
| 5,871,517 A | 2/1999 | Abrams et al. |
| 5,884,626 A | 3/1999 | Kuroda et al. |
| 5,885,976 A | 3/1999 | Sandyk |
| 5,899,867 A | 5/1999 | Collura |
| 5,916,171 A | 6/1999 | Mayevsky |
| 5,920,375 A | 7/1999 | Fahle et al. |
| 5,921,245 A | 7/1999 | O'Donnell, Jr. |
| 5,933,210 A | 8/1999 | Ron |
| 5,938,598 A | 8/1999 | Takeda et al. |
| 5,938,688 A | 8/1999 | Schiff |
| 5,942,954 A | 8/1999 | Galiana et al. |
| 5,970,499 A | 10/1999 | Smith et al. |
| 5,983,129 A | 11/1999 | Cowan et al. |
| 5,995,868 A | 11/1999 | Dorfmeister et al. |
| 6,002,254 A | 12/1999 | Kassai et al. |
| 6,002,952 A | 12/1999 | Diab et al. |
| 6,011,990 A | 1/2000 | Schultz et al. |
| 6,011,991 A | 1/2000 | Mardirossian |
| 6,016,444 A | 1/2000 | John |
| 6,021,345 A | 2/2000 | Karagueuzian et al. |
| 6,023,161 A | 2/2000 | Dantsker et al. |
| 6,032,072 A | 2/2000 | Greenwald et al. |
| 6,033,073 A | 3/2000 | Potapova et al. |
| 6,042,548 A | 3/2000 | Giuffre |
| 6,044,292 A | 3/2000 | Heyrend et al. |
| 6,050,940 A | 4/2000 | Braun et al. |
| 6,050,962 A | 4/2000 | Kramer et al. |
| 6,052,619 A | 4/2000 | John |
| 6,066,084 A | 5/2000 | Edrich et al. |
| 6,067,462 A | 5/2000 | Diab et al. |
| 6,067,467 A | 5/2000 | John |
| 6,069,369 A | 5/2000 | Nishino et al. |
| 6,070,098 A | 5/2000 | Moore-Ede et al. |
| 6,071,246 A | 6/2000 | Sturzebecher et al. |
| 6,076,003 A | 6/2000 | Rogel |
| 6,080,164 A | 6/2000 | Oshio et al. |
| 6,081,735 A | 6/2000 | Diab et al. |
| 6,088,611 A | 7/2000 | Lauterbur et al. |
| 6,091,334 A | 7/2000 | Galiana et al. |
| 6,092,058 A | 7/2000 | Smyth |
| 6,097,980 A | 8/2000 | Monastra et al. |
| 6,097,981 A | 8/2000 | Freer |

(56) References Cited

U.S. PATENT DOCUMENTS

| | | | |
|---|---|---|---|
| 6,099,319 A | 8/2000 | Zaltman et al. |
| 6,115,631 A | 9/2000 | Heyrend et al. |
| 6,117,075 A | 9/2000 | Barnea |
| 6,117,092 A | 9/2000 | Weinstein et al. |
| 6,129,681 A | 10/2000 | Kuroda et al. |
| 6,144,872 A | 11/2000 | Graetz |
| 6,149,586 A | 11/2000 | Elkind |
| 6,154,026 A | 11/2000 | Dantsker et al. |
| 6,154,699 A | 11/2000 | Williams |
| 6,155,966 A | 12/2000 | Parker |
| 6,155,993 A | 12/2000 | Scott |
| 6,157,850 A | 12/2000 | Diab et al. |
| 6,157,857 A | 12/2000 | Dimpfel |
| 6,161,031 A | 12/2000 | Hochman et al. |
| 6,164,278 A | 12/2000 | Nissani |
| 6,167,298 A | 12/2000 | Levin |
| 6,167,311 A | 12/2000 | Rezai |
| 6,171,239 B1 | 1/2001 | Humphrey |
| 6,171,258 B1 | 1/2001 | Karakasoglu et al. |
| 6,195,576 B1 | 2/2001 | John |
| 6,196,972 B1 | 3/2001 | Moehring |
| 6,224,549 B1 | 5/2001 | Drongelen |
| 6,230,037 B1 | 5/2001 | Tsukada et al. |
| 6,231,187 B1 | 5/2001 | Munoz et al. |
| 6,236,872 B1 | 5/2001 | Diab et al. |
| 6,239,145 B1 | 5/2001 | Utsumi et al. |
| 6,240,308 B1 | 5/2001 | Hardy et al. |
| 6,241,686 B1 | 6/2001 | Balkin et al. |
| 6,263,189 B1 | 7/2001 | Reagor |
| 6,270,466 B1 | 8/2001 | Weinstein et al. |
| 6,272,370 B1 | 8/2001 | Gillies et al. |
| 6,280,393 B1 | 8/2001 | Granger et al. |
| 6,287,328 B1 | 9/2001 | Snyder et al. |
| 6,290,638 B1 | 9/2001 | Canedo et al. |
| 6,292,688 B1 | 9/2001 | Patton |
| 6,293,904 B1 | 9/2001 | Blazey et al. |
| 6,298,259 B1 | 10/2001 | Kucharczyk et al. |
| 6,305,943 B1 | 10/2001 | Pougatchev et al. |
| 6,306,077 B1 | 10/2001 | Prabhu et al. |
| 6,309,342 B1 | 10/2001 | Blazey et al. |
| 6,309,361 B1 | 10/2001 | Thornton |
| 6,315,736 B1 | 11/2001 | Tsutsumi et al. |
| 6,317,627 B1 | 11/2001 | Ennen et al. |
| 6,319,205 B1 | 11/2001 | Goor et al. |
| 6,322,515 B1 | 11/2001 | Goor et al. |
| 6,325,475 B1 | 12/2001 | Hayes et al. |
| 6,325,761 B1 | 12/2001 | Jay |
| 6,331,164 B1 | 12/2001 | Shaw et al. |
| 6,338,713 B1 | 1/2002 | Chamoun et al. |
| 6,343,229 B1 | 1/2002 | Siebler et al. |
| 6,346,887 B1 | 2/2002 | Van Orden et al. |
| 6,349,231 B1 | 2/2002 | Musha |
| 6,354,087 B1 | 3/2002 | Nakahara et al. |
| 6,356,079 B1 | 3/2002 | Mizoguchi et al. |
| 6,356,781 B1 | 3/2002 | Lee et al. |
| 6,358,201 B1 | 3/2002 | Childre et al. |
| 6,366,813 B1 | 4/2002 | DiLorenzo |
| 6,370,414 B1 | 4/2002 | Robinson |
| 6,370,423 B1 | 4/2002 | Guerrero et al. |
| 6,374,131 B1 | 4/2002 | Tomita et al. |
| 6,375,614 B1 | 4/2002 | Braun et al. |
| 6,377,833 B1 | 4/2002 | Albert |
| 6,385,479 B1 | 5/2002 | Sibbitt et al. |
| 6,385,486 B1 | 5/2002 | John et al. |
| 6,390,979 B1 | 5/2002 | Njemanze |
| 6,394,963 B1 | 5/2002 | Blazey et al. |
| 6,402,520 B1 | 6/2002 | Freer |
| 6,402,689 B1 | 6/2002 | Scarantino et al. |
| 6,418,344 B1 | 7/2002 | Rezai et al. |
| 6,419,629 B1 | 7/2002 | Balkin et al. |
| 6,428,490 B1 | 8/2002 | Kramer et al. |
| 6,442,421 B1 | 8/2002 | Le Van Quyen et al. |
| 6,442,948 B1 | 9/2002 | Takeda |
| 6,466,816 B2 | 10/2002 | Granger et al. |
| 6,470,220 B1 | 10/2002 | Kraus, Jr. et al. |
| 6,475,163 B1 | 11/2002 | Smits et al. |
| 6,482,165 B1 | 11/2002 | Patton et al. |
| 6,488,617 B1 | 12/2002 | Katz |
| 6,490,472 B1 | 12/2002 | Li et al. |
| 6,493,577 B1 | 12/2002 | Williams |
| 6,496,724 B1 | 12/2002 | Levendowski et al. |
| 6,497,658 B2 | 12/2002 | Roizen et al. |
| 6,503,085 B1 | 1/2003 | Elkind |
| 6,507,754 B2 | 1/2003 | Le Van Quyen et al. |
| 6,510,340 B1 | 1/2003 | Jordan |
| 6,511,424 B1 | 1/2003 | Moore-Ede et al. |
| 6,516,246 B2 | 2/2003 | Derakhshan |
| 6,520,905 B1 | 2/2003 | Surve et al. |
| 6,520,921 B1 | 2/2003 | Patton et al. |
| 6,522,906 B1 | 2/2003 | Salisbury, Jr. et al. |
| 6,524,249 B2 | 2/2003 | Moehring et al. |
| 6,526,297 B1 | 2/2003 | Merilainen |
| 6,526,415 B2 | 2/2003 | Smith et al. |
| 6,527,715 B2 | 3/2003 | Balkin et al. |
| 6,527,730 B2 | 3/2003 | Blazey et al. |
| 6,529,759 B1 | 3/2003 | Tucker et al. |
| 6,529,773 B1 | 3/2003 | Dewan |
| 6,530,884 B2 | 3/2003 | Balkin et al. |
| 6,538,436 B1 | 3/2003 | Simola et al. |
| 6,539,245 B2 | 3/2003 | Tsukada et al. |
| 6,539,263 B1 | 3/2003 | Schiff et al. |
| 6,544,170 B1 | 4/2003 | Kajihara et al. |
| 6,545,650 B1 | 4/2003 | Yamada et al. |
| 6,546,378 B1 | 4/2003 | Cook |
| 6,547,736 B1 | 4/2003 | Moehring et al. |
| 6,547,746 B1 | 4/2003 | Marino |
| 6,549,804 B1 | 4/2003 | Osorio et al. |
| 6,551,243 B2 | 4/2003 | Bocionek et al. |
| 6,553,252 B2 | 4/2003 | Balkin et al. |
| 6,556,695 B1 | 4/2003 | Packer et al. |
| 6,556,861 B1 | 4/2003 | Prichep |
| 6,557,558 B1 | 5/2003 | Tajima et al. |
| 6,565,518 B2 | 5/2003 | Blazey et al. |
| 6,574,513 B1 | 6/2003 | Collura et al. |
| 6,574,573 B1 | 6/2003 | Asano |
| 6,587,729 B2 | 7/2003 | O'Loughlin et al. |
| 6,591,132 B2 | 7/2003 | Gotman et al. |
| 6,594,524 B2 | 7/2003 | Esteller et al. |
| 6,602,202 B2 | 8/2003 | John et al. |
| 6,609,030 B1 | 8/2003 | Rezai et al. |
| 6,611,698 B1 | 8/2003 | Yamashita et al. |
| 6,616,611 B1 | 9/2003 | Moehring |
| 6,622,036 B1 | 9/2003 | Suffin |
| 6,625,485 B2 | 9/2003 | Levendowski et al. |
| 6,626,676 B2 | 9/2003 | Freer |
| 6,640,122 B2 | 10/2003 | Manoli et al. |
| 6,644,976 B2 | 11/2003 | Kullok et al. |
| 6,648,822 B2 | 11/2003 | Hamamoto et al. |
| 6,648,880 B2 | 11/2003 | Chauvet et al. |
| 6,650,917 B2 | 11/2003 | Diab et al. |
| 6,652,458 B2 | 11/2003 | Blazey et al. |
| 6,652,470 B2 | 11/2003 | Patton et al. |
| 6,654,632 B2 | 11/2003 | Lange et al. |
| 6,654,729 B1 | 11/2003 | Hickman et al. |
| 6,656,137 B1 | 12/2003 | Tyldsley et al. |
| 6,658,287 B1 | 12/2003 | Litt et al. |
| 6,663,571 B1 | 12/2003 | Njemanze |
| 6,665,552 B2 | 12/2003 | Yokosawa et al. |
| 6,665,553 B2 | 12/2003 | Kandori et al. |
| 6,665,560 B2 | 12/2003 | Becker et al. |
| 6,665,562 B2 | 12/2003 | Gluckman et al. |
| 6,669,627 B1 | 12/2003 | Campbell et al. |
| 6,678,548 B1 | 1/2004 | Echauz et al. |
| 6,681,774 B2 | 1/2004 | Dewan |
| 6,684,098 B2 | 1/2004 | Oshio et al. |
| 6,687,525 B2 | 2/2004 | Llinas et al. |
| 6,695,761 B2 | 2/2004 | Oschman et al. |
| 6,697,660 B1 | 2/2004 | Robinson |
| RE38,476 E | 3/2004 | Diab et al. |
| 6,699,194 B1 | 3/2004 | Diab et al. |
| 6,701,173 B2 | 3/2004 | Nowinski et al. |
| 6,708,051 B1 | 3/2004 | Durousseau |
| 6,708,064 B2 | 3/2004 | Rezai |
| 6,708,184 B2 | 3/2004 | Smith et al. |

(56)                    References Cited

U.S. PATENT DOCUMENTS

| | | | |
|---|---|---|---|
| 6,709,399 | B1 | 3/2004 | Shen et al. |
| 6,710,051 | B1 | 3/2004 | Trier |
| 6,725,080 | B2 | 4/2004 | Melkent et al. |
| 6,726,624 | B2 | 4/2004 | Keirsbilck et al. |
| 6,728,564 | B2 | 4/2004 | Lahteenmaki |
| 6,731,975 | B1 | 5/2004 | Viertio-Oja et al. |
| 6,735,460 | B2 | 5/2004 | Tsukada et al. |
| 6,735,467 | B2 | 5/2004 | Wilson |
| 6,740,032 | B2 | 5/2004 | Balkin et al. |
| 6,743,167 | B2 | 6/2004 | Balkin et al. |
| 6,743,182 | B2 | 6/2004 | Miller et al. |
| 6,745,060 | B2 | 6/2004 | Diab et al. |
| 6,745,156 | B2 | 6/2004 | Cook |
| 6,746,409 | B2 | 6/2004 | Keirsbilck et al. |
| 6,751,499 | B2 | 6/2004 | Lange et al. |
| 6,758,813 | B2 | 7/2004 | Meadows |
| 6,768,920 | B2 | 7/2004 | Lange et al. |
| 6,773,400 | B2 | 8/2004 | Njemanze |
| 6,774,929 | B1 | 8/2004 | Kopp |
| 6,785,409 | B1 | 8/2004 | Suri |
| 6,795,724 | B2 | 9/2004 | Hogan |
| 6,798,898 | B1 | 9/2004 | Fedorovskaya et al. |
| 6,801,648 | B2 | 10/2004 | Cheng |
| 6,801,803 | B2 | 10/2004 | Viertio-Oja |
| 6,804,661 | B2 | 10/2004 | Cook |
| 6,815,949 | B2 | 11/2004 | Kandori et al. |
| 6,816,744 | B2 | 11/2004 | Garfield et al. |
| 6,819,956 | B2 | 11/2004 | DiLorenzo |
| 6,826,426 | B2 | 11/2004 | Lange et al. |
| 6,842,670 | B2 | 1/2005 | Lin et al. |
| 6,843,774 | B2 | 1/2005 | Foust et al. |
| 6,853,186 | B2 | 2/2005 | Li |
| 6,856,830 | B2 | 2/2005 | He |
| 6,865,494 | B2 | 3/2005 | Duensing et al. |
| 6,873,872 | B2 | 3/2005 | Gluckman et al. |
| 6,875,174 | B2 | 4/2005 | Braun et al. |
| 6,876,196 | B1 | 4/2005 | Taulu et al. |
| 6,882,881 | B1 | 4/2005 | Lesser et al. |
| 6,885,192 | B2 | 4/2005 | Clarke et al. |
| 6,886,964 | B2 | 5/2005 | Gardiner et al. |
| 6,893,407 | B1 | 5/2005 | Brooks et al. |
| 6,896,655 | B2 | 5/2005 | Patton et al. |
| RE38,749 | E | 6/2005 | Dardik |
| 6,907,280 | B2 | 6/2005 | Becerra et al. |
| 6,915,241 | B2 | 7/2005 | Kohlmorgen et al. |
| 6,926,921 | B2 | 8/2005 | Stasiak et al. |
| 6,928,354 | B2 | 8/2005 | Ryu et al. |
| 6,931,274 | B2 | 8/2005 | Williams |
| 6,931,275 | B2 | 8/2005 | Collura |
| 6,936,012 | B2 | 8/2005 | Wells |
| 6,947,790 | B2 | 9/2005 | Gevins et al. |
| 6,950,697 | B2 | 9/2005 | Jordan |
| 6,950,698 | B2 | 9/2005 | Sarkela et al. |
| 6,963,770 | B2 | 11/2005 | Scarantino et al. |
| 6,963,771 | B2 | 11/2005 | Scarantino et al. |
| 6,978,179 | B1 | 12/2005 | Flagg et al. |
| 6,980,863 | B2 | 12/2005 | van Venrooij et al. |
| 6,981,947 | B2 | 1/2006 | Melker |
| 6,983,184 | B2 | 1/2006 | Price |
| 6,983,264 | B2 | 1/2006 | Shimizu |
| 6,985,769 | B2 | 1/2006 | Jordan |
| 6,988,056 | B2 | 1/2006 | Cook |
| 6,993,380 | B1 | 1/2006 | Modarres |
| 6,996,261 | B2 | 2/2006 | deCharms |
| 7,010,340 | B2 | 3/2006 | Scarantino et al. |
| 7,011,410 | B2 | 3/2006 | Bolger et al. |
| 7,011,814 | B2 | 3/2006 | Suddarth et al. |
| 7,014,613 | B2 | 3/2006 | John et al. |
| 7,016,722 | B2 | 3/2006 | Prichep |
| 7,022,083 | B2 | 4/2006 | Tanaka et al. |
| 7,023,206 | B2 | 4/2006 | Viehland et al. |
| 7,024,247 | B2 | 4/2006 | Gliner et al. |
| 7,035,685 | B2 | 4/2006 | Ryu et al. |
| 7,035,686 | B2 | 4/2006 | Hogan |
| 7,037,260 | B2 | 5/2006 | Keirsbilck et al. |
| 7,038,450 | B2 | 5/2006 | Romalis et al. |
| 7,039,266 | B1 | 5/2006 | Doty |
| 7,039,547 | B2 | 5/2006 | Wilson |
| 7,043,293 | B1 | 5/2006 | Baura |
| 7,053,610 | B2 | 5/2006 | Clarke et al. |
| 7,054,454 | B2 | 5/2006 | Causevic et al. |
| 7,062,391 | B2 | 6/2006 | Wilson |
| 7,070,571 | B2 | 7/2006 | Kramer et al. |
| 7,079,977 | B2 | 7/2006 | Osorio et al. |
| 7,089,927 | B2 | 8/2006 | John et al. |
| 7,092,748 | B2 | 8/2006 | Valdes Sosa et al. |
| 7,099,714 | B2 | 8/2006 | Houben |
| 7,103,398 | B2 | 9/2006 | Sieburg |
| 7,104,947 | B2 | 9/2006 | Riehl |
| 7,104,963 | B2 | 9/2006 | Melker et al. |
| 7,105,824 | B2 | 9/2006 | Stoddart et al. |
| 7,107,090 | B2 | 9/2006 | Salisbury, Jr. et al. |
| 7,116,102 | B2 | 10/2006 | Clarke et al. |
| 7,120,486 | B2 | 10/2006 | Leuthardt et al. |
| 7,123,955 | B1 | 10/2006 | Gao et al. |
| 7,128,713 | B2 | 10/2006 | Moehring et al. |
| 7,130,673 | B2 | 10/2006 | Tolvanen-Laakso et al. |
| 7,130,675 | B2 | 10/2006 | Ewing et al. |
| 7,130,691 | B2 | 10/2006 | Falci |
| 7,145,333 | B2 | 12/2006 | Romalis et al. |
| 7,146,211 | B2 | 12/2006 | Frei et al. |
| 7,146,218 | B2 | 12/2006 | Esteller et al. |
| 7,149,572 | B2 | 12/2006 | Frei et al. |
| 7,150,710 | B2 | 12/2006 | Haber et al. |
| 7,150,715 | B2 | 12/2006 | Collura et al. |
| 7,150,718 | B2 | 12/2006 | Okada et al. |
| 7,162,295 | B2 | 1/2007 | Ryu et al. |
| 7,163,512 | B1 | 1/2007 | Childre et al. |
| 7,164,941 | B2 | 1/2007 | Misczynski et al. |
| 7,171,252 | B1 | 1/2007 | Scarantino et al. |
| 7,171,339 | B2 | 1/2007 | Repucci et al. |
| 7,176,680 | B1 | 2/2007 | Veryaskin |
| 7,177,675 | B2 | 2/2007 | Suffin et al. |
| 7,183,381 | B2 | 2/2007 | Varadhachary et al. |
| 7,186,209 | B2 | 3/2007 | Jacobson et al. |
| 7,187,169 | B2 | 3/2007 | Clarke et al. |
| 7,190,826 | B2 | 3/2007 | Russell et al. |
| 7,190,995 | B2 | 3/2007 | Chervin et al. |
| 7,193,413 | B2 | 3/2007 | Kandori et al. |
| 7,196,514 | B2 | 3/2007 | Li |
| 7,197,352 | B2 | 3/2007 | Gott et al. |
| 7,199,708 | B2 | 4/2007 | Terauchi et al. |
| 7,207,948 | B2 | 4/2007 | Coyle |
| 7,209,787 | B2 | 4/2007 | DiLorenzo |
| 7,209,788 | B2 | 4/2007 | Nicolelis et al. |
| 7,212,851 | B2 | 5/2007 | Donoghue et al. |
| 7,215,986 | B2 | 5/2007 | Diab et al. |
| 7,215,994 | B2 | 5/2007 | Huiku |
| 7,218,104 | B2 | 5/2007 | Clarke et al. |
| 7,222,964 | B2 | 5/2007 | Gotze et al. |
| 7,224,282 | B2 | 5/2007 | Terauchi et al. |
| 7,225,013 | B2 | 5/2007 | Geva et al. |
| 7,228,169 | B2 | 6/2007 | Viertio-Oja et al. |
| 7,228,171 | B2 | 6/2007 | Lesser et al. |
| 7,228,178 | B2 | 6/2007 | Carroll et al. |
| 7,231,245 | B2 | 6/2007 | Greenwald et al. |
| 7,231,254 | B2 | 6/2007 | DiLorenzo |
| 7,242,984 | B2 | 7/2007 | DiLorenzo |
| 7,248,928 | B2 | 7/2007 | Yagi |
| 7,254,433 | B2 | 8/2007 | Diab et al. |
| 7,254,439 | B2 | 8/2007 | Misczynski et al. |
| 7,254,500 | B2 | 8/2007 | Makeig et al. |
| 7,258,659 | B2 | 8/2007 | Anninou et al. |
| 7,260,430 | B2 | 8/2007 | Wu et al. |
| 7,267,652 | B2 | 9/2007 | Coyle et al. |
| 7,269,455 | B2 | 9/2007 | Pineda |
| 7,269,456 | B2 | 9/2007 | Collura |
| 7,269,516 | B2 | 9/2007 | Brunner et al. |
| 7,277,758 | B2 | 10/2007 | DiLorenzo |
| 7,280,861 | B2 | 10/2007 | Thomas et al. |
| 7,280,867 | B2 | 10/2007 | Frei et al. |
| 7,280,870 | B2 | 10/2007 | Nurmikko et al. |
| 7,282,030 | B2 | 10/2007 | Frei et al. |
| 7,283,861 | B2 | 10/2007 | Bystritsky |

(56)                References Cited

U.S. PATENT DOCUMENTS

| | | | |
|---|---|---|---|
| 7,286,871 | B2 | 10/2007 | Cohen |
| 7,288,066 | B2 | 10/2007 | Drew |
| 7,297,110 | B2 | 11/2007 | Goyal et al. |
| 7,299,088 | B1 | 11/2007 | Thakor et al. |
| 7,313,442 | B2 | 12/2007 | Velasco et al. |
| 7,321,837 | B2 | 1/2008 | Osorio et al. |
| 7,324,845 | B2 | 1/2008 | Mietus et al. |
| 7,324,851 | B1 | 1/2008 | DiLorenzo |
| 7,328,053 | B1 | 2/2008 | Diab et al. |
| 7,330,032 | B2 | 2/2008 | Donnangelo |
| 7,333,619 | B2 | 2/2008 | Causevic et al. |
| 7,333,851 | B2 | 2/2008 | Echauz et al. |
| 7,334,892 | B2 | 2/2008 | Goodall et al. |
| 7,338,171 | B2 | 3/2008 | Hsieh et al. |
| 7,338,455 | B2 | 3/2008 | White et al. |
| 7,340,125 | B1 | 3/2008 | Doty |
| 7,340,289 | B2 | 3/2008 | Kandori et al. |
| 7,343,198 | B2 | 3/2008 | Behbehani et al. |
| 7,346,382 | B2 | 3/2008 | McIntyre et al. |
| 7,346,395 | B2 | 3/2008 | Lozano et al. |
| 7,353,064 | B2 | 4/2008 | Gliner et al. |
| 7,353,065 | B2 | 4/2008 | Morrell |
| 7,367,949 | B2 | 5/2008 | Korhonen et al. |
| 7,369,896 | B2 | 5/2008 | Gesotti |
| 7,371,365 | B2 | 5/2008 | Poduslo et al. |
| 7,373,198 | B2 | 5/2008 | Bibian et al. |
| 7,376,453 | B1 | 5/2008 | Diab et al. |
| 7,376,459 | B2 | 5/2008 | Rosenfeld |
| 7,378,056 | B2 | 5/2008 | Black |
| 7,381,185 | B2 | 6/2008 | Zhirnov et al. |
| 7,383,070 | B2 | 6/2008 | Diab et al. |
| 7,392,079 | B2 | 6/2008 | Donoghue et al. |
| 7,394,246 | B2 | 7/2008 | Chieh et al. |
| 7,395,292 | B2 | 7/2008 | Johnson |
| 7,396,333 | B2 | 7/2008 | Stahmann et al. |
| 7,399,282 | B2 | 7/2008 | John et al. |
| 7,400,984 | B2 | 7/2008 | Kandori et al. |
| 7,403,124 | B2 | 7/2008 | Arakawa et al. |
| 7,403,809 | B2 | 7/2008 | Tsukada et al. |
| 7,403,814 | B2 | 7/2008 | Cox et al. |
| 7,403,815 | B2 | 7/2008 | Katz et al. |
| 7,403,820 | B2 | 7/2008 | DiLorenzo |
| 7,407,485 | B2 | 8/2008 | Huiku |
| 7,409,321 | B2 | 8/2008 | Repucci et al. |
| 7,418,290 | B2 | 8/2008 | Devlin et al. |
| 7,420,033 | B2 | 9/2008 | Varadhachary et al. |
| 7,429,247 | B2 | 9/2008 | Okada et al. |
| 7,437,196 | B2 | 10/2008 | Wyler et al. |
| 7,440,789 | B2 | 10/2008 | Hannula et al. |
| 7,448,751 | B2 | 11/2008 | Kiderman et al. |
| 7,450,986 | B2 | 11/2008 | Nguyen et al. |
| 7,453,263 | B2 | 11/2008 | Kim et al. |
| 7,454,240 | B2 | 11/2008 | Diab et al. |
| 7,454,387 | B2 | 11/2008 | Abercrombie et al. |
| 7,457,653 | B2 | 11/2008 | Fujimaki |
| 7,460,903 | B2 | 12/2008 | Pineda et al. |
| 7,461,045 | B1 | 12/2008 | Chaovalitwongse et al. |
| 7,462,151 | B2 | 12/2008 | Childre et al. |
| 7,462,155 | B2 | 12/2008 | England |
| 7,463,024 | B2 | 12/2008 | Simola et al. |
| 7,463,142 | B2 | 12/2008 | Lindsay |
| 7,466,132 | B2 | 12/2008 | Clarke et al. |
| 7,468,040 | B2 | 12/2008 | Hartley et al. |
| 7,468,350 | B2 | 12/2008 | Gong et al. |
| 7,469,697 | B2 | 12/2008 | Lee et al. |
| 7,471,971 | B2 | 12/2008 | Diab et al. |
| 7,471,978 | B2 | 12/2008 | John et al. |
| 7,478,108 | B2 | 1/2009 | Townsend et al. |
| 7,482,298 | B2 | 1/2009 | Nepela |
| 7,488,294 | B2 | 2/2009 | Torch |
| 7,489,958 | B2 | 2/2009 | Diab et al. |
| 7,489,964 | B2 | 2/2009 | Suffin et al. |
| 7,490,085 | B2 | 2/2009 | Walker et al. |
| 7,491,173 | B2 | 2/2009 | Heim |
| 7,496,393 | B2 | 2/2009 | Diab et al. |
| 7,497,828 | B1 | 3/2009 | Wilk et al. |
| 7,499,741 | B2 | 3/2009 | Diab et al. |
| 7,499,745 | B2 | 3/2009 | Littrup et al. |
| 7,502,720 | B2 | 3/2009 | Taulu |
| 7,509,154 | B2 | 3/2009 | Diab et al. |
| 7,509,161 | B2 | 3/2009 | Viertio-Oja |
| 7,509,163 | B1 | 3/2009 | Luo et al. |
| 7,510,531 | B2 | 3/2009 | Lee et al. |
| 7,510,699 | B2 | 3/2009 | Black et al. |
| 7,515,054 | B2 | 4/2009 | Torch |
| 7,520,614 | B2 | 4/2009 | Joos et al. |
| 7,530,955 | B2 | 5/2009 | Diab et al. |
| 7,537,568 | B2 | 5/2009 | Moehring |
| 7,539,528 | B2 | 5/2009 | Xiong et al. |
| 7,539,532 | B2 | 5/2009 | Tran |
| 7,539,533 | B2 | 5/2009 | Tran |
| 7,539,543 | B2 | 5/2009 | Schiff et al. |
| 7,546,158 | B2 | 6/2009 | Allison et al. |
| 7,547,284 | B2 | 6/2009 | Brainard, II |
| 7,553,810 | B2 | 6/2009 | Gong et al. |
| 7,554,549 | B2 | 6/2009 | Sagar et al. |
| 7,555,344 | B2 | 6/2009 | Maschino et al. |
| 7,558,622 | B2 | 7/2009 | Tran |
| 7,559,903 | B2 | 7/2009 | Moussavi et al. |
| 7,565,193 | B2 | 7/2009 | Laken |
| 7,565,200 | B2 | 7/2009 | Wyler et al. |
| 7,565,809 | B2 | 7/2009 | Takeda |
| 7,567,693 | B2 | 7/2009 | deCharms |
| 7,570,054 | B1 | 8/2009 | Lin |
| 7,570,991 | B2 | 8/2009 | Milgramm et al. |
| 7,572,225 | B2 | 8/2009 | Stahmann et al. |
| 7,573,264 | B2 | 8/2009 | Xu et al. |
| 7,573,268 | B2 | 8/2009 | Volegov et al. |
| 7,574,007 | B2 | 8/2009 | Shaw et al. |
| 7,574,254 | B2 | 8/2009 | Milgramm et al. |
| 7,577,472 | B2 | 8/2009 | Li et al. |
| 7,580,742 | B2 | 8/2009 | Tan et al. |
| 7,580,798 | B2 | 8/2009 | Brunner et al. |
| 7,593,767 | B1 | 9/2009 | Modarres |
| 7,594,122 | B2 | 9/2009 | Milgramm et al. |
| 7,596,535 | B2 | 9/2009 | de Voir et al. |
| 7,597,665 | B2 | 10/2009 | Wilk et al. |
| 7,599,735 | B2 | 10/2009 | Viertio-Oja et al. |
| 7,603,168 | B2 | 10/2009 | Bibian et al. |
| 7,603,174 | B2 | 10/2009 | De Ridder |
| 7,604,603 | B2 | 10/2009 | Sackner et al. |
| 7,608,579 | B2 | 10/2009 | Gong et al. |
| 7,610,094 | B2 | 10/2009 | Stahmann et al. |
| 7,613,502 | B2 | 11/2009 | Yamamoto et al. |
| 7,613,519 | B2 | 11/2009 | De Ridder |
| 7,613,520 | B2 | 11/2009 | De Ridder |
| 7,620,456 | B2 | 11/2009 | Gliner et al. |
| 7,623,912 | B2 | 11/2009 | Akselrod et al. |
| 7,623,927 | B2 | 11/2009 | Rezai |
| 7,623,928 | B2 | 11/2009 | DiLorenzo |
| 7,624,293 | B2 | 11/2009 | Osorio et al. |
| 7,625,340 | B2 | 12/2009 | Sarkela |
| 7,627,370 | B2 | 12/2009 | Marks |
| 7,630,757 | B2 | 12/2009 | Dorfmeister et al. |
| 7,639,146 | B2 | 12/2009 | Baura |
| 7,640,055 | B2 | 12/2009 | Geva et al. |
| 7,643,655 | B2 | 1/2010 | Liang et al. |
| 7,647,097 | B2 | 1/2010 | Flaherty et al. |
| 7,647,098 | B2 | 1/2010 | Prichep |
| 7,649,351 | B2 | 1/2010 | Kajola et al. |
| 7,653,433 | B2 | 1/2010 | Lozano et al. |
| 7,654,948 | B2 | 2/2010 | Kaplan et al. |
| 7,665,845 | B2 | 2/2010 | Kiderman et al. |
| 7,668,579 | B2 | 2/2010 | Lynn |
| 7,668,591 | B2 | 2/2010 | Lee et al. |
| 7,672,707 | B2 | 3/2010 | Takeda |
| 7,672,717 | B1 | 3/2010 | Zikov et al. |
| 7,676,263 | B2 | 3/2010 | Harris et al. |
| 7,678,041 | B2 | 3/2010 | Prenzel et al. |
| 7,678,061 | B2 | 3/2010 | Lee et al. |
| 7,678,767 | B2 | 3/2010 | Gong et al. |
| 7,680,526 | B2 | 3/2010 | McIntyre et al. |
| 7,682,024 | B2 | 3/2010 | Plant et al. |
| 7,684,856 | B2 | 3/2010 | Virtanen et al. |

(56) References Cited

U.S. PATENT DOCUMENTS

| | | | |
|---|---|---|---|
| D613,267 S | 4/2010 | Suwalski et al. |
| 7,697,979 B2 | 4/2010 | Martinerie et al. |
| 7,702,502 B2 | 4/2010 | Ricci et al. |
| 7,706,871 B2 | 4/2010 | Devlin et al. |
| 7,706,992 B2 | 4/2010 | Ricci et al. |
| 7,711,417 B2 | 5/2010 | John et al. |
| 7,715,894 B2 | 5/2010 | Dunseath et al. |
| 7,715,910 B2 | 5/2010 | Hargrove et al. |
| 7,715,919 B2 | 5/2010 | Osorio et al. |
| 7,720,519 B2 | 5/2010 | Ruohonen |
| 7,720,530 B2 | 5/2010 | Causevic |
| 7,725,174 B2 | 5/2010 | Kern et al. |
| 7,727,161 B2 | 6/2010 | Coyle et al. |
| 7,729,740 B2 | 6/2010 | Kraus, Jr. et al. |
| 7,729,753 B2 | 6/2010 | Kremliovsky et al. |
| 7,729,755 B2 | 6/2010 | Laken |
| 7,729,773 B2 | 6/2010 | Sloan |
| 7,731,360 B2 | 6/2010 | MacDougall et al. |
| 7,733,224 B2 | 6/2010 | Tran |
| 7,733,973 B2 | 6/2010 | Moriya et al. |
| 7,734,334 B2 | 6/2010 | Mietus et al. |
| 7,734,340 B2 | 6/2010 | De Ridder |
| 7,737,687 B2 | 6/2010 | Na et al. |
| 7,740,592 B2 | 6/2010 | Graham et al. |
| 7,742,820 B2 | 6/2010 | Wyler et al. |
| 7,746,979 B2 | 6/2010 | Dilmanian et al. |
| 7,747,325 B2 | 6/2010 | Dilorenzo |
| 7,747,326 B2 | 6/2010 | Velasco et al. |
| 7,747,551 B2 | 6/2010 | Snyder |
| 7,749,155 B1 | 7/2010 | Anderson et al. |
| 7,751,877 B2 | 7/2010 | Flaherty et al. |
| 7,751,878 B1 | 7/2010 | Merkle et al. |
| 7,753,523 B2 | 7/2010 | Kiderman et al. |
| 7,754,190 B2 | 7/2010 | Suffin |
| 7,756,564 B2 | 7/2010 | Matsui et al. |
| 7,756,568 B2 | 7/2010 | Scarantino et al. |
| 7,757,690 B2 | 7/2010 | Stahmann et al. |
| 7,758,503 B2 | 7/2010 | Lynn et al. |
| 7,763,588 B2 | 7/2010 | van Praag et al. |
| 7,764,283 B2 | 7/2010 | Scott et al. |
| 7,764,987 B2 | 7/2010 | Dorr et al. |
| 7,766,827 B2 | 8/2010 | Balkin et al. |
| 7,769,424 B2 | 8/2010 | Sato |
| 7,769,431 B2 | 8/2010 | Scarantino et al. |
| 7,771,341 B2 | 8/2010 | Rogers |
| 7,771,364 B2 | 8/2010 | Arbel et al. |
| 7,773,767 B2 | 8/2010 | Wahl et al. |
| 7,774,052 B2 | 8/2010 | Burton et al. |
| 7,774,064 B2 | 8/2010 | Meyer et al. |
| 7,778,692 B2 | 8/2010 | Scarantino et al. |
| 7,778,693 B2 | 8/2010 | Barbour et al. |
| 7,783,332 B2 | 8/2010 | Laufer et al. |
| 7,787,937 B2 | 8/2010 | Scarantino et al. |
| 7,787,946 B2 | 8/2010 | Stahmann et al. |
| 7,792,575 B2 | 9/2010 | Fujimaki et al. |
| 7,794,403 B2 | 9/2010 | Schaafsma |
| 7,794,406 B2 | 9/2010 | Reisfeld et al. |
| 7,797,040 B2 | 9/2010 | Pesaran et al. |
| 7,800,493 B2 | 9/2010 | Terauchi et al. |
| 7,801,591 B1 | 9/2010 | Shusterman |
| 7,801,592 B2 | 9/2010 | Shan et al. |
| 7,801,593 B2 | 9/2010 | Behbehani et al. |
| 7,801,686 B2 | 9/2010 | Hyde et al. |
| 7,803,118 B2 | 9/2010 | Reisfeld et al. |
| 7,803,119 B2 | 9/2010 | Reisfeld |
| 7,809,433 B2 | 10/2010 | Keenan |
| 7,809,434 B2 | 10/2010 | Kofol et al. |
| 7,811,279 B2 | 10/2010 | John |
| 7,819,794 B2 | 10/2010 | Becker |
| 7,819,812 B2 | 10/2010 | John et al. |
| D626,949 S | 11/2010 | Wahl et al. |
| D627,476 S | 11/2010 | Gaw et al. |
| 7,831,302 B2 | 11/2010 | Thomas |
| 7,831,305 B2 | 11/2010 | Gliner |
| 7,833,966 B2 | 11/2010 | Peyman |
| 7,834,627 B2 | 11/2010 | Sakai et al. |
| 7,835,498 B2 | 11/2010 | Bonfiglio et al. |
| 7,835,787 B2 | 11/2010 | Sajda et al. |
| 7,840,039 B2 | 11/2010 | Fuchs |
| 7,840,248 B2 | 11/2010 | Fuchs et al. |
| 7,840,250 B2 | 11/2010 | Tucker |
| 7,840,257 B2 | 11/2010 | Chance |
| 7,853,329 B2 | 12/2010 | DiLorenzo |
| 7,856,264 B2 | 12/2010 | Firlik et al. |
| 7,860,548 B2 | 12/2010 | McIntyre et al. |
| 7,860,552 B2 | 12/2010 | Borsook et al. |
| 7,860,561 B1 | 12/2010 | Modarres |
| 7,865,234 B1 | 1/2011 | Modarres |
| 7,865,235 B2 | 1/2011 | Le et al. |
| 7,865,244 B2 | 1/2011 | Giftakis et al. |
| 7,866,818 B2 | 1/2011 | Schroeder et al. |
| 7,872,235 B2 | 1/2011 | Rousso et al. |
| 7,872,635 B2 | 1/2011 | Mitchell |
| 7,873,411 B2 | 1/2011 | Eda et al. |
| 7,878,965 B2 | 2/2011 | Haber et al. |
| 7,879,043 B2 | 2/2011 | Meneghini et al. |
| 7,881,760 B2 | 2/2011 | Matsui et al. |
| 7,881,770 B2 | 2/2011 | Melkent et al. |
| 7,881,780 B2 | 2/2011 | Flaherty |
| 7,882,135 B2 | 2/2011 | Brunner et al. |
| 7,885,419 B2 | 2/2011 | Wahl et al. |
| 7,887,493 B2 | 2/2011 | Stahmann et al. |
| 7,890,176 B2 | 2/2011 | Jaax et al. |
| 7,891,814 B2 | 2/2011 | Harada et al. |
| 7,892,764 B2 | 2/2011 | Xiong et al. |
| 7,894,890 B2 | 2/2011 | Sun et al. |
| 7,894,903 B2 | 2/2011 | John |
| 7,895,033 B2 | 2/2011 | Joublin et al. |
| 7,896,807 B2 | 3/2011 | Clancy et al. |
| 7,899,524 B2 | 3/2011 | Kozel |
| 7,899,525 B2 | 3/2011 | John et al. |
| 7,904,134 B2 | 3/2011 | McIntyre et al. |
| 7,904,139 B2 | 3/2011 | Chance |
| 7,904,144 B2 | 3/2011 | Causevic et al. |
| 7,904,507 B2 | 3/2011 | Jung et al. |
| 7,907,994 B2 | 3/2011 | Stolarski et al. |
| 7,907,998 B2 | 3/2011 | Arad (Abboud) |
| 7,908,009 B2 | 3/2011 | Wyler et al. |
| 7,909,771 B2 | 3/2011 | Meyer et al. |
| 7,912,530 B2 | 3/2011 | Seki et al. |
| 7,917,206 B2 | 3/2011 | Frei et al. |
| 7,917,221 B2 | 3/2011 | Tass |
| 7,917,225 B2 | 3/2011 | Wyler et al. |
| 7,918,779 B2 | 4/2011 | Haber et al. |
| 7,918,807 B2 | 4/2011 | Lau et al. |
| 7,920,914 B2 | 4/2011 | Shieh et al. |
| 7,929,693 B2 | 4/2011 | Terauchi et al. |
| 7,930,035 B2 | 4/2011 | DiLorenzo |
| 7,932,225 B2 | 4/2011 | Gong et al. |
| 7,933,645 B2 | 4/2011 | Strychacz et al. |
| 7,933,646 B2 | 4/2011 | Frei et al. |
| 7,933,727 B2 | 4/2011 | Taulu et al. |
| 7,937,138 B2 | 5/2011 | Liley |
| 7,937,152 B1 | 5/2011 | Lozano |
| 7,938,782 B2 | 5/2011 | Stahmann et al. |
| 7,938,785 B2 | 5/2011 | Aguilar et al. |
| 7,941,209 B2 | 5/2011 | Hughes et al. |
| 7,942,824 B1 | 5/2011 | Kayyali et al. |
| 7,944,551 B2 | 5/2011 | Addison et al. |
| 7,945,304 B2 | 5/2011 | Feinberg |
| 7,945,316 B2 | 5/2011 | Giftakis et al. |
| 7,962,204 B2 | 6/2011 | Suffin et al. |
| 7,967,439 B2 | 6/2011 | Shelhamer et al. |
| 7,970,734 B2 | 6/2011 | Townsend et al. |
| 7,972,278 B2 | 7/2011 | Graham et al. |
| 7,974,696 B1 | 7/2011 | DiLorenzo |
| 7,974,787 B2 | 7/2011 | Hyde et al. |
| 7,976,465 B2 | 7/2011 | Frei et al. |
| 7,983,740 B2 | 7/2011 | Culver et al. |
| 7,983,741 B2 | 7/2011 | Chance |
| 7,983,757 B2 | 7/2011 | Miyazawa et al. |
| 7,986,991 B2 | 7/2011 | Prichep |
| 7,988,613 B2 | 8/2011 | Becker |
| 7,988,969 B2 | 8/2011 | Poduslo et al. |

(56)  References Cited

U.S. PATENT DOCUMENTS

| | | | |
|---|---|---|---|
| 7,991,461 B2 | 8/2011 | Flaherty et al. |
| 7,993,279 B2 | 8/2011 | Hartley et al. |
| 7,996,075 B2 | 8/2011 | Korzinov et al. |
| 7,996,076 B2 | 8/2011 | Burns et al. |
| 8,000,767 B2 | 8/2011 | Eden et al. |
| 8,000,773 B2 | 8/2011 | Rousso et al. |
| 8,000,793 B2 | 8/2011 | Libbus |
| 8,000,794 B2 | 8/2011 | Lozano |
| 8,001,179 B2 | 8/2011 | Jung et al. |
| 8,002,553 B2 | 8/2011 | Hatlestad et al. |
| 8,005,534 B2 | 8/2011 | Greenwald et al. |
| 8,005,624 B1 | 8/2011 | Starr |
| 8,005,766 B2 | 8/2011 | Tian et al. |
| 8,005,894 B2 | 8/2011 | Jung et al. |
| 8,010,178 B2 | 8/2011 | Seki et al. |
| 8,010,347 B2 | 8/2011 | Ricci et al. |
| 8,012,107 B2 | 9/2011 | Einav et al. |
| 8,014,847 B2 | 9/2011 | Shastri et al. |
| 8,014,870 B2 | 9/2011 | Seidman |
| 8,019,400 B2 | 9/2011 | Diab et al. |
| 8,019,410 B1 | 9/2011 | Bharmi et al. |
| 8,021,299 B2 | 9/2011 | Miesel et al. |
| 8,024,032 B1 | 9/2011 | Osorio et al. |
| 8,025,404 B2 | 9/2011 | Bolger et al. |
| 8,027,730 B2 | 9/2011 | John |
| 8,029,553 B2 | 10/2011 | Nemenov |
| 8,032,209 B2 | 10/2011 | He et al. |
| 8,032,486 B2 | 10/2011 | Townsend et al. |
| 8,032,842 B2 | 10/2011 | Kwon et al. |
| 8,033,996 B2 | 10/2011 | Behar |
| 8,036,434 B2 | 10/2011 | Hewett et al. |
| 8,036,728 B2 | 10/2011 | Diab et al. |
| 8,036,736 B2 | 10/2011 | Snyder et al. |
| 8,041,136 B2 | 10/2011 | Causevic |
| 8,041,418 B2 | 10/2011 | Giftakis et al. |
| 8,041,419 B2 | 10/2011 | Giftakis et al. |
| 8,046,041 B2 | 10/2011 | Diab et al. |
| 8,046,042 B2 | 10/2011 | Diab et al. |
| 8,055,591 B2 | 11/2011 | Jung et al. |
| 8,055,722 B2 | 11/2011 | Hille |
| 8,059,879 B2 | 11/2011 | Tsukimoto |
| 8,060,194 B2 | 11/2011 | Flaherty |
| 8,065,011 B2 | 11/2011 | Echauz et al. |
| 8,065,360 B2 | 11/2011 | Jung et al. |
| 8,066,637 B2 | 11/2011 | Childre et al. |
| 8,066,647 B2 | 11/2011 | Armitstead |
| 8,068,904 B2 | 11/2011 | Sun et al. |
| 8,068,911 B2 | 11/2011 | Giftakis et al. |
| 8,069,125 B2 | 11/2011 | Jung et al. |
| 8,073,534 B2 | 12/2011 | Low |
| 8,073,631 B2 | 12/2011 | Wilber et al. |
| 8,075,499 B2 | 12/2011 | Nathan et al. |
| 8,079,953 B2 | 12/2011 | Braun et al. |
| 8,082,031 B2 | 12/2011 | Ochs |
| 8,082,215 B2 | 12/2011 | Jung et al. |
| 8,083,786 B2 | 12/2011 | Gafni et al. |
| 8,085,902 B2 | 12/2011 | Bonfiglio et al. |
| 8,086,294 B2 | 12/2011 | Echauz et al. |
| 8,086,296 B2 | 12/2011 | Bystritsky |
| 8,086,563 B2 | 12/2011 | Jung et al. |
| 8,088,057 B2 | 1/2012 | Honeycutt et al. |
| 8,089,283 B2 | 1/2012 | Kaplan et al. |
| 8,095,209 B2 | 1/2012 | Flaherty |
| 8,095,210 B2 | 1/2012 | Burdick et al. |
| 8,103,333 B2 | 1/2012 | Tran |
| 8,108,036 B2 | 1/2012 | Tran |
| 8,108,038 B2 | 1/2012 | Giftakis et al. |
| 8,108,039 B2 | 1/2012 | Saliga et al. |
| 8,108,046 B2 | 1/2012 | Giftakis et al. |
| 8,112,148 B2 | 2/2012 | Giftakis et al. |
| 8,112,153 B2 | 2/2012 | Giftakis et al. |
| 8,114,021 B2 | 2/2012 | Robertson et al. |
| 8,116,874 B2 | 2/2012 | Tass |
| 8,116,877 B2 | 2/2012 | Lozano |
| 8,121,673 B2 | 2/2012 | Tran |
| 8,121,694 B2 | 2/2012 | Molnar et al. |
| 8,121,695 B2 | 2/2012 | Gliner et al. |
| 8,126,528 B2 | 2/2012 | Diab et al. |
| 8,128,422 B2 | 3/2012 | Mellott et al. |
| 8,128,572 B2 | 3/2012 | Diab et al. |
| 8,131,354 B2 | 3/2012 | Arad (Abboud) |
| 8,133,172 B2 | 3/2012 | Shachar et al. |
| 8,135,957 B2 | 3/2012 | Dinges et al. |
| 8,137,269 B2 | 3/2012 | Sheikhzadeh-Nadjar et al. |
| 8,137,270 B2 | 3/2012 | Keenan et al. |
| 8,145,310 B2 | 3/2012 | Dong et al. |
| 8,150,523 B2 | 4/2012 | Schiff et al. |
| 8,150,796 B2 | 4/2012 | Jung et al. |
| 8,152,732 B2 | 4/2012 | Lynn et al. |
| 8,155,726 B2 | 4/2012 | Seki et al. |
| 8,155,736 B2 | 4/2012 | Sullivan et al. |
| 8,160,273 B2 | 4/2012 | Visser et al. |
| 8,160,287 B2 | 4/2012 | Slippy et al. |
| 8,160,689 B2 | 4/2012 | Jadidi |
| 8,162,479 B2 | 4/2012 | Humphries et al. |
| 8,167,784 B1 | 5/2012 | Honeycutt et al. |
| 8,170,637 B2 | 5/2012 | Lee et al. |
| 8,172,766 B1 | 5/2012 | Kayyali et al. |
| 8,175,696 B2 | 5/2012 | Liley et al. |
| 8,177,724 B2 | 5/2012 | Derchak et al. |
| 8,177,726 B2 | 5/2012 | John |
| 8,177,727 B2 | 5/2012 | Kwak |
| 8,177,732 B2 | 5/2012 | Einav et al. |
| 8,180,420 B2 | 5/2012 | Diab et al. |
| 8,180,601 B2 | 5/2012 | Butson et al. |
| 8,185,207 B2 | 5/2012 | Molnar et al. |
| 8,185,382 B2 | 5/2012 | Joublin et al. |
| 8,187,181 B2 | 5/2012 | Osorio et al. |
| 8,187,201 B2 | 5/2012 | Lynn |
| 8,190,227 B2 | 5/2012 | Diab et al. |
| 8,190,248 B2 | 5/2012 | Besio et al. |
| 8,190,249 B1 | 5/2012 | Gharieb et al. |
| 8,190,251 B2 | 5/2012 | Molnar et al. |
| 8,190,264 B2 | 5/2012 | Lozano et al. |
| 8,192,376 B2 | 6/2012 | Lovett et al. |
| 8,195,593 B2 | 6/2012 | Jung et al. |
| 8,197,395 B2 | 6/2012 | Jassemidis et al. |
| 8,197,437 B2 | 6/2012 | Kalafut et al. |
| 8,200,319 B2 | 6/2012 | Pu et al. |
| 8,202,840 B2 | 6/2012 | Peyman |
| 8,203,530 B2 | 6/2012 | Chiang |
| 8,204,583 B2 | 6/2012 | Sackellares et al. |
| 8,204,597 B2 | 6/2012 | Gerber et al. |
| 8,209,009 B2 | 6/2012 | Giftakis et al. |
| 8,209,019 B2 | 6/2012 | Giftakis et al. |
| 8,209,224 B2 | 6/2012 | Pradeep et al. |
| 8,211,035 B2 | 7/2012 | Melker et al. |
| 8,212,556 B1 | 7/2012 | Schwindt et al. |
| 8,213,670 B2 | 7/2012 | Lai |
| 8,214,007 B2 | 7/2012 | Baker et al. |
| 8,214,035 B2 | 7/2012 | Giftakis et al. |
| 8,222,378 B2 | 7/2012 | Masure |
| 8,224,433 B2 | 7/2012 | Suffin et al. |
| 8,229,540 B2 | 7/2012 | Sami et al. |
| 8,233,682 B2 | 7/2012 | Fessler et al. |
| 8,233,965 B2 | 7/2012 | Bjornerud et al. |
| 8,235,907 B2 | 8/2012 | Wilk et al. |
| 8,236,005 B2 | 8/2012 | Meneghini et al. |
| 8,236,038 B2 | 8/2012 | Nofzinger |
| 8,239,014 B2 | 8/2012 | Ochs |
| 8,239,029 B2 | 8/2012 | De Ridder |
| 8,239,030 B1 | 8/2012 | Hagedorn et al. |
| 8,241,213 B2 | 8/2012 | Lynn et al. |
| 8,244,340 B2 | 8/2012 | Wu et al. |
| 8,244,341 B2 | 8/2012 | Hinrikus et al. |
| 8,244,475 B2 | 8/2012 | Aguilar et al. |
| 8,244,552 B2 | 8/2012 | Firminger et al. |
| 8,244,553 B2 | 8/2012 | Firminger et al. |
| 8,248,069 B2 | 8/2012 | Buracas |
| 8,249,316 B2 | 8/2012 | Hu et al. |
| 8,249,698 B2 | 8/2012 | Mugler et al. |
| 8,259,169 B2 | 9/2012 | Sugio et al. |
| 8,262,714 B2 | 9/2012 | Hulvershorn et al. |
| 8,265,743 B2 | 9/2012 | Aguilar et al. |

(56)                    References Cited

U.S. PATENT DOCUMENTS

| | | | |
|---|---|---|---|
| 8,267,851 | B1 | 9/2012 | Kroll |
| 8,270,814 | B2 | 9/2012 | Pradeep et al. |
| 8,271,075 | B2 | 9/2012 | Chuang et al. |
| 8,271,077 | B1 | 9/2012 | Rotenberg |
| 8,271,411 | B2 | 9/2012 | Kaplan |
| 8,280,502 | B2 | 10/2012 | Hargrove et al. |
| 8,280,503 | B2 | 10/2012 | Linderman |
| 8,280,514 | B2 | 10/2012 | Lozano et al. |
| 8,280,515 | B2 | 10/2012 | Greenspan |
| 8,284,233 | B2 | 10/2012 | Bennett et al. |
| 8,285,351 | B2 | 10/2012 | Johnson et al. |
| 8,285,368 | B2 | 10/2012 | Chen et al. |
| 8,290,208 | B2 | 10/2012 | Kurtz et al. |
| 8,290,563 | B2 | 10/2012 | Jin et al. |
| 8,290,575 | B2 | 10/2012 | Tarassenko et al. |
| 8,290,596 | B2 | 10/2012 | Wei et al. |
| 8,295,914 | B2 | 10/2012 | Kalafut et al. |
| 8,295,934 | B2 | 10/2012 | Leyde |
| 8,296,108 | B2 | 10/2012 | Tanaka |
| 8,298,078 | B2 | 10/2012 | Sutton et al. |
| 8,298,140 | B2 | 10/2012 | Beck-Nielsen et al. |
| 8,301,218 | B2 | 10/2012 | Nguyen et al. |
| 8,301,222 | B2 | 10/2012 | Rongen et al. |
| 8,301,232 | B2 | 10/2012 | Albert et al. |
| 8,301,233 | B2 | 10/2012 | Zhang et al. |
| 8,301,257 | B2 | 10/2012 | Hsu et al. |
| D671,523 | S | 11/2012 | Daniel |
| 8,303,636 | B2 | 11/2012 | Schiffer |
| 8,304,246 | B2 | 11/2012 | Cook et al. |
| 8,305,078 | B2 | 11/2012 | Savukov et al. |
| 8,306,607 | B1 | 11/2012 | Levi et al. |
| 8,306,610 | B2 | 11/2012 | Mirow |
| 8,308,646 | B2 | 11/2012 | Belohlavek et al. |
| 8,309,530 | B2 | 11/2012 | Szentirmai et al. |
| 8,311,622 | B2 | 11/2012 | Snyder et al. |
| 8,313,441 | B2 | 11/2012 | Dalton |
| 8,314,707 | B2 | 11/2012 | Kobetski et al. |
| 8,315,703 | B2 | 11/2012 | Lozano |
| 8,315,970 | B2 | 11/2012 | Zalay et al. |
| 8,318,485 | B2 | 11/2012 | Gavrilova et al. |
| 8,320,649 | B2 | 11/2012 | Shahaf et al. |
| 8,323,188 | B2 | 12/2012 | Tran |
| 8,323,189 | B2 | 12/2012 | Tran et al. |
| 8,323,204 | B2 | 12/2012 | Stahmann et al. |
| 8,326,433 | B2 | 12/2012 | Blum et al. |
| 8,328,718 | B2 | 12/2012 | Tran |
| 8,332,017 | B2 | 12/2012 | Tarassenko et al. |
| 8,332,024 | B2 | 12/2012 | Rapoport et al. |
| 8,334,690 | B2 | 12/2012 | Kitching et al. |
| 8,335,561 | B1 | 12/2012 | Modarres |
| 8,335,664 | B2 | 12/2012 | Eberle |
| 8,335,715 | B2 | 12/2012 | Pradeep et al. |
| 8,335,716 | B2 | 12/2012 | Pradeep et al. |
| 8,337,404 | B2 | 12/2012 | Osorio |
| 8,340,752 | B2 | 12/2012 | Cox et al. |
| 8,340,753 | B2 | 12/2012 | Hardt |
| 8,343,026 | B2 | 1/2013 | Gardiner et al. |
| 8,343,066 | B1 | 1/2013 | Eagleman et al. |
| 8,345,191 | B2 | 1/2013 | Yan et al. |
| 8,346,331 | B2 | 1/2013 | Bunce et al. |
| 8,346,342 | B2 | 1/2013 | Kalafut |
| 8,346,349 | B2 | 1/2013 | Guttag et al. |
| 8,350,804 | B1 | 1/2013 | Moll |
| 8,352,023 | B2 | 1/2013 | John et al. |
| 8,353,837 | B2 | 1/2013 | John et al. |
| 8,354,438 | B2 | 1/2013 | Chez |
| 8,354,881 | B2 | 1/2013 | Denison |
| 8,355,768 | B2 | 1/2013 | Masmanidis et al. |
| 8,356,004 | B2 | 1/2013 | Jung et al. |
| 8,356,594 | B2 | 1/2013 | Ujhazy et al. |
| 8,357,101 | B2 | 1/2013 | Sugio et al. |
| 8,358,818 | B2 | 1/2013 | Miga et al. |
| 8,359,080 | B2 | 1/2013 | Diab et al. |
| 8,364,226 | B2 | 1/2013 | Diab et al. |
| 8,364,254 | B2 | 1/2013 | Jacquin et al. |
| 8,364,255 | B2 | 1/2013 | Isenhart et al. |
| 8,364,271 | B2 | 1/2013 | De Ridder |
| 8,369,940 | B2 | 2/2013 | Sun et al. |
| 8,374,412 | B2 | 2/2013 | Kimura |
| 8,374,690 | B2 | 2/2013 | Ma |
| 8,374,696 | B2 | 2/2013 | Sanchez et al. |
| 8,374,703 | B2 | 2/2013 | Imran |
| 8,376,965 | B2 | 2/2013 | Schuette et al. |
| 8,379,952 | B2 | 2/2013 | McIntyre et al. |
| 8,380,289 | B2 | 2/2013 | Zellers et al. |
| 8,380,290 | B2 | 2/2013 | Scarantino et al. |
| 8,380,296 | B2 | 2/2013 | Lee et al. |
| 8,380,314 | B2 | 2/2013 | Panken et al. |
| 8,380,316 | B2 | 2/2013 | Hagedorn et al. |
| 8,380,658 | B2 | 2/2013 | Jung et al. |
| 8,382,667 | B2 | 2/2013 | Osorio |
| 8,386,244 | B2 | 2/2013 | Ricci et al. |
| 8,386,261 | B2 | 2/2013 | Mellott et al. |
| 8,386,312 | B2 | 2/2013 | Pradeep et al. |
| 8,386,313 | B2 | 2/2013 | Pradeep et al. |
| RE44,097 | E | 3/2013 | Wilber et al. |
| 8,388,530 | B2 | 3/2013 | Shusterman |
| 8,391,942 | B2 | 3/2013 | Benni |
| 8,391,956 | B2 | 3/2013 | Zellers et al. |
| 8,391,966 | B2 | 3/2013 | Luo et al. |
| 8,392,250 | B2 | 3/2013 | Pradeep et al. |
| 8,392,251 | B2 | 3/2013 | Pradeep et al. |
| 8,392,253 | B2 | 3/2013 | Pradeep et al. |
| 8,392,254 | B2 | 3/2013 | Pradeep et al. |
| 8,392,255 | B2 | 3/2013 | Pradeep et al. |
| 8,396,529 | B2 | 3/2013 | Lee et al. |
| 8,396,542 | B2 | 3/2013 | Johnson et al. |
| 8,396,545 | B2 | 3/2013 | Berridge et al. |
| 8,396,546 | B2 | 3/2013 | Hirata et al. |
| 8,396,557 | B2 | 3/2013 | DiLorenzo |
| 8,396,744 | B2 | 3/2013 | Pradeep et al. |
| 8,398,538 | B2 | 3/2013 | Dothie et al. |
| 8,400,313 | B2 | 3/2013 | Noguchi et al. |
| 8,401,624 | B2 | 3/2013 | Govari |
| 8,401,626 | B2 | 3/2013 | Mietus et al. |
| 8,401,655 | B2 | 3/2013 | De Ridder |
| 8,403,848 | B2 | 3/2013 | Mietus et al. |
| 8,405,610 | B1 | 3/2013 | Cole |
| 8,406,838 | B2 | 3/2013 | Kato |
| 8,406,841 | B2 | 3/2013 | Lin et al. |
| 8,406,848 | B2 | 3/2013 | Wu et al. |
| 8,406,862 | B2 | 3/2013 | Hopenfeld |
| 8,406,890 | B2 | 3/2013 | Goetz |
| 8,412,337 | B2 | 4/2013 | Lozano |
| 8,412,655 | B2 | 4/2013 | Colman et al. |
| 8,417,185 | B2 | 4/2013 | Braho et al. |
| 8,419,654 | B2 | 4/2013 | Sugio et al. |
| 8,423,125 | B2 | 4/2013 | Rousso et al. |
| 8,423,144 | B2 | 4/2013 | Tass et al. |
| 8,423,297 | B2 | 4/2013 | Wilber |
| 8,425,415 | B2 | 4/2013 | Tran |
| 8,425,583 | B2 | 4/2013 | Nofzinger |
| 8,428,696 | B2 | 4/2013 | Foo |
| 8,428,703 | B2 | 4/2013 | Hopenfeld |
| 8,428,704 | B2 | 4/2013 | Johnson et al. |
| 8,429,225 | B2 | 4/2013 | Jung et al. |
| 8,430,510 | B2 | 4/2013 | Sugio et al. |
| 8,431,537 | B2 | 4/2013 | Gong et al. |
| 8,433,388 | B2 | 4/2013 | Blunt et al. |
| 8,433,414 | B2 | 4/2013 | Gliner et al. |
| 8,433,418 | B2 | 4/2013 | DeRidder |
| 8,434,868 | B2 | 5/2013 | Sato et al. |
| 8,437,843 | B1 | 5/2013 | Kayyali et al. |
| 8,437,844 | B2 | 5/2013 | Syed Momen et al. |
| 8,438,659 | B2 | 5/2013 | Shen |
| 8,439,845 | B2 | 5/2013 | Folkerts et al. |
| 8,441,356 | B1 | 5/2013 | Tedesco et al. |
| 8,442,626 | B2 | 5/2013 | Zavoronkovs et al. |
| 8,444,571 | B2 | 5/2013 | Folkerts et al. |
| 8,445,021 | B2 | 5/2013 | Akhtari et al. |
| 8,445,851 | B2 | 5/2013 | Rousso et al. |
| 8,447,407 | B2 | 5/2013 | Talathi et al. |
| 8,449,116 | B2 | 5/2013 | Sato et al. |
| 8,449,471 | B2 | 5/2013 | Tran |

(56)                    References Cited

U.S. PATENT DOCUMENTS

| | | |
|---|---|---|
| 8,452,544 B2 | 5/2013 | Hymel |
| 8,454,555 B2 | 6/2013 | Struijk et al. |
| 8,456,164 B2 | 6/2013 | Subbarao |
| 8,457,730 B2 | 6/2013 | Makinen |
| 8,457,746 B2 | 6/2013 | Libbus |
| 8,461,988 B2 | 6/2013 | Tran |
| 8,463,007 B2 | 6/2013 | Steinberg et al. |
| 8,463,349 B2 | 6/2013 | Diab et al. |
| 8,463,370 B2 | 6/2013 | Korhonen et al. |
| 8,463,371 B2 | 6/2013 | Guan et al. |
| 8,463,374 B2 | 6/2013 | Hudson et al. |
| 8,463,378 B2 | 6/2013 | Tass |
| 8,463,386 B2 | 6/2013 | Tass |
| 8,463,387 B2 | 6/2013 | De Ridder |
| 8,464,288 B2 | 6/2013 | Pradeep et al. |
| 8,465,408 B2 | 6/2013 | Phillips et al. |
| 8,466,875 B2 | 6/2013 | Nakada et al. |
| 8,467,877 B2 | 6/2013 | Imran |
| 8,467,878 B2 | 6/2013 | Lozano et al. |
| 8,473,024 B2 | 6/2013 | Causevic et al. |
| 8,473,044 B2 | 6/2013 | Lee et al. |
| 8,473,306 B2 | 6/2013 | Seely |
| 8,473,345 B2 | 6/2013 | Pradeep et al. |
| 8,475,354 B2 | 7/2013 | Phillips et al. |
| 8,475,368 B2 | 7/2013 | Tran et al. |
| 8,475,371 B2 | 7/2013 | Derchak et al. |
| 8,475,387 B2 | 7/2013 | Derchak et al. |
| 8,477,425 B2 | 7/2013 | Border et al. |
| 8,478,389 B1 | 7/2013 | Brockway et al. |
| 8,478,394 B2 | 7/2013 | Prichep et al. |
| 8,478,402 B2 | 7/2013 | Wahlstrand et al. |
| 8,480,554 B2 | 7/2013 | Phillips et al. |
| 8,482,859 B2 | 7/2013 | Border et al. |
| 8,483,795 B2 | 7/2013 | Okada |
| 8,483,815 B2 | 7/2013 | Liley |
| 8,483,816 B1 | 7/2013 | Payton et al. |
| 8,484,081 B2 | 7/2013 | Pradeep et al. |
| 8,484,270 B2 | 7/2013 | Kurtz et al. |
| 8,485,979 B2 | 7/2013 | Giftakis et al. |
| 8,487,760 B2 | 7/2013 | Kangas et al. |
| 8,488,246 B2 | 7/2013 | Border et al. |
| 8,492,336 B2 | 7/2013 | Masure |
| 8,494,507 B1 | 7/2013 | Tedesco et al. |
| 8,494,610 B2 | 7/2013 | Pradeep et al. |
| 8,494,829 B2 | 7/2013 | Teixeira |
| 8,494,857 B2 | 7/2013 | Pakhomov |
| 8,494,905 B2 | 7/2013 | Pradeep et al. |
| 8,498,697 B2 | 7/2013 | Yong et al. |
| 8,498,699 B2 | 7/2013 | Wells et al. |
| 8,498,708 B2 | 7/2013 | Bentwich |
| RE44,408 E | 8/2013 | Lindsay |
| 8,500,282 B2 | 8/2013 | Bolger et al. |
| 8,500,636 B2 | 8/2013 | Tran |
| 8,509,879 B2 | 8/2013 | Durkin et al. |
| 8,509,881 B2 | 8/2013 | Thiagarajan et al. |
| 8,509,885 B2 | 8/2013 | Snyder et al. |
| 8,509,904 B2 | 8/2013 | Rickert et al. |
| 8,512,221 B2 | 8/2013 | Kaplan et al. |
| 8,512,240 B1 | 8/2013 | Zuckerman-Stark et al. |
| 8,515,535 B2 | 8/2013 | Hopper et al. |
| 8,517,909 B2 | 8/2013 | Honeycutt et al. |
| 8,517,912 B2 | 8/2013 | Clare |
| 8,519,705 B2 | 8/2013 | Savukov et al. |
| 8,519,853 B2 | 8/2013 | Eskandarian et al. |
| 8,521,284 B2 | 8/2013 | Kim et al. |
| 8,525,673 B2 | 9/2013 | Tran |
| 8,525,687 B2 | 9/2013 | Tran |
| 8,525,788 B2 | 9/2013 | Chiang |
| 8,527,029 B2 | 9/2013 | Okada |
| 8,527,035 B2 | 9/2013 | Diamond |
| 8,527,435 B1 | 9/2013 | Han et al. |
| 8,529,463 B2 | 9/2013 | Della Santina et al. |
| 8,531,291 B2 | 9/2013 | Tran |
| 8,532,756 B2 | 9/2013 | Schalk et al. |
| 8,532,757 B2 | 9/2013 | Molnar et al. |
| 8,533,042 B2 | 9/2013 | Pradeep et al. |
| 8,538,512 B1 | 9/2013 | Bibian et al. |
| 8,538,513 B2 | 9/2013 | Molnar et al. |
| 8,538,514 B2 | 9/2013 | Sun et al. |
| 8,538,536 B2 | 9/2013 | Rezai et al. |
| 8,538,705 B2 | 9/2013 | Greenwald |
| 8,542,900 B2 | 9/2013 | Tolkowsky et al. |
| 8,542,916 B2 | 9/2013 | Tognoli et al. |
| 8,543,189 B2 | 9/2013 | Paitel et al. |
| 8,543,199 B2 | 9/2013 | Snyder et al. |
| 8,543,219 B2 | 9/2013 | Tass |
| 8,545,416 B1 | 10/2013 | Kayyali et al. |
| 8,545,420 B2 | 10/2013 | Einav et al. |
| 8,545,436 B2 | 10/2013 | Robertson et al. |
| 8,548,555 B2 | 10/2013 | Jin et al. |
| 8,548,558 B2 | 10/2013 | Dunagan et al. |
| 8,548,786 B2 | 10/2013 | Plenz |
| 8,548,852 B2 | 10/2013 | Pradeep et al. |
| 8,552,860 B2 | 10/2013 | Baughman et al. |
| 8,553,956 B2 | 10/2013 | Wu et al. |
| 8,554,311 B2 | 10/2013 | Warner et al. |
| 8,554,325 B2 | 10/2013 | Molnar et al. |
| 8,559,645 B2 | 10/2013 | Corona-Strauss et al. |
| 8,560,034 B1 | 10/2013 | Diab et al. |
| 8,560,041 B2 | 10/2013 | Flaherty et al. |
| 8,560,073 B2 | 10/2013 | Osorio |
| 8,562,525 B2 | 10/2013 | Nakashima et al. |
| 8,562,526 B2 | 10/2013 | Heneghan et al. |
| 8,562,527 B2 | 10/2013 | Braun et al. |
| 8,562,540 B2 | 10/2013 | Goodall et al. |
| 8,562,548 B2 | 10/2013 | Shimada et al. |
| 8,562,951 B2 | 10/2013 | Suffin et al. |
| 8,565,606 B2 | 10/2013 | Kim et al. |
| 8,568,231 B2 | 10/2013 | Solanki et al. |
| 8,568,329 B2 | 10/2013 | Lee et al. |
| 8,570,176 B2 | 10/2013 | Farbos |
| 8,571,629 B2 | 10/2013 | Faro et al. |
| 8,571,642 B2 | 10/2013 | Gill et al. |
| 8,574,279 B2 | 11/2013 | Schiffer |
| 8,579,786 B2 | 11/2013 | Osorio et al. |
| 8,579,793 B1 | 11/2013 | Honeycutt et al. |
| 8,579,795 B2 | 11/2013 | Martel |
| 8,585,568 B2 | 11/2013 | Phillips et al. |
| 8,586,019 B2 | 11/2013 | Satchi-Fainaro et al. |
| 8,586,932 B2 | 11/2013 | Rousso et al. |
| 8,587,304 B2 | 11/2013 | Budker et al. |
| 8,588,933 B2 | 11/2013 | Floyd et al. |
| 8,591,419 B2 | 11/2013 | Tyler |
| 8,591,498 B2 | 11/2013 | John |
| 8,593,141 B1 | 11/2013 | Radparvar et al. |
| 8,597,171 B2 | 12/2013 | Altman et al. |
| 8,597,193 B2 | 12/2013 | Grunwald et al. |
| 8,600,493 B2 | 12/2013 | Tanner et al. |
| 8,600,502 B2 | 12/2013 | Lovett et al. |
| 8,600,696 B2 | 12/2013 | Zafiris |
| 8,602,555 B2 | 12/2013 | Backus et al. |
| 8,603,790 B2 | 12/2013 | Deisseroth et al. |
| 8,606,349 B2 | 12/2013 | Rousso et al. |
| 8,606,351 B2 | 12/2013 | Wheeler |
| 8,606,356 B2 | 12/2013 | Lee et al. |
| 8,606,360 B2 | 12/2013 | Butson et al. |
| 8,606,592 B2 | 12/2013 | Hyde et al. |
| 8,606,923 B2 | 12/2013 | Tekwani |
| 8,612,005 B2 | 12/2013 | Rezai et al. |
| 8,613,695 B2 | 12/2013 | Von Ohlsen et al. |
| 8,613,905 B2 | 12/2013 | El-Agnaf |
| 8,614,254 B2 | 12/2013 | Llinas et al. |
| 8,614,873 B1 | 12/2013 | Beran |
| 8,615,293 B2 | 12/2013 | Jacobson et al. |
| 8,615,479 B2 | 12/2013 | Jung et al. |
| 8,615,664 B2 | 12/2013 | Jung et al. |
| 8,618,799 B1 | 12/2013 | Radparvar et al. |
| 8,620,021 B2 | 12/2013 | Knudson et al. |
| 8,620,206 B2 | 12/2013 | Brown et al. |
| 8,620,419 B2 | 12/2013 | Rotenberg et al. |
| 8,626,264 B1 | 1/2014 | Beran |
| 8,626,301 B2 | 1/2014 | Libbus |
| 8,628,328 B2 | 1/2014 | Palacios |
| 8,628,462 B2 | 1/2014 | Berka et al. |

(56)                References Cited

U.S. PATENT DOCUMENTS

| | | | |
|---|---|---|---|
| 8,628,480 B2 | 1/2014 | Derchak |
| 8,630,633 B1 | 1/2014 | Tedesco et al. |
| 8,630,699 B2 | 1/2014 | Baker et al. |
| 8,632,465 B1 | 1/2014 | Brockway |
| 8,632,750 B2 | 1/2014 | Suffin et al. |
| 8,634,892 B2 | 1/2014 | Lee et al. |
| 8,635,105 B2 | 1/2014 | Pradeep et al. |
| 8,636,640 B2 | 1/2014 | Chang |
| 8,638,950 B2 | 1/2014 | Anderson et al. |
| 8,641,632 B2 | 2/2014 | Quintin et al. |
| 8,644,754 B2 | 2/2014 | Brown |
| 8,644,910 B2 | 2/2014 | Rousso et al. |
| 8,644,914 B2 | 2/2014 | Hunt |
| 8,644,921 B2 | 2/2014 | Wilson |
| 8,647,278 B2 | 2/2014 | Ji et al. |
| 8,648,017 B2 | 2/2014 | Umansky et al. |
| 8,649,866 B2 | 2/2014 | Brooke |
| 8,652,038 B2 | 2/2014 | Tran et al. |
| 8,652,189 B2 | 2/2014 | Gafni et al. |
| 8,655,428 B2 | 2/2014 | Pradeep et al. |
| 8,655,437 B2 | 2/2014 | Pradeep et al. |
| 8,655,817 B2 | 2/2014 | Hasey et al. |
| 8,657,756 B2 | 2/2014 | Stahmann et al. |
| 8,658,149 B2 | 2/2014 | Satchi-Fainaro et al. |
| 8,659,397 B2 | 2/2014 | Vargo et al. |
| 8,660,649 B2 | 2/2014 | Ruffini et al. |
| 8,660,799 B2 | 2/2014 | Watson et al. |
| 8,666,099 B2 | 3/2014 | Nielsen et al. |
| 8,666,467 B2 | 3/2014 | Lynn et al. |
| 8,666,478 B2 | 3/2014 | La Violette et al. |
| 8,668,496 B2 | 3/2014 | Nolen |
| 8,669,864 B1 | 3/2014 | Tedesco et al. |
| 8,670,603 B2 | 3/2014 | Tolkowsky et al. |
| 8,670,833 B2 | 3/2014 | Makous et al. |
| 8,672,852 B2 | 3/2014 | Gavish |
| 8,676,230 B2 | 3/2014 | Alexander et al. |
| 8,679,009 B2 | 3/2014 | Osorio |
| 8,679,013 B2 | 3/2014 | Ziarno et al. |
| 8,680,991 B2 | 3/2014 | Tran |
| 8,682,422 B2 | 3/2014 | Hopenfeld |
| 8,682,441 B2 | 3/2014 | De Ridder |
| 8,682,687 B2 | 3/2014 | Hyde et al. |
| 8,684,742 B2 | 4/2014 | Siefert |
| 8,684,900 B2 | 4/2014 | Tran |
| 8,684,922 B2 | 4/2014 | Tran |
| 8,684,926 B2 | 4/2014 | Arndt |
| 8,688,208 B2 | 4/2014 | Kapoor et al. |
| 8,688,209 B2 | 4/2014 | Verbitskiy |
| 8,690,748 B1 | 4/2014 | Fu |
| 8,693,756 B2 | 4/2014 | Tolkowsky et al. |
| 8,693,765 B2 | 4/2014 | Mercier et al. |
| 8,694,087 B2 | 4/2014 | Schiff |
| 8,694,089 B2 | 4/2014 | Arad (Abboud) |
| 8,694,107 B2 | 4/2014 | Falci |
| 8,694,157 B2 | 4/2014 | Wenderow et al. |
| 8,696,113 B2 | 4/2014 | Lewis |
| 8,696,722 B2 | 4/2014 | Deisseroth et al. |
| 8,699,747 B2 | 4/2014 | Rodriguez |
| 8,700,137 B2 | 4/2014 | Albert |
| 8,700,141 B2 | 4/2014 | Causevic |
| 8,700,142 B2 | 4/2014 | John et al. |
| 8,700,167 B2 | 4/2014 | Sabel |
| 8,703,114 B2 | 4/2014 | Satchi-Fainaro et al. |
| 8,706,183 B2 | 4/2014 | Cui et al. |
| 8,706,205 B2 | 4/2014 | Shahaf et al. |
| 8,706,206 B2 | 4/2014 | Kanai et al. |
| 8,706,207 B2 | 4/2014 | Flint |
| 8,706,241 B2 | 4/2014 | Firlik et al. |
| 8,706,518 B2 | 4/2014 | Hyde et al. |
| 8,708,903 B2 | 4/2014 | Tran |
| 8,712,507 B2 | 4/2014 | Cazares et al. |
| 8,712,512 B2 | 4/2014 | Doidge et al. |
| 8,712,513 B1 | 4/2014 | Modarres |
| 8,716,447 B2 | 5/2014 | Deisseroth et al. |
| 8,717,292 B2 | 5/2014 | Niikawa |
| 8,717,430 B2 | 5/2014 | Simon et al. |
| 8,718,747 B2 | 5/2014 | Bjornerud et al. |
| 8,721,341 B2 | 5/2014 | Mitchell |
| 8,721,695 B2 | 5/2014 | Tass et al. |
| 8,725,238 B2 | 5/2014 | Liu et al. |
| 8,725,243 B2 | 5/2014 | Dilorenzo et al. |
| 8,725,264 B2 | 5/2014 | Soler Fernandez et al. |
| 8,725,311 B1 | 5/2014 | Breed |
| 8,725,668 B2 | 5/2014 | Georgopoulos |
| 8,725,669 B1 | 5/2014 | Fu |
| 8,725,796 B2 | 5/2014 | Serena |
| 8,726,294 B2 | 5/2014 | Benedek et al. |
| 8,727,978 B2 | 5/2014 | Tran et al. |
| 8,728,001 B2 | 5/2014 | Lynn |
| 8,731,650 B2 | 5/2014 | Sajda et al. |
| 8,733,290 B2 | 5/2014 | Gerashchenko |
| 8,733,927 B1 | 5/2014 | Lewis |
| 8,733,928 B1 | 5/2014 | Lewis |
| 8,738,121 B2 | 5/2014 | Virag et al. |
| 8,738,136 B2 | 5/2014 | Frei et al. |
| 8,738,395 B2 | 5/2014 | Hyde et al. |
| 8,744,562 B2 | 6/2014 | Giftakis et al. |
| 8,744,563 B2 | 6/2014 | Yoshida |
| 8,747,313 B2 | 6/2014 | Tran et al. |
| 8,747,336 B2 | 6/2014 | Tran |
| 8,747,382 B2 | 6/2014 | D'Souza et al. |
| 8,750,971 B2 | 6/2014 | Tran |
| 8,750,974 B2 | 6/2014 | Baker et al. |
| 8,750,992 B2 | 6/2014 | Hopper et al. |
| 8,751,670 B2 | 6/2014 | Xu |
| 8,753,296 B2 | 6/2014 | Einav et al. |
| 8,755,854 B2 | 6/2014 | Addison et al. |
| 8,755,856 B2 | 6/2014 | Diab et al. |
| 8,755,868 B2 | 6/2014 | Yazicioglu |
| 8,755,869 B2 | 6/2014 | Zhang et al. |
| 8,755,871 B2 | 6/2014 | Weng et al. |
| 8,755,877 B2 | 6/2014 | Zoica |
| 8,755,879 B2 | 6/2014 | Hang et al. |
| 8,761,866 B2 | 6/2014 | Chance |
| 8,761,868 B2 | 6/2014 | Giftakis et al. |
| 8,761,869 B2 | 6/2014 | Leuthardt et al. |
| 8,761,889 B2 | 6/2014 | Wingeier et al. |
| 8,762,065 B2 | 6/2014 | DiLorenzo |
| 8,762,202 B2 | 6/2014 | Pradeep et al. |
| 8,762,852 B2 | 6/2014 | Davis et al. |
| 8,764,193 B2 | 7/2014 | Kiderman et al. |
| 8,764,651 B2 | 7/2014 | Tran |
| 8,764,652 B2 | 7/2014 | Lee et al. |
| 8,764,653 B2 | 7/2014 | Kaminska et al. |
| 8,764,673 B2 | 7/2014 | McCraty et al. |
| 8,766,819 B2 | 7/2014 | Dorfmann et al. |
| 8,768,022 B2 | 7/2014 | Miga et al. |
| 8,768,427 B2 | 7/2014 | Sjaaheim et al. |
| 8,768,447 B2 | 7/2014 | Ermes et al. |
| 8,768,449 B2 | 7/2014 | Pesaran et al. |
| 8,771,194 B2 | 7/2014 | John et al. |
| 8,774,784 B2 | 7/2014 | Kader |
| 8,775,340 B2 | 7/2014 | Waxman et al. |
| 8,780,512 B2 | 7/2014 | Sullivan |
| 8,781,193 B2 | 7/2014 | Steinberg et al. |
| 8,781,197 B2 | 7/2014 | Wang et al. |
| 8,781,557 B2 | 7/2014 | Dean et al. |
| 8,781,563 B2 | 7/2014 | Foo |
| 8,781,570 B2 | 7/2014 | Chuang et al. |
| 8,781,595 B2 | 7/2014 | Grevious et al. |
| 8,781,597 B2 | 7/2014 | DiLorenzo |
| 8,781,796 B2 | 7/2014 | Mott et al. |
| 8,784,322 B2 | 7/2014 | Kim et al. |
| 8,786,624 B2 | 7/2014 | Echauz et al. |
| 8,788,030 B1 | 7/2014 | Payton et al. |
| 8,790,255 B2 | 7/2014 | Behar |
| 8,790,272 B2 | 7/2014 | Sackner et al. |
| 8,790,297 B2 | 7/2014 | Bromander et al. |
| 8,792,974 B2 | 7/2014 | Rothman |
| 8,798,598 B2 | 8/2014 | Rossmann |
| 8,798,717 B2 | 8/2014 | Roscher |
| 8,798,735 B1 | 8/2014 | Bibian et al. |
| 8,798,736 B2 | 8/2014 | Sullivan et al. |
| 8,801,620 B2 | 8/2014 | Melker et al. |

(56) References Cited

U.S. PATENT DOCUMENTS

| | | | |
|---|---|---|---|
| 8,805,489 B1 | 8/2014 | Ofek |
| 8,805,516 B2 | 8/2014 | Bentwich |
| 8,812,075 B2 | 8/2014 | Nguyen et al. |
| 8,812,098 B2 | 8/2014 | Giftakis et al. |
| 8,814,923 B2 | 8/2014 | Nissila et al. |
| 8,815,582 B2 | 8/2014 | Deisseroth et al. |
| 8,816,861 B2 | 8/2014 | Shepherd et al. |
| 8,821,376 B2 | 9/2014 | Tolkowsky |
| 8,821,397 B2 | 9/2014 | Al-Ali et al. |
| 8,821,408 B2 | 9/2014 | Hu et al. |
| 8,825,149 B2 | 9/2014 | Kraus et al. |
| 8,825,167 B2 | 9/2014 | Tass et al. |
| 8,825,428 B2 | 9/2014 | Addison et al. |
| 8,827,912 B2 | 9/2014 | Bukhman |
| 8,827,917 B2 | 9/2014 | Watson et al. |
| 8,830,164 B2 | 9/2014 | Sakata et al. |
| 8,831,705 B2 | 9/2014 | Dobak |
| 8,831,731 B2 | 9/2014 | Blum et al. |
| 8,834,546 B2 | 9/2014 | Deisseroth et al. |
| 8,838,225 B2 | 9/2014 | Ahonen et al. |
| 8,838,226 B2 | 9/2014 | Bibian et al. |
| 8,838,227 B2 | 9/2014 | Causevic et al. |
| 8,838,247 B2 | 9/2014 | Hagedorn et al. |
| 8,843,199 B2 | 9/2014 | Kim et al. |
| 8,843,202 B2 | 9/2014 | Greenspan |
| 8,843,210 B2 | 9/2014 | Simon et al. |
| 8,845,545 B2 | 9/2014 | Folkerts et al. |
| 8,849,368 B2 | 9/2014 | Madsen et al. |
| 8,849,390 B2 | 9/2014 | Echauz et al. |
| 8,849,392 B2 | 9/2014 | Lozano |
| 8,849,632 B2 | 9/2014 | Sparks et al. |
| 8,849,681 B2 | 9/2014 | Hargrove et al. |
| 8,849,727 B2 | 9/2014 | Lu et al. |
| 8,852,073 B2 | 10/2014 | Genereux et al. |
| 8,852,100 B2 | 10/2014 | Osorio |
| 8,852,103 B2 | 10/2014 | Rothberg et al. |
| 8,855,758 B2 | 10/2014 | Rodriquez-Villegas et al. |
| 8,855,773 B2 | 10/2014 | Kokones et al. |
| 8,855,775 B2 | 10/2014 | Leyde |
| 8,858,440 B2 | 10/2014 | Tyler |
| 8,858,449 B2 | 10/2014 | Inan et al. |
| 8,862,196 B2 | 10/2014 | Lynn |
| 8,862,210 B2 | 10/2014 | Yazicioglu et al. |
| 8,862,217 B2 | 10/2014 | McKinley et al. |
| 8,862,219 B2 | 10/2014 | Garcia Molina et al. |
| 8,862,581 B2 | 10/2014 | Zhang et al. |
| 8,864,310 B2 | 10/2014 | Gross et al. |
| 8,868,039 B2 | 10/2014 | Rodriguez |
| 8,868,148 B2 | 10/2014 | Engelbrecht et al. |
| 8,868,163 B2 | 10/2014 | Guttag et al. |
| 8,868,172 B2 | 10/2014 | Leyde et al. |
| 8,868,173 B2 | 10/2014 | Nelson et al. |
| 8,868,174 B2 | 10/2014 | Sato et al. |
| 8,868,175 B2 | 10/2014 | Arad (Abboud) |
| 8,868,216 B2 | 10/2014 | Dunagan |
| 8,870,737 B2 | 10/2014 | Phillips et al. |
| 8,872,640 B2 | 10/2014 | Horseman |
| 8,874,439 B2 | 10/2014 | Kim et al. |
| D717,956 S | 11/2014 | Alexander et al. |
| 8,878,782 B1 | 11/2014 | Cole |
| 8,880,207 B2 | 11/2014 | Abeyratne et al. |
| 8,880,576 B2 | 11/2014 | Ochs et al. |
| 8,886,299 B2 | 11/2014 | Yazicioglu et al. |
| 8,888,672 B2 | 11/2014 | Phillips et al. |
| 8,888,673 B2 | 11/2014 | Phillips et al. |
| 8,888,702 B2 | 11/2014 | Osorio |
| 8,888,708 B2 | 11/2014 | Diab et al. |
| 8,888,723 B2 | 11/2014 | Einav |
| 8,893,120 B2 | 11/2014 | Pinsky et al. |
| 8,897,859 B2 | 11/2014 | Shimuta et al. |
| 8,898,037 B2 | 11/2014 | Watson et al. |
| 8,898,344 B2 | 11/2014 | Frank et al. |
| 8,898,443 B2 | 11/2014 | Reeves et al. |
| 8,902,070 B2 | 12/2014 | Kobetski et al. |
| 8,903,479 B2 | 12/2014 | Zoicas |
| 8,903,483 B2 | 12/2014 | Sun et al. |
| 8,903,494 B2 | 12/2014 | Goldwasser et al. |
| 8,907,668 B2 | 12/2014 | Okada |
| 8,914,100 B2 | 12/2014 | Adachi et al. |
| 8,914,119 B2 | 12/2014 | Wu et al. |
| 8,915,741 B2 | 12/2014 | Hatlestad et al. |
| 8,915,871 B2 | 12/2014 | Einav |
| 8,918,162 B2 | 12/2014 | Prokoski |
| 8,918,176 B2 | 12/2014 | Nelson et al. |
| 8,918,178 B2 | 12/2014 | Simon et al. |
| 8,922,376 B2 | 12/2014 | Kangas et al. |
| 8,922,788 B2 | 12/2014 | Addison et al. |
| 8,923,958 B2 | 12/2014 | Gupta et al. |
| 8,924,235 B2 | 12/2014 | Seely |
| 8,932,199 B2 | 1/2015 | Berka et al. |
| 8,932,218 B1 | 1/2015 | Thompson |
| 8,932,227 B2 | 1/2015 | Lynn |
| 8,933,696 B2 | 1/2015 | Nishikawa |
| 8,934,965 B2 | 1/2015 | Rogers et al. |
| 8,934,986 B2 | 1/2015 | Goetz |
| 8,936,630 B2 | 1/2015 | Denison et al. |
| 8,938,289 B2 | 1/2015 | Einav et al. |
| 8,938,290 B2 | 1/2015 | Wingeier et al. |
| 8,938,301 B2 | 1/2015 | Hagedorn |
| 8,939,579 B2 | 1/2015 | Agurok |
| 8,942,777 B2 | 1/2015 | Diab et al. |
| 8,942,813 B1 | 1/2015 | Hagedorn et al. |
| 8,948,834 B2 | 2/2015 | Diab et al. |
| 8,948,849 B2 | 2/2015 | Diamond et al. |
| 8,948,860 B2 | 2/2015 | Causevic |
| 8,951,189 B2 | 2/2015 | Osorio |
| 8,951,190 B2 | 2/2015 | Chmiel et al. |
| 8,951,192 B2 | 2/2015 | Osorio |
| 8,954,139 B2 | 2/2015 | Hopenfeld et al. |
| 8,954,146 B2 | 2/2015 | Hopper et al. |
| 8,954,293 B2 | 2/2015 | Klinkenbusch |
| 8,955,010 B2 | 2/2015 | Pradeep et al. |
| 8,955,974 B2 | 2/2015 | Gross et al. |
| 8,956,277 B2 | 2/2015 | Mishelevich |
| 8,958,868 B2 | 2/2015 | Ghovanloo et al. |
| 8,958,882 B1 | 2/2015 | Hagedorn |
| 8,961,187 B2 | 2/2015 | Boers et al. |
| 8,961,386 B2 | 2/2015 | Phillips et al. |
| 8,964,298 B2 | 2/2015 | Haddick et al. |
| 8,965,492 B2 | 2/2015 | Baker et al. |
| 8,965,513 B2 | 2/2015 | Wingeier et al. |
| 8,968,176 B2 | 3/2015 | Altman et al. |
| 8,968,195 B2 | 3/2015 | Tran |
| 8,971,936 B2 | 3/2015 | Derchak |
| 8,972,295 B2 | 3/2015 | Johnson et al. |
| 8,974,365 B2 | 3/2015 | Best |
| 8,977,024 B1 | 3/2015 | Rex et al. |
| 8,977,110 B2 | 3/2015 | Pradeep et al. |
| 8,977,362 B2 | 3/2015 | Saab |
| 8,983,155 B2 | 3/2015 | McIntyre et al. |
| 8,983,591 B2 | 3/2015 | Leininger et al. |
| 8,983,628 B2 | 3/2015 | Simon et al. |
| 8,983,629 B2 | 3/2015 | Simon et al. |
| 8,986,207 B2 | 3/2015 | Li et al. |
| 8,988,350 B2 | 3/2015 | Karmarkar et al. |
| 8,989,835 B2 | 3/2015 | Badower et al. |
| 8,989,836 B2 | 3/2015 | Machon et al. |
| 8,992,230 B2 | 3/2015 | Tuchschmid et al. |
| 8,993,623 B2 | 3/2015 | Goodenowe |
| 8,996,112 B2 | 3/2015 | Brooke |
| 8,998,828 B2 | 4/2015 | Reichow et al. |
| 9,002,458 B2 | 4/2015 | Pal et al. |
| 9,004,687 B2 | 4/2015 | Stack |
| 9,005,126 B2 | 4/2015 | Beach et al. |
| 9,008,367 B2 | 4/2015 | Tolkowsky et al. |
| 9,008,754 B2 | 4/2015 | Steinberg et al. |
| 9,008,771 B2 | 4/2015 | Dong et al. |
| 9,013,264 B2 | 4/2015 | Parshionikar et al. |
| 9,014,216 B2 | 4/2015 | Lazar et al. |
| 9,014,453 B2 | 4/2015 | Steinberg et al. |
| 9,014,661 B2 | 4/2015 | deCharms |
| 9,014,811 B2 | 4/2015 | Pal et al. |
| 9,014,819 B2 | 4/2015 | Lee et al. |
| 9,015,057 B2 | 4/2015 | Phillips et al. |

(56) References Cited

U.S. PATENT DOCUMENTS

| | | | |
|---|---|---|---|
| 9,015,087 | B2 | 4/2015 | Li et al. |
| 9,020,576 | B2 | 4/2015 | Nagatani |
| 9,020,585 | B2 | 4/2015 | John et al. |
| 9,020,586 | B2 | 4/2015 | Yamada et al. |
| 9,020,789 | B2 | 4/2015 | Butson et al. |
| 9,022,936 | B2 | 5/2015 | Rothberg et al. |
| 9,025,800 | B2 | 5/2015 | Kidmose et al. |
| 9,026,194 | B2 | 5/2015 | Okada |
| 9,026,202 | B2 | 5/2015 | Albert |
| 9,026,217 | B2 | 5/2015 | Kokones et al. |
| 9,026,218 | B2 | 5/2015 | Lozano et al. |
| 9,026,372 | B2 | 5/2015 | O'Donnell, Jr. et al. |
| 9,026,709 | B2 | 5/2015 | Reeves et al. |
| 9,028,405 | B2 | 5/2015 | Tran |
| 9,028,412 | B2 | 5/2015 | Rothberg et al. |
| 9,031,631 | B2 | 5/2015 | Tong et al. |
| 9,031,644 | B2 | 5/2015 | Johnson et al. |
| 9,031,653 | B2 | 5/2015 | Mashiach |
| 9,031,658 | B2 | 5/2015 | Chiao et al. |
| 9,032,110 | B2 | 5/2015 | Frank et al. |
| 9,033,884 | B2 | 5/2015 | Rothberg et al. |
| 9,034,055 | B2 | 5/2015 | Vinjamuri et al. |
| 9,034,923 | B2 | 5/2015 | Goodenowe |
| 9,037,224 | B1 | 5/2015 | Fu |
| 9,037,225 | B1 | 5/2015 | Saliga et al. |
| 9,037,530 | B2 | 5/2015 | Tan et al. |
| 9,042,074 | B1 | 5/2015 | Beran |
| 9,042,201 | B2 | 5/2015 | Tyler et al. |
| 9,042,952 | B2 | 5/2015 | Lynn et al. |
| 9,042,958 | B2 | 5/2015 | Karmarkar et al. |
| 9,042,988 | B2 | 5/2015 | DiLorenzo |
| 9,044,188 | B2 | 6/2015 | DiLorenzo et al. |
| 9,050,470 | B2 | 6/2015 | Carlton et al. |
| 9,053,516 | B2 | 6/2015 | Stempora |
| 9,055,871 | B2 | 6/2015 | Inan et al. |
| 9,055,974 | B2 | 6/2015 | Goetz |
| 9,058,200 | B2 | 6/2015 | Frank et al. |
| 9,058,473 | B2 | 6/2015 | Navratil et al. |
| 9,060,671 | B2 | 6/2015 | Badower et al. |
| 9,060,683 | B2 | 6/2015 | Tran |
| 9,060,695 | B2 | 6/2015 | Peters |
| 9,060,722 | B2 | 6/2015 | Teixeira |
| 9,060,746 | B2 | 6/2015 | Weng et al. |
| 9,063,183 | B2 | 6/2015 | Toda et al. |
| 9,063,798 | B2 | 6/2015 | Benedek et al. |
| 9,064,036 | B2 | 6/2015 | Hyde et al. |
| 9,067,052 | B2 | 6/2015 | Moses et al. |
| 9,069,031 | B2 | 6/2015 | Guedes et al. |
| 9,070,492 | B2 | 6/2015 | Yarmush et al. |
| 9,071,649 | B2 | 6/2015 | Tekwani |
| 9,072,482 | B2 | 7/2015 | Sarkela et al. |
| 9,072,832 | B2 | 7/2015 | Frei et al. |
| 9,072,870 | B2 | 7/2015 | Wu et al. |
| 9,072,905 | B2 | 7/2015 | Kokones et al. |
| 9,074,976 | B2 | 7/2015 | Adolphi et al. |
| 9,078,577 | B2 | 7/2015 | He et al. |
| 9,078,584 | B2 | 7/2015 | Jorge et al. |
| 9,079,940 | B2 | 7/2015 | Deisseroth et al. |
| 9,081,890 | B2 | 7/2015 | An et al. |
| 9,084,549 | B2 | 7/2015 | Desain et al. |
| 9,084,584 | B2 | 7/2015 | Weiland et al. |
| 9,084,896 | B2 | 7/2015 | Kokones et al. |
| 9,086,884 | B1 | 7/2015 | Frank et al. |
| 9,089,310 | B2 | 7/2015 | Isenhart et al. |
| 9,089,400 | B2 | 7/2015 | Nofzinger |
| 9,089,683 | B2 | 7/2015 | Mishelevich |
| 9,092,556 | B2 | 7/2015 | Amble et al. |
| 9,095,266 | B1 | 8/2015 | Fu |
| 9,095,268 | B2 | 8/2015 | Kurtz et al. |
| 9,095,295 | B2 | 8/2015 | Eagleman et al. |
| 9,095,303 | B2 | 8/2015 | Osorio |
| 9,095,618 | B2 | 8/2015 | Satchi-Fainaro et al. |
| 9,095,713 | B2 | 8/2015 | Foster et al. |
| 9,098,437 | B2 | 8/2015 | Benedek et al. |
| 9,100,758 | B2 | 8/2015 | Adachi et al. |
| 9,101,263 | B2 | 8/2015 | Jung et al. |
| 9,101,276 | B2 | 8/2015 | Georgopoulos |
| 9,101,279 | B2 | 8/2015 | Ritchey et al. |
| 9,101,296 | B2 | 8/2015 | Schroeder et al. |
| 9,102,717 | B2 | 8/2015 | Huang et al. |
| 9,104,467 | B2 | 8/2015 | Frank et al. |
| 9,104,969 | B1 | 8/2015 | Frank et al. |
| 9,107,586 | B2 | 8/2015 | Tran |
| 9,107,595 | B1 | 8/2015 | Smyth |
| 9,107,616 | B2 | 8/2015 | Kiderman et al. |
| 9,107,622 | B2 | 8/2015 | Nistico et al. |
| 9,113,777 | B2 | 8/2015 | Mittal |
| 9,113,801 | B2 | 8/2015 | DiLorenzo |
| 9,113,803 | B2 | 8/2015 | Zhang |
| 9,113,830 | B2 | 8/2015 | Galen et al. |
| 9,116,201 | B2 | 8/2015 | Shah et al. |
| 9,116,835 | B1 | 8/2015 | Smyth |
| 9,118,775 | B2 | 8/2015 | Lim et al. |
| 9,119,551 | B2 | 9/2015 | Qi et al. |
| 9,119,583 | B2 | 9/2015 | Tass |
| 9,119,597 | B2 | 9/2015 | Dripps et al. |
| 9,119,598 | B2 | 9/2015 | Engelbrecht et al. |
| 9,125,574 | B2 | 9/2015 | Zia et al. |
| 9,125,581 | B2 | 9/2015 | Wu et al. |
| 9,125,788 | B2 | 9/2015 | Tee et al. |
| 9,128,281 | B2 | 9/2015 | Osterhout et al. |
| 9,129,478 | B2 | 9/2015 | Smith et al. |
| 9,131,864 | B2 | 9/2015 | Korenberg |
| 9,133,024 | B2 | 9/2015 | Phan et al. |
| 9,134,534 | B2 | 9/2015 | Border et al. |
| 9,135,221 | B2 | 9/2015 | Shahaf et al. |
| 9,135,400 | B2 | 9/2015 | McIntyre et al. |
| 9,138,156 | B2 | 9/2015 | Wu et al. |
| 9,138,183 | B2 | 9/2015 | McKenna et al. |
| 9,142,145 | B2 | 9/2015 | Tuchschmid et al. |
| 9,142,185 | B2 | 9/2015 | Fateh |
| 9,144,392 | B2 | 9/2015 | Santosh et al. |
| 9,146,618 | B2 | 9/2015 | Tait et al. |
| RE45,766 | E | 10/2015 | Lindsay |
| 9,149,214 | B2 | 10/2015 | Adachi et al. |
| 9,149,226 | B2 | 10/2015 | Jadidi |
| 9,149,255 | B2 | 10/2015 | Rothberg et al. |
| 9,149,577 | B2 | 10/2015 | Robertson et al. |
| 9,149,719 | B2 | 10/2015 | Guan et al. |
| 9,152,582 | B2 | 10/2015 | Reeves et al. |
| 9,155,373 | B2 | 10/2015 | Allen et al. |
| 9,155,484 | B2 | 10/2015 | Baker et al. |
| 9,155,487 | B2 | 10/2015 | Linderman et al. |
| 9,155,521 | B2 | 10/2015 | Rothberg et al. |
| 9,160,796 | B2 | 10/2015 | Reeves et al. |
| 9,161,715 | B2 | 10/2015 | Jung et al. |
| 9,165,472 | B2 | 10/2015 | Hagedorn et al. |
| 9,167,356 | B2 | 10/2015 | Higgins et al. |
| 9,167,970 | B2 | 10/2015 | Gratton et al. |
| 9,167,976 | B2 | 10/2015 | Wingeier et al. |
| 9,167,977 | B2 | 10/2015 | Wingeier et al. |
| 9,167,978 | B2 | 10/2015 | Wingeier et al. |
| 9,167,979 | B2 | 10/2015 | Skidmore et al. |
| 9,171,131 | B2 | 10/2015 | Meyer et al. |
| 9,171,366 | B2 | 10/2015 | Declerck et al. |
| D743,039 | S | 11/2015 | Hagedorn |
| 9,173,582 | B2 | 11/2015 | Popovic et al. |
| 9,173,609 | B2 | 11/2015 | Nelson |
| 9,173,610 | B2 | 11/2015 | Navakatikyan |
| 9,179,850 | B2 | 11/2015 | Wingeier et al. |
| 9,179,854 | B2 | 11/2015 | Doidge et al. |
| 9,179,855 | B2 | 11/2015 | Burdea et al. |
| 9,179,858 | B2 | 11/2015 | Hasson et al. |
| 9,179,875 | B2 | 11/2015 | Hua |
| 9,179,876 | B2 | 11/2015 | Ochs et al. |
| 9,183,351 | B2 | 11/2015 | Shusterman |
| 9,183,580 | B2 | 11/2015 | Rhoads et al. |
| 9,186,105 | B2 | 11/2015 | Leininger et al. |
| 9,191,764 | B2 | 11/2015 | Baughman et al. |
| 9,192,300 | B2 | 11/2015 | Jung et al. |
| 9,192,309 | B1 | 11/2015 | Hopenfeld et al. |
| 9,198,571 | B2 | 12/2015 | Kiderman et al. |
| 9,198,621 | B2 | 12/2015 | Fernstrom et al. |
| 9,198,637 | B2 | 12/2015 | Rothberg et al. |

(56) References Cited

U.S. PATENT DOCUMENTS

| | | | |
|---|---|---|---|
| 9,198,707 | B2 | 12/2015 | McKay et al. |
| 9,202,360 | B1 | 12/2015 | Tedesco et al. |
| 9,204,835 | B2 | 12/2015 | Parsey et al. |
| 9,208,558 | B2 | 12/2015 | Dean et al. |
| 9,210,517 | B2 | 12/2015 | Pontoppidan et al. |
| 9,211,076 | B2 | 12/2015 | Kim |
| 9,211,077 | B2 | 12/2015 | Jung et al. |
| 9,211,078 | B2 | 12/2015 | Meggiolaro et al. |
| 9,211,212 | B2 | 12/2015 | Nofzinger et al. |
| 9,211,411 | B2 | 12/2015 | Wu et al. |
| 9,211,417 | B2 | 12/2015 | Heldman et al. |
| 9,213,074 | B2 | 12/2015 | van der Kouwe et al. |
| 9,213,076 | B2 | 12/2015 | Liu |
| 9,213,185 | B1 | 12/2015 | Starner et al. |
| 9,213,403 | B1 | 12/2015 | Raffle et al. |
| 9,213,406 | B2 | 12/2015 | Ou-Yang et al. |
| 9,215,978 | B2 | 12/2015 | Knight et al. |
| 9,218,530 | B2 | 12/2015 | Davis et al. |
| 9,223,893 | B2 | 12/2015 | Rodriguez |
| 9,224,309 | B2 | 12/2015 | Mutlu et al. |
| D747,495 | S | 1/2016 | Attal et al. |
| 9,229,080 | B2 | 1/2016 | Lin |
| 9,230,539 | B2 | 1/2016 | Pakhomov |
| 9,232,910 | B2 | 1/2016 | Alshaer et al. |
| 9,232,984 | B2 | 1/2016 | Guthart et al. |
| 9,233,244 | B2 | 1/2016 | Pal et al. |
| 9,235,685 | B2 | 1/2016 | McIntyre et al. |
| 9,238,142 | B2 | 1/2016 | Heldman et al. |
| 9,238,150 | B2 | 1/2016 | Deisseroth et al. |
| 9,239,615 | B2 | 1/2016 | Frank et al. |
| 9,240,021 | B2 | 1/2016 | Rodriguez |
| 9,241,665 | B2 | 1/2016 | deCharms |
| 9,242,067 | B2 | 1/2016 | Shore et al. |
| 9,247,870 | B2 | 2/2016 | Kiderman et al. |
| 9,247,890 | B2 | 2/2016 | Turnbull et al. |
| 9,247,911 | B2 | 2/2016 | Galloway et al. |
| 9,247,924 | B2 | 2/2016 | Rothberg et al. |
| 9,248,003 | B2 | 2/2016 | Wright et al. |
| 9,248,286 | B2 | 2/2016 | Simon et al. |
| 9,248,288 | B2 | 2/2016 | Panken et al. |
| 9,249,200 | B2 | 2/2016 | Deisseroth et al. |
| 9,249,234 | B2 | 2/2016 | Deisseroth et al. |
| 9,251,566 | B1 | 2/2016 | Bajic |
| 9,254,097 | B2 | 2/2016 | Espy et al. |
| 9,254,099 | B2 | 2/2016 | Connor |
| 9,254,383 | B2 | 2/2016 | Simon et al. |
| 9,258,301 | B2 | 2/2016 | Dabbiere |
| 9,259,180 | B2 | 2/2016 | McCaffrey |
| 9,259,482 | B2 | 2/2016 | Satchi-Fainaro et al. |
| 9,259,591 | B2 | 2/2016 | Brown et al. |
| 9,261,573 | B1 | 2/2016 | Radparvar et al. |
| 9,265,943 | B2 | 2/2016 | Yun et al. |
| 9,265,965 | B2 | 2/2016 | Fox et al. |
| 9,268,014 | B2 | 2/2016 | Rothberg et al. |
| 9,268,015 | B2 | 2/2016 | Rothberg et al. |
| 9,268,905 | B2 | 2/2016 | Garripoli |
| 9,271,651 | B2 | 3/2016 | Avinash et al. |
| 9,271,660 | B2 | 3/2016 | Luo et al. |
| 9,271,674 | B2 | 3/2016 | Deisseroth et al. |
| 9,271,679 | B2 | 3/2016 | Cho et al. |
| 9,275,191 | B2 | 3/2016 | Dean et al. |
| 9,277,871 | B2 | 3/2016 | Keenan et al. |
| 9,277,873 | B2 | 3/2016 | Sarma et al. |
| 9,280,784 | B2 | 3/2016 | Barnett et al. |
| 9,282,927 | B2 | 3/2016 | Hyde et al. |
| 9,282,930 | B2 | 3/2016 | Machon et al. |
| 9,282,934 | B2 | 3/2016 | Liley et al. |
| 9,283,279 | B2 | 3/2016 | Satchi-Fainaro et al. |
| 9,284,353 | B2 | 3/2016 | Deisseroth et al. |
| 9,285,249 | B2 | 3/2016 | Schober et al. |
| 9,286,515 | B2 | 3/2016 | Nakamura et al. |
| 9,289,143 | B2 | 3/2016 | Wingeier et al. |
| 9,289,595 | B2 | 3/2016 | Floyd et al. |
| 9,289,603 | B1 | 3/2016 | Giuffrida et al. |
| 9,292,858 | B2 | 3/2016 | Marci et al. |
| 9,292,895 | B2 | 3/2016 | Rodriguez et al. |
| 9,292,920 | B2 | 3/2016 | Dean et al. |
| 9,301,675 | B2 | 4/2016 | Kiderman et al. |
| 9,302,069 | B2 | 4/2016 | Tass et al. |
| 9,302,110 | B2 | 4/2016 | Kokones et al. |
| 9,307,925 | B2 | 4/2016 | Russell et al. |
| 9,307,944 | B2 | 4/2016 | Colman et al. |
| 9,308,372 | B2 | 4/2016 | Sparks et al. |
| 9,309,296 | B2 | 4/2016 | Deisseroth et al. |
| 9,311,640 | B2 | 4/2016 | Filler |
| 9,317,457 | B2 | 4/2016 | Reeves et al. |
| 9,320,449 | B2 | 4/2016 | Gu |
| 9,320,450 | B2 | 4/2016 | Badower |
| 9,320,900 | B2 | 4/2016 | DiLorenzo |
| 9,322,895 | B2 | 4/2016 | Santosh et al. |
| 9,324,234 | B2 | 4/2016 | Ricci et al. |
| 9,326,705 | B2 | 5/2016 | Derchak |
| 9,326,720 | B2 | 5/2016 | McLaughlin |
| 9,326,742 | B2 | 5/2016 | Hirschman et al. |
| 9,327,069 | B2 | 5/2016 | Foster et al. |
| 9,329,758 | B2 | 5/2016 | Guzak et al. |
| 9,330,206 | B2 | 5/2016 | Dean et al. |
| 9,330,497 | B2 | 5/2016 | Byrd et al. |
| 9,330,523 | B2 | 5/2016 | Sutton et al. |
| 9,331,841 | B2 | 5/2016 | Kim et al. |
| 9,332,939 | B2 | 5/2016 | Osorio |
| 9,333,334 | B2 | 5/2016 | Jeffery et al. |
| 9,336,302 | B1 | 5/2016 | Swamy |
| 9,336,535 | B2 | 5/2016 | Pradeep et al. |
| 9,336,611 | B2 | 5/2016 | Bilgic et al. |
| 9,339,227 | B2 | 5/2016 | D'arcy et al. |
| 9,339,495 | B2 | 5/2016 | During |
| 9,345,609 | B2 | 5/2016 | Hyde et al. |
| 9,351,651 | B2 | 5/2016 | Nagasaka |
| 9,352,145 | B2 | 5/2016 | Whitehurst et al. |
| 9,354,445 | B1 | 5/2016 | Weaver et al. |
| 9,354,778 | B2 | 5/2016 | Cornaby et al. |
| 9,357,240 | B2 | 5/2016 | Pradeep et al. |
| 9,357,298 | B2 | 5/2016 | Hiroe |
| 9,357,329 | B2 | 5/2016 | Jeffery et al. |
| 9,357,938 | B2 | 6/2016 | Ang et al. |
| 9,357,941 | B2 | 6/2016 | Simon |
| 9,357,970 | B2 | 6/2016 | Clark et al. |
| 9,358,393 | B1 | 6/2016 | Lozano |
| 9,359,449 | B2 | 6/2016 | Deisseroth et al. |
| 9,364,462 | B2 | 6/2016 | Simpson, Jr. |
| 9,365,628 | B2 | 6/2016 | Deisseroth et al. |
| 9,367,131 | B2 | 6/2016 | Klappert et al. |
| 9,367,288 | B2 | 6/2016 | Wilber |
| 9,367,738 | B2 | 6/2016 | Harumatsu et al. |
| 9,368,018 | B2 | 6/2016 | Kangas et al. |
| 9,368,265 | B2 | 6/2016 | Park et al. |
| 9,370,302 | B2 | 6/2016 | Krueger |
| 9,370,309 | B2 | 6/2016 | Ko et al. |
| 9,370,667 | B2 | 6/2016 | Schmidt |
| 9,375,145 | B2 | 6/2016 | Chin et al. |
| 9,375,151 | B1 | 6/2016 | Hopenfeld et al. |
| 9,375,171 | B2 | 6/2016 | Teixeira |
| 9,375,564 | B2 | 6/2016 | Wingeier et al. |
| 9,375,571 | B2 | 6/2016 | Errico et al. |
| 9,375,573 | B2 | 6/2016 | Dilorenzo |
| 9,377,348 | B2 | 6/2016 | Kataoka |
| 9,377,515 | B2 | 6/2016 | Kim et al. |
| 9,377,869 | B2 | 6/2016 | Tait et al. |
| 9,381,352 | B2 | 7/2016 | Yun et al. |
| 9,383,208 | B2 | 7/2016 | Mohanty |
| 9,387,320 | B2 | 7/2016 | Wingeier et al. |
| 9,389,685 | B1 | 7/2016 | Pathirage et al. |
| 9,391,988 | B2 | 7/2016 | Cronin |
| 9,392,955 | B2 | 7/2016 | Folkerts et al. |
| 9,392,956 | B2 | 7/2016 | Luo et al. |
| 9,394,347 | B2 | 7/2016 | Deisseroth et al. |
| 9,395,425 | B2 | 7/2016 | Diamond et al. |
| 9,396,669 | B2 | 7/2016 | Karkanias et al. |
| 9,398,873 | B2 | 7/2016 | Van Dooren et al. |
| 9,399,126 | B2 | 7/2016 | Pal et al. |
| 9,400,805 | B2 | 7/2016 | Knudson |
| 9,401,033 | B2 | 7/2016 | Bajic |
| 9,401,977 | B1 | 7/2016 | Gaw |

(56)                    References Cited

U.S. PATENT DOCUMENTS

| | | | |
|---|---|---|---|
| 9,402,099 B2 | 7/2016 | Rodriguez |
| 9,402,558 B2 | 8/2016 | John et al. |
| 9,403,038 B2 | 8/2016 | Tyler |
| 9,405,366 B2 | 8/2016 | Segal |
| 9,408,575 B2 | 8/2016 | Bordoley et al. |
| 9,408,997 B2 | 8/2016 | Kelley |
| 9,410,885 B2 | 8/2016 | Schober et al. |
| 9,411,033 B2 | 8/2016 | He et al. |
| 9,412,233 B1 | 8/2016 | Bagherzadeh et al. |
| 9,414,029 B2 | 8/2016 | Miyazaki et al. |
| 9,414,776 B2 | 8/2016 | Sillay et al. |
| 9,414,780 B2 | 8/2016 | Rhoads |
| 9,414,907 B2 | 8/2016 | Wortz et al. |
| 9,415,219 B2 | 8/2016 | Simon et al. |
| 9,415,222 B2 | 8/2016 | DiLorenzo |
| 9,418,368 B2 | 8/2016 | Jung et al. |
| 9,420,970 B2 | 8/2016 | Dagum |
| 9,421,373 B2 | 8/2016 | DiLorenzo |
| 9,424,761 B2 | 8/2016 | Tuchschmid et al. |
| 9,426,582 B2 | 8/2016 | Pontoppidan |
| 9,427,474 B2 | 8/2016 | Satchi-Fainaro et al. |
| 9,427,581 B2 | 8/2016 | Simon et al. |
| 9,430,615 B2 | 8/2016 | Michaelis et al. |
| 9,432,501 B2 | 8/2016 | Vishwanath |
| 9,432,777 B2 | 8/2016 | Lunner et al. |
| 9,436,279 B2 | 9/2016 | Beaty |
| 9,436,989 B2 | 9/2016 | Uber, III |
| 9,438,650 B2 | 9/2016 | Serena |
| 9,439,593 B2 | 9/2016 | Shepherd et al. |
| 9,439,595 B2 | 9/2016 | Leininger et al. |
| 9,439,596 B2 | 9/2016 | Leininger et al. |
| 9,439,736 B2 | 9/2016 | Olson |
| 9,440,064 B2 | 9/2016 | Wingeier et al. |
| 9,440,070 B2 | 9/2016 | Goldwasser et al. |
| 9,442,525 B2 | 9/2016 | Choi et al. |
| 9,443,141 B2 | 9/2016 | Mirowski et al. |
| 9,444,998 B2 | 9/2016 | Kim et al. |
| 9,445,730 B2 | 9/2016 | Snyder et al. |
| 9,445,739 B1 | 9/2016 | Payton et al. |
| 9,445,763 B2 | 9/2016 | Davis et al. |
| 9,445,768 B2 | 9/2016 | Alexander et al. |
| 9,446,028 B2 | 9/2016 | During |
| 9,446,238 B2 | 9/2016 | Lozano |
| 9,448,289 B2 | 9/2016 | Wang et al. |
| 9,451,303 B2 | 9/2016 | Kothuri et al. |
| 9,451,406 B2 | 9/2016 | Cornaby et al. |
| 9,451,734 B2 | 9/2016 | Onuma et al. |
| 9,451,883 B2 | 9/2016 | Gallant et al. |
| 9,451,886 B2 | 9/2016 | Teixeira |
| 9,451,899 B2 | 9/2016 | Ritchey et al. |
| 9,454,646 B2 | 9/2016 | Siefert |
| 9,454,777 B2 | 9/2016 | Kruglick |
| 9,456,740 B2 | 10/2016 | Leinonen et al. |
| 9,458,208 B2 | 10/2016 | Deisseroth et al. |
| 9,459,597 B2 | 10/2016 | Kahn et al. |
| 9,460,400 B2 | 10/2016 | De Bruin et al. |
| 9,462,433 B2 | 10/2016 | Rodriguez |
| 9,462,733 B2 | 10/2016 | Hokari |
| 9,462,956 B2 | 10/2016 | Pandia et al. |
| 9,462,975 B2 | 10/2016 | Sackner et al. |
| 9,462,977 B2 | 10/2016 | Horseman |
| 9,463,327 B2 | 10/2016 | Lempka et al. |
| 9,468,541 B2 | 10/2016 | Contreras-Vidal et al. |
| 9,470,728 B2 | 10/2016 | George et al. |
| 9,471,978 B2 | 10/2016 | Chen et al. |
| 9,474,481 B2 | 10/2016 | Dagum |
| 9,474,852 B2 | 10/2016 | Lozano et al. |
| 9,477,290 B2 | 10/2016 | Frank et al. |
| 9,477,317 B1 | 10/2016 | Clements |
| 9,477,701 B1 | 10/2016 | Kundu et al. |
| RE46,189 E | 11/2016 | Prichep et al. |
| RE46,209 E | 11/2016 | Gong et al. |
| 9,480,402 B2 | 11/2016 | Leuthardt et al. |
| 9,480,425 B2 | 11/2016 | Culver et al. |
| 9,480,429 B2 | 11/2016 | Nakada et al. |
| 9,480,812 B1 | 11/2016 | Thompson |
| 9,480,845 B2 | 11/2016 | Harris et al. |
| 9,480,854 B2 | 11/2016 | Von Ohlsen et al. |
| 9,482,606 B2 | 11/2016 | Kim et al. |
| 9,483,117 B2 | 11/2016 | Karkkainen et al. |
| 9,486,168 B2 | 11/2016 | Bonmassar et al. |
| 9,486,332 B2 | 11/2016 | Harshbarger et al. |
| 9,486,381 B2 | 11/2016 | Juto et al. |
| 9,486,389 B2 | 11/2016 | Tass |
| 9,486,618 B2 | 11/2016 | Wingeier et al. |
| 9,486,632 B2 | 11/2016 | Saab |
| 9,489,854 B2 | 11/2016 | Haruta et al. |
| 9,492,084 B2 | 11/2016 | Behar et al. |
| 9,492,114 B2 | 11/2016 | Reiman |
| 9,492,120 B2 | 11/2016 | Horseman |
| 9,492,313 B2 | 11/2016 | Nofzinger |
| 9,492,432 B2 | 11/2016 | Vavvas et al. |
| 9,492,630 B2 | 11/2016 | Cho et al. |
| 9,495,684 B2 | 11/2016 | Jung et al. |
| 9,497,017 B1 | 11/2016 | Kim et al. |
| 9,497,530 B1 | 11/2016 | Campbell et al. |
| 9,498,134 B1 | 11/2016 | Trobaugh et al. |
| 9,498,634 B2 | 11/2016 | De Ridder |
| 9,500,722 B2 | 11/2016 | Takahashi |
| 9,503,772 B2 | 11/2016 | Azam |
| 9,504,410 B2 | 11/2016 | Gal |
| 9,504,420 B2 | 11/2016 | Davis et al. |
| 9,504,788 B2 | 11/2016 | Hyde et al. |
| 9,505,817 B2 | 11/2016 | Deisseroth et al. |
| 9,507,974 B1 | 11/2016 | Todeschini |
| 9,510,752 B2 | 12/2016 | Klin et al. |
| 9,510,790 B2 | 12/2016 | Kang et al. |
| 9,511,877 B2 | 12/2016 | Masson |
| 9,516,430 B2 | 12/2016 | Jensen et al. |
| 9,517,031 B2 | 12/2016 | Jung |
| 9,517,222 B2 | 12/2016 | Goodenowe |
| 9,519,981 B2 | 12/2016 | Sudarsky et al. |
| 9,521,958 B2 | 12/2016 | Nagasaka et al. |
| 9,521,976 B2 | 12/2016 | Greco |
| 9,522,278 B1 | 12/2016 | Heldman et al. |
| 9,526,419 B2 | 12/2016 | Derchak et al. |
| 9,526,906 B2 | 12/2016 | Mashiach |
| 9,531,708 B2 | 12/2016 | Cornell et al. |
| 9,532,748 B2 | 1/2017 | Denison et al. |
| 9,533,113 B2 | 1/2017 | Lain et al. |
| 9,534,044 B2 | 1/2017 | El-Agnaf |
| 9,538,062 B2 | 1/2017 | Cronin |
| 9,538,635 B1 | 1/2017 | Beran |
| 9,538,934 B2 | 1/2017 | Ang et al. |
| 9,538,948 B2 | 1/2017 | Dagum |
| 9,539,118 B2 | 1/2017 | Leuthardt et al. |
| 9,541,383 B2 | 1/2017 | Abovitz et al. |
| 9,545,221 B2 | 1/2017 | Adhikari et al. |
| 9,545,222 B2 | 1/2017 | Derchak et al. |
| 9,545,225 B2 | 1/2017 | Cavuoto et al. |
| 9,545,285 B2 | 1/2017 | Ghaffari et al. |
| 9,548,050 B2 | 1/2017 | Gruber et al. |
| 9,554,484 B2 | 1/2017 | Rogers et al. |
| 9,556,487 B2 | 1/2017 | Umansky et al. |
| 9,557,957 B2 | 1/2017 | Guan et al. |
| 9,558,558 B2 | 1/2017 | Stehle et al. |
| 9,560,458 B2 | 1/2017 | Lunner et al. |
| 9,560,967 B2 | 2/2017 | Hyde et al. |
| 9,560,984 B2 | 2/2017 | Pradeep et al. |
| 9,560,986 B2 | 2/2017 | Varcoe |
| 9,563,273 B2 | 2/2017 | Mann |
| 9,563,740 B2 | 2/2017 | Abdelghani et al. |
| 9,563,927 B2 | 2/2017 | Sinclair |
| 9,563,950 B2 | 2/2017 | Raj |
| 9,563,998 B2 | 2/2017 | Hoyos et al. |
| 9,568,564 B2 | 2/2017 | Ma et al. |
| 9,569,986 B2 | 2/2017 | Levine et al. |
| 9,572,996 B2 | 2/2017 | Tass et al. |
| 9,577,992 B2 | 2/2017 | Zizi et al. |
| 9,579,035 B2 | 2/2017 | Sarkela |
| 9,579,048 B2 | 2/2017 | Rayner et al. |
| 9,579,060 B1 | 2/2017 | Lisy et al. |
| 9,582,072 B2 | 2/2017 | Connor |
| 9,582,925 B2 | 2/2017 | Durand et al. |

(56)  References Cited

U.S. PATENT DOCUMENTS

| | | | |
|---|---|---|---|
| 9,584,928 | B2 | 2/2017 | Laudanski et al. |
| 9,585,581 | B1 | 3/2017 | Mullins et al. |
| 9,588,203 | B2 | 3/2017 | Zhu et al. |
| 9,588,490 | B2 | 3/2017 | Tsang |
| 9,590,986 | B2 | 3/2017 | Zizi et al. |
| 9,592,383 | B2 | 3/2017 | Schiff et al. |
| 9,592,384 | B2 | 3/2017 | Tass |
| 9,592,389 | B2 | 3/2017 | Moffitt |
| 9,592,409 | B2 | 3/2017 | Yoo et al. |
| 9,594,500 | B2 | 3/2017 | Clements |
| 9,595,059 | B2 | 3/2017 | Knudson et al. |
| 9,596,224 | B2 | 3/2017 | Woods et al. |
| 9,596,584 | B2 | 3/2017 | Hyde et al. |
| 9,596,986 | B2 | 3/2017 | Kiderman et al. |
| 9,597,493 | B2 | 3/2017 | Wingeier et al. |
| 9,597,494 | B2 | 3/2017 | Wingeier et al. |
| 9,599,492 | B2 | 3/2017 | Hwang |
| 9,600,138 | B2 | 3/2017 | Thomas et al. |
| 9,604,073 | B2 | 3/2017 | Deisseroth et al. |
| 9,607,023 | B1 | 3/2017 | Swamy |
| 9,609,453 | B2 | 3/2017 | Jabri |
| 9,612,295 | B2 | 4/2017 | Toda et al. |
| 9,615,746 | B2 | 4/2017 | Horseman |
| 9,615,749 | B2 | 4/2017 | Clifton et al. |
| 9,615,789 | B2 | 4/2017 | Deisseroth et al. |
| 9,616,166 | B2 | 4/2017 | Kalafut et al. |
| 9,618,591 | B1 | 4/2017 | Radparvar et al. |
| 9,618,759 | B2 | 4/2017 | Morifuji et al. |
| 9,619,613 | B2 | 4/2017 | Meyer et al. |
| 9,622,660 | B2 | 4/2017 | Le et al. |
| 9,622,672 | B2 | 4/2017 | Yoshida et al. |
| 9,622,675 | B2 | 4/2017 | Leyde et al. |
| 9,622,676 | B2 | 4/2017 | Masmanidis et al. |
| 9,622,702 | B2 | 4/2017 | Badower et al. |
| 9,622,703 | B2 | 4/2017 | Badower et al. |
| 9,623,240 | B2 | 4/2017 | Simon et al. |
| 9,626,561 | B2 | 4/2017 | Cho et al. |
| 9,626,756 | B2 | 4/2017 | Dean et al. |
| 9,629,568 | B2 | 4/2017 | Hagedorn et al. |
| 9,630,008 | B2 | 4/2017 | McLaughlin et al. |
| 9,632,585 | B2 | 4/2017 | Niikawa |
| 9,635,605 | B2 | 4/2017 | Hyde et al. |
| 9,636,019 | B2 | 5/2017 | Hendler et al. |
| 9,636,063 | B2 | 5/2017 | Arbas |
| 9,640,167 | B2 | 5/2017 | DeFranks et al. |
| 9,641,665 | B2 | 5/2017 | Lee et al. |
| 9,642,552 | B2 | 5/2017 | Hua |
| 9,642,553 | B2 | 5/2017 | Hokari |
| 9,642,554 | B2 | 5/2017 | Simola et al. |
| 9,642,699 | B2 | 5/2017 | Wortz et al. |
| 9,643,019 | B2 | 5/2017 | Higgins et al. |
| 9,646,248 | B1 | 5/2017 | Benvenuto et al. |
| 9,649,030 | B2 | 5/2017 | Gross et al. |
| 9,649,036 | B2 | 5/2017 | Teixeira |
| 9,649,501 | B2 | 5/2017 | Best |
| 9,651,368 | B2 | 5/2017 | Abovitz et al. |
| 9,652,626 | B2 | 5/2017 | Son et al. |
| 9,655,573 | B2 | 5/2017 | Majewski et al. |
| 9,655,669 | B2 | 5/2017 | Palti et al. |
| 9,658,473 | B2 | 5/2017 | Lewis |
| 9,659,186 | B2 | 5/2017 | Pinsky et al. |
| 9,659,229 | B2 | 5/2017 | Clifton et al. |
| 9,662,045 | B2 | 5/2017 | Skelton et al. |
| 9,662,049 | B2 | 5/2017 | Scarantino et al. |
| 9,662,492 | B1 | 5/2017 | Tucker et al. |
| 9,664,856 | B2 | 5/2017 | Nagasaka |
| 9,665,824 | B2 | 5/2017 | Chang et al. |
| 9,665,987 | B2 | 5/2017 | Fateh |
| 9,668,694 | B2 | 6/2017 | Badower |
| 9,669,185 | B2 | 6/2017 | Nofzinger |
| 9,672,302 | B2 | 6/2017 | Dean et al. |
| 9,672,617 | B2 | 6/2017 | Dean et al. |
| 9,672,760 | B1 | 6/2017 | Breuer et al. |
| 9,675,292 | B2 | 6/2017 | Fadem |
| 9,678,810 | B2 | 6/2017 | Reeves et al. |
| 9,681,814 | B2 | 6/2017 | Galloway et al. |
| 9,681,820 | B2 | 6/2017 | Wagner |
| 9,682,232 | B2 | 6/2017 | Shore et al. |
| 9,684,051 | B2 | 6/2017 | Nieminen et al. |
| 9,684,335 | B2 | 6/2017 | Kim et al. |
| 9,685,600 | B2 | 6/2017 | Washington, II et al. |
| 9,687,187 | B2 | 6/2017 | Dagum |
| 9,687,562 | B2 | 6/2017 | Satchi-Fainaro et al. |
| 9,692,756 | B2 | 6/2017 | Poisner et al. |
| 9,693,684 | B2 | 7/2017 | Lopez et al. |
| 9,693,724 | B2 | 7/2017 | Dagum |
| 9,693,734 | B2 | 7/2017 | Horseman |
| 9,694,155 | B2 | 7/2017 | Panova et al. |
| 9,694,178 | B2 | 7/2017 | Ruffini et al. |
| 9,694,197 | B2 | 7/2017 | Segal |
| 9,700,261 | B2 | 7/2017 | Lunner |
| 9,704,205 | B2 | 7/2017 | Akutagawa et al. |
| 9,706,060 | B2 | 7/2017 | Hyde et al. |
| 9,706,237 | B2 | 7/2017 | Chen et al. |
| 9,706,382 | B2 | 7/2017 | Hyde et al. |
| 9,706,910 | B1 | 7/2017 | Blaha et al. |
| 9,706,957 | B2 | 7/2017 | Wu et al. |
| 9,706,963 | B2 | 7/2017 | Gupta et al. |
| 9,707,372 | B2 | 7/2017 | Smith |
| 9,707,396 | B2 | 7/2017 | Su et al. |
| 9,710,788 | B2 | 7/2017 | Horseman |
| 9,712,736 | B2 | 7/2017 | Kearns et al. |
| 9,713,013 | B2 | 7/2017 | Hyde et al. |
| 9,713,428 | B2 | 7/2017 | Chon et al. |
| 9,713,433 | B2 | 7/2017 | Gadot et al. |
| 9,713,444 | B2 | 7/2017 | Severson |
| 9,713,712 | B2 | 7/2017 | Wingeier et al. |
| 9,717,440 | B2 | 8/2017 | Abdelghani et al. |
| 9,722,472 | B2 | 8/2017 | Horseman et al. |
| 9,723,422 | B2 | 8/2017 | Jensen et al. |
| 9,723,981 | B2 | 8/2017 | Kiderman et al. |
| 9,724,357 | B2 | 8/2017 | Vavvas et al. |
| 9,729,252 | B2 | 8/2017 | Tyler et al. |
| 9,730,583 | B2 | 8/2017 | Kiderman et al. |
| 9,736,603 | B2 | 8/2017 | Osborne et al. |
| 9,737,231 | B2 | 8/2017 | Tveit |
| 9,740,285 | B2 | 8/2017 | Beaty |
| 9,756,096 | B1 | 9/2017 | Lilienthal et al. |
| 9,760,236 | B2 | 9/2017 | Sivakumar et al. |
| 9,763,613 | B2 | 9/2017 | Shepherd et al. |
| 9,764,109 | B2 | 9/2017 | Brewer et al. |
| 9,775,545 | B2 | 10/2017 | Al-Ali et al. |
| 9,775,554 | B2 | 10/2017 | Jung et al. |
| 9,779,575 | B1 | 10/2017 | Bagherzadeh et al. |
| 9,781,521 | B2 | 10/2017 | Kofod-Hansen et al. |
| 9,781,554 | B2 | 10/2017 | Hyde et al. |
| 9,782,122 | B1 | 10/2017 | Pulliam et al. |
| 9,783,162 | B2 | 10/2017 | Hoyos et al. |
| 9,785,242 | B2 | 10/2017 | Parshionikar |
| 9,788,714 | B2 | 10/2017 | Krueger |
| 9,794,672 | B2 | 10/2017 | Campbell et al. |
| 9,795,324 | B2 | 10/2017 | Sales et al. |
| 9,800,717 | B2 | 10/2017 | Ma et al. |
| 9,805,339 | B2 | 10/2017 | Horseman |
| 9,805,381 | B2 | 10/2017 | Frank et al. |
| 9,807,582 | B2 | 10/2017 | Hyde et al. |
| 9,808,156 | B2 | 11/2017 | Horseman |
| 9,811,154 | B2 | 11/2017 | Raffle et al. |
| 9,813,887 | B2 | 11/2017 | Hyde et al. |
| 9,814,426 | B2 | 11/2017 | Connor |
| 9,818,150 | B2 | 11/2017 | Rhoads et al. |
| 9,820,120 | B2 | 11/2017 | deCharms |
| 9,821,162 | B2 | 11/2017 | Wu et al. |
| 9,824,607 | B1 | 11/2017 | Bhattacharyya et al. |
| 9,829,971 | B2 | 11/2017 | San Agustin Lopez et al. |
| 9,830,576 | B2 | 11/2017 | Horseman |
| 9,830,577 | B2 | 11/2017 | Horseman |
| 9,832,353 | B2 | 11/2017 | Weaver et al. |
| 9,833,142 | B2 | 12/2017 | Horseman |
| 9,833,185 | B2 | 12/2017 | Leininger et al. |
| 9,835,864 | B2 | 12/2017 | Morifuji et al. |
| 9,836,896 | B2 | 12/2017 | Zizi et al. |
| 9,836,931 | B1 | 12/2017 | Rivaud et al. |
| 9,841,812 | B2 | 12/2017 | Kitazawa et al. |

(56)                    References Cited

U.S. PATENT DOCUMENTS

| | | | |
|---|---|---|---|
| 9,842,299 | B2 | 12/2017 | Stolarz et al. |
| 9,843,917 | B2 | 12/2017 | Hyde et al. |
| 9,844,344 | B2 | 12/2017 | Horseman |
| 9,853,976 | B2 | 12/2017 | Zizi et al. |
| 9,854,987 | B2 | 1/2018 | Chang et al. |
| 9,857,590 | B2 | 1/2018 | Hall, Jr. |
| 9,858,540 | B2 | 1/2018 | Firminger et al. |
| 9,858,745 | B1 | 1/2018 | Bagherzadeh et al. |
| 9,860,273 | B2 | 1/2018 | Myron |
| 9,861,307 | B2 | 1/2018 | Klin et al. |
| 9,864,431 | B2 | 1/2018 | Keskin et al. |
| 9,865,093 | B1 | 1/2018 | Mullins |
| 9,866,706 | B2 | 1/2018 | Hyde et al. |
| 9,867,546 | B2 | 1/2018 | Tzvieli et al. |
| 9,872,968 | B2 | 1/2018 | de Zambotti et al. |
| 9,883,396 | B2 | 1/2018 | Rodriguez |
| D809,474 | S | 2/2018 | Attal et al. |
| 9,886,493 | B2 | 2/2018 | Coleman et al. |
| 9,886,729 | B2 | 2/2018 | Firminger et al. |
| 9,886,981 | B2 | 2/2018 | Pradeep et al. |
| 9,888,090 | B2 | 2/2018 | Poisner et al. |
| 9,889,271 | B2 | 2/2018 | Adamczyk et al. |
| 9,892,435 | B2 | 2/2018 | Firminger et al. |
| 9,895,077 | B2 | 2/2018 | Shahaf et al. |
| 9,898,082 | B1 | 2/2018 | Greenwald |
| 9,898,793 | B2 | 2/2018 | Rodriguez |
| 9,900,669 | B2 | 2/2018 | Touma et al. |
| 9,904,891 | B2 | 2/2018 | Stolarz et al. |
| 9,904,892 | B2 | 2/2018 | Stolarz et al. |
| 9,905,239 | B2 | 2/2018 | Chang et al. |
| 9,910,298 | B1 | 3/2018 | Sales et al. |
| 9,911,165 | B2 | 3/2018 | Firminger et al. |
| 9,916,010 | B2 | 3/2018 | Harris et al. |
| 9,921,663 | B2 | 3/2018 | Niikawa |
| 9,922,053 | B1 | 3/2018 | Caughey |
| 9,923,764 | B2 | 3/2018 | Garg et al. |
| 9,927,872 | B2 | 3/2018 | Yang et al. |
| 9,930,155 | B2 | 3/2018 | Gaw |
| 9,936,250 | B2 | 4/2018 | Marci et al. |
| 9,936,916 | B2 | 4/2018 | Sahin |
| 9,943,698 | B2 | 4/2018 | Chase et al. |
| 9,946,344 | B2 | 4/2018 | Ayaz et al. |
| 9,949,640 | B2 | 4/2018 | Horseman |
| 9,953,650 | B1 | 4/2018 | Falevsky |
| 9,955,895 | B2 | 5/2018 | Jin et al. |
| 9,955,902 | B2 | 5/2018 | Frank et al. |
| 9,955,905 | B2 | 5/2018 | Intrator |
| 9,962,082 | B2 | 5/2018 | Kim et al. |
| 9,962,083 | B2 | 5/2018 | Horseman |
| 9,965,860 | B2 | 5/2018 | Nguyen et al. |
| 9,968,297 | B2 | 5/2018 | Connor |
| 9,968,780 | B2 | 5/2018 | Pal et al. |
| 9,978,095 | B2 | 5/2018 | Davis et al. |
| 9,980,114 | B2 | 5/2018 | Hyde et al. |
| 9,983,670 | B2 | 5/2018 | Coleman et al. |
| 9,990,727 | B2 | 6/2018 | Yoon et al. |
| 9,993,190 | B2 | 6/2018 | Preminger |
| 9,993,386 | B2 | 6/2018 | Racette |
| 9,993,517 | B2 | 6/2018 | Vavvas et al. |
| 9,994,228 | B2 | 6/2018 | Krueger |
| 9,996,151 | B2 | 6/2018 | Iwasaki et al. |
| 9,996,154 | B2 | 6/2018 | Kim et al. |
| 9,996,983 | B2 | 6/2018 | Mullins |
| 10,009,644 | B2 | 6/2018 | Aimone et al. |
| 10,016,156 | B2 | 7/2018 | Klin et al. |
| 10,019,060 | B2 | 7/2018 | Cash |
| 10,026,138 | B2 | 7/2018 | Sinclair |
| 10,029,067 | B2 | 7/2018 | Gerdes et al. |
| 10,031,580 | B2 | 7/2018 | Cruz-Hernandez |
| 10,037,636 | B2 | 7/2018 | Ho et al. |
| 10,039,445 | B1 | 8/2018 | Torch |
| 10,039,682 | B2 | 8/2018 | Einav et al. |
| 10,042,038 | B1 | 8/2018 | Lord |
| 10,042,993 | B2 | 8/2018 | Beigi |
| 10,052,023 | B2 | 8/2018 | Horseman |
| 10,052,057 | B2 | 8/2018 | Klin et al. |
| 10,052,066 | B2 | 8/2018 | Rogers et al. |
| 10,052,452 | B2 | 8/2018 | Schoonover et al. |
| 10,058,285 | B2 | 8/2018 | Horseman |
| 10,064,578 | B2 | 9/2018 | Garcia Molina et al. |
| 10,068,373 | B2 | 9/2018 | Lee et al. |
| 10,073,519 | B2 | 9/2018 | Mun et al. |
| 10,074,224 | B2 | 9/2018 | Ho et al. |
| 10,075,581 | B2 | 9/2018 | Cohen et al. |
| 10,075,896 | B2 | 9/2018 | Kim et al. |
| 10,079,788 | B2 | 9/2018 | Park et al. |
| 10,080,506 | B2 | 9/2018 | Fu |
| 10,086,268 | B2 | 10/2018 | Ishihara |
| 10,089,074 | B2 | 10/2018 | Motamedi et al. |
| 10,095,191 | B2 | 10/2018 | Heo et al. |
| 10,108,783 | B2 | 10/2018 | Horseman |
| 10,109,056 | B2 | 10/2018 | Nguyen et al. |
| 10,110,805 | B2 | 10/2018 | Pomerantz et al. |
| 10,111,603 | B2 | 10/2018 | Macri et al. |
| 10,111,615 | B2 | 10/2018 | Russell et al. |
| 10,113,913 | B2 | 10/2018 | Tzvieli et al. |
| 10,120,413 | B2 | 11/2018 | Aimone et al. |
| 10,123,133 | B2 | 11/2018 | Pontoppidan et al. |
| 10,123,134 | B2 | 11/2018 | Jensen et al. |
| 10,126,816 | B2 | 11/2018 | Segal |
| 10,129,325 | B2 | 11/2018 | Kelani et al. |
| 10,130,278 | B2 | 11/2018 | Jordan et al. |
| 10,130,279 | B2 | 11/2018 | Moon et al. |
| 10,130,766 | B1 | 11/2018 | Bibian et al. |
| 10,130,788 | B2 | 11/2018 | Garcia Molina et al. |
| 10,131,322 | B2 | 11/2018 | Hoyos et al. |
| 10,136,856 | B2 | 11/2018 | Tzvieli et al. |
| 10,136,862 | B2 | 11/2018 | Chafe et al. |
| 10,137,363 | B2 | 11/2018 | Parshionikar |
| 10,143,415 | B2 | 12/2018 | Girouard et al. |
| 10,149,161 | B2 | 12/2018 | Choi et al. |
| 10,149,884 | B2 | 12/2018 | Vavvas et al. |
| 10,149,958 | B1 | 12/2018 | Tran et al. |
| 10,152,957 | B2 | 12/2018 | Lenhert |
| 10,154,333 | B2 | 12/2018 | Campbell et al. |
| 10,154,815 | B2 | 12/2018 | Al-Ali et al. |
| 10,156,888 | B2 | 12/2018 | Lee et al. |
| 10,162,707 | B2 | 12/2018 | Kong et al. |
| 10,165,949 | B2 | 1/2019 | Tzvieli et al. |
| 10,165,977 | B2 | 1/2019 | Wu et al. |
| 10,166,091 | B2 | 1/2019 | Cowburn et al. |
| 10,168,704 | B2 | 1/2019 | Zhang et al. |
| 10,168,772 | B2 | 1/2019 | Kim et al. |
| 10,168,793 | B2 | 1/2019 | Komaki et al. |
| 10,169,712 | B2 | 1/2019 | Stolarz et al. |
| 10,173,059 | B2 | 1/2019 | Wallbridge et al. |
| 10,176,894 | B2 | 1/2019 | Park et al. |
| 10,180,339 | B1 | 1/2019 | Long et al. |
| 10,182,736 | B2 | 1/2019 | Coleman et al. |
| 10,185,147 | B2 | 1/2019 | Lewis |
| 10,186,014 | B2 | 1/2019 | Cho et al. |
| 10,188,307 | B2 | 1/2019 | Henson et al. |
| 10,191,545 | B1 | 1/2019 | Laszlo et al. |
| 10,191,558 | B2 | 1/2019 | Parshionikar |
| 10,192,173 | B2 | 1/2019 | Stephens et al. |
| 10,195,455 | B2 | 2/2019 | Stubbeman |
| 10,198,068 | B2 | 2/2019 | Holz et al. |
| 10,198,505 | B2 | 2/2019 | Frank et al. |
| 10,203,751 | B2 | 2/2019 | Keskin et al. |
| 10,204,251 | B1 | 2/2019 | Fenty, III et al. |
| 10,206,625 | B2 | 2/2019 | Horseman |
| 10,209,779 | B2 | 2/2019 | Roh et al. |
| 10,212,593 | B2 | 2/2019 | Rodriguez |
| 10,213,156 | B2 | 2/2019 | Min et al. |
| 10,219,736 | B2 | 3/2019 | Davis et al. |
| 10,223,633 | B2 | 3/2019 | Breuer et al. |
| 10,223,710 | B2 | 3/2019 | Purves et al. |
| 10,226,209 | B2 | 3/2019 | Girouard |
| 10,227,063 | B2 | 3/2019 | Abreu |
| 10,231,650 | B2 | 3/2019 | Skelton et al. |
| 10,231,673 | B2 | 3/2019 | Jain et al. |
| 10,234,942 | B2 | 3/2019 | Connor |
| 10,244,033 | B2 | 3/2019 | Grimstrup et al. |
| 10,254,785 | B2 | 4/2019 | Simon et al. |

(56)                    References Cited

U.S. PATENT DOCUMENTS

| | | |
|---|---|---|
| 10,257,177 B2 | 4/2019 | Hwang et al. |
| 10,257,555 B2 | 4/2019 | Chen et al. |
| 10,258,243 B2 | 4/2019 | LeBoeuf et al. |
| 10,258,291 B2 | 4/2019 | Coleman et al. |
| 10,258,798 B2 | 4/2019 | Panken et al. |
| 10,261,947 B2 | 4/2019 | Frank et al. |
| 10,262,356 B2 | 4/2019 | Davis et al. |
| 10,264,019 B2 | 4/2019 | Myron |
| 10,264,990 B2 | 4/2019 | Pasley et al. |
| 10,265,527 B2 | 4/2019 | Lim et al. |
| 10,271,087 B2 | 4/2019 | Klappert et al. |
| 10,275,027 B2 | 4/2019 | Segal |
| 10,279,192 B2 | 5/2019 | Malchano et al. |
| 10,285,634 B2 | 5/2019 | Jain et al. |
| 10,290,225 B1 | 5/2019 | Danyluk et al. |
| 10,291,977 B2 | 5/2019 | Mackellar et al. |
| 10,292,613 B2 | 5/2019 | Hatakeyama |
| 10,293,177 B2 | 5/2019 | Malchano et al. |
| 10,299,210 B2 | 5/2019 | Kim et al. |
| 10,300,240 B2 | 5/2019 | Weiss et al. |
| 10,303,258 B2 | 5/2019 | Todeschini |
| 10,303,971 B2 | 5/2019 | Geva et al. |
| 10,303,988 B1 | 5/2019 | Long et al. |
| 10,307,085 B2 | 6/2019 | Sales et al. |
| 10,307,104 B2 | 6/2019 | Horseman |
| 10,307,611 B2 | 6/2019 | Malchano et al. |
| 10,314,508 B2 | 6/2019 | Desain et al. |
| 10,319,471 B2 | 6/2019 | Firminger et al. |
| 2001/0009975 A1 | 7/2001 | Tsukada et al. |
| 2001/0020127 A1 | 9/2001 | Oshio et al. |
| 2001/0021800 A1 | 9/2001 | Balkin et al. |
| 2001/0031930 A1 | 10/2001 | Roizen et al. |
| 2001/0049480 A1 | 12/2001 | John et al. |
| 2001/0051774 A1 | 12/2001 | Littrup et al. |
| 2002/0005784 A1 | 1/2002 | Balkin et al. |
| 2002/0016552 A1 | 2/2002 | Granger et al. |
| 2002/0017994 A1 | 2/2002 | Balkin et al. |
| 2002/0024450 A1 | 2/2002 | Townsend et al. |
| 2002/0033454 A1 | 3/2002 | Cheng et al. |
| 2002/0035317 A1 | 3/2002 | Cheng et al. |
| 2002/0035338 A1 | 3/2002 | Dear et al. |
| 2002/0037095 A1 | 3/2002 | Cheng |
| 2002/0042563 A1 | 4/2002 | Becerra et al. |
| 2002/0055675 A1 | 5/2002 | Llinas et al. |
| 2002/0058867 A1 | 5/2002 | Breiter et al. |
| 2002/0059159 A1 | 5/2002 | Cook |
| 2002/0077534 A1 | 6/2002 | DuRousseau |
| 2002/0077536 A1 | 6/2002 | Diab et al. |
| 2002/0082513 A1 | 6/2002 | Ennen et al. |
| 2002/0085174 A1 | 7/2002 | Bolger et al. |
| 2002/0091319 A1 | 7/2002 | Moehring et al. |
| 2002/0091335 A1 | 7/2002 | John et al. |
| 2002/0095099 A1 | 7/2002 | Quyen et al. |
| 2002/0099273 A1 | 7/2002 | Bocionek et al. |
| 2002/0099295 A1 | 7/2002 | Gil et al. |
| 2002/0099306 A1 | 7/2002 | Shaw et al. |
| 2002/0103428 A1 | 8/2002 | deCharms |
| 2002/0103429 A1 | 8/2002 | deCharms |
| 2002/0103512 A1 | 8/2002 | Echauz et al. |
| 2002/0107454 A1 | 8/2002 | Collura et al. |
| 2002/0112732 A1 | 8/2002 | Blazey et al. |
| 2002/0117176 A1 | 8/2002 | Mantzaridis et al. |
| 2002/0128540 A1 | 9/2002 | Kim et al. |
| 2002/0128544 A1 | 9/2002 | Diab et al. |
| 2002/0128638 A1 | 9/2002 | Chauvet et al. |
| 2002/0138013 A1 | 9/2002 | Guerrero et al. |
| 2002/0151771 A1 | 10/2002 | Braun et al. |
| 2002/0158631 A1 | 10/2002 | Kandori et al. |
| 2002/0173714 A1 | 11/2002 | Tsukada et al. |
| 2002/0177882 A1 | 11/2002 | DiLorenzo |
| 2002/0182574 A1 | 12/2002 | Freer |
| 2002/0183644 A1 | 12/2002 | Levendowski et al. |
| 2002/0193670 A1 | 12/2002 | Garfield et al. |
| 2003/0001098 A1 | 1/2003 | Stoddart et al. |
| 2003/0004429 A1 | 1/2003 | Price |
| 2003/0009078 A1 | 1/2003 | Fedorovskaya et al. |
| 2003/0009096 A1 | 1/2003 | Lahteenmaki |
| 2003/0013981 A1 | 1/2003 | Gevins et al. |
| 2003/0018277 A1 | 1/2003 | He |
| 2003/0018278 A1 | 1/2003 | Jordan |
| 2003/0023183 A1 | 1/2003 | Williams |
| 2003/0028081 A1 | 2/2003 | Blazey et al. |
| 2003/0028121 A1 | 2/2003 | Blazey et al. |
| 2003/0032870 A1 | 2/2003 | Farwell |
| 2003/0032888 A1 | 2/2003 | Dewan |
| 2003/0032889 A1 | 2/2003 | Wells |
| 2003/0035301 A1 | 2/2003 | Gardiner et al. |
| 2003/0036689 A1 | 2/2003 | Diab et al. |
| 2003/0040660 A1 | 2/2003 | Jackowski et al. |
| 2003/0046018 A1 | 3/2003 | Kohlmorgen et al. |
| 2003/0055355 A1 | 3/2003 | Viertio-Oja |
| 2003/0068605 A1 | 4/2003 | Kullok et al. |
| 2003/0069516 A1 | 4/2003 | Becker et al. |
| 2003/0070685 A1 | 4/2003 | Patton et al. |
| 2003/0074032 A1 | 4/2003 | Gliner |
| 2003/0081818 A1 | 5/2003 | Fujimaki |
| 2003/0083596 A1 | 5/2003 | Kramer et al. |
| 2003/0093004 A1 | 5/2003 | Sosa et al. |
| 2003/0093005 A1 | 5/2003 | Tucker |
| 2003/0093129 A1 | 5/2003 | Nicolelis et al. |
| 2003/0097159 A1 | 5/2003 | Schiff et al. |
| 2003/0100844 A1 | 5/2003 | Miller et al. |
| 2003/0105408 A1 | 6/2003 | Gotman et al. |
| 2003/0120140 A1 | 6/2003 | Bango |
| 2003/0120172 A1 | 6/2003 | Foust et al. |
| 2003/0128801 A1 | 7/2003 | Eisenberg et al. |
| 2003/0130709 A1 | 7/2003 | D.C. et al. |
| 2003/0135128 A1 | 7/2003 | Suffin et al. |
| 2003/0139681 A1 | 7/2003 | Melker et al. |
| 2003/0139683 A1 | 7/2003 | Ryu et al. |
| 2003/0144601 A1 | 7/2003 | Prichep |
| 2003/0149351 A1 | 8/2003 | Nowinski et al. |
| 2003/0149678 A1 | 8/2003 | Cook |
| 2003/0150465 A1 | 8/2003 | Dewan |
| 2003/0153818 A1 | 8/2003 | Bocionek et al. |
| 2003/0158466 A1 | 8/2003 | Lynn et al. |
| 2003/0158495 A1 | 8/2003 | Hogan |
| 2003/0158496 A1 | 8/2003 | Keirsbilck et al. |
| 2003/0158497 A1 | 8/2003 | Graham et al. |
| 2003/0158587 A1 | 8/2003 | Esteller et al. |
| 2003/0160622 A1 | 8/2003 | Duensing et al. |
| 2003/0163027 A1 | 8/2003 | Balkin et al. |
| 2003/0163028 A1 | 8/2003 | Balkin et al. |
| 2003/0167019 A1 | 9/2003 | Viertio-Oja et al. |
| 2003/0171658 A1 | 9/2003 | Keirsbilck et al. |
| 2003/0171685 A1 | 9/2003 | Lesser et al. |
| 2003/0171689 A1 | 9/2003 | Millan et al. |
| 2003/0176804 A1 | 9/2003 | Melker |
| 2003/0181821 A1 | 9/2003 | Greenwald et al. |
| 2003/0185408 A1 | 10/2003 | Causevic et al. |
| 2003/0187359 A1 | 10/2003 | Njemanze |
| 2003/0195429 A1 | 10/2003 | Wilson |
| 2003/0199749 A1 | 10/2003 | Lowery, Jr. et al. |
| 2003/0204135 A1 | 10/2003 | Bystritsky |
| 2003/0216654 A1 | 11/2003 | Xu et al. |
| 2003/0225335 A1 | 12/2003 | Njemanze |
| 2003/0225340 A1 | 12/2003 | Collura |
| 2003/0229291 A1 | 12/2003 | Collura |
| 2003/0236458 A1 | 12/2003 | Hochman |
| 2004/0002635 A1 | 1/2004 | Hargrove et al. |
| 2004/0006265 A1 | 1/2004 | Alhussiny |
| 2004/0006376 A1 | 1/2004 | Falci |
| 2004/0010203 A1 | 1/2004 | Bibian et al. |
| 2004/0013609 A1 | 1/2004 | Trier |
| 2004/0019257 A1 | 1/2004 | Meadows |
| 2004/0019370 A1 | 1/2004 | Gliner et al. |
| 2004/0024287 A1 | 2/2004 | Patton et al. |
| 2004/0030585 A1 | 2/2004 | Sariel |
| 2004/0034299 A1 | 2/2004 | Kandori et al. |
| 2004/0039268 A1 | 2/2004 | Barbour et al. |
| 2004/0049484 A1 | 3/2004 | Kamba |
| 2004/0059203 A1 | 3/2004 | Guerrero et al. |
| 2004/0059241 A1 | 3/2004 | Suffin |
| 2004/0064020 A1 | 4/2004 | Diab et al. |

(56)                    References Cited

U.S. PATENT DOCUMENTS

| | | |
|---|---|---|
| 2004/0064066 A1 | 4/2004 | John et al. |
| 2004/0068164 A1 | 4/2004 | Diab et al. |
| 2004/0068172 A1 | 4/2004 | Nowinski et al. |
| 2004/0068199 A1 | 4/2004 | Echauz et al. |
| 2004/0070729 A1 | 4/2004 | Wiebe et al. |
| 2004/0072133 A1 | 4/2004 | Kullok et al. |
| 2004/0073098 A1 | 4/2004 | Geva et al. |
| 2004/0073129 A1 | 4/2004 | Caldwell et al. |
| 2004/0077960 A1 | 4/2004 | Tanaka et al. |
| 2004/0077967 A1 | 4/2004 | Jordan |
| 2004/0079372 A1 | 4/2004 | John et al. |
| 2004/0082862 A1 | 4/2004 | Chance |
| 2004/0082876 A1 | 4/2004 | Viertio-Oja et al. |
| 2004/0092809 A1 | 5/2004 | DeCharms |
| 2004/0096395 A1 | 5/2004 | Xiong et al. |
| 2004/0097802 A1 | 5/2004 | Cohen |
| 2004/0101146 A1 | 5/2004 | Laitinen et al. |
| 2004/0102843 A1 | 5/2004 | Yagi |
| 2004/0116784 A1 | 6/2004 | Gavish |
| 2004/0116791 A1 | 6/2004 | Miyauchi |
| 2004/0116798 A1 | 6/2004 | Cancro et al. |
| 2004/0116825 A1 | 6/2004 | Sturzebecher |
| 2004/0117098 A1 | 6/2004 | Ryu et al. |
| 2004/0122787 A1 | 6/2004 | Avinash et al. |
| 2004/0122790 A1 | 6/2004 | Walker et al. |
| 2004/0127803 A1 | 7/2004 | Berkes et al. |
| 2004/0133119 A1 | 7/2004 | Osorio et al. |
| 2004/0133120 A1 | 7/2004 | Frei et al. |
| 2004/0133390 A1 | 7/2004 | Osorio et al. |
| 2004/0138536 A1 | 7/2004 | Frei et al. |
| 2004/0138580 A1 | 7/2004 | Frei et al. |
| 2004/0138711 A1 | 7/2004 | Osorio et al. |
| 2004/0143170 A1 | 7/2004 | DuRousseau |
| 2004/0144925 A1 | 7/2004 | Stoddart et al. |
| 2004/0152958 A1 | 8/2004 | Frei et al. |
| 2004/0152995 A1 | 8/2004 | Cox et al. |
| 2004/0158119 A1 | 8/2004 | Osorio et al. |
| 2004/0158300 A1 | 8/2004 | Gardiner |
| 2004/0163648 A1 | 8/2004 | Burton |
| 2004/0166536 A1 | 8/2004 | Kerkman et al. |
| 2004/0167418 A1 | 8/2004 | Nguyen et al. |
| 2004/0181162 A1 | 9/2004 | Wilson |
| 2004/0181168 A1 | 9/2004 | Plant et al. |
| 2004/0186542 A1 | 9/2004 | van Venrooij et al. |
| 2004/0193037 A1 | 9/2004 | Tsukada et al. |
| 2004/0193068 A1 | 9/2004 | Burton et al. |
| 2004/0199482 A1 | 10/2004 | Wilson |
| 2004/0204636 A1 | 10/2004 | Diab et al. |
| 2004/0204637 A1 | 10/2004 | Diab et al. |
| 2004/0204656 A1 | 10/2004 | Tolvanen-Laakso et al. |
| 2004/0204659 A1 | 10/2004 | John et al. |
| 2004/0210127 A1 | 10/2004 | Kandori et al. |
| 2004/0210146 A1 | 10/2004 | Diab et al. |
| 2004/0210156 A1 | 10/2004 | Hogan |
| 2004/0215082 A1 | 10/2004 | Chance |
| 2004/0220494 A1 | 11/2004 | Sturzebecher |
| 2004/0220704 A1 | 11/2004 | Lin et al. |
| 2004/0220782 A1 | 11/2004 | Cook |
| 2004/0225179 A1 | 11/2004 | Kaplan et al. |
| 2004/0227699 A1 | 11/2004 | Mitchell |
| 2004/0230105 A1 | 11/2004 | Geva et al. |
| 2004/0243017 A1 | 12/2004 | Causevic |
| 2004/0249237 A1 | 12/2004 | Campbell et al. |
| 2004/0254493 A1 | 12/2004 | Chervin et al. |
| 2004/0260169 A1 | 12/2004 | Sternnickel |
| 2004/0263162 A1 | 12/2004 | Kandori et al. |
| 2004/0267152 A1 | 12/2004 | Pineda |
| 2005/0004489 A1 | 1/2005 | Sarkela et al. |
| 2005/0007091 A1 | 1/2005 | Makeig et al. |
| 2005/0010091 A1 | 1/2005 | Woods et al. |
| 2005/0010116 A1 | 1/2005 | Korhonen et al. |
| 2005/0015205 A1 | 1/2005 | Repucci et al. |
| 2005/0017870 A1 | 1/2005 | Allison et al. |
| 2005/0018858 A1 | 1/2005 | John |
| 2005/0019734 A1 | 1/2005 | Peled |
| 2005/0020918 A1 | 1/2005 | Wilk et al. |
| 2005/0025704 A1 | 2/2005 | Keirsbilck et al. |
| 2005/0027284 A1 | 2/2005 | Lozano et al. |
| 2005/0033122 A1 | 2/2005 | Balkin et al. |
| 2005/0033154 A1 | 2/2005 | deCharms |
| 2005/0033174 A1 | 2/2005 | Moehring et al. |
| 2005/0033379 A1 | 2/2005 | Lozano et al. |
| 2005/0038354 A1 | 2/2005 | Miller et al. |
| 2005/0043652 A1 | 2/2005 | Lovett et al. |
| 2005/0043774 A1 | 2/2005 | Devlin et al. |
| 2005/0059874 A1 | 3/2005 | Fuchs et al. |
| 2005/0075568 A1 | 4/2005 | Moehring |
| 2005/0079474 A1 | 4/2005 | Lowe |
| 2005/0079636 A1 | 4/2005 | White et al. |
| 2005/0080349 A1 | 4/2005 | Okada et al. |
| 2005/0080828 A1 | 4/2005 | Johnson |
| 2005/0085744 A1 | 4/2005 | Beverina et al. |
| 2005/0096517 A1 | 5/2005 | Diab et al. |
| 2005/0099601 A1 | 5/2005 | MacDougall et al. |
| 2005/0106713 A1 | 5/2005 | Phan et al. |
| 2005/0107654 A1 | 5/2005 | Riehl |
| 2005/0110950 A1 | 5/2005 | Thorpe et al. |
| 2005/0113713 A1 | 5/2005 | Foust et al. |
| 2005/0119547 A1 | 6/2005 | Shastri et al. |
| 2005/0119586 A1 | 6/2005 | Coyle et al. |
| 2005/0124848 A1 | 6/2005 | Holzner |
| 2005/0124851 A1 | 6/2005 | Patton et al. |
| 2005/0124863 A1 | 6/2005 | Cook |
| 2005/0131311 A1 | 6/2005 | Leuthardt et al. |
| 2005/0135102 A1 | 6/2005 | Gardiner et al. |
| 2005/0136002 A1 | 6/2005 | Fossheim et al. |
| 2005/0137493 A1 | 6/2005 | Ryu et al. |
| 2005/0137494 A1 | 6/2005 | Viertio-Oja |
| 2005/0148828 A1 | 7/2005 | Lindsay |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0149123 A1 | 7/2005 | Lesser et al. |
| 2005/0153268 A1 | 7/2005 | Junkin et al. |
| 2005/0154290 A1 | 7/2005 | Langleben |
| 2005/0154426 A1 | 7/2005 | Boveja et al. |
| 2005/0159670 A1 | 7/2005 | Sneddon |
| 2005/0159671 A1 | 7/2005 | Sneddon |
| 2005/0167588 A1 | 8/2005 | Donnangelo |
| 2005/0182287 A1 | 8/2005 | Becker |
| 2005/0182456 A1 | 8/2005 | Ziobro et al. |
| 2005/0192514 A1 | 9/2005 | Kearby et al. |
| 2005/0195165 A1 | 9/2005 | Mitchell |
| 2005/0197590 A1 | 9/2005 | Osorio et al. |
| 2005/0209517 A1 | 9/2005 | Diab et al. |
| 2005/0215916 A1 | 9/2005 | Fadem et al. |
| 2005/0216071 A1 | 9/2005 | Devlin et al. |
| 2005/0222639 A1 | 10/2005 | Seifritz et al. |
| 2005/0228451 A1 | 10/2005 | Jaax et al. |
| 2005/0228785 A1 | 10/2005 | Wolcott et al. |
| 2005/0240087 A1 | 10/2005 | Keenan et al. |
| 2005/0240253 A1 | 10/2005 | Tyler et al. |
| 2005/0245796 A1 | 11/2005 | Woods et al. |
| 2005/0251055 A1 | 11/2005 | Zhirnov et al. |
| 2005/0256378 A1 | 11/2005 | Takai et al. |
| 2005/0256385 A1 | 11/2005 | Diab et al. |
| 2005/0256418 A1 | 11/2005 | Mietus et al. |
| 2005/0267343 A1 | 12/2005 | Woods et al. |
| 2005/0267344 A1 | 12/2005 | Woods et al. |
| 2005/0267362 A1 | 12/2005 | Mietus et al. |
| 2005/0273017 A1 | 12/2005 | Gordon |
| 2005/0277813 A1 | 12/2005 | Katz et al. |
| 2005/0277912 A1 | 12/2005 | John |
| 2005/0283053 A1 | 12/2005 | deCharms |
| 2005/0283090 A1 | 12/2005 | Wells |
| 2006/0004298 A1 | 1/2006 | Kennedy et al. |
| 2006/0004422 A1 | 1/2006 | De Ridder |
| 2006/0009704 A1 | 1/2006 | Okada et al. |
| 2006/0015034 A1 | 1/2006 | Martinerie et al. |
| 2006/0018525 A1 | 1/2006 | Barbour |
| 2006/0020184 A1 | 1/2006 | Woods et al. |
| 2006/0036152 A1 | 2/2006 | Kozel |
| 2006/0036153 A1 | 2/2006 | Laken |
| 2006/0041201 A1 | 2/2006 | Behbehani et al. |

(56)                References Cited

U.S. PATENT DOCUMENTS

| | | |
|---|---|---|
| 2006/0047187 A1 | 3/2006 | Goyal et al. |
| 2006/0047216 A1 | 3/2006 | Dorr et al. |
| 2006/0047324 A1 | 3/2006 | Tass |
| 2006/0051814 A1 | 3/2006 | Jackowski et al. |
| 2006/0052706 A1 | 3/2006 | Hynynen et al. |
| 2006/0058590 A1 | 3/2006 | Shaw et al. |
| 2006/0058683 A1 | 3/2006 | Chance |
| 2006/0061544 A1 | 3/2006 | Min et al. |
| 2006/0064140 A1 | 3/2006 | Whitehurst et al. |
| 2006/0071934 A1 | 4/2006 | Sagar et al. |
| 2006/0074290 A1 | 4/2006 | Chen et al. |
| 2006/0074298 A1 | 4/2006 | Borsook et al. |
| 2006/0074334 A1 | 4/2006 | Coyle |
| 2006/0074822 A1 | 4/2006 | Eda et al. |
| 2006/0077064 A1 | 4/2006 | Baura |
| 2006/0078183 A1 | 4/2006 | deCharms |
| 2006/0082727 A1 | 4/2006 | Bolger et al. |
| 2006/0084858 A1 | 4/2006 | Marks |
| 2006/0084877 A1 | 4/2006 | Ujhazy et al. |
| 2006/0087746 A1 | 4/2006 | Lipow |
| 2006/0089541 A1 | 4/2006 | Braun et al. |
| 2006/0089549 A1 | 4/2006 | Diab et al. |
| 2006/0094968 A1 | 5/2006 | Drew |
| 2006/0094974 A1 | 5/2006 | Cain |
| 2006/0100526 A1 | 5/2006 | Yamamoto et al. |
| 2006/0100530 A1 | 5/2006 | Kliot et al. |
| 2006/0102171 A1 | 5/2006 | Gavish |
| 2006/0106434 A1 | 5/2006 | Padgitt et al. |
| 2006/0111644 A1 | 5/2006 | Guttag et al. |
| 2006/0116556 A1 | 6/2006 | Duhamel |
| 2006/0122481 A1 | 6/2006 | Sievenpiper et al. |
| 2006/0129277 A1 | 6/2006 | Wu et al. |
| 2006/0129324 A1 | 6/2006 | Rabinoff et al. |
| 2006/0135877 A1 | 6/2006 | Giftakis et al. |
| 2006/0135879 A1 | 6/2006 | Liley |
| 2006/0135880 A1 | 6/2006 | Sarkela |
| 2006/0135881 A1 | 6/2006 | Giftakis et al. |
| 2006/0136006 A1 | 6/2006 | Giftakis et al. |
| 2006/0145457 A1 | 7/2006 | Prenzel et al. |
| 2006/0149144 A1 | 7/2006 | Lynn et al. |
| 2006/0149160 A1 | 7/2006 | Kofol et al. |
| 2006/0153396 A1 | 7/2006 | John |
| 2006/0155206 A1 | 7/2006 | Lynn |
| 2006/0155207 A1 | 7/2006 | Lynn et al. |
| 2006/0155495 A1 | 7/2006 | Osorio et al. |
| 2006/0161071 A1 | 7/2006 | Lynn et al. |
| 2006/0161075 A1 | 7/2006 | Kurtz |
| 2006/0161218 A1 | 7/2006 | Danilov |
| 2006/0161384 A1 | 7/2006 | Osorio et al. |
| 2006/0167370 A1 | 7/2006 | Greenwald et al. |
| 2006/0167722 A1 | 7/2006 | MRF Struys et al. |
| 2006/0173364 A1 | 8/2006 | Clancy et al. |
| 2006/0173510 A1 | 8/2006 | Besio et al. |
| 2006/0178709 A1 | 8/2006 | Foster et al. |
| 2006/0184059 A1 | 8/2006 | Jadidi |
| 2006/0189866 A1 | 8/2006 | Thomas et al. |
| 2006/0189880 A1 | 8/2006 | Lynn et al. |
| 2006/0189882 A1 | 8/2006 | Thomas |
| 2006/0195144 A1 | 8/2006 | Giftakis et al. |
| 2006/0200013 A1 | 9/2006 | Smith et al. |
| 2006/0200016 A1 | 9/2006 | Diab et al. |
| 2006/0200034 A1 | 9/2006 | Ricci et al. |
| 2006/0200035 A1 | 9/2006 | Ricci et al. |
| 2006/0204532 A1 | 9/2006 | John |
| 2006/0206033 A1 | 9/2006 | Guerrero et al. |
| 2006/0206165 A1 | 9/2006 | Jaax et al. |
| 2006/0206174 A1 | 9/2006 | Honeycutt et al. |
| 2006/0217609 A1 | 9/2006 | Diab et al. |
| 2006/0217781 A1 | 9/2006 | John |
| 2006/0217816 A1 | 9/2006 | Pesaran et al. |
| 2006/0224067 A1 | 10/2006 | Giftakis et al. |
| 2006/0225437 A1 | 10/2006 | Kazami |
| 2006/0233390 A1 | 10/2006 | Causevic et al. |
| 2006/0235315 A1 | 10/2006 | Akselrod et al. |
| 2006/0235324 A1 | 10/2006 | Lynn |
| 2006/0241373 A1 | 10/2006 | Strychacz et al. |
| 2006/0241382 A1 | 10/2006 | Li et al. |
| 2006/0241562 A1 | 10/2006 | John et al. |
| 2006/0241718 A1 | 10/2006 | Tyler et al. |
| 2006/0247728 A1 | 11/2006 | Foster et al. |
| 2006/0251303 A1 | 11/2006 | He et al. |
| 2006/0252978 A1 | 11/2006 | Vesely et al. |
| 2006/0252979 A1 | 11/2006 | Vesely et al. |
| 2006/0253003 A1 | 11/2006 | Laufer et al. |
| 2006/0255956 A1 | 11/2006 | Arakawa et al. |
| 2006/0258896 A1 | 11/2006 | Haber et al. |
| 2006/0258950 A1 | 11/2006 | Hargrove et al. |
| 2006/0265022 A1 | 11/2006 | John et al. |
| 2006/0276695 A9 | 12/2006 | Lynn et al. |
| 2006/0281543 A1 | 12/2006 | Sutton et al. |
| 2006/0281980 A1 | 12/2006 | Randlov et al. |
| 2006/0293578 A1 | 12/2006 | Rennaker |
| 2007/0005115 A1 | 1/2007 | Lozano et al. |
| 2007/0005391 A1 | 1/2007 | Repucci et al. |
| 2007/0007454 A1 | 1/2007 | Stoddart et al. |
| 2007/0008172 A1 | 1/2007 | Hewett et al. |
| 2007/0010748 A1 | 1/2007 | Rauch et al. |
| 2007/0015976 A1 | 1/2007 | Miesel et al. |
| 2007/0015985 A1 | 1/2007 | Tolvanen-Laakso et al. |
| 2007/0016095 A1 | 1/2007 | Low et al. |
| 2007/0016264 A1 | 1/2007 | Falci |
| 2007/0017534 A1 | 1/2007 | Thorpe |
| 2007/0021673 A1 | 1/2007 | Arbel et al. |
| 2007/0021675 A1 | 1/2007 | Childre et al. |
| 2007/0032733 A1 | 2/2007 | Burton |
| 2007/0032737 A1 | 2/2007 | Causevic et al. |
| 2007/0036355 A1 | 2/2007 | Terauchi et al. |
| 2007/0038067 A1 | 2/2007 | Kandori et al. |
| 2007/0038264 A1 | 2/2007 | Jaax et al. |
| 2007/0038382 A1 | 2/2007 | Keenan |
| 2007/0040691 A1 | 2/2007 | Lau et al. |
| 2007/0043392 A1 | 2/2007 | Gliner et al. |
| 2007/0043401 A1 | 2/2007 | John |
| 2007/0049844 A1 | 3/2007 | Rosenfeld |
| 2007/0050715 A1 | 3/2007 | Behar |
| 2007/0055145 A1 | 3/2007 | Zelnik et al. |
| 2007/0060830 A1 | 3/2007 | Le et al. |
| 2007/0060831 A1 | 3/2007 | Le et al. |
| 2007/0066403 A1 | 3/2007 | Conkwright |
| 2007/0066914 A1 | 3/2007 | Le et al. |
| 2007/0066915 A1 | 3/2007 | Frei et al. |
| 2007/0078077 A1 | 4/2007 | Peyman |
| 2007/0083128 A1 | 4/2007 | Cote et al. |
| 2007/0093721 A1 | 4/2007 | Lynn et al. |
| 2007/0100246 A1 | 5/2007 | Hyde |
| 2007/0100251 A1 | 5/2007 | Prichep |
| 2007/0100278 A1 | 5/2007 | Frei et al. |
| 2007/0100666 A1 | 5/2007 | Stivoric et al. |
| 2007/0121068 A1 | 5/2007 | MacDougall et al. |
| 2007/0129647 A1 | 6/2007 | Lynn |
| 2007/0132841 A1 | 6/2007 | MacDougall et al. |
| 2007/0135724 A1 | 6/2007 | Ujhazy et al. |
| 2007/0135728 A1 | 6/2007 | Snyder et al. |
| 2007/0138886 A1 | 6/2007 | Krebs et al. |
| 2007/0142862 A1 | 6/2007 | Dilorenzo |
| 2007/0142873 A1 | 6/2007 | Esteller et al. |
| 2007/0146368 A1 | 6/2007 | Scott et al. |
| 2007/0149860 A1 | 6/2007 | Lynn et al. |
| 2007/0156457 A1 | 7/2007 | Brown |
| 2007/0161919 A1 | 7/2007 | DiLorenzo |
| 2007/0162086 A1 | 7/2007 | DiLorenzo |
| 2007/0165915 A1 | 7/2007 | Fuchs |
| 2007/0167694 A1 | 7/2007 | Causevic et al. |
| 2007/0167723 A1 | 7/2007 | Park et al. |
| 2007/0167853 A1 | 7/2007 | Melker et al. |
| 2007/0167858 A1 | 7/2007 | Virtanen et al. |
| 2007/0167991 A1 | 7/2007 | DiLorenzo |
| 2007/0173733 A1 | 7/2007 | Le et al. |
| 2007/0179395 A1 | 8/2007 | Sotos et al. |
| 2007/0179396 A1 | 8/2007 | Le et al. |
| 2007/0179534 A1 | 8/2007 | Firlik et al. |
| 2007/0179558 A1 | 8/2007 | Gliner et al. |
| 2007/0179734 A1 | 8/2007 | Chmiel et al. |
| 2007/0184507 A1 | 8/2007 | Jackowski et al. |

(56) References Cited

U.S. PATENT DOCUMENTS

| | | |
|---|---|---|
| 2007/0185697 A1 | 8/2007 | Tan et al. |
| 2007/0191688 A1 | 8/2007 | Lynn |
| 2007/0191691 A1 | 8/2007 | Polanco |
| 2007/0191697 A1 | 8/2007 | Lynn et al. |
| 2007/0191704 A1 | 8/2007 | DeCharms |
| 2007/0191727 A1 | 8/2007 | Fadem |
| 2007/0197930 A1 | 8/2007 | Sarkela |
| 2007/0203401 A1 | 8/2007 | Gordon et al. |
| 2007/0203448 A1 | 8/2007 | Melker et al. |
| 2007/0208212 A1 | 9/2007 | DiLorenzo |
| 2007/0208269 A1 | 9/2007 | Mumford et al. |
| 2007/0209669 A1 | 9/2007 | Derchak |
| 2007/0213786 A1 | 9/2007 | Sackellares et al. |
| 2007/0225581 A1 | 9/2007 | Diab et al. |
| 2007/0225674 A1 | 9/2007 | Molnar et al. |
| 2007/0225932 A1 | 9/2007 | Halford |
| 2007/0238934 A1 | 10/2007 | Viswanathan |
| 2007/0238939 A1 | 10/2007 | Giftakis et al. |
| 2007/0239054 A1 | 10/2007 | Giftakis et al. |
| 2007/0239059 A1 | 10/2007 | McIver |
| 2007/0239060 A1 | 10/2007 | Giftakis et al. |
| 2007/0239230 A1 | 10/2007 | Giftakis et al. |
| 2007/0249918 A1 | 10/2007 | Diab et al. |
| 2007/0249952 A1 | 10/2007 | Rubin et al. |
| 2007/0250119 A1 | 10/2007 | Tyler et al. |
| 2007/0250138 A1 | 10/2007 | Nofzinger |
| 2007/0255122 A1 | 11/2007 | Vol et al. |
| 2007/0255135 A1 | 11/2007 | Kalafut et al. |
| 2007/0255164 A1 | 11/2007 | Viertio-Oja et al. |
| 2007/0259323 A1 | 11/2007 | Brown et al. |
| 2007/0260147 A1 | 11/2007 | Giftakis et al. |
| 2007/0260151 A1 | 11/2007 | Clifford |
| 2007/0260286 A1 | 11/2007 | Giftakis et al. |
| 2007/0260289 A1 | 11/2007 | Giftakis et al. |
| 2007/0265508 A1 | 11/2007 | Sheikhzadeh-Nadjar et al. |
| 2007/0265533 A1 | 11/2007 | Tran |
| 2007/0265536 A1 | 11/2007 | Giftakis et al. |
| 2007/0265677 A1 | 11/2007 | Giftakis et al. |
| 2007/0273504 A1 | 11/2007 | Tran |
| 2007/0273611 A1 | 11/2007 | Torch |
| 2007/0276270 A1 | 11/2007 | Tran |
| 2007/0276278 A1 | 11/2007 | Coyle et al. |
| 2007/0276279 A1 | 11/2007 | Echauz et al. |
| 2007/0276609 A1 | 11/2007 | Greenwald |
| 2007/0282228 A1 | 12/2007 | Einav et al. |
| 2007/0287896 A1 | 12/2007 | Derchak et al. |
| 2007/0291832 A1 | 12/2007 | Diab et al. |
| 2007/0293760 A1 | 12/2007 | Schaafsma |
| 2007/0299370 A1 | 12/2007 | Bystritsky |
| 2007/0299371 A1 | 12/2007 | Einav et al. |
| 2008/0001600 A1 | 1/2008 | deCharms |
| 2008/0001735 A1 | 1/2008 | Tran |
| 2008/0004514 A1 | 1/2008 | Diab et al. |
| 2008/0004550 A1 | 1/2008 | Einav et al. |
| 2008/0004904 A1 | 1/2008 | Tran |
| 2008/0009685 A1 | 1/2008 | Kim et al. |
| 2008/0009772 A1 | 1/2008 | Tyler et al. |
| 2008/0013747 A1 | 1/2008 | Tran |
| 2008/0015458 A1 | 1/2008 | Buarque de Macedo et al. |
| 2008/0021332 A1 | 1/2008 | Brainard |
| 2008/0021336 A1 | 1/2008 | Dobak |
| 2008/0021340 A1 | 1/2008 | Sarkela |
| 2008/0021341 A1 | 1/2008 | Harris et al. |
| 2008/0021342 A1 | 1/2008 | Echauz et al. |
| 2008/0021345 A1 | 1/2008 | Kern et al. |
| 2008/0027346 A1 | 1/2008 | Litt et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033266 A1 | 2/2008 | Diab et al. |
| 2008/0033291 A1 | 2/2008 | Rousso et al. |
| 2008/0033297 A1 | 2/2008 | Sliwa |
| 2008/0033490 A1 | 2/2008 | Giftakis et al. |
| 2008/0033502 A1 | 2/2008 | Harris et al. |
| 2008/0033508 A1 | 2/2008 | Frei et al. |
| 2008/0036752 A1 | 2/2008 | Diab et al. |
| 2008/0039677 A1 | 2/2008 | Adams |
| 2008/0039698 A1 | 2/2008 | Burton |
| 2008/0039737 A1 | 2/2008 | Breiter et al. |
| 2008/0039904 A1 | 2/2008 | Bulkes et al. |
| 2008/0042067 A1 | 2/2008 | Rousso et al. |
| 2008/0045823 A1 | 2/2008 | Diab et al. |
| 2008/0045844 A1 | 2/2008 | Arbel et al. |
| 2008/0049186 A1 | 2/2008 | MacDougall et al. |
| 2008/0049187 A1 | 2/2008 | Joos et al. |
| 2008/0051669 A1 | 2/2008 | Meyer et al. |
| 2008/0051858 A1 | 2/2008 | Haber et al. |
| 2008/0058664 A1 | 3/2008 | Mirro |
| 2008/0058668 A1 | 3/2008 | Seyed Momen et al. |
| 2008/0064934 A1 | 3/2008 | Frei et al. |
| 2008/0074307 A1 | 3/2008 | Boric-Lubecke et al. |
| 2008/0074618 A1 | 3/2008 | Qi |
| 2008/0077010 A1 | 3/2008 | Cohen-Solal et al. |
| 2008/0077015 A1 | 3/2008 | Boric-Lubecke et al. |
| 2008/0081963 A1 | 4/2008 | Naghavi et al. |
| 2008/0082018 A1 | 4/2008 | Sackner et al. |
| 2008/0091118 A1 | 4/2008 | Georgopoulos |
| 2008/0097197 A1 | 4/2008 | Kalafut et al. |
| 2008/0097235 A1 | 4/2008 | Ofek et al. |
| 2008/0097785 A1 | 4/2008 | Ali |
| 2008/0119716 A1 | 5/2008 | Boric-Lubecke et al. |
| 2008/0119747 A1 | 5/2008 | Mietus et al. |
| 2008/0119763 A1 | 5/2008 | Wiener |
| 2008/0119900 A1 | 5/2008 | DiLorenzo |
| 2008/0123927 A1 | 5/2008 | Miga et al. |
| 2008/0125669 A1 | 5/2008 | Suffin et al. |
| 2008/0128626 A1 | 6/2008 | Rousso et al. |
| 2008/0132383 A1 | 6/2008 | Einav et al. |
| 2008/0139953 A1 | 6/2008 | Baker et al. |
| 2008/0140403 A1 | 6/2008 | Hughes et al. |
| 2008/0154111 A1 | 6/2008 | Wu et al. |
| 2008/0154126 A1 | 6/2008 | Culver et al. |
| 2008/0154148 A1 | 6/2008 | Chung et al. |
| 2008/0167535 A1 | 7/2008 | Stivoric et al. |
| 2008/0167540 A1 | 7/2008 | Korhonen et al. |
| 2008/0167569 A1 | 7/2008 | Ermes et al. |
| 2008/0167571 A1 | 7/2008 | Gevins |
| 2008/0177195 A1 | 7/2008 | Armitstead |
| 2008/0177196 A1 | 7/2008 | Burdick et al. |
| 2008/0177197 A1 | 7/2008 | Lee et al. |
| 2008/0181452 A1 | 7/2008 | Kwon et al. |
| 2008/0183314 A1 | 7/2008 | Klouzal et al. |
| 2008/0188765 A1 | 8/2008 | Stolarski et al. |
| 2008/0188777 A1 | 8/2008 | Bedziouk et al. |
| 2008/0195166 A1 | 8/2008 | Sun et al. |
| 2008/0200831 A1 | 8/2008 | Sturzebecher |
| 2008/0208072 A1 | 8/2008 | Fadem et al. |
| 2008/0208073 A1 | 8/2008 | Causevic |
| 2008/0214902 A1 | 9/2008 | Lee et al. |
| 2008/0221400 A1 | 9/2008 | Lee et al. |
| 2008/0221401 A1 | 9/2008 | Derchak et al. |
| 2008/0221441 A1 | 9/2008 | Bjornerud et al. |
| 2008/0221472 A1 | 9/2008 | Lee et al. |
| 2008/0221969 A1 | 9/2008 | Lee et al. |
| 2008/0228077 A1 | 9/2008 | Wilk et al. |
| 2008/0228100 A1 | 9/2008 | Navakatikyan |
| 2008/0228239 A1 | 9/2008 | Tyler et al. |
| 2008/0229408 A1 | 9/2008 | Dinges et al. |
| 2008/0230702 A1 | 9/2008 | Rousso et al. |
| 2008/0230705 A1 | 9/2008 | Rousso et al. |
| 2008/0234113 A1 | 9/2008 | Einav |
| 2008/0234598 A1 | 9/2008 | Snyder et al. |
| 2008/0234601 A1 | 9/2008 | Wexelman |
| 2008/0235164 A1 | 9/2008 | Tian et al. |
| 2008/0242521 A1 | 10/2008 | Einav |
| 2008/0243014 A1 | 10/2008 | Moussavi et al. |
| 2008/0243017 A1 | 10/2008 | Moussavi et al. |
| 2008/0243021 A1 | 10/2008 | Causevic et al. |
| 2008/0249430 A1 | 10/2008 | John et al. |
| 2008/0252850 A1 | 10/2008 | Plagwitz et al. |
| 2008/0253519 A1 | 10/2008 | Bonfiglio et al. |
| 2008/0255469 A1 | 10/2008 | Shieh et al. |
| 2008/0255949 A1 | 10/2008 | Genco et al. |
| 2008/0257349 A1 | 10/2008 | Hedner et al. |

(56)                References Cited

U.S. PATENT DOCUMENTS

| | | | |
|---|---|---|---|
| 2008/0260212 A1 | 10/2008 | Moskal et al. |
| 2008/0262327 A1 | 10/2008 | Kato |
| 2008/0262367 A1 | 10/2008 | Mugler et al. |
| 2008/0262371 A1 | 10/2008 | Causevic |
| 2008/0262373 A1 | 10/2008 | Burns et al. |
| 2008/0273084 A1 | 11/2008 | MacDougall et al. |
| 2008/0275327 A1 | 11/2008 | Faarbaek et al. |
| 2008/0275340 A1 | 11/2008 | Beach et al. |
| 2008/0278685 A1 | 11/2008 | MacDougall et al. |
| 2008/0294019 A1 | 11/2008 | Tran |
| 2008/0294063 A1 | 11/2008 | Bibian et al. |
| 2008/0300449 A1 | 12/2008 | Gerber et al. |
| 2008/0304691 A1 | 12/2008 | Lai |
| 2008/0304731 A1 | 12/2008 | Kimura |
| 2008/0306365 A1 | 12/2008 | Bunce et al. |
| 2008/0309855 A1 | 12/2008 | Yan et al. |
| 2008/0311549 A1 | 12/2008 | Belitsiotis |
| 2008/0319326 A1 | 12/2008 | Behbehani et al. |
| 2008/0319430 A1 | 12/2008 | Zenzie et al. |
| 2008/0319505 A1 | 12/2008 | Boyden et al. |
| 2009/0005667 A1 | 1/2009 | Cui et al. |
| 2009/0005675 A1 | 1/2009 | Grunwald et al. |
| 2009/0009284 A1 | 1/2009 | Sako |
| 2009/0012387 A1 | 1/2009 | Hanson et al. |
| 2009/0018407 A1 | 1/2009 | Jung et al. |
| 2009/0018419 A1 | 1/2009 | Torch |
| 2009/0018429 A1 | 1/2009 | Saliga et al. |
| 2009/0018431 A1 | 1/2009 | Feiweier et al. |
| 2009/0018432 A1 | 1/2009 | He et al. |
| 2009/0018462 A1 | 1/2009 | Bell |
| 2009/0022825 A1 | 1/2009 | Kerkman et al. |
| 2009/0024007 A1 | 1/2009 | Lee et al. |
| 2009/0024050 A1 | 1/2009 | Jung et al. |
| 2009/0024449 A1 | 1/2009 | Pradeep et al. |
| 2009/0025023 A1 | 1/2009 | Pradeep et al. |
| 2009/0030476 A1 | 1/2009 | Hargrove |
| 2009/0033333 A1 | 2/2009 | Gribova et al. |
| 2009/0036755 A1 | 2/2009 | Pradeep et al. |
| 2009/0036756 A1 | 2/2009 | Pradeep et al. |
| 2009/0036791 A1 | 2/2009 | Plenz |
| 2009/0043221 A1 | 2/2009 | Kaplan et al. |
| 2009/0048507 A1 | 2/2009 | Feiweier et al. |
| 2009/0048530 A1 | 2/2009 | Sarkela et al. |
| 2009/0054788 A1 | 2/2009 | Hauger et al. |
| 2009/0054800 A1 | 2/2009 | Martinerie et al. |
| 2009/0054801 A1 | 2/2009 | Hinrikus et al. |
| 2009/0054958 A1 | 2/2009 | Nofzinger |
| 2009/0058660 A1 | 3/2009 | Torch |
| 2009/0062629 A1 | 3/2009 | Pradeep et al. |
| 2009/0062660 A1 | 3/2009 | Chance |
| 2009/0062670 A1 | 3/2009 | Sterling et al. |
| 2009/0062676 A1 | 3/2009 | Kruglikov et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0062696 A1 | 3/2009 | Nathan et al. |
| 2009/0062698 A1 | 3/2009 | Einav et al. |
| 2009/0063255 A1 | 3/2009 | Pradeep et al. |
| 2009/0063256 A1 | 3/2009 | Pradeep et al. |
| 2009/0076339 A1 | 3/2009 | Quintin et al. |
| 2009/0076399 A1 | 3/2009 | Arbel et al. |
| 2009/0076400 A1 | 3/2009 | Diab et al. |
| 2009/0076406 A1 | 3/2009 | Graham et al. |
| 2009/0076407 A1 | 3/2009 | John et al. |
| 2009/0078875 A1 | 3/2009 | Rousso et al. |
| 2009/0082688 A1 | 3/2009 | Wagner |
| 2009/0082689 A1 | 3/2009 | Guttag et al. |
| 2009/0082690 A1 | 3/2009 | Phillips et al. |
| 2009/0082829 A1 | 3/2009 | Panken et al. |
| 2009/0083071 A1 | 3/2009 | Phillips et al. |
| 2009/0088658 A1 | 4/2009 | Luo et al. |
| 2009/0094305 A1 | 4/2009 | Johnson |
| 2009/0099474 A1 | 4/2009 | Pineda et al. |
| 2009/0099627 A1 | 4/2009 | Molnar et al. |
| 2009/0099783 A1 | 4/2009 | Reisberg |
| 2009/0105785 A1 | 4/2009 | Wei et al. |
| 2009/0112077 A1 | 4/2009 | Nguyen et al. |
| 2009/0112117 A1 | 4/2009 | Rewari |
| 2009/0112273 A1 | 4/2009 | Wingeier et al. |
| 2009/0112277 A1 | 4/2009 | Wingeier et al. |
| 2009/0112278 A1 | 4/2009 | Wingeier et al. |
| 2009/0112279 A1 | 4/2009 | Wingeier et al. |
| 2009/0112280 A1 | 4/2009 | Wingeier et al. |
| 2009/0112281 A1 | 4/2009 | Miyazawa et al. |
| 2009/0112523 A1 | 4/2009 | Townsend et al. |
| 2009/0118610 A1 | 5/2009 | Karmarkar et al. |
| 2009/0118622 A1 | 5/2009 | Durkin et al. |
| 2009/0118636 A1 | 5/2009 | Collura |
| 2009/0124869 A1 | 5/2009 | Hu et al. |
| 2009/0124921 A1 | 5/2009 | Milgramm et al. |
| 2009/0124922 A1 | 5/2009 | Milgramm et al. |
| 2009/0124923 A1 | 5/2009 | Sackellares et al. |
| 2009/0131995 A1 | 5/2009 | Sloan et al. |
| 2009/0137915 A1 | 5/2009 | Childre et al. |
| 2009/0137923 A1 | 5/2009 | Suffin et al. |
| 2009/0149148 A1 | 6/2009 | Kurtz et al. |
| 2009/0149736 A1 | 6/2009 | Skidmore et al. |
| 2009/0156907 A1 | 6/2009 | Jung et al. |
| 2009/0156925 A1 | 6/2009 | Jin et al. |
| 2009/0156954 A1 | 6/2009 | Cox et al. |
| 2009/0156955 A1 | 6/2009 | Jung et al. |
| 2009/0156956 A1 | 6/2009 | Milgramm et al. |
| 2009/0157323 A1 | 6/2009 | Jung et al. |
| 2009/0157481 A1 | 6/2009 | Jung et al. |
| 2009/0157482 A1 | 6/2009 | Jung et al. |
| 2009/0157625 A1 | 6/2009 | Jung et al. |
| 2009/0157662 A1 | 6/2009 | Suffin et al. |
| 2009/0157751 A1 | 6/2009 | Jung et al. |
| 2009/0157813 A1 | 6/2009 | Jung et al. |
| 2009/0163777 A1 | 6/2009 | Jung et al. |
| 2009/0164131 A1 | 6/2009 | Jung et al. |
| 2009/0164132 A1 | 6/2009 | Jung et al. |
| 2009/0171164 A1 | 7/2009 | Jung et al. |
| 2009/0171232 A1 | 7/2009 | Hu et al. |
| 2009/0171240 A1 | 7/2009 | Aguilar et al. |
| 2009/0172540 A1 | 7/2009 | Jung et al. |
| 2009/0177050 A1 | 7/2009 | Griffiths et al. |
| 2009/0177090 A1 | 7/2009 | Grunwald et al. |
| 2009/0177108 A1 | 7/2009 | Shieh et al. |
| 2009/0177144 A1 | 7/2009 | Masmanidis et al. |
| 2009/0179642 A1 | 7/2009 | deCharms |
| 2009/0182211 A1 | 7/2009 | Diab et al. |
| 2009/0191131 A1 | 7/2009 | Fossheim et al. |
| 2009/0192394 A1 | 7/2009 | Guttag et al. |
| 2009/0192556 A1 | 7/2009 | Wu et al. |
| 2009/0198144 A1 | 8/2009 | Phillips et al. |
| 2009/0198145 A1 | 8/2009 | Chow |
| 2009/0204015 A1 | 8/2009 | Phillips et al. |
| 2009/0209831 A1 | 8/2009 | Kucharczyk et al. |
| 2009/0209835 A1 | 8/2009 | Diab et al. |
| 2009/0209845 A1 | 8/2009 | Christen et al. |
| 2009/0214060 A1 | 8/2009 | Chuang et al. |
| 2009/0214485 A1 | 8/2009 | Gavrilova et al. |
| 2009/0216091 A1 | 8/2009 | Arndt |
| 2009/0216146 A1 | 8/2009 | Teicher et al. |
| 2009/0216288 A1 | 8/2009 | Schiff et al. |
| 2009/0220425 A1 | 9/2009 | Moxon et al. |
| 2009/0220429 A1 | 9/2009 | Johnsen et al. |
| 2009/0221928 A1 | 9/2009 | Einav et al. |
| 2009/0221930 A1 | 9/2009 | Laken |
| 2009/0227876 A1 | 9/2009 | Tran |
| 2009/0227877 A1 | 9/2009 | Tran |
| 2009/0227882 A1 | 9/2009 | Foo |
| 2009/0227889 A2 | 9/2009 | John et al. |
| 2009/0240119 A1 | 9/2009 | Schwaibold et al. |
| 2009/0246138 A1 | 10/2009 | Santosh et al. |
| 2009/0247893 A1 | 10/2009 | Lapinlampi et al. |
| 2009/0247894 A1 | 10/2009 | Causevic |
| 2009/0264785 A1 | 10/2009 | Causevic et al. |
| 2009/0264789 A1 | 10/2009 | Molnar et al. |
| 2009/0264952 A1 | 10/2009 | Jassemidis et al. |
| 2009/0265298 A1 | 10/2009 | Kaplan |
| 2009/0267758 A1 | 10/2009 | Hyde et al. |
| 2009/0270687 A1 | 10/2009 | Hyde et al. |

(56)　　　　　References Cited

U.S. PATENT DOCUMENTS

| | | |
|---|---|---|
| 2009/0270688 A1 | 10/2009 | Hyde et al. |
| 2009/0270692 A1 | 10/2009 | Hyde et al. |
| 2009/0270693 A1 | 10/2009 | Hyde et al. |
| 2009/0270694 A1 | 10/2009 | Hyde et al. |
| 2009/0270758 A1 | 10/2009 | Eagleman et al. |
| 2009/0270786 A1 | 10/2009 | Hyde et al. |
| 2009/0270944 A1 | 10/2009 | Whitehurst et al. |
| 2009/0275853 A1 | 11/2009 | Sarkela |
| 2009/0281400 A1 | 11/2009 | McCraty et al. |
| 2009/0281408 A1 | 11/2009 | Lee et al. |
| 2009/0281448 A1 | 11/2009 | Wright et al. |
| 2009/0287107 A1 | 11/2009 | Beck-Nielsen et al. |
| 2009/0287108 A1 | 11/2009 | Levy |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287274 A1 | 11/2009 | De Ridder |
| 2009/0287467 A1 | 11/2009 | Sparks et al. |
| 2009/0289895 A1 | 11/2009 | Nakada et al. |
| 2009/0292180 A1 | 11/2009 | Mirow |
| 2009/0292223 A1 | 11/2009 | Sugio et al. |
| 2009/0292713 A1 | 11/2009 | Jung et al. |
| 2009/0292724 A1 | 11/2009 | Jung et al. |
| 2009/0295738 A1 | 12/2009 | Chiang |
| 2009/0297000 A1 | 12/2009 | Shahaf et al. |
| 2009/0299169 A1 | 12/2009 | deCharms |
| 2009/0299209 A1 | 12/2009 | Farbos |
| 2009/0304582 A1 | 12/2009 | Rousso et al. |
| 2009/0306531 A1 | 12/2009 | Leuthardt et al. |
| 2009/0306532 A1 | 12/2009 | Tucker |
| 2009/0306534 A1 | 12/2009 | Pizzagalli |
| 2009/0306741 A1 | 12/2009 | Hogle et al. |
| 2009/0311655 A1 | 12/2009 | Karkanias et al. |
| 2009/0312624 A1 | 12/2009 | Berridge et al. |
| 2009/0312646 A1 | 12/2009 | Binder et al. |
| 2009/0312663 A1 | 12/2009 | John et al. |
| 2009/0312664 A1 | 12/2009 | Rodriguez Villegas et al. |
| 2009/0312665 A1 | 12/2009 | Daimoto et al. |
| 2009/0312808 A1 | 12/2009 | Tyler et al. |
| 2009/0312817 A1 | 12/2009 | Hogle et al. |
| 2009/0316925 A1 | 12/2009 | Eisenfeld et al. |
| 2009/0318773 A1 | 12/2009 | Jung et al. |
| 2009/0318779 A1 | 12/2009 | Tran |
| 2009/0318794 A1 | 12/2009 | DeCharms |
| 2009/0319001 A1 | 12/2009 | Schiff |
| 2009/0319004 A1 | 12/2009 | Sabel |
| 2009/0322331 A1 | 12/2009 | Buracas |
| 2009/0323049 A1 | 12/2009 | Addison et al. |
| 2009/0326353 A1 | 12/2009 | Watson et al. |
| 2009/0326404 A1 | 12/2009 | Sajda et al. |
| 2009/0326604 A1 | 12/2009 | Tyler et al. |
| 2009/0327068 A1 | 12/2009 | Pradeep et al. |
| 2009/0328089 A1 | 12/2009 | Pradeep et al. |
| 2010/0004500 A1 | 1/2010 | Gliner et al. |
| 2010/0004977 A1 | 1/2010 | Marci et al. |
| 2010/0010289 A1 | 1/2010 | Clare |
| 2010/0010364 A1 | 1/2010 | Verbitskiy |
| 2010/0010365 A1 | 1/2010 | Terao et al. |
| 2010/0010366 A1 | 1/2010 | Silberstein |
| 2010/0010385 A1 | 1/2010 | Skelton et al. |
| 2010/0010844 A1 | 1/2010 | Isaksen |
| 2010/0021378 A1 | 1/2010 | Rousso et al. |
| 2010/0023089 A1 | 1/2010 | DiLorenzo |
| 2010/0028841 A1 | 2/2010 | Eatough et al. |
| 2010/0030073 A1 | 2/2010 | Kalafut |
| 2010/0030097 A1 | 2/2010 | Silberstein |
| 2010/0030287 A1 | 2/2010 | Jaax et al. |
| 2010/0036211 A1 | 2/2010 | La Rue et al. |
| 2010/0036233 A1 | 2/2010 | Zhu et al. |
| 2010/0036276 A1 | 2/2010 | Ochs |
| 2010/0036290 A1 | 2/2010 | Noguchi et al. |
| 2010/0036453 A1 | 2/2010 | Hulvershorn et al. |
| 2010/0041949 A1 | 2/2010 | Tolkowsky |
| 2010/0041962 A1 | 2/2010 | Causevic et al. |
| 2010/0042011 A1 | 2/2010 | Doidge et al. |
| 2010/0043795 A1 | 2/2010 | Ujhazy et al. |
| 2010/0045932 A1 | 2/2010 | Shelhamer et al. |
| 2010/0049069 A1 | 2/2010 | Tarassenko et al. |
| 2010/0049075 A1 | 2/2010 | Bolger et al. |
| 2010/0049276 A1 | 2/2010 | Blum et al. |
| 2010/0049482 A1 | 2/2010 | He et al. |
| 2010/0056276 A1 | 3/2010 | Silberstein |
| 2010/0056854 A1 | 3/2010 | Chang |
| 2010/0056939 A1 | 3/2010 | Tarassenko et al. |
| 2010/0068146 A1 | 3/2010 | Luther-Forsstrom et al. |
| 2010/0068751 A1 | 3/2010 | Eberle |
| 2010/0069739 A1 | 3/2010 | deCharms |
| 2010/0069762 A1 | 3/2010 | Mietus et al. |
| 2010/0069775 A1 | 3/2010 | Milgramm et al. |
| 2010/0069777 A1 | 3/2010 | Marks |
| 2010/0069780 A1 | 3/2010 | Schuette et al. |
| 2010/0069993 A1 | 3/2010 | Greenspan |
| 2010/0076253 A1 | 3/2010 | Altman et al. |
| 2010/0076274 A1 | 3/2010 | Severson |
| 2010/0076333 A9 | 3/2010 | Burton et al. |
| 2010/0076334 A1 | 3/2010 | Rothblatt |
| 2010/0076338 A1 | 3/2010 | Kwak |
| 2010/0079292 A1 | 4/2010 | Lynn et al. |
| 2010/0081707 A1 | 4/2010 | Ali et al. |
| 2010/0082506 A1 | 4/2010 | Avinash et al. |
| 2010/0087701 A1 | 4/2010 | Berka et al. |
| 2010/0087719 A1 | 4/2010 | Benni |
| 2010/0087900 A1 | 4/2010 | Flint |
| 2010/0090835 A1 | 4/2010 | Liu et al. |
| 2010/0092934 A1 | 4/2010 | Silberstein |
| 2010/0094097 A1 | 4/2010 | Liu et al. |
| 2010/0094103 A1 | 4/2010 | Kaplan et al. |
| 2010/0094152 A1 | 4/2010 | Semmlow |
| 2010/0094154 A1 | 4/2010 | Schalk et al. |
| 2010/0094155 A1 | 4/2010 | Prichep |
| 2010/0098289 A1 | 4/2010 | Tognoli et al. |
| 2010/0099954 A1 | 4/2010 | Dickinson et al. |
| 2010/0099975 A1 | 4/2010 | Faro et al. |
| 2010/0100001 A1 | 4/2010 | Aguilar et al. |
| 2010/0106041 A1 | 4/2010 | Ghovanloo et al. |
| 2010/0106043 A1 | 4/2010 | Robinson et al. |
| 2010/0106044 A1 | 4/2010 | Linderman |
| 2010/0113959 A1 | 5/2010 | Pascual-Leone et al. |
| 2010/0114193 A1 | 5/2010 | Lozano et al. |
| 2010/0114237 A1 | 5/2010 | Giftakis et al. |
| 2010/0114813 A1 | 5/2010 | Zalay et al. |
| 2010/0125219 A1 | 5/2010 | Harris et al. |
| 2010/0130812 A1 | 5/2010 | Martel |
| 2010/0130869 A1 | 5/2010 | Hauger et al. |
| 2010/0131034 A1 | 5/2010 | Gliner et al. |
| 2010/0137728 A1 | 6/2010 | Govari |
| 2010/0137937 A1 | 6/2010 | John et al. |
| 2010/0143256 A1 | 6/2010 | Suffin et al. |
| 2010/0152621 A1 | 6/2010 | Janna et al. |
| 2010/0160737 A1 | 6/2010 | Shachar et al. |
| 2010/0163027 A1 | 7/2010 | Hyde et al. |
| 2010/0163028 A1 | 7/2010 | Hyde et al. |
| 2010/0163035 A1 | 7/2010 | Hyde et al. |
| 2010/0165093 A1 | 7/2010 | Sugio et al. |
| 2010/0165593 A1 | 7/2010 | Townsend et al. |
| 2010/0168525 A1 | 7/2010 | Hyde et al. |
| 2010/0168529 A1 | 7/2010 | Hyde et al. |
| 2010/0168602 A1 | 7/2010 | Hyde et al. |
| 2010/0174161 A1 | 7/2010 | Lynn |
| 2010/0174533 A1 | 7/2010 | Pakhomov |
| 2010/0177929 A1 | 7/2010 | Kurtz et al. |
| 2010/0179447 A1 | 7/2010 | Hunt |
| 2010/0185113 A1 | 7/2010 | Peot et al. |
| 2010/0189318 A1 | 7/2010 | Chang et al. |
| 2010/0191095 A1 | 7/2010 | Felblinger et al. |
| 2010/0191124 A1 | 7/2010 | Prokoski |
| 2010/0191139 A1 | 7/2010 | Jacquin et al. |
| 2010/0191305 A1 | 7/2010 | Imran et al. |
| 2010/0195770 A1 | 8/2010 | Ricci et al. |
| 2010/0196396 A1 | 8/2010 | Szentirmai et al. |
| 2010/0197610 A1 | 8/2010 | Lian et al. |
| 2010/0198090 A1 | 8/2010 | Hudson et al. |
| 2010/0198098 A1 | 8/2010 | Osorio et al. |
| 2010/0198101 A1 | 8/2010 | Song et al. |

(56)                    References Cited

U.S. PATENT DOCUMENTS

| | | |
|---|---|---|
| 2010/0201621 A1 | 8/2010 | Niikawa |
| 2010/0201780 A1 | 8/2010 | Bennett et al. |
| 2010/0204604 A1 | 8/2010 | Liley et al. |
| 2010/0204608 A1 | 8/2010 | Sugio et al. |
| 2010/0204614 A1 | 8/2010 | Lindquist et al. |
| 2010/0204748 A1 | 8/2010 | Lozano et al. |
| 2010/0204750 A1 | 8/2010 | Hargrove et al. |
| 2010/0217100 A1 | 8/2010 | LeBoeuf et al. |
| 2010/0217146 A1 | 8/2010 | Osvath |
| 2010/0217348 A1 | 8/2010 | DiLorenzo |
| 2010/0219820 A1 | 9/2010 | Skidmore et al. |
| 2010/0222640 A1 | 9/2010 | Anderson et al. |
| 2010/0222694 A1 | 9/2010 | Causevic |
| 2010/0224188 A1 | 9/2010 | John et al. |
| 2010/0228695 A1 | 9/2010 | Kaplan |
| 2010/0234705 A1 | 9/2010 | Lynn |
| 2010/0234752 A1 | 9/2010 | Sullivan et al. |
| 2010/0234753 A1 | 9/2010 | Ma |
| 2010/0241449 A1 | 9/2010 | Firminger et al. |
| 2010/0245093 A1 | 9/2010 | Kobetski et al. |
| 2010/0248275 A1 | 9/2010 | Jackowski et al. |
| 2010/0249573 A1 | 9/2010 | Marks |
| 2010/0249627 A1 | 9/2010 | Zhang et al. |
| 2010/0249635 A1 | 9/2010 | Van Der Reijden |
| 2010/0249636 A1 | 9/2010 | Pradeep et al. |
| 2010/0249638 A1 | 9/2010 | Liley |
| 2010/0258126 A1 | 10/2010 | Ujhazy et al. |
| 2010/0261977 A1 | 10/2010 | Seely |
| 2010/0261993 A1 | 10/2010 | van der Kouwe et al. |
| 2010/0262377 A1 | 10/2010 | Jensen |
| 2010/0268055 A1 | 10/2010 | Jung et al. |
| 2010/0268057 A1 | 10/2010 | Firminger et al. |
| 2010/0268108 A1 | 10/2010 | Firminger et al. |
| 2010/0274577 A1 | 10/2010 | Firminger et al. |
| 2010/0274578 A1 | 10/2010 | Firminger et al. |
| 2010/0280338 A1 | 11/2010 | Chou |
| 2010/0280372 A1 | 11/2010 | Poolman et al. |
| 2010/0280403 A1 | 11/2010 | Erdogmus et al. |
| 2010/0283972 A1 | 11/2010 | Plant et al. |
| 2010/0286549 A1 | 11/2010 | John et al. |
| 2010/0286747 A1 | 11/2010 | Sabesan et al. |
| 2010/0292752 A1 | 11/2010 | Bardakjian et al. |
| 2010/0293002 A1 | 11/2010 | Firminger et al. |
| 2010/0293115 A1 | 11/2010 | Seyed Momen |
| 2010/0298624 A1 | 11/2010 | Becker |
| 2010/0298735 A1 | 11/2010 | Suffin |
| 2010/0303101 A1 | 12/2010 | Lazar et al. |
| 2010/0305962 A1 | 12/2010 | Firminger et al. |
| 2010/0305963 A1 | 12/2010 | Firminger et al. |
| 2010/0312188 A1 | 12/2010 | Robertson et al. |
| 2010/0312579 A1 | 12/2010 | Firminger et al. |
| 2010/0318025 A1 | 12/2010 | John |
| 2010/0324441 A1 | 12/2010 | Hargrove et al. |
| 2010/0331649 A1 | 12/2010 | Chou |
| 2010/0331715 A1 | 12/2010 | Addison et al. |
| 2010/0331976 A1 | 12/2010 | Pesaran et al. |
| 2011/0004089 A1 | 1/2011 | Chou |
| 2011/0004115 A1 | 1/2011 | Shahaf et al. |
| 2011/0004412 A1 | 1/2011 | Shahaf et al. |
| 2011/0009715 A1 | 1/2011 | O'Reilly et al. |
| 2011/0009729 A1 | 1/2011 | Shin et al. |
| 2011/0009752 A1 | 1/2011 | Chen et al. |
| 2011/0009777 A1 | 1/2011 | Reichow et al. |
| 2011/0015467 A1 | 1/2011 | Dothie et al. |
| 2011/0015495 A1 | 1/2011 | Dothie et al. |
| 2011/0015501 A1 | 1/2011 | Lynn et al. |
| 2011/0015515 A1 | 1/2011 | deCharms |
| 2011/0015536 A1 | 1/2011 | Milgramm et al. |
| 2011/0015539 A1 | 1/2011 | deCharms |
| 2011/0026678 A1 | 2/2011 | Bonfiglio et al. |
| 2011/0028802 A1 | 2/2011 | Addison et al. |
| 2011/0028827 A1 | 2/2011 | Sitaram et al. |
| 2011/0028859 A1 | 2/2011 | Chian |
| 2011/0034821 A1 | 2/2011 | Ekpar |
| 2011/0034822 A1 | 2/2011 | Phillips et al. |
| 2011/0035231 A1 | 2/2011 | Firminger et al. |
| 2011/0038515 A1 | 2/2011 | Jacquin et al. |
| 2011/0039790 A1 | 2/2011 | Peyman |
| 2011/0040202 A1 | 2/2011 | Luo et al. |
| 2011/0040713 A1 | 2/2011 | Colman et al. |
| 2011/0043759 A1 | 2/2011 | Bushinsky |
| 2011/0046473 A1 | 2/2011 | Pradeep et al. |
| 2011/0046491 A1 | 2/2011 | Diamond |
| 2011/0046502 A1 | 2/2011 | Pradeep et al. |
| 2011/0046510 A1 | 2/2011 | Laufer et al. |
| 2011/0054272 A1 | 3/2011 | Derchak |
| 2011/0054279 A1 | 3/2011 | Reisfeld et al. |
| 2011/0054345 A1 | 3/2011 | Nagatani |
| 2011/0054562 A1 | 3/2011 | Gliner |
| 2011/0060423 A1 | 3/2011 | Bonfiglio et al. |
| 2011/0066005 A1 | 3/2011 | Rotenberg |
| 2011/0066041 A1 | 3/2011 | Pandia et al. |
| 2011/0066042 A1 | 3/2011 | Pandia et al. |
| 2011/0066053 A1 | 3/2011 | Yazicioglu |
| 2011/0074396 A1 | 3/2011 | Liao et al. |
| 2011/0077503 A1 | 3/2011 | Bonilha et al. |
| 2011/0077538 A1 | 3/2011 | Liu et al. |
| 2011/0077548 A1 | 3/2011 | Torch |
| 2011/0082360 A1 | 4/2011 | Fuchs et al. |
| 2011/0082381 A1 | 4/2011 | Uthman et al. |
| 2011/0087082 A1 | 4/2011 | Giftakis et al. |
| 2011/0087125 A1 | 4/2011 | Causevic |
| 2011/0092800 A1 | 4/2011 | Yoo et al. |
| 2011/0092834 A1 | 4/2011 | Yazicioglu et al. |
| 2011/0092839 A1 | 4/2011 | Alshaer et al. |
| 2011/0092882 A1 | 4/2011 | Firlik et al. |
| 2011/0096294 A1 | 4/2011 | Peyman |
| 2011/0098583 A1 | 4/2011 | Pandia et al. |
| 2011/0105859 A1 | 5/2011 | Popovic et al. |
| 2011/0105913 A1 | 5/2011 | Giftakis et al. |
| 2011/0105915 A1 | 5/2011 | Bauer et al. |
| 2011/0105938 A1 | 5/2011 | Hardt |
| 2011/0106206 A1 | 5/2011 | Schiff |
| 2011/0110868 A1 | 5/2011 | Akhtari et al. |
| 2011/0112379 A1 | 5/2011 | Li et al. |
| 2011/0112381 A1 | 5/2011 | Sun et al. |
| 2011/0112394 A1 | 5/2011 | Mishelevich |
| 2011/0112426 A1 | 5/2011 | Causevic |
| 2011/0112427 A1 | 5/2011 | Phillips et al. |
| 2011/0115624 A1 | 5/2011 | Tran |
| 2011/0118536 A1 | 5/2011 | Phillips et al. |
| 2011/0118618 A1 | 5/2011 | John et al. |
| 2011/0118619 A1 | 5/2011 | Burton et al. |
| 2011/0119212 A1 | 5/2011 | De Bruin et al. |
| 2011/0125046 A1 | 5/2011 | Burton et al. |
| 2011/0125048 A1 | 5/2011 | Causevic et al. |
| 2011/0125077 A1 | 5/2011 | Denison et al. |
| 2011/0125078 A1 | 5/2011 | Denison et al. |
| 2011/0125238 A1 | 5/2011 | Nofzinger |
| 2011/0129129 A1 | 6/2011 | Avinash et al. |
| 2011/0130643 A1 | 6/2011 | Derchak et al. |
| 2011/0130675 A1 | 6/2011 | Bibian et al. |
| 2011/0137372 A1 | 6/2011 | Makous et al. |
| 2011/0144520 A1 | 6/2011 | Causevic et al. |
| 2011/0144521 A1 | 6/2011 | Molnar et al. |
| 2011/0144522 A1 | 6/2011 | Sajda et al. |
| 2011/0150253 A1 | 6/2011 | Corona-Strauss et al. |
| 2011/0152710 A1 | 6/2011 | Kim et al. |
| 2011/0160543 A1 | 6/2011 | Parsey et al. |
| 2011/0160607 A1 | 6/2011 | John et al. |
| 2011/0160608 A1 | 6/2011 | Hargrove |
| 2011/0160795 A1 | 6/2011 | Osorio |
| 2011/0161011 A1 | 6/2011 | Hasson et al. |
| 2011/0162645 A1 | 7/2011 | John et al. |
| 2011/0162879 A1 | 7/2011 | Bunyan et al. |
| 2011/0166430 A1 | 7/2011 | Harris et al. |
| 2011/0170066 A1 | 7/2011 | Sugio et al. |
| 2011/0170067 A1 | 7/2011 | Sato et al. |
| 2011/0172500 A1 | 7/2011 | Van Dooren et al. |
| 2011/0172509 A1 | 7/2011 | Chance |
| 2011/0172553 A1 | 7/2011 | John et al. |
| 2011/0172725 A1 | 7/2011 | Wells et al. |
| 2011/0178359 A1 | 7/2011 | Hirschman et al. |
| 2011/0178441 A1 | 7/2011 | Tyler |

(56)         References Cited

U.S. PATENT DOCUMENTS

| | | |
|---|---|---|
| 2011/0178442 A1 | 7/2011 | Mishelevich |
| 2011/0178581 A1 | 7/2011 | Haber et al. |
| 2011/0178784 A1 | 7/2011 | Sato et al. |
| 2011/0181422 A1 | 7/2011 | Tran |
| 2011/0182501 A1 | 7/2011 | Mercier et al. |
| 2011/0184305 A1 | 7/2011 | Liley |
| 2011/0184650 A1 | 7/2011 | Hymel |
| 2011/0190600 A1 | 8/2011 | McKenna et al. |
| 2011/0190846 A1 | 8/2011 | Ruffini et al. |
| 2011/0191350 A1 | 8/2011 | Zhang et al. |
| 2011/0196693 A1 | 8/2011 | Hargrove et al. |
| 2011/0207988 A1 | 8/2011 | Ruohonen et al. |
| 2011/0208094 A1 | 8/2011 | Mishelevich |
| 2011/0208539 A1 | 8/2011 | Lynn |
| 2011/0213200 A1 | 9/2011 | Mishelevich |
| 2011/0217240 A1 | 9/2011 | Ferris |
| 2011/0218405 A1 | 9/2011 | Avinash et al. |
| 2011/0218453 A1 | 9/2011 | Hirata et al. |
| 2011/0218456 A1 | 9/2011 | Graham et al. |
| 2011/0218950 A1 | 9/2011 | Mirowski et al. |
| 2011/0224503 A1 | 9/2011 | Cusimano Reaston et al. |
| 2011/0224569 A1 | 9/2011 | Isenhart et al. |
| 2011/0224570 A1 | 9/2011 | Causevic |
| 2011/0224571 A1 | 9/2011 | Pascual-Leone et al. |
| 2011/0224602 A1 | 9/2011 | Struijk et al. |
| 2011/0227813 A1 | 9/2011 | Haddick et al. |
| 2011/0230738 A1 | 9/2011 | Chance |
| 2011/0238685 A1 | 9/2011 | Garcia Molina et al. |
| 2011/0245709 A1 | 10/2011 | Greenwald |
| 2011/0251511 A1 | 10/2011 | Desain et al. |
| 2011/0251583 A1 | 10/2011 | Miyazawa et al. |
| 2011/0251985 A1 | 10/2011 | Waxman et al. |
| 2011/0256520 A1 | 10/2011 | Siefert |
| 2011/0257517 A1 | 10/2011 | Guttag et al. |
| 2011/0257519 A1 | 10/2011 | Bjørnerud et al. |
| 2011/0263962 A1 | 10/2011 | Marks |
| 2011/0263968 A1 | 10/2011 | Quattrocki-Knight et al. |
| 2011/0263995 A1 | 10/2011 | Chen |
| 2011/0270074 A1 | 11/2011 | deCharms |
| 2011/0270095 A1 | 11/2011 | Bukhman |
| 2011/0270117 A1 | 11/2011 | Warwick et al. |
| 2011/0270579 A1 | 11/2011 | Watson et al. |
| 2011/0270914 A1 | 11/2011 | Jung et al. |
| 2011/0275927 A1 | 11/2011 | Wagner et al. |
| 2011/0282230 A9 | 11/2011 | Liley |
| 2011/0282234 A1 | 11/2011 | Ochs |
| 2011/0288400 A1 | 11/2011 | Russell et al. |
| 2011/0288424 A1 | 11/2011 | Kanai et al. |
| 2011/0288431 A1 | 11/2011 | Alshaer et al. |
| 2011/0289030 A1 | 11/2011 | Lu et al. |
| 2011/0295086 A1 | 12/2011 | Nakada et al. |
| 2011/0295142 A1 | 12/2011 | Chakravarthy et al. |
| 2011/0295143 A1 | 12/2011 | Leuthardt et al. |
| 2011/0295166 A1 | 12/2011 | Dalton |
| 2011/0295338 A1 | 12/2011 | Rickert et al. |
| 2011/0298702 A1 | 12/2011 | Sakata et al. |
| 2011/0298706 A1 | 12/2011 | Mann |
| 2011/0301436 A1 | 12/2011 | Teixeira |
| 2011/0301439 A1 | 12/2011 | Albert et al. |
| 2011/0301441 A1 | 12/2011 | Bandic et al. |
| 2011/0301448 A1 | 12/2011 | deCharms |
| 2011/0301486 A1 | 12/2011 | Van Hek et al. |
| 2011/0301487 A1 | 12/2011 | Abeyratne et al. |
| 2011/0301488 A1 | 12/2011 | Schuette et al. |
| 2011/0306845 A1 | 12/2011 | Osorio |
| 2011/0306846 A1 | 12/2011 | Osorio |
| 2011/0307029 A1 | 12/2011 | Hargrove |
| 2011/0307030 A1 | 12/2011 | John |
| 2011/0307079 A1 | 12/2011 | Oweiss et al. |
| 2011/0310238 A1 | 12/2011 | Koh et al. |
| 2011/0313268 A1 | 12/2011 | Kokones et al. |
| 2011/0313274 A1 | 12/2011 | Subbarao |
| 2011/0313308 A1 | 12/2011 | Zavoronkovs et al. |
| 2011/0313487 A1 | 12/2011 | Kokones et al. |
| 2011/0313760 A1 | 12/2011 | Ricci et al. |
| 2011/0319056 A1 | 12/2011 | Toy et al. |
| 2011/0319482 A1 | 12/2011 | Blower et al. |
| 2011/0319724 A1 | 12/2011 | Cox |
| 2011/0319785 A1 | 12/2011 | Snyder et al. |
| 2012/0003615 A1 | 1/2012 | Ochs |
| 2012/0004518 A1 | 1/2012 | D'Souza et al. |
| 2012/0004561 A1 | 1/2012 | John |
| 2012/0004564 A1 | 1/2012 | Dobak |
| 2012/0004579 A1 | 1/2012 | Luo et al. |
| 2012/0004749 A1 | 1/2012 | Abeyratne et al. |
| 2012/0010536 A1 | 1/2012 | Bolger et al. |
| 2012/0016218 A1 | 1/2012 | Lau et al. |
| 2012/0016252 A1 | 1/2012 | Melker et al. |
| 2012/0021394 A1 | 1/2012 | deCharms |
| 2012/0022336 A1 | 1/2012 | Teixeira |
| 2012/0022343 A1 | 1/2012 | Shastri et al. |
| 2012/0022350 A1 | 1/2012 | Teixeira |
| 2012/0022351 A1 | 1/2012 | Starr |
| 2012/0022365 A1 | 1/2012 | Mansfield |
| 2012/0022384 A1 | 1/2012 | Teixeira |
| 2012/0022392 A1 | 1/2012 | Leuthardt et al. |
| 2012/0022844 A1 | 1/2012 | Teixeira |
| 2012/0022884 A1 | 1/2012 | Chillemi |
| 2012/0023243 A1 | 1/2012 | Xu |
| 2012/0029320 A1 | 2/2012 | Watson et al. |
| 2012/0029378 A1 | 2/2012 | Low |
| 2012/0029379 A1 | 2/2012 | Sivadas |
| 2012/0035431 A1 | 2/2012 | Sun et al. |
| 2012/0035433 A1 | 2/2012 | Chance |
| 2012/0035765 A1 | 2/2012 | Sato et al. |
| 2012/0036004 A1 | 2/2012 | Pradeep et al. |
| 2012/0041279 A1 | 2/2012 | Freeman et al. |
| 2012/0041330 A1 | 2/2012 | Prichep et al. |
| 2012/0046531 A1 | 2/2012 | Hua |
| 2012/0046535 A1 | 2/2012 | Lin et al. |
| 2012/0046569 A1 | 2/2012 | Johnstone et al. |
| 2012/0046711 A1 | 2/2012 | Osorio |
| 2012/0046971 A1 | 2/2012 | Walker et al. |
| 2012/0052905 A1 | 3/2012 | Lim et al. |
| 2012/0053394 A1 | 3/2012 | Honeycutt |
| 2012/0053433 A1 | 3/2012 | Chamoun et al. |
| 2012/0053449 A1 | 3/2012 | Moses et al. |
| 2012/0053473 A1 | 3/2012 | Johnson et al. |
| 2012/0053476 A1 | 3/2012 | Hopenfeld |
| 2012/0053478 A1 | 3/2012 | Johnson et al. |
| 2012/0053479 A1 | 3/2012 | Hopenfeld |
| 2012/0053483 A1 | 3/2012 | Doidge et al. |
| 2012/0053491 A1 | 3/2012 | Nathan et al. |
| 2012/0053508 A1 | 3/2012 | Wu et al. |
| 2012/0059273 A1 | 3/2012 | Meggiolaro et al. |
| 2012/0065536 A1 | 3/2012 | Causevic et al. |
| 2012/0066393 A1 | 3/2012 | Tekwani |
| 2012/0071771 A1 | 3/2012 | Behar |
| 2012/0075168 A1 | 3/2012 | Osterhout et al. |
| 2012/0078115 A1 | 3/2012 | Lonky |
| 2012/0078327 A1 | 3/2012 | Sloan et al. |
| 2012/0078820 A1 | 3/2012 | Azam |
| 2012/0081666 A1 | 4/2012 | Kiderman et al. |
| 2012/0083700 A1 | 4/2012 | Osorio |
| 2012/0083701 A1 | 4/2012 | Osorio |
| 2012/0083708 A1 | 4/2012 | Rajdev et al. |
| 2012/0084480 A1 | 4/2012 | Reeves et al. |
| 2012/0084481 A1 | 4/2012 | Reeves et al. |
| 2012/0084542 A1 | 4/2012 | Reeves et al. |
| 2012/0084791 A1 | 4/2012 | Benedek et al. |
| 2012/0084792 A1 | 4/2012 | Benedek et al. |
| 2012/0088987 A1 | 4/2012 | Braun et al. |
| 2012/0088992 A1 | 4/2012 | Armitstead |
| 2012/0089004 A1 | 4/2012 | Hsu et al. |
| 2012/0089906 A1 | 4/2012 | Reeves et al. |
| 2012/0092156 A1 | 4/2012 | Tran |
| 2012/0092157 A1 | 4/2012 | Tran |
| 2012/0095352 A1 | 4/2012 | Tran |
| 2012/0095357 A1 | 4/2012 | Tran |
| 2012/0100514 A1 | 4/2012 | Desain et al. |
| 2012/0101387 A1 | 4/2012 | Ji et al. |
| 2012/0101401 A1 | 4/2012 | Faul et al. |
| 2012/0101402 A1 | 4/2012 | Nguyen |
| 2012/0101430 A1 | 4/2012 | Robertson et al. |

(56)                    References Cited

U.S. PATENT DOCUMENTS

| | | |
|---|---|---|
| 2012/0108909 A1 | 5/2012 | Slobounov et al. |
| 2012/0108918 A1 | 5/2012 | Jarvik et al. |
| 2012/0108995 A1 | 5/2012 | Pradeep et al. |
| 2012/0108997 A1 | 5/2012 | Guan et al. |
| 2012/0108998 A1 | 5/2012 | Molnar et al. |
| 2012/0108999 A1 | 5/2012 | Leininger et al. |
| 2012/0112909 A1 | 5/2012 | Baughman et al. |
| 2012/0116235 A1 | 5/2012 | Trumble et al. |
| 2012/0116559 A1 | 5/2012 | Davis et al. |
| 2012/0123232 A1 | 5/2012 | Najarian et al. |
| 2012/0123290 A1 | 5/2012 | Kidmose et al. |
| 2012/0125337 A1 | 5/2012 | Asanoi |
| 2012/0127426 A1 | 5/2012 | Backus et al. |
| 2012/0130204 A1 | 5/2012 | Basta et al. |
| 2012/0130228 A1 | 5/2012 | Zellers et al. |
| 2012/0130229 A1 | 5/2012 | Zellers et al. |
| 2012/0134548 A1 | 5/2012 | Rhoads et al. |
| 2012/0136242 A1 | 5/2012 | Qi et al. |
| 2012/0136274 A1 | 5/2012 | Burdea et al. |
| 2012/0136605 A1 | 5/2012 | Addison et al. |
| 2012/0143038 A1 | 6/2012 | Georgopoulos |
| 2012/0143074 A1 | 6/2012 | Shin et al. |
| 2012/0143075 A1 | 6/2012 | Tansey |
| 2012/0143104 A1 | 6/2012 | Tee et al. |
| 2012/0145152 A1 | 6/2012 | Lain et al. |
| 2012/0149042 A1 | 6/2012 | Jackowski et al. |
| 2012/0149997 A1 | 6/2012 | Diab et al. |
| 2012/0150262 A1 | 6/2012 | Gliner et al. |
| 2012/0150545 A1 | 6/2012 | Simon |
| 2012/0154633 A1 | 6/2012 | Rodriguez |
| 2012/0157804 A1 | 6/2012 | Rogers et al. |
| 2012/0157963 A1 | 6/2012 | Imran |
| 2012/0159656 A1 | 6/2012 | Gerber et al. |
| 2012/0163689 A1 | 6/2012 | Bottger et al. |
| 2012/0165624 A1 | 6/2012 | Diab et al. |
| 2012/0165631 A1 | 6/2012 | Diab et al. |
| 2012/0165899 A1 | 6/2012 | Gliner |
| 2012/0165904 A1 | 6/2012 | Lee et al. |
| 2012/0172682 A1 | 7/2012 | Linderman et al. |
| 2012/0172689 A1 | 7/2012 | Albert et al. |
| 2012/0172743 A1 | 7/2012 | Aguilar et al. |
| 2012/0176302 A1 | 7/2012 | Mangoubi et al. |
| 2012/0177233 A1 | 7/2012 | Kidmose et al. |
| 2012/0184826 A1 | 7/2012 | Keenan et al. |
| 2012/0190959 A1 | 7/2012 | Hayakawa et al. |
| 2012/0191000 A1 | 7/2012 | Adachi et al. |
| 2012/0191542 A1 | 7/2012 | Nurmi |
| 2012/0194781 A1 | 8/2012 | Agurok |
| 2012/0197092 A1 | 8/2012 | Luo et al. |
| 2012/0197153 A1 | 8/2012 | Kraus et al. |
| 2012/0197163 A1 | 8/2012 | Mishelevich |
| 2012/0200601 A1 | 8/2012 | Osterhout et al. |
| 2012/0203079 A1 | 8/2012 | McLaughlin |
| 2012/0203087 A1 | 8/2012 | McKenna et al. |
| 2012/0203130 A1 | 8/2012 | Bernhard |
| 2012/0203131 A1 | 8/2012 | DiLorenzo |
| 2012/0203133 A1 | 8/2012 | Jadidi |
| 2012/0203725 A1 | 8/2012 | Stoica |
| 2012/0209126 A1 | 8/2012 | Amos et al. |
| 2012/0209136 A1 | 8/2012 | Ma |
| 2012/0209139 A1 | 8/2012 | John |
| 2012/0210233 A1 | 8/2012 | Davis et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0215114 A1 | 8/2012 | Gratton et al. |
| 2012/0219195 A1 | 8/2012 | Wu et al. |
| 2012/0219507 A1 | 8/2012 | Santosh et al. |
| 2012/0220843 A1 | 8/2012 | Diab et al. |
| 2012/0220889 A1 | 8/2012 | Sullivan et al. |
| 2012/0221075 A1 | 8/2012 | Bentwich |
| 2012/0221310 A1 | 8/2012 | Sarrafzadeh et al. |
| 2012/0226091 A1 | 9/2012 | Mishelevich |
| 2012/0226185 A1 | 9/2012 | Chung et al. |
| 2012/0226334 A1 | 9/2012 | Gardiner et al. |
| 2012/0229248 A1 | 9/2012 | Parshionikar et al. |
| 2012/0232327 A1 | 9/2012 | Lozano et al. |
| 2012/0232376 A1 | 9/2012 | Crevecoeur et al. |
| 2012/0232433 A1 | 9/2012 | Mishelevich |
| 2012/0235887 A1 | 9/2012 | Border et al. |
| 2012/0236030 A1 | 9/2012 | Border et al. |
| 2012/0238890 A1 | 9/2012 | Baker et al. |
| 2012/0242501 A1 | 9/2012 | Tran et al. |
| 2012/0245437 A1 | 9/2012 | Lovett et al. |
| 2012/0245450 A1 | 9/2012 | Lee et al. |
| 2012/0245464 A1 | 9/2012 | Tran |
| 2012/0245474 A1 | 9/2012 | Ofek et al. |
| 2012/0245481 A1 | 9/2012 | Blanco et al. |
| 2012/0245493 A1 | 9/2012 | Mishelevich |
| 2012/0249274 A1 | 10/2012 | Toda et al. |
| 2012/0250197 A1 | 10/2012 | Sullivan |
| 2012/0253141 A1 | 10/2012 | Addison et al. |
| 2012/0253168 A1 | 10/2012 | Hu et al. |
| 2012/0253219 A1 | 10/2012 | Suffin et al. |
| 2012/0253249 A1 | 10/2012 | Wilson |
| 2012/0253261 A1 | 10/2012 | Poletto et al. |
| 2012/0253434 A1 | 10/2012 | Nissila et al. |
| 2012/0256833 A1 | 10/2012 | Chiang |
| 2012/0262558 A1 | 10/2012 | Boger et al. |
| 2012/0265080 A1 | 10/2012 | Yu et al. |
| 2012/0265267 A1 | 10/2012 | Blum et al. |
| 2012/0265271 A1 | 10/2012 | Goetz |
| 2012/0271148 A1 | 10/2012 | Nelson |
| 2012/0271151 A1 | 10/2012 | LaVoilette et al. |
| 2012/0271190 A1 | 10/2012 | Mortensen et al. |
| 2012/0271376 A1 | 10/2012 | Kokones et al. |
| 2012/0271377 A1 | 10/2012 | Hagedorn et al. |
| 2012/0277545 A1 | 11/2012 | Teixeira |
| 2012/0277548 A1 | 11/2012 | Burton |
| 2012/0277618 A1 | 11/2012 | Giftakis et al. |
| 2012/0277816 A1 | 11/2012 | Zhang et al. |
| 2012/0283502 A1 | 11/2012 | Mishelevich et al. |
| 2012/0283604 A1 | 11/2012 | Mishelevich |
| 2012/0284012 A1 | 11/2012 | Rodriguez et al. |
| 2012/0289854 A1 | 11/2012 | Yamada et al. |
| 2012/0289869 A1 | 11/2012 | Tyler |
| 2012/0295589 A1 | 11/2012 | Alexander et al. |
| 2012/0296182 A1 | 11/2012 | Hornero Sanchez et al. |
| 2012/0296241 A1 | 11/2012 | Mishelevich |
| 2012/0296253 A1 | 11/2012 | Mathews et al. |
| 2012/0296476 A1 | 11/2012 | Cale et al. |
| 2012/0296569 A1 | 11/2012 | Shahaf et al. |
| 2012/0300972 A1 | 11/2012 | Rodriguez |
| 2012/0302842 A1 | 11/2012 | Kurtz et al. |
| 2012/0302845 A1 | 11/2012 | Lynn et al. |
| 2012/0302856 A1 | 11/2012 | Chang et al. |
| 2012/0302867 A1 | 11/2012 | Ichimura |
| 2012/0302894 A1 | 11/2012 | Diab et al. |
| 2012/0303548 A1 | 11/2012 | Johnson et al. |
| 2012/0310100 A1 | 12/2012 | Galen et al. |
| 2012/0310105 A1 | 12/2012 | Feingold et al. |
| 2012/0310106 A1 | 12/2012 | Cavuoto |
| 2012/0310107 A1 | 12/2012 | Doidge et al. |
| 2012/0310298 A1 | 12/2012 | Besio et al. |
| 2012/0316793 A1 | 12/2012 | Jung et al. |
| 2012/0321759 A1 | 12/2012 | Marinkovich et al. |
| 2012/0323132 A1 | 12/2012 | Warner et al. |
| 2012/0323229 A1 | 12/2012 | Zenzie et al. |
| 2012/0330109 A1 | 12/2012 | Tran |
| 2012/0330178 A1 | 12/2012 | Kraft et al. |
| 2012/0330869 A1 | 12/2012 | Durham |
| 2013/0006124 A1 | 1/2013 | Eyal et al. |
| 2013/0009783 A1 | 1/2013 | Tran |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0012804 A1 | 1/2013 | deCharms |
| 2013/0012830 A1 | 1/2013 | Leininger et al. |
| 2013/0013327 A1 | 1/2013 | Horseman |
| 2013/0013667 A1 | 1/2013 | Serena |

(56)     References Cited

U.S. PATENT DOCUMENTS

| | | |
|---|---|---|
| 2013/0023783 A1 | 1/2013 | Snyder et al. |
| 2013/0023951 A1 | 1/2013 | Greenspan |
| 2013/0030241 A1 | 1/2013 | Smith |
| 2013/0030257 A1 | 1/2013 | Nakata et al. |
| 2013/0033677 A1 | 2/2013 | MacDougall et al. |
| 2013/0035578 A1 | 2/2013 | Chiu et al. |
| 2013/0035579 A1 | 2/2013 | Le et al. |
| 2013/0035734 A1 | 2/2013 | Soler Fernandez et al. |
| 2013/0039498 A1 | 2/2013 | Adachi et al. |
| 2013/0039509 A1 | 2/2013 | Chuang et al. |
| 2013/0041235 A1 | 2/2013 | Rogers et al. |
| 2013/0041243 A1 | 2/2013 | Byrd et al. |
| 2013/0041281 A1 | 2/2013 | Park et al. |
| 2013/0044055 A1 | 2/2013 | Karmarkar et al. |
| 2013/0046151 A1 | 2/2013 | Bsoul et al. |
| 2013/0046193 A1 | 2/2013 | Guttag et al. |
| 2013/0046206 A1 | 2/2013 | Preminger |
| 2013/0046715 A1 | 2/2013 | Castermans et al. |
| 2013/0060110 A1 | 3/2013 | Lynn et al. |
| 2013/0060125 A1 | 3/2013 | Zeman et al. |
| 2013/0060158 A1 | 3/2013 | Perez-Velazquez et al. |
| 2013/0063434 A1 | 3/2013 | Miga et al. |
| 2013/0063550 A1 | 3/2013 | Ritchey et al. |
| 2013/0066183 A1 | 3/2013 | Jin et al. |
| 2013/0066184 A1 | 3/2013 | Nguyen et al. |
| 2013/0066350 A1 | 3/2013 | Mishelevich |
| 2013/0066391 A1 | 3/2013 | Hulvershorn et al. |
| 2013/0066392 A1 | 3/2013 | Simon et al. |
| 2013/0066394 A1 | 3/2013 | Saab |
| 2013/0066395 A1 | 3/2013 | Simon et al. |
| 2013/0069780 A1 | 3/2013 | Tran et al. |
| 2013/0070929 A1 | 3/2013 | Adachi et al. |
| 2013/0072292 A1 | 3/2013 | Sutton et al. |
| 2013/0072775 A1 | 3/2013 | Rogers et al. |
| 2013/0072780 A1 | 3/2013 | Espy et al. |
| 2013/0072807 A1 | 3/2013 | Tran |
| 2013/0076885 A1 | 3/2013 | Kobetski et al. |
| 2013/0079606 A1 | 3/2013 | McGonigle et al. |
| 2013/0079621 A1 | 3/2013 | Shoham et al. |
| 2013/0079647 A1 | 3/2013 | McGonigle et al. |
| 2013/0079656 A1 | 3/2013 | Dripps et al. |
| 2013/0079657 A1 | 3/2013 | Ochs et al. |
| 2013/0080127 A1 | 3/2013 | Shahaf et al. |
| 2013/0080489 A1 | 3/2013 | Ochs et al. |
| 2013/0085678 A1 | 4/2013 | Jung et al. |
| 2013/0094702 A1 | 4/2013 | Rodriguez |
| 2013/0095459 A1 | 4/2013 | Tran |
| 2013/0096391 A1 | 4/2013 | Osorio et al. |
| 2013/0096393 A1 | 4/2013 | Osorio et al. |
| 2013/0096394 A1 | 4/2013 | Gupta et al. |
| 2013/0096408 A1 | 4/2013 | He et al. |
| 2013/0096440 A1 | 4/2013 | Kiraly |
| 2013/0096441 A1 | 4/2013 | Osorio |
| 2013/0096453 A1 | 4/2013 | Chung et al. |
| 2013/0096454 A1 | 4/2013 | Jang et al. |
| 2013/0096575 A1 | 4/2013 | Olson |
| 2013/0096839 A1 | 4/2013 | Osorio et al. |
| 2013/0096840 A1 | 4/2013 | Osorio et al. |
| 2013/0097630 A1 | 4/2013 | Rodriguez |
| 2013/0102833 A1 | 4/2013 | John et al. |
| 2013/0102897 A1 | 4/2013 | Kalafut et al. |
| 2013/0109995 A1 | 5/2013 | Rothman et al. |
| 2013/0109996 A1 | 5/2013 | Turnbull et al. |
| 2013/0110616 A1 | 5/2013 | Bakalash et al. |
| 2013/0113816 A1 | 5/2013 | Sudarsky et al. |
| 2013/0116520 A1 | 5/2013 | Roham et al. |
| 2013/0116561 A1 | 5/2013 | Rothberg et al. |
| 2013/0116588 A1 | 5/2013 | Yazicioglu et al. |
| 2013/0118494 A1 | 5/2013 | Ujhazy et al. |
| 2013/0120246 A1 | 5/2013 | Schuette et al. |
| 2013/0123584 A1 | 5/2013 | Sun et al. |
| 2013/0123607 A1 | 5/2013 | Leuthardt et al. |
| 2013/0127708 A1 | 5/2013 | Jung et al. |
| 2013/0127980 A1 | 5/2013 | Haddick et al. |
| 2013/0130799 A1 | 5/2013 | Van Hulle et al. |
| 2013/0131438 A1 | 5/2013 | Brewer et al. |
| 2013/0131461 A1 | 5/2013 | Jorge et al. |
| 2013/0131537 A1 | 5/2013 | Tam |
| 2013/0131755 A1 | 5/2013 | Panken et al. |
| 2013/0137642 A1 | 5/2013 | Vavvas et al. |
| 2013/0137936 A1 | 5/2013 | Baker, Jr. et al. |
| 2013/0137938 A1 | 5/2013 | Peters |
| 2013/0138002 A1 | 5/2013 | Weng et al. |
| 2013/0138011 A1 | 5/2013 | Ang et al. |
| 2013/0138177 A1 | 5/2013 | DeRidder |
| 2013/0144106 A1 | 6/2013 | Phillips et al. |
| 2013/0144107 A1 | 6/2013 | Phillips et al. |
| 2013/0144108 A1 | 6/2013 | Phillips et al. |
| 2013/0144183 A1 | 6/2013 | John et al. |
| 2013/0150121 A1 | 6/2013 | Jeffery et al. |
| 2013/0150650 A1 | 6/2013 | Phillips et al. |
| 2013/0150651 A1 | 6/2013 | Phillips et al. |
| 2013/0150659 A1 | 6/2013 | Shaw et al. |
| 2013/0150702 A1 | 6/2013 | Hokari |
| 2013/0159041 A1 | 6/2013 | Jayaraman et al. |
| 2013/0165766 A1 | 6/2013 | Nishikawa et al. |
| 2013/0165804 A1 | 6/2013 | Johnson et al. |
| 2013/0165812 A1 | 6/2013 | Aksenova et al. |
| 2013/0167159 A1 | 6/2013 | Ricci et al. |
| 2013/0167360 A1 | 7/2013 | Masmanidis et al. |
| 2013/0172663 A1 | 7/2013 | Leonard |
| 2013/0172686 A1 | 7/2013 | Addison et al. |
| 2013/0172691 A1 | 7/2013 | Tran |
| 2013/0172716 A1 | 7/2013 | Lozano et al. |
| 2013/0172763 A1 | 7/2013 | Wheeler |
| 2013/0172767 A1 | 7/2013 | Dripps et al. |
| 2013/0172772 A1 | 7/2013 | Alshaer et al. |
| 2013/0172774 A1 | 7/2013 | Crowder et al. |
| 2013/0174047 A1 | 7/2013 | Sivakumar et al. |
| 2013/0177883 A1 | 7/2013 | Barnehama et al. |
| 2013/0178693 A1 | 7/2013 | Neuvonen et al. |
| 2013/0178718 A1 | 7/2013 | Tran et al. |
| 2013/0178733 A1 | 7/2013 | Langleben |
| 2013/0179087 A1 | 7/2013 | Garripoli |
| 2013/0182860 A1 | 7/2013 | Adachi et al. |
| 2013/0184516 A1 | 7/2013 | Genereux et al. |
| 2013/0184552 A1 | 7/2013 | Westermann et al. |
| 2013/0184558 A1 | 7/2013 | Gallant et al. |
| 2013/0184597 A1 | 7/2013 | Hopenfeld |
| 2013/0184603 A1 | 7/2013 | Rothman |
| 2013/0184728 A1 | 7/2013 | Mishelevich |
| 2013/0184786 A1 | 7/2013 | Goetz |
| 2013/0185144 A1 | 7/2013 | Pradeep et al. |
| 2013/0188854 A1 | 7/2013 | Bilgic et al. |
| 2013/0189663 A1 | 7/2013 | Tuchschmid et al. |
| 2013/0190577 A1 | 7/2013 | Brunner et al. |
| 2013/0190642 A1 | 7/2013 | Muesch et al. |
| 2013/0197321 A1 | 8/2013 | Wilson |
| 2013/0197322 A1 | 8/2013 | Tran |
| 2013/0197328 A1 | 8/2013 | Diab et al. |
| 2013/0197339 A1 | 8/2013 | Bardakjian et al. |
| 2013/0197401 A1 | 8/2013 | Sato et al. |
| 2013/0203019 A1 | 8/2013 | Nolen |
| 2013/0204085 A1 | 8/2013 | Alexander et al. |
| 2013/0204122 A1 | 8/2013 | Hendler et al. |
| 2013/0204150 A1 | 8/2013 | Similowski et al. |
| 2013/0208234 A1 | 8/2013 | Lewis |
| 2013/0211224 A1 | 8/2013 | Isenhart et al. |
| 2013/0211226 A1 | 8/2013 | Lee et al. |
| 2013/0211238 A1 | 8/2013 | DeCharms |
| 2013/0211276 A1 | 8/2013 | Luo et al. |
| 2013/0211291 A1 | 8/2013 | Tran |
| 2013/0217982 A1 | 8/2013 | Behzadi |
| 2013/0218043 A1 | 8/2013 | Yoshida |
| 2013/0218053 A1 | 8/2013 | Kaiser et al. |
| 2013/0218233 A1 | 8/2013 | Warschewske et al. |
| 2013/0221961 A1 | 8/2013 | Liu |
| 2013/0223709 A1 | 8/2013 | Wagner |
| 2013/0225940 A1 | 8/2013 | Fujita et al. |
| 2013/0225992 A1 | 8/2013 | Osorio |
| 2013/0226261 A1 | 8/2013 | Sparks et al. |
| 2013/0226464 A1 | 8/2013 | Marci et al. |
| 2013/0231574 A1 | 9/2013 | Tran |
| 2013/0231580 A1 | 9/2013 | Chen et al. |

(56)      References Cited

U.S. PATENT DOCUMENTS

| | | |
|---|---|---|
| 2013/0231947 A1 | 9/2013 | Shusterman |
| 2013/0234823 A1 | 9/2013 | Kahn et al. |
| 2013/0237867 A1 | 9/2013 | Alexander et al. |
| 2013/0237874 A1 | 9/2013 | Zoicas |
| 2013/0238049 A1 | 9/2013 | Simon et al. |
| 2013/0238050 A1 | 9/2013 | Simon et al. |
| 2013/0238063 A1 | 9/2013 | Nofzinger |
| 2013/0242262 A1 | 9/2013 | Lewis |
| 2013/0245416 A1 | 9/2013 | Yarmush et al. |
| 2013/0245422 A1 | 9/2013 | D'arcy et al. |
| 2013/0245424 A1 | 9/2013 | deCharms |
| 2013/0245485 A1 | 9/2013 | Mashour et al. |
| 2013/0245486 A1 | 9/2013 | Simon et al. |
| 2013/0245711 A1 | 9/2013 | Simon et al. |
| 2013/0245712 A1 | 9/2013 | Simon et al. |
| 2013/0251641 A1 | 9/2013 | Akhtari et al. |
| 2013/0255586 A1 | 10/2013 | Gerashchenko |
| 2013/0259297 A1 | 10/2013 | Knudson |
| 2013/0260361 A1 | 10/2013 | Mutlu et al. |
| 2013/0260727 A1 | 10/2013 | Knudson et al. |
| 2013/0261490 A1 | 10/2013 | Truccolo et al. |
| 2013/0261506 A1 | 10/2013 | Mishelevich |
| 2013/0266163 A1 | 10/2013 | Morikawa et al. |
| 2013/0267760 A1 | 10/2013 | Jin |
| 2013/0267866 A1 | 10/2013 | Nakashima et al. |
| 2013/0267928 A1 | 10/2013 | Imran et al. |
| 2013/0274562 A1 | 10/2013 | Ghaffari et al. |
| 2013/0274580 A1 | 10/2013 | Madsen et al. |
| 2013/0274586 A1 | 10/2013 | Miyazaki et al. |
| 2013/0274625 A1 | 10/2013 | Sarma et al. |
| 2013/0275159 A1 | 10/2013 | Seely |
| 2013/0278492 A1 | 10/2013 | Stolarz et al. |
| 2013/0278631 A1 | 10/2013 | Border et al. |
| 2013/0279726 A1 | 10/2013 | Baughman et al. |
| 2013/0281759 A1 | 10/2013 | Hagedorn et al. |
| 2013/0281811 A1 | 10/2013 | Imran |
| 2013/0281879 A1 | 10/2013 | Raniere |
| 2013/0281890 A1 | 10/2013 | Mishelevich |
| 2013/0282339 A1 | 10/2013 | Ricci et al. |
| 2013/0289360 A1 | 10/2013 | Hyde et al. |
| 2013/0289364 A1 | 10/2013 | Colman et al. |
| 2013/0289385 A1 | 10/2013 | Lozano et al. |
| 2013/0289386 A1 | 10/2013 | Deisseroth et al. |
| 2013/0289401 A1 | 10/2013 | Colbaugh et al. |
| 2013/0289413 A1 | 10/2013 | Ochs et al. |
| 2013/0289417 A1 | 10/2013 | Grunwald et al. |
| 2013/0289424 A1 | 10/2013 | Brockway et al. |
| 2013/0289433 A1 | 10/2013 | Jin et al. |
| 2013/0293844 A1 | 11/2013 | Gross et al. |
| 2013/0295016 A1 | 11/2013 | Gerber et al. |
| 2013/0295898 A1 | 11/2013 | Kader |
| 2013/0300573 A1 | 11/2013 | Brown et al. |
| 2013/0303828 A1 | 11/2013 | Hargrove |
| 2013/0303934 A1 | 11/2013 | Collura |
| 2013/0304153 A1 | 11/2013 | Hargrove et al. |
| 2013/0304472 A1 | 11/2013 | Pakhomov |
| 2013/0308099 A1 | 11/2013 | Stack |
| 2013/0310422 A1 | 11/2013 | Brown et al. |
| 2013/0310660 A1 | 11/2013 | Zuckerman-Stark et al. |
| 2013/0310909 A1 | 11/2013 | Simon et al. |
| 2013/0311329 A1 | 11/2013 | Knudson et al. |
| 2013/0317380 A1 | 11/2013 | Liley et al. |
| 2013/0318546 A1 | 11/2013 | Kothuri et al. |
| 2013/0324880 A1 | 12/2013 | Adachi et al. |
| 2013/0325567 A1 | 12/2013 | Bradley et al. |
| 2013/0326333 A1 | 12/2013 | Hashmi |
| 2013/0338449 A1 | 12/2013 | Warwick et al. |
| 2013/0338459 A1 | 12/2013 | Lynn et al. |
| 2013/0338518 A1 | 12/2013 | Zoica |
| 2013/0338738 A1 | 12/2013 | Garcia Molina et al. |
| 2013/0338803 A1 | 12/2013 | Maoz et al. |
| 2013/0340775 A1 | 12/2013 | Juster et al. |
| 2013/0343584 A1 | 12/2013 | Bennett et al. |
| 2013/0343585 A1 | 12/2013 | Bennett et al. |
| 2013/0344465 A1 | 12/2013 | Dickinson et al. |
| 2013/0345522 A1 | 12/2013 | Sun et al. |
| 2013/0345523 A1 | 12/2013 | Diab et al. |
| 2013/0345524 A1 | 12/2013 | Meyer et al. |
| 2014/0000630 A1 | 1/2014 | Ford |
| 2014/0005518 A1 | 1/2014 | Ko et al. |
| 2014/0005988 A1 | 1/2014 | Brockway |
| 2014/0012061 A1 | 1/2014 | Song et al. |
| 2014/0012110 A1 | 1/2014 | Watson et al. |
| 2014/0012111 A1 | 1/2014 | Snyder et al. |
| 2014/0012133 A1 | 1/2014 | Sverdlik et al. |
| 2014/0012152 A1 | 1/2014 | Gentry et al. |
| 2014/0012153 A1 | 1/2014 | Greenwald |
| 2014/0018694 A1 | 1/2014 | Ang et al. |
| 2014/0018792 A1 | 1/2014 | Gang et al. |
| 2014/0019165 A1 | 1/2014 | Horseman |
| 2014/0020089 A1 | 1/2014 | Perini |
| 2014/0023999 A1 | 1/2014 | Greder |
| 2014/0024598 A1 | 1/2014 | Vavvas et al. |
| 2014/0025396 A1 | 1/2014 | Horseman |
| 2014/0025397 A1 | 1/2014 | Horseman |
| 2014/0031703 A1 | 1/2014 | Rayner et al. |
| 2014/0031889 A1 | 1/2014 | Mashiach |
| 2014/0031903 A1 | 1/2014 | Mashiach |
| 2014/0032466 A1 | 1/2014 | Kaplan |
| 2014/0038147 A1 | 2/2014 | Morrow |
| 2014/0039279 A1 | 2/2014 | Jarvik et al. |
| 2014/0039975 A1 | 2/2014 | Hill |
| 2014/0046208 A1 | 2/2014 | Sejdic et al. |
| 2014/0051044 A1 | 2/2014 | Badower et al. |
| 2014/0051960 A1 | 2/2014 | Badower et al. |
| 2014/0051961 A1 | 2/2014 | Badower et al. |
| 2014/0052213 A1 | 2/2014 | Osorio |
| 2014/0055284 A1 | 2/2014 | Tran et al. |
| 2014/0055746 A1 | 2/2014 | Nistico et al. |
| 2014/0057232 A1 | 2/2014 | Wetmore et al. |
| 2014/0058189 A1 | 2/2014 | Stubbeman |
| 2014/0058218 A1 | 2/2014 | Randlov et al. |
| 2014/0058219 A1 | 2/2014 | Kiraly |
| 2014/0058241 A1 | 2/2014 | Apparies et al. |
| 2014/0058292 A1 | 2/2014 | Alford et al. |
| 2014/0058528 A1 | 2/2014 | Contreras-Vidal et al. |
| 2014/0059566 A1 | 2/2014 | Benedek et al. |
| 2014/0062472 A1 | 3/2014 | Nishikawa |
| 2014/0066739 A1 | 3/2014 | He et al. |
| 2014/0066763 A2 | 3/2014 | Rothberg et al. |
| 2014/0067557 A1 | 3/2014 | van Niekerk et al. |
| 2014/0070958 A1 | 3/2014 | Foo |
| 2014/0072127 A1 | 3/2014 | Adachi et al. |
| 2014/0072130 A1 | 3/2014 | Adachi et al. |
| 2014/0073298 A1 | 3/2014 | Rossmann |
| 2014/0073863 A1 | 3/2014 | Engelbrecht et al. |
| 2014/0073864 A1 | 3/2014 | Engelbrecht et al. |
| 2014/0073866 A1 | 3/2014 | Engelbrecht et al. |
| 2014/0073870 A1 | 3/2014 | Engelbrecht et al. |
| 2014/0073875 A1 | 3/2014 | Engelbrecht et al. |
| 2014/0073876 A1 | 3/2014 | Rodriguez-Llorente et al. |
| 2014/0073877 A1 | 3/2014 | Wooder |
| 2014/0073878 A1 | 3/2014 | Engelbrecht et al. |
| 2014/0073898 A1 | 3/2014 | Engelbrecht et al. |
| 2014/0073948 A1 | 3/2014 | Engelbrecht et al. |
| 2014/0073949 A1 | 3/2014 | Engelbrecht et al. |
| 2014/0073951 A1 | 3/2014 | Engelbrecht et al. |
| 2014/0073953 A1 | 3/2014 | Engelbrecht et al. |
| 2014/0073954 A1 | 3/2014 | Engelbrecht et al. |
| 2014/0073955 A1 | 3/2014 | Engelbrecht et al. |
| 2014/0073956 A1 | 3/2014 | Engelbrecht et al. |
| 2014/0073960 A1 | 3/2014 | Rodriguez-Llorente et al. |
| 2014/0073961 A1 | 3/2014 | Rodriguez-Llorente et al. |
| 2014/0073963 A1 | 3/2014 | Engelbrecht et al. |
| 2014/0073965 A1 | 3/2014 | Engelbrecht et al. |
| 2014/0073966 A1 | 3/2014 | Engelbrecht et al. |
| 2014/0073967 A1 | 3/2014 | Engelbrecht et al. |
| 2014/0073968 A1 | 3/2014 | Engelbrecht et al. |
| 2014/0073969 A1 | 3/2014 | Zou et al. |
| 2014/0073974 A1 | 3/2014 | Engelbrecht |
| 2014/0073975 A1 | 3/2014 | Engelbrecht et al. |
| 2014/0074060 A1 | 3/2014 | Imran |
| 2014/0074179 A1 | 3/2014 | Heldman et al. |
| 2014/0074180 A1 | 3/2014 | Heldman et al. |

(56) References Cited

U.S. PATENT DOCUMENTS

| | | |
|---|---|---|
| 2014/0077612 A1 | 3/2014 | Onuma et al. |
| 2014/0077946 A1 | 3/2014 | Tran |
| 2014/0078049 A1 | 3/2014 | Parshionikar |
| 2014/0081114 A1 | 3/2014 | Shachar et al. |
| 2014/0081115 A1 | 3/2014 | Gu |
| 2014/0081117 A1 | 3/2014 | Kato et al. |
| 2014/0088341 A1 | 3/2014 | Altman et al. |
| 2014/0088377 A1 | 3/2014 | Manzke et al. |
| 2014/0089202 A1 | 3/2014 | Bond et al. |
| 2014/0089462 A1 | 3/2014 | Tekwani |
| 2014/0094710 A1 | 4/2014 | Sarma et al. |
| 2014/0094719 A1 | 4/2014 | Mishelevich |
| 2014/0094720 A1 | 4/2014 | Tyler |
| 2014/0096210 A1 | 4/2014 | Dabbiere |
| 2014/0098981 A1 | 4/2014 | Lunner et al. |
| 2014/0099623 A1 | 4/2014 | Amit et al. |
| 2014/0100467 A1 | 4/2014 | Baker et al. |
| 2014/0101084 A1 | 4/2014 | Li et al. |
| 2014/0104059 A1 | 4/2014 | Tran |
| 2014/0105436 A1 | 4/2014 | Adachi et al. |
| 2014/0106710 A1 | 4/2014 | Rodriguez |
| 2014/0107401 A1 | 4/2014 | Anderson et al. |
| 2014/0107464 A1 | 4/2014 | Aksenova et al. |
| 2014/0107519 A1 | 4/2014 | Musha et al. |
| 2014/0107520 A1 | 4/2014 | Hang et al. |
| 2014/0107521 A1 | 4/2014 | Galan |
| 2014/0107525 A1 | 4/2014 | Tass |
| 2014/0108842 A1 | 4/2014 | Frank et al. |
| 2014/0111335 A1 | 4/2014 | Kleiss et al. |
| 2014/0114165 A1 | 4/2014 | Walker et al. |
| 2014/0114205 A1 | 4/2014 | Braun et al. |
| 2014/0114207 A1 | 4/2014 | Patterson |
| 2014/0114242 A1 | 4/2014 | Eckle |
| 2014/0114889 A1 | 4/2014 | Dagum |
| 2014/0119621 A1 | 5/2014 | Uber |
| 2014/0121017 A1 | 5/2014 | Mandryk et al. |
| 2014/0121446 A1 | 5/2014 | Phillips et al. |
| 2014/0121476 A1 | 5/2014 | Tran et al. |
| 2014/0121554 A1 | 5/2014 | Sarma et al. |
| 2014/0121565 A1 | 5/2014 | Kim |
| 2014/0122255 A1 | 5/2014 | Snyder |
| 2014/0128762 A1 | 5/2014 | Han et al. |
| 2014/0128763 A1 | 5/2014 | Fadem |
| 2014/0128764 A1 | 5/2014 | Gandhi |
| 2014/0135642 A1 | 5/2014 | Ekpar |
| 2014/0135873 A1 | 5/2014 | An et al. |
| 2014/0135879 A1 | 5/2014 | Flint |
| 2014/0136585 A1 | 5/2014 | Brockway |
| 2014/0140567 A1 | 5/2014 | LeBoeuf et al. |
| 2014/0142448 A1 | 5/2014 | Bae et al. |
| 2014/0142654 A1 | 5/2014 | Simon et al. |
| 2014/0143064 A1 | 5/2014 | Tran |
| 2014/0146987 A1 | 5/2014 | Pontoppidan et al. |
| 2014/0148657 A1 | 5/2014 | Hendler et al. |
| 2014/0148715 A1 | 5/2014 | Alexander et al. |
| 2014/0148716 A1 | 5/2014 | Hopenfeld et al. |
| 2014/0148723 A1 | 5/2014 | Nierenberg et al. |
| 2014/0148726 A1 | 5/2014 | Wagner |
| 2014/0151563 A1 | 6/2014 | Rousso et al. |
| 2014/0152673 A1 | 6/2014 | Lynn et al. |
| 2014/0154647 A1 | 6/2014 | Nolen |
| 2014/0155706 A1 | 6/2014 | Kochs et al. |
| 2014/0155714 A1 | 6/2014 | Gavish |
| 2014/0155730 A1 | 6/2014 | Bansal et al. |
| 2014/0155952 A1 | 6/2014 | Lozano et al. |
| 2014/0156000 A1 | 6/2014 | Campin et al. |
| 2014/0159862 A1 | 6/2014 | Yang et al. |
| 2014/0160250 A1 | 6/2014 | Pomerantz et al. |
| 2014/0161412 A1 | 6/2014 | Chase et al. |
| 2014/0163328 A1 | 6/2014 | Geva et al. |
| 2014/0163330 A1 | 6/2014 | Horseman |
| 2014/0163331 A1 | 6/2014 | Horseman |
| 2014/0163332 A1 | 6/2014 | Horseman |
| 2014/0163333 A1 | 6/2014 | Horseman |
| 2014/0163335 A1 | 6/2014 | Horseman |
| 2014/0163336 A1 | 6/2014 | Horseman |
| 2014/0163337 A1 | 6/2014 | Horseman |
| 2014/0163368 A1 | 6/2014 | Rousso et al. |
| 2014/0163385 A1 | 6/2014 | Kelleher et al. |
| 2014/0163409 A1 | 6/2014 | Arndt |
| 2014/0163425 A1 | 6/2014 | Tran |
| 2014/0163897 A1 | 6/2014 | Lynn et al. |
| 2014/0164056 A1 | 6/2014 | Johnson et al. |
| 2014/0171749 A1 | 6/2014 | Chin et al. |
| 2014/0171757 A1 | 6/2014 | Kawato et al. |
| 2014/0171819 A1 | 6/2014 | Patterson |
| 2014/0171820 A1 | 6/2014 | Causevic |
| 2014/0174277 A1 | 6/2014 | Mann |
| 2014/0175261 A1 | 6/2014 | Addison et al. |
| 2014/0176944 A1 | 6/2014 | Addison et al. |
| 2014/0179980 A1 | 6/2014 | Phillips et al. |
| 2014/0179986 A1 | 6/2014 | Kelley |
| 2014/0180088 A1 | 6/2014 | Rothberg et al. |
| 2014/0180092 A1 | 6/2014 | Rothberg et al. |
| 2014/0180093 A1 | 6/2014 | Rothberg et al. |
| 2014/0180094 A1 | 6/2014 | Rothberg et al. |
| 2014/0180095 A1 | 6/2014 | Rothberg et al. |
| 2014/0180096 A1 | 6/2014 | Rothberg et al. |
| 2014/0180097 A1 | 6/2014 | Rothberg et al. |
| 2014/0180099 A1 | 6/2014 | Rothberg et al. |
| 2014/0180100 A1 | 6/2014 | Rothberg et al. |
| 2014/0180112 A1 | 6/2014 | Rothberg et al. |
| 2014/0180113 A1 | 6/2014 | Rothberg et al. |
| 2014/0180145 A1 | 6/2014 | Kanai et al. |
| 2014/0180153 A1 | 6/2014 | Zia et al. |
| 2014/0180160 A1 | 6/2014 | Brown et al. |
| 2014/0180161 A1 | 6/2014 | Bolger et al. |
| 2014/0180176 A1 | 6/2014 | Rothberg et al. |
| 2014/0180177 A1 | 6/2014 | Rothberg et al. |
| 2014/0180597 A1 | 6/2014 | Brown et al. |
| 2014/0184550 A1 | 7/2014 | Hennessey et al. |
| 2014/0187901 A1 | 7/2014 | Cui et al. |
| 2014/0187994 A1 | 7/2014 | Thornton |
| 2014/0188006 A1 | 7/2014 | Alshaer et al. |
| 2014/0188311 A1 | 7/2014 | Masson |
| 2014/0188770 A1 | 7/2014 | Agrafioti et al. |
| 2014/0193336 A1 | 7/2014 | Rousso et al. |
| 2014/0194702 A1 | 7/2014 | Tran |
| 2014/0194726 A1 | 7/2014 | Mishelevich et al. |
| 2014/0194758 A1 | 7/2014 | Korenberg |
| 2014/0194759 A1 | 7/2014 | Weiland et al. |
| 2014/0194768 A1 | 7/2014 | Nierenberg et al. |
| 2014/0194769 A1 | 7/2014 | Nierenberg et al. |
| 2014/0194780 A1 | 7/2014 | Alshaer et al. |
| 2014/0194793 A1 | 7/2014 | Nakata et al. |
| 2014/0195221 A1 | 7/2014 | Frank et al. |
| 2014/0198936 A1 | 7/2014 | Higgins et al. |
| 2014/0200414 A1 | 7/2014 | Osorio |
| 2014/0200432 A1 | 7/2014 | Banerji et al. |
| 2014/0201256 A1 | 7/2014 | Pinheiro et al. |
| 2014/0203797 A1 | 7/2014 | Stivoric et al. |
| 2014/0204025 A1 | 7/2014 | Niikawa |
| 2014/0204029 A1 | 7/2014 | Lopez et al. |
| 2014/0206981 A1 | 7/2014 | Nagasaka |
| 2014/0210709 A1 | 7/2014 | Alexander et al. |
| 2014/0211593 A1 | 7/2014 | Tyler et al. |
| 2014/0213937 A1 | 7/2014 | Bianchi et al. |
| 2014/0214330 A1 | 7/2014 | Iyer et al. |
| 2014/0214335 A1 | 7/2014 | Siefert |
| 2014/0221779 A1 | 8/2014 | Schoonover et al. |
| 2014/0221855 A1 | 8/2014 | McCaffrey |
| 2014/0221866 A1 | 8/2014 | Quy |
| 2014/0222612 A1 | 8/2014 | Knudson et al. |
| 2014/0223462 A1 | 8/2014 | Aimone et al. |
| 2014/0226131 A1 | 8/2014 | Lopez et al. |
| 2014/0228649 A1 | 8/2014 | Rayner et al. |
| 2014/0228651 A1 | 8/2014 | Causevic et al. |
| 2014/0228653 A1 | 8/2014 | Kiraly |
| 2014/0228701 A1 | 8/2014 | Chizeck et al. |
| 2014/0228702 A1 | 8/2014 | Shahaf et al. |
| 2014/0232516 A1 | 8/2014 | Stivoric et al. |
| 2014/0235965 A1 | 8/2014 | Tran |
| 2014/0236039 A1 | 8/2014 | Strokova Aksenova et al. |
| 2014/0236077 A1 | 8/2014 | Robertson et al. |

(56)　　　　　　　　References Cited

U.S. PATENT DOCUMENTS

| | | |
|---|---|---|
| 2014/0237073 A1 | 8/2014 | Schiff |
| 2014/0243608 A1 | 8/2014 | Hunt |
| 2014/0243614 A1 | 8/2014 | Rothberg et al. |
| 2014/0243621 A1 | 8/2014 | Weng et al. |
| 2014/0243628 A1 | 8/2014 | Ochs et al. |
| 2014/0243647 A1 | 8/2014 | Clark et al. |
| 2014/0243652 A1 | 8/2014 | Pashko |
| 2014/0243694 A1 | 8/2014 | Baker et al. |
| 2014/0243714 A1 | 8/2014 | Ward et al. |
| 2014/0244514 A1 | 8/2014 | Rodriguez et al. |
| 2014/0245191 A1 | 8/2014 | Serena |
| 2014/0249360 A1 | 9/2014 | Jaeger et al. |
| 2014/0249429 A1 | 9/2014 | Tran |
| 2014/0249445 A1 | 9/2014 | Deadwyler et al. |
| 2014/0249447 A1 | 9/2014 | Sereno et al. |
| 2014/0257047 A1 | 9/2014 | Sillay et al. |
| 2014/0257073 A1 | 9/2014 | Machon et al. |
| 2014/0257128 A1 | 9/2014 | Moxon et al. |
| 2014/0257147 A1 | 9/2014 | John et al. |
| 2014/0257833 A1 | 9/2014 | Williams |
| 2014/0258110 A1 | 9/2014 | Davis et al. |
| 2014/0266696 A1 | 9/2014 | Addison et al. |
| 2014/0266787 A1 | 9/2014 | Tran |
| 2014/0269441 A1 | 9/2014 | Hyde et al. |
| 2014/0269442 A1 | 9/2014 | Hyde et al. |
| 2014/0269443 A1 | 9/2014 | Hyde et al. |
| 2014/0270438 A1 | 9/2014 | Declerck et al. |
| 2014/0271483 A1 | 9/2014 | Satchi-Fainaro et al. |
| 2014/0273924 A1 | 9/2014 | Hyde et al. |
| 2014/0273934 A1 | 9/2014 | Hyde et al. |
| 2014/0273935 A1 | 9/2014 | Hyde et al. |
| 2014/0273937 A1 | 9/2014 | Hyde et al. |
| 2014/0273939 A1 | 9/2014 | Hyde et al. |
| 2014/0273940 A1 | 9/2014 | Hyde et al. |
| 2014/0273947 A1 | 9/2014 | Hyde et al. |
| 2014/0274056 A1 | 9/2014 | Hyde et al. |
| 2014/0274078 A1 | 9/2014 | Hyde et al. |
| 2014/0275741 A1 | 9/2014 | Vandenbelt et al. |
| 2014/0275807 A1 | 9/2014 | Redei |
| 2014/0275851 A1 | 9/2014 | Amble et al. |
| 2014/0275886 A1 | 9/2014 | Teixeira |
| 2014/0275889 A1 | 9/2014 | Addison et al. |
| 2014/0275891 A1 | 9/2014 | Muehlemann et al. |
| 2014/0276013 A1 | 9/2014 | Muehlemann et al. |
| 2014/0276014 A1 | 9/2014 | Khanicheh et al. |
| 2014/0276090 A1 | 9/2014 | Breed |
| 2014/0276123 A1 | 9/2014 | Yang |
| 2014/0276130 A1 | 9/2014 | Mirelman et al. |
| 2014/0276181 A1 | 9/2014 | Sun et al. |
| 2014/0276183 A1 | 9/2014 | Badower |
| 2014/0276187 A1 | 9/2014 | Iasemidis et al. |
| 2014/0276702 A1 | 9/2014 | McKay et al. |
| 2014/0276944 A1 | 9/2014 | Farritor et al. |
| 2014/0277292 A1 | 9/2014 | Steel |
| 2014/0277582 A1 | 9/2014 | Leuthardt et al. |
| 2014/0278786 A1 | 9/2014 | Liu-Qiu-Yan |
| 2014/0279341 A1 | 9/2014 | Bhardwaj et al. |
| 2014/0279475 A1 | 9/2014 | Castrechini et al. |
| 2014/0279541 A1 | 9/2014 | Castrechini et al. |
| 2014/0279746 A1 | 9/2014 | De Bruin et al. |
| 2014/0282772 A1 | 9/2014 | Chen et al. |
| 2014/0288381 A1 | 9/2014 | Faarbaek et al. |
| 2014/0288614 A1 | 9/2014 | Hagedorn et al. |
| 2014/0288667 A1 | 9/2014 | Oxley |
| 2014/0288953 A1 | 9/2014 | Lynn et al. |
| 2014/0289172 A1 | 9/2014 | Rothman et al. |
| 2014/0296646 A1 | 10/2014 | Wingeier et al. |
| 2014/0296655 A1 | 10/2014 | Akhbardeh et al. |
| 2014/0296724 A1 | 10/2014 | Guttag et al. |
| 2014/0296733 A1 | 10/2014 | Omurtag et al. |
| 2014/0296750 A1 | 10/2014 | Einav et al. |
| 2014/0297397 A1 | 10/2014 | Bakalash et al. |
| 2014/0300532 A1 | 10/2014 | Karkkainen et al. |
| 2014/0303424 A1 | 10/2014 | Glass |
| 2014/0303425 A1 | 10/2014 | Pilla et al. |
| 2014/0303428 A1 | 10/2014 | Berka et al. |
| 2014/0303453 A1 | 10/2014 | Seely et al. |
| 2014/0303454 A1 | 10/2014 | Clifton et al. |
| 2014/0303486 A1 | 10/2014 | Baumgartner et al. |
| 2014/0303508 A1 | 10/2014 | Plotnik-Peleg et al. |
| 2014/0303511 A1 | 10/2014 | Sajda et al. |
| 2014/0304122 A1 | 10/2014 | Rhoads et al. |
| 2014/0304773 A1 | 10/2014 | Woods et al. |
| 2014/0307878 A1 | 10/2014 | Osborne et al. |
| 2014/0309484 A1 | 10/2014 | Chang |
| 2014/0309614 A1 | 10/2014 | Frei et al. |
| 2014/0309943 A1 | 10/2014 | Grundlehner et al. |
| 2014/0313303 A1 | 10/2014 | Davis et al. |
| 2014/0313488 A1 | 10/2014 | Kiderman et al. |
| 2014/0315169 A1 | 10/2014 | Bohbot |
| 2014/0316191 A1 | 10/2014 | de Zambotti et al. |
| 2014/0316192 A1 | 10/2014 | de Zambotti et al. |
| 2014/0316217 A1 | 10/2014 | Purdon et al. |
| 2014/0316221 A1 | 10/2014 | Rothman |
| 2014/0316230 A1 | 10/2014 | Denison et al. |
| 2014/0316235 A1 | 10/2014 | Davis et al. |
| 2014/0316248 A1 | 10/2014 | deCharms |
| 2014/0316278 A1 | 10/2014 | Addison et al. |
| 2014/0320808 A1 | 10/2014 | Kiderman et al. |
| 2014/0320817 A1 | 10/2014 | Kiderman et al. |
| 2014/0321682 A1 | 10/2014 | Kofod-Hansen et al. |
| 2014/0323455 A1 | 10/2014 | Vavvas |
| 2014/0323849 A1 | 10/2014 | Deisseroth et al. |
| 2014/0323899 A1 | 10/2014 | Silberstein |
| 2014/0323900 A1 | 10/2014 | Bibian et al. |
| 2014/0324118 A1 | 10/2014 | Simon et al. |
| 2014/0327881 A1 | 11/2014 | Kiderman et al. |
| 2014/0328487 A1 | 11/2014 | Hiroe |
| 2014/0330093 A1 | 11/2014 | Pedro |
| 2014/0330102 A1 | 11/2014 | Zbrzeski et al. |
| 2014/0330157 A1 | 11/2014 | Snook |
| 2014/0330159 A1 | 11/2014 | Costa et al. |
| 2014/0330268 A1 | 11/2014 | Palti et al. |
| 2014/0330334 A1 | 11/2014 | Errico et al. |
| 2014/0330335 A1 | 11/2014 | Errico et al. |
| 2014/0330336 A1 | 11/2014 | Errico et al. |
| 2014/0330394 A1 | 11/2014 | Leuthardt et al. |
| 2014/0330404 A1 | 11/2014 | Abdelghani et al. |
| 2014/0330580 A1 | 11/2014 | Grima et al. |
| 2014/0333529 A1 | 11/2014 | Kim et al. |
| 2014/0335489 A1 | 11/2014 | DeCharms |
| 2014/0336473 A1 | 11/2014 | Greco |
| 2014/0336489 A1 | 11/2014 | Angotzi et al. |
| 2014/0336547 A1 | 11/2014 | Tass et al. |
| 2014/0340084 A1 | 11/2014 | Alon |
| 2014/0342818 A1 | 11/2014 | Smith et al. |
| 2014/0343397 A1 | 11/2014 | Kim et al. |
| 2014/0343399 A1 | 11/2014 | Posse |
| 2014/0343408 A1 | 11/2014 | Tolkowsky |
| 2014/0343882 A1 | 11/2014 | Taulu et al. |
| 2014/0347265 A1 | 11/2014 | Aimone et al. |
| 2014/0347491 A1 | 11/2014 | Connor |
| 2014/0348183 A1 | 11/2014 | Kim et al. |
| 2014/0350353 A1 | 11/2014 | Connor |
| 2014/0350380 A1 | 11/2014 | Eidelberg |
| 2014/0350431 A1 | 11/2014 | Hagedorn |
| 2014/0350436 A1 | 11/2014 | Nathan et al. |
| 2014/0350634 A1 | 11/2014 | Grill et al. |
| 2014/0350864 A1 | 11/2014 | Fang et al. |
| 2014/0354278 A1 | 12/2014 | Subbarao |
| 2014/0357507 A1 | 12/2014 | Umansky et al. |
| 2014/0357932 A1 | 12/2014 | Lozano |
| 2014/0357935 A1 | 12/2014 | Ilmoniemi et al. |
| 2014/0357962 A1 | 12/2014 | Harrington et al. |
| 2014/0358025 A1 | 12/2014 | Parhi et al. |
| 2014/0358067 A1 | 12/2014 | Deisseroth et al. |
| 2014/0362346 A1 | 12/2014 | Leinonen et al. |
| 2014/0364721 A1 | 12/2014 | Lee et al. |
| 2014/0364746 A1 | 12/2014 | Addison et al. |
| 2014/0368601 A1 | 12/2014 | deCharms |
| 2014/0369537 A1 | 12/2014 | Pontoppidan et al. |
| 2014/0369550 A1 | 12/2014 | Davis et al. |
| 2014/0370479 A1 | 12/2014 | Gazzaley |
| 2014/0371516 A1 | 12/2014 | Tsai et al. |

(56) References Cited

U.S. PATENT DOCUMENTS

| 2014/0371544 A1 | 12/2014 | Wu et al. |
| 2014/0371573 A1 | 12/2014 | Komoto et al. |
| 2014/0371599 A1 | 12/2014 | Wu et al. |
| 2014/0371611 A1 | 12/2014 | Kim |
| 2014/0378809 A1 | 12/2014 | Weitnauer et al. |
| 2014/0378810 A1 | 12/2014 | Davis et al. |
| 2014/0378815 A1 | 12/2014 | Huang et al. |
| 2014/0378830 A1 | 12/2014 | Li |
| 2014/0378941 A1 | 12/2014 | Su et al. |
| 2014/0379620 A1 | 12/2014 | Sarrafzadeh et al. |
| 2015/0000025 A1 | 1/2015 | clements |
| 2015/0002815 A1 | 1/2015 | Gross et al. |
| 2015/0003698 A1 | 1/2015 | Davis et al. |
| 2015/0003699 A1 | 1/2015 | Davis et al. |
| 2015/0005592 A1 | 1/2015 | Osorio |
| 2015/0005594 A1 | 1/2015 | Chamoun et al. |
| 2015/0005640 A1 | 1/2015 | Davis et al. |
| 2015/0005644 A1 | 1/2015 | Rhoads |
| 2015/0005646 A1 | 1/2015 | Balakrishnan et al. |
| 2015/0005660 A1 | 1/2015 | Kraus et al. |
| 2015/0005680 A1 | 1/2015 | Lipani |
| 2015/0005840 A1 | 1/2015 | Pal et al. |
| 2015/0005841 A1 | 1/2015 | Pal et al. |
| 2015/0006186 A1 | 1/2015 | Davis et al. |
| 2015/0008916 A1 | 1/2015 | Le Prado et al. |
| 2015/0011866 A1 | 1/2015 | Baumgartner |
| 2015/0011877 A1 | 1/2015 | Baumgartner |
| 2015/0011907 A1 | 1/2015 | Purdon et al. |
| 2015/0012111 A1 | 1/2015 | Contreras-Vidal et al. |
| 2015/0012426 A1 | 1/2015 | Purves et al. |
| 2015/0016618 A1 | 1/2015 | Adachi et al. |
| 2015/0016664 A1 | 1/2015 | Rodriguez |
| 2015/0016674 A1 | 1/2015 | Cho et al. |
| 2015/0017115 A1 | 1/2015 | Satchi-Fainaro et al. |
| 2015/0018665 A1 | 1/2015 | Jasanoff et al. |
| 2015/0018699 A1 | 1/2015 | Zeng et al. |
| 2015/0018702 A1 | 1/2015 | Galloway et al. |
| 2015/0018705 A1 | 1/2015 | Barlow et al. |
| 2015/0018706 A1 | 1/2015 | Segal |
| 2015/0018758 A1 | 1/2015 | John |
| 2015/0018905 A1 | 1/2015 | Nofzinger et al. |
| 2015/0019266 A1 | 1/2015 | Stempora |
| 2015/0024356 A1 | 1/2015 | Hillyer et al. |
| 2015/0025351 A1 | 1/2015 | Govari |
| 2015/0025408 A1 | 1/2015 | Wingeier et al. |
| 2015/0025422 A1 | 1/2015 | Tyler |
| 2015/0025610 A1 | 1/2015 | Wingeier et al. |
| 2015/0025917 A1 | 1/2015 | Stempora |
| 2015/0026446 A1 | 1/2015 | Kim et al. |
| 2015/0029087 A1 | 1/2015 | Klappert et al. |
| 2015/0030220 A1 | 1/2015 | Cho et al. |
| 2015/0032017 A1 | 1/2015 | Babaeizadeh et al. |
| 2015/0033056 A1 | 1/2015 | Frank et al. |
| 2015/0033245 A1 | 1/2015 | Klappert et al. |
| 2015/0033258 A1 | 1/2015 | Klappert et al. |
| 2015/0033259 A1 | 1/2015 | Klappert et al. |
| 2015/0033262 A1 | 1/2015 | Klappert et al. |
| 2015/0033266 A1 | 1/2015 | Klappert et al. |
| 2015/0033363 A1 | 1/2015 | Pinsky et al. |
| 2015/0035745 A1 | 2/2015 | Ou-Yang et al. |
| 2015/0035959 A1 | 2/2015 | Amble et al. |
| 2015/0038804 A1 | 2/2015 | Younes |
| 2015/0038812 A1 | 2/2015 | Ayaz et al. |
| 2015/0038822 A1 | 2/2015 | Wingeier et al. |
| 2015/0038869 A1 | 2/2015 | Simon et al. |
| 2015/0039066 A1 | 2/2015 | Wingeier et al. |
| 2015/0039110 A1 | 2/2015 | Abeyratne et al. |
| 2015/0039710 A1 | 2/2015 | Feghali |
| 2015/0040139 A1 | 2/2015 | Frank et al. |
| 2015/0042477 A1 | 2/2015 | Kobetski et al. |
| 2015/0044138 A1 | 2/2015 | Lansbergen et al. |
| 2015/0045007 A1 | 2/2015 | Cash |
| 2015/0045606 A1 | 2/2015 | Hagedorn et al. |
| 2015/0045686 A1 | 2/2015 | Lynn |
| 2015/0051663 A1 | 2/2015 | Hagedorn |
| 2015/0054731 A1 | 2/2015 | Mun et al. |
| 2015/0057512 A1 | 2/2015 | Kapoor |
| 2015/0058611 A1 | 2/2015 | Reeves et al. |
| 2015/0065813 A1 | 3/2015 | Wochlik et al. |
| 2015/0065838 A1 | 3/2015 | Wingeier et al. |
| 2015/0065839 A1 | 3/2015 | Farah et al. |
| 2015/0065845 A1 | 3/2015 | Takiguchi |
| 2015/0069846 A1 | 3/2015 | Hokari |
| 2015/0071600 A1 | 3/2015 | Azam |
| 2015/0072394 A1 | 3/2015 | Deisseroth et al. |
| 2015/0072728 A1 | 3/2015 | Rodriguez et al. |
| 2015/0073237 A1 | 3/2015 | Osorio |
| 2015/0073249 A1 | 3/2015 | Musha |
| 2015/0073294 A1 | 3/2015 | Zhang et al. |
| 2015/0073306 A1 | 3/2015 | Abeyratne et al. |
| 2015/0073505 A1 | 3/2015 | Errico et al. |
| 2015/0073907 A1 | 3/2015 | Purves et al. |
| 2015/0079949 A1 | 3/2015 | Vishwanath |
| 2015/0080671 A1 | 3/2015 | Christensen et al. |
| 2015/0080695 A1 | 3/2015 | Rogers et al. |
| 2015/0080703 A1 | 3/2015 | Reiman |
| 2015/0080746 A1 | 3/2015 | Bleich et al. |
| 2015/0080753 A1 | 3/2015 | Miyazaki et al. |
| 2015/0080985 A1 | 3/2015 | Yun et al. |
| 2015/0081226 A1 | 3/2015 | Baki |
| 2015/0081299 A1 | 3/2015 | Jasinschi et al. |
| 2015/0087931 A1 | 3/2015 | Banerjee et al. |
| 2015/0088024 A1 | 3/2015 | Sackellares et al. |
| 2015/0088093 A1 | 3/2015 | Goetz |
| 2015/0088120 A1 | 3/2015 | Garcia et al. |
| 2015/0088224 A1 | 3/2015 | Goldwasser et al. |
| 2015/0091730 A1 | 4/2015 | Kangas et al. |
| 2015/0091791 A1 | 4/2015 | Segal |
| 2015/0092050 A1 | 4/2015 | Cho et al. |
| 2015/0092949 A1 | 4/2015 | Adachi et al. |
| 2015/0092983 A1 | 4/2015 | Nguyen et al. |
| 2015/0093729 A1 | 4/2015 | Plans et al. |
| 2015/0094914 A1 | 4/2015 | Abreu |
| 2015/0096564 A1 | 4/2015 | Cosnek |
| 2015/0099941 A1 | 4/2015 | Tran |
| 2015/0099946 A1 | 4/2015 | Sahin |
| 2015/0099959 A1 | 4/2015 | Bonmassar et al. |
| 2015/0099962 A1 | 4/2015 | Weiss et al. |
| 2015/0103360 A1 | 4/2015 | Addison et al. |
| 2015/0105111 A1 | 4/2015 | Rodriguez |
| 2015/0105631 A1 | 4/2015 | Tran et al. |
| 2015/0105641 A1 | 4/2015 | Austin et al. |
| 2015/0105701 A1 | 4/2015 | Mayer et al. |
| 2015/0105837 A1* | 4/2015 | Aguilar Domingo . A61B 5/374 607/45 |
| 2015/0105844 A1 | 4/2015 | Tass et al. |
| 2015/0112153 A1 | 4/2015 | Nahum |
| 2015/0112222 A1 | 4/2015 | Sun et al. |
| 2015/0112403 A1 | 4/2015 | Ruffini et al. |
| 2015/0112409 A1 | 4/2015 | Hagedorn |
| 2015/0112899 A1 | 4/2015 | Dagum |
| 2015/0119652 A1 | 4/2015 | Hyde et al. |
| 2015/0119658 A1 | 4/2015 | Osorio |
| 2015/0119689 A1 | 4/2015 | Pascual-Leone et al. |
| 2015/0119698 A1 | 4/2015 | Eyal et al. |
| 2015/0119743 A1 | 4/2015 | Maksym et al. |
| 2015/0119745 A1 | 4/2015 | Similowski et al. |
| 2015/0119746 A1 | 4/2015 | Conradsen |
| 2015/0120007 A1 | 4/2015 | Guez et al. |
| 2015/0121474 A1 | 4/2015 | Korkishko et al. |
| 2015/0123653 A1 | 5/2015 | Nagasaka |
| 2015/0123984 A1 | 5/2015 | Kim et al. |
| 2015/0124220 A1 | 5/2015 | Gross et al. |
| 2015/0126281 A1 | 5/2015 | Lewis |
| 2015/0126821 A1 | 5/2015 | Kempfner et al. |
| 2015/0126845 A1 | 5/2015 | Jin et al. |
| 2015/0126848 A1 | 5/2015 | Baker et al. |
| 2015/0126873 A1 | 5/2015 | Connor |
| 2015/0126892 A1 | 5/2015 | Kim et al. |
| 2015/0131159 A1 | 5/2015 | Lewis |
| 2015/0133811 A1 | 5/2015 | Suzuki et al. |
| 2015/0133812 A1 | 5/2015 | deCharms |
| 2015/0133830 A1 | 5/2015 | Dirks et al. |
| 2015/0134264 A1 | 5/2015 | Tansey |

(56)                    References Cited

U.S. PATENT DOCUMENTS

| | | |
|---|---|---|
| 2015/0135309 A1 | 5/2015 | Karmarkar et al. |
| 2015/0137988 A1 | 5/2015 | Gravenstein et al. |
| 2015/0138089 A1 | 5/2015 | Angerbauer et al. |
| 2015/0140528 A1 | 5/2015 | Sikstrom et al. |
| 2015/0141529 A1 | 5/2015 | Hargrove |
| 2015/0141773 A1 | 5/2015 | Einav et al. |
| 2015/0141789 A1 | 5/2015 | Knight et al. |
| 2015/0141794 A1 | 5/2015 | Foo |
| 2015/0142082 A1 | 5/2015 | Simon et al. |
| 2015/0145676 A1 | 5/2015 | Adhikari et al. |
| 2015/0148619 A1 | 5/2015 | Berg et al. |
| 2015/0148621 A1 | 5/2015 | Sier |
| 2015/0148700 A1 | 5/2015 | Mhuircheartaigh et al. |
| 2015/0150122 A1 | 5/2015 | Son et al. |
| 2015/0150473 A1 | 6/2015 | Knight et al. |
| 2015/0150475 A1 | 6/2015 | Varcoe |
| 2015/0150753 A1 | 6/2015 | Racette |
| 2015/0151142 A1 | 6/2015 | Tyler et al. |
| 2015/0153477 A1 | 6/2015 | Wikelski et al. |
| 2015/0154721 A1 | 6/2015 | Thompson |
| 2015/0154764 A1 | 6/2015 | Xie et al. |
| 2015/0154889 A1 | 6/2015 | Tuchschmid et al. |
| 2015/0157235 A1 | 6/2015 | Jelen et al. |
| 2015/0157255 A1 | 6/2015 | Nduka |
| 2015/0157266 A1 | 6/2015 | Machon et al. |
| 2015/0157271 A1 | 6/2015 | Zhang |
| 2015/0161738 A1 | 6/2015 | Stempora |
| 2015/0162802 A1 | 6/2015 | Horseman et al. |
| 2015/0163345 A1 | 6/2015 | Cornaby et al. |
| 2015/0164349 A1 | 6/2015 | Gopalakrishnan et al. |
| 2015/0164362 A1 | 6/2015 | Morrow |
| 2015/0164375 A1 | 6/2015 | Schindhelm et al. |
| 2015/0164404 A1 | 6/2015 | Euliano et al. |
| 2015/0164431 A1 | 6/2015 | Terry et al. |
| 2015/0165239 A1 | 6/2015 | Mishelevich |
| 2015/0174362 A1 | 6/2015 | Panova et al. |
| 2015/0174403 A1 | 6/2015 | Pal et al. |
| 2015/0174418 A1 | 6/2015 | Tyler et al. |
| 2015/0177529 A1 | 6/2015 | Zhao et al. |
| 2015/0178388 A1 | 6/2015 | Winnemoeller et al. |
| 2015/0178631 A1 | 6/2015 | Thomas et al. |
| 2015/0178978 A1 | 6/2015 | Durand et al. |
| 2015/0181840 A1 | 7/2015 | Tupin, Jr. et al. |
| 2015/0182417 A1 | 7/2015 | Nagatani |
| 2015/0182753 A1 | 7/2015 | Harris et al. |
| 2015/0185482 A1 | 7/2015 | Lewis |
| 2015/0185506 A1 | 7/2015 | Lewis |
| 2015/0186923 A1 | 7/2015 | Gurumoorthy et al. |
| 2015/0190062 A1 | 7/2015 | Han et al. |
| 2015/0190070 A1 | 7/2015 | Bonmassar et al. |
| 2015/0190077 A1 | 7/2015 | Kim et al. |
| 2015/0190085 A1 | 7/2015 | Nathan et al. |
| 2015/0190094 A1 | 7/2015 | Lee et al. |
| 2015/0190636 A1 | 7/2015 | Simon et al. |
| 2015/0190637 A1 | 7/2015 | Simon et al. |
| 2015/0192532 A1 | 7/2015 | Clevenson et al. |
| 2015/0192776 A1 | 7/2015 | Lee et al. |
| 2015/0195482 A1 | 7/2015 | Wise |
| 2015/0196213 A1 | 7/2015 | Pandia et al. |
| 2015/0196249 A1 | 7/2015 | Brown et al. |
| 2015/0196800 A1 | 7/2015 | Macri et al. |
| 2015/0199010 A1 | 7/2015 | Coleman et al. |
| 2015/0200046 A1 | 7/2015 | Park et al. |
| 2015/0201879 A1 | 7/2015 | Hargrove |
| 2015/0202330 A1 | 7/2015 | Yang et al. |
| 2015/0202447 A1 | 7/2015 | Afshar et al. |
| 2015/0203822 A1 | 7/2015 | Tremolada et al. |
| 2015/0205482 A1 | 7/2015 | Johnson et al. |
| 2015/0206051 A1 | 7/2015 | McIntosh et al. |
| 2015/0206174 A1 | 7/2015 | Barnett et al. |
| 2015/0208940 A1 | 7/2015 | Addison et al. |
| 2015/0208975 A1 | 7/2015 | Ghajar |
| 2015/0208994 A1 | 7/2015 | Rapoport |
| 2015/0212168 A1 | 7/2015 | Shah et al. |
| 2015/0212830 A1 | 7/2015 | Reeves et al. |
| 2015/0213012 A1 | 7/2015 | Marvit et al. |
| 2015/0213019 A1 | 7/2015 | Marvit et al. |
| 2015/0213020 A1 | 7/2015 | Marvit et al. |
| 2015/0213191 A1 | 7/2015 | Abdelghani et al. |
| 2015/0213722 A1 | 7/2015 | Nypl et al. |
| 2015/0215412 A1 | 7/2015 | Marvit et al. |
| 2015/0216436 A1 | 8/2015 | Bosl et al. |
| 2015/0216439 A1 | 8/2015 | Muraskin et al. |
| 2015/0216468 A1 | 8/2015 | Vidal-Naquet et al. |
| 2015/0216762 A1 | 8/2015 | Oohashi et al. |
| 2015/0217082 A1 | 8/2015 | Kang et al. |
| 2015/0219729 A1 | 8/2015 | Takahashi |
| 2015/0219732 A1 | 8/2015 | Diamond et al. |
| 2015/0220486 A1 | 8/2015 | Karakonstantis et al. |
| 2015/0220830 A1 | 8/2015 | Li et al. |
| 2015/0223683 A1 | 8/2015 | Davidovics et al. |
| 2015/0223721 A1 | 8/2015 | De Ridder |
| 2015/0223731 A1 | 8/2015 | Sahin |
| 2015/0223743 A1 | 8/2015 | Pathangay et al. |
| 2015/0223905 A1 | 8/2015 | Karmarkar et al. |
| 2015/0226813 A1 | 8/2015 | Yu et al. |
| 2015/0227193 A1 | 8/2015 | Frank et al. |
| 2015/0227702 A1 | 8/2015 | Krishna et al. |
| 2015/0227844 A1 | 8/2015 | Frank et al. |
| 2015/0227922 A1 | 8/2015 | Filler |
| 2015/0230719 A1 | 8/2015 | Berg et al. |
| 2015/0230744 A1 | 8/2015 | Faubert et al. |
| 2015/0230750 A1 | 8/2015 | McDarby et al. |
| 2015/0231330 A1 | 8/2015 | Lozano et al. |
| 2015/0231395 A1 | 8/2015 | Saab |
| 2015/0231405 A1 | 8/2015 | Okada |
| 2015/0231408 A1 | 8/2015 | Williams et al. |
| 2015/0234477 A1 | 8/2015 | Abovitz et al. |
| 2015/0235088 A1 | 8/2015 | Abovitz et al. |
| 2015/0235134 A1 | 8/2015 | Guan et al. |
| 2015/0235370 A1 | 8/2015 | Abovitz et al. |
| 2015/0235441 A1 | 8/2015 | Abovitz et al. |
| 2015/0235447 A1 | 8/2015 | Abovitz et al. |
| 2015/0238104 A1 | 8/2015 | Tass |
| 2015/0238106 A1 | 8/2015 | Lappalainen et al. |
| 2015/0238112 A1 | 8/2015 | Park et al. |
| 2015/0238137 A1 | 8/2015 | Eyal et al. |
| 2015/0241705 A1 | 8/2015 | Abovitz et al. |
| 2015/0241916 A1 | 8/2015 | Choi et al. |
| 2015/0241959 A1 | 8/2015 | Abovitz et al. |
| 2015/0242120 A1 | 8/2015 | Rodriguez |
| 2015/0242575 A1 | 8/2015 | Abovitz et al. |
| 2015/0242608 A1 | 8/2015 | Kim et al. |
| 2015/0242943 A1 | 8/2015 | Abovitz et al. |
| 2015/0243100 A1 | 8/2015 | Abovitz et al. |
| 2015/0243105 A1 | 8/2015 | Abovitz et al. |
| 2015/0243106 A1 | 8/2015 | Abovitz et al. |
| 2015/0245800 A1 | 9/2015 | Sorensen et al. |
| 2015/0246238 A1 | 9/2015 | Moses et al. |
| 2015/0247723 A1 | 9/2015 | Abovitz et al. |
| 2015/0247921 A1 | 9/2015 | Rothberg et al. |
| 2015/0247975 A1 | 9/2015 | Abovitz et al. |
| 2015/0247976 A1 | 9/2015 | Abovitz et al. |
| 2015/0248167 A1 | 9/2015 | Turbell et al. |
| 2015/0248169 A1 | 9/2015 | Abovitz et al. |
| 2015/0248170 A1 | 9/2015 | Abovitz et al. |
| 2015/0248470 A1 | 9/2015 | Coleman et al. |
| 2015/0248615 A1 | 9/2015 | Parra et al. |
| 2015/0248651 A1 | 9/2015 | Akutagawa et al. |
| 2015/0248764 A1 | 9/2015 | Keskin et al. |
| 2015/0248765 A1 | 9/2015 | Criminisi et al. |
| 2015/0248787 A1 | 9/2015 | Abovitz et al. |
| 2015/0248788 A1 | 9/2015 | Abovitz et al. |
| 2015/0248789 A1 | 9/2015 | Abovitz et al. |
| 2015/0248791 A1 | 9/2015 | Abovitz et al. |
| 2015/0248792 A1 | 9/2015 | Abovitz et al. |
| 2015/0248793 A1 | 9/2015 | Abovitz et al. |
| 2015/0250393 A1 | 9/2015 | Tran |
| 2015/0250401 A1 | 9/2015 | Tveit |
| 2015/0250415 A1 | 9/2015 | Leininger et al. |
| 2015/0253391 A1 | 9/2015 | Toda et al. |
| 2015/0253410 A1 | 9/2015 | Warfield et al. |
| 2015/0256593 A1 | 9/2015 | Kelani et al. |
| 2015/0256956 A1 | 9/2015 | Jensen et al. |

(56) References Cited

U.S. PATENT DOCUMENTS

| | | |
|---|---|---|
| 2015/0257104 A1 | 9/2015 | Choi et al. |
| 2015/0257645 A1 | 9/2015 | Bae et al. |
| 2015/0257673 A1 | 9/2015 | Lawrence et al. |
| 2015/0257674 A1 | 9/2015 | Jordan et al. |
| 2015/0257697 A1 | 9/2015 | Sepah |
| 2015/0257700 A1 | 9/2015 | Fu |
| 2015/0257712 A1 | 9/2015 | Sarrafzadeh et al. |
| 2015/0261003 A1 | 9/2015 | Morifuji et al. |
| 2015/0262016 A1 | 9/2015 | Rothblatt |
| 2015/0264028 A1 | 9/2015 | Kim et al. |
| 2015/0264492 A1 | 9/2015 | Laudanski et al. |
| 2015/0265164 A1 | 9/2015 | Gopalakrishnan et al. |
| 2015/0265207 A1 | 9/2015 | Wu et al. |
| 2015/0265679 A1 | 9/2015 | Miller et al. |
| 2015/0268483 A1 | 9/2015 | Lewis |
| 2015/0269825 A1 | 9/2015 | Tran |
| 2015/0272461 A1 | 10/2015 | Morimoto et al. |
| 2015/0272465 A1 | 10/2015 | Ishii |
| 2015/0272496 A1 | 10/2015 | Klappert et al. |
| 2015/0272508 A1 | 10/2015 | Chiouchang et al. |
| 2015/0272510 A1 | 10/2015 | Chin |
| 2015/0272652 A1 | 10/2015 | Ghaffari et al. |
| 2015/0277560 A1 | 10/2015 | Beaty |
| 2015/0278980 A1 | 10/2015 | Sinclair |
| 2015/0282705 A1 | 10/2015 | Avital |
| 2015/0282730 A1 | 10/2015 | Knight et al. |
| 2015/0282749 A1 | 10/2015 | Zand et al. |
| 2015/0282755 A1 | 10/2015 | Deriche et al. |
| 2015/0282760 A1 | 10/2015 | Badower et al. |
| 2015/0283019 A1 | 10/2015 | Feingold |
| 2015/0283393 A1 | 10/2015 | Schmidt |
| 2015/0287403 A1 | 10/2015 | Holzer Zaslansky et al. |
| 2015/0289065 A1 | 10/2015 | Jensen et al. |
| 2015/0289217 A1 | 10/2015 | Ban et al. |
| 2015/0289779 A1 | 10/2015 | Fischl et al. |
| 2015/0289813 A1 | 10/2015 | Lipov |
| 2015/0289929 A1 | 10/2015 | Toth et al. |
| 2015/0290420 A1 | 10/2015 | Nofzinger |
| 2015/0290453 A1 | 10/2015 | Tyler et al. |
| 2015/0290454 A1 | 10/2015 | Tyler et al. |
| 2015/0293004 A1 | 10/2015 | Adolphi et al. |
| 2015/0293592 A1 | 10/2015 | Cheong et al. |
| 2015/0294074 A1 | 10/2015 | Kawato et al. |
| 2015/0296288 A1 | 10/2015 | Anastas |
| 2015/0297106 A1 | 10/2015 | Pasley et al. |
| 2015/0297108 A1 | 10/2015 | Chase et al. |
| 2015/0297109 A1 | 10/2015 | Garten et al. |
| 2015/0297139 A1 | 10/2015 | Toth |
| 2015/0297141 A1 | 10/2015 | Siegel et al. |
| 2015/0297444 A1 | 10/2015 | Tass |
| 2015/0297719 A1 | 10/2015 | Deisseroth et al. |
| 2015/0297893 A1 | 10/2015 | Kokones et al. |
| 2015/0302543 A1 | 10/2015 | Weaver et al. |
| 2015/0304048 A1 | 10/2015 | Kim et al. |
| 2015/0304101 A1 | 10/2015 | Gupta et al. |
| 2015/0305685 A1 | 10/2015 | Shahaf et al. |
| 2015/0305686 A1 | 10/2015 | Coleman et al. |
| 2015/0305689 A1 | 10/2015 | Gourmelon et al. |
| 2015/0305799 A1 | 10/2015 | Trieu |
| 2015/0305800 A1 | 10/2015 | Trieu |
| 2015/0305801 A1 | 10/2015 | Trieu |
| 2015/0306057 A1 | 10/2015 | Goodenowe |
| 2015/0306340 A1 | 10/2015 | Giap et al. |
| 2015/0306390 A1 | 10/2015 | Zalay et al. |
| 2015/0306391 A1 | 10/2015 | Wu et al. |
| 2015/0309563 A1 | 10/2015 | Connor |
| 2015/0309582 A1 | 10/2015 | Gupta |
| 2015/0310862 A1 | 10/2015 | Dauphin et al. |
| 2015/0313496 A1 | 11/2015 | Connor |
| 2015/0313498 A1 | 11/2015 | Coleman et al. |
| 2015/0313535 A1 | 11/2015 | Alshaer et al. |
| 2015/0313539 A1 | 11/2015 | Connor |
| 2015/0313540 A1 | 11/2015 | Deuchar et al. |
| 2015/0313903 A1 | 11/2015 | During |
| 2015/0313949 A1 | 11/2015 | Cutillo |
| 2015/0313971 A1 | 11/2015 | Haslett et al. |
| 2015/0315554 A1 | 11/2015 | Shekdar et al. |
| 2015/0317447 A1 | 11/2015 | Helleputte et al. |
| 2015/0317796 A1 | 11/2015 | Schett et al. |
| 2015/0320591 A1 | 11/2015 | Smith et al. |
| 2015/0323986 A1 | 11/2015 | Frank et al. |
| 2015/0324544 A1 | 11/2015 | Maslowski et al. |
| 2015/0324568 A1 | 11/2015 | Publicover et al. |
| 2015/0324692 A1 | 11/2015 | Ritchey et al. |
| 2015/0325151 A1 | 11/2015 | Tuchschmid et al. |
| 2015/0327813 A1 | 11/2015 | Fu |
| 2015/0327837 A1 | 11/2015 | Qi et al. |
| 2015/0328330 A1 | 11/2015 | Satchi-Fainaro et al. |
| 2015/0331929 A1 | 11/2015 | El-Saban et al. |
| 2015/0335240 A1 | 11/2015 | Kiderman et al. |
| 2015/0335281 A1 | 11/2015 | Scroggins |
| 2015/0335288 A1 | 11/2015 | Toth et al. |
| 2015/0335292 A1 | 11/2015 | Mittal |
| 2015/0335294 A1 | 11/2015 | Witcher et al. |
| 2015/0335295 A1 | 11/2015 | Park et al. |
| 2015/0335876 A1 | 11/2015 | Jeffery et al. |
| 2015/0335877 A1 | 11/2015 | Jeffery et al. |
| 2015/0338915 A1 | 11/2015 | Publicover et al. |
| 2015/0338917 A1 | 11/2015 | Steiner et al. |
| 2015/0339363 A1 | 11/2015 | Moldoveanu et al. |
| 2015/0342478 A1 | 12/2015 | Galen et al. |
| 2015/0342493 A1 | 12/2015 | Hardt |
| 2015/0343242 A1 | 12/2015 | Tyler et al. |
| 2015/0347734 A1 | 12/2015 | Beigi |
| 2015/0350794 A1 | 12/2015 | Pontoppidan |
| 2015/0350820 A1 | 12/2015 | Son et al. |
| 2015/0351655 A1 | 12/2015 | Coleman |
| 2015/0351690 A1 | 12/2015 | Toth et al. |
| 2015/0351695 A1 | 12/2015 | Cronin |
| 2015/0351698 A1 | 12/2015 | Cronin |
| 2015/0351701 A1 | 12/2015 | Moxon et al. |
| 2015/0352085 A1 | 12/2015 | During |
| 2015/0358316 A1 | 12/2015 | Cronin |
| 2015/0358526 A1 | 12/2015 | Cronin |
| 2015/0359431 A1 | 12/2015 | Bakalash et al. |
| 2015/0359441 A1 | 12/2015 | Giovangrandi et al. |
| 2015/0359450 A1 | 12/2015 | Lee et al. |
| 2015/0359452 A1 | 12/2015 | Giovangrandi et al. |
| 2015/0359467 A1 | 12/2015 | Tran |
| 2015/0359482 A1 | 12/2015 | Garcia Molina et al. |
| 2015/0359486 A1 | 12/2015 | Kovacs et al. |
| 2015/0359492 A1 | 12/2015 | Giovangrandi et al. |
| 2015/0360039 A1 | 12/2015 | Lempka et al. |
| 2015/0363986 A1 | 12/2015 | Hoyos et al. |
| 2015/0366482 A1 | 12/2015 | Lee |
| 2015/0366497 A1 | 12/2015 | Cavuoto et al. |
| 2015/0366503 A1 | 12/2015 | Sjaaheim et al. |
| 2015/0366504 A1 | 12/2015 | Connor |
| 2015/0366516 A1 | 12/2015 | Dripps et al. |
| 2015/0366518 A1 | 12/2015 | Sampson |
| 2015/0366656 A1 | 12/2015 | Wortz et al. |
| 2015/0366659 A1 | 12/2015 | Wortz et al. |
| 2015/0367133 A1 | 12/2015 | Schiff et al. |
| 2015/0369864 A1 | 12/2015 | Marlow et al. |
| 2015/0370320 A1 | 12/2015 | Connor |
| 2015/0370325 A1 | 12/2015 | Jarosiewicz et al. |
| 2015/0374250 A1 | 12/2015 | Hatano et al. |
| 2015/0374285 A1 | 12/2015 | Chang et al. |
| 2015/0374292 A1 | 12/2015 | Wyeth et al. |
| 2015/0374300 A1 | 12/2015 | Najarian et al. |
| 2015/0375006 A1 | 12/2015 | Denison et al. |
| 2015/0379370 A1 | 12/2015 | Clifton et al. |
| 2015/0380009 A1 | 12/2015 | Chang et al. |
| 2016/0000348 A1 | 1/2016 | Kitajo et al. |
| 2016/0000354 A1 | 1/2016 | Hagedorn et al. |
| 2016/0000383 A1 | 1/2016 | Lee et al. |
| 2016/0001065 A1 | 1/2016 | Wingeier et al. |
| 2016/0001096 A1 | 1/2016 | Mishelevich |
| 2016/0001098 A1 | 1/2016 | Wingeier et al. |
| 2016/0004298 A1 | 1/2016 | Mazed et al. |
| 2016/0005176 A1 | 1/2016 | Nguyen et al. |
| 2016/0005229 A1 | 1/2016 | Lee et al. |
| 2016/0005235 A1 | 1/2016 | Fateh |
| 2016/0005320 A1 | 1/2016 | deCharms et al. |

(56) References Cited

U.S. PATENT DOCUMENTS

| | | |
|---|---|---|
| 2016/0007849 A1 | 1/2016 | Krueger |
| 2016/0007899 A1 | 1/2016 | Durkee et al. |
| 2016/0007915 A1 | 1/2016 | Berka et al. |
| 2016/0007918 A1 | 1/2016 | Badower et al. |
| 2016/0008489 A1 | 1/2016 | Korzus |
| 2016/0008568 A1 | 1/2016 | Attia et al. |
| 2016/0008598 A1 | 1/2016 | McLaughlin et al. |
| 2016/0008620 A1 | 1/2016 | Stubbeman |
| 2016/0008632 A1 | 1/2016 | Wetmore et al. |
| 2016/0012011 A1 | 1/2016 | Llinas et al. |
| 2016/0012583 A1 | 1/2016 | Cales et al. |
| 2016/0012749 A1 | 1/2016 | Connor |
| 2016/0014224 A1 | 1/2016 | Tekwani |
| 2016/0015281 A1 | 1/2016 | McKenna et al. |
| 2016/0015289 A1 | 1/2016 | Simon et al. |
| 2016/0015673 A1 | 1/2016 | Goodenowe |
| 2016/0019434 A1 | 1/2016 | Caldwell |
| 2016/0019693 A1 | 1/2016 | Silbersweig et al. |
| 2016/0022141 A1 | 1/2016 | Mittal et al. |
| 2016/0022156 A1 | 1/2016 | Kovacs et al. |
| 2016/0022164 A1 | 1/2016 | Brockway et al. |
| 2016/0022165 A1 | 1/2016 | Sackellares et al. |
| 2016/0022167 A1 | 1/2016 | Simon |
| 2016/0022168 A1 | 1/2016 | Luczak et al. |
| 2016/0022206 A1 | 1/2016 | Simon et al. |
| 2016/0022207 A1 | 1/2016 | Roberts et al. |
| 2016/0022981 A1 | 1/2016 | Wingeier et al. |
| 2016/0023016 A1 | 1/2016 | Bonmassar et al. |
| 2016/0026913 A1 | 1/2016 | Moon et al. |
| 2016/0027293 A1 | 1/2016 | Esteller et al. |
| 2016/0027342 A1 | 1/2016 | Ben-Haim |
| 2016/0027423 A1 | 1/2016 | Deuel et al. |
| 2016/0029883 A1 | 2/2016 | Cox |
| 2016/0029896 A1 | 2/2016 | Lee et al. |
| 2016/0029917 A1 | 2/2016 | Baker et al. |
| 2016/0029918 A1 | 2/2016 | Baker et al. |
| 2016/0029946 A1 | 2/2016 | Simon et al. |
| 2016/0029947 A1 | 2/2016 | Girouard et al. |
| 2016/0029950 A1 | 2/2016 | Chang et al. |
| 2016/0029958 A1 | 2/2016 | Le et al. |
| 2016/0029959 A1 | 2/2016 | Le et al. |
| 2016/0029965 A1 | 2/2016 | Simon |
| 2016/0029998 A1 | 2/2016 | Brister et al. |
| 2016/0030666 A1 | 2/2016 | Lozano et al. |
| 2016/0030702 A1 | 2/2016 | Yang |
| 2016/0030834 A1 | 2/2016 | Brown et al. |
| 2016/0038037 A1 | 2/2016 | Kovacs |
| 2016/0038038 A1 | 2/2016 | Kovacs |
| 2016/0038042 A1 | 2/2016 | Mulligan et al. |
| 2016/0038043 A1 | 2/2016 | Mulligan et al. |
| 2016/0038049 A1 | 2/2016 | Geva et al. |
| 2016/0038069 A1 | 2/2016 | Stack |
| 2016/0038091 A1 | 2/2016 | Krishnaswamy et al. |
| 2016/0038469 A1 | 2/2016 | During |
| 2016/0038559 A1 | 2/2016 | Palmer et al. |
| 2016/0038770 A1 | 2/2016 | Tyler et al. |
| 2016/0042123 A1 | 2/2016 | Meyer et al. |
| 2016/0044460 A1 | 2/2016 | Cornaby et al. |
| 2016/0045128 A1 | 2/2016 | Sitt et al. |
| 2016/0045150 A1 | 2/2016 | Leininger et al. |
| 2016/0045756 A1 | 2/2016 | Phillips et al. |
| 2016/0048659 A1 | 2/2016 | Pereira et al. |
| 2016/0048948 A1 | 2/2016 | Bajic |
| 2016/0048965 A1 | 2/2016 | Stehle et al. |
| 2016/0051161 A1 | 2/2016 | Labyt et al. |
| 2016/0051162 A1 | 2/2016 | Durand et al. |
| 2016/0051187 A1 | 2/2016 | Damadian |
| 2016/0051195 A1 | 2/2016 | Pang et al. |
| 2016/0051793 A1 | 2/2016 | Gibson-Horn |
| 2016/0051812 A1 | 2/2016 | Montgomery, Jr. et al. |
| 2016/0054568 A1 | 2/2016 | Lewis |
| 2016/0054569 A1 | 2/2016 | Lewis |
| 2016/0055236 A1 | 2/2016 | Frank et al. |
| 2016/0055304 A1 | 2/2016 | Russell et al. |
| 2016/0055415 A1 | 2/2016 | Baxi |
| 2016/0055842 A1 | 2/2016 | DeFranks et al. |
| 2016/0058301 A1 | 3/2016 | Shusterman |
| 2016/0058304 A1 | 3/2016 | Emblem et al. |
| 2016/0058322 A1 | 3/2016 | Brister et al. |
| 2016/0058354 A1 | 3/2016 | Phan et al. |
| 2016/0058366 A1 | 3/2016 | Choi et al. |
| 2016/0058376 A1 | 3/2016 | Baek et al. |
| 2016/0058392 A1 | 3/2016 | Hasson et al. |
| 2016/0058673 A1 | 3/2016 | Francis |
| 2016/0060926 A1 | 3/2016 | Kim et al. |
| 2016/0062459 A1 | 3/2016 | Publicover et al. |
| 2016/0062596 A1 | 3/2016 | Lee et al. |
| 2016/0062807 A1 | 3/2016 | Reeves et al. |
| 2016/0063207 A1 | 3/2016 | Schmidt |
| 2016/0063611 A1 | 3/2016 | Davis et al. |
| 2016/0063883 A1 | 3/2016 | Jeyanandarajan |
| 2016/0065557 A1 | 3/2016 | Hwang et al. |
| 2016/0065724 A1 | 3/2016 | Lee et al. |
| 2016/0065840 A1 | 3/2016 | Kim et al. |
| 2016/0066788 A1 | 3/2016 | Tran et al. |
| 2016/0066828 A1 | 3/2016 | Phan et al. |
| 2016/0066838 A1 | 3/2016 | DeCharms |
| 2016/0067494 A1 | 3/2016 | Lipani |
| 2016/0070334 A1 | 3/2016 | Frank et al. |
| 2016/0070436 A1 | 3/2016 | Thomas et al. |
| 2016/0071390 A1 | 3/2016 | Sales et al. |
| 2016/0073886 A1 | 3/2016 | Connor |
| 2016/0073916 A1 | 3/2016 | Aksenova et al. |
| 2016/0073947 A1 | 3/2016 | Anderson |
| 2016/0074661 A1 | 3/2016 | Lipani |
| 2016/0074749 A1 | 3/2016 | Choi |
| 2016/0077547 A1 | 3/2016 | Aimone et al. |
| 2016/0078366 A1 | 3/2016 | Kaplan |
| 2016/0078657 A1 | 3/2016 | McCord |
| 2016/0078780 A1 | 3/2016 | Alexander et al. |
| 2016/0081577 A1 | 3/2016 | Sridhar et al. |
| 2016/0081613 A1 | 3/2016 | Braun et al. |
| 2016/0081616 A1 | 3/2016 | Li |
| 2016/0081623 A1 | 3/2016 | Lunner |
| 2016/0081625 A1 | 3/2016 | Kim et al. |
| 2016/0081793 A1 | 3/2016 | Galstian et al. |
| 2016/0082180 A1 | 3/2016 | Toth et al. |
| 2016/0082319 A1 | 3/2016 | Macri et al. |
| 2016/0084925 A1 | 3/2016 | Le Prado et al. |
| 2016/0085302 A1 | 3/2016 | Publicover et al. |
| 2016/0086622 A1 | 3/2016 | Yamamoto |
| 2016/0087603 A1 | 3/2016 | Ricci et al. |
| 2016/0089031 A1 | 3/2016 | Hu |
| 2016/0095838 A1 | 4/2016 | Satchi-Fainaro et al. |
| 2016/0097824 A1 | 4/2016 | Fujii et al. |
| 2016/0100769 A1 | 4/2016 | Kim et al. |
| 2016/0101260 A1 | 4/2016 | Austin et al. |
| 2016/0103322 A1 | 4/2016 | Hall, Jr. |
| 2016/0103487 A1 | 4/2016 | Crawford et al. |
| 2016/0103963 A1 | 4/2016 | Mishra |
| 2016/0104006 A1 | 4/2016 | Son et al. |
| 2016/0106331 A1 | 4/2016 | Zorick et al. |
| 2016/0106344 A1 | 4/2016 | Nazari |
| 2016/0106950 A1 | 4/2016 | Vasapollo |
| 2016/0107309 A1 | 4/2016 | Walsh et al. |
| 2016/0109851 A1 | 4/2016 | Tsang |
| 2016/0109954 A1 | 4/2016 | Harris et al. |
| 2016/0109959 A1 | 4/2016 | Heo |
| 2016/0112022 A1 | 4/2016 | Butts |
| 2016/0112684 A1 | 4/2016 | Connor |
| 2016/0113517 A1 | 4/2016 | Lee et al. |
| 2016/0113539 A1 | 4/2016 | Sinharay et al. |
| 2016/0113545 A1 | 4/2016 | Kim et al. |
| 2016/0113567 A1 | 4/2016 | Osvath et al. |
| 2016/0113587 A1 | 4/2016 | Kothe et al. |
| 2016/0116472 A1 | 4/2016 | Ay |
| 2016/0116553 A1 | 4/2016 | Kim et al. |
| 2016/0117829 A1 | 4/2016 | Yoon et al. |
| 2016/0119726 A1 | 4/2016 | Pontoppidan et al. |
| 2016/0120048 A1 | 4/2016 | Seo et al. |
| 2016/0120428 A1 | 5/2016 | Yoshida et al. |
| 2016/0120432 A1 | 5/2016 | Sridhar et al. |
| 2016/0120433 A1 | 5/2016 | Hughes et al. |
| 2016/0120434 A1 | 5/2016 | Park et al. |

(56) References Cited

U.S. PATENT DOCUMENTS

| | | |
|---|---|---|
| 2016/0120436 A1 | 5/2016 | Silberstein |
| 2016/0120437 A1 | 5/2016 | Graham et al. |
| 2016/0120457 A1 | 5/2016 | Wu et al. |
| 2016/0120464 A1 | 5/2016 | Lau et al. |
| 2016/0120474 A1 | 5/2016 | Connor |
| 2016/0120480 A1 | 5/2016 | Turnbull et al. |
| 2016/0121074 A1 | 5/2016 | Ashby |
| 2016/0125228 A1 | 5/2016 | Son et al. |
| 2016/0125572 A1 | 5/2016 | Yoo et al. |
| 2016/0128589 A1 | 5/2016 | Tabib-Azar |
| 2016/0128596 A1 | 5/2016 | Morshed et al. |
| 2016/0128597 A1 | 5/2016 | Lin et al. |
| 2016/0128629 A1 | 5/2016 | Crow et al. |
| 2016/0128632 A1 | 5/2016 | Wiebe et al. |
| 2016/0128864 A1 | 5/2016 | Nofzinger et al. |
| 2016/0129249 A1 | 5/2016 | Yun et al. |
| 2016/0131723 A1 | 5/2016 | Nagasaka |
| 2016/0132189 A1 | 5/2016 | Choi et al. |
| 2016/0132654 A1 | 5/2016 | Rothman et al. |
| 2016/0133052 A1 | 5/2016 | Choi et al. |
| 2016/0135691 A1 | 5/2016 | Dripps et al. |
| 2016/0135727 A1 | 5/2016 | Osorio |
| 2016/0135748 A1 | 5/2016 | Lin et al. |
| 2016/0135754 A1 | 5/2016 | Marshall et al. |
| 2016/0139215 A1 | 5/2016 | Fujii |
| 2016/0140834 A1 | 5/2016 | Tran |
| 2016/0140887 A1 | 5/2016 | Kim |
| 2016/0140975 A1 | 5/2016 | Kamamoto et al. |
| 2016/0142252 A1 | 5/2016 | Garg et al. |
| 2016/0142407 A1 | 5/2016 | Chun et al. |
| 2016/0143540 A1 | 5/2016 | Gencer et al. |
| 2016/0143541 A1 | 5/2016 | He et al. |
| 2016/0143554 A1 | 5/2016 | Lim et al. |
| 2016/0143560 A1 | 5/2016 | Grunwald et al. |
| 2016/0143574 A1 | 5/2016 | Jones et al. |
| 2016/0143582 A1 | 5/2016 | Connor |
| 2016/0143594 A1 | 5/2016 | Moorman et al. |
| 2016/0144173 A1 | 5/2016 | Wallbridge et al. |
| 2016/0144175 A1 | 5/2016 | Simon et al. |
| 2016/0147301 A1 | 5/2016 | Iwasaki et al. |
| 2016/0148077 A1 | 5/2016 | Cox et al. |
| 2016/0148400 A1 | 5/2016 | Bajic |
| 2016/0148531 A1 | 5/2016 | Bleich et al. |
| 2016/0150582 A1 | 5/2016 | Jung et al. |
| 2016/0150955 A1 | 6/2016 | Kiderman et al. |
| 2016/0150988 A1 | 6/2016 | Prerau et al. |
| 2016/0151014 A1 | 6/2016 | Ujhazy et al. |
| 2016/0151018 A1 | 6/2016 | Machon et al. |
| 2016/0151628 A1 | 6/2016 | Simon et al. |
| 2016/0156575 A1 | 6/2016 | Jeong et al. |
| 2016/0156682 A1 | 6/2016 | Jeon et al. |
| 2016/0157742 A1 | 6/2016 | Huang et al. |
| 2016/0157773 A1 | 6/2016 | Baek et al. |
| 2016/0157777 A1 | 6/2016 | Attal et al. |
| 2016/0157828 A1 | 6/2016 | Sumi et al. |
| 2016/0158553 A1 | 6/2016 | Panken et al. |
| 2016/0162016 A1 | 6/2016 | Lee et al. |
| 2016/0162652 A1 | 6/2016 | Siekmeier |
| 2016/0164813 A1 | 6/2016 | Anderson et al. |
| 2016/0164949 A1 | 6/2016 | Grimstrup et al. |
| 2016/0165852 A1 | 6/2016 | Goldfain |
| 2016/0165853 A1 | 6/2016 | Goldfain |
| 2016/0166169 A1 | 6/2016 | Badower et al. |
| 2016/0166197 A1 | 6/2016 | Venkatraman et al. |
| 2016/0166199 A1 | 6/2016 | Sun et al. |
| 2016/0166207 A1 | 6/2016 | Falconer |
| 2016/0166208 A1 | 6/2016 | Girouard et al. |
| 2016/0166219 A1 | 6/2016 | Majewski et al. |
| 2016/0167672 A1 | 6/2016 | Krueger |
| 2016/0168137 A1 | 6/2016 | Van Leyen et al. |
| 2016/0170996 A1 | 6/2016 | Frank et al. |
| 2016/0170998 A1 | 6/2016 | Frank et al. |
| 2016/0171514 A1 | 6/2016 | Frank et al. |
| 2016/0174099 A1 | 6/2016 | Goldfain |
| 2016/0174862 A1 | 6/2016 | Yu et al. |
| 2016/0174863 A1 | 6/2016 | Foerster et al. |
| 2016/0174867 A1 | 6/2016 | Hatano et al. |
| 2016/0174907 A1 | 6/2016 | Colman et al. |
| 2016/0175557 A1 | 6/2016 | Tass |
| 2016/0175607 A1 | 6/2016 | Deisseroth et al. |
| 2016/0176053 A1 | 6/2016 | Rognini et al. |
| 2016/0178392 A1 | 6/2016 | Goldfain |
| 2016/0180054 A1 | 6/2016 | Luo et al. |
| 2016/0183812 A1 | 6/2016 | Zhang et al. |
| 2016/0183828 A1 | 6/2016 | Ouyang et al. |
| 2016/0183861 A1 | 6/2016 | Hayes et al. |
| 2016/0183881 A1 | 6/2016 | Keenan et al. |
| 2016/0184029 A1 | 6/2016 | Peng et al. |
| 2016/0184599 A1 | 6/2016 | Segal |
| 2016/0191269 A1 | 6/2016 | Niruyi et al. |
| 2016/0191517 A1 | 6/2016 | Bae et al. |
| 2016/0192166 A1 | 6/2016 | deCharms |
| 2016/0192841 A1 | 7/2016 | Inagaki et al. |
| 2016/0192842 A1 | 7/2016 | Inagaki |
| 2016/0192847 A1 | 7/2016 | Inagaki |
| 2016/0192879 A1 | 7/2016 | Yamashita |
| 2016/0193442 A1 | 7/2016 | Adamczyk et al. |
| 2016/0193499 A1 | 7/2016 | Kim et al. |
| 2016/0196185 A1 | 7/2016 | Gu et al. |
| 2016/0196393 A1 | 7/2016 | Avinash et al. |
| 2016/0196635 A1 | 7/2016 | Cho et al. |
| 2016/0196758 A1 | 7/2016 | Causevic et al. |
| 2016/0198950 A1 | 7/2016 | Gross et al. |
| 2016/0198963 A1 | 7/2016 | Addison et al. |
| 2016/0198966 A1 | 7/2016 | Uematsu et al. |
| 2016/0198968 A1 | 7/2016 | Plenz et al. |
| 2016/0198973 A1 | 7/2016 | Fukuda et al. |
| 2016/0199241 A1 | 7/2016 | Rapoport |
| 2016/0199577 A1 | 7/2016 | Hyde et al. |
| 2016/0202755 A1 | 7/2016 | Connor |
| 2016/0203597 A1 | 7/2016 | Chang et al. |
| 2016/0203726 A1 | 7/2016 | Hibbs et al. |
| 2016/0204937 A1 | 7/2016 | Edwards et al. |
| 2016/0205450 A1 | 7/2016 | Gartseev et al. |
| 2016/0205489 A1 | 7/2016 | Jabri |
| 2016/0206241 A1 | 7/2016 | Cho et al. |
| 2016/0206380 A1 | 7/2016 | Sparks et al. |
| 2016/0206581 A1 | 7/2016 | Wittkowski |
| 2016/0206871 A1 | 7/2016 | Weisend |
| 2016/0206877 A1 | 7/2016 | Hargrove |
| 2016/0206880 A1 | 7/2016 | Koubeissi |
| 2016/0210552 A1 | 7/2016 | Kasabov et al. |
| 2016/0210872 A1 | 7/2016 | Roberts et al. |
| 2016/0212708 A1 | 7/2016 | Kim et al. |
| 2016/0213261 A1 | 7/2016 | Fleischer et al. |
| 2016/0213276 A1 | 7/2016 | Gadot et al. |
| 2016/0213314 A1 | 7/2016 | Zuckerman-Stark et al. |
| 2016/0213317 A1 | 7/2016 | Richardson et al. |
| 2016/0213354 A1 | 7/2016 | Levin et al. |
| 2016/0216760 A1 | 7/2016 | Trutna et al. |
| 2016/0219000 A1 | 7/2016 | Park et al. |
| 2016/0219345 A1 | 7/2016 | Knight et al. |
| 2016/0220133 A1 | 8/2016 | Inagaki |
| 2016/0220134 A1 | 8/2016 | Inagaki |
| 2016/0220136 A1 | 8/2016 | Schultz |
| 2016/0220163 A1 | 8/2016 | Yamada et al. |
| 2016/0220166 A1 | 8/2016 | Thornton |
| 2016/0220439 A1 | 8/2016 | Wojciechowski et al. |
| 2016/0220821 A1 | 8/2016 | O'Connell et al. |
| 2016/0220836 A1 | 8/2016 | Parks |
| 2016/0220837 A1 | 8/2016 | Jin |
| 2016/0220850 A1 | 8/2016 | Tyler |
| 2016/0222073 A1 | 8/2016 | Deisseroth et al. |
| 2016/0223622 A1 | 8/2016 | Yu et al. |
| 2016/0223627 A1 | 8/2016 | Shah et al. |
| 2016/0224757 A1 | 8/2016 | Melkonyan |
| 2016/0224803 A1 | 8/2016 | Frank et al. |
| 2016/0226542 A1 | 8/2016 | Tran et al. |
| 2016/0228019 A1 | 8/2016 | Grunwald et al. |
| 2016/0228028 A1 | 8/2016 | Van Der Kooi et al. |
| 2016/0228029 A1 | 8/2016 | Ware |
| 2016/0228059 A1 | 8/2016 | Badower |
| 2016/0228064 A1 | 8/2016 | Jung et al. |
| 2016/0228418 A1 | 8/2016 | During |

(56)  References Cited

U.S. PATENT DOCUMENTS

| | | | |
|---|---|---|---|
| 2016/0228640 A1 | 8/2016 | Pindado et al. |
| 2016/0228702 A1 | 8/2016 | Kempe et al. |
| 2016/0228705 A1 | 8/2016 | Crowder et al. |
| 2016/0231401 A1 | 8/2016 | Wang et al. |
| 2016/0232625 A1 | 8/2016 | Akutagawa et al. |
| 2016/0232811 A9 | 8/2016 | Connor |
| 2016/0235323 A1 | 8/2016 | Tadi et al. |
| 2016/0235324 A1 | 8/2016 | Mershin et al. |
| 2016/0235341 A1 | 8/2016 | Choi et al. |
| 2016/0235351 A1 | 8/2016 | Intrator |
| 2016/0235352 A1 | 8/2016 | DiLorenzo |
| 2016/0235359 A1 | 8/2016 | Cho et al. |
| 2016/0235980 A1 | 8/2016 | Berman et al. |
| 2016/0235983 A1 | 8/2016 | Berman et al. |
| 2016/0238673 A1 | 8/2016 | Honkura |
| 2016/0239084 A1 | 8/2016 | Connor |
| 2016/0239966 A1 | 8/2016 | Parsey et al. |
| 2016/0239968 A1 | 8/2016 | Parsey et al. |
| 2016/0240212 A1 | 8/2016 | Wilson et al. |
| 2016/0240765 A1 | 8/2016 | Washington et al. |
| 2016/0242645 A1 | 8/2016 | Muller |
| 2016/0242659 A1 | 8/2016 | Yamashita et al. |
| 2016/0242665 A1 | 8/2016 | Galloway et al. |
| 2016/0242669 A1 | 8/2016 | Muraskin et al. |
| 2016/0242670 A1 | 8/2016 | Suzuki et al. |
| 2016/0242690 A1 | 8/2016 | Principe et al. |
| 2016/0242699 A1 | 8/2016 | Das et al. |
| 2016/0245670 A1 | 8/2016 | Nelson et al. |
| 2016/0245766 A1 | 8/2016 | Nelson et al. |
| 2016/0247064 A1 | 8/2016 | Yoo et al. |
| 2016/0248434 A1 | 8/2016 | Govari |
| 2016/0248994 A1 | 8/2016 | Liu |
| 2016/0249826 A1 | 9/2016 | Derchak |
| 2016/0249841 A1 | 9/2016 | Gerber et al. |
| 2016/0249857 A1 | 9/2016 | Choi et al. |
| 2016/0249864 A1 | 9/2016 | Kang et al. |
| 2016/0250189 A1 | 9/2016 | Vavvas et al. |
| 2016/0250355 A1 | 9/2016 | Macknik |
| 2016/0250473 A1 | 9/2016 | Alberts et al. |
| 2016/0256063 A1 | 9/2016 | Friedman et al. |
| 2016/0256086 A1 | 9/2016 | Byrd et al. |
| 2016/0256105 A1 | 9/2016 | Boyle et al. |
| 2016/0256108 A1 | 9/2016 | Yun et al. |
| 2016/0256112 A1 | 9/2016 | Brockway et al. |
| 2016/0256118 A1 | 9/2016 | Iyer et al. |
| 2016/0256130 A1 | 9/2016 | Hamilton et al. |
| 2016/0257957 A1 | 9/2016 | Greenberg et al. |
| 2016/0259905 A1 | 9/2016 | Park et al. |
| 2016/0260216 A1 | 9/2016 | Wu et al. |
| 2016/0262608 A1 | 9/2016 | Krueger |
| 2016/0262664 A1 | 9/2016 | Linderman |
| 2016/0262680 A1 | 9/2016 | Martucci et al. |
| 2016/0262685 A1 | 9/2016 | Wagner et al. |
| 2016/0262695 A1 | 9/2016 | Zhang et al. |
| 2016/0262703 A1 | 9/2016 | Maccallum |
| 2016/0262704 A1 | 9/2016 | Min et al. |
| 2016/0265952 A1 | 9/2016 | Hwang |
| 2016/0267809 A1 | 9/2016 | deCharms et al. |
| 2016/0269999 A1 | 9/2016 | Hwang |
| 2016/0270656 A1 | 9/2016 | Samec et al. |
| 2016/0270723 A1 | 9/2016 | Deisseroth et al. |
| 2016/0271475 A1 | 9/2016 | Jeffery et al. |
| 2016/0274660 A1 | 9/2016 | Publicover et al. |
| 2016/0275536 A1 | 9/2016 | Anderson |
| 2016/0278651 A1 | 9/2016 | Lu et al. |
| 2016/0278653 A1 | 9/2016 | Clark et al. |
| 2016/0278662 A1 | 9/2016 | Brister et al. |
| 2016/0278672 A1 | 9/2016 | Cho et al. |
| 2016/0278687 A1 | 9/2016 | Xia |
| 2016/0278697 A1 | 9/2016 | John et al. |
| 2016/0278713 A1 | 9/2016 | Shoaran et al. |
| 2016/0278736 A1 | 9/2016 | Hamilton et al. |
| 2016/0279267 A1 | 9/2016 | Deisseroth et al. |
| 2016/0282113 A1 | 9/2016 | Lee |
| 2016/0282941 A1 | 9/2016 | Aksenova et al. |
| 2016/0287117 A1 | 10/2016 | Breakspear et al. |
| 2016/0287118 A1 | 10/2016 | Sarma et al. |
| 2016/0287120 A1 | 10/2016 | Sun et al. |
| 2016/0287142 A1 | 10/2016 | Han et al. |
| 2016/0287157 A1 | 10/2016 | Simpson |
| 2016/0287162 A1 | 10/2016 | Bardakjian et al. |
| 2016/0287166 A1 | 10/2016 | Tran |
| 2016/0287169 A1 | 10/2016 | Kortelainen et al. |
| 2016/0287308 A1 | 10/2016 | Grant et al. |
| 2016/0287334 A1 | 10/2016 | Grant et al. |
| 2016/0287436 A1 | 10/2016 | Wingeier et al. |
| 2016/0287869 A1 | 10/2016 | Errico et al. |
| 2016/0287871 A1 | 10/2016 | Bardakjian et al. |
| 2016/0287895 A1 | 10/2016 | Deisseroth et al. |
| 2016/0296157 A1 | 10/2016 | Girouard |
| 2016/0296746 A1 | 10/2016 | Wingeier et al. |
| 2016/0299568 A1 | 10/2016 | Segal |
| 2016/0300252 A1 | 10/2016 | Frank et al. |
| 2016/0300352 A1 | 10/2016 | Raj |
| 2016/0302683 A1 | 10/2016 | Lawrence et al. |
| 2016/0302704 A9 | 10/2016 | Lynn et al. |
| 2016/0302709 A1 | 10/2016 | Mossbridge |
| 2016/0302711 A1 | 10/2016 | Frank et al. |
| 2016/0302720 A1 | 10/2016 | John et al. |
| 2016/0302737 A1 | 10/2016 | Watson et al. |
| 2016/0303396 A9 | 10/2016 | Deisseroth et al. |
| 2016/0303397 A1 | 10/2016 | Hirschman et al. |
| 2016/0303402 A1 | 10/2016 | Tyler |
| 2016/0306844 A1 | 10/2016 | Frank et al. |
| 2016/0306942 A1 | 10/2016 | Rapaka et al. |
| 2016/0307380 A1 | 10/2016 | Ho et al. |
| 2016/0310031 A1 | 10/2016 | Sarkar |
| 2016/0310070 A1 | 10/2016 | Sabesan |
| 2016/0310071 A1 | 10/2016 | Kim |
| 2016/0310698 A1 | 10/2016 | Schoonover et al. |
| 2016/0310838 A1 | 10/2016 | Poisner et al. |
| 2016/0313408 A1 | 10/2016 | Hatano et al. |
| 2016/0313417 A1 | 10/2016 | Kawabata et al. |
| 2016/0313418 A1 | 10/2016 | Fujii et al. |
| 2016/0313798 A1 | 10/2016 | Connor |
| 2016/0316288 A1 | 10/2016 | Mendez Estrada |
| 2016/0317056 A1 | 11/2016 | Moon et al. |
| 2016/0317060 A1 | 11/2016 | Connor |
| 2016/0317077 A1 | 11/2016 | Sillay |
| 2016/0317383 A1 | 11/2016 | Stanfield et al. |
| 2016/0317834 A1 | 11/2016 | Kirk et al. |
| 2016/0320210 A1 | 11/2016 | Nelson et al. |
| 2016/0320930 A1 | 11/2016 | Byrd et al. |
| 2016/0321742 A1 | 11/2016 | Phillips et al. |
| 2016/0323431 A1 | 11/2016 | Gaw |
| 2016/0324445 A1 | 11/2016 | Kim et al. |
| 2016/0324457 A1 | 11/2016 | Dagum |
| 2016/0324465 A1 | 11/2016 | Osvath et al. |
| 2016/0324478 A1 | 11/2016 | Goldstein |
| 2016/0324580 A1 | 11/2016 | Esterberg |
| 2016/0324677 A1 | 11/2016 | Hyde et al. |
| 2016/0324942 A1 | 11/2016 | Lester et al. |
| 2016/0331264 A1 | 11/2016 | Helms-Tillery et al. |
| 2016/0331307 A1 | 11/2016 | Purdon et al. |
| 2016/0331925 A1 | 11/2016 | Kelley |
| 2016/0334475 A1 | 11/2016 | Ueno |
| 2016/0334866 A9 | 11/2016 | Mazed et al. |
| 2016/0337857 A1 | 11/2016 | Carron et al. |
| 2016/0338608 A1 | 11/2016 | Nagasaka et al. |
| 2016/0338634 A1 | 11/2016 | Neu et al. |
| 2016/0338644 A1 | 11/2016 | Connor |
| 2016/0338798 A1 | 11/2016 | Vora et al. |
| 2016/0338825 A1 | 11/2016 | Wortz et al. |
| 2016/0339243 A1 | 11/2016 | Wingeier et al. |
| 2016/0339300 A1 | 11/2016 | Todasco |
| 2016/0341684 A1 | 11/2016 | Choi |
| 2016/0342241 A1 | 11/2016 | Chung et al. |
| 2016/0342644 A1 | 11/2016 | Stolarz et al. |
| 2016/0344569 A1 | 11/2016 | Chun et al. |
| 2016/0345895 A1 | 12/2016 | Loetsch et al. |
| 2016/0345901 A1 | 12/2016 | Connor |
| 2016/0345911 A1 | 12/2016 | Leuthardt et al. |
| 2016/0346530 A1 | 12/2016 | Jeffery et al. |
| 2016/0346542 A1 | 12/2016 | Simon et al. |

(56) References Cited

U.S. PATENT DOCUMENTS

| | | |
|---|---|---|
| 2016/0349841 A1 | 12/2016 | Beaty |
| 2016/0354003 A1 | 12/2016 | Baker et al. |
| 2016/0354027 A1 | 12/2016 | Benson et al. |
| 2016/0357003 A1 | 12/2016 | Hauger et al. |
| 2016/0357256 A1 | 12/2016 | Siefert |
| 2016/0358091 A1 | 12/2016 | Stolarz et al. |
| 2016/0358092 A1 | 12/2016 | Stolarz et al. |
| 2016/0360100 A1 | 12/2016 | Kim et al. |
| 2016/0360965 A1 | 12/2016 | Tran |
| 2016/0360970 A1 | 12/2016 | Tzvieli et al. |
| 2016/0360990 A1 | 12/2016 | Altshuler et al. |
| 2016/0360992 A1 | 12/2016 | Guger et al. |
| 2016/0361021 A1 | 12/2016 | Salehizadeh et al. |
| 2016/0361027 A1 | 12/2016 | Jang et al. |
| 2016/0361041 A1 | 12/2016 | Barsimantov et al. |
| 2016/0361532 A1 | 12/2016 | Wingeier et al. |
| 2016/0361534 A9 | 12/2016 | Weisend |
| 2016/0361546 A1 | 12/2016 | Salam et al. |
| 2016/0361602 A1 | 12/2016 | Lagree |
| 2016/0363483 A1 | 12/2016 | Tzvieli et al. |
| 2016/0364586 A1 | 12/2016 | Todeschini |
| 2016/0366462 A1 | 12/2016 | Klappert et al. |
| 2016/0367138 A1 | 12/2016 | Kim et al. |
| 2016/0367186 A1 | 12/2016 | Freeman et al. |
| 2016/0367195 A1 | 12/2016 | Park et al. |
| 2016/0367198 A1 | 12/2016 | Chon et al. |
| 2016/0367204 A1 | 12/2016 | Won et al. |
| 2016/0367619 A1 | 12/2016 | Vavvas et al. |
| 2016/0370774 A1 | 12/2016 | Lamti et al. |
| 2016/0371387 A1 | 12/2016 | Serena |
| 2016/0371721 A1 | 12/2016 | Bogdon et al. |
| 2016/0374581 A1 | 12/2016 | Jensen |
| 2016/0374594 A1 | 12/2016 | Garcia Molina et al. |
| 2016/0374616 A1 | 12/2016 | Mullins et al. |
| 2016/0374618 A1 | 12/2016 | Giovangrandi |
| 2016/0378608 A1 | 12/2016 | Kong et al. |
| 2016/0378965 A1 | 12/2016 | Choe et al. |
| 2016/0381621 A1 | 12/2016 | Kim et al. |
| 2017/0000324 A1 | 1/2017 | Samec et al. |
| 2017/0000325 A1 | 1/2017 | Samec et al. |
| 2017/0000326 A1 | 1/2017 | Samec et al. |
| 2017/0000329 A1 | 1/2017 | Samec et al. |
| 2017/0000330 A1 | 1/2017 | Samec et al. |
| 2017/0000331 A1 | 1/2017 | Samec et al. |
| 2017/0000332 A1 | 1/2017 | Samec et al. |
| 2017/0000333 A1 | 1/2017 | Samec et al. |
| 2017/0000334 A1 | 1/2017 | Samec et al. |
| 2017/0000335 A1 | 1/2017 | Samec et al. |
| 2017/0000337 A1 | 1/2017 | Samec et al. |
| 2017/0000340 A1 | 1/2017 | Samec et al. |
| 2017/0000341 A1 | 1/2017 | Samec et al. |
| 2017/0000342 A1 | 1/2017 | Samec et al. |
| 2017/0000343 A1 | 1/2017 | Samec et al. |
| 2017/0000345 A1 | 1/2017 | Samec et al. |
| 2017/0000404 A1 | 1/2017 | Leininger et al. |
| 2017/0000422 A1 | 1/2017 | Moturu et al. |
| 2017/0000454 A1 | 1/2017 | Samec et al. |
| 2017/0000683 A1 | 1/2017 | Samec et al. |
| 2017/0000970 A1 | 1/2017 | Garcia Molina et al. |
| 2017/0001016 A1 | 1/2017 | De Ridder |
| 2017/0001032 A1 | 1/2017 | Samec et al. |
| 2017/0003741 A1 | 1/2017 | Ding |
| 2017/0003742 A1 | 1/2017 | Ding |
| 2017/0006217 A1 | 1/2017 | Ding |
| 2017/0006931 A1 | 1/2017 | Guez et al. |
| 2017/0007111 A1 | 1/2017 | Samec et al. |
| 2017/0007115 A1 | 1/2017 | Samec et al. |
| 2017/0007116 A1 | 1/2017 | Samec et al. |
| 2017/0007122 A1 | 1/2017 | Samec et al. |
| 2017/0007123 A1 | 1/2017 | Samec et al. |
| 2017/0007165 A1 | 1/2017 | Jain et al. |
| 2017/0007173 A1 | 1/2017 | Adamczyk et al. |
| 2017/0007182 A1 | 1/2017 | Samec et al. |
| 2017/0007450 A1 | 1/2017 | Samec et al. |
| 2017/0007799 A1 | 1/2017 | Samec et al. |
| 2017/0007843 A1 | 1/2017 | Samec et al. |
| 2017/0010469 A1 | 1/2017 | Samec et al. |
| 2017/0010470 A1 | 1/2017 | Samec et al. |
| 2017/0010647 A1 | 1/2017 | Frank et al. |
| 2017/0010677 A1 | 1/2017 | Roh et al. |
| 2017/0011178 A1 | 1/2017 | Hendrickson et al. |
| 2017/0011210 A1 | 1/2017 | Cheong et al. |
| 2017/0013562 A1 | 1/2017 | Lim et al. |
| 2017/0014037 A1 | 1/2017 | Coppola et al. |
| 2017/0014080 A1 | 1/2017 | Macia Barber et al. |
| 2017/0014083 A1 | 1/2017 | Diab et al. |
| 2017/0017083 A1 | 1/2017 | Samec et al. |
| 2017/0020388 A1 | 1/2017 | Kiderman et al. |
| 2017/0020434 A1 | 1/2017 | Walker et al. |
| 2017/0020447 A1 | 1/2017 | Grossman et al. |
| 2017/0020454 A1 | 1/2017 | Keteyian et al. |
| 2017/0020627 A1 | 1/2017 | Tesar et al. |
| 2017/0021158 A1 | 1/2017 | Wingeier et al. |
| 2017/0021161 A1 | 1/2017 | De Ridder |
| 2017/0027467 A1 | 2/2017 | Hagedorn |
| 2017/0027517 A9 | 2/2017 | Le et al. |
| 2017/0027521 A1 | 2/2017 | Geva et al. |
| 2017/0027539 A1 | 2/2017 | Uber |
| 2017/0027651 A1 | 2/2017 | Esterberg |
| 2017/0027812 A1 | 2/2017 | Hyde et al. |
| 2017/0028563 A1 | 2/2017 | Hemken |
| 2017/0031440 A1 | 2/2017 | Randolph |
| 2017/0031441 A1 | 2/2017 | Muller et al. |
| 2017/0032098 A1 | 2/2017 | Ghorbanian et al. |
| 2017/0032221 A1 | 2/2017 | Wu et al. |
| 2017/0032527 A1 | 2/2017 | Murthy et al. |
| 2017/0032584 A1 | 2/2017 | Moran et al. |
| 2017/0034638 A1 | 2/2017 | Anastas |
| 2017/0035309 A1 | 2/2017 | Kang et al. |
| 2017/0035317 A1 | 2/2017 | Jung et al. |
| 2017/0035344 A1 | 2/2017 | Tzvieli et al. |
| 2017/0035392 A1 | 2/2017 | Grunwald et al. |
| 2017/0039045 A1 | 2/2017 | Abrahami et al. |
| 2017/0039591 A1 | 2/2017 | Knight et al. |
| 2017/0039706 A1 | 2/2017 | Mikhno et al. |
| 2017/0041205 A1 | 2/2017 | Rangel et al. |
| 2017/0041699 A1 | 2/2017 | Mackellar et al. |
| 2017/0042418 A1 | 2/2017 | Leinonen et al. |
| 2017/0042430 A1 | 2/2017 | Kovacs |
| 2017/0042439 A1 | 2/2017 | Yeow et al. |
| 2017/0042444 A1 | 2/2017 | Bardy et al. |
| 2017/0042469 A1 | 2/2017 | Prerau et al. |
| 2017/0042474 A1 | 2/2017 | Widge et al. |
| 2017/0042475 A1 | 2/2017 | Verghese et al. |
| 2017/0042476 A1 | 2/2017 | Reiman |
| 2017/0042485 A1 | 2/2017 | Chung et al. |
| 2017/0042827 A1 | 2/2017 | Margel et al. |
| 2017/0043160 A1 | 2/2017 | Goodall et al. |
| 2017/0043166 A1 | 2/2017 | Choi et al. |
| 2017/0043167 A1 | 2/2017 | Widge et al. |
| 2017/0045601 A1 | 2/2017 | Akhtari |
| 2017/0046052 A1 | 2/2017 | Lee et al. |
| 2017/0048626 A1 | 2/2017 | Jensen et al. |
| 2017/0049395 A1 | 2/2017 | Cao |
| 2017/0049524 A1 | 2/2017 | Olson |
| 2017/0052170 A1 | 2/2017 | Shekdar et al. |
| 2017/0053082 A1 | 2/2017 | Pereira et al. |
| 2017/0053088 A1 | 2/2017 | Walker et al. |
| 2017/0053461 A1 | 2/2017 | Pal et al. |
| 2017/0053513 A1 | 2/2017 | Savolainen et al. |
| 2017/0053665 A1 | 2/2017 | Quatieri, Jr. et al. |
| 2017/0055839 A1 | 3/2017 | Levinson et al. |
| 2017/0055868 A1 | 3/2017 | Hatakeyama |
| 2017/0055898 A1 | 3/2017 | Bandyopadhyay et al. |
| 2017/0055900 A1 | 3/2017 | Jain et al. |
| 2017/0055913 A1 | 3/2017 | Bandyopadhyay et al. |
| 2017/0056363 A1 | 3/2017 | Goodenowe |
| 2017/0056467 A1 | 3/2017 | Deisseroth et al. |
| 2017/0056642 A1 | 3/2017 | Moffitt et al. |
| 2017/0056655 A1 | 3/2017 | Lineaweaver |
| 2017/0060298 A1 | 3/2017 | Hwang et al. |
| 2017/0061034 A1 | 3/2017 | Ritchey et al. |
| 2017/0061760 A1 | 3/2017 | Lee et al. |
| 2017/0064434 A1 | 3/2017 | Campbell et al. |

(56)                    References Cited

U.S. PATENT DOCUMENTS

| | | |
|---|---|---|
| 2017/0065199 A1 | 3/2017 | Meisel |
| 2017/0065218 A1 | 3/2017 | Leininger et al. |
| 2017/0065229 A1 | 3/2017 | Howard |
| 2017/0065349 A1 | 3/2017 | Ourselin et al. |
| 2017/0065379 A1 | 3/2017 | Cowburn et al. |
| 2017/0065816 A1 | 3/2017 | Wingeier et al. |
| 2017/0066806 A1 | 3/2017 | Deisseroth et al. |
| 2017/0068920 A1 | 3/2017 | Dow et al. |
| 2017/0068921 A1 | 3/2017 | Dow et al. |
| 2017/0069306 A1 | 3/2017 | Asaei et al. |
| 2017/0071495 A1 | 3/2017 | Denison et al. |
| 2017/0071521 A1 | 3/2017 | Mestha et al. |
| 2017/0071523 A1 | 3/2017 | Jain et al. |
| 2017/0071529 A1 | 3/2017 | Haugland et al. |
| 2017/0071532 A1 | 3/2017 | Greco |
| 2017/0071537 A1 | 3/2017 | Jain et al. |
| 2017/0071546 A1 | 3/2017 | Jain et al. |
| 2017/0071551 A1 | 3/2017 | Jain et al. |
| 2017/0071552 A1 | 3/2017 | Harpe et al. |
| 2017/0076520 A1 | 3/2017 | Ho et al. |
| 2017/0078883 A1 | 3/2017 | Rodriguez |
| 2017/0079538 A1 | 3/2017 | Liang et al. |
| 2017/0079543 A1 | 3/2017 | Sadeghian-Motahar |
| 2017/0079588 A1 | 3/2017 | Ghaffari et al. |
| 2017/0079589 A1 | 3/2017 | Ghaffari et al. |
| 2017/0079596 A1 | 3/2017 | Teixeira |
| 2017/0080050 A1 | 3/2017 | Deisseroth et al. |
| 2017/0080256 A1 | 3/2017 | Kim et al. |
| 2017/0080320 A1 | 3/2017 | Smith |
| 2017/0080332 A1 | 3/2017 | Poisner et al. |
| 2017/0083312 A1 | 3/2017 | Pindado et al. |
| 2017/0085547 A1 | 3/2017 | De Aguiar et al. |
| 2017/0085855 A1 | 3/2017 | Roberts et al. |
| 2017/0086672 A1 | 3/2017 | Tran |
| 2017/0086695 A1 | 3/2017 | Mullins et al. |
| 2017/0086727 A1 | 3/2017 | Dagum |
| 2017/0086729 A1 | 3/2017 | Bruno |
| 2017/0086763 A1 | 3/2017 | Verma et al. |
| 2017/0087330 A1 | 3/2017 | Kahn et al. |
| 2017/0087367 A1 | 3/2017 | Weisend |
| 2017/0087453 A1 | 3/2017 | Poisner et al. |
| 2017/0090475 A1 | 3/2017 | Choi et al. |
| 2017/0091418 A1 | 3/2017 | Chen et al. |
| 2017/0091532 A1 | 3/2017 | Son et al. |
| 2017/0091567 A1 | 3/2017 | Wang et al. |
| 2017/0093848 A1 | 3/2017 | Poisner et al. |
| 2017/0094385 A1 | 3/2017 | Lee et al. |
| 2017/0095157 A1 | 4/2017 | Tzvieli et al. |
| 2017/0095174 A1 | 4/2017 | Fokas et al. |
| 2017/0095199 A1 | 4/2017 | Kranck |
| 2017/0095383 A1 | 4/2017 | Li et al. |
| 2017/0095670 A1 | 4/2017 | Ghaffari et al. |
| 2017/0095721 A1 | 4/2017 | Bleich et al. |
| 2017/0099479 A1 | 4/2017 | Browd et al. |
| 2017/0099713 A1 | 4/2017 | Perez et al. |
| 2017/0100051 A1 | 4/2017 | Honkura |
| 2017/0100540 A1 | 4/2017 | Hyde et al. |
| 2017/0102767 A1 | 4/2017 | Kim et al. |
| 2017/0103440 A1 | 4/2017 | Xing et al. |
| 2017/0103668 A1 | 4/2017 | Chatterjee et al. |
| 2017/0104787 A1 | 4/2017 | Myron |
| 2017/0104928 A1 | 4/2017 | Chase et al. |
| 2017/0105647 A1 | 4/2017 | Duffy |
| 2017/0107575 A1 | 4/2017 | Umansky et al. |
| 2017/0108926 A1 | 4/2017 | Moon et al. |
| 2017/0112379 A1 | 4/2017 | Swiston et al. |
| 2017/0112403 A1 | 4/2017 | Doidge et al. |
| 2017/0112427 A1 | 4/2017 | Simon et al. |
| 2017/0112446 A1 | 4/2017 | Dagum |
| 2017/0112577 A1 | 4/2017 | Bonutti et al. |
| 2017/0112671 A1 | 4/2017 | Goldstein |
| 2017/0113046 A1 | 4/2017 | Fried et al. |
| 2017/0113056 A1 | 4/2017 | Stocco et al. |
| 2017/0113057 A1 | 4/2017 | Goodall et al. |
| 2017/0115742 A1 | 4/2017 | Xing et al. |
| 2017/0119270 A1 | 5/2017 | Juan et al. |
| 2017/0119271 A1 | 5/2017 | Leuthardt et al. |
| 2017/0119994 A1 | 5/2017 | Argaman |
| 2017/0120041 A1 | 5/2017 | Wenger et al. |
| 2017/0120043 A1 | 5/2017 | John |
| 2017/0120066 A1 | 5/2017 | Phillips et al. |
| 2017/0127946 A1 | 5/2017 | Levinson et al. |
| 2017/0127975 A1 | 5/2017 | Bozkurt |
| 2017/0128006 A1 | 5/2017 | Seo et al. |
| 2017/0128015 A1 | 5/2017 | Rogers et al. |
| 2017/0131293 A1 | 5/2017 | Haslett et al. |
| 2017/0132816 A1 | 5/2017 | Aston et al. |
| 2017/0132861 A1 | 5/2017 | Ho et al. |
| 2017/0133009 A1 | 5/2017 | Cho et al. |
| 2017/0133576 A1 | 5/2017 | Marcus et al. |
| 2017/0133577 A1 | 5/2017 | Cybart et al. |
| 2017/0135594 A1 | 5/2017 | Hartings et al. |
| 2017/0135597 A1 | 5/2017 | Mann |
| 2017/0135604 A1 | 5/2017 | Kent et al. |
| 2017/0135626 A1 | 5/2017 | Singer |
| 2017/0135629 A1 | 5/2017 | Kent et al. |
| 2017/0135631 A1 | 5/2017 | Zuckerman-Stark et al. |
| 2017/0135633 A1 | 5/2017 | Connor |
| 2017/0135640 A1 | 5/2017 | Gunasekar et al. |
| 2017/0136240 A1 | 5/2017 | Mogul |
| 2017/0136264 A1 | 5/2017 | Hyde et al. |
| 2017/0136265 A1 | 5/2017 | Hyde et al. |
| 2017/0139484 A1 | 5/2017 | Todeschini |
| 2017/0140124 A1 | 5/2017 | Sehgal et al. |
| 2017/0142656 A1 | 5/2017 | Hong et al. |
| 2017/0143231 A1 | 5/2017 | Ostberg et al. |
| 2017/0143249 A1 | 5/2017 | Davis et al. |
| 2017/0143255 A1 | 5/2017 | Babaeizadeh et al. |
| 2017/0143257 A1 | 5/2017 | Kent et al. |
| 2017/0143259 A1 | 5/2017 | Kent et al. |
| 2017/0143266 A1 | 5/2017 | Kovacs et al. |
| 2017/0143267 A1 | 5/2017 | Kovacs et al. |
| 2017/0143268 A1 | 5/2017 | Kovacs et al. |
| 2017/0143273 A1 | 5/2017 | Osorio et al. |
| 2017/0143280 A1 | 5/2017 | Kent et al. |
| 2017/0143282 A1 | 5/2017 | Kovacs et al. |
| 2017/0143442 A1 | 5/2017 | Tesar et al. |
| 2017/0143960 A1 | 5/2017 | Kent et al. |
| 2017/0143963 A1 | 5/2017 | Osorio |
| 2017/0143986 A1 | 5/2017 | Deisseroth et al. |
| 2017/0146386 A1 | 5/2017 | Wiard et al. |
| 2017/0146387 A1 | 5/2017 | Wiard et al. |
| 2017/0146390 A1 | 5/2017 | Kovacs |
| 2017/0146391 A1 | 5/2017 | Kovacs et al. |
| 2017/0146615 A1 | 5/2017 | Wolf et al. |
| 2017/0146801 A1 | 5/2017 | Stempora |
| 2017/0147578 A1 | 5/2017 | Hecht et al. |
| 2017/0147754 A1 | 5/2017 | Kovacs |
| 2017/0148213 A1 | 5/2017 | Thomas et al. |
| 2017/0148240 A1 | 5/2017 | Kovacs et al. |
| 2017/0148340 A1 | 5/2017 | Popa-Simil et al. |
| 2017/0148592 A1 | 5/2017 | Tabib-Azir |
| 2017/0149945 A1 | 5/2017 | Lee et al. |
| 2017/0150896 A9 | 6/2017 | Lu et al. |
| 2017/0150897 A1 | 6/2017 | Komaki |
| 2017/0150898 A1 | 6/2017 | Liu et al. |
| 2017/0150916 A1 | 6/2017 | Osorio |
| 2017/0150925 A1 | 6/2017 | Jung |
| 2017/0151435 A1 | 6/2017 | Deadwyler et al. |
| 2017/0151436 A1 | 6/2017 | Flaherty et al. |
| 2017/0154167 A1 | 6/2017 | Ovtchinnikov |
| 2017/0156593 A1 | 6/2017 | Ferber et al. |
| 2017/0156606 A1 | 6/2017 | Ferber et al. |
| 2017/0156655 A1 | 6/2017 | Austin et al. |
| 2017/0156662 A1 | 6/2017 | Goodall et al. |
| 2017/0156674 A1 | 6/2017 | Hochman |
| 2017/0157435 A1 | 6/2017 | Choi |
| 2017/0160360 A1 | 6/2017 | Deisseroth et al. |
| 2017/0160703 A1 | 6/2017 | Heo et al. |
| 2017/0162072 A1 | 6/2017 | Horseman et al. |
| 2017/0164293 A1 | 6/2017 | Hwang |
| 2017/0164861 A1 | 6/2017 | Cahan et al. |
| 2017/0164862 A1 | 6/2017 | Dolev et al. |
| 2017/0164876 A1 | 6/2017 | Hyde et al. |

(56) References Cited

U.S. PATENT DOCUMENTS

| | | |
|---|---|---|
| 2017/0164878 A1 | 6/2017 | Connor |
| 2017/0164893 A1 | 6/2017 | Narayan et al. |
| 2017/0164894 A1 | 6/2017 | Yoo et al. |
| 2017/0164901 A1 | 6/2017 | Shusterman |
| 2017/0165020 A1 | 6/2017 | Martel |
| 2017/0165481 A1 | 6/2017 | Menon |
| 2017/0168121 A1 | 6/2017 | Yu et al. |
| 2017/0168568 A1 | 6/2017 | Petrov |
| 2017/0169176 A1 | 6/2017 | Abiola |
| 2017/0169295 A1 | 6/2017 | Park et al. |
| 2017/0169714 A1 | 6/2017 | Lin et al. |
| 2017/0171441 A1 | 6/2017 | Kearns et al. |
| 2017/0172414 A1 | 6/2017 | Nierenberg et al. |
| 2017/0172445 A1 | 6/2017 | Dang et al. |
| 2017/0172446 A1 | 6/2017 | Kuzum et al. |
| 2017/0172499 A1 | 6/2017 | Yoo |
| 2017/0172501 A1 | 6/2017 | Badower et al. |
| 2017/0172520 A1 | 6/2017 | Kannan et al. |
| 2017/0172527 A1 | 6/2017 | Uber |
| 2017/0173262 A1 | 6/2017 | Veltz |
| 2017/0173326 A1 | 6/2017 | Bloch et al. |
| 2017/0173391 A1 | 6/2017 | Wiebe et al. |
| 2017/0174180 A1 | 6/2017 | Hoyos et al. |
| 2017/0175280 A1 | 6/2017 | Dang et al. |
| 2017/0177023 A1 | 6/2017 | Simon et al. |
| 2017/0178001 A1 | 6/2017 | Anderson et al. |
| 2017/0178340 A1 | 6/2017 | Schadewaldt et al. |
| 2017/0180558 A1 | 6/2017 | Li et al. |
| 2017/0180882 A1 | 6/2017 | Lunner et al. |
| 2017/0181252 A1 | 6/2017 | Wouhaybi et al. |
| 2017/0181693 A1 | 6/2017 | Kim et al. |
| 2017/0182176 A1 | 6/2017 | Satchi-Fainaro et al. |
| 2017/0185149 A1 | 6/2017 | Oluwafemi et al. |
| 2017/0185150 A1 | 6/2017 | Yang et al. |
| 2017/0185714 A1 | 6/2017 | Halter et al. |
| 2017/0185762 A1 | 6/2017 | Chang et al. |
| 2017/0188862 A1 | 7/2017 | Kale et al. |
| 2017/0188865 A1 | 7/2017 | Nierenberg et al. |
| 2017/0188866 A1 | 7/2017 | Kale et al. |
| 2017/0188868 A1 | 7/2017 | Kale et al. |
| 2017/0188869 A1 | 7/2017 | Kale et al. |
| 2017/0188870 A1 | 7/2017 | Hilty |
| 2017/0188872 A1 | 7/2017 | Hughes et al. |
| 2017/0188905 A1 | 7/2017 | Lee et al. |
| 2017/0188916 A1 | 7/2017 | Wang et al. |
| 2017/0188922 A1 | 7/2017 | Lee et al. |
| 2017/0188932 A1 | 7/2017 | Singer et al. |
| 2017/0188933 A1 | 7/2017 | Huggins et al. |
| 2017/0188947 A1 | 7/2017 | Connor |
| 2017/0188992 A1 | 7/2017 | O'Brien et al. |
| 2017/0189640 A1 | 7/2017 | Sadwick |
| 2017/0189691 A1 | 7/2017 | De Ridder |
| 2017/0190765 A1 | 7/2017 | El-Agnaf |
| 2017/0193314 A1 | 7/2017 | Kim et al. |
| 2017/0193831 A1 | 7/2017 | Walter et al. |
| 2017/0196497 A1 | 7/2017 | Ray et al. |
| 2017/0196501 A1 | 7/2017 | Watson et al. |
| 2017/0196503 A1 | 7/2017 | Narayan et al. |
| 2017/0196519 A1 | 7/2017 | Miller et al. |
| 2017/0197081 A1 | 7/2017 | Charlesworth et al. |
| 2017/0198017 A1 | 7/2017 | Deisseroth et al. |
| 2017/0199251 A1 | 7/2017 | Fujii et al. |
| 2017/0201619 A1 | 7/2017 | Cohen et al. |
| 2017/0202474 A1 | 7/2017 | Banerjee et al. |
| 2017/0202475 A1 | 7/2017 | Leuthardt |
| 2017/0202476 A1 | 7/2017 | Desain et al. |
| 2017/0202518 A1 | 7/2017 | Furman et al. |
| 2017/0202633 A1 | 7/2017 | Liu |
| 2017/0203154 A1 | 7/2017 | Solinsky |
| 2017/0205259 A1 | 7/2017 | Jang et al. |
| 2017/0206654 A1 | 7/2017 | Shiroishi et al. |
| 2017/0206691 A1 | 7/2017 | Harrises et al. |
| 2017/0206913 A1 | 7/2017 | Nahman et al. |
| 2017/0209043 A1 | 7/2017 | Gross et al. |
| 2017/0209044 A1 | 7/2017 | Ito et al. |
| 2017/0209053 A1 | 7/2017 | Pantelopoulos et al. |
| 2017/0209062 A1 | 7/2017 | Iwasaki et al. |
| 2017/0209083 A1 | 7/2017 | Zarandi et al. |
| 2017/0209094 A1 | 7/2017 | Derchak et al. |
| 2017/0209225 A1 | 7/2017 | Wu |
| 2017/0209389 A1 | 7/2017 | Toth et al. |
| 2017/0209737 A1 | 7/2017 | Tadi et al. |
| 2017/0212188 A1 | 7/2017 | Kikitsu et al. |
| 2017/0213311 A1 | 7/2017 | Sinclair |
| 2017/0214786 A1 | 7/2017 | Lee et al. |
| 2017/0215011 A1 | 7/2017 | Goldstein |
| 2017/0215757 A1 | 8/2017 | Gil Da Costa et al. |
| 2017/0216393 A1 | 8/2017 | Vavvas et al. |
| 2017/0221121 A1 | 8/2017 | Davis et al. |
| 2017/0221463 A1 | 8/2017 | Lenhert |
| 2017/0238831 A1 | 8/2017 | Cho et al. |
| 2017/0243023 A1 | 8/2017 | Lee et al. |
| 2017/0243203 A1 | 8/2017 | Bond et al. |
| 2017/0244702 A1 | 8/2017 | Jwa et al. |
| 2017/0245145 A1 | 8/2017 | Choi et al. |
| 2017/0249009 A1 | 8/2017 | Parshionikar |
| 2017/0251945 A1 | 9/2017 | Nick et al. |
| 2017/0255981 A1 | 9/2017 | Van Niekerk et al. |
| 2017/0258319 A1 | 9/2017 | Weffers-albu et al. |
| 2017/0258390 A1 | 9/2017 | Howard |
| 2017/0259167 A1 | 9/2017 | Cook et al. |
| 2017/0262943 A1 | 9/2017 | Akutagawa et al. |
| 2017/0265807 A1 | 9/2017 | Stopek |
| 2017/0270636 A1 | 9/2017 | Shtukater |
| 2017/0272699 A1 | 9/2017 | Stopek |
| 2017/0272842 A1 | 9/2017 | Touma et al. |
| 2017/0276956 A1 | 9/2017 | Morifuji et al. |
| 2017/0281001 A1 | 10/2017 | Stopek |
| 2017/0293846 A1 | 10/2017 | Zyglowicz et al. |
| 2017/0300654 A1 | 10/2017 | Stein et al. |
| 2017/0300998 A1 | 10/2017 | Knudson et al. |
| 2017/0304587 A1 | 10/2017 | Santostasi et al. |
| 2017/0304623 A1 | 10/2017 | Tandon |
| 2017/0308172 A1 | 10/2017 | Niikawa |
| 2017/0309152 A1 | 10/2017 | Dinkins |
| 2017/0311023 A1 | 10/2017 | Chen et al. |
| 2017/0311097 A1 | 10/2017 | Nielsen et al. |
| 2017/0311832 A1 | 11/2017 | Barthelemy et al. |
| 2017/0311837 A1 | 11/2017 | Wei |
| 2017/0311878 A1 | 11/2017 | Wu et al. |
| 2017/0312622 A1 | 11/2017 | Ishihara |
| 2017/0316707 A1 | 11/2017 | Lawrenson et al. |
| 2017/0319109 A1 | 11/2017 | Skelton et al. |
| 2017/0319815 A1 | 11/2017 | Nofzinger et al. |
| 2017/0323073 A1 | 11/2017 | Westermann et al. |
| 2017/0329401 A1 | 11/2017 | Mitchell |
| 2017/0330248 A1 | 11/2017 | Gomariz et al. |
| 2017/0331563 A1 | 11/2017 | Tyler et al. |
| 2017/0332964 A1 | 11/2017 | Attal et al. |
| 2017/0333729 A1 | 11/2017 | Olcese |
| 2017/0337834 A1 | 11/2017 | Shindi |
| 2017/0344991 A1 | 11/2017 | Mark et al. |
| 2017/0345239 A9 | 11/2017 | Ho et al. |
| 2017/0346851 A1 | 11/2017 | Drake |
| 2017/0347181 A1 | 11/2017 | Campbell et al. |
| 2017/0347906 A1 | 12/2017 | Intrator |
| 2017/0347947 A1 | 12/2017 | Liang et al. |
| 2017/0347948 A1 | 12/2017 | Thein et al. |
| 2017/0352233 A1 | 12/2017 | Rivaud et al. |
| 2017/0354327 A1 | 12/2017 | Kiderman et al. |
| 2017/0360360 A1 | 12/2017 | Alqurashi |
| 2017/0360363 A1 | 12/2017 | Fonseca et al. |
| 2017/0367606 A1 | 12/2017 | Lee |
| 2017/0367610 A1 | 12/2017 | Girouard |
| 2017/0367651 A1 | 12/2017 | Tzvieli et al. |
| 2017/0368348 A1 | 12/2017 | Le Van Quyen et al. |
| 2017/0371421 A1 | 12/2017 | Parshionikar |
| 2018/0000255 A1 | 1/2018 | Youngblood et al. |
| 2018/0004287 A1 | 1/2018 | Yoo et al. |
| 2018/0005442 A1 | 1/2018 | Mullins |
| 2018/0009417 A1 | 1/2018 | Hoyos et al. |
| 2018/0011676 A1 | 1/2018 | Han et al. |
| 2018/0011689 A1 | 1/2018 | Motamedi et al. |
| 2018/0012009 A1 | 1/2018 | Furman et al. |

(56) References Cited

U.S. PATENT DOCUMENTS

| | | | |
|---|---|---|---|
| 2018/0014130 A1 | 1/2018 | Lunner et al. | |
| 2018/0014741 A1 | 1/2018 | Chou | |
| 2018/0025368 A1 | 1/2018 | Frank et al. | |
| 2018/0027176 A1 | 1/2018 | Agell et al. | |
| 2018/0027347 A1 | 1/2018 | Osborne et al. | |
| 2018/0032103 A1 | 2/2018 | Eskilsson et al. | |
| 2018/0034855 A1 | 2/2018 | Myron | |
| 2018/0042513 A1 | 2/2018 | Connor | |
| 2018/0042523 A1 | 2/2018 | Sales et al. | |
| 2018/0046248 A1 | 2/2018 | San Agustin Lopez et al. | |
| 2018/0047216 A1 | 2/2018 | Mullins | |
| 2018/0056026 A1 | 3/2018 | Harkness et al. | |
| 2018/0068581 A1 | 3/2018 | Skorheim et al. | |
| 2018/0070823 A1 | 3/2018 | Blackwell et al. | |
| 2018/0075364 A1 | 3/2018 | Stolarz et al. | |
| 2018/0081430 A1 | 3/2018 | Konz | |
| 2018/0081439 A1 | 3/2018 | Daniels | |
| 2018/0088678 A1 | 3/2018 | Komaki et al. | |
| 2018/0089531 A1 | 3/2018 | Geva et al. | |
| 2018/0092557 A1 | 4/2018 | Bickford et al. | |
| 2018/0092566 A1 | 4/2018 | Guger et al. | |
| 2018/0092600 A1 | 4/2018 | Simons et al. | |
| 2018/0093092 A1 | 4/2018 | Howard | |
| 2018/0095532 A1 | 4/2018 | Cheng et al. | |
| 2018/0098710 A1 | 4/2018 | Gavas et al. | |
| 2018/0098908 A1 | 4/2018 | Chien | |
| 2018/0103859 A1 | 4/2018 | Provenzano | |
| 2018/0103867 A1 | 4/2018 | Stephens et al. | |
| 2018/0103917 A1 | 4/2018 | Kim et al. | |
| 2018/0108191 A9 | 4/2018 | Ho et al. | |
| 2018/0108192 A1 | 4/2018 | Ho et al. | |
| 2018/0110960 A1 | 4/2018 | Youngblood et al. | |
| 2018/0110991 A1 | 4/2018 | Molnar et al. | |
| 2018/0113509 A1 | 4/2018 | Kim et al. | |
| 2018/0113669 A1 | 4/2018 | Szeto | |
| 2018/0115808 A1 | 4/2018 | Buga | |
| 2018/0116543 A1 | 5/2018 | Miller et al. | |
| 2018/0125356 A1 | 5/2018 | Yamada | |
| 2018/0125386 A1 | 5/2018 | Lim et al. | |
| 2018/0125405 A1 | 5/2018 | Yamada | |
| 2018/0125406 A1 | 5/2018 | Yamada | |
| 2018/0133431 A1 | 5/2018 | Malchano et al. | |
| 2018/0133504 A1 | 5/2018 | Malchano et al. | |
| 2018/0133507 A1 | 5/2018 | Malchano et al. | |
| 2018/0139518 A1 | 5/2018 | Touma et al. | |
| 2018/0140249 A1 | 5/2018 | Frohlich | |
| 2018/0146879 A9 | 5/2018 | Fadem et al. | |
| 2018/0146916 A1 | 5/2018 | Howard et al. | |
| 2018/0150762 A1 | 5/2018 | Stolarz et al. | |
| 2018/0154104 A1 | 6/2018 | Gerdes et al. | |
| 2018/0157336 A1 | 6/2018 | Harris et al. | |
| 2018/0157379 A1 | 6/2018 | Sivakumar et al. | |
| 2018/0158133 A1 | 6/2018 | Davis et al. | |
| 2018/0160982 A1 | 6/2018 | Laszlo et al. | |
| 2018/0165593 A1 | 6/2018 | Stolarz et al. | |
| 2018/0166157 A1 | 6/2018 | Firminger et al. | |
| 2018/0168905 A1 | 6/2018 | Goodall et al. | |
| 2018/0169411 A1 | 6/2018 | Goodall et al. | |
| 2018/0169412 A1 | 6/2018 | Goodall et al. | |
| 2018/0169430 A1* | 6/2018 | Kamei | A61N 5/06 |
| 2018/0173220 A1 | 6/2018 | Wang et al. | |
| 2018/0177393 A1 | 6/2018 | Muniraju | |
| 2018/0177451 A1 | 6/2018 | Sahin | |
| 2018/0182161 A1 | 6/2018 | Chaudhari et al. | |
| 2018/0184002 A1 | 6/2018 | Thukral et al. | |
| 2018/0184964 A1 | 7/2018 | Simon et al. | |
| 2018/0189678 A1 | 7/2018 | Gupta et al. | |
| 2018/0190376 A1 | 7/2018 | Hill et al. | |
| 2018/0192936 A1 | 7/2018 | Widge et al. | |
| 2018/0193589 A1 | 7/2018 | McLaughlin et al. | |
| 2018/0196511 A1 | 7/2018 | Chae | |
| 2018/0196512 A1 | 7/2018 | Kim et al. | |
| 2018/0197636 A1 | 7/2018 | Firminger et al. | |
| 2018/0214020 A1 | 8/2018 | Ohlendorf et al. | |
| 2018/0214028 A1 | 8/2018 | Zhang et al. | |
| 2018/0214768 A1 | 8/2018 | Macri et al. | |
| 2018/0217666 A1 | 8/2018 | Gil Da Costa et al. | |
| 2018/0219729 A1 | 8/2018 | Garg et al. | |
| 2018/0220957 A1 | 8/2018 | Fuerst et al. | |
| 2018/0221620 A1* | 8/2018 | Metzger | A61B 5/38 |
| 2018/0228423 A1 | 8/2018 | Intrator | |
| 2018/0232507 A1 | 8/2018 | Zizi et al. | |
| 2018/0234479 A1 | 8/2018 | Lilienthal et al. | |
| 2018/0234847 A1 | 8/2018 | Rodriguez | |
| 2018/0236202 A1 | 8/2018 | Weiss et al. | |
| 2018/0242902 A1 | 8/2018 | Martinmaki et al. | |
| 2018/0246570 A1 | 8/2018 | Coleman et al. | |
| 2018/0250494 A1 | 9/2018 | Hanbury | |
| 2018/0256094 A1 | 9/2018 | Russell et al. | |
| 2018/0260801 A1 | 9/2018 | Chiarella et al. | |
| 2018/0263562 A1 | 9/2018 | Laplante-Levesque et al. | |
| 2018/0271362 A1 | 9/2018 | Palczewski et al. | |
| 2018/0275747 A1 | 9/2018 | Campbell | |
| 2018/0276833 A1 | 9/2018 | Yoon et al. | |
| 2018/0278984 A1 | 9/2018 | Aimone et al. | |
| 2018/0279902 A1 | 10/2018 | Liu | |
| 2018/0279939 A1 | 10/2018 | Madsen et al. | |
| 2018/0279960 A1 | 10/2018 | Li et al. | |
| 2018/0284886 A1 | 10/2018 | Mardanbegi et al. | |
| 2018/0289310 A1 | 10/2018 | Girouard et al. | |
| 2018/0289318 A1 | 10/2018 | Howard | |
| 2018/0292902 A1 | 10/2018 | Min | |
| 2018/0296112 A1 | 10/2018 | Girouard et al. | |
| 2018/0299953 A1 | 10/2018 | Selker et al. | |
| 2018/0301061 A1 | 10/2018 | Paudyal et al. | |
| 2018/0303370 A1 | 10/2018 | Kanayama et al. | |
| 2018/0303805 A1 | 10/2018 | During | |
| 2018/0310851 A1 | 11/2018 | Das et al. | |
| 2018/0310855 A1 | 11/2018 | Connor | |
| 2018/0311462 A1 | 11/2018 | Garcia Molina | |
| 2018/0317794 A1 | 11/2018 | Mackellar et al. | |
| 2018/0317795 A1* | 11/2018 | Couser | A61B 5/6803 |
| 2018/0321700 A1 | 11/2018 | Kwak et al. | |
| 2018/0321898 A1 | 11/2018 | Okubo et al. | |
| 2018/0324516 A1 | 11/2018 | Campbell et al. | |
| 2018/0328917 A1 | 11/2018 | Ilan | |
| 2018/0333585 A1 | 11/2018 | Gaddam et al. | |
| 2018/0333587 A1 | 11/2018 | Howard | |
| 2018/0338068 A1 | 11/2018 | Weaver et al. | |
| 2018/0341328 A1 | 11/2018 | Agell et al. | |
| 2018/0341848 A1 | 11/2018 | Breuer et al. | |
| 2018/0343219 A1 | 11/2018 | Anderson et al. | |
| 2018/0344969 A1 | 12/2018 | Stoneman et al. | |
| 2018/0348764 A1 | 12/2018 | Zhang et al. | |
| 2018/0352326 A1 | 12/2018 | Restuccia et al. | |
| 2018/0364810 A1 | 12/2018 | Parshionikar | |
| 2018/0368717 A1 | 12/2018 | Soulet De Brugiere et al. | |
| 2018/0368722 A1 | 12/2018 | Lunner et al. | |
| 2018/0368755 A1 | 12/2018 | Garcia Molina et al. | |
| 2018/0369847 A1 | 12/2018 | Kihm et al. | |
| 2018/0373272 A1 | 12/2018 | Kihm et al. | |
| 2019/0001039 A1 | 1/2019 | Heide et al. | |
| 2019/0004325 A1 | 1/2019 | Connor | |
| 2019/0008992 A1 | 1/2019 | Kihm et al. | |
| 2019/0011612 A1 | 1/2019 | Mastrangelo et al. | |
| 2019/0012758 A1 | 1/2019 | Sinclair et al. | |
| 2019/0013960 A1 | 1/2019 | Sadwick | |
| 2019/0020554 A1 | 1/2019 | Lilienthal et al. | |
| 2019/0020610 A1 | 1/2019 | Park et al. | |
| 2019/0026871 A1 | 1/2019 | Han et al. | |
| 2019/0029528 A1 | 1/2019 | Tzvieli et al. | |
| 2019/0029587 A1 | 1/2019 | Walker et al. | |
| 2019/0029595 A1 | 1/2019 | Sekitani et al. | |
| 2019/0033914 A1 | 1/2019 | Aimone et al. | |
| 2019/0033968 A1 | 1/2019 | Segal | |
| 2019/0034164 A1 | 1/2019 | Motamedi et al. | |
| 2019/0037067 A1 | 1/2019 | Cohen et al. | |
| 2019/0043154 A1 | 2/2019 | Lawrence | |
| 2019/0046119 A1 | 2/2019 | Oxley | |
| 2019/0053731 A1 | 2/2019 | Moon et al. | |
| 2019/0053756 A1 | 2/2019 | Ayers et al. | |
| 2019/0053766 A1 | 2/2019 | Mijovic et al. | |
| 2019/0054899 A1 | 2/2019 | Hoyos et al. | |
| 2019/0056438 A1 | 2/2019 | Jaroch | |

(56)          References Cited

U.S. PATENT DOCUMENTS

| | | |
|---|---|---|
| 2019/0059771 A1 | 2/2019 | Fu |
| 2019/0060602 A1 | 2/2019 | Tran et al. |
| 2019/0070386 A1 | 3/2019 | Raut et al. |
| 2019/0073029 A1 | 3/2019 | Filatov et al. |
| 2019/0073044 A1 | 3/2019 | Komaki et al. |
| 2019/0073605 A1 | 3/2019 | Keller |
| 2019/0077409 A1 | 3/2019 | Zandi et al. |
| 2019/0079580 A1 | 3/2019 | Ura et al. |
| 2019/0082990 A1 | 3/2019 | Poltorak |
| 2019/0082991 A1 | 3/2019 | Barthelemy et al. |
| 2019/0083212 A1 | 3/2019 | Cowburn et al. |
| 2019/0086919 A1 | 3/2019 | Zhang et al. |
| 2019/0097430 A1 | 3/2019 | Bae et al. |
| 2019/0099076 A1 | 4/2019 | Fujikado et al. |
| 2019/0099104 A1 | 4/2019 | Macri et al. |
| 2019/0099467 A1 | 4/2019 | Vavvas et al. |
| 2019/0101985 A1 | 4/2019 | Sajda et al. |
| 2019/0103034 A1 | 4/2019 | Walter et al. |
| 2019/0107888 A1 | 4/2019 | Sereshkeh et al. |
| 2019/0108191 A1 | 4/2019 | Frank et al. |
| 2019/0110726 A1 | 4/2019 | Chatterjee et al. |
| 2019/0113973 A1 | 4/2019 | Coleman et al. |
| 2019/0117062 A1 | 4/2019 | Yeo et al. |
| 2019/0117933 A1 | 4/2019 | Couser |
| 2019/0121682 A1 | 4/2019 | Adiletta et al. |
| 2019/0126033 A1 | 5/2019 | Pradeep |
| 2019/0130353 A1 | 5/2019 | Fenty et al. |
| 2019/0130750 A1 | 5/2019 | Cole et al. |
| 2019/0130777 A1 | 5/2019 | Dey et al. |
| 2019/0133445 A1 | 5/2019 | Eteminan et al. |
| 2019/0142349 A1 | 5/2019 | Schorey et al. |
| 2019/0143073 A1 | 5/2019 | Grossman et al. |
| 2019/0146580 A1 | 5/2019 | Baugh et al. |
| 2019/0151337 A1 | 5/2019 | Tsuruda et al. |
| 2019/0158717 A1 | 5/2019 | Nomura et al. |
| 2019/0159675 A1 | 5/2019 | Sengupta et al. |
| 2019/0159715 A1 | 5/2019 | Mishra Ramanathan et al. |
| 2019/0167179 A1 | 6/2019 | Arzy |
| 2019/0167370 A1 | 6/2019 | Olson |
| 2019/0174237 A1 | 6/2019 | Lunner et al. |
| 2019/0174238 A1 | 6/2019 | Lunner et al. |

FOREIGN PATENT DOCUMENTS

| | | |
|---|---|---|
| EP | 0483698 | 5/1992 |
| EP | 1090583 | 4/2001 |
| EP | 1304073 A2 | 4/2003 |
| EP | 1304073 A3 | 9/2003 |
| EP | 1776922 | 4/2007 |
| JP | 4582509 | 4/2007 |
| JP | 4699694 | 4/2007 |
| JP | 4801839 | 4/2007 |
| JP | 4829231 | 4/2007 |
| KR | 100895297 | 4/2007 |
| RU | 2563433 | 9/2015 |
| WO | WO2000025668 A1 | 9/2015 |
| WO | WO2001087153 A1 | 9/2015 |
| WO | WO2015143031 | 9/2015 |

* cited by examiner

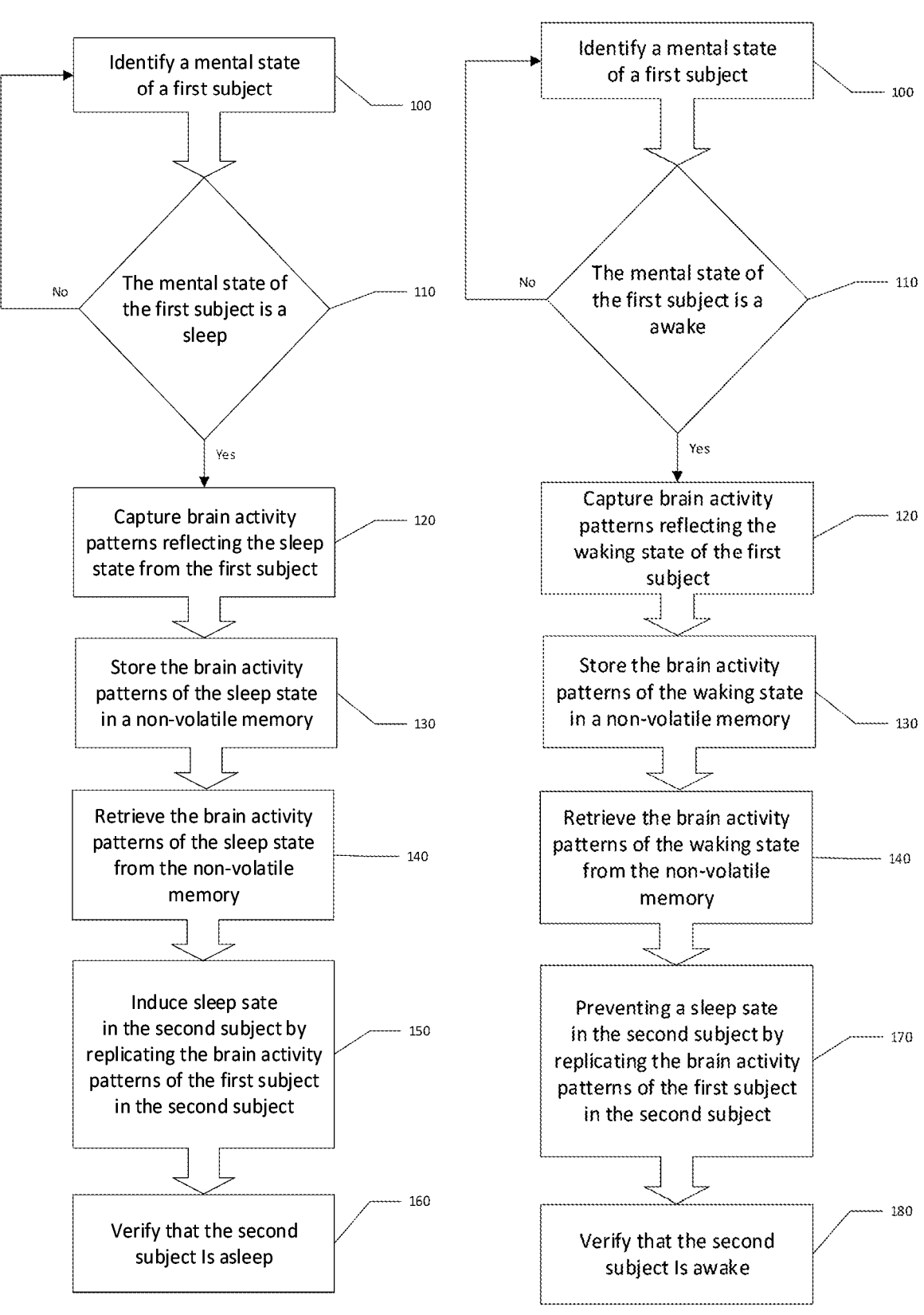
Fig. 1                              Fig. 2

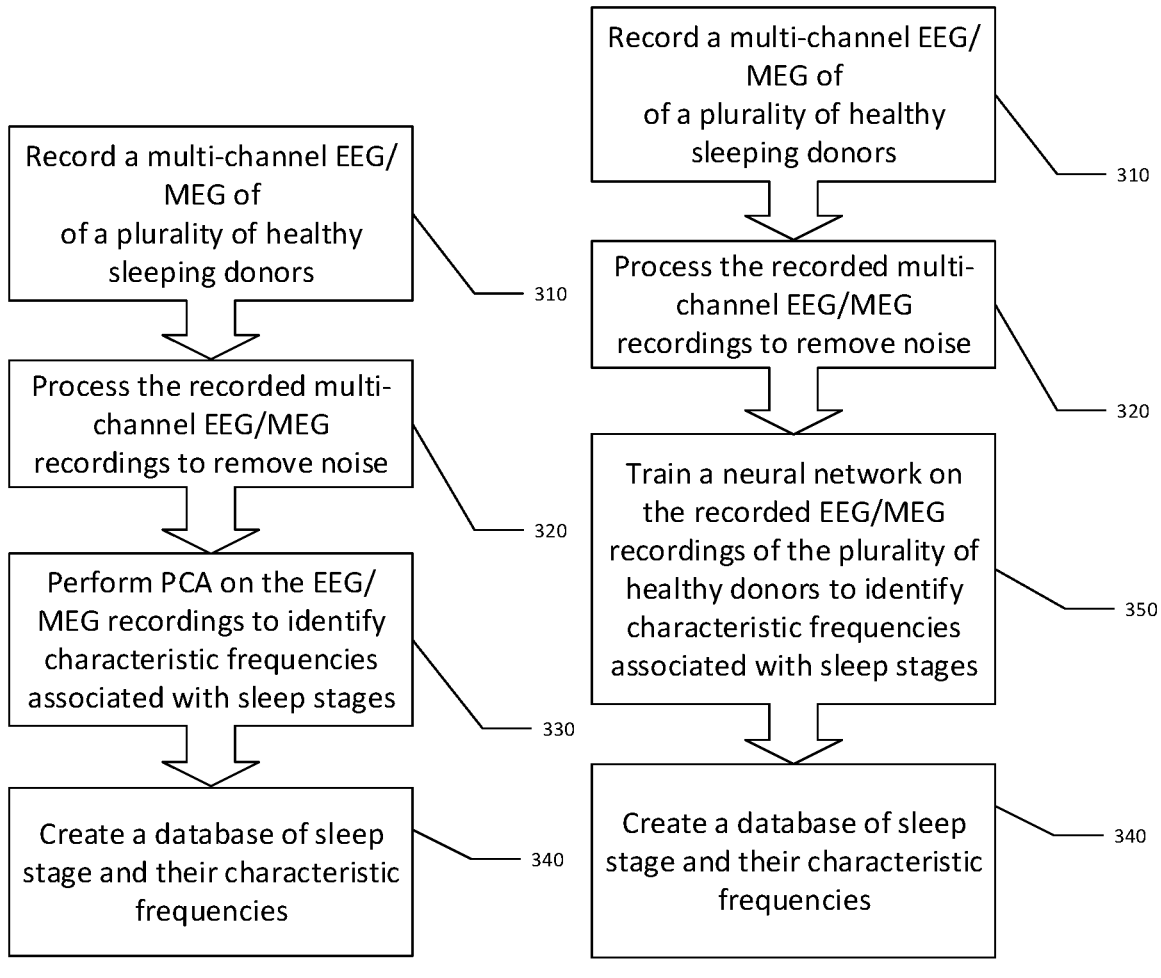
Fig. 5                    Fig. 6

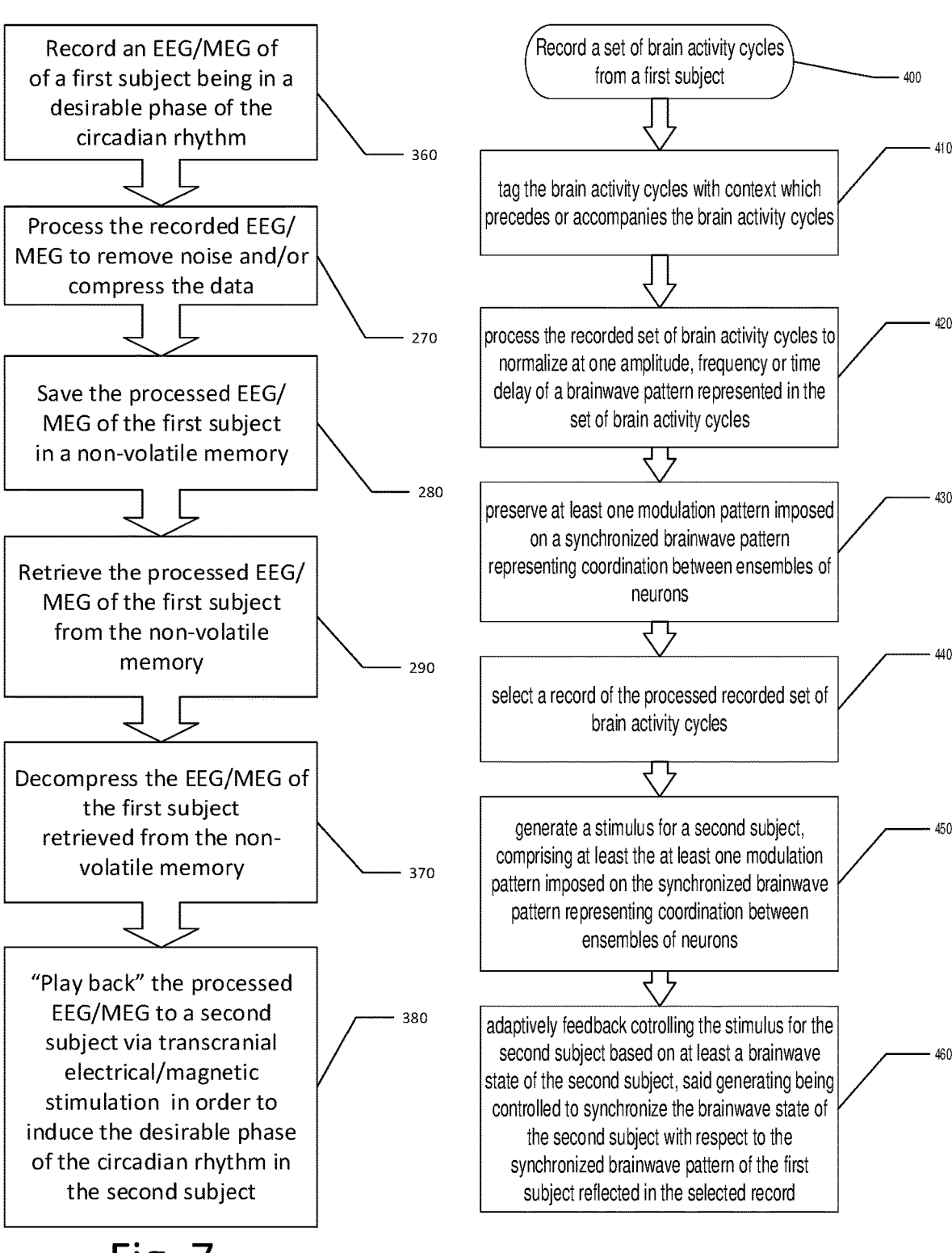

Record an EEG/MEG of of a first subject being in a desirable phase of the circadian rhythm
— 360

Process the recorded EEG/MEG to remove noise and/or compress the data
— 270

Save the processed EEG/MEG of the first subject in a non-volatile memory
— 280

Retrieve the processed EEG/MEG of the first subject from the non-volatile memory
— 290

Decompress the EEG/MEG of the first subject retrieved from the non-volatile memory
— 370

"Play back" the processed EEG/MEG to a second subject via transcranial electrical/magnetic stimulation in order to induce the desirable phase of the circadian rhythm in the second subject
— 380

Fig. 7

Record a set of brain activity cycles from a first subject
— 400 tag the brain activity cycles with context which precedes or accompanies the brain activity cycles
— 410 process the recorded set of brain activity cycles to normalize at one amplitude, frequency or time delay of a brainwave pattern represented in the set of brain activity cycles
— 420 preserve at least one modulation pattern imposed on a synchronized brainwave pattern representing coordination between ensembles of neurons
— 430 select a record of the processed recorded set of brain activity cycles
— 440 generate a stimulus for a second subject, comprising at least the at least one modulation pattern imposed on the synchronized brainwave pattern representing coordination between ensembles of neurons
— 450 adaptively feedback cotrolling the stimulus for the second subject based on at least a brainwave state of the second subject, said generating being controlled to synchronize the brainwave state of the second subject with respect to the synchronized brainwave pattern of the first subject reflected in the selected record
— 460

Fig. 8

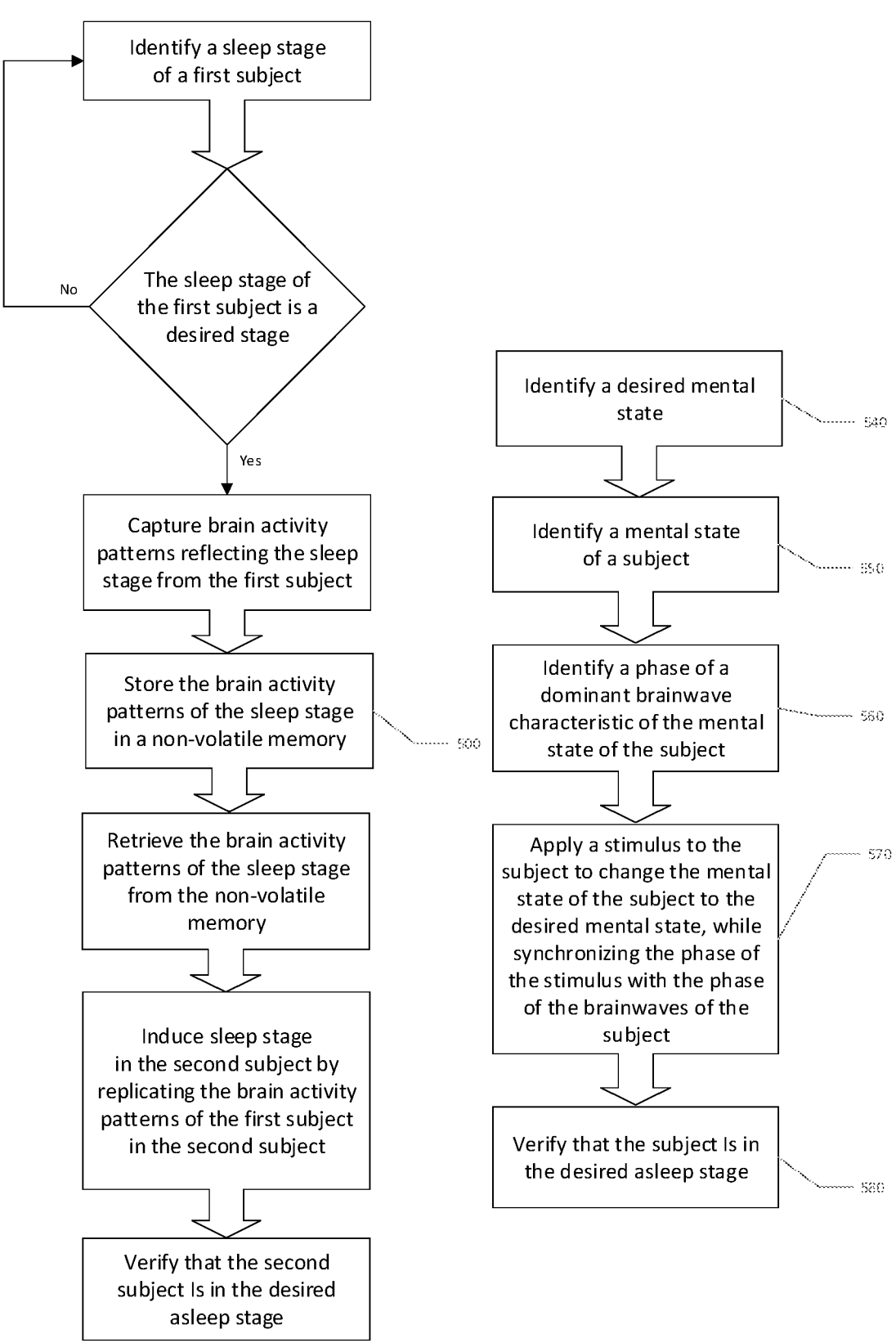
Fig. 9                    Fig. 10

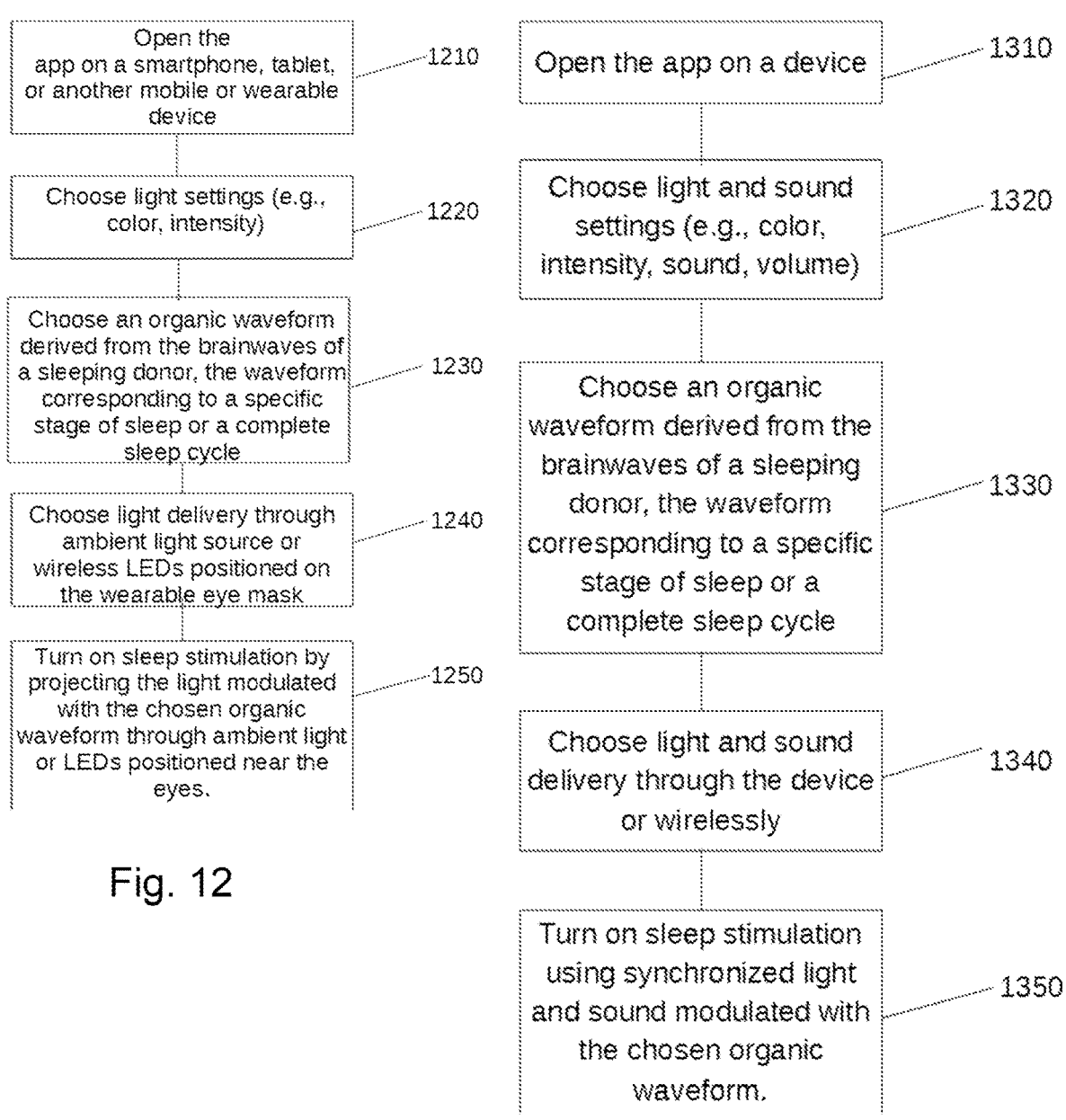

Open the app on a smartphone, tablet, or another mobile or wearable device — 1210

Choose light settings (e.g., color, intensity) — 1220

Choose an organic waveform derived from the brainwaves of a sleeping donor, the waveform corresponding to a specific stage of sleep or a complete sleep cycle — 1230

Choose light delivery through ambient light source or wireless LEDs positioned on the wearable eye mask — 1240

Turn on sleep stimulation by projecting the light modulated with the chosen organic waveform through ambient light or LEDs positioned near the eyes. — 1250

Fig. 12

Open the app on a device — 1310

Choose light and sound settings (e.g., color, intensity, sound, volume) — 1320

Choose an organic waveform derived from the brainwaves of a sleeping donor, the waveform corresponding to a specific stage of sleep or a complete sleep cycle — 1330

Choose light and sound delivery through the device or wirelessly — 1340

Turn on sleep stimulation using synchronized light and sound modulated with the chosen organic waveform. — 1350

Fig. 13

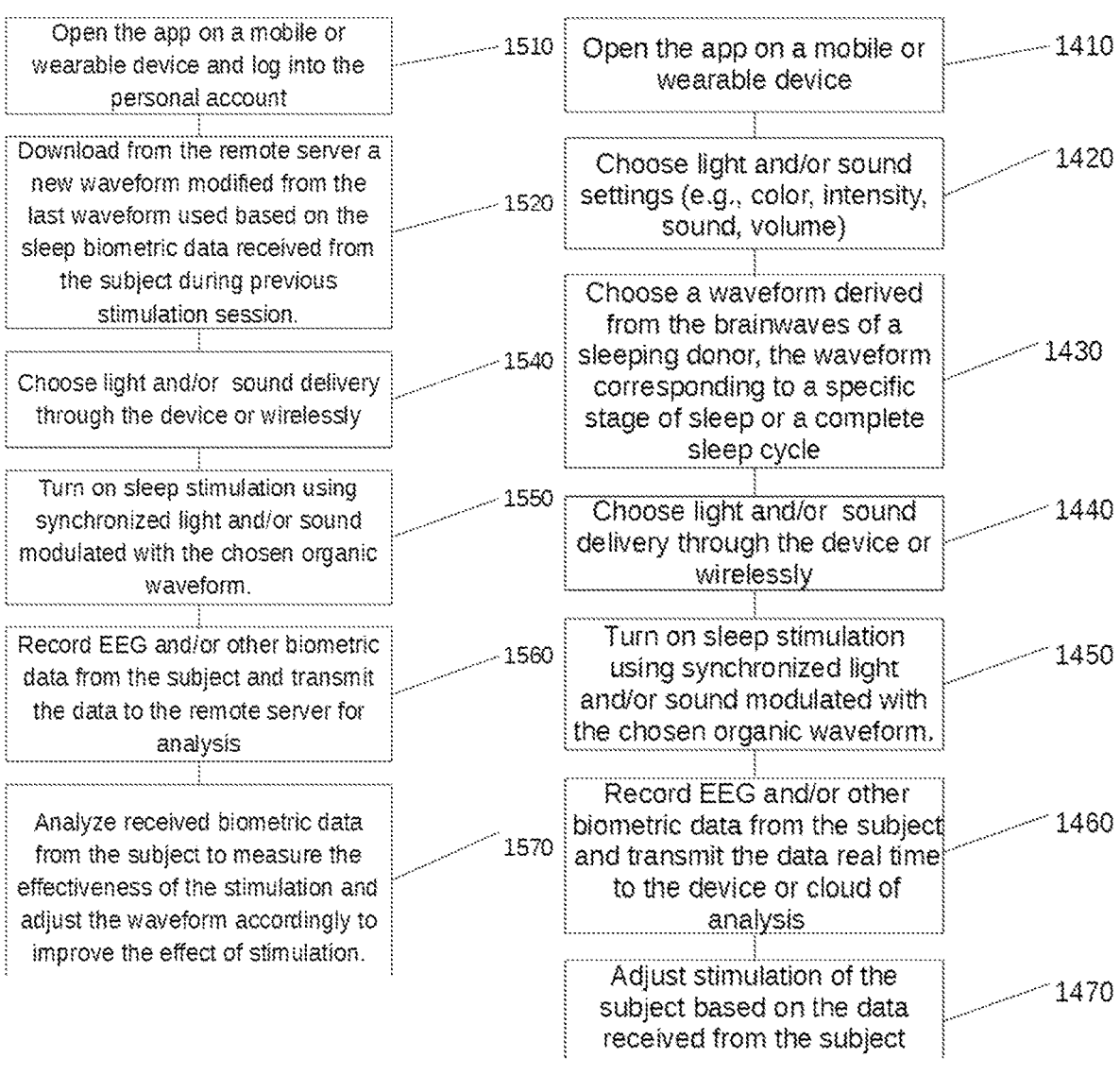

Open the app on a mobile or wearable device and log into the personal account — 1510

Download from the remote server a new waveform modified from the last waveform used based on the sleep biometric data received from the subject during previous stimulation session. — 1520

Choose light and/or sound delivery through the device or wirelessly — 1540

Turn on sleep stimulation using synchronized light and/or sound modulated with the chosen organic waveform. — 1550

Record EEG and/or other biometric data from the subject and transmit the data to the remote server for analysis — 1560

Analyze received biometric data from the subject to measure the effectiveness of the stimulation and adjust the waveform accordingly to improve the effect of stimulation. — 1570

Fig. 14

Open the app on a mobile or wearable device — 1410

Choose light and/or sound settings (e.g., color, intensity, sound, volume) — 1420

Choose a waveform derived from the brainwaves of a sleeping donor, the waveform corresponding to a specific stage of sleep or a complete sleep cycle — 1430

Choose light and/or sound delivery through the device or wirelessly — 1440

Turn on sleep stimulation using synchronized light and/or sound modulated with the chosen organic waveform. — 1450

Record EEG and/or other biometric data from the subject and transmit the data real time to the device or cloud of analysis — 1460

Adjust stimulation of the subject based on the data received from the subject — 1470

Fig. 15

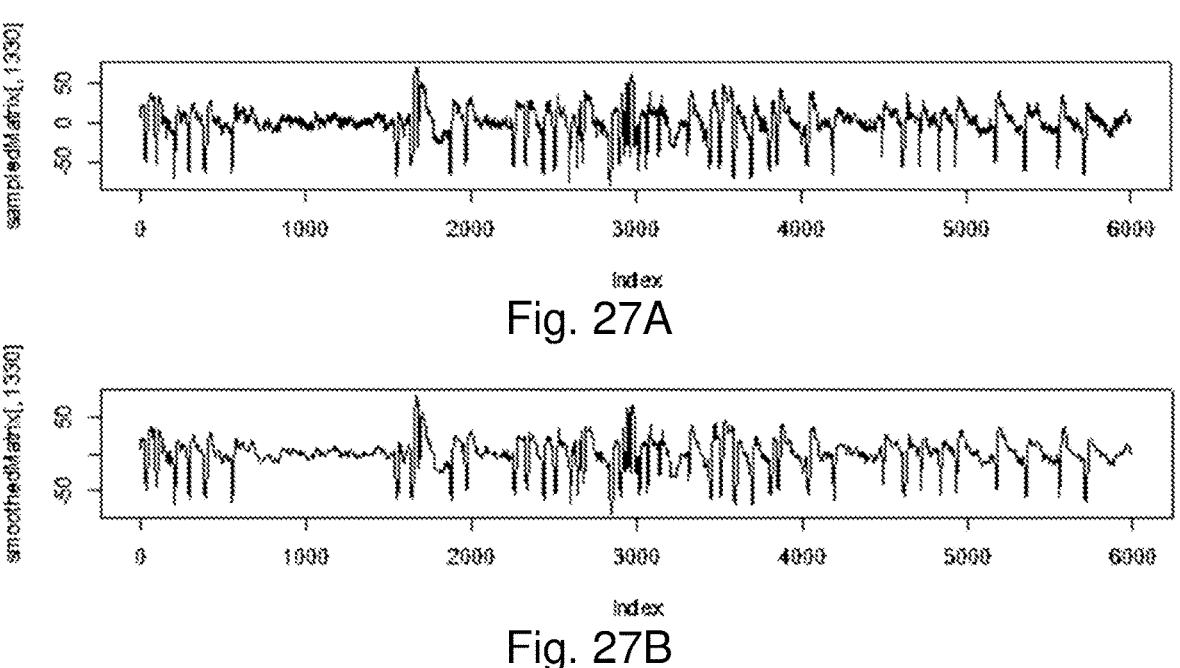
Fig. 27A
Fig. 27B
Replicating Mental States
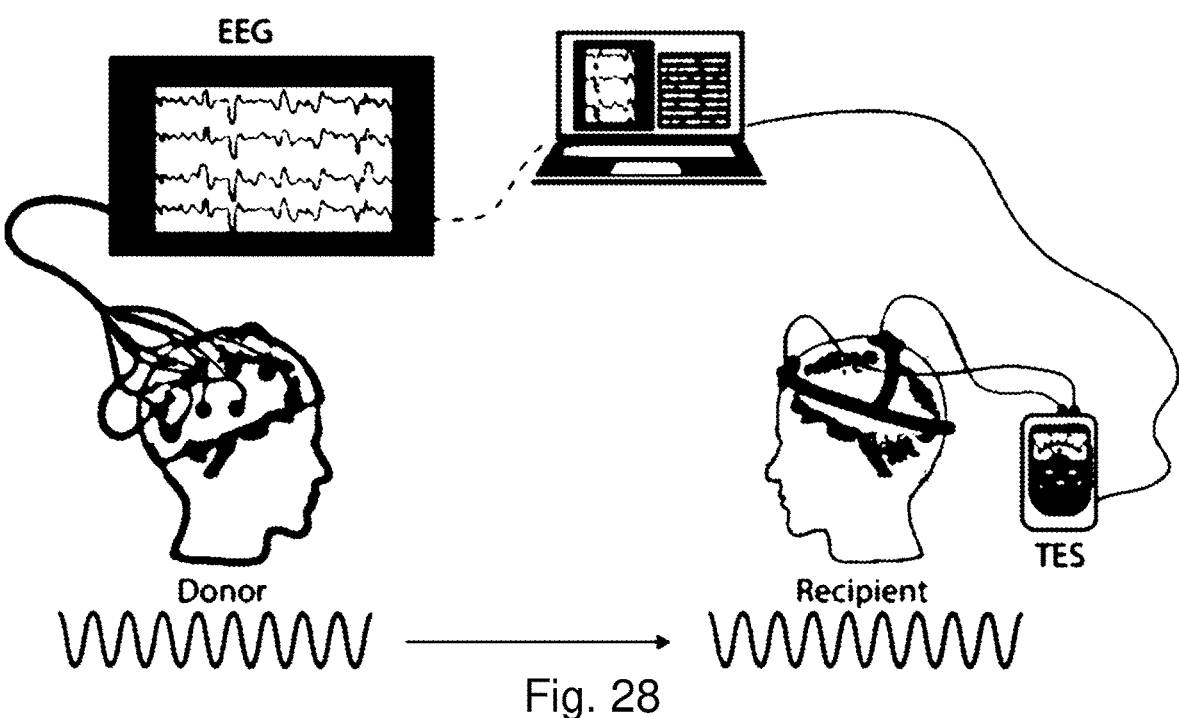
Fig. 28

DEVICE, METHOD, AND APP FOR FACILITATING SLEEP

CROSS REFERENCE TO RELATED APPLICATIONS

The present application is a Continuation of U.S. patent application Ser. No. 16/883,541, filed May 26, 2020, now U.S. Pat. No. 11,786,694, issued Oct. 17, 2023, which is a Non-provisional of, and claims benefit of priority under 35 U.S.C. § 119 (e) from U.S. Provisional Patent Application No. 62/862,656, filed Jun. 17, 2019, and from U.S. Provisional Patent Application No. 62/852,877, filed May 24, 2019, each of which is expressly incorporated herein by reference in its entirety.

FIELD OF THE INVENTION

The present invention generally relates to the field of neuromodulation and neuroenhancement, and more specifically to systems, methods and applications for improving achievement and/or maintenance of sleep.

BACKGROUND OF THE INVENTION

Each reference and document cited herein is expressly incorporated herein by reference in its entirety, for all purposes.

Brain Computer Interface (BCI): sometimes called a neural-control interface (NCI), mind-machine interface (MMI), direct neural interface (DNI), or brain-machine interface (BMI), is a communication pathway between a brain and an external computerized device. BCI may allows for bidirectional information flow. BCIs are often directed at researching, mapping, assisting, augmenting, or repairing human cognitive or sensory-motor functions. See, en.wikipedia.org/wiki/Brain-computer_interface. A bidirectional adaptive BCI controlling computer buzzer by an anticipatory brain potential, the Contingent Negative Variation (CNV) potential has been reported. The experiment described how an expectation state of the brain, manifested by CNV, controls in a feedback loop the S2 buzzer in the S1-S2-CNV paradigm. The obtained cognitive wave representing the expectation learning in the brain is named Electroexpectogram (EXG). Electroencephalography (EEG) is the most studied non-invasive interface, mainly due to its fine temporal resolution, ease of use, portability and low set-up cost. See Reference List 1.

Time in a biological manner: Almost everything in biology is subject to change over time. These changes occur on many different time scales, which vary greatly. For example, there are evolutionary changes that affect entire populations over time rather than a single organism. Evolutionary changes are often slower than a human time scale that spans many years (usually a human lifetime). Faster variations of the timing and duration of biological activity in living organisms occur, for example, in many essential biological processes in everyday life: in humans and animals, these variations occur, for example, in eating, sleeping, mating, hibernating, migration, cellular regeneration, etc. Other fast changes may include the transmission of a neural signal, for example, through a synapse such as the calyx of held, a particularly large synapse in the auditory central nervous system of mammals that can reach transmission frequencies of up to 50 Hz. With recruitment modulation, the effective frequencies can be higher. A single nerve impulse can reach a speed as high as one hundred meters (0.06 mile) per second (Kraus, David. Concepts in Modern Biology. New York: Globe Book Company, 1969:170.). Myelination of axons can increase the speed of transmission by segmenting the membrane depolarization process.

Many of these changes over time are repetitive or rhythmic and are described as some frequency or oscillation. The field of chronobiology, for example, examines such periodic (cyclic) phenomena in living organisms and their adaptation, for example, to solar and lunar-related rhythms [DeCoursey et al. (2003).] These cycles are also known as biological rhythms. The related terms chronomics and chronome have been used in some cases to describe either the molecular mechanisms involved in chronobiological phenomena or the more quantitative aspects of chronobiology, particularly where comparison of cycles between organisms is required. Chronobiological studies include, but are not limited to, comparative anatomy, physiology, genetics, molecular biology, and behavior of organisms within biological rhythms mechanics [DeCoursey et al. (2003).]. Other aspects include epigenetics, development, reproduction, ecology, and evolution.

The most important rhythms in chronobiology are the circadian rhythms, roughly 24-hour cycles shown by physiological processes in all these organisms. It is regulated by circadian clocks. The circadian rhythms can be further broken down into routine cycles during the 24-hour day [Nelson R J. 2005. An Introduction to Behavioral Endocrinology. Sinauer Associates, Inc.: Massachusetts. Pg. 587.] All animals can be classified according to their activity cycles: Diurnal, which describes organisms active during daytime; Nocturnal, which describes organisms active in the night; and Crepuscular, which describes animals primarily active during the dawn and dusk hours (ex: white-tailed deer, some bats).

While circadian rhythms are defined as regulated by endogenous processes, other biological cycles may be regulated by exogenous signals. In some cases, multi-trophic systems may exhibit rhythms driven by the circadian clock of one of the members (which may also be influenced or reset by external factors).

Many other important cycles are also studied, including Infradian rhythms, which are cycles longer than a day. Examples include circannual or annual cycles that govern migration or reproduction cycles in many plants and animals, or the human menstrual cycle; Ultradian rhythms, which are cycles shorter than 24 hours, such as the 90-minute REM cycle, the 4-hour nasal cycle, or the 3-hour cycle of growth hormone production; Tidal rhythms, commonly observed in marine life, which follow the roughly 12.4-hour transition from high to low tide and back; Lunar rhythms, which follow the lunar month (29.5 days). They are relevant, for example, to marine life, as the level of the tides is modulated across the lunar cycle; and Gene oscillations; some genes are expressed more during certain hours of the day than during other hours.

Within each cycle, the time period during which the process is more active is called the acrophase [Refinetti, Roberto (2006). Circadian Physiology. CRC Press/Taylor & Francis Group. ISBN 0-8493-2233-2. Lay summary]. When the process is less active, the cycle is in its bathyphase or trough phase. The particular moment of highest activity is the peak or maximum; the lowest point is the nadir. How high (or low) the process gets is measured by the amplitude.

The sleep cycle and the ultradian rhythms: The normal cycle of sleep and wakefulness implies that, at specific times, various neural systems are being activated while others are being turned off. A key to the neurobiology of sleep is, therefore, to understand the various stages of sleep. In 1953, Nathaniel Kleitman and Eugene Aserinksy showed, using EEG recordings from normal human subjects, that sleep comprises different stages that occur in a characteristic sequence.

Humans descend into sleep in stages that succeed each other over the first hour or so after retiring. These characteristic stages are defined primarily by EEG criteria. Initially, during "drowsiness," the frequency spectrum of the EEG is shifted toward lower values, and the amplitude of the cortical waves slightly increases. This drowsy period, called stage I sleep, eventually gives way to light or stage II sleep, which is characterized by a further decrease in the frequency of the EEG waves and an increase in their amplitude, together with intermittent high-frequency spike clusters called sleep spindles. Sleep spindles are periodic bursts of activity at about 10-12 Hz that generally last 1 or 2 seconds and arise as a result of interactions between thalamic and cortical neurons. In stage III sleep, which represents moderate to deep sleep, the number of spindles decreases, whereas the amplitude of low-frequency waves increases still more. In the deepest level of sleep, stage IV sleep, the predominant EEG activity consists of low-frequency (1-4 Hz), high-amplitude fluctuations called delta waves, the characteristic slow waves for which this phase of sleep is named. The entire sequence from drowsiness to deep stage IV sleep usually takes about an hour.

These four sleep stages are called non-rapid eye movement (non-REM or NREM) sleep, and its most prominent feature is the slow-wave (stage IV) sleep. Sometimes, stages III and IV are combined and referred to jointly as the stage III sleep. It is most difficult to awaken people from slow-wave sleep; hence, it is considered to be the deepest stage of sleep. Following a period of slow-wave sleep, however, EEG recordings show that the stages of sleep reverse to reach a quite different state called rapid eye movement, or REM, sleep. In REM sleep, the EEG recordings are remarkably similar to that of the awake state. This mode is bizarre: a dreamer's brain becomes highly active while the body's muscles are paralyzed, and breathing and heart rate become erratic. After about 10 minutes in REM sleep, the brain typically cycles back through the non-REM sleep stages. Slow-wave sleep usually occurs again in the second period of this continual cycling, but not during the rest of the night. On average, four additional periods of REM sleep occur, each having longer than the preceding cycle durations.

The sleep cycle is an oscillation between the non-REM (including slow-waves) and REM phases of sleep. It is sometimes called the ultradian sleep cycle, sleep-dream cycle, or REM-NREM cycle, to distinguish it from the circadian alternation between sleep and wakefulness. In humans, this cycle takes on average between 1 and 2 hours (approximately 90 min).

The timing of sleep cycles can be observed on EEG by marked distinction in brainwaves manifested during REM and non-REM sleep. Delta wave activity, correlating with slow-wave (deep) sleep, in particular, shows regular oscillations throughout a night's sleep. Secretions of various hormones, including renin, growth hormone, and prolactin, correlate positively with delta-wave activity, whereas secretion of thyroid-stimulating hormone correlates inversely. Heart rate variability, well-known to increase during REM, also correlates inversely with delta-wave oscillations over the ~90-minute cycle.

Homeostatic functions, especially thermoregulation, normally occur during non-REM sleep, but not during REM sleep. During REM sleep, body temperature tends to drift from its mean level, and during non-REM sleep, to return to normal. The alternation between the stages, therefore, maintains body temperature within an acceptable range.

In humans, the transition between non-REM and REM is abrupt; in other animals, less so.

Different models have been proposed to elucidate the complex rhythm of electrochemical processes that result in the regular alternation of REM and non-REM sleep. Monoamines are active during non-REM stages but not during REM stages, whereas acetylcholine is more active during REM sleep. The reciprocal interaction model proposed in the 1970s suggested a cyclic give and take between these two systems. More recent theories such as the "flip-flop" model proposed in the 2000s include the regulatory role of in inhibitory neurotransmitter gamma-aminobutyric acid (GABA).

The average length of the sleep cycle in an adult man is 90 minutes. N1 (NREM stage 1) is when the person is drowsy or awake to falling asleep. Brain waves and muscle activity start to decrease at this stage. N2 is when the person experiences a light sleep. Eye movement has stopped by this time. Brain wave frequency and muscle tonus is decreased. The heart rate and body temperature go down. N3 or even N4 is the most difficult stages to be awakened. Every part of the body is now relaxed, breathing is slowed, blood pressure and body temperature are reduced. REM sleep is a unique state, in which dreams usually occur. The brain is awake, and body paralyzed. This unique stage is usually when the person is in the deepest stage of sleep and dreams. The average length of a sleep cycle usually thought of as 90 min. Some sources give it 90-110 minutes or an even wider range of 80-120 minutes. A seven-eight-hour sleep usually includes five cycles, the middle two of which tend to be longer. REM takes up more of the cycle as the night goes on.

When falling asleep, a series of highly orchestrated events puts the brain to sleep in the above-mentioned stages. Technically, sleep starts in the brain areas that produce slow-wave sleep (SWS). It has been shown that two groups of cells—the ventrolateral preoptic nucleus in the hypothalamus and the parafacial zone in the brain stem—are involved in prompting SWS. When these cells are activated, it triggers a loss of consciousness. After SWS, REM sleep begins. The purpose of REM sleep remains a biological mystery, despite our growing understanding of its biochemistry and neurobiology. It has been shown that a small group of cells in the brain stem, called the subcoeruleus nucleus, control REM sleep. When these cells become injured or diseased, people do not experience the muscle paralysis associated with REM sleep, which can lead to REM sleep behavior disorder—a serious condition in which the afflicted violently act out their dreams. For reasons that are not clear, the amount of REM sleep each day decreases from about 8 hours at birth to 2 hours at 20 years, to only about 45 minutes at 70 years of age.

See Mallick, B. N.; S. R. Pandi-Perumal; Robert W. McCarley; and Adrian R. Morrison (2011). *Rapid Eye Movement Sleep: Regulation and Function*. Cambridge University Press. ISBN 978-0-521-11680-0.

Nir, and Tononi, "Dreaming and the Brain: from Phenomenology to Neurophysiology." *Trends in Cognitive Sciences*, vol. 14, no. 2, 2010, pp. 88-100.

Varela, F., Engel, J., Wallace, B., & Thupten, Jinpa. (1997). *Sleeping, dreaming, and dying: An exploration of consciousness with the Dalai Lama.*

Mental State: A mental state is a state of mind that a subject is in. Some mental states are pure and unambiguous, while humans are capable of complex states that are a combination of mental representations, which may have in their pure state contradictory characteristics. There are several paradigmatic states of mind that a subject has: love, hate, pleasure, fear, and pain. Mental states can also include a waking state, a sleeping state, a flow (or being in the "zone"), and a mood (a mental state). A mental state is a hypothetical state that corresponds to thinking and feeling and consists of a conglomeration of mental representations. A mental state is related to an emotion, though it can also relate to cognitive processes. Because the mental state itself is complex and potentially possess inconsistent attributes, clear interpretation of mental state through external analysis (other than self-reporting) is difficult or impossible. However, some studies report that certain attributes of mental state or thought processes may, in fact, be determined through passive monitoring, such as EEG, or fMRI with some degree of statistical reliability. In most studies, the characterization of mental state was an endpoint, and the raw signals, after statistical classification or semantic labeling, are superseded. The remaining signal energy treated as noise. Current technology does not permit a precise abstract encoding or characterization of the full range of mental states based on neural correlates of mental state.

Brain: The brain is a key part of the central nervous system, enclosed in the skull. In humans, and mammals more generally, the brain controls both autonomic processes, as well as cognitive processes. The brain (and to a lesser extent, the spinal cord) controls all volitional functions of the body and interprets information from the outside world. Intelligence, memory, emotions, speech, thoughts, movements, and creativity are controlled by the brain. The central nervous system also controls autonomic functions and many homeostatic and reflex actions, such as breathing, heart rate, etc. The human brain consists of the cerebrum, cerebellum, and brainstem. The brainstem includes the midbrain, the pons, and the medulla oblongata. Sometimes the diencephalon, the caudal part of the forebrain, is included.

The brainstem has many basic functions, including heart rate, breathing, sleeping, and eating. The skull imposes a barrier to electrical access to the brain functions, and in a healthy human, breaching the dura to access the brain is highly disfavored. The result is that electrical readings of brain activity are filtered by the dura, the cerebrospinal fluid, the skull, the scalp, skin appendages (e.g., hair), resulting in a loss of potential spatial resolution and amplitude of signals emanating from the brain. While magnetic fields resulting from brain electrical activity are accessible, the spatial resolution using feasible sensors is also limited.

The brain is composed of neurons, neuroglia (a.k.a., glia), and other cell types in connected networks that integrate sensory inputs, control movements, facilitate learning and memory, activate and express emotions, and control all other behavioral and cognitive functions. A neuron is a fundamental unit of the nervous system, which comprises the autonomic nervous system and the central nervous system. Neurons communicate primarily through electrochemical pulses that transmit signals between connected cells within and between brain areas. Thus, the desire to noninvasively capture and replicate neural activity associated with cognitive states has been a subject of interest to behavioral and cognitive neuroscientists. Nerve electrical activity may be detected through the skull.

Technological advances now allow for the non-invasive recording of large quantities of information from the brain at multiple spatial and temporal scales. Examples include electroencephalogram ("EEG") data using multi-channel electrode arrays placed on the scalp or inside the brain, magnetoencephalography ("MEG"), magnetic resonance imaging ("MRI"), functional data using functional magnetic resonance imaging ("fMRI"), positron emission tomography ("PET"), near-infrared spectroscopy ("NIRS"), single-photon emission computed tomography ("SPECT"), and others.

Noninvasive neuromodulation technologies have also been developed that can modulate the pattern of neural activity, and thereby cause altered behavior, cognitive states, perception, and motor output. Integration of noninvasive measurement and neuromodulation techniques for identifying and transplanting brain states from neural activity would be very valuable for clinical therapies, such as brain stimulation and related technologies often attempting to treat disorders of cognition.

Mehmetali Gülpınar, Berrak C Yeğen, "The Physiology of Learning and Memory: Role of Peptides and Stress", Current Protein and Peptide Science, 2004(5) www.researchgate.net/publication/8147320_The_Physiology_of_Learning_and_Memory_Role_of_Peptides_and-_Stress. Deep brain stimulation is described in NIH Research Matters, "A noninvasive deep brain stimulation technique", (2017), Brainworks, "QEEG Brain Mapping".

Carmon, A., Mor, J., & Goldberg, J. (1976). Evoked cerebral responses to noxious thermal stimuli in humans. Experimental Brain Research, 25(1), 103-107.

Mental State: A number of studies report that certain attributes of mental state or thought processes may, in fact, be determined through passive monitoring, such as EEG, with some degree of statistical reliability. In most studies, the characterization of mental state was an endpoint, and the raw signals, after statistical classification or semantic labeling, are superseded and the remaining signal energy treated as noise.

Neural Correlates: A neural correlate of a sleep state is an electro-neuro-biological state or the state assumed by some biophysical subsystem of the brain, whose presence necessarily and regularly correlates with such specific sleep states. All properties credited to the mind, including consciousness, emotion, and desires are thought to have direct neural correlates. Neural correlates of a sleep state can be defined as the minimal set of neuronal oscillations that correspond to the given sleep stage.

Brainwaves: At the root of all our thoughts, emotions, and behaviors is the communication between neurons within our brains, a rhythmic or repetitive neural activity in the central nervous system. The oscillation can be produced by a single neuron or by synchronized electrical pulses from ensembles of neurons communicating with each other. The interaction between neurons can give rise to oscillations at a different frequency than the firing frequency of individual neurons. The synchronized activity of large numbers of neurons produces macroscopic oscillations, which can be observed in an electroencephalogram. They are divided into bandwidths to describe their purported functions or functional relationships. Oscillatory activity in the brain is widely observed at different levels of organization and is thought to play a key role in processing neural information. Numerous experimental studies support a functional role of neural oscillations. A unified interpretation, however, is still not determined. Neural oscillations and synchronization have been linked to many cognitive functions such as information transfer, perception, motor control, and memory. EEG signals are relatively easy and safe to acquire, have a long history of analysis, and can have high dimensionality, e.g., up to 128 or 256 separate recording electrodes. While the information represented in each electrode is not independent of the others, and the noise in the signals high, there is much information available through such signals that has not been fully characterized to date.

Brainwaves have been widely studied in neural activity generated by large groups of neurons, mostly by EEG. In general, EEG signals reveal oscillatory activity (groups of neurons periodically firing in synchrony), in specific frequency bands: alpha (7.5-12.5 Hz) that can be detected from the occipital lobe during relaxed wakefulness and which increases when the eyes are closed; delta (1-4 Hz), theta (4-8 Hz), beta (13-30 Hz), low gamma (30-70 Hz), and high gamma (70-150 Hz) frequency bands, where faster rhythms such as gamma activity have been linked to cognitive processing. Higher frequencies imply multiple groups of neurons firing in coordination, either in parallel or in series, or both, since individual neurons do not fire at rates of 100 Hz. Neural oscillations of specific characteristics have been linked to cognitive states, such as awareness and consciousness and different sleep stages. See, Chang-Hwan Im, Computational EEG Analysis: Methods and Applications (Biological and Medical Physics, Biomedical Engineering), Sep. 11, 2019.

Nyquist Theorem states that the highest frequency that can be accurately represented is one-half of the sampling rate. Practically, the sampling rate should be ten times higher than the highest frequency of the signal. (See, www.slideshare.net/ertvk/eeg-examples). While EEG signals are largely band limited, the superimposed noise may not be. Further, the EEG signals themselves represent components from a large number of neurons, which fire independently. Therefore, large bandwidth signal acquisition may have utility.

It is a useful analogy to think of brainwaves as musical notes. Like in a symphony, the higher and lower frequencies link and cohere with each other through harmonics, especially when one considers that neurons may be coordinated not only based on transitions, but also on phase delay. Oscillatory activity is observed throughout the central nervous system at all levels of organization. The dominant neuro oscillation frequency is associated with a respective mental state.

The functions of brainwaves are wide-ranging and vary for different types of oscillatory activity. Neural oscillations also play an important role in many neurological disorders.

In standard EEG recording practice, 19 recording electrodes are placed uniformly on the scalp (the International 10-20 System). In addition, one or two reference electrodes (often placed on earlobes) and a ground electrode (often placed on the nose to provide amplifiers with reference voltages) are required. However, additional electrodes may add minimal useful information unless supplemented by computer algorithms to reduce raw EEG data to a manageable form. When large numbers of electrodes are employed, the potential at each location may be measured with respect to the average of all potentials (the common average reference), which often provides a good estimate of potential at infinity. The common average reference is not appropriate when electrode coverage is sparse (perhaps less than 64 electrodes). See, Paul L. Nunez and Ramesh Srinivasan (2007) Electroencephalogram. Scholarpedia, 2(2):1348, scholarpedia.org/article/Electroencephalogram. Dipole localization algorithms may be useful to determine spatial emission patterns in EEG.

Scalp potential may be expressed as a volume integral of dipole moment per unit volume over the entire brain provided P(r,t) is defined generally rather than in columnar terms. For the important case of dominant cortical sources, scalp potential may be approximated by the following integral over the cortical volume $\theta$, $VS(r,t)=\iiint\theta G(r,r')\cdot P(r',t)d\theta(r')$. If the volume element $d\theta(r')$ is defined in terms of cortical columns, the volume integral may be reduced to an integral over the folded cortical surface. The time-dependence of scalp potential is the weighted sum of all dipole time variations in the brain, although deep dipole volumes typically make negligible contributions. The vector Green's function $G(r,r')$ contains all geometric and conductive information about the head volume conductor and weights the integral accordingly. Thus, each scalar component of the Green's function is essentially an inverse electrical distance between each source component and scalp location. For the idealized case of sources in an infinite medium of constant conductivity, the electrical distance equals the geometric distance. The Green's function accounts for the tissue's finite spatial extent and its inhomogeneity and anisotropy. The forward problem in EEG consists of choosing a head model to provide $G(r,r')$ and carrying out the integral for some assumed source distribution. The inverse problem consists of using the recorded scalp potential distribution $VS(r,t)$ plus some constraints (usual assumptions) on $P(r,t)$ to find the best fit source distribution $P(r,t)$. Since the inverse problem has no unique solution, any inverse solution depends critically on the chosen constraints, for example, only one or two isolated sources, distributed sources confined to the cortex, or spatial and temporal smoothness criteria. High-resolution EEG uses the experimental scalp potential $VS(r,t)$ to predict the potential on the dura surface (the unfolded membrane surrounding the cerebral cortex) $VD(r,t)$. This may be accomplished using a head model Green's function $G(r,r')$ or by estimating the surface Laplacian with either spherical or 3D splines. These two approaches typically provide very similar dura potentials $VD(r,t)$; the estimates of dura potential distribution are unique subject to head model, electrode density, and noise issues.

In an EEG recording system, each electrode is connected to one input of a differential amplifier (one amplifier per pair of electrodes); a common system reference electrode (or synthesized reference) is connected to the other input of each differential amplifier. These amplifiers amplify the voltage between the active electrode and the reference (typically 1,000-100,000 times, or 60-100 dB of voltage gain). The amplified signal is digitized via an analog-to-digital converter, after being passed through an anti-aliasing filter. Analog-to-digital sampling typically occurs at 256-512 Hz in clinical scalp EEG; sampling rates of up to 20 KHz are used in some research applications. The EEG signals can be captured with open source hardware such as OpenBCI, and the signal can be processed by freely available EEG software such as EEGLAB or the Neurophysiological Biomarker Toolbox. A typical adult human EEG signal is about 10 μV to 100 μV in amplitude when measured from the scalp and is about 10-20 mV when measured from subdural electrodes.

Delta wave (en.wikipedia.org/wiki/Delta_wave) is the frequency range up to 4 Hz. It tends to be the highest in amplitude and the slowest waves. It is normally seen in adults in NREM (en.wikipedia.org/wiki/NREM). It is also seen normally in babies. It may occur focally with subcortical lesions and in general distribution with diffuse lesions, metabolic encephalopathy hydrocephalus or deep midline lesions. It is, usually, most prominent frontally in adults (e.g., FIRDA-frontal intermittent rhythmic delta) and posteriorly in children (e.g., OIRDA-occipital intermittent rhythmic delta).

Theta is the frequency range from 4 Hz to 7 Hz. Theta is normally seen in young children. It may be seen in drowsiness or arousal in older children and adults; it can also be seen in meditation. Excess theta for age represents abnormal activity. It can be seen as a focal disturbance in focal subcortical lesions; it can be seen in the generalized distribution in diffuse disorder or metabolic encephalopathy or deep midline disorders or some instances of hydrocephalus. On the contrary, this range has been associated with reports of relaxed, meditative, and creative states.

Alpha is the frequency range from 7 Hz to 14 Hz. This was the "posterior basic rhythm" (also called the "posterior dominant rhythm" or the "posterior alpha rhythm"), seen in the posterior regions of the head on both sides, higher in amplitude on the dominant side. It emerges with the closing of the eyes and with relaxation and attenuates with eye opening or mental exertion. The posterior basic rhythm is slower than 8 Hz in young children (therefore technically in the theta range). In addition to the posterior basic rhythm, there are other normal alpha rhythms such as the sensorimotor, or mu rhythm (alpha activity in the contralateral sensory and motor cortical areas) that emerges when the hands and arms are idle; and the "third rhythm" (alpha activity in the temporal or frontal lobes). Alpha can be abnormal; for example, an EEG that has diffuse alpha occurring in a coma and is not responsive to external stimuli is referred to as "alpha coma."

Beta is the frequency range from 15 Hz to about 30 Hz. It is usually seen on both sides in symmetrical distribution and is most evident frontally. Beta activity is closely linked to motor behavior and is generally attenuated during active movements. Low-amplitude beta with multiple and varying frequencies is often associated with active, busy, or anxious thinking and active concentration. Rhythmic beta with a dominant set of frequencies is associated with various pathologies, such as Dup15q syndrome, and drug effects, especially benzodiazepines. It may be absent or reduced in areas of cortical damage. It is the dominant rhythm in patients who are alert or anxious or who have their eyes open.

Gamma is the frequency range of approximately 30-100 Hz. Gamma rhythms are thought to represent binding of different populations of neurons together into a network to carry out a certain cognitive or motor function.

Mu range is 8-13 Hz and partly overlaps with other frequencies. It reflects the synchronous firing of motor neurons in a rest state. Mu suppression is thought to reflect motor mirror neuron systems because when an action is observed, the pattern extinguishes, possibly because of the normal neuronal system and the mirror neuron system "go out of sync" and interfere with each other. (en.wikipedia.org/wiki/Electroencephalography). See Reference List 2. All sleep stages are associated with frequencies below 13 Hz-delta (1-4 Hz), theta (4-8 Hz), and alpha (8-12 Hz). While these frequencies may be reproduced in transcranial electric (or magnetic) stimulation, or via sensory stimulation with light, any attempts to reproduce these frequencies for stimulation via sound ran into problems associated with infrasound, defined as any sound below 20 Hz frequency. Firstly, it is difficult to generate infrasound through acoustic speakers. Earbuds are too small for that and so are most regular speakers. Specialized large subwoofers with circular design or sound guides may be used, but tend to be impractical.

A more serious problem is the effect of the infrasound on human health. While many animals (e.g., elephants and whales) communicate via infrasound, in humans, infrasound causes undesirable effects including send of panic, fear, and anxiety. Prolonged exposure to infrasound could be dangerous to human health. See, for example, Persinger, M. A. Nat Hazards (2014) 70:501. doi.org/10.1007/s11069-013-0827-3. These problems are addressed using binaural beats.

Binaural beats: (See en.wikipedia.org/wiki/Beat_(acoustics)#Binaural_beats) A binaural beat is an auditory illusion perceived when two different pure-tone sine waves, both with frequencies lower than 1500 Hz, with less than a 40 Hz difference between them, are presented to a listener dichotically (one through each ear).

For example, if a 530 Hz pure tone is presented to a subject's right ear, while a 520 Hz pure tone is presented to the subject's left ear, the listener will perceive the auditory illusion of a third tone, in addition to the two pure-tones presented to each ear. The third sound is called a binaural beat, and in this example would have a perceived pitch correlating to a frequency of 10 Hz, that being the difference between the 530 Hz and 520 Hz pure tones presented to each ear.

Binaural-beat perception originates in the inferior colliculus of the midbrain and the superior olivary complex of the brainstem, where auditory signals from each ear are integrated and precipitate electrical impulses along neural pathways through the reticular formation up the midbrain to the thalamus, auditory cortex, and other cortical regions. Binaural beats are widely used in brain stimulation.

EEG AND qEEG: An EEG electrode will mainly detect the neuronal activity in the brain region just beneath it. However, the electrodes receive the activity from thousands of neurons. One square millimeter of cortex surface, for example, has more than 100,000 neurons. It is only when the input to a region is synchronized with electrical activity occurring at the same time that simple periodic waveforms in the EEG become distinguishable. The temporal pattern associated with specific brainwaves can be digitized and encoded a non-transient memory, and embodied in or referenced by, computer software.

EEG and MEG are available technologies to monitor brain electrical activity. Each generally has sufficient temporal resolution to follow dynamic changes in brain electrical activity. EEG and quantitative EEG (qEEG) are electrophysiological monitoring methods that analyze the electrical activity of the brain to measure and display patterns that correspond to cognitive states and/or diagnostic information. It is typically noninvasive, with the electrodes placed on the scalp, although invasive electrodes are also used in some cases. EEG signals may be captured and analyzed by a mobile device, often referred to as "brain wearables." There are a variety of "brain wearables" readily available on the market today. EEGs can be obtained with a non-invasive method where the aggregate oscillations of brain electric potentials are recorded with numerous electrodes attached to the scalp of a person. Most EEG signals originate in the brain's outer layer (the cerebral cortex), believed largely responsible for our thoughts, emotions, and behavior. Cortical synaptic action generates electrical signals that change in the 10 to 100-millisecond range. Transcutaneous EEG signals are limited by the relatively insulating nature of the skull surrounding the brain, the conductivity of the cerebrospinal fluid and brain tissue, relatively low amplitude of individual cellular electrical activity, and distances between the cellular current flows and the electrodes. EEG is characterized by: (1) Voltage; (2) Frequency; (3) Spatial location; (4) Inter-hemispheric symmetries; (5) Reactivity (reaction to state change); (6) Character of waveform occurrence (random, serial, continuous); and (7) Morphology of transient events. EEGs can be separated into two main categories. Spontaneous EEG which occur in the absence of specific sensory stimuli and evoked potentials (EPs) which are associated with sensory stimuli like repeated light flashes, auditory tones, finger pressure, or mild electric shocks. The latter is recorded, for example, by time averaging to remove effects of spontaneous EEG. Non-sensory triggered potentials are also known. EP's typically are time synchronized with the trigger, and thus have an organization principle. Event-related potentials (ERPs) provide evidence of a direct link between cognitive events and brain electrical activity in a wide range of cognitive paradigms. It has generally been held that an ERP is the result of a set of discrete stimulus-evoked brain events. Event-related potentials (ERPs) are recorded in the same way as EPs, but occur at longer latencies from the stimuli and are more associated with an endogenous brain state.

Typically, a magnetic sensor with sufficient sensitivity to individual cell depolarization or small groups is a superconducting quantum interference device (SQUID), which requires cryogenic temperature operation, either at liquid nitrogen temperatures (high-temperature superconductors, HTS) or liquid helium temperatures (low-temperature superconductors, LTS). However, current research shows the possible feasibility of room temperature superconductors (20C). Magnetic sensing has an advantage, due to the dipole nature of sources, of having better potential volumetric localization; however, due to this added information, the complexity of signal analysis is increased.

In general, the electromagnetic signals detected represent action potentials, an automatic response of a nerve cell to depolarization beyond a threshold, which briefly opens conduction channels. The cells have ion pumps which seek to maintain a depolarized state. Once triggered, the action potential propagates along the membrane in two-dimensions, causing a brief high level of depolarizing ion flow. There is a quiescent period after depolarization that generally prevents oscillation within a single cell. Since the exon extends from the body of the neuron, the action potential will typically proceed along the length of the axon, which terminates in a synapse with another cell. While direct electrical connections between cells occur, often the axon releases a neurotransmitter compound into the synapse, which causes depolarization or hyperpolarization of the target cell. Indeed, the result may also be the release of a hormone or peptide, which may have a local or more distant effect.

The electrical fields detectable externally tend to not include signals which low-frequency signals, such as static levels of polarization, or cumulative depolarizing or hyperpolarizing effects between action potentials. In myelinated tracts, the current flows at the segments tend to be small, and therefore, the signals from individual cells are small. Therefore, the largest signal components are from the synapses and cell bodies. In the cerebrum and cerebellum, these structures are mainly in the cortex, which is largely near the skull, making EEG useful, since it provides spatial discrimination based on electrode location. However, deep signals are attenuated and poorly localized. Magnetoencephalography detects dipoles, which derive from current flow, rather than voltage changes. In the case of a radially or spherically symmetric current flow within a short distance, the dipoles will tend to cancel, while net current flows long axons will reinforce. Therefore, an electroencephalogram reads a different signal than a magnetoencephalogram.

EEG-based studies of emotional specificity at the single-electrode level demonstrated that asymmetric activity at the frontal site, especially in the alpha (8-12 Hz) band, is associated with emotion. Voluntary facial expressions of smiles of enjoyment produce higher left frontal activation. Decreased left frontal activity is observed during the voluntary facial expressions of fear. In addition to alpha-band activity, theta band power at the frontal midline (Fm) has also been found to relate to emotional states. Pleasant (as opposed to unpleasant) emotions are associated with an increase in frontal midline theta power. Many studies have sought to utilize pattern classification, such as neural networks, statistical classifiers, clustering algorithms, etc., to differentiate between various emotional states reflected in EEG. Ekman and Davidson found that voluntary facial expressions of smiles of enjoyment produced higher left frontal activation (Ekman P, Davidson R J (1993) Voluntary Smiling Changes Regional Brain Activity. Psychol Sci 4:342-345). Another study by Coan et al. found decreased left frontal activity during the voluntary facial expressions of fear (Coan J A, Allen J J, Harmon-Jones E (2001) Voluntary facial expression and hemispheric asymmetry over the frontal cortex. Psychophysiology 38:912-925). Sammler and colleagues, for example, showed that pleasant (as opposed to unpleasant) emotion is associated with an increase in frontal midline theta power (Sammler D, Grigutsch M, Fritz T, Koelsch S (2007) Music and emotion: Electrophysiological correlates of the processing of pleasant and unpleasant music. Psychophysiology 44:293-304). To further demonstrate whether these emotion-specific EEG characteristics are strong enough to differentiate between various emotional states, some studies have utilized a pattern classification analysis approach.

Detecting different emotional states by EEG may be more appropriate using EEG-based functional connectivity. There are various ways to estimate EEG-based functional brain connectivity: correlation, coherence, and phase synchronization indices between each pair of EEG electrodes had been used. The assumption is that a higher correlation map indicates a stronger relationship between two signals. (Brazier M A, Casby J U (1952) Cross-correlation and autocorrelation studies of EEG potentials. Electroen clin neuro 4:201-211). Coherence gives information similar to correlation but also includes the covariation between two signals as a function of frequency. (Cantero J L, Atienza M, Salas R M, Gomez C M (1999) Alpha EEG coherence in different brain states: an electrophysiological index of the arousal level in human subjects. Neurosci lett 271:167-70.) The assumption is that higher correlation indicates a stronger relationship between two signals. (Guevara M A, Corsi-Cabrera M (1996) EEG coherence or EEG correlation? Int J Psychophysiology 23:145-153; Cantero J L, Atienza M, Salas R M, Gomez C M (1999) Alpha EEG coherence in different brain states: an electrophysiological index of the arousal level in human subjects. Neurosci lett 271:167-70; Adler G, Brassen S, Jajcevic A (2003) EEG coherence in Alzheimer's dementia. J Neural Transm 110:1051-1058; Deeny S P, Hillman C H, Janelle C M, Hatfield B D (2003) Cortico-cortical communication and superior performance in skilled marksmen: An EEG coherence analysis. J Sport Exercise Psy 25:188-204.) Phase synchronization among the neuronal groups estimated based on the phase difference between two signals is another way to estimate the EEG-based functional connectivity among brain areas. It is. (Franaszczuk P J, Bergey G K (1999) An autoregressive method for the measurement of synchronization of interictal and ictal EEG signals. Biol Cybern 81:3-9.)

A number of groups have examined emotional specificity using EEG-based functional brain connectivity. For example, Shin and Park showed that when emotional states become more negative at high room temperatures, correlation coefficients between the channels in temporal and occipital sites increase (Shin J-H, Park D-H. (2011) Analysis for Characteristics of Electroencephalogram (EEG) and Influence of Environmental Factors According to Emotional Changes. In Lee G, Howard D, Ślęzak D, editors. Convergence and Hybrid Information Technology. Springer Berlin Heidelberg, 488-500.) Hinrichs and Machleidt demonstrated that coherence decreases in the alpha band during sadness, compared to happiness (Hinrichs H, Machleidt W (1992) Basic emotions reflected in EEG-coherences. Int J Psychophysiol 13:225-232). Miskovic and Schmidt found that EEG coherence between the prefrontal cortex and the posterior cortex increased while viewing highly emotionally arousing (i.e., threatening) images, compared to viewing neutral images (Miskovic V, Schmidt L A (2010) Cross-regional cortical synchronization during affective image viewing. Brain Res 1362:102-111). Costa and colleagues applied the synchronization index to detect interaction in different brain sites under different emotional states (Costa T, Rognoni E, Galati D (2006) EEG phase synchronization during emotional response to positive and negative film stimuli. Neurosci Lett 406:159-164). Costa's results showed an overall increase in the synchronization index among frontal channels during emotional stimulation, particularly during negative emotion (i.e., sadness). Furthermore, phase synchronization patterns were found to differ between positive and negative emotions. Costa also found that sadness was more synchronized than happiness at each frequency band and was associated with a wider synchronization both between the right and left frontal sites and within the left hemisphere. In contrast, happiness was associated with a wider synchronization between the frontal and occipital sites.

Different connectivity indices are sensitive to different characteristics of EEG signals. Correlation is sensitive to phase and polarity but is independent of amplitudes. Changes in both amplitude and phase lead to a change in coherence (Guevara M A, Corsi-Cabrera M (1996) EEG coherence or EEG correlation? Int J Psychophysiol 23:145-153). The phase synchronization index is only sensitive to a change in phase (Lachaux J P, Rodriguez E, Martinerie J, Varela F J (1999) Measuring phase synchrony in brain signals. Hum Brain Mapp 8:194-208).

A number of studies have tried to classify emotional states by means of recording and statistically analyzing EEG signals from the central nervous systems. See, for example:

Lin Y P, Wang C H, Jung T P, Wu T L, Jeng S K, et al. (2010) EEG-Based Emotion Recognition in Music Listening. IEEE T Bio Med Eng 57:1798-1806

Murugappan M, Nagarajan R, Yaacob S (2010) Classification of human emotion from EEG using discrete wavelet transform. J Biomed Sci Eng 3:390-396.

Murugappan M, Nagarajan R, Yaacob S (2011) Combining Spatial Filtering and Wavelet Transform for Classifying Human Emotions Using EEG Signals. J Med. Bio. Eng. 31:45-51.

Berkman E, Wong D K, Guimaraes M P, Uy E T, Gross J J, et al. (2004) Brain wave recognition of emotions in EEG. Psychophysiology 41: S71-S71.

Chanel G, Kronegg J, Grandjean D, Pun T (2006) Emotion assessment: Arousal evaluation using EEG's and peripheral physiological signals. Multimedia Content Representation, Classification and Security 4105:530-537.

Hagiwara KlaM (2003) A Feeling Estimation System Using a Simple Electroencephalograph. IEEE International Conference on Systems, Man and Cybernetics. 4204-4209.

You-Yun Lee and Shulan Hsieh studied different emotional states by means of EEG-based functional connectivity patterns. They used emotional film clips to elicit three different emotional states.

The dimensional theory of emotion, which asserts that there are neutral, positive, and negative emotional states, may be used to classify emotional states because numerous studies have suggested that the responses of the central nervous system correlate with emotional valence and arousal. (See, for example, Davidson R J (1993) Cerebral Asymmetry and Emotion-Conceptual and Methodological Conundrums. Cognition Emotion 7:115-138; Jones N A, Fox N A (1992) Electroencephalogram asymmetry during emotionally evocative films and its relation to positive and negative affectivity. Brain Cogn 20:280-299; Schmidt L A, Trainor L J (2001) Frontal brain electrical activity (EEG) distinguishes valence and intensity of musical emotions. Cognition Emotion 15:487-500; Tomarken A J, Davidson R J, Henriques J B (1990) Resting frontal brain asymmetry predicts affective responses to films. J Pers Soc Psychol 59:791-801.) As suggested by Mauss and Robins (2009), "measures of emotional responding appear to be structured along dimensions (e.g., valence, arousal) rather than discrete emotional states (e.g., sadness, fear, anger)".

EEG-based functional connectivity change was found to be significantly different among emotional states of neutral, positive, or negative. Lee Y—Y, Hsieh S (2014) Classifying Different Emotional States by Means of EEG-Based Functional Connectivity Patterns. PLOS ONE 9 (4): e95415. doi.org/10.1371/journal.pone.0095415. A connectivity pattern may be detected by pattern classification analysis using Quadratic Discriminant Analysis. The results indicated that the classification rate was better than chance. They concluded that estimating EEG-based functional connectivity provides a useful tool for studying the relationship between brain activity and emotional states.

Emotions affects learning. Intelligent Tutoring Systems (ITS) learner model initially composed of a cognitive module was extended to include a psychological module and an emotional module. Alicia Heraz et al. introduced an emomental agent. It interacts with an ITS to communicate the emotional state of the learner based upon his mental state. The mental state was obtained from the learner's brainwaves. The agent learns to predict the learner's emotions by using machine learning techniques. (Alicia Heraz, Ryad Razaki; Claude Frasson, "Using machine learning to predict learner emotional state from brainwaves" Advanced Learning Technologies, 2007. ICALT 2007. Seventh IEEE International Conference on Advanced Learning Technologies (ICALT 2007)) See also:

Ella T. Mampusti, Jose S. Ng, Jarren James I. Quinto, Grizelda L. Teng, Merlin Teodosia C. Suarez, Rhia S. Trogo, "Measuring Academic Affective States of Students via Brainwave Signals", Knowledge and Systems Engineering (KSE) 2011 Third International Conference on, pp. 226-231, 2011

Judith J. Azcarraga, John Francis Ibanez Jr., lanne Robert Lim, Nestor Lumanas Jr., "Use of Personality Profile in Predicting Academic Emotion Based on Brainwaves Signals and Mouse Behavior", Knowledge and Systems Engineering (KSE) 2011 Third International Conference on, pp. 239-244, 2011.

Yi-Hung Liu, Chien-Te Wu, Yung-Hwa Kao, Ya-Ting Chen, "Single-trial EEG-based emotion recognition using kernel Eigen-emotion pattern and adaptive support vector machine", Engineering in Medicine and Biology Society (EMBC) 2013 35th Annual International Conference of the IEEE, pp. 4306-4309, 2013, ISSN 1557-170X.

Thong Tri Vo, Nam Phuong Nguyen, Toi Vo Van, IFMBE Proceedings, vol. 63, pp. 621, 2018, ISSN 1680-0737, ISBN 978-981-10-4360-4.

Adrian Rodriguez Aguinaga, Miguel Angel Lopez Ramirez, Lecture Notes in Computer Science, vol. 9456, pp. 177, 2015, ISSN 0302-9743, ISBN 978-3-319-26507-0.

Judith Azcarraga, Merlin Teodosia Suarez, "Recognizing Student Emotions using Brainwaves and Mouse Behavior Data", International Journal of Distance Education Technologies, vol. 11, pp. 1, 2013, ISSN 1539-3100.

Tri Thong Vo, Phuong Nam Nguyen, Van Toi Vo, IFMBE Proceedings, vol. 61, pp. 67, 2017, ISSN 1680-0737, ISBN 978-981-10-4219-5.

Alicia Heraz, Claude Frasson, Lecture Notes in Computer Science, vol. 5535, pp. 367, 2009, ISSN 0302-9743, ISBN 978-3-642-02246-3.

Hamwira Yaacob, Wahab Abdul, Norhaslinda Kamaruddin, "Classification of EEG signals using MLP based on categorical and dimensional perceptions of emotions", Information and Communication Technology for the Muslim World (ICT4M) 2013 5th International Conference on, pp. 1-6, 2013.

Yuan-Pin Lin, Chi-Hong Wang, Tzyy-Ping Jung, Tien-Lin Wu, Shyh-Kang Jeng, Jeng-Ren Duann, Jyh-Horng Chen, "EEG-Based Emotion Recognition in Music Listening", Biomedical Engineering IEEE Transactions on, vol. 57, pp. 1798-1806, 2010, ISSN 0018-9294.

Yi-Hung Liu, Wei-Teng Cheng, Yu-Tsung Hsiao, Chien-Te Wu, Mu-Der Jeng, "EEG-based emotion recognition based on kernel Fisher's discriminant analysis and spectral powers", Systems Man and Cybernetics (SMC) 2014 IEEE International Conference on, pp. 2221-2225, 2014.

Using EEG to assess the emotional state has numerous practical applications. One of the first such applications was the development of a travel guide based on emotions by measuring brainwaves by the Singapore tourism group. "By studying the brainwaves of a family on vacation, the researchers drew up the Singapore Emotion Travel Guide, which advises future visitors of the emotions they can expect to experience at different attractions." (www.lonelyplanet-.com/news/2017/04/12/singapore-emotion-travel-guide) Joel Pearson at University of New South Wales and his group developed the protocol of measuring brainwaves of travelers using EEG and decoding specific emotional states.

Another recently released application pertains to virtual reality (VR) technology. On Sep. 18, 2017 Looxid Labs launched a technology that harnesses EEG from a subject waring a VR headset. Looxid Labs intention is to factor in brainwaves into VR applications in order to accurately infer emotions. Other products such as MindMaze and even Samsung have tried creating similar applications through facial muscles recognition. (scottamyx.com/2017/10/13/looxid-labs-vr-brain-waves-human-emotions/). According to its website (looxidlabs.com/device-2/), the Looxid Labs Development Kit provides a VR headset embedded with miniaturized eye and brain sensors. It uses 6 EEG channels: Fp1, Fp2, AF7, AF8, AF3, AF4 in the international 10-20 system.

To assess a user's state of mind, a computer may be used to analyze the EEG signals produced by the brain of the user. However, the emotional states of a brain are complex, and the brainwaves associated with specific emotions seem to change over time. Wei-Long Zheng at Shanghai Jiao Tong University used machine learning to identify the emotional brain states and to repeat it reliably. The machine learning algorithm found a set of patterns that clearly distinguished positive, negative, and neutral emotions that worked for different subjects and for the same subjects over time with an accuracy of about 80 percent. (See Wei-Long Zheng, Jia-Yi Zhu, Bao-Liang Lu, Identifying Stable Patterns over Time for Emotion Recognition from EEG, arxiv.org/abs/1601.02197; see also How One Intelligent Machine Learned to Recognize Human Emotions, MIT Technology Review, Jan. 23, 2016.)

MEG: Magnetoencephalography (MEG) is a functional neuroimaging technique for mapping brain activity by recording magnetic fields produced by electrical currents occurring naturally in the brain, using very sensitive magnetometers. Arrays of SQUIDs (superconducting quantum interference devices) are currently the most common magnetometer, while the SERF (spin exchange relaxation-free) magnetometer is being investigated (Hämäläinen, Matti; Hari, Riitta; Ilmoniemi, Risto J.; Knuutila, Jukka; Lounasmaa, Olli V. (1993). "Magnetoencephalography-theory, instrumentation, and applications to noninvasive studies of the working human brain". Reviews of Modern Physics. 65 (2): 413-497. ISSN 0034-6861. doi: 10.1103/RevModPhys.65.413.) It is known that "neuronal activity causes local changes in cerebral blood flow, blood volume, and blood oxygenation" (Dynamic magnetic resonance imaging of human brain activity during primary sensory stimulation. K. K. Kwong, J. W. Belliveau, D. A. Chesler, I. E. Goldberg, R. M. Weisskoff, B. P. Poncelet, D. N. Kennedy, B. E. Hoppel, M. S. Cohen, and R. Turner). Using "a 122-channel D. C. SQUID magnetometer with a helmet-shaped detector array covering the subject's head" it has been shown that the "system allows simultaneous recording of magnetic activity all over the head." (122-channel squid instrument for investigating the magnetic signals from the human brain.) A. I. Ahonen, M. S. Hämäläinen, M. J. Kajola, J. E. T. Knuutila, P. P. Laine, O. V. Lounasmaa, L. T. Parkkonen, J. T. Simola, and C. D. Tesche Physica Scripta, Volume 1993, T49A).

In some cases, magnetic fields cancel, and thus the detectable electrical activity may fundamentally differ from the detectable electrical activity obtained via EEG. However, the main types of brain rhythms are detectable by both methods.

See: U.S. Pub. App. and U.S. Pat. Nos. 5,059,814; 5,118, 606; 5,136,687; 5,224,203; 5,303,705; 5,325,862; 5,461, 699; 5,522,863; 5,640,493; 5,715,821; 5,719,561; 5,722, 418; 5,730,146; 5,736,543; 5,737,485; 5,747,492; 5,791, 342; 5,816,247; 6,497,658; 6,510,340; 6,654,729; 6,893, 407; 6,950,697; 8,135,957; 8,620,206; 8,644,754; 9,118, 775; 9,179,875; 9,642,552; 20030018278; 20030171689; 20060293578; 20070156457; 20070259323; 20080015458; 20080154148; 20080229408; 20100010365; 20100076334; 20100090835; 20120046531; 20120052905; 20130041281; 20150081299; 20150262016. See EP1304073A2; EP1304073A3; WO2000025668A1; and WO2001087153A1.

MEG seeks to detect the magnetic dipole emission from an electrical discharge in cells, e.g., neural action potentials.

Typical sensors for MEGs are superconducting quantum interference devices (SQUIDs). These currently require cooling to liquid nitrogen or liquid helium temperatures. However, the development of room temperature, or near room temperature superconductors, and miniature cryocoolers, may permit field deployments and portable or mobile detectors. Because MEGs are less influenced by medium conductivity and dielectric properties, and because they inherently detect the magnetic field vector, MEG technology permits volumetric mapping of brain activity and distinction of complementary activity that might suppress detectable EEG signals. MEG technology also supports vector mapping of fields, since magnetic emitters are inherently dipoles, and therefore a larger amount of information is inherently available. See, Reference List 3.

EEGs and MEGs can monitor the state of consciousness. For example, states of deep sleep are associated with slower EEG oscillations of larger amplitude. Various signal analysis methods allow for robust identifications of distinct sleep stages, depth of anesthesia, epileptic seizures, and connections to detailed cognitive events.

Neurofeedback: Neurofeedback (NFB), also called neurotherapy or neurobiofeedback, is a type of biofeedback that uses real-time displays of brain activity-most commonly EEG, to teach self-regulation of brain function. Typically, sensors are placed on the scalp to measure activity, with measurements displayed using video displays or sound. The feedback may be in various other forms as well. Typically, the feedback is sought to be presented through primary sensory inputs, but this is not a limitation on the technique.

The applications of neurofeedback to enhance performance extend to the arts in fields such as music, dance, and acting. A study with conservatoire musicians found that alpha-theta training benefitted the three music domains of musicality, communication, and technique. Historically, alpha-theta training, a form of neurofeedback, was created to assist creativity by inducing hypnagogia, a "borderline waking state associated with creative insights", through the facilitation of neural connectivity. Alpha-theta training has also been shown to improve novice singing in children. Alpha-theta neurofeedback, in conjunction with heart rate variability training, a form of biofeedback, has also produced benefits in dance by enhancing performance in competitive ballroom dancing and increasing cognitive creativity in contemporary dancers. Additionally, neurofeedback has also been shown to instill a superior flow state in actors, possibly due to greater immersion while performing.

Several studies of brain wave activity in experts while performing a task related to their respective area of expertise revealed certain characteristic telltale signs of so-called "flow" associated with top-flight performance. Mihaly Csikszentmihalyi (University of Chicago) found that the most skilled chess players showed less EEG activity in the prefrontal cortex, which is typically associated with higher cognitive processes such as working memory and verbalization, during a game.

Chris Berka et al., Advanced Brain Monitoring, Carlsbad, California, The International J. Sport and Society, vol 1, p 87, looked at the brainwaves of Olympic archers and professional golfers. A few seconds before the archers fired off an arrow or the golfers hit the ball, the team spotted a small increase in alpha band patterns. This may correspond to the contingent negative variation observed in evoked potential studies, and the Bereitschaftspotential or BP (from German, "readiness potential"), also called the pre-motor potential or readiness potential (RP), a measure of activity in the motor cortex and supplementary motor area of the brain leading up to voluntary muscle movement. Berka also trained novice marksmen using neurofeedback. Each person was hooked up to electrodes that tease out and display specific brainwaves, along with a monitor that measured their heartbeat. By controlling their breathing and learning to deliberately manipulate the waveforms on the screen in front of them, the novices managed to produce the alpha waves characteristic of the flow state. This, in turn, helped them improve their accuracy at hitting the targets.

Low Energy Neurofeedback System (LENS): The LENS, or Low Energy Neurofeedback System, uses a very low power electromagnetic field, to carry feedback to the person receiving it. The feedback travels down the same wires carrying the brainwaves to the amplifier and computer. Although the feedback signal is weak, it produces a measurable change in the brainwaves without conscious effort from the individual receiving the feedback. The system is software controlled, to receive input from EEG electrodes, to control the stimulation. Through the scalp. Neurofeedback uses a feedback frequency that is different from, but correlates with, the dominant brainwave frequency. When exposed to this feedback frequency, the EEG amplitude distribution changes in power. Most of the time, the brainwaves reduce in power, but at times they also increase in power. In either case, the result is a changed brainwave state and much greater ability for the brain to regulate itself.

Content-Based Brainwave Analysis: Memories are not unique. Janice Chen, Nature Neuroscience, DOI: 10.1038/nn.4450, showed that when people describe the episode from Sherlock Holmes drama, their brain activity patterns were almost exactly the same as each other's, for each scene. Moreover, there is also evidence that, when a person tells someone else about it, they implant that same activity into their brain as well. Moreover, research in which people who have not seen a movie listen to someone else's description of it, Chen et al. have found that the listener's brain activity looks much like that of the person who has seen it. See also "Our brains record and remember things in exactly the same way" by Andy Coghlan, New Scientist, Dec. 5, 2016 (www.newscientist.com/article/2115093-our-brains-record-and-remember-things-in-exactly-the-same-way/) Brian Pasley, Frontiers in Neuroengineering, doi.org/whb, developed a technique for reading thoughts. The team hypothesized that hearing speech and thinking to oneself might spark some of the same neural signatures in the brain. They supposed that an algorithm trained to identify speech heard out loud might also be able to identify words that are thought. In the experiment, the decoder trained on speech was able to reconstruct which words several of the volunteers were thinking, using neural activity alone. See also "Hearing our inner voice" by Helen Thomson. New Scientist, Oct. 29, 2014 (www.newscientist.com/article/mg22429934-000-brain-decoder-can-eavesdrop-on-your-inner-voice/)

Jack Gallant et al. were able to detect which of a set of images someone was looking at from a brain scan, using software that compared the subject's brain activity while looking at an image with that captured while they were looking at "training" photographs. The program then picked the most likely match from a set of previously unseen pictures.

Ann Graybiel and Mark Howe used electrodes to analyze brainwaves in the ventromedial striatum of rats while they were taught to navigate a maze. As rats were learning the task, their brain activity showed bursts of fast gamma waves. Once the rats mastered the task, their brainwaves slowed to almost a quarter of their initial frequency, becoming beta waves. Graybiel's team posited that this transition reflects when learning becomes a habit.

Bernard Balleine, Proceedings of the National Academy of Sciences, DOI: 10.1073/pnas. 1113158108. See also "Habits form when brainwaves slow down" by Wendy Zukerman. New Scientist, Sep. 26, 2011 (www.newscientist.com/article/dn20964-habits-form-when-brainwaves-slow-down/) posits that the slower brainwaves may be the brain weeding out excess activity to refine behavior. He suggests it might be possible to boost the rate at which they learn a skill by enhancing such beta-wave activity.

U.S. Pat. No. 9,763,592 provides a system for instructing a user behavior change comprising: collecting and analyzing bioelectrical signal datasets; and providing a behavior change suggestion based upon the analysis. A stimulus may be provided to prompt an action by the user, which may be visual, auditory, or haptic. See also U.S. Pat. No. 9,622,660, 20170041699; 20130317384; 20130317382; 20130314243; 20070173733; and 20070066914.

The chess game is a good example of a cognitive task which needs a lot of training and experience. A number of EEG studies have been done on chess players. Pawel Stepien, Wlodzimierz Klonowski and Nikolay Suvorov, Nonlinear analysis of EEG in chess players, EPJ Nonlinear Biomedical Physics 20153:1, showed better applicability of Higuchi Fractal Dimension method for analysis of EEG signals related to chess tasks than that of Sliding Window Empirical Mode Decomposition. The paper shows that the EEG signal during the game is more complex, non-linear, and non-stationary even when there are no significant differences between the game and relaxed state in the contribution of different EEG bands to the total power of the signal. There is the need for gathering more data from more chess experts and of comparing them with data from novice chess players. See also Junior, L. R. S., Cesar, F. H. G., Rocha, F. T., and Thomaz, C. E. EEG and Eye Movement Maps of Chess Players. Proceedings of the Sixth International Conference on Pattern Recognition Applications and Methods. (ICPRAM 2017) pp. 343-441. (fei.edu.br/~cet/icpram17_LaercioJunior.pdf).

Estimating EEG-based functional connectivity provides a useful tool for studying the relationship between brain activity and emotional states. See You-Yun Lee, Shulan Hsieh. Classifying Different Emotional States by Means of EEG-Based Functional Connectivity Patterns. Apr. 17, 2014, (doi.org/10.1371/journal.pone.0095415), which aimed to classify different emotional states by means of EEG-based functional connectivity patterns, and showed that the EEG-based functional connectivity change was significantly different among emotional states. Furthermore, the connectivity pattern was detected by pattern classification analysis using Quadratic Discriminant Analysis. The results indicated that the classification rate was better than chance. Estimating EEG-based functional connectivity provides a useful tool for studying the relationship between brain activity and emotional states.

Sensory Stimulation: Light, sound or electromagnetic fields may be used to remotely convey a temporal pattern of brainwaves. See Reference List 4.

Light Stimulation: The functional relevance of brain oscillations in the alpha frequency range (8-13 Hz) has been repeatedly investigated through the use of rhythmic visual stimulation. There are two hypotheses on the origin of steady-state visual evoked potential (SSVEP) measured in EEG during rhythmic stimulation: entrainment of brain oscillations and superposition of event-related responses (ERPs). The entrainment but not the superposition hypothesis justifies rhythmic visual stimulation as a means to manipulate brain oscillations because superposition assumes a linear summation of single responses, independent from ongoing brain oscillations. Participants stimulated with the rhythmic flickering light of different frequencies and intensities, and entrainment was measured by comparing the phase coupling of brain oscillations stimulated by rhythmic visual flicker with the oscillations induced by arrhythmic jittered stimulation, varying the time, stimulation frequency, and intensity conditions. Phase coupling was found to be more pronounced with increasing stimulation intensity as well as at stimulation frequencies closer to each participant's intrinsic frequency. Even in a single sequence of an SSVEP, non-linear features (intermittency of phase locking) was found that contradict the linear summation of single responses, as assumed by the superposition hypothesis. Thus, evidence suggests that visual rhythmic stimulation entrains brain oscillations, validating the approach of rhythmic stimulation as manipulation of brain oscillations. See, Notbohm A, Kurths J, Herrmann C S, Modification of Brain Oscillations via Rhythmic Light Stimulation Provides Evidence for Entrainment but Not for Superposition of Event-Related Responses, Front Hum Neurosci. 2016 Feb. 3; 10:10. doi: 10.3389/fnhum.2016.00010. eCollection 2016.

It is also known that periodic visual stimulation can trigger epileptic seizures.

It is known to analyze EEG patterns to extract an indication of certain volitional activity (U.S. Pat. No. 6,011, 991). This technique describes that an EEG recording can be matched against a stored normalized signal using a computer. This matched signal is then translated into the corresponding reference. The patent application describes a method "a system capable of identifying particular nodes in an individual's brain, the firings of which affect characteristics such as appetite, hunger, thirst, communication skills" and "devices mounted to the person (e.g. underneath the scalp) may be energized in a predetermined manner or sequence to remotely cause particular identified brain node(s) to be fired in order to cause a predetermined feeling or reaction in the individual" without technical description of implementation. This patent also describes, that "brain activity [is monitored] by way of electroencephalograph (EEG) methods, magnetoencephalograph (MEG) methods, and the like." For example, see U.S. Pat. Nos. 5,816,247 and 5,325, 862. See also Reference List 5.

Brain Entrainment: Brain entrainment, also referred to as brainwave synchronization and neural entrainment, refers to the capacity of the brain to naturally synchronize its brainwave frequencies with the rhythm of periodic external stimuli, most commonly auditory, visual, or tactile. Brainwave entrainment technologies are used to induce various brain states, such as relaxation or sleep, by creating stimuli that occur at regular, periodic intervals to mimic electrical cycles of the brain during the desired states, thereby "training" the brain to consciously alter states. Recurrent acoustic frequencies, flickering lights, or tactile vibrations are the most common examples of stimuli applied to generate different sensory responses. It is hypothesized that listening to these beats of certain frequencies one can induce a desired state of consciousness that corresponds with specific neural activity. Patterns of neural firing, measured in Hz, correspond with alertness states such as focused attention, deep sleep, etc.

Neural oscillations are rhythmic or repetitive electrochemical activity in the brain and central nervous system. Such oscillations can be characterized by their frequency, amplitude, and phase. Neural tissue can generate oscillatory activity driven by mechanisms within individual neurons, as well as by interactions between them. They may also adjust frequency to synchronize with the periodic vibration of external acoustic or visual stimuli. The functional role of neural oscillations is still not fully understood; however, they have been shown to correlate with emotional responses, motor control, and a number of cognitive functions including information transfer, perception, and memory. Specifically, neural oscillations, in particular theta activity, are extensively linked to memory function, and coupling between theta and gamma activity is considered to be vital for memory functions, including episodic memory. EEG has been most widely used in the study of neural activity generated by large groups of neurons, known as neural ensembles, including investigations of the changes that occur in EEG profiles during cycles of sleep and wakefulness. EEG signals change dramatically during sleep and show a transition from faster frequencies to increasingly slower frequencies, indicating a relationship between the frequency of neural oscillations and cognitive states, including awareness and consciousness.

The term "entrainment" has been used to describe a shared tendency of many physical and biological systems to synchronize their periodicity and rhythm through interaction. This tendency has been identified as specifically pertinent to the study of sound and music generally, and acoustic rhythms specifically. The most ubiquitous and familiar examples of neuromotor entrainment to acoustic stimuli are observable in spontaneous foot or finger tapping to the rhythmic beat of a song. Exogenous rhythmic entrainment, which occurs outside the body, has been identified and documented for a variety of human activities, which include the way people adjust the rhythm of their speech patterns to those of the subject with whom they communicate, and the rhythmic unison of an audience clapping. Even among groups of strangers, the rate of breathing, locomotive, and subtle expressive motor movements, and rhythmic speech patterns have been observed to synchronize and entrain, in response to an auditory stimulus, such as a piece of music with a consistent rhythm. Furthermore, motor synchronization to repetitive tactile stimuli occurs in animals, including cats and monkeys as well as humans, with accompanying shifts in electroencephalogram (EEG) readings. Examples of endogenous entrainment, which occurs within the body, include the synchronizing of human circadian sleep-wake cycles to the 24-hour cycle of light and dark, and the frequency following response of humans to sounds and music.

Brainwaves, or neural oscillations, share the fundamental constituents with acoustic and optical waves, including frequency, amplitude, and periodicity. The synchronous electrical activity of cortical neural ensembles can synchronize in response to external acoustic or optical stimuli and also entrain or synchronize their frequency and phase to that of a specific stimulus. Brainwave entrainment is a colloquialism for such 'neural entrainment', which is a term used to denote the way in which the aggregate frequency of oscillations produced by the synchronous electrical activity in ensembles of cortical neurons can adjust to synchronize with the periodic vibration of an external stimuli, such as a sustained acoustic frequency perceived as pitch, a regularly repeating pattern of intermittent sounds, perceived as rhythm, or of a regularly rhythmically intermittent flashing light.

Changes in neural oscillations, demonstrable through electroencephalogram (EEG) measurements, are precipitated by listening to music, which can modulate autonomic arousal ergotropically and trophotropically, increasing and decreasing arousal respectively. Musical auditory stimulation has also been demonstrated to improve immune function, facilitate relaxation, improve mood, and contribute to the alleviation of stress.

The Frequency following response (FFR), also referred to as Frequency Following Potential (FFP), is a specific response to hearing sound and music, by which neural oscillations adjust their frequency to match the rhythm of auditory stimuli. The use of sound with intent to influence cortical brainwave frequency is called auditory driving, by which frequency of neural oscillation is 'driven' to entrain with that of the rhythm of a sound source. See Reference List 6.

Baseline correction of event-related time-frequency measure may be made by taking pre-event baseline activity into consideration. In general, a baseline period is defined by the average of the values within a time window preceding the time-locking event. There are at least four common methods for baseline correction in time-frequency analysis. The methods include various baseline value normalizations. See, Reference List 7.

The question of whether different emotional states are associated with specific patterns of physiological response has long being a subject of neuroscience research See, for example:

Electroencephalograms (EEG) and functional Magnetic Resonance Imaging, fMRI have been used to study specific brain activity associated with different emotional states. Mauss and Robinson, in their review paper, have indicated that "emotional state is likely to involve circuits rather than any brain region considered in isolation" (Mauss I B, Robinson M D (2009) Measures of emotion: A review. Cogn Emot 23:209-237.)

The amplitude, latency from the stimulus, and covariance (in the case of multiple electrode sites) of each component can be examined in connection with a cognitive task (ERP) or with no task (EP). Steady-state visually evoked potentials (SSVEPs) use a continuous sinusoidally-modulated flickering light, typically superimposed in front of a TV monitor displaying a cognitive task. The brain response in a narrow frequency band containing the stimulus frequency is measured. Magnitude, phase, and coherence (in the case of multiple electrode sites) may be related to different parts of the cognitive task. Brain entrainment may be detected through EEG or MEG activity.

Brain entrainment may be detected through EEG or MEG activity. See Reference List 8.

The entrainment hypothesis (Thut and Miniussi, 2009; Thut et al., 2011a, 2012), suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop (Buzsaki, 2006). Because of the variety of experimental protocols for brain stimulation, limits on descriptions of the actual protocols employed, and limited controls, consistency of reported studies is lacking, and extrapolability is limited. Thus, while there is various consensus in various aspects of the effects of extracranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, studies that employ feedback control are lacking.

Different cognitive states are associated with different oscillatory patterns in the brain (Buzsàki, 2006; Canolty and Knight, 2010; Varela et al., 2001). Thut et al. (2011b) directly tested the entrainment hypothesis by means of a concurrent EEG-TMS experiment. They first determined the individual source of the parietal-occipital alpha modulation and the individual alpha frequency (magnetoencephalography study). They then applied rTMS at the individual alpha power while recording the EEG activity at rest. The results confirmed the three predictions of the entrainment hypothesis: the induction of a specific frequency after TMS, the enhancement of oscillation during TMS stimulation due to synchronization, and phase alignment of the induced frequency and the ongoing activity (Thut et al., 2011b).

If associative stimulation is a general principle for human neural plasticity in which the timing and strength of activation are critical factors, it is possible that synchronization within or between areas using an external force to phase/align oscillations can also favor efficient communication and associative plasticity (or alter communication). In this respect associative, cortico-cortical stimulation has been shown to enhance the coherence of oscillatory activity between the stimulated areas (Plewnia et al., 2008).

In a coherence resonance (Longtin, 1997), the addition of a certain amount of noise in an excitable system results in the most coherent and proficient oscillatory responses. The brain's response to external timing-embedded stimulation can result in a decrease in phase variance and an enhanced alignment (clustering) of the phase components of the ongoing EEG activity (entraining, phase resetting) that can change the signal-to-noise ratio and increase (or decrease) signal efficacy.

If one considers neuron activity within the brain as a set of loosely coupled oscillators, then the various parameters that might be controlled include the size of the region of neurons, frequency of oscillation, resonant frequency or time-constant, oscillator damping, noise, amplitude, coupling to other oscillators, and of course, external influences that may include stimulation and/or power loss. In a human brain, pharmacological intervention may be significant. For example, drugs that alter excitability, such as caffeine, neurotransmitter release and reuptake, nerve conductance, etc. can all influence operation of the neural oscillators. Likewise, sub-threshold external stimulation effects, including DC, AC, and electromagnetic effects, can also influence the operation of the neural oscillators.

Phase resetting or shifting can synchronize inputs and favor communication and, eventually, Hebbian plasticity (Hebb, 1949). Thus, rhythmic stimulation may induce a statistically higher degree of coherence in spiking neurons, which facilitates the induction of a specific cognitive process (or hinders that process). Here, the perspective is slightly different (coherence resonance), but the underlining mechanisms are similar to the ones described so far (stochastic resonance), and the additional key factor is the repetition at a specific rhythm of the stimulation.

In the 1970s, the British biophysicist and psychobiologist, C. Maxwell Cade, monitored the brainwave patterns of advanced meditators and 300 of his students. Here he found that the most advanced meditators have a specific brainwave pattern that was different from the rest of his students. He noted that these meditators showed the high activity of alpha brainwaves accompanied by beta, theta, and even delta waves that were about half the amplitude of the alpha waves.

See, Cade "The Awakened Mind: Biofeedback and the Development of Higher States of Awareness" (Dell, 1979). Anna Wise extended Cade's studies, and found that extraordinary achievers which included composers, inventors, artists, athletes, dancers, scientists, mathematicians, CEO's and presidents of large corporations have brainwave patterns differ from average performers, with a specific balance between Beta, Alpha, Theta and Delta brainwaves where Alpha had the strongest amplitude. See, Anna Wise, "The High-Performance Mind: Mastering Brainwaves for Insight, Healing, and Creativity".

Entrainment is plausible because of the characteristics of the demonstrated EEG responses to a single TMS pulse, which have a spectral composition which resembles the spontaneous oscillations of the stimulated cortex. For example, TMS of the "resting" visual (Rosanova et al., 2009) or motor cortices (Veniero et al., 2011) triggers alpha-waves, the natural frequency at the resting state of both types of cortices. With the entrainment hypothesis, the noise generation framework moves to a more complex and extended level in which noise is synchronized with on-going activity. Nevertheless, the model to explain the outcome will not change, stimulation will interact with the system, and the final result will depend on introducing or modifying the noise level. The entrainment hypothesis makes clear predictions with respect to online repetitive TMS paradigms' frequency engagement as well as the possibility of inducing phase alignment, i.e., a reset of ongoing brain oscillations via external spTMS (Thut et al., 2011a, 2012; Veniero et al., 2011). The entrainment hypothesis is superior to the localization approach in gaining knowledge about how the brain works, rather than where or when a single process occurs. TMS pulses may phase-align the natural, ongoing oscillation of the target cortex. When additional TMS pulses are delivered in synchrony with the phase-aligned oscillation (i.e., at the same frequency), further synchronized phase-alignment will occur, which will bring the oscillation of the target area in resonance with the TMS train. Thus, entrainment may be expected when TMS is frequency-tuned to the underlying brain oscillations (Veniero et al., 2011).

Binaural Beats: Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm. The binaural-beat appears to be associated with an EEG frequency-following response in the brain.

Uses of audio with embedded binaural beats that are mixed with music or various pink or background sound are diverse. They range from relaxation, meditation, stress reduction, pain management, improved sleep quality, decrease in sleep requirements, super learning, enhanced creativity and intuition, remote viewing, telepathy, and out-of-body experience and lucid dreaming. Audio embedded with binaural beats is often combined with various meditation techniques, as well as positive affirmations and visualization.

When signals of two different frequencies are presented, one to each ear, the brain detects phase differences between these signals. "Under natural circumstances, a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat—is heard. The binaural beat is perceived as a fluctuating rhythm at the frequency of the difference between the two auditory inputs. Evidence suggests that the binaural beats are generated in the brainstem's superior olivary nucleus, the first site of contralateral integration in the auditory system. Studies also suggest that the frequency-following response originates from the inferior colliculus. This activity is conducted to the cortex where it can be recorded by scalp electrodes. Binaural beats can easily be heard at the low frequencies (<30 Hz) that are characteristic of the EEG spectrum.

Synchronized brainwaves have long been associated with meditative and hypnogogic states, and audio with embedded binaural beats has the ability to induce and improve such states of consciousness. The reason for this is physiological. Each ear is "hardwired" (so to speak) to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnogogic states of consciousness. Brain function is also enhanced through the increase of cross-collosal communication between the left and right hemispheres of the brain. See Reference List 9.

Isochronic Tones: Isochronic tones are regular beats of a single tone that are used alongside monaural beats and binaural beats in the process called brainwave entrainment. At its simplest level, an isochronic tone is a tone that is being turned on and off rapidly. They create sharp, distinctive pulses of sound. See Reference List 10.

Time-Frequency Analysis: Brian J. Roach and Daniel H. Mathalon, "Event-related EEG time-frequency analysis: an overview of measures and analysis of early gamma band phase locking in schizophrenia. Schizophrenia Bull. USA. 2008; 34:5:907-926., describes a mechanism for EEG time-frequency analysis. Fourier and wavelet transforms (and their inverse) may be performed on EEG signals. See Reference List 11.

There are many approaches to time-frequency decomposition of EEG data, including the short-term Fourier transform (STFT), (Gabor D. Theory of Communication. J. Inst. Electr. Engrs. 1946; 93:429-457) continuous (Daubechies I. Ten Lectures on Wavelets. Philadelphia, Pa: Society for Industrial and Applied Mathematics; 1992:357. 21. Combes J M, Grossmann A, Tchamitchian P. Wavelets: Time-Frequency Methods and Phase Space-Proceedings of the International Conference; Dec. 14-18, 1987; Marseille, France) or discrete (Mallat S G. A theory for multiresolution signal decomposition: the wavelet representation. IEEE Trans Pattern Anal Mach Intell. 1989; 11:674-693) wavelet transforms, Hilbert transform (Lyons R G. Understanding Digital Signal Processing. 2nd ed. Upper Saddle River, NJ: Prentice Hall PTR; 2004:688), and matching pursuits (Mallat S, Zhang Z. Matching pursuits with time-frequency dictionaries. IEEE Trans. Signal Proc. 1993; 41 (12): 3397-3415). Prototype analysis systems may be implemented using, for example, MatLab with the Wavelet Toolbox, www.math-works.com/products/wavelet.html. See Reference List 12.

Single instruction, multiple data processors, such as graphics processing units including the nVidia CUDA environment or AMD Firepro high-performance computing environment are known, and may be employed for general purpose computing, finding particular application in data matrix transformations. See Reference List 13.

Statistical analysis may be presented in a form that permits parallelization, which can be efficiently implemented using various parallel processors, a common form of which is a SIMD (single instruction, multiple data) processor, found in typical graphics processors (GPUs). Artificial neural networks have been employed to analyze EEG signals.

See Reference List 14.

Principal Component Analysis: Principal component analysis (PCA) is a statistical procedure that uses an orthogonal transformation to convert a set of observations of possibly correlated variables into a set of values of linearly uncorrelated variables called principal components. If there are n observations with p variables, then the number of distinct principal components is min $(n-1,p)$. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables. PCA is the simplest of the true eigenvector-based multivariate analyses. Often, its operation can be thought of as revealing the internal structure of the data in a way that best explains the variance in the data. If a multivariate dataset is visualized as a set of coordinates in high-dimensional data space (1 axis per variable), PCA can supply the user with a lower-dimensional picture, a projection of this object when viewed from its most informative viewpoint. This is done by using only the first few principal components so that the dimensionality of the transformed data is reduced. PCA is closely related to factor analysis. Factor analysis typically incorporates more domain specific assumptions about the underlying structure and solves eigenvectors of a slightly different matrix. PCA is also related to canonical correlation analysis (CCA). CCA defines coordinate systems that optimally describe the cross-covariance between two datasets while PCA defines a new orthogonal coordinate system that optimally describes variance in a single dataset. See, en.wikipedia.org/wiki/Principal_component_analysis.

A general model for confirmatory factor analysis is expressed as $x=\alpha+\Lambda\xi+\varepsilon$. The covariance matrix is expressed as $E[(x-\mu)(x-u)']=\Lambda\Phi\Lambda'+\Theta$. If residual covariance matrix $\Theta=0$ and correlation matrix among latent factors $\Phi=I$, then factor analysis is equivalent to principal component analysis and the resulting covariance matrix is simplified to $\Sigma=\Lambda\Lambda'$.

When there are p number of variables and all p components (or factors) are extracted, this covariance matrix can alternatively be expressed into $\Sigma = D\Lambda D'$, or $\Sigma = \lambda DAD'$, where $D = n \times p$ orthogonal matrix of eigenvectors, and $\Lambda = \lambda A$, $p \times p$ matrix of eigenvalues, where $\lambda$ is a scalar, and A is a diagonal matrix whose elements are proportional to the eigenvalues of $\Sigma$. The following three components determine the geometric features of the observed data: $\lambda$ parameterizes the volume of the observation, D indicates the orientation, and A represents the shape of the observation.

When population heterogeneity is explicitly hypothesized as in model-based cluster analysis, the observed covariance matrix is decomposed into the following general form $$\sum\nolimits_k = \lambda_k D_k A_k D_k^T,$$

where $\lambda_k$ parameterizes the volume of the $k^{th}$ cluster, $D_k$ indicates the orientation of that cluster, and $A_k$ represents the shape of that cluster. The subscript k indicates that each component (or cluster) can have different volume, shape, and orientation.

Assume a random vector X, taking values in $\mathfrak{R}^m$, has a mean and covariance matrix of $\mu_X$ and $\Sigma_X$, respectively. $\lambda_1 > \lambda_2 > \ldots > \lambda_m > 0$ are ordered eigenvalues of $\Sigma_X$, such that the $i^{th}$ eigenvalue of $\Sigma_X$ means the $i^{th}$ largest of them. Similarly, a vector $\alpha_i$ is the $i^{th}$ eigenvector of $\Sigma_X$ when it corresponds to the $i^{th}$ eigenvalue of $\Sigma_X$. To derive the form of principal components (PCs), consider the optimization problem of maximizing $$\mathrm{var}[\alpha_1^T X] = \alpha_1^T \sum\nolimits_X \alpha_1,$$

subject to $$\alpha_1^T \alpha_1 = 1.$$

The Lagrange multiplier method is used to solve this question.

$$L(\alpha_1, \phi_1) = \alpha_1^T \sum\nolimits_X \alpha_1 + \phi_1(\alpha_1^T \alpha_1 - 1)$$

$$\frac{\partial L}{\partial \alpha_1} =$$

$$2\Sigma_X \alpha_1 + 2\phi\alpha_1 = 0 \Rightarrow \Sigma_X \alpha_1 = -\phi_1\alpha_1 \Rightarrow \mathrm{var}[\alpha_1^T X] = -\phi_1\alpha_1^T \alpha_1 = -\phi_1.$$

Because $-\phi_1$ is the eigenvalue of $\Sigma_X$, with $\alpha_1$ being the corresponding normalized eigenvector, $$\mathrm{var}[\alpha_1^T X]$$

is maximized by choosing $\alpha_1$ to be the first eigenvector of $\Sigma_X$. In this case, $$z_1 = \alpha_1^T X$$

is named the first PC of X, $\alpha_1$ is the vector of coefficients for $z_1$ and $\mathrm{var}(z_1) = \lambda_1$.

To find the second PC, $$z_2 = \alpha_2^T X,$$

we need to maximize $$\mathrm{var}[\alpha_2^T X] = \alpha_2^T \sum\nolimits_X \alpha_2$$

subject to $z_2$ being uncorrelated with $z_1$. Because $$\mathrm{cov}(\alpha_1^T X, \alpha_2^T X) = 0 \Rightarrow \alpha_1^T \sum\nolimits_X \alpha_2 = 0 \Rightarrow \alpha_1^T \alpha_2 = 0,$$

this problem is equivalently set as maximizing $$\alpha_2^T \sum\nolimits_X \alpha_2,$$

subject to $$\alpha_1^T \alpha_2 = 0, \text{ and } \alpha_2^T \alpha_2 = 1.$$

We still make use of the Lagrange multiplier method.

$$L(\alpha_2, \phi, \phi_2) = \alpha_2^T \Sigma_X \alpha_2 + \phi_1 \alpha_1^T \alpha_2 + \phi_2(\alpha_2^T \alpha_2 - 1)$$

$$\frac{\partial L}{\partial \alpha_2} = 2\Sigma_X \alpha_2 + \phi_1 \alpha_1 + 2\phi_2 \alpha_2 = 0 \Rightarrow \alpha_1^T(2\Sigma_X \alpha_2 + \phi_1 \alpha_1 + 2\phi_2 \alpha_2) =$$

$$0 \Rightarrow \phi_1 = 0 \Rightarrow \Sigma_X \alpha_2 = -\phi_2 \alpha_2 \Rightarrow \alpha_2^T \Sigma_X \alpha_2 = -\phi_2.$$

Because $-\phi_2$ is the eigenvalue of $\Sigma_X$, with $\alpha_2$ being the corresponding normalized eigenvector, $$\mathrm{var}[\alpha_2^T X]$$

is maximized by choosing $\alpha_2$ to be the second eigenvector of $\Sigma_X$. In this case, $$z_2 = \alpha_2^T X$$

is named the second PC of X, $\alpha_2$ is the vector of coefficients for $z_2$, and $\mathrm{var}(z_2) = \lambda_2$. Continuing in this way, it can be shown that the i-th PC $$z_i = \alpha_i^T X$$

is constructed by selecting $\alpha_i$ to be the $i_{th}$ eigenvector of $\Sigma_X$, and has a variance of $\lambda_i$. The key result in regards to PCA is that the principal components are the only set of linear functions of original data that are uncorrelated and have orthogonal vectors of coefficients.

For any positive integer $p \le m$, let $B=[\beta_1, \beta_2, \ldots, \beta_p]$ be an real m×P matrix with orthonormal columns, i.e., $$\beta_i^T \beta_j = \delta_{ij}, \text{ and } Y = B^T X.$$

Then the trace of covariance matrix of Y is maximized by taking $B=[\alpha_1, \alpha_2, \ldots, \beta_p]$, where $\alpha_i$ is the i-th eigenvector of $\Sigma_X$. Because $\Sigma_X$ is symmetric with all distinct eigenvalues, so $\{\alpha_1, \alpha_2, \ldots, \alpha_m\}$ is an orthonormal basis with $\alpha_i$ being the i-th eigenvector of $\Sigma_X$, and we can represent the columns of B as $$\beta_i = \sum_{j=1}^{m} c_{ji}\alpha_j, i = 1, \ldots, p,$$

So we have B=PC, where $P=[\alpha_1, \ldots, \alpha_m]$, $C=\{c_{ij}\}$ is an m×p matrix. Then, $P^T \Sigma_X P = \Lambda$, with $\Lambda$ being a diagonal matrix whose k-th diagonal element is $\lambda_k$, and the covariance matrix of Y is, $$\sum_Y = B^T \sum_X B = C^T P^T \sum_X PC = C^T \Lambda C = \lambda_1 c_1 c_1^T + \ldots + \lambda_m c_m c_m^T$$

where $$c_i^T$$

is the i-th row of C. So, $$\text{trace}(\Sigma_Y) = \sum_{i=1}^{m} \lambda_i \text{trace}(c_i c_i^T) = \sum_{i=1}^{m} \lambda_i \text{trace}(c_i^T c_i) = \sum_{i=1}^{m} \lambda_i c_i^T c_i = \sum_{i=1}^{m} \left( \sum_{j=1}^{p} c_{ij}^2 \right) \lambda_i.$$

Because $C^T C = B^T PP^T B = B^T B = I$, so $$\text{trace}(C^T C) = \sum_{i=1}^{m} \sum_{j=i}^{p} c_{ij}^2 = p,$$

and the columns of C are orthonormal. By the Gram-Schmidt method, C can expand to D, such that D has its columns as an orthonormal basis of $\mathfrak{R}^m$ and contains C as its first P columns. D is square shape, thus being an orthogonal matrix and having its rows as another orthonormal basis of $\mathfrak{R}^m$. One row of C is a part of one row of D, so $$\sum_{j=1}^{p} c_{ij}^2 < 1, i = 1, \ldots, m.$$

Considering the constraints $$\sum_{j=1}^{p} c_{ij}^2 < 1, \sum_{i=1}^{m} \sum_{j=1}^{p} c_{ij}^2 = p$$

and the objective $$\sum_{i=1}^{m} \left( \sum_{j=1}^{p} c_{ij}^2 \right) \lambda_i.$$

We derive that trace($\Sigma_Y$) is maximized if $$\sum_{j=1}^{p} c_{ij}^2 = 1 \text{ for } i = 1, \ldots, p, \text{ and } \sum_{j=1}^{p} c_{ij}^2 = 0 \text{ for } i = p+1, \ldots, m.$$

When $B=[\alpha_1, \alpha_2, \ldots, \alpha_p]$ straightforward calculation yields that C is an all-zero matrix except $c_{ii}=1$, i=1, ..., P. This fulfills the maximization condition. Actually, by taking $B=[\gamma_1, \gamma_2, \ldots, \gamma_p]$, where $\{\gamma_1, \gamma_2, \ldots, \gamma_p\}$ is any orthonormal basis of the subspace of span$\{\alpha_1, \alpha_2, \ldots, \alpha_p\}$, the maximization condition is also satisfied, yielding the same trace of the covariance matrix of Y Suppose that we wish to approximate the random vector X by its projection onto a subspace spanned by columns of B, where $B=[\beta_1, \beta_2, \ldots, \beta_p]$ is a real m×p matrix with orthonormal columns, i.e., $$\beta_i^T \beta_j = \delta_{ij}.$$

If $$\sigma_i^2$$

is the residual variance for each component of X, then $$\sum_{i=1}^{m} \sigma_i^2$$

is minimized if $B=[\alpha_1, \alpha_2, \ldots, \alpha_p]$, where $\{\alpha_1, \alpha_2, \ldots, \alpha_p\}$ are the first p eigenvectors of $\Sigma_X$. In other words, the trace of the covariance matrix of $X-BB^T X$ is minimized if $B=[\alpha_1, \alpha_2, \ldots, \alpha_p]$. When E(X)=0, which is a commonly applied preprocessing step in data analysis methods, this property is saying that $E\|X-BB^T X\|^2$ is minimized if $B=[\alpha_1, \alpha_2, \ldots, \alpha_p]$.

The projection of a random vector X onto a subspace spanned by columns of B is $\hat{X}=BB^T X$. Then the residual vector is $\varepsilon=X-BB^T X$, which has a covariance matrix $\Sigma_\varepsilon = (I-BB^T)\Sigma_X(I-BB^T)$. Then, $$\sum_{i=1}^{m} \sigma_i^2 = \text{trace}\left(\sum_\varepsilon\right) = \text{trace}\left(\sum_X - \sum_X BB^T - BB^T \sum_X + BB^T \sum_X BB^T\right).$$

Also, we know:

$$\text{trace}(\Sigma_X BB^T) = \text{trace}(BB^T \Sigma_X) = \text{trace}(B^T \Sigma_X B)$$

$$\text{trace}(BB^T \Sigma_X BB^T) = \text{trace}(B^T \Sigma_X BB^T B) = \text{trace}(B^T \Sigma_X B).$$

The last equation comes from the fact that B has ortho- normal columns. So, $$\sum_{i=1}^{m} \sigma_i^2 = \text{trace}\left(\sum_X\right) - \text{trace}\left(B^T \sum_X B\right).$$

To minimize $$\sum_{i=1}^{m} \sigma_i^2,$$

it suffices to maximize $\text{trace}(B^T \Sigma_X B)$. This can be done by choosing $B = [\alpha_1, \alpha_2, \ldots, \alpha_p]$, where $\{\alpha_1, \alpha_2, \ldots, \alpha_p\}$ are the first p eigenvectors of $\Sigma_X$, as above.

See, Pietro Amenta, Luigi D'Ambra, "Generalized Constrained Principal Component Analysis with External Information," (2000). We assume that data on K sets of explanatory variables and S criterion variables of n statistical units are collected in matrices $X_k$ (k=1, . . . , K) and $Y_s$ (s=1, . . . , S) of orders (n×p$_1$), . . . , (n×p$_K$) and (n×q$_1$), . . . , (n×q$_s$), respectively. We suppose, without loss of generality, identity matrices for the metrics of the spaces of variables of $X_k$ and $Y_s$ with $D_n$=diag(1/n), weight matrix of statistical units. We assume, moreover, that $X_k$'s and $Y_s$'s are centered as to the weights $D_n$.

Let $X = [X_1 | \ldots | X_K]$ and $Y = [Y_1 | \ldots | Y_S]$, respectively, be K and S matrices column linked to orders (n×$\Sigma_k$ p$_k$) and (n×$\Sigma_s$q$_s$) Let be, also, $W_Y$=YY' while we denote $v_k$ the coefficients vector (p$_k$,1) of the linear combination for each $X_k$ such that $z_x = X_k v_k$. Let $C_k$ be the matrix of dimension p$_k$×m (m≤p$_k$), associated to the external information explanatory variables of set k.

Generalized CPCA (GCPCA) (Amenta, D'Ambra, 1999) with external information consists in seeking for K coefficients vectors $v_k$ (or, in same way, K linear combinations $z_k$) subject to the restriction $$C_k' v_k = 0$$

simultaneously, such that:

$$\begin{cases} \max \sum_{i=1}^{K}\sum_{j=1}^{K} \langle Y'X_i v_i, Y'X_j v_j \rangle \\ \\ \text{with the constraints} \begin{array}{l} \sum_{k=1}^{K} \|X_k v_k\|^2 = 1 \\ \sum_{k=1}^{K} C_k' v_k = 0 \end{array} \end{cases}$$

or, in equivalent way, $$\begin{cases} \max v'(A'A)v \\ \text{with the constraints} \begin{array}{l} v'Bv = 1 \\ C'v = 0 \end{array} \end{cases} \text{ or } \begin{cases} \max f'B^{-0.5}A'AB^{-0.5}f \\ \text{with the constraints} \begin{array}{l} f'f = 1 \\ C'v = 0 \end{array} \end{cases}$$

where $$A = Y'X, B = \text{diag}(X_1'X_1, \ldots, X_K'X_K), C' = [C_1' | \ldots | C_k'], v' = (v_1' | \ldots | v_k')$$

and $f = B^{0.5}v$, with $$A'A = \begin{bmatrix} X_1'YY'X_1 & \cdots & X_1'YY'X_K \\ \vdots & \ddots & \vdots \\ X_K'YY'X_1 & \cdots & X_k'YY'X_k \end{bmatrix}.$$

The constrained maximum problem turns out to be an extension of criterion $\sup_{\Sigma_k \|z_k\|^2 = 1} \Sigma_i \Sigma_k \langle z_i, z_k \rangle$ (Sabatier, 1993) with more sets of criterion variables with external information. The solution of this constrained maximum problem leads to solve the eigen-equation $$(P_X - P_{XB^{-1}C}) W_Y g = \lambda g$$

where $$g = Xv, P_X - P_{XB^{-1}C} = \sum_{k=1}^{K}\left(P_{X_k} - P_{X_k(X_k'X_k)^{-1}C_k}\right)$$

is the oblique projector operator associated to the direct sum decomposition of $\mathfrak{R}^n$, $\mathfrak{R}^n = \text{Im}(P_X - P_{XB^{-1}C}) \oplus \text{Im}(P_C) \oplus \text{Ker}(P_X)$ with $$P_{X_k} = X_k(X_k'X_k)^{-1}X_k' \text{ and } P_C = C(C'B^{-1}C)^{-1}C'B^{-1},$$

respectively, $/$ and $B^{-1}$ orthogonal projector operators onto the subspaces spanned by the columns of matrices $X_k$ and C. Furthermore, $P_{XB^{-1}C} = XB^{-1}C(C'B^{-1}C)^{-1}C'B^{-1}X'$ is the orthogonal projector operator onto the subspace spanned the columns of the matrix $XB^{-1}C$. Starting from the relation $(P_{X_k} - P_{X_k(X_k'X_k)^{-1}C_k})W_Y g = \lambda X_k v_k$ (which is obtained from the expression $(I - P_C)$ $X'W_Y g = \lambda Bv$) the coefficients vectors $v_k$ and the linear combinations $z_k = X_k v_k$ maximizing (1) can be given by the relations $$v_k = \frac{1}{\lambda}(X_k'X_k)^{-1}(I - P_{C_k})X_k'W_Y Xv \text{ and } z_k = \frac{1}{\lambda}\left(P_{X_k} - P_{X_k(X_k'X_k)^{-1}C_k}\right)W_Y Xv,$$

respectively.

The solution eigenvector g can be written, as the sum of the linear combinations $z_k$: $g = \Sigma_k X_k v_k$. Notice that the eigenvalues associated to the eigen-system are, according to the Sturm theorem, lower or equal than those of GCPCA eigensystem:

$$\sum_{k=1}^{K} P_{X_k} W_Y g = \lambda g.$$

See Reference List 15.

Spatial Principal Component Analysis

Let J(t, i; α, s) be the current density in voxel i, as estimated by LORETA, in condition α at t time-frames after stimulus onset for subject s. Let area:Voxel→fBA be a function, which assigns to each voxel i∈Voxel the corresponding fBA b∈fBA. In a first pre-processing step, we calculate for each subject s the value of the current density averaged over each Fba $$x(t, b; \alpha, s) = \frac{1}{N_b} \sum_{i \in b} J(t, i; \alpha, s)$$

where $N_b$ is the number of voxels in the fBA b, in condition ox for subject s.

In the second analysis stage, the mean current density x(t, b; α, s) from each fBA b, for every subject s and condition α, was subjected to spatial PCA analysis of the correlation matrix and varimax rotation In the present study, the spatial PCA uses the above-defined fBAs as variables sampled along the time epoch for which EEG has been sampled (0-1000 ms; 512 time-frames), and the inverse solution was estimated. Spatial matrices (each matrix was sized b×t=36×512 elements) for every subject and condition were collected, and subjected to PCA analyses, including the calculation of the covariance matrix; eigenvalue decomposition and varimax rotation, in order to maximize factor loadings. In other words, in the spatial PCA analysis, we approximate the mean current density for each subject in each condition as $$x(t; \alpha, s) \approx x_0(\alpha, s) + \sum_k c_k(t) x_k(\alpha, s),$$

where here x(t; α, s)∈$R^{36}$ is a vector, which denotes the time-dependent activation of the fBAs, $x_0(\alpha,s)$ is their mean activation, and $x_k(\alpha, s)$ and $c_k$ are the principal components and their corresponding coefficients (factor loadings) as computed using the principal component analysis.

See, download.lww.com/wolterskluwer.com/WNR_1_1_2010_03_22_ARZY_1_SDC1.doc.

Singular spectrum analysis (SSA): SSA is a nonparametric spectral estimation method. It combines elements of classical time series analysis, multivariate statistics, multivariate geometry, dynamical systems, and signal processing. SSA can be an aid in the decomposition of time series into a sum of components, each having a meaningful interpretation. The name "singular spectrum analysis" relates to the spectrum of eigenvalues in a singular value decomposition of a covariance matrix, and not directly to a frequency domain decomposition. (see en.wikipedia.org/wiki/Singular_spectrum_analysis.)

In practice, SSA is a nonparametric spectral estimation method based on embedding a time series {X(t): t=1, . . . , N} in a vector space of dimension M. SSA proceeds by diagonalizing the M×M lag-covariance matrix $C_X$ of X(t) to obtain spectral information on the time series, assumed to be stationary in the weak sense. The matrix $C_X$ can be estimated directly from the data as a Toeplitz matrix with constant diagonals, i.e., its entries $c_{ij}$ depend only on the lag |i−j|:

$$c_{ij} = \frac{1}{N - |i - j|} \sum_{t=1}^{N-|i-j|} X(t) X(t + |i - j|)$$

An alternative way to compute $C_X$, is by using the N'×M "trajectory matrix" D that is formed by M lag-shifted copies of X(t), which are N'=N−M+1 long; then $$C_X = \frac{1}{N'} D^t D$$

The M eigenvectors $E_k$ of the lag-covariance matrix $C_X$ are called temporal empirical orthogonal functions (EOFs). The eigenvalues $\lambda_k$ of $C_X$ account for the partial variance in the direction $E_k$ and the sum of the eigenvalues, i.e., the trace of $C_X$, gives the total variance of the original time series X(t). The name of the method derives from the singular values $\lambda_k^{1/2}$ of $C_X$. Projecting the time series onto each EOF yields the corresponding temporal principal components (PCs) $A_k$:

$$A_k(t) = \sum_{j=1}^{M} X(t + j - 1) E_k(j).$$

An oscillatory mode is characterized by a pair of nearly equal SSA eigenvalues and associated PCs that are in approximate phase quadrature. Such a pair can represent efficiently a nonlinear, nonharmonic oscillation. This is due to the fact that a single pair of data-adaptive SSA eigenmodes often will capture better the basic periodicity of an oscillatory mode than methods with fixed basis functions, such as the sines and cosines used in the Fourier transform.

The window width M determines the longest periodicity captured by SSA. Signal-to-noise separation can be obtained by merely inspecting the slope break in a "scree diagram" of eigenvalues $\lambda_k$ or singular values $\lambda_k^{1/2}$ vs. k. The point k*=S at which this break occurs should not be confused with a "dimension" D of the underlying deterministic dynamics.

A Monte-Carlo test can be applied to ascertain the statistical significance of the oscillatory pairs detected by SSA. The entire time series or parts of it that correspond to trends, oscillatory modes or noise can be reconstructed by using linear combinations of the PCs and EOFs, which provide the reconstructed components (RCs) $R_K$:

$$R_K(t) = \frac{1}{M_t} \sum_{k \in K} \sum_{j=L_t}^{U_t} A_k(t - j + 1) E_k(j);$$

here K is the set of EOFs on which the reconstruction is based. The values of the normalization factor $M_t$, as well as of the lower and upper bound of summation $L_t$ and $U_t$, differ between the central part of the time series and the vicinity of its endpoints.

Multi-channel SSA (or M-SSA) is a natural extension of SSA to an L-channel time series of vectors or maps with N data points {$X_l(t)$: l=1, . . . , L; t=1, . . . , N}. The extended EOF (EEOF) analysis is sometimes assumed to be synonymous with M-SSA. The two methods are both extensions of classical principal component analysis (PCA) but they differ in emphasis: EEOF analysis typically utilizes a number L of spatial channels much greater than the number M of temporal lags, thus limiting the temporal and spectral information. In M-SSA, on the other hand, one usually chooses L≤M. Often M-SSA is applied to a few leading PCs of the spatial data, with M chosen large enough to extract detailed temporal and spectral information from the multivariate time series.

To avoid a loss of spectral properties, VARIMAX rotation of the spatio-temporal EOFs (ST-EOFs) of the M-SSA and its variations are sometimes used. Alternatively, a closed matrix formulation of the algorithm for the simultaneous rotation of the EOFs by iterative SVD decompositions has been proposed.

Nonlinear Dimensionality Reduction: High-dimensional data, meaning data that requires more than two or three dimensions to represent, can be difficult to interpret. One approach to simplification is to assume that the data of interest lie on an embedded non-linear manifold within the higher-dimensional space. If the manifold is of low enough dimension, the data can be visualized in the low-dimensional space. Non-linear methods can be broadly classified into two groups: those that provide a mapping (either from the high-dimensional space to the low-dimensional embedding or vice versa), and those that just give a visualization. In the context of machine learning, mapping methods may be viewed as a preliminary feature extraction step, after which pattern recognition algorithms are applied. Typically, those that just give a visualization are based on proximity data—that is, distance measurements. Related Linear Decomposition Methods include Independent component analysis (ICA), Principal component analysis (PCA) (also called Karhunen-Loève transform–KLT), Singular value decomposition (SVD), and Factor analysis.

The self-organizing map (SOM, also called Kohonen map) and its probabilistic variant generative topographic mapping (GTM) use a point representation in the embedded space to form a latent variable model based on a non-linear mapping from the embedded space to the high-dimensional space. These techniques are related to work on density networks, which also are based around the same probabilistic model.

Principal curves and manifolds give the natural geometric framework for nonlinear dimensionality reduction and extend the geometric interpretation of PCA by explicitly constructing an embedded manifold, and by encoding using standard geometric projection onto the manifold. How to define the "simplicity" of the manifold is problem-dependent. However, it is commonly measured by the intrinsic dimensionality and/or the smoothness of the manifold. Usually, the principal manifold is defined as a solution to an optimization problem. The objective function includes quality of data approximation and some penalty terms for the bending of the manifold. The popular initial approximations are generated by linear PCA, Kohonen's SOM or autoencoders. The elastic map method provides the expectation-maximization algorithm for principal manifold learning with minimization of quadratic energy functional at the "maximization" step.

An autoencoder is a feed-forward neural network which is trained to approximate the identity function. That is, it is trained to map from a vector of values to the same vector. When used for dimensionality reduction purposes, one of the hidden layers in the network is limited to contain only a small number of network units. Thus, the network must learn to encode the vector into a small number of dimensions and then decode it back into the original space. Thus, the first half of the network is a model which maps from high to low-dimensional space, and the second half maps from low to high-dimensional space. Although the idea of autoencoders is quite old, training of deep autoencoders has only recently become possible through the use of restricted Boltzmann machines and stacked denoising autoencoders. Related to autoencoders is the NeuroScale algorithm, which uses stress functions inspired by multidimensional scaling and Sammon mappings (see below) to learn a non-linear mapping from the high-dimensional to the embedded space. The mappings in NeuroScale are based on radial basis function networks.

Gaussian process latent variable models (GPLVM) are probabilistic dimensionality reduction methods that use Gaussian Processes (GPs) to find a lower dimensional non-linear embedding of high dimensional data. They are an extension of the Probabilistic formulation of PCA. The model is defined probabilistically, and the latent variables are then marginalized, and parameters are obtained by maximizing the likelihood. Like kernel PCA they use a kernel function to form a nonlinear mapping (in the form of a Gaussian process). However, in the GPLVM the mapping is from the embedded (latent) space to the data space (like density networks and GTM) whereas in kernel PCA it is in the opposite direction. It was originally proposed for visualization of high dimensional data but has been extended to construct a shared manifold model between two observation spaces. GPLVM and its many variants have been proposed specially for human motion modeling, e.g., back constrained GPLVM, GP dynamic model (GPDM), balanced GPDM (B-GPDM) and topologically constrained GPDM. To capture the coupling effect of the pose and gait manifolds in the gait analysis, a multi-layer joint gait-pose manifold was proposed.

Curvilinear component analysis (CCA) looks for the configuration of points in the output space that preserves original distances as much as possible while focusing on small distances in the output space (conversely to Sammon's mapping which focuses on small distances in original space). It should be noticed that CCA, as an iterative learning algorithm, actually starts with a focus on large distances (like the Sammon algorithm), then gradually change focus to small distances. The small distance information will overwrite the large distance information if compromises between the two have to be made. The stress function of CCA is related to a sum of right Bregman divergences. Curvilinear distance analysis (CDA) trains a self-organizing neural network to fit the manifold and seeks to preserve geodesic distances in its embedding. It is based on Curvilinear Component Analysis (which extended Sammon's mapping), but uses geodesic distances instead. Diffeomorphic Dimensionality Reduction or Diffeomap learns a smooth diffeomorphic mapping which transports the data onto a lower-dimensional linear subspace. The method solves for a smooth time indexed vector field such that flows along the field which starts at the data points will end at a lower-dimensional linear subspace, thereby attempting to preserve pairwise differences under both the forward and inverse mapping.

Perhaps the most widely used algorithm for manifold learning is Kernel principal component analysis (kernel PCA). It is a combination of Principal component analysis and the kernel trick. PCA begins by computing the covariance matrix of the M×n Matrix X. It then projects the data onto the first k eigenvectors of that matrix. By comparison, KPCA begins by computing the covariance matrix of the data after being transformed into a higher-dimensional space. It then projects the transformed data onto the first k eigenvectors of that matrix, just like PCA. It uses the kernel trick to factor away much of the computation, such that the entire process can be performed without actually computing $\phi(x)$. Of course, $\phi$ must be chosen such that it has a known corresponding kernel.

Laplacian Eigenmaps, (also known as Local Linear Eigenmaps, LLE) are special cases of kernel PCA, performed by constructing a data-dependent kernel matrix.

KPCA has an internal model, so it can be used to map points onto its embedding that were not available at training time. Laplacian Eigenmaps uses spectral techniques to perform dimensionality reduction. This technique relies on the basic assumption that the data lies in a low-dimensional manifold in a high-dimensional space. This algorithm cannot embed out of sample points, but techniques based on Reproducing kernel Hilbert space regularization exist for adding this capability. Such techniques can be applied to other nonlinear dimensionality reduction algorithms as well. Traditional techniques like principal component analysis do not consider the intrinsic geometry of the data. Laplacian eigenmaps builds a graph from neighborhood information of the data set. Each data point serves as a node on the graph and connectivity between nodes is governed by the proximity of neighboring points (using e.g. the k-nearest neighbor algorithm). The graph thus generated can be considered as a discrete approximation of the low-dimensional manifold in the high-dimensional space. Minimization of a cost function based on the graph ensures that points close to each other on the manifold are mapped close to each other in the low-dimensional space, preserving local distances. The eigenfunctions of the Laplace-Beltrami operator on the manifold serve as the embedding dimensions, since under mild conditions this operator has a countable spectrum that is a basis for square integrable functions on the manifold (compare to Fourier series on the unit circle manifold). Attempts to place Laplacian eigenmaps on solid theoretical ground have met with some success, as under certain nonrestrictive assumptions, the graph Laplacian matrix has been shown to converge to the Laplace-Beltrami operator as the number of points goes to infinity. In classification applications, low dimension manifolds can be used to model data classes which can be defined from sets of observed instances. Each observed instance can be described by two independent factors termed 'content' and 'style', where 'content' is the invariant factor related to the essence of the class and 'style' expresses variations in that class between instances. Unfortunately, Laplacian Eigenmaps may fail to produce a coherent representation of a class of interest when training data consist of instances varying significantly in terms of style. In the case of classes which are represented by multivariate sequences, Structural Laplacian Eigenmaps has been proposed to overcome this issue by adding additional constraints within the Laplacian Eigenmaps neighborhood information graph to better reflect the intrinsic structure of the class. More specifically, the graph is used to encode both the sequential structure of the multivariate sequences and, to minimize stylistic variations, the proximity between data points of different sequences or even within a sequence, if it contains repetitions. Using dynamic time warping, proximity is detected by finding correspondences between and within sections of the multivariate sequences that exhibit high similarity.

Like LLE, Hessian LLE is also based on sparse matrix techniques. It tends to yield results of a much higher quality than LLE. Unfortunately, it has a very costly computational complexity, so it is not well-suited for heavily sampled manifolds. It has no internal model. Modified LLE (MLLE) is another LLE variant which uses multiple weights in each neighborhood to address the local weight matrix conditioning problem which leads to distortions in LLE maps. MLLE produces robust projections similar to Hessian LLE, but without the significant additional computational cost.

Manifold alignment takes advantage of the assumption that disparate data sets produced by similar generating processes will share a similar underlying manifold representation. By learning projections from each original space to the shared manifold, correspondences are recovered and knowledge from one domain can be transferred to another. Most manifold alignment techniques consider only two data sets, but the concept extends to arbitrarily many initial data sets. Diffusion maps leverage the relationship between heat diffusion and a random walk (Markov Chain); an analogy is drawn between the diffusion operator on a manifold and a Markov transition matrix operating on functions defined on the graph whose nodes were sampled from the manifold. The relational perspective map is a multidimensional scaling algorithm. The algorithm finds a configuration of data points on a manifold by simulating a multi-particle dynamic system on a closed manifold, where data points are mapped to particles and distances (or dissimilarity) between data points represent a repulsive force. As the manifold gradually grows in size, the multi-particle system cools down gradually and converges to a configuration that reflects the distance information of the data points. Local tangent space alignment (LTSA) is based on the intuition that when a manifold is correctly unfolded, all of the tangent hyperplanes to the manifold will become aligned. It begins by computing the k-nearest neighbors of every point. It computes the tangent space at every point by computing the d-first principal components in each local neighborhood. It then optimizes to find an embedding that aligns the tangent spaces. Local Multidimensional Scaling performs multidimensional scaling in local regions and then uses convex optimization to fit all the pieces together.

Maximum Variance Unfolding was formerly known as Semidefinite Embedding. The intuition for this algorithm is that when a manifold is properly unfolded, the variance over the points is maximized. This algorithm also begins by finding the k-nearest neighbors of every point. It then seeks to solve the problem of maximizing the distance between all non-neighboring points, constrained such that the distances between neighboring points are preserved. Nonlinear PCA (NLPCA) uses backpropagation to train a multi-layer perceptron (MLP) to fit to a manifold. Unlike typical MLP training, which only updates the weights, NLPCA updates both the weights and the inputs. That is, both the weights and inputs are treated as latent values. After training, the latent inputs are a low-dimensional representation of the observed vectors, and the MLP maps from that low-dimensional representation to the high-dimensional observation space. Manifold Sculpting uses graduated optimization to find an embedding. Like other algorithms, it computes the k-nearest neighbors and tries to seek an embedding that preserves relationships in local neighborhoods. It slowly scales variance out of higher dimensions, while simultaneously adjusting points in lower dimensions to preserve those relationships.

Ruffini (2015) discusses Multichannel transcranial current stimulation (tCS) systems that offer the possibility of EEG-guided optimized, non-invasive brain stimulation. A tCS electric field realistic brain model is used to create a forward "lead-field" matrix and, from that, an EEG inverter is employed for cortical mapping. Starting from EEG, 2D cortical surface dipole fields are defined that could produce the observed EEG electrode voltages.

Schestatsky et al. (2017) discuss transcranial direct current stimulation (tDCS), which stimulates through the scalp with a constant electric current that induces shifts in neuronal membrane excitability, resulting in secondary changes in cortical activity. Although tDCS has most of its neuromodulatory effects on the underlying cortex, tDCS effects can also be observed in distant neural networks. Concomitant EEG monitoring of the effects of tDCS can provide valuable information on the mechanisms of tDCS. EEG findings can be an important surrogate marker for the effects of tDCS and thus can be used to optimize its parameters. This combined EEG-tDCS system can also be used for preventive treatment of neurological conditions characterized by abnormal peaks of cortical excitability, such as seizures. Such a system would be the basis of a non-invasive closed-loop device. tDCS and EEG can be used concurrently. See Reference List 16.

EEG analysis approaches have emerged, in which event-related changes in EEG dynamics in single event-related data records are analyzed. See Allen D. Malony et al., Computational Neuroinformatics for Integrated Electromagnetic Neuroimaging and Analysis, PAR-99-138. Pfurtscheller, reported a method for quantifying the average transient suppression of alpha band (circa 10-Hz) activity following stimulation. Event-related desynchronization (ERD, spectral amplitude decreases), and event-related synchronization (ERS, spectral amplitude increases) are observed in a variety of narrow frequency bands (4-40 Hz) which are systematically dependent on task and cognitive state variables as well as on stimulus parameters. Makeig (1993) was reported on event-related changes in the full EEG spectrum, yielding a 2-D time/frequency measure he called the event-related spectral perturbation (ERSP). This method avoided problems associated with the analysis of a priori narrow frequency bands, since bands of interest for the analysis could be based on significant features of the complete time/frequency transform. Rappelsburger et al. introduced event-related coherence (ERCOH). A wide variety of other signal processing measures have been tested for use on EEG and/or MEG data, including dimensionality measures based on chaos theory and the bispectrum. Use of neural networks has also been proposed for EEG pattern recognition applied to clinical and practical problems, though usually these methods have not been employed with the aim of explicitly modeling the neurodynamics involved. Neurodynamics is the mobilization of the nervous system as an approach to physical treatment. The method relies on influencing pain and other neural physiology via the mechanical treatment of neural tissues and the non-neural structures surrounding the nervous system. The body presents the nervous system with a mechanical interface via the musculoskeletal system. With movement, the musculoskeletal system exerts non-uniform stresses and movement in neural tissues, depending on the local anatomical and mechanical characteristics and the pattern of body movement. This activates an array of mechanical and physiological responses in neural tissues. These responses include neural sliding, pressurization, elongation, tension, and changes in intraneural microcirculation, axonal transport, and impulse traffic.

The availability of and interest in larger and larger numbers of EEG (and MEG) channels led immediately to the question of how to combine data from different channels. Donchin advocated the use of linear factor analysis methods based on principal component analysis (PCA) for this purpose. Temporal PCA assumes that the time course of activation of each derived component is the same in all data conditions. Because this is unreasonable for many data sets, spatial PCA (usually followed by a component rotation procedure such as Varimax or Promax) is of potentially greater interest. To this end, several variants of PCA have been proposed for ERP decomposition.

Bell and Sejnowski published an iterative algorithm based on information theory for decomposing linearly mixed signals into temporally independent by minimizing their mutual information. First approaches to blind source separation minimized third and fourth-order correlations among the observed variables and achieved limited success in simulations. A generalized approach uses a simple neural network algorithm that used joint information maximization or 'infomax' as a training criterion. By using a compressive nonlinearity to transform the data and then following the entropy gradient of the resulting mixtures, ten recorded voice and music sound sources were unmixed. A similar approach was used for performing blind deconvolution, and the 'infomax' method was used for decomposition of visual scenes.

The first applications of blind decomposition to biomedical time series analysis applied the infomax independent component analysis (ICA) algorithm to the decomposition of EEG and event-related potential (ERP) data and reported the use of ICA to monitor alertness. This separated artifacts, and EEG data into constituent components defined by spatial stability and temporal independence. ICA can also be used to remove artifacts from continuous or event-related (single-trial) EEG data prior to averaging. Vigario et al. (1997), using a different ICA algorithm, supported the use of ICA for identifying artifacts in MEG data. Meanwhile, widespread interest in ICA has led to multiple applications to biomedical data as well as to other fields (Jung et al., 2000b). Most relevant to EEG/MEG analysis, ICA is effective in separating functionally independent components of functional magnetic resonance imaging (fMRI) data Since the publication of the original infomax ICA algorithm, several extensions have been proposed. Incorporation of a 'natural gradient' term avoided matrix inversions, greatly speeding the convergence of the algorithm and making it practical for use with personal computers on large data EEG and fMRI data sets. An initial 'sphering' step further increased the reliability of convergence of the algorithm. The original algorithm assumed that sources have 'sparse' (super-Gaussian) distributions of activation values. This restriction has recently been relaxed in an 'extended-ICA' algorithm that allows both super-Gaussian and sub-Gaussian sources to be identified. A number of variant ICA algorithms have appeared in the signal processing literature. In general, these make more specific assumptions about the temporal or spatial structure of the components to be separated and typically are more computationally intensive than the infomax algorithm.

Since individual electrodes (or magnetic sensors) each record a mixture of brain and non-brain sources, spectral measures are difficult to interpret and compare across scalp channels. For example, an increase in coherence between two electrode signals may reflect the activation of a strong brain source projecting to both electrodes or the deactivation of a brain generator projecting mainly to one of the electrodes. If independent components of the EEG (or MEG) data can be considered to measure activity within functionally distinct brain networks, however, event-related coherence between independent components may reveal transient, event-related changes in their coupling and decoupling (at one or more EEG/MEG frequencies). ERCOH analysis has been applied to independent EEG components in a selective attention task.

Electrooculography: Electrooculography (EOG) is a technique for measuring the corneo-retinal standing potential that exists between the front and the back of the human eye. The resulting signal is called the electrooculogram. Primary applications are in the ophthalmological diagnosis and in recording eye movements. Unlike the electroretinogram, the EOG does not measure the response to individual visual stimuli. To measure eye movement, pairs of electrodes are typically placed either above and below the eye or to the left and right of the eye. If the eye moves from a center position toward one of the two electrodes, this electrode "sees" the positive side of the retina and the opposite electrode "sees" the negative side of the retina. Consequently, a potential difference occurs between the electrodes. Assuming that the resting potential is constant, the recorded potential is a measure of the eye's position.

Because sleep patterns have characteristic eye movements, e.g., rapid eye movements (REM), EOG may provide in indication of sleep state.

Electromyography: Electromyography (EMG) is an electrodiagnostic medicine technique for evaluating and recording the electrical activity produced by skeletal muscles. EMG is performed using an instrument called an electromyograph to produce a record called an electromyogram. An electromyograph detects the electric potential generated by muscle cells when these cells are electrically or neurologically activated. EMG reflects muscle tone, which can be indicative of a sleep state. See, Reference List 17.

SUMMARY OF THE INVENTION

The present invention provides a system and method for inducing brain states in a subject human or animal which represent or are conducive to sleep according to a natural sleep cycle, based on brain activity patterns (e.g., brainwaves) from a representative of the same species, or the same individual, which are processed and converted to a stimulatory signal that is then imposed on the subject. At any time, the stimulation of the subject seeks to induce EEG patterns that are representative of a target sleep state. The sequence of sleep states may be from the species or individual, or designed according to an algorithm designed or optimized to achieve the overall sleep pattern comprising the desired sequence of sleep states. Advantageously, the subject is monitored during stimulation to measure response to the stimulation, and/or interruption of the target sleep cycle. In case of interruption of the sleep cycle, the stimulation is restarted based on the state of the subject and, therefore, progresses again through a natural sequence of sleep states.

In some cases, the goal is to achieve a sleep cycle which differs from a normal or natural sleep cycle and may be modified or controlled in the case of organic pathology or mental illness. The preferred stimulation is non-invasive, and also preferably not electrical. However, transcranial magnetic stimulation, e.g., subthreshold PEMF, may be employed, alone or with auditory, visual, or other stimulation. For example, while visual stimulation may be contraindicated for entry into respectively deeper sleep states, it may be advantageously used for moving the subject to a shallower sleep state, and to awaken the subject. However, such auditory or visual stimulation preferably is modulated to synchronize or control brainwave patterns, in addition to any overt sensory effects that may be provided. The measurement of brain activity, and brain stimulation may be according to the known methods described hereinabove, without limitation, though the preferred implementation is such that the subject need not be encumbered by bulky, uncomfortable, expensive, or exotic equipment, and can be used unmonitored in a home environment. However, the invention is not limited by such constraints, so long as the sleep pattern is effectively controlled.

In some cases, the invention is used for other than sleep induction, and may also be used to control other stages of consciousness or other mental or emotional states, and preferably a desired sequence of states based on subject biology.

Brain-states, which correlate with specific cognitive states, may be monitored with non-invasive techniques such as EEG and MEG that indirectly measure cortical activity. These cortical signatures provide insight into the neuronal activity, which has been used to identify abnormal cortical function in numerous neurological and psychiatric conditions. Further, the induction of entrained cortical rhythms via transcranial stimulation is effective in imbuing brain-states correlated with such cortical rhythms. See, Poltorak, Alexander. 2019. "On the Possibility of Transplanting Mental States." OSF Preprints. April 16. doi: 10.31219/osf.io/sjqfx.

It has been suggested by Crick and Koch [Crick F, Koch C. Towards a neurobiological theory of consciousness. Seminars in the Neurosciences, 1990; (2), 263-75.] (see also [Rees G, Kreiman G, Koch C. Neural correlates of consciousness in humans. Nature Reviews. Neuroscience 2002; 3 (4), 261-270. doi.org/10.1038/nrn783]) that every mental state is expressed through unique neural signals, such as frequency oscillations, that are correlated with mood, cognition and motor functions. It is thus possible to induce a desired mental state by replicating its neural correlates.

Functional neuroimaging, such as EEG or MEG, can capture the neuronal activity of localized brain regions which correlate with distinct cognitive or behavioral states (mental states). EEG recordings have demonstrated, for example, that the pattern of brain activity changes during meditative acts, and frontal cortex EEG activity has been associated with emotion induction and regulation (Yu et al. [Yu X, Fumoto M, Nakatani Y, Sekiyama T, Kikuchi H, Seki Y, Sato-Suzuki I, Arita H. Activation of the anterior prefrontal cortex and serotonergic system is associated with improvements in mood and EEG changes induced by Zen meditation practice in novices. Int J of Psychophysiology 2011; 80(2), 103-111. doi.org/10.1016/j.ijpsycho.2011.02.004]; Dennis and Solomon [Dennis T A, Solomon B. Frontal EEG and emotion regulation: electrocortical activity in response to emotional film clips is associated with reduced mood induction and attention interference effects. Biological Psychology 2010; 85 (3), 456-464. doi.org/10.1016/j.biopsycho.2010.09.008]). EEG recordings reflect ionic fluctuations resultant of neuronal communication in the cortex arising from dendritic depolarizations (Nunez and Srinivasan [Nunez P L, Srinivasan R. Electric fields of the brain: the neurophysics of EEG(2 ed). Oxford: Oxford Univ. Press; 2006.]). Alternatively, MEG measurements reflect intracellular ionic fluctuations, which similarly result from action potentials (Hämäläinen et al. [Hämäläinen M, Hari R, Ilmoniemi R J, Knuutila J, Lounasmaa O V. Magnetoencephalography—theory, instrumentation, and applications to noninvasive studies of the working human brain. Rev. Mod. Phys. 1993; 65,413. doi.org/10.1103/revmodphys.65.413]). In both cases, the output measures correlate with localized cortical activity.

These EEG or MEG signatures may be inverted in order to stimulate, rather than record, cortical activity. Specifically, transcranial electric stimulation (TES; Annarumma et al. [Annarumma L, D'Atri A, Alfonsi V, De Gennaro L. The Efficacy of Transcranial Current Stimulation Techniques to Modulate Resting-State EEG, to Affect Vigilance and to Promote Sleepiness. Brain Sci. 2018; 8 (7), 137. doi.org/10.3390/brainsci8070137]), including transcranial alternating current stimulation (tACS) and transcranial direct current stimulation (tDCS; Utz et al. [Utz K S, Dimova V, Oppenländer K, Kerkhoff G. Electrified minds: transcranial direct current stimulation (tDCS) and galvanic vestibular stimulation (GVS) as methods of non-invasive brain stimulation in neuropsychology—a review of current data and future implications. Neuropsychologia 2010; 48(10), 2789-2810]) are used to electrically stimulate cortical activity, while transcranial magnetic stimulation (TMS; see [Lawson McLean A. Publication trends in transcranial magnetic stimulation: a 30-year panorama. Brain Stimulation 2019; in press. doi.org/10.1016/j.brs.2019.01.002]) uses a precise magnetic field in order to achieve a similar endpoint of electric current control. Typical brain entrainment methods utilize a constant stimulus (e.g., tDCS) or a synthetic waveform, which may be a step function modulated on a direct current (such as "electrosleep" [Robinovitch L G. Electric analgesia, and electric resuscitation after heart failure under chloroform or electrocution. Journal of the American Medical Association 1911; LVI (7), 478-481. doi.org/10.1001/jama. 1911.02560070010003]), a sinusoid modulated on an oscillatory direct current (osc-tDCS; D'Atri et al. [D'Atri A, De Simoni E, Gorgoni M, Ferrara M, Ferlazzo F, Rossini P M, De Gennaro L. Electrical stimulation of the frontal cortex enhances slow-frequency EEG activity and sleepiness. Neuroscience 2016; 324, 119-130. doi.org/10.1016/j.neuroscience.2016.03.007]), or a fixed frequency modulated on alternating current (tACS; [Rosa, MA, Lisanby, SH. Somatic treatments for mood disorders. Neuropsychopharmacology 2012; 37 (1), 102-16. 10.1038/npp.2011.225]). Helfrich et al., supra, utilized simultaneous tACS stimulation combined with EEG recordings to show that, when tACS was applied to the parieto-occipital lobe of the brain, alpha wave activity increased and became synchronized with the entrainment frequency.

These techniques may be used in order to record and subsequently induce specific brain states. Thus, EEG/MEG may be used to record mental states, which may then be applied via TES (tDCS, osc-tDCS, tACS) or TMS in order to replicate the cognitive-behavioral state of the "donor." This technique has been previously investigated in the domain of sleep [Gebodh N, Vacchi L, Adair D, Unal G, Poltorak A, Poltorak V, Bikson M. Proceedings #11: Replay of Endogenous Sleep Rhythms to Produce Sleepiness. Brain Stimulation: Basic, Translational, and Clinical Research in Neuromodulation 2019; 12 (2), e71-e72. doi.org/10.1016/j.brs.2018.12.180].

The present technology involves, according to one embodiment, the notion of "transplanting" mental states including sleep, attention, and learning, as well as emotional valence. See FIG. 28. Attention-states in the brain are primarily the result of the cognitive process of suppressing the detection of erroneous stimuli. This cognitive state is associated with specific neuronal oscillations (Schroeder et al. [Schroeder C E, Wilson D A, Radman T, Scharfman H, Lakatos P. Dynamics of Active Sensing and perceptual selection. Current Opinion in Neurobiology 2010; 20 (2), 172-176. doi.org/10.1016/j.conb.2010.02.010]) which may be captured via EEG or MEG. The neural oscillations associated with attention have been shown to be disrupted in a number of conditions including epilepsy (Besle et al., [Besle J, Schevon C A, Mehta A D, Lakatos P, Goodman R R, Mckhann G M, Emerson R G, Schroeder, CE. Tuning of the human neocortex to the temporal dynamics of attended events. The Journal of Neuroscience: The Official Journal of the Society for Neuroscience 2011; 31 (9), 3176-3185. doi.org/10.1523/JNEUROSCI.4518-10.2011]), dyslexia (Thomson et al. [Thomson J M, Goswami U. Rhythmic processing in children with developmental dyslexia: auditory and motor rhythms link to reading and spelling. Journal of Physiology, Paris 2008; 102 (1-3), 120-129. doi.org/10.1016/j.jphysparis.2008.03.007]; Leong et al. [Leong V, Goswami U. Assessment of rhythmic entrainment at multiple timescales in dyslexia: evidence for disruption in syllable timing. Hearing Research 2014; 308, 141-161. doi.org/10.1016/j.heares.2013.07.015]; Soltész et al. [Soltész F, Szűcs D, Leong V, White S, Goswami U. Differential entrainment of neuroelectric delta oscillations in developmental dyslexia. PloS One 2013; 8 (10), e76608. doi.org/10.1371/journal.pone.0076608]), and schizophrenia (Lakatos et al. [Lakatos P, Schroeder C E, Leitman D I, Javitt D C. Predictive suppression of cortical excitability and its deficit in schizophrenia. The Journal of Neuroscience: The Official Journal of the Society for Neuroscience 2013; 33 (28), 11692-11702. doi.org/10.1523/JNEUROSCI.0010-13.2013]). Therefore, the acquisition of a brainwave signature during states of attention in a healthy "donor" may prove valuable when applied to a recipient exhibiting attention deficits associated with disrupted or otherwise irregular cortical oscillations. Previous research shows that memory functions are acutely sensitive to neural entrainment and may be disrupted via TMS (Hanslmayr et al. [Hanslmayr S, Matuschek J, Fellner M-C. Entrainment of Prefrontal Beta Oscillations Induces an Endogenous Echo and Impairs Memory Formation. Current Biology 2014; 24 (8),904-909. doi.org/10.1016/j.cub.2014.03.007]) indicating the possibility of an inverse, positive entrainment of these oscillations.

Similarly, emotional arousal and valence are correlated with distinct cortical signatures observable through EEG (Allen et al. [Allen J J B, Keune P M, Schönenberg M, Nusslock R. Frontal EEG alpha asymmetry and emotion: From neural underpinnings and methodological considerations to psychopathology and social cognition. Psychophysiology 2018; 55 (1). doi.org/10.1111/psyp. 13028]). Previous data indicate that happiness resultant of musical experience, for instance, is associated with increased theta frequency oscillations in the left frontal cortical hemisphere (Rogenmoser et al. [Rogenmoser L, Zollinger N, Elmer S, Jäncke L. Independent component processes underlying emotions during natural music listening. Social Cognitive and Affective Neuroscience 2016; 11 (9), 1428-1439. doi.org/10.1093/scan/nsw048]). Cortical oscillations associated with negative affect conversely correlate with decreased theta frequency oscillations in this same region. Notably, aberrant cortical oscillations have been observed in a range of affective disorders including major depression (Van der Vinne et al. [Van der Vinne N, Vollebregt M A, van Putten MJAM, Arns M. Frontal alpha asymmetry as a diagnostic marker in depression: Fact or fiction? A meta-analysis. NeuroImage. Clinical 2017; 16, 79-87. doi.org/10.1016/j.nicl.2017.07.006]). Indeed, the left frontal hemisphere exhibits disrupted cortical rhythms in patients diagnosed with major depression as compared to healthy controls (Nusslock et al. [Nusslock R, Shackman A J, McMenamin B W, Greischar L L, Davidson R J, Kovacs M. Comorbid anxiety moderates the relationship between depression history and prefrontal EEG asymmetry. Psychophysiology 2018; 55 (1). doi.org/10.1111/psyp.12953]). Similar data have highlighted cortical asymmetry of frontal lobe oscillations in post-traumatic stress disorder (PTSD; Meyer et al. [Meyer T, Quaedflieg CWEM, Weijland K, Schruers K, Merckelbach H, Smeets T. Frontal EEG asymmetry during symptom provocation predicts subjective responses to intrusions in survivors with and without PTSD. Psychophysiology 2018; 55 (1). doi.org/10.1111/psyp. 12779]). Simple cortical entrainment via binaural beat stimulation has already proven adequate for inducing specific emotional states (Chaieb et al. [Chaieb L, Wilpert E C, Reber T P, Fell J. Auditory Beat Stimulation and its Effects on Cognition and Mood States. Frontiers in Psychiatry 2015; 6. doi.org/10.3389/fpsyt.2015.00070]). More directly, cranial electrotherapy has been demonstrated as an efficacious treatment for depression, anxiety, and certain forms of insomnia (Kirsch et al. [Kirsch D L, Nichols F. Cranial Electrotherapy Stimulation for Treatment of Anxiety, Depression, and Insomnia. Psychiatric Clinics of North America 2013; 36 (1), 169-176. doi.org/10.1016/j.psc.2013.01.006]). Certain forms of depression may respond better to transcranial approaches, such as TMS, as has been demonstrated in early data on patients with treatment-resistant major depression (Rosenberg et al. [Rosenberg O, Shoenfeld N, Zangen A, Kotler M, Dannon P N. Deep TMS in a resistant major depressive disorder: a brief report. Depression and Anxiety 2010; 27 (5), 465-469. doi.org/10.1002/da.20689])

This approach to "transplant" (transfer) mental states by replicating neural correlates of the donor's state in a recipient is founded on two main principles. First, a large body of literature has identified distinct, measurable cortical signatures associated with specific brain-states ranging from those defining the sleep/wake cycle to those underlying emotional experience. Second, TES and TMS have been repeatedly demonstrated as efficacious, safe means by which cortical rhythms may be entrained with a high degree of location-specificity. Together, these findings provide the basis for the hypothesis that mental states can be "transplanted" (transferred) and provide the means by which a cortical signature may be obtained via EEG or EMG associated with a desired mental state of a "donor" that may, in turn, be processed, inverted, and subsequently applied to a recipient in order to induce said cognitive state via cortical rhythm entrainment using tACS, TMS or other stimuli such as light or sound. Theoretical considerations suggest that this hypothesis is plausible and deserves experimental verification. Importantly, using cortical signatures acquired from a "donor," rather than a fixed-frequency or synthetic waveform applications as is currently typical for TES techniques, offers the distinct advantage of replicating multi-phasic, temporally dynamic signals are more likely to induce naturalistic mind-states holistically. This technique may, therefore, provide a novel approach to the non-invasive treatment of a variety of disorders whose current treatments are limited to pharmacotherapeutic interventions.

Sleep disorders affect a significant portion of the adult population. Between 50 and 70 million adults in the U.S. have a sleep disorder. (Ohayon M M. Epidemiology of insomnia: what we know and what we still need to learn. Sleep medicine reviews. 2002; 6 (2): 97-111.) Insomnia is the most common specific sleep disorder, with short-term issues reported by about 30% of adults and chronic insomnia by 10%. (Kessler R C, Berglund P A, Coulouvrat C, et al. Insomnia and the performance of US workers: results from the America insomnia survey. Sleep. 2011; 34 (9): 1161-1171; Sateia M J, Doghramji K, Hauri P J, Morin C M. Evaluation of chronic insomnia. An American Academy of Sleep Medicine review. Sleep. 2000; 23 (2): 243-308.) Chronic insomnia is associated with deterioration of memory, adverse effects on endocrine functions and immune responses, and an increase in the risk of obesity and diabetes Sateia et al. 2000; Taylor D J, Mallory L J, Lichstein K L, Durrence H H, Riedel B W, Bush A J. Comorbidity of chronic insomnia with medical problems. Sleep. 2007; 30 (2): 213-218). While at any age, managing insomnia is a challenge, it is especially a critical condition in the elderly due to age-related increases in comorbid medical conditions and medication use, as well as age-related changes in sleep structure, which shorten sleep time and impair sleep quality. (Ancoli-Israel S. Insomnia in the elderly: a review for the primary care practitioner. Sleep. 2000; 23: S23-30; discussion S36-28; Buysse D J. Insomnia, depression, and aging. Assessing sleep and mood interactions in older adults. Geriatrics (Basel, Switzerland). 2004; 59 (2): 47-51; quiz 52.) As a result, decreased sleep quality is one of the most common health complaints of older adults. Medications are widely prescribed for relief from insomnia. However, sleep-promoting agents, such as hypnotic drugs, can produce adverse effects, particularly in the elderly. (Sateia M J, Buysse D J, Krystal A D, Neubauer D N. Adverse Effects of Hypnotic Medications. J Clin Sleep Med. Jun. 15, 2017; 13 (6): 839.) Even natural supplements, such as melatonin, can cause some side effects, including headache, depression, daytime sleepiness, dizziness, stomach cramps, and irritability. (Buscemi N, Vandermeer B, Hooton N, et al. The efficacy and safety of exogenous melatonin for primary sleep disorders a meta-analysis. Journal of general internal medicine. 2005; 20 (12): 1151-1158.)

Aside from the general deterioration of sleep quality with age in adult population, the deterioration in quantity and quality of the slow-wave sleep (SWS), which is non-REM deep sleep, is particularly troubling. (Roth T. Slow wave sleep: does it matter? Journal of clinical sleep medicine: JCSM: official publication of the American Academy of Sleep Medicine. 2009; 5 (2 Suppl): S4). SWS plays an important role in cerebral restoration and recovery in humans. Studies have shown that a 15% reduction in the amounts of SWS and increased number and duration of awakenings are associated with normal aging. (Chinoy E D, Frey D J, Kaslovsky D N, Meyer F G, Wright Jr K P. Age-related changes in slow wave activity rise time and NREM sleep EEG with and without zolpidem in healthy young and older adults. Sleep medicine. 2014; 15 (9): 1037-1045.) Experimental disruption of SWS have been shown to increase shallow sleep, sleep fragmentation, daytime sleep propensity, and impair daytime function. (Dijk D J. Regulation and functional correlates of slow wave sleep. J Clin Sleep Med. Apr. 15 2009; 5 (2 Suppl): S6-15; Restoring Deep, Slow Wave Sleep to Enhance Health and Increase Lifespan, nutritionreview.org/2014/07/restoring-slow-wave-sleep-shown-enhance-health-increase-lifespan/ (2014). Given that SWS contributes to sleep continuity, enhancement of SWS may lead to improvements in sleep quality and daytime function in patients with insomnia and the elderly. Furthermore, accumulating evidence point to the SWS is the time when short-term memory is consolidated into long-term memory. (Born J. Slow-wave sleep and the consolidation of long-term memory. The World Journal of Biological Psychiatry. 2010; 11 (sup1): 16-21.) Recent research connects the deterioration of the SWS with early onset of Alzheimer's disease and other forms of dementia. (Petit D, Gagnon J-F, Fantini M L, Ferini-Strambi L, Montplaisir J. Sleep and quantitative EEG in neurodegenerative disorders. Journal of psychosomatic research. 2004; 56 (5): 487-496; McCurry S M, Ancoli-Israel S. Sleep dysfunction in Alzheimer's disease and other dementias. Current treatment options in neurology. 2003; 5 (3): 261-272). It is also suggested that the loss of SWS stage may play a role in these debilitating age-related diseases. (Mattis J, Sehgal A. Circadian rhythms, sleep, and disorders of aging. Trends in Endocrinology & Metabolism. 2016; 27 (4): 192-203). Unfortunately, most standard sleeping pills, while alleviating insomnia, do little to improve the SWS. (Walsh J K. Enhancement of slow wave sleep: implications for insomnia. Journal of clinical sleep medicine: JCSM: official publication of the American Academy of Sleep Medicine. 2009; 5 (2 Suppl): S27.) Some evidence suggests that some hypnotic drugs change the structure of sleep, adversely affecting the SWS (Sateia et al. (2017); Walsh (2009). Hence, there is an unmet need for non-pharmacological techniques for promoting sleep, particularly, the deep non-REM sleep stage (SWS) lacking in the elderly population.

One of the promising non-pharmacological approaches to promoting sleep is neuromodulation via light, sound, and/or transcranial electric stimulation (TES). Limited human trials conducted by Neuroenhancement Lab in collaboration with the Neuromodulation Laboratory at The City College of New York (CUNY) showed promise in replicating the desired sleep stage o a healthy donor in other subjects (recipients). Electroencephalogram (EEG) of healthy volunteers were recorded as they dozed off entering stage 1 of sleep, as evidenced by the predominance of alpha waves. These EEG recordings were subsequently filtered from noise, inverted, and used for transcranial Endogenous Sleep-Derived stimulation (tESD). Volunteer subjects stimulated with tESD modulated with the indigenous brainwaves recorded in a sleeping donor, quickly dozed off and entered stage 1 of sleep, as evidenced by EEG, heart rate, respiration rate, and post-sleep cognitive test. These results were better as compared to the control arms of the study that included sham stimulation, tDCS, and tACS (10 Hz). These preliminary results suggest that tACS modulated with indigenous brainwaves recorded from a healthy sleeping donor can be used to replicate the desired sleep stage of a healthy donor in another subject.

There is significant research to identify markers of different phases of healthy or pathological sleep; the markers allow to classify observed EEG to one of the phases of sleep/wake categories. The applicants are not aware of any research that aimed at comprehensive identification of all independent components of EEG signals during sleep; and comprehensive analysis of statistically significant inter-dependence of a presence of an independent component with the particular stage of sleep. Comprehensive identification and analysis of independent components associated with sleep would allow to use those components and/or derived signals for a tACS protocol.

EEG recordings of brainwaves are obtained and pre-processed from healthy human subjects during various stages of sleep. EEG recordings of three stages of sleep, and while being awake from at least ten healthy subjects (e.g., through public EEG database), which are then smoothed and filtered. The EEG recordings are analyzed to identify statistically significant waveform components correlated with specific sleep stages. A model (e.g., a linear multivariate model) is developed for the coefficients of the components of the EEG, based on sleep stage/wakefulness status; and the statistical significance of the model is measured. Stimulation protocols are developed that can provide safe and effective neurostimulation to induce desired sleep stage.

Great economic burden and the societal cost is incurred due to sleeping disorders, particularly insomnia. Sleep disturbances are common symptoms in adults and are related to various factors, including the use of caffeine, tobacco, and alcohol; sleep habits; and comorbid diseases. Epidemiologic studies indicate sleep disorders are affecting a significant portion of adult population. Between 50 and 70 million adults in the U.S. have a sleep disorder. Insomnia is the most common specific sleep disorder, with short-term issues reported by about 30% of adults and chronic insomnia by 10%. (Kessler et al. (2011), Sateia et al. (2000), Ancoli- Israel et al. (2000), Ancoli-Israel S, Roth T. Characteristics of insomnia in the United States: results of the 1991 National Sleep Foundation Survey. I. Sleep. 1999; 22: S347-353.). Chronic insomnia is associated with deterioration of memory, adverse effects on endocrine functions and immune responses, and an increase in the risk of obesity and diabetes. (Sateia et al. (2000)). In addition, there is a significant economic burden and societal cost associated with insomnia due to the impact on health care utilization, impact in the work domain, and quality of life. Recent estimates of direct and indirect costs are upwards of 100 billion dollars annually in the United States. (Fullerton D S. The economic impact of insomnia in managed care: a clearer picture emerges. Am J Manag Care. May 2006; 12 (8 Suppl): S246-252.) While at any age, managing insomnia is a challenge, it is especially a critical condition in the elderly due to age-related increases in comorbid medical conditions and medication use, as well as age-related changes in sleep structure, which shorten sleep time and impair sleep quality. (Ancoli-Israel (2000). As a result, decreased subjective sleep quality is one of the most common health complaints of older adults.

There is a deterioration of the slow-wave sleep (SWS) in the elderly. Aside from the general deterioration of sleep quality with age in the adult population, the deterioration in quantity and quality of the slow-wave sleep (SWS), which is the deep non-REM sleep, is particularly troubling. (Roth (2009). SWS plays an important role in cerebral restoration and recovery in humans. It is the most prominent EEG event during sleep and appears as spontaneous large oscillations of the EEG signal occurring approximately once every second in the deepest stage of non-REM sleep. (Achermann P, Dijk D-J, Brunner D P, Borbély AA. A model of human sleep homeostasis based on EEG slow-wave activity: quantitative comparison of data and simulations. Brain research bulletin. 1993; 31 (1-2): 97-113.) Studies have shown that a significant decrease (~15% reduction) in the amounts of SWS and increased number and duration of awakenings are associated with normal aging. (Chinoy et al. (2014). Given that SWS contributes to sleep continuity and experimental disruption of SWS increases shallow sleep and sleep fragmentation, enhances daytime sleep propensity, and impairs daytime function. (Dijk (2009); NutritionReview.org (2014)), enhancement of SWS may lead to improvements in sleep maintenance and daytime function in patients with insomnia and in the elderly. Furthermore, accumulating evidence point to the SWS as the time when short-term memory is consolidated into long-term memory. (Born (2010). Recent research connects the deterioration of the SWS with early onset of Alzheimer's disease and other forms of dementia. (Petit et al. (2010); McCurry et al. (2003). It is also suggested that the loss of SWS stage may be the culprit for these debilitating age-related diseases. (Mattis et al. (2016).

SWS enhancement is a potential non-pharmacological therapy for the elderly. Given the pivotal role of slow waves during sleep, it is not surprising that several efforts have been made to increase sleep efficacy by potentiating SWS. Recently, a number of drugs have been shown to increase SWS. Although acting on different synaptic sites, overall the slow wave enhancing the effect of these drugs is mediated by enhancing GABAergic transmission. Specifically, clinical investigations showed that both tiagabine and gaboxadol increased the duration of SWS after sleep restriction. (Walsh (2009); Mathias S, Wetter T C, Steiger A, Lancel M. The GABA uptake inhibitor tiagabine promotes slow wave sleep in normal elderly subjects. Neurobiology of aging. 2001; 22 (2): 247-253; Walsh J K, Snyder E, Hall J, et al. Slow wave sleep enhancement with gaboxadol reduces daytime sleepiness during sleep restriction. Sleep. May 2008; 31 (5): 659-672; Feld G B, Wilhelm I, Ma Y, et al. Slow wave sleep induced by GABA agonist tiagabine fails to benefit memory consolidation. Sleep. Sep. 1 2013; 36 (9): 1317-1326.). Tiagabine also improved performance on cognitive tasks evaluating executive functions and reduced the negative effects of sleep restriction on alertness. (Walsh J K, Randazzo A C, Stone K, et al. Tiagabine is associated with sustained attention during sleep restriction: evidence for the value of slow-wave sleep enhancement? Sleep-New York Then Westchester-. 2006; 29 (4): 433.). Although these results are positive, pharmacological approaches to sleep enhancement often raise issues related to dependence and tolerance and are commonly associated with residual daytime side effects. Some evidence suggests that some hypnotic drugs, while alleviating insomnia, change the structure of sleep adversely affecting the SWS. (Sateia (2000); Walsh (2009)). Even natural supplements, such as melatonin, can cause some side effects, including headache, short-term feelings of depression, daytime sleepiness, dizziness, stomach cramps, and irritability. (Buscemi et al. (2005)). Hence, there is an unmet need for a non-pharmacological technique for promoting sleep, particularly in the deep non-REM sleep stage lacking in the elderly population.

Brainwaves, e.g., EEG signals, may be acquired in various ways. Traditional signal acquisition by neurologists and encephalography/EEG technicians involves pasted-on electrodes or caps with arrays of electrodes, e.g., 20-256 electrodes positioned on the scalp. However, in some cases, especially where high spatial resolution is not required, and dominant brainwave patterns are sought, simpler and less controlled EEG acquisition systems may be employed, including through commercially available device intended to interface with smartphones. See, kokoon.io, www.think-mindset.com/; www.choosemuse.com (Muse, Muse2); Neurosky; getvi.com (Vi Sense); Strickland, Eliza, "In-Ear EEG Makes Unobtrusive Brain-Hacking Gadgets a Real Possibility", IEEE Spectrum Jul. 7, 2016; Strickland, Eliza, "Wireless Earbuds Will Record Your EEG, Send Brainwave Data To Your Phone", IEEE Spectrum May 17, 2016. The Unicorn "Hybrid Black" wearable EEG headset provides a headset with eight electrode channels and digital data acquisition electronics (24 bit, 250 Hz), intended to provide a brain-computer interface for artistic, control and other tasks. See, www.unicorn-bi.com/. Starkey Laboratories, Inc. US20190166434 discloses an ear-worn electronic device having a plurality of sensors for EEG signals from a wearer's ear, as a brain-computer interface. A number of designs provide in-ear headphones which integrate EEG electrodes that pick up signals from the ear canal. See Reference List 18.

The brain activity of a first subject (a "donor" who is in the desired sleeping state) may be captured by recording neural correlates of the sleep, as expressed by brain activity patterns, such as EEG signals. The representations of the neural correlates of the first subject are used to control stimulation of a second subject (a "recipient"), seeking to induce the same brain activity patterns of the donor in the recipient to assist the recipient in attaining the desired sleep state that had been attained by the donor.

One strategy to enhance deep sleep non-pharmacologically is to stimulate the brain with light, sound, electrical currents, or magnetic fields based on artificial and synthetic stimulation paradigms. Intermittent transcranial direct-current stimulation (tDCS) applied at 0.75 Hz for 5-min intervals separated by 1-min off periods after SWS onset can increase the EEG power in the slow oscillation band (<1 Hz) during the stimulation-free intervals. (Lang N, Siebner H R, Ward N S, et al. How does transcranial DC stimulation of the primary motor cortex alter regional neuronal activity in the human brain? European Journal of Neuroscience. 2005; 22 (2): 495-504; Marshall L, Helgadottir H, Molle M, Born J. Boosting slow oscillations during sleep potentiates memory. Nature. Nov. 30 2006; 444 (7119): 610-613). Similarly, stimulated by tDCS at the beginning of SWS accelerate the SWA homeostatic decay in subjects. (Reato D, Gasca F, Datta A, Bikson M, Marshall L, Parra L C. Transcranial electrical stimulation accelerates human sleep homeostasis. PLOS Comput Biol. 2013; 9 (2): e1002898). Furthermore, slow waves can be triggered by directly perturbing the cortex during non-REM sleep using transcranial magnetic stimulation (TMS). (Massimini M, Ferrarelli F, Esser S K, et al. Triggering sleep slow waves by transcranial magnetic stimulation. Proc Natl Acad Sci USA. May 15 2007; 104 (20): 8496-8501). Other research has focused on the possibility of inducing slow waves in a more physiological natural manner. In a larger study in healthy adults, bilateral electrical stimulation of the vestibular apparatus shortened sleep onset latency in comparison to sham nights where no stimulation was provided. (Krystal A D, Zammit G K, Wyatt J K, et al. The effect of vestibular stimulation in a four-hour sleep phase advance model of transient insomnia. J Clin Sleep Med. Aug. 15 2010; 6 (4): 315-321). The effect of somatosensory and auditory stimulation was also assessed (Krystal et al. 2010; Ngo H V, Martinetz T, Born J, Molle M. Auditory closed-loop stimulation of the sleep slow oscillation enhances memory. Neuron. May 8 2013; 78 (3): 545-553). While the change observed with somatosensory stimulation was minor, acoustic stimulation was particularly efficacious in enhancing sleep slow waves. Specifically, using an intermittent stimulation, in which tones were played in blocks of 15 s spaced out by stimulation-free intervals, slow waves appeared remarkably large and numerous during the stimulation blocks. (Tononi G, Riedner B, Hulse B, Ferrarelli F, Sarasso S. Enhancing sleep slow waves with natural stimuli. Medicamundi. 2010; 54 (2): 73-79; Bellesi M, Riedner B A, Garcia-Molina G N, Cirelli C, Tononi G. Enhancement of sleep slow waves: underlying mechanisms and practical consequences. Frontiers in systems neuroscience. 2014; 8:208). In addition, high-density EEG studies (hdEEG, 256 channels) showed that the morphology, topography, and traveling patterns of induced slow waves were indistinguishable from those of spontaneous slow waves observed during natural sleep. A recent study found that EEG SWA increased following tone presentation during non-REM sleep (Arzi A, Shedlesky L, Ben-Shaul M, et al. Humans can learn new information during sleep. Nature neuroscience. 2012; 15(10): 1460), and slow oscillation activity (0.5-1 Hz) was increased in response to continuous acoustic stimulation at 0.8 Hz starting 2 min before lights were turned off and lasting for 90 min. (Ngo H V, Claussen J C, Born J, Molle M. Induction of slow oscillations by rhythmic acoustic stimulation. J Sleep Res. February 2013; 22(1): 22-31). Unlike the previous neuro-stimulation methods with artificial and synthetic stimulation paradigms, the present stimulation protocol uses source-derived waveforms, extracted from the indigenous brain activity EEG recordings of the healthy subjects, processed by statistical methods (e.g., principal component analysis, independent component analysis (Ungureanu M, Bigan C, Strungaru R, Lazarescu V. Independent component analysis applied in biomedical signal processing. Measurement Science Review. 2004; 4(2): 18) or spatial principal component analysis, autocorrelation, etc.), which separates components of brain activity. These separated brain EEG activities are then modified or modulated and subsequently inverted and used for transcranial Endogenous Sleep-Derived stimulation (tESD). The application of endogenous brain waveform should not only retain the efficacy in triggering SWS but also alleviate the safety concerns that are associated with long-term brain stimulation using synthetic paradigms.

The present technology provides a method of improving sleep by transplanting sleep states—one desired sleep stage, or the sequences of sleep stages—from the first subject (donor) (or from a plurality of donors) to a second subject (recipient). (In some embodiments, the first and the second subject may be the same subject at different points in time, or based on a protocol or algorithm.)

The process seeks to achieve, in the subject, a brainwave pattern, which is derived from a human. The brainwave pattern is complex, representing a superposition of modulated waveforms. The modulation preferably is determined based on brain wave patterns of another subject or plurality of subjects.

Sleep is a natural periodic suspension of consciousness, basically a process that can hardly be influenced in its individual stages by the person sleeping. It is a subconscious (in a technical sense) mental state, representing a resting state, activity pattern, activity rhythm, readiness, receptivity, or other state, often independent of particular inputs. In essence, a sleep state in a particular sleep stage or a sequence of different sleep stages of the first subject (a "donor" who is in a desired sleep stage or goes through a sequence with its individual stages) is captured by recording neural correlates of the sleep state, e.g., as expressed by brain activity patterns, such as EEG or MEG signals. The neural correlates of the first subject, either as direct or recorded representations, may then be used to control a stimulation of the second subject (a "recipient"), seeking to induce the same brain activity patterns in the second subject (recipient) as were present in the first subject (donor), thereby transplanting the sleep state of the first subject (donor), to assist the second subject (recipient) to attain the desired sleep stage that had been attained by the donor. In an alternative embodiment, the signals from the first subject (donor) being in a first sleep stage are employed to prevent the second subject (recipient) from achieving a second sleep stage, wherein the second sleep stage is an undesirable one. Furthermore, the duration and timing of different sleep stages can be controlled in the second subject. This could enable the change of the individual duration or intensity of each sleep stage and the order in which they appear. In some embodiments, the signals from the first subject can be used to trigger sleep in the second subject or to prevent sleep or sleepiness and associated symptoms such as fatigue, lack of concentration, etc.

In one embodiment, brain activity patterns are recorded during a complete sleep cycle or during several such cycles over the course of a normal night sleeping. In some embodiments, the acquiring of the sleep state information is preceded by or followed by identifying the sleep stage, by direct reporting by the first subject (donor) or an observer, or by automated analysis of the physiological parameters (e.g., brain activity patterns, heartbeat, breathing pattern, oxygen saturation in blood, temperature, eye movement, skin impedance, etc.) or both. In other embodiments, the processing of the brain activity patterns does not seek to classify or characterize it, but rather to filter and transform the information to a form suitable for control of the stimulation of the second subject. In particular, according to this embodiment, the subtleties that are not yet reliably classified in traditional brain activity pattern analysis are respected. For example, it is understood that all brain activity is reflected in synaptic currents and other neural modulation and, therefore, theoretically, conscious and subconscious information is, in theory, accessible through brain activity pattern analysis. Since the available processing technology generally fails to distinguish a large number of different brain activity patterns, that available processing technology, is necessarily deficient, but improving. However, just because a computational algorithm is unavailable to extract the information, does not mean that the information is absent. Therefore, this embodiment employs relatively raw brain activity pattern data, such as filtered or unfiltered EEGs, to control the stimulation of the second subject, without a full comprehension or understanding of exactly what information of significance is present. In one embodiment, brainwaves are recorded and "played back" to another subject, similar to recording and playing back music. Such recording-playback may be digital or analog. Typically, the stimulation may include a low dimensionality stimulus, such as stereo-optic, binaural, isotonic tones, tactile, or other sensory stimulation, operating bilaterally, and with control over frequency and phase and/or waveform and/or transcranial stimulation such as TES, tDCS, HD-tDCS, tACS, or TMS. A plurality of different types of stimulation may be applied concurrently, e.g., visual, auditory, other sensory, magnetic, electrical.

Likewise, a present lack of complete understanding of the essential characteristics of the signal components in the brain activity patterns does not prevent their acquisition, storage, communication, and processing (to some extent). The stimulation may be direct, i.e., a visual, auditory, or tactile stimulus corresponding to the brain activity pattern or a derivative or feedback control based on the second subject's brain activity pattern.

To address the foregoing problems, in whole or in part, and/or other problems that may have been observed by persons skilled in the art, the present disclosure provides methods, processes, systems, apparatus, instruments, and/or devices, as described by way of example in implementations set forth below.

While mental states are typically considered internal to the individual, and subjective such states are common across individuals and have determinable physiological and electrophysiological population characteristics. Further, mental states may be externally changed or induced in a manner that bypasses the normal cognitive processes. In some cases, the triggers for the mental state are subjective, and therefore the particular subject-dependent sensory or excitation scheme required to induce a particular state will differ. For example, olfactory stimulation can have different effects on different people, based on differences in the history of exposure, social and cultural norms, and the like. On the other hand, some mental state response triggers are normative, for example, "tear jerker" media.

Mental states are represented in brainwave patterns, and in normal humans, the brainwave patterns and metabolic (e.g. blood flow, oxygen consumption, etc.) follow prototypical patterns. Therefore, by monitoring brainwave patterns in an individual, a state or series of mental states in that person may be determined or estimated. However, the brainwave patterns may be interrelated with context, other activity, and past history. Further, while prototypical patterns may be observed, there are also individual variations in the patterns. The brainwave patterns may include characteristic spatial and temporal patterns indicative of mental state. The brainwave signals of a person may be processed to extract these patterns, which, for example, may be represented as hemispheric signals within a frequency range of 3-100 Hz. These signals may then be synthesized or modulated into one or more stimulation signals, which are then employed to induce a corresponding mental state into a recipient, in a manner seeking to achieve a similar brainwave pattern from the source. The brainwave pattern to be introduced need not be newly acquired for each case. Rather, signals may be acquired from one or more individuals, to obtain an exemplar for various respective mental state. Once determined, the processed signal representation may be stored in non-volatile memory for later use. However, in cases of complex interaction between a mental state and a context or content or activity, it may be appropriate to derive the signals from a single individual whose context or content-environment or activity is appropriate for the circumstances. Further, in some cases, a single mental state, emotion or mood is not described or fully characterized, and therefore acquiring signals from a source is an efficient exercise.

With a library of target brainwave patterns, a system and method is provided in which a target subject may be immersed in a presentation, which includes not only multimedia content but also a series of defined mental states, emotional states or moods that accompany the multimedia content. In this way, the multimedia presentation becomes fully immersive. The stimulus, in this case, may be provided through a headset, such as a virtual reality or augmented reality headset. This headset is provided with a stereoscopic display, binaural audio, and a set of EEG stimulatory electrodes. These electrodes (if provided) typically deliver a subthreshold signal, which is not painful, which is typically an AC signal which corresponds to the desired frequency, phase, and spatial location of the desired target pattern. The electrodes may also be used to counteract undesired signals, by destructively interfering with them while concurrently imposing the desired patterns. The headset may also generate visual and/or auditory signals which correspond to the desired state. For example, the auditory signals may induce binaural beats, which cause brainwave entrainment. The visual signals may include intensity fluctuations or other modulation patterns, especially those which are subliminal, that are also adapted to cause brainwave entrainment or induction of the desired brainwave pattern.

The headset preferably includes EEG electrodes for receiving feedback from the user. That is, the stimulatory system seeks to achieve a mental state, emotion or mood response from the user. The EEG electrodes permit determination of whether that state is achieved, and if not, what the current state is. It may be that achieving the desired brainwave pattern is state dependent, and therefore that characteristics of the stimulus to achieve the desired state depend on the starting state of the subject. Other ways of determining mental state, emotion, or mood include analysis of facial expression, electromyography (EMG) analysis of facial muscles, explicit user feedback, etc.

An authoring system is provided which permits a content designer to determine what mental states are desired, and then encode those states into media, which is then interpreted by a media reproduction system in order to generate appropriate stimuli. As noted above, the stimuli may be audio, visual, multimedia, other senses, or electrical or magnetic brain stimulation, and therefore a VR headset with transcranial electrical or magnetic stimulation is not required. Further, in some embodiments, the patterns may be directly encoded into the audiovisual content, subliminally encoded. In some cases, the target mental state may be derived from an expert, actor or professional exemplar. The states may be read based on facial expressions, EMG, EEG, or other means, from the actor or exemplar. For example, a prototype exemplar engages in an activity that triggers a response, such as viewing the Grand Canyon or artworks within the Louvre. The responses of the exemplar are then recorded or represented, and preferably brainwave patterns recorded that represent the responses. A representation of the same experience is then presented to the target, with a goal of the target also experiencing the same experience as the exemplar. This is typically a voluntary and disclosed process, so the target will seek to willingly comply with the desired experiences. In some cases, the use of the technology is not disclosed to the target, for example in advertising presentations or billboards. In order for an actor to serve as the exemplar, the emotions achieved by that person must be authentic. However, so-called "method actors" do authentically achieve the emotions they convey. However, in some cases, for example, where facial expressions are used as the indicator of mental state, an actor can present desired facial expressions with inauthentic mental states. The act of making a face corresponding to an emotion often achieves the targeted mental state.

In general, the present technology is directed toward inducing sleep. Note that certain kinds of content are known to assist in induction of sleep, e.g., a lullaby. However, the present technology encompasses both human comprehensible signals and incomprehensible (noise-like) signals.

In order to calibrate the system, the brain pattern of a person may be measured while in the desired state. The brain patterns acquired for calibration or feedback need not be of the same quality, or precision, or data depth, and indeed may represent responses rather than primary indicia. That is, there may be some asymmetry in the system, between the brainwave patterns representative of a mental state, and the stimulus patterns appropriate for inducing the brain state.

The present invention generally relates to achieving a mental state in a subject by conveying to the brain of the subject patterns of brainwaves. These brainwaves may be artificial or synthetic, or derived from the brain of a second subject (e.g., a person experiencing an authentic experience or engaged in an activity). Typically, the wave patterns of the second subject are derived while the second subject is experiencing an authentic experience.

A special case is where the first and second subjects are the same individual. For example, brainwave patterns are recorded while a subject is in a particular mental state. That same pattern may assist in achieving the same mental state at another time. Thus, there may be a time delay between the acquisition of the brainwave information from the second subject, and exposing the first subject to corresponding stimulation. The signals may be recorded and transmitted.

The temporal pattern may be conveyed or induced non-invasively via light (visible or infrared), sound (or infrasound). Alternately, non-sensory stimulation may be employed, e.g., transcranial direct or alternating current stimulation (tDCS or tACS), transcranial magnetic stimulation (TMS), Deep transcranial magnetic stimulation (Deep TMS, or dTMS), Repetitive Transcranial Magnetic Stimulation (rTMS) olfactory stimulation, tactile stimulation, or any other means capable of conveying frequency patterns. In a preferred embodiment, normal human senses are employed to stimulate the subject, such as light, sound, smell, and touch. Combinations of stimuli may be employed. In some cases, the stimulus or combination is innate, and therefore largely pan-subject. In other cases, response to a context is learned, and therefore subject-specific. Therefore, feedback from the subject may be appropriate to determine the triggers and stimuli appropriate to achieve a mental state.

This technology may be advantageously used to enhance mental response to a stimulus or context. Still another aspect provides for a change in the mental state. The technology may be used in humans or animals.

The present technology may employ an event-correlated EEG time and/or frequency analysis performed on neuronal activity patterns. In a time-analysis, the signal is analyzed temporally and spatially, generally looking for changes with respect to time and space. In a frequency analysis, over an epoch of analysis, the data, which is typically a time-sequence of samples, is transformed, using e.g., a Fourier transform (FT, or one implementation, the Fast Fourier Transform, FFT), into a frequency domain representation, and the frequencies present during the epoch are analyzed. The window of analysis may be rolling, and so the frequency analysis may be continuous. In a hybrid time-frequency analysis, for example, a wavelet analysis, the data during the epoch is transformed using a "wavelet transform", e.g., the Discrete Wavelet Transform (DWT) or continuous wavelet transform (CWT), which has the ability to construct a time-frequency representation of a signal that offers very good time and frequency localization. Changes in transformed data over time and space may be analyzed. In general, the spatial aspect of the brainwave analysis is anatomically modeled. In most cases, anatomy is considered universal, but in some cases, there are significant differences. For example, brain injury, psychiatric disease, age, race, native language, training, sex, handedness, and other factors may lead to distinct spatial arrangement of brain function, and therefore when transferring mood from one individual to another, it is preferred to normalize the brain anatomy of both individuals by experiencing roughly the same experiences, and measuring spatial parameters of the EEG or MEG. Note that spatial organization of the brain is highly persistent, absent injury or disease, and therefore, this need only be performed infrequently. However, since electrode placement may be inexact, a spatial calibration may be performed after electrode placement.

Different aspects of EEG magnitude and phase relationships may be captured, to reveal details of the neuronal activity. The "time-frequency analysis" reveals the brain's parallel processing of information, with oscillations at various frequencies within various regions of the brain reflecting multiple neural processes co-occurring and interacting. See, Lisman J, Buzsaki G. A neural coding scheme formed by the combined function of gamma and theta oscillations. Schizophr Bull. Jun. 16, 2008; doi: 10.1093/schbul/sbn060. Such a time-frequency analysis may take the form of a wavelet transform analysis. This may be used to assist in integrative and dynamically adaptive information processing. Of course, the transform may be essentially lossless and may be performed in any convenient information domain representation. These EEG-based data analyses reveal the frequency-specific neuronal oscillations and their synchronization in brain functions ranging from sensory processing to higher-order cognition. Therefore, these patterns may be selectively analyzed, for transfer to or induction in, a subject.

A statistical clustering analysis may be performed in high dimension space to isolate or segment regions which act as signal sources, and to characterize the coupling between various regions. This analysis may also be used to establish signal types within each brain region and decision boundaries characterizing transitions between different signal types. These transitions may be state dependent, and therefore the transitions may be detected based on a temporal analysis, rather than merely a concurrent oscillator state.

The various measures make use of the magnitude and/or phase angle information derived from the complex data extracted from the EEG during spectral decomposition and/or temporal/spatial/spectral analysis. Some measures estimate the magnitude or phase consistency of the EEG within one channel across trials, whereas others estimate the consistency of the magnitude or phase differences between channels across trials. Beyond these two families of calculations, there are also measures that examine the coupling between frequencies, within trials and recording sites. Of course, in the realm of time-frequency analysis, many types of relationships can be examined beyond those already mentioned.

These sensory processing specific neuronal oscillations, e.g., brainwave patterns, e.g., of a subject (a "source") or to a person trained (for example, an actor trained in "the method") to create the desired state, and can be stored on a tangible medium and/or can be simultaneously conveyed to a recipient making use of the brain's frequency following response nature. See, Galbraith, Gary C., Darlene M. Olfman, and Todd M. Huffman. "Selective attention affects human brain stem frequency-following response." Neuroreport 14, no. 5 (2003): 735-738, journals.lww.com/neuroreport/Abstract/2003/04150/Selective_attention_affects_human_brain_stem.15.aspx.

According to one embodiment, the stimulation of the second subject is combined with a feedback process, to verify that the second subject has appropriately responded to the stimulation, e.g., has a predefined similarity to the sleep stage as the first subject, has a sleep stage with a predefined difference from the first subject, or has the desired change from a baseline sleep stage. The feedback may be based on brain activity per se, or neural correlates of sleep stage or, alternatively, or, in addition, physical, psychological, or behavioral effects that may be measured, reported or observed.

The feedback typically is provided to a controller with at least partial model basis, for the stimulator, which alters stimulation parameters to optimize the stimulation.

As discussed above, the model is typically difficult to define. Therefore, the model-based controller is incompletely defined, and the existence of errors and artifacts is to be expected. However, by employing a model-based controller, those parameters that are defined may be used to improve response over the corresponding controller, which lacks the model.

For example, it is believed that brainwaves represent a form of resonance, where ensembles of neurons interact in a coordinated fashion. The frequency of the wave is related to neural responsiveness to neurotransmitters, distances along neural pathways, diffusion limitations, etc. That is, the same sleep stage may be represented by slightly different frequencies in two different individuals, based on differences in the size of their brains, neuromodulators present, other anatomical, morphological and physiological differences, etc. These differences may be measured in microseconds or less, resulting in small changes in frequency. Therefore, the model component of the controller can determine the parameters of neural transmission and ensemble characteristics, vis-à-vis stimulation, and resynthesize the stimulus signal to match the correct frequency and phase of the subject's brainwave, with the optimization of the waveform adaptively determined. This may not be as simple as speeding up or slowing down playback of the signal, as different elements of the various brainwaves representing neural correlates of a sleep stage may have different relative differences between subjects.

Of course, in some cases, one or more components of the stimulation of the target subject (recipient) may be represented as abstract or semantically defined signals, and, more generally, the processing of the signals to define the stimulation will involve high-level modulation or transformation between the source signal received from the first subject (donor) or plurality of donors, to define the target signal for stimulation of the second subject (recipient).

Preferably, each component represents a subset of the neural correlates reflecting brain activity that has a high autocorrelation in space and time, or in a hybrid representation such as wavelet. These may be separated by optimal filtering (e.g., spatial PCA), once the characteristics of the signal are known, and bearing in mind that the signal is accompanied by a modulation pattern and that the two components themselves may have some weak coupling and interaction.

For example, if the first subject (donor) is listening to music, there will be significant components of the neural correlates that are synchronized with the particular music. On the other hand, the music per se may not be part of the desired stimulation of the target subject (recipient). Further, the target subject (recipient) may be in a different acoustic environment, and it may be appropriate to modify the residual signal dependent on the acoustic environment of the recipient, so that the stimulation is appropriate for achieving the desired effect, and does not represent phantoms, distractions, or irrelevant or inappropriate content. In order to perform signal processing, it is convenient to store the signals or a partially processed representation, though a complete real-time signal processing chain may be implemented. According to another embodiment, a particular stage of the sleep state of at least one first subject (donor) is identified, and the neural correlates of brain activity are captured, and the second subject (recipient) is subject to stimulation based on the captured neural correlates and the identified sleep stage. The sleep stage is typically represented as a semantic variable within a limited classification space. The sleep stage identification need not be through analysis of the neural correlates signal and may be a volitional self-identification by the first subject, e.g., based on other body signals or by an observer, or a manual classification by third parties using, for example, observation, fMRI or psychological assessment. The identified sleep stage is useful, for example, because it represents a target toward (or, in some cases, against) which the second subject (recipient) can be steered.

The stimulation may be one or more stimulus applied to the second subject (trainee or recipient), which may be a sensory stimulation (e.g., visual, auditory, or tactile), mechanical stimulation, ultrasonic stimulation, etc., and controlled with respect to waveform, frequency, phase, intensity/amplitude, duration, or controlled via feedback, self-reported effect by the second subject, manual classification by third parties, automated analysis of brain activity, behavior, physiological parameters, etc. of the second subject (recipient).

Typically, the goal of the process is to improve sleep in a recipient by transplanting the desired sleep stages, or a sequence of stages, of at least one first subject (donor) to the second subject (recipient) by inducing in the second subject (recipient) neural correlates of the sleep stage (or a sequence of stages) of at least one first subject (donor) corresponding to the sleep stage of the first subject, through the use of stimulation parameters comprising a waveform over a period of time derived from the neural correlates of the sleep stage of the first subject.

Typically, the first and the second subjects are spatially remote from each other and may be temporally remote as well. In some cases, the first and second subject are the same subject (human or animal), temporally displaced. In other cases, the first and the second subject are spatially proximate to each other. These different embodiments differ principally in the transfer of the signal from at least one first subject (donor) to the second subject (recipient). However, when the first and the second subjects share a common environment, the signal processing of the neural correlates and, especially of real-time feedback of neural correlates from the second subject, may involve interactive algorithms with the neural correlates of the first subject.

According to another embodiment, the first and second subjects are each subject to stimulation. In one particularly interesting embodiment, the first subject and the second subject communicate with each other in real-time, with the first subject receiving stimulation based on the second subject, and the second subject receiving feedback based on the first subject. This can lead to synchronization of neural correlates (e.g., neuronal oscillations, or brainwaves) and, consequently, of sleep stage between the two subjects. The neural correlates may be neuronal oscillations resulting in brainwaves that are detectable as, for example, EEG, qEEG, or MEG signals. Traditionally, these signals are found to have dominant frequencies, which may be determined by various analyses, such as spectral analysis, wavelet analysis, or principal component analysis (PCA), for example. One embodiment provides that the modulation pattern of a brainwave of at least one first subject (donor) is determined independently of the dominant frequency of the brainwave (though, typically, within the same class of brainwaves), and this modulation imposed on a brainwave corresponding to the dominant frequency of the second subject (recipient). That is, once the second subject achieves that same brainwave pattern as the first subject (which may be achieved by means other than electromagnetic, mechanical, or sensory stimulation), the modulation pattern of the first subject is imposed as a way of guiding the sleep stage of the second subject.

According to another embodiment, the second subject (recipient) is stimulated with a stimulation signal, which faithfully represents the frequency composition of a defined component of the neural correlates of at least one first subject (donor). The defined component may be determined based on principal component analysis, independent component analysis (ICI), eigenvector-based multivariable analysis, factor analysis, canonical correlation analysis (CCA), nonlinear dimensionality reduction (NLDR), or related technique.

The stimulation may be performed, for example, by using a light stimulation, a sound stimulation, a tactile stimulation, or olfactory stimulation. An auditory stimulus may be, for example, binaural beats or isochronic tones. Non-sensory stimulation may include a TES device, such as a tDCS device, a high-definition tDCS device, an osc-tDCS device, a pulse-tDCS ("electrosleep") device, an osc-tDCS, a tACS device, a CES device, a TMS device, rTMS device, a deep TMS device, a light source, or a sound source configured to modulate the dominant frequency on respectively the light signal or the sound signal. The stimulus may be a light signal, a sonic signal (sound), an electric signal, a magnetic field, olfactory or tactile stimulation. The current signal may be a pulse signal or an oscillating signal. The stimulus may be applied via a cranial electric stimulation (CES), a transcranial electric stimulation (TES), a deep electric stimulation, a transcranial magnetic stimulation (TMS), a deep magnetic stimulation, The technology also provides a processor configured to process the neural correlates of sleep stage from the first subject (donor), and to produce or define a stimulation pattern for the second subject (recipient) selectively dependent on a waveform pattern of the neural correlates from the first subject. Typically, the processor performs signal analysis and calculates at least a dominant frequency of the brainwaves of the first subject, and preferably also spatial and phase patterns within the brain of the first subject. The processor may also perform a PCA, a spatial PCA, an independent component analysis (ICA), eigenvalue decomposition, eigenvector-based multivariate analyses, factor analysis, an autoencoder neural network with a linear hidden layer, linear discriminant analysis, network component analysis, nonlinear dimensionality reduction (NLDR), or another statistical method of data analysis.

A signal is presented to a second apparatus, configured to stimulate the second subject (recipient), which may be an open loop stimulation dependent on a non-feedback-controlled algorithm, or a closed loop feedback dependent algorithm. The second apparatus produces a stimulation intended to induce in the second subject (recipient) the desired sleep stage, e.g., representing the same sleep stage as was present in the first subject (donor).

A typical process performed on the neural correlates is filtering to remove noise. In some embodiments, noise filters may be provided, for example, at 50 Hz, 60 Hz, 100 Hz, 120 Hz, and additional overtones (e.g., tertiary and higher harmonics). The stimulator associated with the second subject (recipient) would typically perform decoding, decompression, decryption, inverse transformation, modulation, etc.

Alternately, an authentic wave or hash thereof may be authenticated via a blockchain, and thus authenticatable by an immutable record. In some cases, it is possible to use the stored encrypted signal in its encrypted form, without decryption. For example, with an asymmetric encryption scheme, which supports distance determination.

Due to different brain sizes, and other anatomical, morphological, and/or physiological differences, dominant frequencies associated with the same sleep stage may be different in different subjects. Consequently, it may not be optimal to forcefully impose on the recipient the frequency of the donor that may or may not precisely correspond to the recipient's frequency associated with the same sleep stage. Accordingly, in some embodiments, the donor's frequency may be used to start the process of inducing the desired sleep stage in a recipient. As some point, when the recipient is closed to achieving the desired sleep state, the stimulation is either stopped or replaced with neurofeedback allowing the brain of the recipient to find its optimal frequency associated with the desired sleep stage.

In one embodiment, the feedback signal from the second subject may be correspondingly encoded as per the source signal, and the error between the two minimized. According to one embodiment, the processor may perform a noise reduction distinct from frequency-band filtering. According to one embodiment, the neural correlates are transformed into a sparse matrix, and in the transform domain, components having a high probability of representing noise are masked, while components having a high probability of representing signal are preserved. That is, in some cases, the components that represent modulation that are important may not be known a priori. However, dependent on their effect in inducing the desired response in the second subject (recipient), the "important" components may be identified, and the remainder filtered or suppressed. The transformed signal may then be inverse-transformed and used as a basis for a stimulation signal.

According to another embodiment, a method of sleep stage modification, e.g., brain entrainment, is provided, comprising: ascertaining a sleep stage in a plurality of first subjects (donors); acquiring brainwaves of the plurality of first subjects (donors), e.g., using one of EEG and MEG, to create a dataset containing brainwaves corresponding to different sleep stages. The database may be encoded with a classification of sleep stages, activities, environment, or stimulus patterns, applied to the plurality of first subjects, and the database may include acquired brainwaves across a large number of sleep stages, activities, environment, or stimulus patterns, for example. In many cases, the database records will reflect a characteristic or dominant frequency of the respective brainwaves.

Sleep stages, activities, environment, or stimulus patterns, for example, and a stimulation pattern for a second subject (recipient) defined based on the database records of one or more subjects (donors).

The record(s) thus retrieved are used to define a stimulation pattern for the second subject (recipient). As a relatively trivial example, a female recipient could be stimulated principally based on records from female donors. Similarly, a child recipient of a certain age could be stimulated principally based on the records from children donors of a similar age. Likewise, various demographic, personality, and/or physiological parameters may be matched to ensure a high degree of correspondence to between the source and target subjects. In the target subject, a guided or genetic algorithm may be employed to select modification parameters from the various components of the signal, which best achieve the desired target state based on feedback from the target subject.

Of course, a more nuanced approach is to process the entirety of the database and stimulate the second subject based on a global brainwave-stimulus model, though this is not required, and also, the underlying basis for the model may prove unreliable or inaccurate. It may be preferred to derive a stimulus waveform from only a single first subject (donor), in order to preserve micro-modulation aspects of the signal, which, as discussed above, have not been fully characterized. However, the selection of the donor(s) need not be static and can change frequently. The selection of donor records may be based on population statistics of other users of the records, i.e., whether or not the record had the expected effect, filtering donors whose response pattern correlates highest with a given recipient, etc. The selection of donor records may also be based on feedback patterns from the recipient.

The process of stimulation typically seeks to target the desired sleep stage in the recipient, which is automatically or semi-automatically determined or manually entered. In one embodiment, the records are used to define a modulation waveform of a synthesized carrier or set of carriers, and the process may include a frequency domain multiplexed multi-subcarrier signal (which is not necessarily orthogonal). A plurality of stimuli may be applied concurrently, through the different subchannels and/or through different stimulator electrodes, electric current stimulators, magnetic field generators, mechanical stimulators, sensory stimulators, etc. The stimulus may be applied to achieve brain entrainment (i.e., synchronization) of the second subject (recipient) with one or more first subjects (donors). If the plurality of donors are mutually entrained, then each will have a corresponding brainwave pattern dependent on brainwave entrainment. This link between donors may help determine compatibility between a respective donor and the recipient. For example, characteristic patterns in the entrained brainwaves may be determined, even for different target sleep stages, and the characteristic patterns may be correlated to find relatively close matches and to exclude relatively poor matches.

This technology may also provide a basis for a social network, dating site, employment, mission (e.g., space or military), or vocational testing, or other interpersonal environments, wherein people may be matched with each other based on entrainment characteristics. For example, people who efficiently entrain with each other may have better compatibility and, therefore, a better marriage, work, or social relationships than those who do not. The entrainment effect need not be limited to sleep stages and may arise across any context.

As discussed above, the plurality of first subjects (donors) may have their respective brainwave patterns stored in separate database records. However, they may also be combined into a more global model. One such model is a neural network or a deep neural network. Typically, such a network would have recurrent features. Data from a plurality of first subjects (donors) is used to train the neural network, which is then accessed by inputting the target stage and/or feedback information, and which outputs a stimulation pattern or parameters for controlling a stimulator(s). When multiple first subjects (donors) form the basis for the stimulation pattern, it is preferred that the neural network output parameters of the stimulation, derived from and comprising features of the brainwave patterns or other neural correlates of sleep stage from the plurality of first subject (donors), which are then used to control a stimulator which, for example, generates its own carrier wave(s) which are then modulated based on the output of the neural network. A trained neural network need not periodically retrieve records and, therefore, may operate in a more time-continuous manner, rather than the more segmented scheme of record-based control.

In any of the feedback dependent methods, the brainwave patterns or other neural correlates of sleep stages may be processed by a neural network, to produce an output that guides or controls the stimulation. The stimulation, is, for example, at least one of a light signal, a sound signal, an electric signal, a magnetic field, an olfactory signal, a chemical signal, and vibration or mechanical stimulus. The process may employ a relational database of sleep stages and brainwave patterns, e.g., frequencies/neural correlate waveform patterns associated with the respective sleep stages. The relational database may comprise a first table, the first table further comprising a plurality of data records of brainwave patterns, and a second table, the second table comprising a plurality of sleep stages, each of the sleep stages being linked to at least one brainwave pattern. Data related to sleep stages and brainwave patterns associated with the sleep stages are stored in the relational database and maintained. The relational database is accessed by receiving queries for selected (existing or desired) sleep stages, and data records are returned representing the associated brainwave pattern. The brainwave pattern retrieved from the relational database may then be used for modulating a stimulator seeking to produce an effect selectively dependent on the desired sleep stage.

A further aspect of the technology provides a computer apparatus for creating and maintaining a relational database of sleep stages and frequencies associated with the sleep stage. The computer apparatus may comprise a non-volatile memory for storing a relational database of sleep stages and neural correlates of brain activity associated with the sleep stages, the database comprising a first table comprising a plurality of data records of neural correlates of brain activity associated with the sleep stages, and a second table comprising a plurality of sleep stages, each of the sleep stages being linked to one or more records in the first table; a processor coupled with the non-volatile memory, and is configured to process relational database queries, which are then used for searching the database; RAM coupled with the processor and the non-volatile memory for temporary holding database queries and data records retrieved from the relational database; and an IO interface configured to receive database queries and deliver data records retrieved from the relational database. A structured query language (SQL) or alternate to SQL (e.g., noSQL) database may also be used to store and retrieve records. A relational database described above, maintained and operated by a general-purpose computer, improves the operations of the general-purpose computer by making searches of specific sleep stages and brainwaves associated therewith more efficient thereby, inter alia, reducing the demand on computing power.

A further aspect of the technology provides a method of brain entrainment comprising: ascertaining a sleep stage in at least one first subject (donor), recording brainwaves of said at least one first subject (donor) using at least one channel of EEG and/or MEG; storing the recorded brainwaves in a physical memory device, retrieving the brainwaves from the memory device, applying a stimulus signal comprising a brainwave pattern derived from at least one-channel of the EEG and/or MEG to a second subject (recipient) via sensory stimulation, whereby the sleep stage desired by the second subject (recipient) is achieved. The stimulation may be of the same dimension (number of channels) as the EEG or MEG, or a different number of channels, typically reduced. For example, the EEG or MEG may comprise 64, 128, or 256 channels.

One of the advantages of transforming the data is the ability to select a transform that separates the information of interest represented in the raw data, from noise or other information. Some transforms preserve the spatial and state transition history and may be used for a more global analysis. Another advantage of a transform is that it can present the information of interest in a form where relatively simple linear or statistical functions of a low order may be applied. In some cases, it is desired to perform an inverse transform on the data. For example, if the raw data includes noise, such as 50 or 60 Hz interference, a frequency transform may be performed, followed by a narrow band filtering of the interference and its higher order intermodulation products. An inverse transform may be performed to return the data to its time-domain representation for further processing. (In the case of simple filtering, a finite impulse response (FIR) or infinite impulse response (IIR) filter could be employed). In other cases, the analysis is continued in the transformed domain.

Transforms may be part of an efficient algorithm to compress data for storage or analysis, by making the representation of the information of interest consume fewer bits of information (if in digital form) and/or allow it to be communicated using lower bandwidth. Typically, compression algorithms will not be lossless, and as a result, the compression is irreversible with respect to truncated information.

Typically, the transformation(s) and filtering of the signal are conducted using traditional computer logic, according to defined algorithms. The intermediate stages may be stored and analyzed. However, in some cases, neural networks or deep neural networks may be used, convolutional neural network architectures, or even analog signal processing. According to one set of embodiments, the transforms (if any) and analysis are implemented in a parallel processing environment. Such as using a SIMD processor such as a GPU (or GPGPU). Algorithms implemented in such systems are characterized by an avoidance of data-dependent branch instructions, with many threads concurrently executing the same instructions.

EEG signals are analyzed to determine the location (e.g., voxel or brain region) from which an electrical activity pattern is emitted, and the wave pattern characterized. The spatial processing of the EEG signals will typically precede the content analysis, since noise and artifacts may be useful for spatial resolution. Further, the signal from one brain region will typically be noise or interference in the signal analysis from another brain region; so the spatial analysis may represent part of the comprehension analysis. The spatial analysis is typically in the form of a geometrically and/or anatomically-constrained statistical model, employing all of the raw inputs in parallel. For example, where the input data is transcutaneous electroencephalogram information, from 32 EEG electrodes, the 32 input channels, sampled at e.g., 500 sps, 1 ksps or 2 ksps, are processed in a four or higher dimensional matrix, to permit mapping of locations and communication of impulses over time, space and state.

The matrix processing may be performed in a standard computing environment, e.g., an i9-9900K, i9-9980HK, processor, under the Windows 10 operating system, executing Matlab (Mathworks, Woburn M A) software platform. Alternately, the matrix processing may be performed in a computer cluster or grid or cloud computing environment. The processing may also employ parallel processing, in either a distributed and loosely coupled environment, or asynchronous environment. One preferred embodiment employs a single instruction, multiple data processors, such as a graphics processing unit such as the nVidia CUDA environment or AMD Firepro high-performance computing environment.

Artificial intelligence (AI) and machine learning methods, such as artificial neural networks, deep neural networks, etc., may be implemented to extract the signals of interest. Neural networks act as an optimized statistical classifier and may have arbitrary complexity. A so-called deep neural network having multiple hidden layers may be employed. The processing is typically dependent on labeled training data, such as EEG data, or various processed, transformed, or classified representations of the EEG data. The label represents the emotion, mood, context, or state of the subject during acquisition. In order to handle the continuous stream of data represented by the EEG, a recurrent neural network architecture may be implemented. Depending preprocessing before the neural network, formal implementations of recurrence may be avoided. A four or more dimensional data matrix may be derived from the traditional spatial-temporal processing of the EEG and fed to a neural network. Since the time parameter is represented in the input data, a neural network temporal memory is not required, though this architecture may require a larger number of inputs. Principal component analysis (PCA, en.wikipedia.org/wiki/Principal-_component_analysis), spatial PCA (arxiv.org/pdf/1501.03221v3.pdf, adegenet.r-forge.r-project.org/files/tutorial-spca.pdf, www.ncbi.nlm.nih.gov/pubmed/1510870); and clustering analysis may also be employed (en.wikipe-dia.org/wiki/Cluster_analysis, see U.S. Pat. Nos. 9,336,302, 9,607,023 and cited references).

In general, a neural network of this type of implementation will, in operation, be able to receive unlabeled EEG data, and produce the output signals representative of the predicted or estimated task, performance, context, or state of the subject during the acquisition of the unclassified EEG. Of course, statistical classifiers may be used rather than neural networks.

The analyzed EEG, either by conventional processing, neural network processing, or both, serves two purposes. First, it permits one to deduce which areas of the brain are subject to which kinds of electrical activity under which conditions. Second, it permits feedback during the training of a trainee (assuming proper spatial and anatomical correlates between the trainer and trainee), to help the system achieve the desired state, or as may be appropriate, the desired series of states and/or state transitions. According to one aspect of the technology, the applied stimulation is dependent on a measured starting state or status (which may represent a complex context and history-dependent matrix of parameters), and therefore the target represents a desired complex vector change. Therefore, this aspect of the technology seeks to understand a complex time-space-brain activity associated with an activity or task in a trainer, and to seek a corresponding complex time-space-brain activity associated with the same activity or task in a trainee, such that the complex time-space-brain activity state in the trainor is distinct from the corresponding state sought to be achieved in the trainee. This permits the transfer of training paradigms from qualitatively different persons, in different contexts, and, to some extent, to achieve a different result.

The conditions of data acquisition from the trainer will include both task data, and sensory-stimulation data. That is, a preferred application of the system is to acquire EEG data from a trainer or skilled individual, which will then be used to transfer learning, or more likely, learning readiness states, to a naïve trainee. The goal for the trainee is to produce a set of stimulation parameters that will achieve, in the trainee, the corresponding neural activity resulting in the EEG state of the trainer at the time of or preceding the learning of a skill or a task, or performance of the task.

It is noted that EEG is not the only neural or brain activity or state data that may be acquired, and, of course, any and all such data may be included within the scope of the technology, and therefore EEG is a representative example only of the types of data that may be used. Other types include fMRI, magnetoencephalogram, motor neuron activity, PET, etc.

While mapping the stimulus-response patterns distinct from the task is not required in the trainer, it is advantageous to do so, because the trainer may be available for an extended period, the stimulus of the trainee may influence the neural activity patterns, and it is likely that the trainer will have correlated stimulus-response neural activity patterns with the trainee(s). It should be noted that the foregoing has suggested that the trainer is a single individual, while in practice, the trainer may be a population of trainers or skilled individuals. The analysis and processing of brain activity data may, therefore, be adaptive, both for each respective individual and for the population as a whole.

For example, the system may determine that not all human subjects have common stimulus-response brain activity correlates, and therefore that the population needs to be segregated and clustered. If the differences may be normalized, then a normalization matrix or other correction may be employed. On the other hand, if the differences do not permit feasible normalization, the population(s) may be segmented, with different trainers for the different segments. For example, in some tasks, male brains have different activity patterns and capabilities than female brains. This, coupled with anatomical differences between the sexes, implies that the system may provide gender-specific implementations. Similarly, age differences may provide a rational and scientific basis for segmentation of the population. However, depending on the size of the information base and matrices required, and some other factors, each system may be provided with substantially all parameters required for the whole population, with a user-specific implementation based on a user profile or initial setup, calibration, and system training session.

According to one aspect of the present invention, a source subject is instrumented with sensors to determine localized brain activity during experiencing an event. The objective is to identify regions of the brain involved in processing this response.

The sensors will typically seek to determine neuron firing patterns and brain region excitation patterns, which can be detected by implanted electrodes, transcutaneous electroencephalograms, magnetoencephalograms, fMRI, and other technologies. Where appropriate, transcutaneous EEG is preferred, since this is non-invasive and relatively simple.

The source is observed with the sensors in a quiet state, a state in which he or she is experiencing an event, and various control states in which the source is at rest or engaged in different activities resulting in different states. The data may be obtained for a sufficiently long period of time and over repeated trials to determine the effect of duration. The data may also be a population statistical result, and need not be derived from only a single individual at a single time.

The sensor data is then processed using a 4D (or higher) model to determine the characteristic location-dependent pattern of brain activity over time associated with the state of interest. Where the data is derived from a population with various degrees of arousal, the model maintains this arousal state variable dimension.

A recipient is then prepared for receipt of the mental state. The mental state of the recipient may be assessed. This can include responses to a questionnaire, self-assessment, or other psychological assessment methods. Further, the transcutaneous EEG (or other brain activity data) of the recipient may be obtained, to determine the starting state for the recipient, as well as an activity during experiencing the desired mental state.

In addition, a set of stimuli, such as visual patterns, acoustic patterns, vestibular, smell, taste, touch (light touch, deep touch, proprioception, stretch, hot, cold, pain, pleasure, electric stimulation, acupuncture, etc.), vagus nerve (e.g., parasympathetic), are imposed on the subject, optionally over a range of baseline brain states, to acquire data defining the effect of individual and various combinations of sensory stimulation on the brain state of the recipient. Population data may also be used for this aspect.

The data from the source or population of sources (see above) may then be processed in conjunction with the recipient or population of recipient data, to extract information defining the optimal sensory stimulation over time of the recipient to achieve the desired brain state resulting in the desired mental state.

In general, for populations of sources and recipients, the data processing task is immense. However, the statistical analysis will generally be of a form that permits parallelization of mathematical transforms for processing the data, which can be efficiently implemented using various parallel processors, a common form of which is a SIMD (single instruction, multiple data) processor, found in typical graphics processors (GPUs). Because of the cost-efficiency of GPUs, it is referred to implement the analysis using efficient parallelizable algorithms, even if the computational complexity is nominally greater than a CISC-type processor implementation.

During stimulation of the recipient, the EEG pattern may be monitored to determine if the desired state is achieved through the sensory stimulation. A closed loop feedback control system may be implemented to modify the stimulation seeking to achieve the target. An evolving genetic algorithm may be used to develop a user model, which relates the mental state, arousal, and valence, sensory stimulation, and brain activity patterns, both to optimize the current session of stimulation and learning, as well as to facilitate future sessions, where the mental states of the recipient have further enhanced, and to permit use of the system for a range of mental states.

The technology may be embodied in apparatuses for acquiring the brain activity information from the source, processing the brain activity information to reveal a target brain activity state and a set of stimuli, which seek to achieve that state in a recipient, and generating stimuli for the recipient to achieve and maintain the target brain activity state over a period of time and potential state transitions. The generated stimuli may be feedback controlled. A general-purpose computer may be used for the processing of the information, a microprocessor, an FPGA, an ASIC, a system-on-a-chip, or a specialized system, which employs a customized configuration to efficiently achieve the information transformations required. Typically, the source and recipient act asynchronously, with the brain activity of the source recorded and later processed. However, real-time processing and brain activity transfer are also possible. In the case of a general purpose programmable processor implementation or portions of the technology, computer instructions may be stored on a nontransient computer readable medium. Typically, the system will have special-purpose components, such as a sensory stimulator, or a modified audio and/or display system, and therefore the system will not be a general purpose system. Further, even in a general purpose system, the operation per se is enhanced according to the present technology.

Mental states may be induced in a subject non-invasively via light, sound, or other means capable of conveying frequency patterns.

The transmission of the brainwaves can be accomplished through direct electrical contact with the electrodes implanted in the brain or remotely employing light, sound, electromagnetic waves, and other non-invasive techniques. Light, sound, or electromagnetic fields may be used to remotely convey the temporal pattern of prerecorded brainwaves to a subject by modulating the encoded temporal frequency on the light, sound or electromagnetic filed signal to which the subject is exposed.

Every activity, mental or motor, and emotion is associated with unique brainwaves having specific spatial and temporal patterns, i.e., a characteristic frequency or a characteristic distribution of frequencies over time and space. Such waves can be read and recorded by several known techniques, including EEG, MEG, exact low-resolution brain electromagnetic tomography (eLORETA), sensory evoked potentials (SEP), fMRI, functional near-infrared spectroscopy (fNIRS), etc. The cerebral cortex is composed of neurons that are interconnected in networks. Cortical neurons constantly send and receive nerve impulses-electrical activity-even during sleep. The electrical or magnetic activity measured by an EEG or MEG (or another device) device reflects the intrinsic activity of neurons in the cerebral cortex and the information sent to it by subcortical structures and the sense receptors.

It has been observed that "playing back the brainwaves" to another animal or person by providing decoded temporal pattern through transcranial direct current stimulation (tDCS), transcranial alternating current stimulation (tACS), high definition transcranial alternating current stimulation (HD-tDCS), transcranial magnetic stimulation (TMS), or through electrodes implanted in the brain allows the recipient to achieve the mental state at hand or to increase the speed of achievement. For example, if the brainwaves of a mouse navigated a familiar maze are decoded (by EEG or via implanted electrodes), playing this temporal pattern to another mouse unfamiliar with this maze will allow it to learn to navigate this maze faster.

Similarly, recording brainwaves associated with a specific response of one subject and later "playing back" this response to another subject will induce a similar response in the second subject. More generally, when one animal assumes a mental state, parts of the brain will have characteristic activity patterns. Further, by "artificially" inducing the same pattern in another animal, the other animal will have the same mental state or more easily be induced into that state. The pattern of interest may reside deep in the brain, and thus be overwhelmed in an EEG signal by cortical potentials and patterns. However, techniques other than surface electrode EEG may be used to determine and spatially discriminate deep brain activity, e.g., from the limbic system. For example, various types of magnetic sensors may sense deep brain activity. See, e.g., U.S. Pat. Nos. 9,618,591; 9,261,573; 8,618,799; and 8,593,141.

In some cases, EEGs dominated by cortical excitation patterns may be employed to sense the mental state, since the cortical patterns may correlate with lower-level brain activity. Note that the determination of a state representation of a mental state need not be performed each time the system is used; rather, once the brain spatial and temporal activity patterns and synchronization states associated with a particular mental states are determined, those patterns may be used for multiple targets and over time.

Similarly, while the goal is, for example, to trigger the target to assume the same brain activity patterns are the exemplar, this can be achieved in various ways, and these methods of inducing the desired patterns need not be invasive. Further, user feedback, especially in the case of a human transferee, may be used to tune the process. Finally, using the various senses, especially sight, sound, vestibular, touch, proprioception, taste, smell, vagus afferent, other cranial nerve afferent, etc. can be used to trigger high-level mental activity, that in a particular subject achieves the desired mental state, emotion or mood.

Thus, in an experimental subject, which may include laboratory scale and/or invasive monitoring, a set of brain electrical activity patterns that correspond to particular emotions or mental states is determined. Preferably, these are also correlated with surface EEG findings. For the transferee, a stimulation system is provided that is non-hazardous and non-invasive. For example, audiovisual stimulation may be exclusively used. A set of EEG electrodes is provided to measure brain activity, and an adaptive or genetic algorithm scheme is provided to optimize the audiovisual presentation, seeking to induce in the transferee the target pattern found in the experimental subject. After the stimulation patterns, which may be path dependent, are determined, it is likely that these patterns will be persistent, though over longer time periods, there may be some desensitization to the stimulation pattern(s). In some cases, audiovisual stimulation is insufficient, and TMS, PEMF, or other electromagnetic stimulation (superthreshold, or preferably subthreshold) is employed to assist in achieving the desired state and maintaining it for the desired period.

Employing light, sound or electromagnetic field to remotely convey the temporal pattern of brainwaves (which may be prerecorded) to a subject by modulating the encoded temporal frequency on the light, sound or electromagnetic filed signal to which the subject is exposed.

When a group of neurons fires simultaneously, the activity appears as a brainwave. Different brainwave-frequencies are linked to different mental states in the brain.

The desired mental state may be induced in a target individual (e.g., human, animal), by providing selective stimulation according to a temporal pattern, wherein the temporal pattern is correlated with an EEG pattern of the target when in the desired mental state, or represents a transition which represents an intermediate toward achieving the desired mental state. The temporal pattern may be targeted to a discrete spatial region within the brain, either by a physical arrangement of a stimulator, or natural neural pathways through which the stimulation (or its result) passes.

The EEG pattern may be derived from another individual or individuals, the same individual at a different time, or an in vivo animal model of the desired mental state. The method may, therefore, replicate a mental state of a first subject in a second subject. The mental state typically is not a state of consciousness or an idea, but rather a subconscious (in a technical sense) state, representing an emotion, readiness, receptivity, or another state, often independent of particular thoughts or ideas. In essence, a mental state of the first subject (a "trainer" or "donor" who is in a desired mental state) is captured by recording neural correlates of the mental state, e.g., as expressed by brain activity patterns, such as EEG or MEG signals. The neural correlates of the first subject, either as direct or recorded representations, may then be used to control a stimulation of the second subject (a "trainee" or "recipient"), seeking to induce the same brain activity patterns in the second subject (recipient/trainee) as were present in the first subject (donor/trainer) to assist the second subject (recipient/trainee) to attain the desired mental state that had been attained by the donor/trainer. In an alternative embodiment, the signals from the first subject (donor/trainer) being in the first mental state are employed to prevent the second subject (recipient/trainee) from achieving a second mental state, wherein the second mental state is an undesirable one.

The source brain wave pattern may be acquired through multichannel EEG or MEG, from a human in the desired brain state. A computational model of the brain state is difficult to create. However, such a model is not required according to the present technology. Rather, the signals may be processed by a statistical process (e.g., PCA or a related technology), or a statistically trained process (e.g., a neural network). The processed signals preferably retain information regarding signal source special location, frequency, and phase. In stimulating the recipient's brain, the source may be modified to account for brain size differences, electrode locations, etc. Therefore, the preserved characteristics are normalized spatial characteristics, frequency, phase, and modulation patterns.

The normalization may be based on feedback from the target subject, for example, based on a comparison of a present state of the target subject and a corresponding state of the source subject, or another comparison of known states between the target and source. Typically, the excitation electrodes in the target subject do not correspond to the feedback electrodes or the electrodes on the source subject. Therefore, an additional type of normalization is required, which may also be based on a statistical or statistically trained algorithm.

According to one embodiment, the stimulation of the second subject is associated with a feedback process, to verify that the second subject has appropriately responded to the stimulation, e.g., has a predefined similarity to the mental state as the first subject, has a mental state with a predefined difference from the first subject, or has a desired change from a baseline mental state. Advantageously, the stimulation may be adaptive to the feedback. In some cases, the feedback may be functional, i.e., not based on brain activity per se, or neural correlates of mental state, but rather physical, psychological, or behavioral effects that may be reported or observed.

The feedback typically is provided to a computational model-based controller for the stimulator, which alters stimulation parameters to optimize the stimulation in dependence on a brain and brain state model applicable to the target.

For example, it is believed that brainwaves represent a form of resonance, where ensembles of neurons interact in a coordinated fashion as a set of coupled or interacting oscillators. The frequency of the wave is related to neural responsivity to neurotransmitters, distances along neural pathways, diffusion limitations, etc., and perhaps pacemaker neurons or neural pathways. That is, the same mental state may be represented by different frequencies in two different individuals, based on differences in the size of their brains, neuromodulators present, physiological differences, etc. These differences may be measured in microseconds or less, resulting in fractional changes in frequency. However, if the stimulus is different from the natural or resonant frequency of the target process, the result may be different from that expected. Therefore, the model-based controller can determine the parameters of neural transmission and ensemble characteristics, vis-à-vis stimulation, and resynthesize the stimulus wave to match the correct waveform, with the optimization of the waveform adaptively determined. This may not be as simple as speeding up or slowing down playback of the signal, as different elements of the various waveforms representing neural correlates of mental state may have different relative differences between subjects. Therefore, according to one set of embodiments, the stimulator autocalibrates for the target, based on correspondence (error) of a measured response to the stimulation and the desired mental state sought by the stimulation. In cases where the results are chaotic or unpredictable based on existing data, a genetic algorithm may be employed to explore the range of stimulation parameters, and determine the response of the target.

In some cases, the target has an abnormal or unexpected response to stimulation based on a model maintained within the system. In this case, when the deviance from the expected response is identified, the system may seek to a new model, such as from a model repository that may be online, such as through the Internet. If the models are predictable, a translation may be provided between an applicable model of a source or trainer, and the applicable model of the target, to account for differences. In some cases, the desired mental state is relatively universal, such as sleep and awake. In this case, the brain response model may be a statistical model, rather than a neural network or deep neural network type implementation.

Thus, in one embodiment, a hybrid approach is provided, with the use of donor-derived brainwaves, on the one hand, which may be extracted from the brain activity readings (e.g., EEG or MEG) of the first at least one subject (donor), preferably processed by principal component analysis, or spatial principal component analysis, autocorrelation, or other statistical processing technique (clustering, PCA, etc.) or statistically trained technique (backpropagation of errors, etc.) that separates components of brain activity, which can then be modified or modulated based on high-level parameters, e.g., abstractions. See, ml4a.github.io/ml4a/how_neural_networks_are_trained/. Thus, the stimulator may be programmed to induce a series of brain states defined by name (e.g., sleep stage 1, sleep stage 2, etc.) or as a sequence of "abstract" semantic labels, icons, or other representations, each corresponding to a technical brain state or sequence of sub-states. The sequence may be automatically defined, based on biology and the system training, and thus relieve the programmer of low-level tasks. However, in a general case, the present technology maintains the use of components or subcomponents of the donor's brain activity readings, e.g., EEG or MEG, and does not seek to characterize or abstract them to a semantic level.

According to the present technology, a neural network system or statistical classifier may be employed to characterize the brain wave activity and/or other data from a subject. In addition to the classification or abstraction, a reliability parameter is presented, which predicts the accuracy of the output. Where the accuracy is high, a model-based stimulator may be provided to select and/or parameterize the model and generate a stimulus for a target subject. Where the accuracy is low, a filtered representation of the signal may be used to control the stimulator, bypassing the model(s). The advantage of this hybrid scheme is that when the model-based stimulator is employed, many different parameters may be explicitly controlled independently of the source subject. On the other hand, where the data processing fails to yield a highly useful prediction of the correct model-based stimulator parameters, the model itself may be avoided, in favor of a direct stimulation type system.

Of course, in some cases, one or more components of the stimulation of the target subject may be represented as abstract or semantically defined signals, and more generally the processing of the signals to define the stimulation will involve high-level modulation or transformation between the source signal received from the first subject, to define the target signal for stimulation of the second subject.

Preferably, each component represents a subset of the neural correlates reflecting brain activity that has a high spatial autocorrelation in space and time, or in a hybrid representation such as wavelet. For example, one signal may represent a modulated 10.2 Hz signal, while another signal represents a superposed modulated 15.7 Hz signal, with respectively different spatial origins. These may be separated by optimal filtering, once the spatial and temporal characteristics of the signal are known, and bearing in mind that the signal is accompanied by a modulation pattern, and that the two components themselves may have some weak coupling and interaction.

In some cases, the base frequency, modulation, coupling, noise, phase jitter, or another characteristic of the signal may be substituted. For example, if the first subject is listening to music, there will be significant components of the neural correlates that are synchronized with the particular music. On the other hand, the music per se may not be part of the desired stimulation of the target subject. Therefore, through signal analysis and decomposition, the components of the signal from the first subject, which have a high temporal correlation with the music, may be extracted or suppressed from the resulting signal. Further, the target subject may be in a different acoustic environment, and it may be appropriate to modify the residual signal dependent on the acoustic environment of the target subject, so that the stimulation is appropriate for achieving the desired effect, and does not represent phantoms, distractions, or irrelevant or inappropriate content. In order to perform processing, it is convenient to store the signals or a partially processed representation, though a complete real-time signal processing chain may be implemented. Such a real-time signal processing chain is generally characterized in that the average size of a buffer remains constant, i.e., the lag between output and input is relatively constant, bearing in mind that there may be periodicity to the processing.

The mental state of the first subject may be identified, and the neural correlates of brain activity captured. The second subject is subject to stimulation based on the captured neural correlates and the identified mental state. The mental state may be represented as a semantic variable, within a limited classification space. The mental state identification need not be through analysis of the neural correlates signal and may be a volitional self-identification by the first subject, a manual classification by third parties, or an automated determination. The identified mental state is useful, for example, because it represents a target toward (or against) which the second subject can be steered.

The stimulation may be one or more inputs to the second subject, which may be a sensory stimulation, mechanical stimulation, ultrasonic stimulation, etc., and controlled with respect to waveform, intensity/amplitude, duration, feedback, self-reported effect by the second subject, manual classification by third parties, automated analysis of brain activity, behavior, physiological parameters, etc. of the second subject.

The process may be used to induce in the target subject neural correlates of the desired mental state, which are derived from a different time for the same person, or a different person at the same or a different time. For example, one seeks to induce the neural correlates of the first subject in a desired mental state in a second subject, through the use of stimulation parameters comprising a waveform over a period of time derived from the neural correlates of the mental state of the first subject.

The first and second subjects may be spatially remote from each other and may be temporally remote as well. In some cases, the first and second subject are the same animal (e.g., human), temporally displaced. In other cases, the first and second subject are spatially proximate to each other. In some cases, neural correlates of a desired mental state are derived from a mammal having a simpler brain, which are then extrapolated to a human brain. (Animal brain stimulation is also possible, for example, to enhance training and performance). When the first and second subjects share a common environment, the signal processing of the neural correlates, and especially of real-time feedback of neural correlates from the second subject may involve interactive algorithms with the neural correlates of the first subject.

The first and second subjects may each be subject to stimulators. The first subject and the second subject may communicate with each other in real-time, with the first subject receiving stimulation based on the second subject, and the second subject receiving feedback based on the first subject. This can lead to synchronization of mental state between the two subjects. However, the first subject need not receive stimulation based on real-time signals from the second subject, as the stimulation may derive from a third subject or the first or second subjects at different points in time.

The neural correlates may be, for example, EEG, qEEG, or MEG signals. Traditionally, these signals are found to have dominant frequencies, which may be determined by various analyses. One embodiment provides that the modulation pattern of a brainwave of the first subject is determined independent of the dominant frequency of the brainwave (though typically within the same class of brainwaves), and this modulation imposed on a wave corresponding to the dominant frequency of the second subject. That is, once the second subject achieves that same brainwave pattern as the first subject (which may be achieved by means other than electromagnetic, mechanical, or sensors stimulation), the modulation pattern of the first subject is imposed as a way of guiding the mental state of the second subject.

The second subject may be stimulated with a stimulation signal, which faithfully represents the frequency composition of a defined component of the neural correlates of the first subject.

The stimulation may be performed, for example, by using a source of one of a light signal and a sound signal configured to modulate the dominant frequency on the one of a light signal and a sound signal. The stimulus may be at least one of a light signal, a sound signal, an electric signal, and a magnetic field. The stimulus may be a light stimulation or a sound stimulation. A visual stimulus may be ambient light or direct light. An auditory stimulus may be binaural beats or isochronic tones.

The technology may also provide a processor configured to process the neural correlates of mental state from the first subject, and to produce or define a stimulation pattern for the second subject selectively dependent on a waveform pattern of the neural correlates from the first subject. Typically, the processor performs signal analysis and calculates at least a dominant frequency of the brainwaves of the first subject, and preferably also spatial and phase patterns within the brain of the first subject.

A signal is presented to a second apparatus, configured to stimulate the second subject, which may be an open loop stimulation dependent on a non-feedback controlled algorithm, or a closed loop feedback dependent algorithm. In other cases, analog processing is employed in part or in whole, wherein the algorithm comprises an analog signal processing chain. The second apparatus receives information from the processor (first apparatus), typically comprising a representation of a portion of a waveform represented in the neural correlates. The second apparatus produces a stimulation intended to induce in the second subject the desired mental state, e.g., representing the same mental state as was present in the first subject.

A typical process performed on the neural correlates is filtering to remove noise. For example, notch filters may be provided at 50 Hz, 60 Hz, 100 Hz, 120 Hz, and additional overtones. Other environmental signals may also be filtered in a frequency-selective or waveform-selective (temporal) manner. Higher level filtering may also be employed, as is known in the art. The neural correlates, after noise filtering, may be encoded, compressed (lossy or losslessly), encrypted, or otherwise processed or transformed. The stimulator associated with the second subject would typically perform decoding, decompression, decryption, inverse transformation, etc.

Information security and copy protection technology, similar to that employed for audio signals, may be employed to protect the neural correlate signals from copying or content analysis before use. In some cases, it is possible to use the stored encrypted signal in its encrypted for without decryption. For example, with an asymmetric encryption scheme, which supports distance determination. See U.S. Pat. No. 7,269,277; Sahai and Waters (2005) Annual International Conference on the Theory and Applications of Cryptographic Techniques, pp. 457-473. Springer, Berlin, Heidelberg; Bringer et al. (2009) IEEE International Conference on Communications, pp. 1-6; Juels and Sudan (2006) Designs, Codes and Cryptography 2:237-257; Thaker et al. (2006) IEEE International Conference on Workload Characterization, pp. 142-149; Galil et al. (1987) Conference on the Theory and Application of Cryptographic Techniques, pp. 135-155.

Because the system may act intrusively, it may be desirable to authenticate the stimulator or parameters employed by the stimulator before use. For example, the stimulator and parameters it employs may be authenticated by a distributed ledger, e.g., a blockchain. On the other hand, in a closed system, digital signatures and other hierarchical authentication schemes may be employed. Permissions to perform certain processes may be defined according to smart contracts, which automated permissions (i.e., cryptographic authorization) provided from a blockchain or distributed ledger system. Of course, centralized management may also be employed.

In practice, the feedback signal from the second subject may be correspondingly encoded as per the source signal, and the error between the two minimized. In such an algorithm, the signal sought to be authenticated is typically brought within an error tolerance of the encrypted signal before usable feedback is available. One way to accomplish this is to provide a predetermined range of acceptable authenticatable signals which are then encoded, such that authentication occurs when the putative signal matches any of the predetermined range. In the case of the neural correlates, a large set of digital hash patterns may be provided representing different signals as hash patterns. The net result is relatively weakened encryption, but the cryptographic strength may still be sufficiently high to abate the risks.

The processor may perform a noise reduction distinct from frequency-band filtering. The neural correlates may be transformed into a sparse matrix, and in the transform domain, components representing high probability noise are masked, while components representing high probability signal are preserved. The distinction may be optimized or adaptive. That is, in some cases, the components which represent modulation that are important may not be known a priori. However, dependent on their effect in inducing the desired response in the second subject, the "important" components may be identified, and the remainder filtered or suppressed. The transformed signal may then be inverse-transformed and used as a basis for a stimulation signal.

A mental state modification, e.g., brain entrainment, may be provided, which ascertains a mental state in a plurality of first subjects; acquires brainwaves of the plurality of first subjects, e.g., using one of EEG and MEG, to create a dataset containing representing brainwaves of the plurality of first subjects. The database may be encoded with a classification of mental state, activities, environment, or stimulus patterns, applied to the plurality of first subjects, and the database may include acquired brainwaves across a large number of mental states, activities, environment, or stimulus patterns, for example. In many cases, the database records will reflect a characteristic or dominant frequency of the respective brainwaves. As discussed above, the trainer or first subject is a convenient source of the stimulation parameters but is not the sole available source. The database may be accessed according to its indexing, e.g., mental states, activities, environment, or stimulus patterns, for example, and a stimulation pattern for a second subject defined based on the database records of one or more subjects.

The record(s) thus retrieved are used to define a stimulation pattern for the second subject. The selection of records, and their use, may be dependent on the second subject and/or feedback from the second subject. As a relatively trivial example, a female second subject could be stimulated principally dependent on records from female first subjects. Of course, a more nuanced approach is to process the entirety of the database and stimulate the second subject based on a global brain wave-stimulus model, though this is not required, and also, the underlying basis for the model may prove unreliable or inaccurate. It may be preferred to derive a stimulus waveform from only a single first subject, in order to preserve micro-modulation aspects of the signal, which as discussed above have not been fully characterized. However, the selection of the first subject(s) need not be static and can change frequently. The selection of first subject records may be based on population statistics of other users of the records (i.e., collaborative filtering, i.e., whose response pattern do I correlate highest with? etc.). The selection of first subject records may also be based on feedback patterns from the second user.

The process of stimulation may seek to target a desired mental state in the second subject, which is automatically or semi-automatically determined or manually entered. That target then represents a part of the query against the database to select the desired record(s). The selection of records may be a dynamic process, and reselection of records may be feedback dependent.

The records may be used to define a modulation waveform of a synthesized carrier or set of carriers, and the process may include a frequency domain multiplexed multi-subcarrier signal (which is not necessarily orthogonal). A plurality of stimuli may be applied concurrently, through the suffered subchannels and/or through different stimulator electrodes, magnetic field generators, mechanical stimulators, sensory stimulators, etc. The stimuli for the different subchannels or modalities need not be derived from the same records.

The stimulus may be applied to achieve the desired mental state, e.g., brain entrainment of the second subject with one or more first subjects. Brain entrainment is not the only possible outcome of this process. If the plurality of first subjects is mutually entrained, then each will have a corresponding brain wave pattern dependent based on brainwave entrainment. This link between first subject may help determine compatibility between a respective first subject and the second subject. For example, characteristic patterns in the entrained brainwaves may be determined, even for different target mental states, and the characteristic patterns correlated to find relatively close matches and to exclude relatively poor matches.

This technology may also provide a basis for a social network, dating site, employment or vocational testing, or other interpersonal environments, wherein people may be matched with each other based on entrainment characteristics. For example, people who efficiently entrain with each other may have better social relationships than those who do not. Thus, rather than seeking to match people based on personality profiles, the match could be made based on the ability of each party to efficiently entrain the brainwave pattern of the other party. This enhances non-verbal communication and assists in achieving corresponding states during activities. This can be assessed by monitoring neural responses of each individual to video, and also by providing a test stimulation based on the other party's brainwave correlates of mental state, to see whether coupling is efficiently achieved. On the other hand, the technology could be used to assist in entrainment when the natural coupling is inefficient or to block coupling where the coupling is undesirable. An example of the latter is hostility; when two people are entrained in a hostile environment, emotional escalation ensures. However, if the entrainment is attenuated, undesired escalation may be impeded.

The process may employ a relational database of mental states and brainwave patterns, e.g., frequencies/neural correlate waveform patterns associated with the respective mental states. The relational database may comprise a first table, the first table further comprising a plurality of data records of brainwave patterns, and a second table, the second table comprising a plurality of mental states, each of the mental states being linked to at least one brainwave pattern. Data related to mental states and brainwave patterns associated with the mental states are stored in the relational database and maintained. The relational database is accessed by receiving queries for selected mental states, and data records are returned, representing the associated brainwave pattern. The brainwave pattern retrieved from the relational database may then be used for modulating a stimulator seeking to produce an effect selectively dependent on the mental state at issue.

A computer apparatus may be provided for creating and maintaining a relational database of mental states and frequencies associated with the mental states, the computer apparatus comprising: a non-volatile memory for storing a relational database of mental states and neural correlates of brain activity associated with the mental states, the database comprising a first table, the first table further comprising a plurality of data records of neural correlates of brain activity associated with the mental states, and a second table, the second table comprising a plurality of mental states, each of the mental states being linked to one or more records in the first table; a processor coupled with the non-volatile memory, configured to process relational database queries, which are then used for searching the database; RAM coupled with the processor and the non-volatile memory for temporary holding database queries and data records retrieved from the relational database; and an I/O interface configured to receive database queries and deliver data records retrieved from the relational database. An SQL or noSQL database may also be used to store and retrieve records.

A further aspect of the technology provides a method of brain entrainment comprising: ascertaining a mental state in a first subject; recording brainwaves of the plurality of subjects using at least one channel one of EEG and MEG; storing the recorded brainwaves in a physical memory device; retrieving the brainwaves from the memory device; applying a stimulus signal comprising a brainwave pattern derived from at least one-channel one of the EEG and MEG to a second subject via sensory stimulation, whereby the mental state desired by the second subject is achieved. The stimulation may be of the same order (number of channels)

as the EEG or MEG, or a different number of channels, typically reduced. For example, the EEG or MEG may comprise 128 or 256 channels, while the sensory stimulator may have 8 or fewer channels. Transcranial stimulation of various modalities and patterns may accompany the sensory stimulation.

The present technology may be responsive to chronobiology, and in particular to the subjective sense of time. For a subject, this may be determined volitionally subjectively, but also automatically, for example by judging attention span, using, e.g., eye movements, and analyzing the persistence of brainwave patterns or other physiological parameters after a discrete stimulus. Further, time-constants of the brain, reflected by delays and phase may also be analyzed. Further, the contingent negative variation (CNV) preceding a volitional act may be used, both to determine (or measure) conscious action timing, and also the time relationships between thought and action more generally.

Typically, brainwave activity is measured with a large number of EEG electrodes, which each receive signals from a small area on the scalp, or in the case of a MEG, by several sensitive magnetic field detectors, which are responsive to local field differences. Typically, the brainwave capture is performed in a relatively high number of spatial dimensions, e.g., corresponding to the number of sensors. It is often unfeasible to process the brainwave signals to create a source model, given that the brainwaves are created by billions of neurons, connected through axons, which have long distances. Further, the neurons are generally non-linear and interconnected. However, a source model is not required.

Various types of artificial intelligence techniques may be exploited to analyze the neural correlates of a sleep stage represented in the brain activity data of both the first subject (donor) (or a plurality of donors) and the second subject (recipient). The algorithm or implementation need not be the same, though in some cases, it is useful to confirm the approach of the source processing and feedback processing so that the feedback does not achieve or seek a suboptimal target sleep stage. However, given the possible differences in conditions, resources, equipment, and purpose, there is no necessary coordination of these processes. The artificial intelligence may take the form of neural networks or deep neural networks, though rule/expert-based systems, hybrids, and more classical statistical analysis may be used. In a typical case, an artificial intelligence process will have at least one aspect, which is non-linear in its output response to an input signal, and thus at least the principle of linear superposition is violated. Such systems tend to permit discrimination, since a decision and the process of decision-making are, ultimately, non-linear. An artificially intelligent system requires a base of experience or information upon which to train. This can be supervised (external labels applied to data), unsupervised (self-discrimination of classes), or semi-supervised (a portion of the data is externally labeled).

A self-learning or genetic algorithm may be used to tune the system, including both or either the signal processing at the donor system and the recipient system. In a genetic algorithm feedback-dependent self-learning system, the responsivity of a subject, e.g., the target, to various kinds of stimuli may be determined over a stimulus space. This stimulation may be in the context of use, with a specific target sleep stage provided, or unconstrained. The stimulator may operate using a library of stimulus patterns, or seek to generate synthetic patterns or modifications of patterns.

Over some time, the system will learn to map the desired sleep stage to optimal context-dependent parameters of the stimulus pattern.

The technology may be used for both the creation of a desired sleep stages in the recipient, elimination of existing sleep stages in the recipient. In the latter case, a decision of what end state is to be achieved is less constrained, and therefore, the optimization is distinct. For example, in the former case, it may be hard to achieve a particular sleep stage that is desired, requiring a set of transitions to cause the brain of the recipient to be enabled/prepared to enter the target state. In the case of a system seeking to eliminate an undesired sleep stage, the issue is principally what path to take to most efficiently leave the current state, bearing in mind the various costs, such as the comfort/discomfort of the stimulation, the time value cost, etc. Therefore, the series of states may differ in the implementation of these distinct goals, even if the endpoints are identical, i.e., the optimal algorithm to achieve state B from state A, may be different from the optimal algorithm to exist state A, and end up at state B.

The technology may be used to address sleep stages or sections of them associated with dreaming. Typically, dreaming is associated with many different brain regions. As such, the biology of dreaming is different. Often, dreams have a biochemical or hormonal component and, perhaps, a physiological component, that may be attenuated or absent from cognitive states. Dreaming had long been thought to occur largely during rapid-eye-movement (REM) sleep, but dreams have also been reported to occur during non-REM sleep. However, dreams are typically remembered, if the dreamer wakes us during the REM phase of the sleep. In addition, it has been shown that dreaming, for example, about faces was linked to increased high-frequency activity in the specific region of the brain involved in face recognition, with dreams involving spatial perception, movement and thinking similarly linked to regions of the brain that handle such tasks when awake. Therefore, while the general brainwave or other neural correlates acquisition from a donor may be similar or identical, the stimulus used on the second subject (recipient) may be distinct in modality, spatial location, intensity/waveform, other stimulation parameters, and the types and application of feedback employed.

It is known that people who have more REM sleep and more intense theta (4 Hz-7 Hz) activity during REM are better able to consolidate emotional memories. It was suggested (Blagrove) that if we attempt to hack our dreams by artificially increasing theta waves, it might lead to the incorporation of more waking experiences into our dreams. (See "Dreams act as overnight therapy" New Scientist magazine on 5 May 2018). Transplanting theta frequency brainwaves from a vivid dreamer may also help achieve the same effect. Moreover, instead of stimulating the subject's brain with a synthetic theta frequency (e.g., isotonic tones or ambient sound beats), stimulating the recipient's brain using donor's brainwaves carrying secondary (and higher) harmonics, in addition to the dominant theta frequency, may induce the same category of dreams, i.e., if the donor dreamed of people, the recipient will be more likely to dream of people, albeit different people, because the donor's brainwaves will stimulate the visual cortex of the recipient. This may be helpful in the treatment of PTSD, stress management, phobias and some psychiatric diseases.

In a medical treatment implementation, in some cases it may be appropriate to administer a drug or pharmacological agent, such as melatonin, hypnotic or soporific drug, a sedative (e.g., barbiturates, benzodiazepines, nonbenzodiazepine hypnotics, orexin antagonists, antihistamines, general anesthetics, cannabis and other herbal sedatives, methaqualone and analogues, muscle relaxants, opioids) that assists in achieving the target sleep stage, and for emotional states and/or dreams, this may include certain psychotropic drugs, such as epinephrine, norepinephrine reuptake inhibitors, serotonin reuptake inhibitors, peptide endocrine hormones, such as oxytocin, ACTH fragments, insulin, etc. Combining a drug with stimulation may reduce the required dose of the drug and the associated side effects of the drug.

It is an object to provide a method of brain entrainment to facilitate sleep in a subject using a sleep app executing on a user device, the method comprising: executing the sleep app on the user device, configured to select at least one stimulus selected from the group consisting of at least one of a light signal and a sound signal; selecting a waveform from a menu having a plurality of waveforms derived from brainwaves of at least one sleeping donor, wherein said waveform corresponds to at least one specific stage of sleep; and stimulating the subject with said at least one stimulus, wherein said at least one stimulus is modulated with the selected waveform, to thereby entrain the brain of the subject with the selected waveform to facilitate sleep in the subject. The user device may be, e.g., a mobile device, a wearable device, or an implantable device. The stimulus may be a sound signal, comprising at least one of a predetermined soundtrack, a tone, and white noise. The sound signal may comprise a soundtrack representing at least one of a sound of rainfall, a sound of a waterfall, a sound of ocean waves, a lullaby, a melody, and a polyphony.

The effect of the stimulus may be monitored by feedback, e.g., EEG, body temperature, heart rate, respiration rate, facial expression, muscle tone, vasodilation, which may be measured by non-contact sensors or wearable devices, and other electronic sensors embedded in the bed, blanket, mattress, sheets, pillow, etc. Body movement and eye movement may be observed by a video camera or webcam. The sensor signals are advantageously transmitted back to the user device to adjust the regime of stimulation. Of course, the communication path may be indirect to the user device, or the analysis of the signals may be remote from the user device, e.g., in a cloud computing center. An important aspect of the system is synchronizing the cycles with the context and current state of the subject. For example, if the subject got up to go to the bathroom or woke up for other reasons, the modulation cycle would generally need to restart from sleep stage 1. However, depending on the mental state of the subject, the progression through the sleep states may be varied.

The sound may be amplitude modulated on a carrier waveform, which would generally have higher frequencies that the modulation waveform (typically <100 Hz), and/or frequency modulated. When the sound separation between ears is present, the amplitude, frequency, phase, timing, etc. between ears may be modulated. Similarly, optical signals may be modulated by intensity, color, frequency, phase, etc., in addition to morphological objects and dynamic changes in real time.

The at least one waveform may be derived from an EEG recordings of brainwaves of at least one sleeping donor, processed using at least one of a principal component analysis (PCA), a correspondence analysis (CA), a factor analysis, a K-means clustering, a non-negative matrix factorization (NMF), a sparse PCA, a non-linear PCA, a robust PCA, an independent component analysis (ICA), a network component analysis, and a singular spectral analysis.

Gender of the subject may be determined, and the gender of the subject marched with a gender of said at least one sleeping donor.

The at least one specific stage of sleep may be one of stage 1 of sleep, stage 2 of sleep, stage 3 of sleep, and stage 4 of sleep. In some analyses, 4 different non-REM (NREM) stages are classified, with stages 3 and 4 being deep sleep stages. See, www.sleepassociation.org/about-sleep/stages-of-sleep/, FIG. 17. At least one specific stage of sleep may be one of REM sleep, non-REM sleep, and slow-wave sleep. At least one specific stage of sleep may be at least one complete sleep cycle comprising a natural sequence of sleep stages from stage 1 through stage 4 (REM). The at least one complete sleep cycle may comprise least three sequential complete sleep cycles.

The user device may comprise at least one speaker and wherein the stimulus comprises a sound signal delivered through said at least one speaker, and comprises an isochronic tone. The sound signal may be delivered to the subject through a pair of wireless earbuds, e.g., the modulated selected waveform may comprise binaural beats.

The user device may be configured to control an ambient light, which is selectively controllable to change at least one of brightness and color, and wherein the stimulus comprises a light signal which is presented to the subject through the ambient light. The light signal may be generated by at least one light emitting diode (LED). The LED may be disposed in proximity to the subject's eyes, e.g., in a sleep mask.

The user device may comprise at least one biometric sensor, further comprising the step of monitoring and collecting biometric data of the subject from said at least one biometric sensor.

The method may further comprise monitoring movement of the subject using at least one of a camera in the user device and a webcam coupled with the user device, processed with a neural network configured to classify a subject's sleep as one of a REM sleep, non-REM sleep, and a slow-wave sleep; and adjusting the stimulating of the subject upon determining whether the classification.

The method may further comprise monitoring a facial expression of the subject to determine if the subject is asleep or awake, and controlling a sequence of sleep stages induced by said stimulating in dependence on at least the monitored facial expression. The stimulating may be controlled to progress according to a natural series of sleep stages, further comprising resetting the progress according to the natural series of sleep stages in dependence on an awakening of the subject determined based on the monitored facial expression. The facial expression may be monitored by at least one of a camera in the user device and a webcam communicating with the user device. The facial expression may be monitored according to a signal present in at least one electromyographic electrode.

The method may further comprise obtaining biofeedback from the subject in real time and adjusting the stimulation of the subject in real time according to a biofeedback loop implemented by the user device.

It is also an object to provide a mobile device, comprising a housing; a microprocessor disposed within the housing; and a non-volatile memory disposed within the housing and electrically coupled with the processor, configured to store at least one app for controlling the microprocessor; the at least one app being configured to: (a) select a waveform from a plurality of waveforms derived from brainwaves of at least one sleeping donor, wherein said waveform corresponds to at least one specific stage of sleep; and (b) stimulate a subject with said at least one stimulus, wherein at least one stimulus selected from the group consisting of at least one of an auditory stimulus and a visual stimulus is modulated with the selected waveform, to thereby entrain the brain of the subject with the selected waveform to facilitate sleep in the subject. The mobile device may further comprise a battery electrically coupled with the processor; a display, disposed within the housing, electrically coupled with the microprocessor; a wireless communication transceiver disposed within the housing, electrically coupled with the microprocessor; at least one microphone, electrically coupled with the processor; at least one speaker disposed within the housing, electrically coupled with the processor; and at least one camera electrically coupled with the processor. The mobile device may be wirelessly coupled with a wearable device, wherein said wearable device comprises at least one biometric sensor configured to communicate biometric data from the subject to the mobile device through the wireless communication transceiver. The housing may be wearable by the subject and/or maintained close to the skull of the subject with a headband.

Another object provides a method of brain entrainment to facilitate sleep in a subject using a sleep app, comprising opening the sleep app on a programmable device; choosing at least one stimulus, wherein said at least one stimulus is one of a light signal and a sound signal; choosing a waveform from a menu having a plurality of waveforms derived from brainwaves of at least one sleeping donor, wherein said waveform corresponds to at least one specific stage of sleep; and stimulating the subject's brain with said at least one stimulus, wherein said at least one stimulus is modulated with the chosen waveform to entrain the brain of the subject with frequencies of the brainwaves of the at least one sleeping donor, to facilitate sleep in the subject. The method may further comprise recording a subject's electroencephalogram (EEG) during sleep while stimulated; and adjusting the stimulating based on the subject's electroencephalogram (EEG) in real time using a neurofeedback loop.

A further object provides a method of brain entrainment to facilitate sleep in a subject, comprising: providing a programmable device having a sleep app stored in a non-volatile memory; providing a stimulator, selected from one or more of a light stimulator and a sound stimulator; defining a waveform, by the sleep app, from a plurality of waveforms, each respective waveform being derived from brainwaves of at least one sleeping donor, wherein said waveform corresponds to at least one specific stage of sleep; stimulating the subject with the stimulator, having at least one of a light output or a sound output modulated with the defined waveform, to entrain the brain of the subject with the brainwaves of the at least one sleeping donor, to facilitate sleep in the subject. The method may further comprise recording an electroencephalogram (EEG) from the subject during sleep while being stimulated, and defining at least one new waveform for stimulation, said waveform being selectively dependent on the uploaded recorded electroencephalogram. The at least one new waveform may be used to stimulate the subject one day after the electroencephalogram is recorded. The recorded electroencephalogram may be uploaded to a remote server, and the new waveform for stimulation subsequently downloaded from the remote server.

Another object provides a non-transitory computer readable medium storing instructions for controlling a processor to perform a method comprising: instructions to select a waveform from a plurality of waveforms derived from brainwaves of at least one sleeping donor, wherein said waveform corresponds to at least one specific stage of sleep;

and instructions to stimulate a subject with said at least one stimulus, wherein at least one stimulus selected from the group consisting of at least one of an auditory stimulus and a visual stimulus is modulated with the selected waveform, to thereby entrain the brain of the subject with the selected waveform to facilitate sleep in the subject.

A still further object provides a method of generating a waveform for neuromodulation to improve sleep in a subject, the method comprising: collecting EEG recording from at least one sleeping donor; identifying portions of the EEG recordings corresponding to a specific sleep stage; grouping a plurality of portions of the EEG recordings corresponding to the specific sleep stage, each group corresponding to the specific sleep stage; analyzing each group corresponding to the specific sleep stage using a statistical analysis; extracting a cortical signature corresponding to each specific sleep stage; generating a waveform based on the cortical signature for each sleep stage; and modulating a stimulus for the subject according to the waveform. The modulating of the stimulus may be performed under control of a sleep app executing on a mobile or wearable device. The statistical analysis may be at least one of a principal component analysis (PCA), a correspondence analysis (CA), a factor analysis, a K-means clustering, a non-negative matrix factorization (NMF), a sparse PCA, a non-linear PCA, a robust PCA, an independent component analysis (ICA), a network component analysis, and a singular spectral analysis.

It is, therefore, an object to provide a method of inducing sleep in a second subject comprising: recording brain activity patterns of a first subject (donor) who is asleep; and inducing sleep in the second subject (recipient) by replicating the brain activity patterns of the donor in the recipient.

It is also an object to provide a method of preventing sleep in a second subject (recipient) comprising: recording brain activity patterns of a first subject (donor) who is awake; and preventing sleep in the second subject (recipient) by replicating the brain activity patterns of the donor in the recipient.

It is further an object to provide a method of inducing sleep in a second subject (recipient) comprising: identifying the mental state of a first subject (donor); if the donor is asleep, recording brain activity patterns of the donor; and inducing sleep in the recipient by replicating the brain activity patterns of the donor in the recipient. The method may further comprise verifying that the recipient is asleep.

It is still a further object to provide a method of preventing sleep in a second subject (recipient) comprising: identifying a mental state of a first subject (donor); if the donor is awake, recording brain activity patterns of the first subject; and preventing sleep in the second subject by replicating the brain activity patterns of the second subject. The method may further comprise verifying that the second subject is awake.

Another object is a method of transplanting a desired mental state from a first subject (donor) to a second subject (recipient) comprising: identifying a mental state of the donor; capturing a mental state of the donor by recording brain activity patterns; saving the brain activity patterns in a non-volatile memory; retrieving the brain activity patterns from the non-volatile memory; and transplanting the desired mental state of the donor to the recipient by inducing the brain activity patterns in the recipient, wherein the desired mental state is one a sleeping state and a waking state.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is one a sleep stage 1, 2, and 3.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is one of a REM sleep stage and non-REM sleep stage.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is a slow-wave deep non-REM sleep.

A further object is a method of improving sleep in a recipient by transplanting a mental state of a donor to the recipient comprising: recording brainwaves of the donor; and transplanting the mental state of the donor to the recipient by inducing the recorded brainwaves of the donor in the recipient, wherein the mental state is one of a waking state and a sleeping state.

A still further object is a method of transplanting a desired mental state of a first subject (donor) to a second subject comprising: identifying a mental state of the donor; recording brainwaves of the donor in a desired mental state; and transplanting the desired mental state of the donor to the recipient by inducing the brainwaves of the first subject in the second subject, wherein the desired mental state is one of a sleeping state and a waking state.

Another object is a method of improving sleep in a recipient by transplanting the desired state of a healthy sleep to the recipient comprising: identifying a mental state of the plurality of healthy donors; recording brainwaves of the plurality of healthy donor in a state of sleep; saving the brainwaves in a non-volatile memory; retrieving the brainwaves from the non-volatile memory; and transplanting the state of healthy sleep from the plurality of healthy donors to the recipient by inducing the brainwaves of the donor in the recipient. The method may comprise identifying a mental state of the recipient to verify that the recipient has the desired mental state. The brainwaves may be recorded using EEG, qEEG, or MEG. The method may further comprise filtering the recorded brainwaves from noise and/or performing PCA to determine dominant frequencies and secondary (and, possibly, higher) harmonics.

A further object is a system for transplanting a desired mental state from a first subject (donor) to a second subject (recipient) comprising: a first apparatus for recording brainwaves of the donor in a desired mental state; a non-volatile memory coupled with the first apparatus for storing the recording of the brainwaves; and a second apparatus for inducing the brainwaves in the recipient to transplant to the recipient the desired mental state of the donor, the second apparatus configured to receive the recording of the brainwaves of the donor from the non-volatile memory, wherein the desired mental state is one of a sleeping state and a waking state. The first apparatus may be one of an EEG and an MEG. The second apparatus may be one of a source of light signal or sound signal configured to modulate donor's brainwave frequencies on the light signal or the sound signal.

Another object is a method of transplanting a desired mental state of a first subject (donor) to a second subject (recipient) comprising: identifying a mental state of the donor; recording at least one of EEG and MEG of the donor, said donor being in a desired mental state; processing the EEG or MEG signal; saving the processed signal in a nonvolatile memory; retrieving the processed signal from the nonvolatile memory; modulating the processed signal on at least one stimulus; and transplanting the desired mental state of the first subject to the second subject by stimulating the second subject with said at least one stimulus, wherein the desired mental state is a sleeping state or a waking state. The processing may comprise removing noise from the EEG or MEG signal; and/or compressing the EEG or MEG signal. The EEG or MEG signal retrieved from the nonvolatile memory may be decompressed. The stimulus may be a light signal, a sound signal, or a combination thereof. The light stimulation may be an ambient light or a direct light. The sound stimulation may be binaural beats or isochronic tones.

A still another object is a system for transplanting a desired mental state of a first subject (donor) to a second subject (recipient) comprising: an EEG or an MEG for recoding brainwaves of the donor, the donor being in a desired mental state; a processor coupled with an EEG or MEG, the processor configured to perform signal analysis and calculate at least one dominant frequency of the brainwaves of the donor; a nonvolatile memory coupled with the first processor for storing the at least one frequency of the brainwaves of the donor; a second apparatus for inducing the brainwaves in the recipient to transplant to the recipient the desired mental state of the donor, the second apparatus configured to receive said at least one dominant frequency of the brainwaves of the donor from the non-volatile memory, wherein the desired mental state is one of a sleeping state and a waking state.

The second apparatus may be a light source capable of modulating said at least one dominant frequency on the light, a sound source capable of modulating said at least one dominant frequency on the sound, or a combination thereof. The sound source may be binaural beats source or isochronic tones source.

A further object is a method of transplanting a circadian rhythm of a first subject (donor) to a second subject (recipient) comprising: recording EEG or MEG of the donor, the donor having a desirable phase of the circadian rhythm; processing the recorded EEG or MEG to remove noise; saving the processed EEG or MEG in a nonvolatile memory; retrieving the processed EEG or MEG from the nonvolatile memory; and transplanting the desired phase of the circadian rhythm of the donor to the recipient by "playing back" the processed EEG or MEG of the donor to the recipient via sensory stimulation or other one or more stimulus on which the donor's EEG or MEG is modulated. The method may further comprise compressing the recorded EEG or MEG, before saving it in the non-volatile memory; and decompressing the recorded EEG or MEG after retrieving compressed EEG or MEG from the non-volatile memory.

Yet another object is a system for transplanting a circadian rhythm of a first subject (donor) to a second subject (recipient) comprising: an EEG or MEG for recording EEG or MEG signals respectively; a first processor coupled to the EEG or MEG and configured for digital signal processing for removing noise from the recorded EEG or MEG; a non-volatile memory coupled with the processor for storing the processed EEG or MEG; and a stimulation device coupled to the non-volatile memory for playing back the processed EEG or MEG to the recipient to induce the circadian rhythm of the donor to the recipient. The stimulation device may be a sensory stimulation device, a source of light or a source of the sound, each capable of modulating recorded EEG or MEG on a light signal or a sound signal respectively. The first processor may be further configured to compress the processed EEG or MEG. A second processor configured to decompress compressed EEG or MEG may be coupled to the non-volatile memory and to the stimulation device.

The technology may be used to modify or alter a mental state (e.g., from sleep to waking and vice versa) in a subject. Typically, the starting mental state, brain state, or brainwave pattern is assessed, such as by EEG, MEG, observation, stimulus-response amplitude and/or delay, or the like. Of particular interest in uncontrolled environments are automated mental state assessments, which do not rely on human observation or EEG signals, and rather may be acquired through MEG (e.g., SQID, optically-pumped magnetometer), EMG, MMG (magnetomyogram), mechanical (e.g., accelerometer, gyroscope, etc.), data from physiological sensors (e.g., EKG, heartrate, respiration rate, temperature, galvanic skim potential, etc.), or automated camera sensors.

For example, cortical stimulus-response pathways and reflexes may be exercised automatically, to determine their characteristics on a generally continuous basis. These characteristics may include, for example, a delay between stimulus and the observed central (e.g., EEG) or peripheral response (e.g., EMG, limb accelerometer, video). Typically, the same modality will be used to assess the pre-stimulation state, stimulus response, and post-stimulation state, though this is not a limitation.

In order to change the mental state, a stimulus is applied in a way designed to alter the mental state in the desired manner. A state transition table, or algorithm, may be employed to optimize the transition from a starting mental state to a desired mental state. The stimulus may be provided in an open loop (predetermined stimulus protocol) or closed loop (feedback adapted stimulus protocol), based on observed changes in a monitored variable.

Advantageously, a characteristic delay between application of stimulus and determination of response varies with the brain or mental state. For example, some mental states may lead to an increased delay or greater variability in delay, while others may lead to decreased or lower variability. Further, some states may lead to attenuation of response, while others may lead to an exaggerated response. In addition, different mental states can be associated with qualitatively different responses. Typically, the mere assessment of the brain or mental state should not itself alter the state, though in some cases the assessment and transition influence may be combined. For example, in seeking to assist in achieving a deep sleep state, the excitation that disturbs sleep is contraindicated.

In cases where a brainwave pattern is itself determined by EEG (which may be limited to relatively controlled environments), brainwaves representing that pattern represent coherent firing of an ensemble of neurons, defining a phase. One way to change the state is to advance or retard the triggering of the neuronal excitation, which can be a direct or indirect excitation or inhibition, caused, for example, by electrical, magnetic, mechanical, or sensory stimulation.

This stimulation may be time-synchronized with the detected (e.g., by EEG) brainwaves, for example with a phase lead or lag with respect to the detected pattern. Further, the excitation can steer the brainwave signal by continually advancing to the desired state, which through the continual phase rotation represents a different frequency. After the desired new state is achieved, the stimulus may cease, or be maintained in a phase-locked manner to hold the desired state.

A predictive model may be used to determine the current mental state, optimal transition to a desired mental state, when the subject has achieved the desired mental state, and how to maintain the desired mental state. The desired mental state itself may represent a dynamic sequence (e.g., stage 1→stage 2→stage 3, etc.), such that the subject's mental state is held for the desired period in a defined condition. Accordingly, the stimulus may be time-synchronized with respect to the measured brainwave pattern.

Direct measurement or determination of brainwaves or their phase relationships is not necessarily required. Rather, the system may determine tremor or reflex patterns. Typically, the reflex patterns of interest involve central pathways, and more preferably brain reflex pathways, and not spinal cord mediated reflexes, which are less dependent on instantaneous brain state. The central reflex patterns can reflect a time delay between stimulation and motor response, an amplitude of motor response, distribution of response through various afferent pathways, the variability of response, tremor or other modulation of motor activity, etc. Combinations of these characteristics may be employed, and different subsets may be employed at different times or to reflect different states. Similar to evoked potentials, the stimulus may be any sense, especially sight, sound, touch/proprioception/pain/etc., though the other senses, such as taste, smell, balance, etc., may also be exercised. A direct electrical or magnetic excitation is also possible. As discussed, the response may be determined through EEG, MEG, or peripheral afferent pathways.

A further object provides a system and method for enhancing deep non-REM sleep, comprising statistically separating slow-wave sleep components from acquired brainwave patterns; defining a stimulation pattern based on the statistically separating slow-wave sleep components, and stimulating a subject with the defined stimulation pattern. The neurological stimulator comprises a memory configured to store acquired brainwave patterns; at least one processor configured to: statistically separate slow-wave non-REM sleep components from the acquired brainwave patterns; and define a brain stimulation pattern based on the statistically separating slow-wave non-REM deep sleep components; and an output signal generator configured to defined brain stimulation pattern.

A still further object provides a system and method for enhancing deep sleep, comprising: extracting brainwave patterns representing a deep sleep state comprising slow wave sleep, from indigenous brain activity EEG recordings of at least one subject; processing the extracted brainwave patterns using a statistical processing algorithm to separate slow wave sleep components from the indigenous brain activity EEG recordings of the at least one subject; inverting the processed extracted brainwave patterns; and stimulating a subject with the inverted processed extracted brainwave patterns. The corresponding system for enhancing deep sleep comprises a memory configured to store brainwave patterns representing a deep sleep state comprising slow wave sleep, from indigenous brain activity EEG recordings of at least one subject; at least one processor configured to process the extracted brainwave patterns using a statistical processing algorithm to separate slow wave sleep components from the indigenous brain activity EEG recordings of the at least one subject; and a stimulator, configured to generate a stimulation signal based on the processed extracted brainwave patterns. The stimulator may comprise a sensory stimulator (e.g., sight, sound, vestibular, touch, taste, smell, etc.). In order to format the signal for stimulating the brain, it may be inverted. Normalization of brain activity information may be spatial and/or temporal.

See also US 2016/0066838 (DeCharms); US 2009/0099623 (Bentwich); US201210289869 A1 (Tyler); US 2004/0131998 (Marmon et al.); U.S. Pat. No. 5,356,368 (Monroe); US 2002/0198577 (Jaillet); and US 2015/0294074 (Advanced Telecommunications Research Institute International). DeCharms discloses a computer-assisted method for treating pain in a subject comprising measuring activity of one or more internal voxels of a brain of said subject associated with pain; communicating instructions to said subject which modulate the activity of said voxel, and training said subject to control said internal voxel. DeCharms provides methods, software, and systems that may be used to provide and enhance the activation and control of one or more regions of interest, particularly through training and exercising those regions of interest. Data analysis/behavioral control software performs computations of brain scan image data to produce activity metrics that are measures of physiological activity in brain regions of interest. The results and other information and ongoing collected data may be stored to data files of progress and a record of the stimuli used. The selected instruction, measured information, or stimulus, is then presented via a display to a subject. This encourages the subject to engage in imagined or performed behaviors or exercises or to perceive stimuli. If the subject undertakes overt behaviors, such as responding to questions, the responses and other behavioral measurements are fed to the data analysis/behavioral control software. According to DeCharms, a subject can be trained to control the activation of a region of interest of that subject's brain, and then exercise the use of that region to further increase the strength and control of its activation. This training and exercise can have beneficial effects on the subject. In the case of regions that release endogenous neuromodulatory agents, this control can serve a role similar to that of externally applied drugs.

It is also an object to provide a method of generating a waveform for neuromodulation to improve sleep in a subject, the method comprising: collecting EEG recordings from at least one sleeping donor for a plurality of sleep stages; grouping a plurality of portions of the EEG recordings corresponding to the plurality of sleep stages, into a plurality of groups corresponding to the plurality of sleep stages; analyzing each group using a statistical analysis; extracting a cortical signature corresponding characteristic of each analyzed group; generating a waveform based on the characteristic cortical signature for each of the plurality of sleep stages; and modulating a stimulus for the subject according to the generated waveforms for the plurality of sleep stages.

It is a further object to provide a mobile device contained within a housing, comprising: a microprocessor; an electrical power source, electrically coupled with the microprocessor; a wireless communication transceiver, electrically coupled with the microprocessor; at least one microphone port, electrically coupled with the microprocessor, configured to receive an electrical signal corresponding to a sound; at least one camera port electrically coupled with the microprocessor, configured to receive an electrical signal corresponding to an image; a display, electrically coupled with the microprocessor; at least one speaker port, electrically coupled with the microprocessor, configured to generate an electrical signal corresponding to a sound; a non-volatile memory and electrically coupled with the microprocessor, configured to store at least one app downloadable through the wireless communication transceiver for controlling the microprocessor, said at least one downloadable app being configured to: (a) select a waveform from a plurality of waveforms derived from brainwaves of at least one sleeping donor, wherein said waveform corresponds to at least one a specific stage of sleep, a gender, and an age group; and (b) define a stimulus for stimulation of a subject, selected from the group consisting of at least one of an auditory stimulus generated through the at least one speaker, and a visual stimulus generated through the display, modulated with the selected waveform, and adapted to entrain the brain of the subject with the selected waveform to facilitate sleep in the subject; wherein at least one of the selection of the waveform and the definition of the stimulus is responsive to the at least one microphone or the at least one camera.

It is another object to provide a method of facilitating sleep, comprising: providing data defining a plurality of waveforms in a memory; retrieving a selected waveform from the memory, selectively dependent on at least one of a determined sleep phase of a human subject and a predetermined sequence; and stimulating the human subject with a stimulus modulated according to the selected waveform; to thereby entrain the brain of the human subject with the selected waveform to facilitate sleep in the subject.

The plurality of waveforms in the memory may be derived from brain activity measurements acquired during at least one sleep cycle of at least one human, or from brain activity measurements acquired during at least one sleep cycle of the human subject.

The method may further comprise acquiring brain activity measurements during at least one sleep cycle of at least one human; and processing the acquired brain activity measurements to define the plurality of waveforms in the memory.

The stimulus may be modulated in a human subject device, according to a sleep app stored within the human subject device, the sleep app being downloadable and upgradable from a remote server.

The predetermined sequence may be defined by a human user interface menu of a human subject device for selecting at least one respective waveform.

The sleep phase of the human subject may be determined based on at least EEG activity of the human subject or based on at least bioelectric signals received from the human subject.

The stimulus modulated according to the selected waveform may entrain the brain of the human subject with the selected waveform to facilitate sleep in the human subject.

The stimulus modulated according to the selected waveform may be one of a light stimulus and a sound stimulus.

The selected waveform may correspond to at least one specific stage of sleep.

Each of the plurality of waveforms may be derived from recordings of brainwaves of at least one sleeping donor, processed using a statistical decision analysis.

The method may further comprise adaptively defining a sequence of sleep stages dependent on biometric information received from a sleeping human subject; and selecting waveforms from the memory in dependence on a correspondence to a respective sleep stage of the adaptively defined sequence of sleep stages; wherein said stimulating the human subject comprises altering a sleep stage of the human subject dependent on both the determined sleep phase of a human subject and the adaptively defined sequence of sleep stages.

The human subject may be stimulated with at least one audio transducer and wherein the stimulus comprises at least one of an isochronic tone and binaural beats or with an ambient light stimulus, selectively modulated according to the selected waveform to change at least one of brightness and color. The ambient light stimulus may be emitted by at least one light emitting diode disposed in a sleep mask proximate the human subject's eyes.

The method may further comprise providing at least one sensor to determine at least one of an eye movement and a facial expression of the human subject, to at least one of determine a current determined sleep phase of a human subject or select the predetermined sequence.

The predetermined sequence may be a natural series of sleep stages, the method further comprising reselling the progress according to the natural series of sleep stages in dependence on an awakening of the human subject.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

FIG. 1 shows a flowchart according to one embodiment of the invention illustrating a process of replicating a sleep state from one subject to another subject.

FIG. 2 shows a flowchart according to one embodiment of the invention illustrating a process of replicating a waking stage from one subject to another subject by recording and replicating brainwaves associated with the waking stage, according to one embodiment of the invention.

FIG. 5 shows a flowchart according to one embodiment of the invention illustrating the creation of a database of sleep stages and their associated frequencies for later brain entrainment.

FIG. 6 shows a flowchart according to one embodiment of the invention illustrating using a neural network in the creation of a database of sleep stages and their associated frequencies for later brain entrainment.

FIG. 7 shows a flowchart according to one embodiment of the invention illustrating a method of recording a mental state of a first subject in a desirable state of the subject's circadian rhythm and transplanting this mental state into another subject to replicated the desirable state of the circadian rhythm.

FIG. 8 shows a flowchart according to a further embodiment of the invention.

FIG. 9 shows a flowchart according to one embodiment of the invention illustrating a process of replicating the desired sleep stage from one subject to another subject.

FIG. 10 shows a flowchart according to an embodiment of the invention.

FIG. 12 shows a flowchart according to an embodiment of the invention.

FIG. 13 shows a flowchart according to an embodiment of the invention.

FIG. 14 shows a flowchart according to an embodiment of the invention.

FIG. 15 shows a flowchart according to an embodiment of the invention.

FIGS. 27A and 27B show an EEG for a 25 years old male in sleep stage W.

FIG. 28 shows a schematic diagram of a mental state transfer system.

DETAILED DESCRIPTION OF THE PREFERRED EMBODIMENTS

Figures 3, 4:
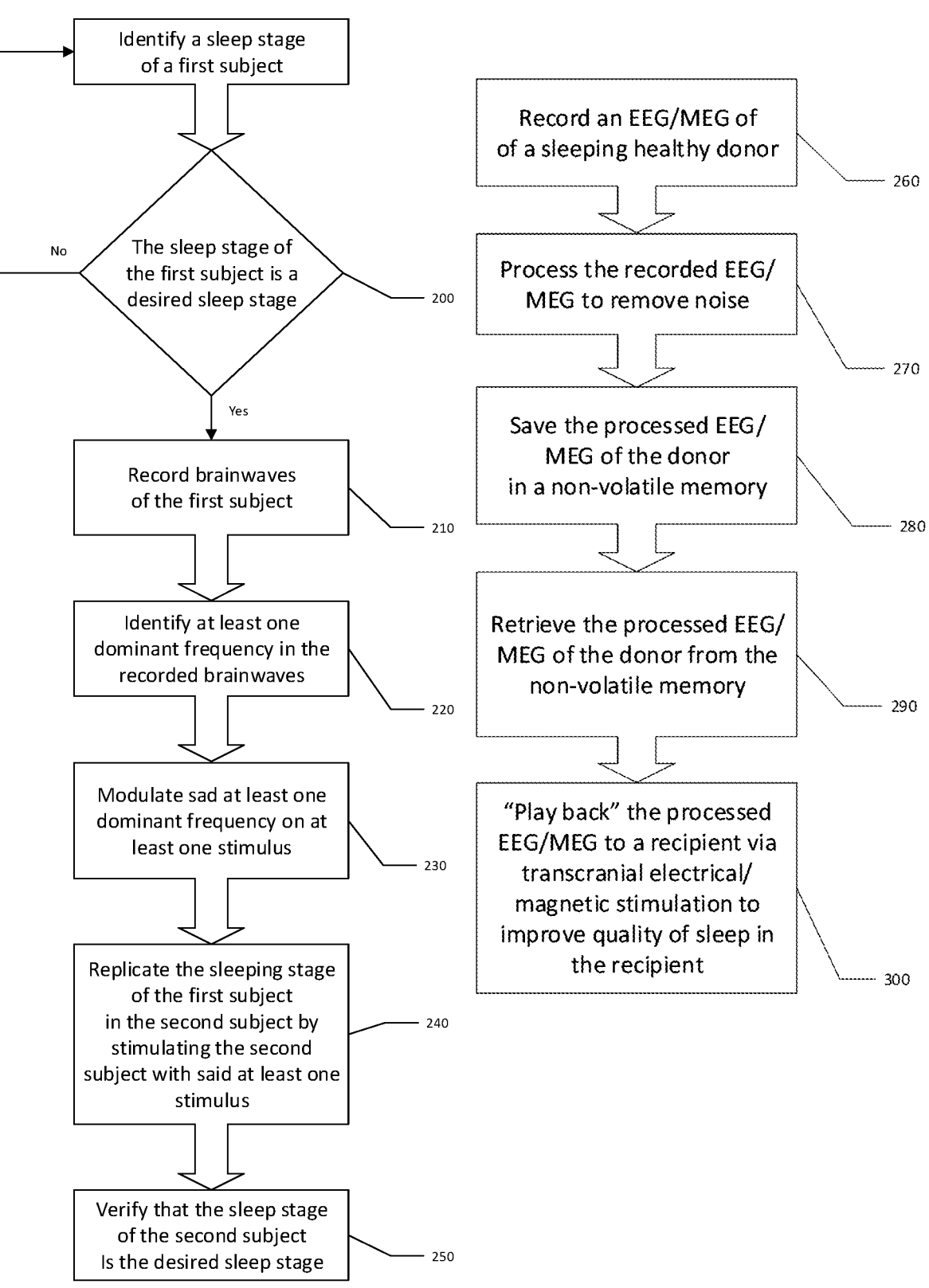
FIG. 3 shows a flowchart according to one embodiment of the invention illustrating a process of replicating a sleep stage from at least one first subject to another subject by recording electroencephalogram (EEG) of said least one first subject, extracting at least one dominant frequency from the EEG and replicating the sleep stage of said at least one first subject in a second subject by stimulating the second subject with stimuli having the dominant frequency associated with the desired sleep stage, according to one embodiment of the invention.
FIG. 4 shows a flowchart according to one embodiment of the invention illustrating a method of improving sleep in a recipient by recording EEG or MEG of a healthy donor and "playing it back" to the recipient via transcranial stimulation.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

FIG. 1 shows a flowchart of a first embodiment according to the present invention. A first subject (donor), having a mental state, is interrogated, observed or sensed, to determine or identify his or her mental state 100. The first subject is typically human, though this is not a limit of the technology and the subject may be an animal. In this embodiment, the process seeks to identify a characteristic sleep pattern, and therefore the mental state of the first subject is monitored until a sleep state occurs 110. When the first subject (donor) is asleep, brain activity patterns reflecting or characterizing the sleep state are captured 120. This step may be done by recording EEG or MEG of the first subject (donor). And the brain activity patterns are stored in a non-volatile memory 130. These stored patterns may be optionally processed, statistically aggregated, analyzed for perturbations or anomalies, filtered, compressed, etc. Stages of sleep may be determined. It is noted that brain activity patterns change over time during sleep from stage to stage, and therefore, the stored patterns may encompass one or more stages of sleep.

The stored data from the first subject (donor) is then used to induce sleep in a second subject (a recipient—also typically a human, but may be an animal) by replicating the brain activity patterns (or sequences of brain activity patterns) of the first subject (donor) in the second subject (recipient) 150. The replication of brain activity patterns, dependent on the stored patterns, typically seeks to stimulate or induce the brain of the second subject (recipient) by modulating a stimulus (or several stimuli) in a manner synchronized with the frequency, phase and/or waveform pattern represented in the brain activity patterns of the first subject (donor) in the sleep state. Typically, when the second subject (recipient) achieves the sleep state 160 (assuming that the first subject and second subject are physiologically compatible—a donor and a recipient should both be either human or animals), the brain activity patterns of the first and second subject will be corresponding.

According to the present technology, the modulation of stimulation, which is, for example, a sensory stimulation, whose waveform is modulated to correspond to the raw or processed brainwave pattern of the first subject (donor) for the brain region associated with the stimulation electrode.

For example, the brain activity pattern of the first subject (donor) is measured by EEG electrodes. In a sleep state, it may assume various wave patterns, over the range<1 Hz to about 25 Hz, which vary in amplitude, frequency, spatial location, and relative phase. For example, the first stage of sleep is initially dominated by alpha brainwaves with a frequency of 8 Hz to 13 Hz. Typically, brain activity pattern measurement from the first subject (donor) has a higher spatial resolution, e.g., 64 or 128 electrode EEGs, than the stimulator for the second subject (recipient), and the stimulus electrodes tend to be larger than the EEG electrode. The stimulus for the second subject (recipient) is therefore processed using a dimensionality (or spatial) reduction algorithm to account for these differences, which will tend to filter the stimulus signal. By applying this stimulus modulated with the brain activity of the first subject (donor), the second subject (recipient) is made susceptible to synchronization with the brain activity pattern of the first subject (donor). For example, by temporally modulating the polarization level of the cells near the electrode, the cells will better couple to excitation stimuli in the brain of the second subject (recipient) having the characteristics of the brain activity pattern of the first subject (donor).

The donor's indigenous brainwaves may be modulated on light, sound, vibrations or any number of other stimuli amenable to frequency modulation. For example, donor's brainwaves may be modulated on ambient light, on binaural beats, or isochronic tones.

The verification that the recipient has achieved the desired sleep state may optionally be done by visual observation, by EEG, EKG, measuring heart and/or respiration rate, body temperature or any number of other physiological parameters that will be well understood by a person skilled in the art. These measurements should be, preferably, done automatically via biosensors.

FIG. 2 shows a flowchart of the second embodiment according to the present invention. A first subject (donor), having a mental state, is interrogated, observed or sensed, to determine or identify of his or her mental state 100. The first subject is typically human, though this is not a limit of the invention (which equally applies to any animal). In this embodiment, the interrogation seeks to identify a characteristic alert/awake pattern, and therefore the mental state of the first subject is monitored until an alert state occurs 111. When the first subject (donor) is awake, brain activity patterns reflecting or characterizing the waking state are captured 120, and stored in a non-volatile memory 130. For example, one may seek to capture the patterns that represent awakening, and therefore, the monitoring commences on a sleeping subject. These stored patterns may be optionally processed, statistically aggregated, analyzed for perturbations or anomalies, filtered, compressed, etc. Stages of awakening may be determined. It is noted that the brain activity patterns change over time during awakening, and therefore, the stored patterns may encompass one or more stages of the waking process.

The stored data from the first subject (donor) is then retrieved from the non-volatile memory 140 and used to "transplant" the state of alertness to prevent sleep, or maintain alertness, in a second subject (a recipient—also typically, but not necessarily, a human) by replicating the awake brain activity patterns of the first subject (donor), or sequences of brain activity patterns, in the second subject (recipient) 170. The replication of brain activity patterns, dependent on the stored patterns, typically seeks to stimulate or induce the brain of the second subject (recipient) by modulating indigenous brainwaves of the donor on a stimulus in a manner synchronized with the frequency, and preferably phase and/or waveform pattern represented in the brain activity patterns of the first subject (donor) in the awake or wakening state. Typically, when the second subject is awake or wakes up, 180, the brain activity patterns of the first and second subject will be corresponding.

FIG. 3 shows a flowchart of a third embodiment, in which the technology is generalized. A first subject (donor), having a mental state, is interrogated, observed or sensed, to determine or identify his or her mental state 190. The mental state of the first subject is monitored until the desired state is achieved 200. When the first subject achieves that state, brain activity patterns reflecting or characterizing the state are captured 210 by, for example, recording EEG or MEG of the first subject, and optionally stored in non-volatile memory. The brain activity pattern is, e.g., brainwaves (e.g., EEG) 210.

The brainwaves are analyzed using statistical data mining techniques such as PCA to determine a set of linearly-uncorrelated variables—principal components. At least one dominant frequency in the recorded brainwaves is identified 220. Optionally, secondary and higher harmonics may be identified as well. It will be well-understood by a person skilled in the art that any number of similar statistical data analysis technics may be used, such as signal processing, independent component analysis, network component analysis, correspondence analysis, multiple correspondence analysis, factor analysis, canonical correlation, functional PCA, independent component analysis, singular spectrum analysis, weighted PCA, sparse PCA, principal geodesic analysis, eigenvector-based multivariate analyses, etc.

The stored data from the first subject is then retrieved, at least the dominant frequency is modulated on at least one stimulus and used to "transplant" the desired mental state of the donor in a second subject (recipient) by seeking to replicate the brain activity patterns of the first subject (donor), or sequences of brain activity patterns, in the second subject (recipient) 240. The second subject (recipient) is then monitored for induction of the desired mental state 250.

FIG. 4 shows a flowchart according to the fourth embodiment, in which an EEG or EMG of a first subject (healthy donor), while in a state of sleep, is recorded 260, optionally processed to remove noise 270, and stored 280. The data may optionally be compressed. The stored data is retrieved 290 and decompressed as necessary. The data is then played back to a second subject (recipient), to improve the quality of sleep 300.

FIG. 5 shows a flowchart according to the fifth embodiment, in which a multichannel EEG/EMG of a first subject (donor) is recorded 310, and processed to remove noise (and/or artifacts) and/or compress the data 320. It is optionally stored in non-volatile memory. PCA analysis is performed on the data to determine characteristic frequencies associated with sleep stages 330. A database is created, storing the recorded EEG/MEG, the associated characteristic frequencies, and corresponding sleep stages, so that a characteristic frequency may be retrieved for any given sleep stage 340. This database can be a relational database or any other type of searchable database as will be readily understood by anyone skilled in the art. According to the sixth embodiment, a multichannel EEG/EMG of a first subject (donor) is recorded 310, and processed to remove noise (and/or artifacts) and/or compress the data 320. It is optionally stored in non-volatile memory. An artificial neural network is trained on this data to determine characteristic frequencies associated with sleep stages 350. A deep neural network, as well as other AI machine-learning tools, may be used as will be readily understood by a person skilled in the art. A database is created, storing the recording of the EEG/MEG, the associated characteristic frequencies, and corresponding sleep stages, so that a characteristic frequency may be retrieved for any given sleep stage 340.

FIG. 6 shows a flowchart according to an embodiment of the invention. A multichannel EEG or EMG of a plurality of healthy sleeping donors is recorded 310. The multichannel EEG/EMG recordings are processed too, e.g., remove noise 320. A neural network is trained on the recorded EEG/EMG recordings to identify characteristic frequencies associated with sleep stages 350. A database of sleep stage characteristic frequencies is created.

FIG. 7 shows a flowchart according to a further embodiment of the present invention illustrating a process in which a first subject (donor) is monitored with respect to phases of his or her circadian rhythm with his or her EEG or EMG recorded 360, processed to remove noise (and/or artifacts), and, optionally, compressed 270, and then stored in a non-volatile memory 280. In this case, the stored signals are tagged with the circadian cycle phase, unless only a single phase is captured, or pattern recognition used to identify the cycle stage. The stored data is then retrieved 290, decompressed 370, and played back to a second subject (recipient) 380, using sensory stimulation, or other stimuli, to induce a desired circadian rhythm state. In this case, the technology may also be used to prolong states in the second subject or hasten the transition from one state to another. It may also be used to treat circadian rhythm disorders, by reinforcing healthy or normal circadian rhythm patterns in a second subject with an otherwise abnormal cycle.

FIG. 8 shows a flowchart according to a further embodiment of the present invention illustrating a process of replicating the desired sleep stage from one subject (donor)

to another subject (recipient). In general, the sleep stage of the source subject is determined in a traditional manner, which may include brain signal analysis, other biometrics, and/or observation. The data may be acquired 400 over one or more sleep cycles, and during or after different types of environmental conditions or stimulation. For example, various types of music may be played, seeking to entrain a conscious or subconscious rhythm. Lights can flash, and various other sensory stimulation may occur. The brain signal readings are synchronized and tagged with the stimulation parameters 410 so that the stimulation is associated with its respective effect. Similarly, before sleep, the subject may be presented with certain experiences, such that during sleep, the memory processing within the brain is dependent on these experiences.

After the various data is acquired from the subject 400, along with information about the pre-sleep experience and or context 410, and sensory stimulation during sleep, a memory, database, statistical model, the rule-based model is generated, and/or neural network is trained, reflecting the subject (donor). Data may be aggregated from a plurality of subjects (donors), but typically, these are processed for the particular subject before aggregation. Based on single or multiple subject data, a normalization process may occur 420. The normalization may be spatial and/or temporal. For example, the EEG electrodes between sessions or for the different subject may be in different locations, leading to a distortion of the multichannel spatial arrangement. Further, the head size and shape of different individuals are different, and this needs to be normalized and/or encoded as well. The size and shape of the head/skull and/or brain may also lead to temporal differences in the signals, such as characteristic time delays, resonant or characteristic frequencies, etc.

One way to account for these effects is through the use of a time-space transform, such as a wavelet-type transform. It is noted that, in a corresponding way that statistical processes are subject to frequency decomposition analysis through Fourier transforms, they are also subject to time-frequency decomposition through wavelet transforms. Typically, the wavelet transform is a discrete wavelet transform (DWT), though more complex and less regular transforms may be employed. As discussed above, PCA and spatial PCA may be used to analyze signals, presuming linearity (linear superposition) and statistical independence of components. However, these presumptions technically do not apply to brainwave data, and practically, one would normally expect interaction between brain wave components (non-independence) and lack of linearity (since "neural networks" by their nature are non-linear), defeating the use of PCA or spatial PCA unmodified. However, a field of nonlinear dimensionality reduction provides various techniques to permit corresponding analyses under the presumptions of non-linearity and non-independence. See, en.wikipedia.org/wiki/Nonlinear_dimensionality_reduction, www.image.ucar.edu/pub/toyIV/monahan_5_16.pdf (An Introduction to Nonlinear Principal Component Analysis, Adam Monahan), Nonlinear PCA toolbox for MATLAB (www.nlpca.org), Nonlinear PCA (www.comp.nus.edu.sg/~cs5240/lecture/nonlinear-pca.pdf), Nonlinear Principal Components Analysis: Introduction and Application (open-access.leidenuniv.nl/bitstream/handle/1887/12386/Chapter2.pdf?sequence=10, 2007), Nonlinear Principal Component Analysis: Neural Network Models and Applications (pdfs.semanticscholar.org/9d31/23542031a227d2f4c4602066cf8ebceaeb7a.pdf), Karl Friston, "Nonlinear PCA: characterizing interactions between modes of brain activity" (www.fil.ion.ucl.ac.uk/~karl/Nonlinear PCA.pdf, 2000), Howard et al., "Distinct Variation Pattern Discovery Using Alternating Nonlinear Principal Component Analysis", IEEE Trans Neural Network Learn Syst. 2018 January; 29 (1): 156-166. doi: 10.1109/TNNLS.2016.2616145. Epub 2016 Oct. 26 (www.ncbi.nlm-.nih.gov/pubmed/27810837); Jolliffe, I. T., "Principal Component Analysis, Second Edition", Springer 2002, cda.psych.uiuc.edu/statistical_learning_course/Jolliffe I. Principal Component Analysis (2ed., Springer, 2002) (518s) _MVsa_.pdf, Stone, James V. "Blind source separation using temporal predictability." Neural computation 13, no. 7 (2001): 1559-1574.; Barros, Allan Kardec, and Andrzej Cichocki. "Extraction of specific signals with temporal structure." Neural computation 13, no. 9 (2001): 1995-2003.; Lee, Soo-Young. "Blind source separation and independent component analysis: A review." Neural Information Processing-Letters and Reviews 6, no. 1 (2005): 1-57.; Hyvärinen, Aapo, and Patrik Hoyer. "Emergence of phase- and shift-invariant features by decomposition of natural images into independent feature subspaces." Neural computation 12, no. 7 (2000): 1705-1720.; Wahlund, Björn, Włodzimierz Klonowski, Pawel Stepien, Robert Stepien, Tatjana von Rosen, and Dietrich von Rosen. "EEG data, fractal dimension and multivariate statistics." Journal of Computer Science and Engineering 3, no. 1 (2010): 10-14.; Yu, Xianchuan, Dan Hu, and Jindong Xu. Blind source separation: theory and applications. John Wiley & Sons, 2013.; Parida, Shantipriya, Satchidananda Dehuri, and Sung-Bae Cho. "Machine Learning Approaches for Cognitive State Classification and Brain Activity Prediction: A Survey." Current Bioinformatics 10, no. 4 (2015): 344-359.; Friston, Karl J., Andrew P. Holmes, Keith J. Worsley, J-P. Poline, Chris D. Frith, and Richard S J Frackowiak. "Statistical parametric maps in functional imaging: a general linear approach." Human brain mapping 2, no. 4 (1994): 189-210.; Wang, Yan, Matthew T. Sutherland, Lori L. Sanfratello, and Akaysha C. Tang. "Single-trial classification of ERPS using second-order blind identification (SOBI)." In Machine Learning and Cybernetics, 2004. Proceedings of 2004 International Conference on, vol. 7, pp. 4246-4251. IEEE, 2004.; Jutten, Christian, and Massoud Babaie-Zadeh. "Source separation: Principles, current advances and applications." IAR Annu Meet Nancy Fr 110 (2006).; Saproo, Sameer, Victor Shih, David C. Jangraw, and Paul Sajda. "Neural mechanisms underlying catastrophic failure in human-machine interaction during aerial navigation." Journal of neural engineering 13, no. 6 (2016): 066005.; Valente, Giancarlo. "Separazione cieca di sorgenti in ambienti reali: nuovi algoritmi, applicazioni e implementazioni." (2006).; SAPIENZA, LA. "Blind Source Separation in real-world environments: new algorithms, applications and implementations Separazione cieca di sorgenti in ambienti reali: nuovi algoritmi, applicazioni e."; Ewald, Arne. "Novel multivariate data analysis techniques to determine functionally connected networks within the brain from EEG or MEG data." (2014).; Friston, Karl J. "Basic concepts and overview." SPMcourse, Short course; Crainiceanu, Ciprian M., Ana-Maria Staicu, Shubankar Ray, and Naresh Punjabi. "Statistical inference on the difference in the means of two correlated functional processes: an application to sleep EEG power spectra." Johns Hopkins University, Dept. of Biostatistics Working Papers (2011): 225.; Konar, Amit, and Aruna Chakraborty. Emotion recognition: A pattern analysis approach. John Wiley & Sons, 2014.; Kohl, Florian. "Blind separation of dependent source signals for MEG sensory stimulation experiments." (2013).; Onken, Arno, Jian K. Liu, PP Chamanthi R. Karunasekara, loannis Delis, Tim Gollisch, and Stefano Panzeri. "Using matrix and tensor factorizations for the single-trial analysis of population spike trains." PLOS computational biology 12, no. 11 (2016): e1005189.; Tressoldi, Patrizio, Luciano Pederzoli, Marco Bilucaglia, Patrizio Caini, Pasquale Fedele, Alessandro Ferrini, Simone Melloni, Diana Richeldi, Florentina Richeldi, and Agostino Accardo. "Brain-to-Brain (Mind-to-Mind) Interaction at Distance: A Confirmatory Study." (2014). f1000researchdata. s3.amazonaws.com/manuscripts/5914/5adbf847-787a-4fc1-ac04-2e1cd61ca972_4336_-patrizio_tressoldi_v3.pdf?doi=10.12688/f1000research.4336.3; Tsiaparas, Nikolaos N. "Wavelet analysis in coherence estimation of electroencephalographic signals in children for the detection of dyslexia-related abnormalities." PhD diss., 2006.

FIG. 9 shows a flowchart of an embodiment of the invention. A sleep stage of a first subject is identified, and then it is determined whether the sleep stage is the desired sleep stage. If not, the first subject is further monitored. If the sleep stage is the one desired, the brain activity of the first subject is captured, reflecting the sleep stage, and the brain activity patterns of the first subject while in the desired sleep stage stored in non-volatile memory 500. The stored brain activity patterns are subsequently retrieved and used to induce the sleep stage in a second subject by replicating the brain activity patterns of the first subject in the second subject by appropriate stimulation of the second subject. The second subject may be monitored to verify that the second subject is in the desired sleep stage.

As shown in FIG. 10, a human brain state or mental state in a subject is modified or altered. In some implementations, a current brainwave pattern of the subject, a phase of a characteristic wave of the current brainwave pattern of the subject, a characteristic timing of a stimulus-response dependent on the mental state, or temporal relationships in monitored neurological or motor patterns of the subject is determined. The desired change in the current brain wave pattern of the subject is determined or defined. A stimulus is applied, e.g., electrical, magnetic, acoustic or ultrasound, sensory, etc., which can be for determining the current state, changing the state, or both. For example, a characteristic timing of a stimulus-response dependent on the mental state may be extracted, or temporal relationships in monitored neurological or motor patterns of the subject determined. The stimulus may be asynchronous, or time-synchronized with respect to the phase state, or dependent on at least the determined temporal relationships. In a closed-loop excitation, the brain wave pattern of the subject after at least one stimulus is monitored or the response parameters, e.g., characteristic timing measured or assessed. The stimulus may be controlled dependent on the observed or monitored changes, indicative of an effective alteration or modification of the brain state or mental state in the subject. FIG. 10 thus shows a flowchart of an embodiment of the invention. A desired mental state is identified 540. The mental state of a subject identified 550, and a phase of a dominant brainwave, characteristic of the mental state of the subject identified 560. A stimulus is applied to the subject to change the mental state of the subject to the desired mental state, while synchronizing the phase of the stimulus with the phase of the dominant brainwave of the subject 570. The subject is monitored to determine if the desired mental state is achieved. If the desired mental state is sleep, the sleep state of the subject may be verified 580.

Figure 11:
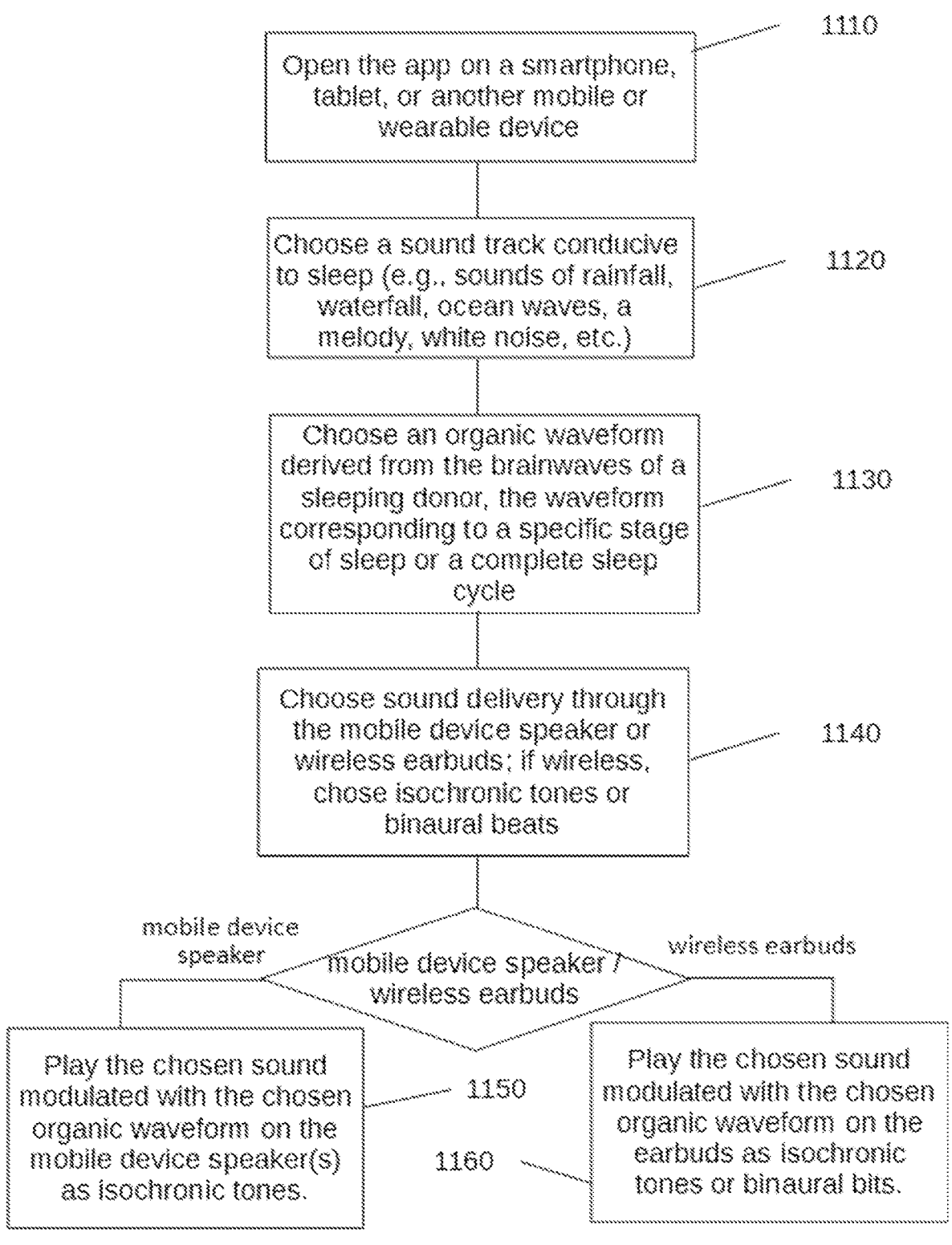
FIG. 11 shows a flowchart according to an embodiment of the invention.

FIG. 11 shows a flowchart of a further embodiment of the invention. An app is opened on a smartphone, tablet or another mobile or wearable device 1110. Note that in some applications, the device need not be mobile, and for example may be part of a headboard, nightstand, clock radio, etc. A soundtrack conducive to sleep, e.g., sounds of rainfall, waterfall, ocean waves, a melody, white noise, pink noise, etc., is chosen 1120. An organic waveform is chosen, derived from brainwaves of a sleeping donor, corresponding to a specific stage of a sleep cycle or a complete sleep cycle 1130. The sound delivery may be chosen to be through a mobile device speaker, earphones, wireless earbuds. If separate sound delivery to each ear, the sound may be isochronic tones or binaural beats 1140, while if not isolated, isochronic tones may be played 1160.

FIG. 12 shows a flowchart of a still further embodiment of the invention. An app may be opened on a smartphone, tablet or wearable device 110. Light settings, such as color and intensity, are chosen 1220. An organic waveform derived from brainwaves of a sleeping donor, corresponding to a specific stage or stages of sleep, or a complete sleep cycle is chosen 1230. Light delivery may be chosen through an ambient light source or e.g., LEDs positioned on a wearable eye mask 1240, which is wirelessly connected to the device. Sleep stimulation is turned on by projecting the light modulated with the chosen organic waveform through ambient light or LEDs positioned near the eyes 1250.

FIG. 13 shows a flowchart of an embodiment of the invention. The subject opens an app on a device 1310, and chooses light and sound settings, e.g., color, intensity, sound, volume, etc. 1320. An organic waveform derived from the brainwaves of a sleeping donor is chosen, e.g., automatically by the app, corresponding to a specific stage(s) of sleep or a complete sleep cycle 1330. The stimulus is chosen as light or sound delivery through the device or wirelessly 1340. Sleep stimulation is turned using synchronized light and sound modulated with the chosen organic waveform 1350.

FIG. 14 shows a flowchart of an embodiment of the invention. The subject opens an app on e.g., a mobile or wearable device 1410, and chooses light and/or sound settings, e.g., color, intensity, sound, volume, etc. 1420. An organic waveform derived from the brainwaves of a sleeping donor is chosen, e.g., automatically by the app, corresponding to a specific stage(s) of sleep or a complete sleep cycle 1430. The stimulus is chosen as light and/or sound delivery through the device or wirelessly 1440. Sleep stimulation is turned using synchronized light and/or sound modulated with the chosen organic waveform 1450. EEG and/or other biometric data is recorded from the subject and transmitted in real time to the device or a cloud computing resource for analysis 1460. The stimulation of the subject is adjusted based on the data received from the subject 1470.

FIG. 15 shows a flowchart of an embodiment of the invention. The subject opens an app on, e.g., a mobile or wearable device and logs in to a personal account 1510. A new waveform, modified from the last waveform used based on biometric sleep data received from the subject during a previous stimulation session 1520. Light and/or sound delivery through the device or through a wireless peripheral is chosen 1540. Sleep stimulation is turned using synchronized light and/or sound modulated with the chosen organic waveform 1550. EEG and/or other biometric data is recorded from the subject and transmitted to a remote for analysis 1560. The received biometric data from the subject is analyzed, to measure the effectiveness of the stimulation and to adjust the waveform accordingly, to improve the effect of the stimulation 1570.

Therefore, statistical approaches are available for separating EEG signals from other signals, and for analyzing components of EEG signals themselves. According to the present invention, various components that might be considered noise in other contexts, e.g., according to prior technologies, such as a modulation pattern of a brainwave, are preserved. Likewise, interactions and characteristic delays between significant brainwave events are preserved. This information may be stored either integrated with the brainwave pattern in which it occurs or as a separated modulation pattern that can then be recombined with an unmodulated brainwave pattern to approximate the original subject.

According to the present technology, lossy "perceptual" encoding (i.e., functionally optimized with respect to a subjective response) of the brainwaves may be employed to process, store, and communicate the brainwave information. In a testing scenario, the "perceptual" features may be tested, so that important information is preserved over information that does not strongly correspond to the effective signal. Thus, while one might not know a priori which components represent useful information, a genetic algorithm may empirically determine which features or data reduction algorithms or parameter sets optimize retention of useful information vs. information efficiency. It is noted that subjects may differ in their response to signal components, and therefore the "perceptual" encoding may be subjective with respect to the recipient. On the other hand, different donors may have different information patterns, and therefore, each donor may also require individual processing. As a result, pairs of donor and recipient may require optimization, to ensure accurate and efficient communication of the relevant information. According to the present invention, sleep/wake mental states and their corresponding patterns are sought to be transferred. In the recipient, these patterns have characteristic brainwave patterns. Thus, the donor may be used, under a variety of alternate processing schemes, to stimulate the recipient, and the sleep/wake response of the recipient determined based on objective criteria, such as resulting brainwave patterns or expert observer reports, or subjective criteria, such as recipient self-reporting, survey or feedback. Thus, after a training period, optimized processing of the donor, which may include filtering, dominant frequency resynthesis, feature extraction, etc., may be employed, which is optimized for both donor and recipient. In other cases, the donor characteristics may be sufficiently normalized, that only recipient characteristics need be compensated. In a trivial case, there is only one exemplar donor, and the signal is oversampled and losslessly recorded, leaving only recipient variation as a significant factor.

Because dominant frequencies tend to have low information content (as compared to the modulation of these frequencies and interrelation of various sources within the brain), one efficient way to encode the main frequencies is by location, frequency, phase, and amplitude. The modulation of a wave may also be represented as a set of parameters. By decomposing the brainwaves according to functional attributes, it becomes possible, during stimulation, to modify the sequence of "events" from the donor, so that the recipient need not experience the same events, in the same order, and in the same duration, as the donor. Rather, a high-level control may select states, dwell times, and transitions between states, based on classified patterns of the donor brainwaves. The extraction and analysis of the brainwaves of the donors, and response of the recipient, may be performed using statistical processes, such as principal components analysis (PCA), independent component analysis (ICA), and related techniques; clustering, classification, dimensionality reduction and related techniques; neural networks and other known technologies. These algorithms may be implemented on general purpose CPUs, array processors such as GPUs, and other technologies.

In practice, a brainwave pattern of the first subject may be analyzed by a PCA technique that respects the non-linearity and non-independence of the brainwave signals, to extract the major cyclic components, their respective modulation patterns, and their respective interrelation. The major cyclic components may be resynthesized by a waveform synthesizer, and thus may be efficiently coded. Further, a waveform synthesizer may modify frequencies or relationships of components from the donor based on normalization and recipient characteristic parameters. For example, the brain of the second subject (recipient) may have characteristic classified brainwave frequencies 3% lower than the donor (or each type of wave may be separately parameterized), and therefore the resynthesis may take this difference into account. The modulation patterns and interrelations may then be reimposed onto the resynthesized patterns. The normalization of the modulation patterns and interrelations may be distinct from the underlying major cyclic components, and this correction may also be made, and the normalized modulation patterns and interrelations included in the resynthesis. If the temporal modifications are not equal, the modulation patterns and interrelations may be decimated or interpolated to provide a correct continuous time sequence of the stimulator. The stimulator may include one or more stimulation channels, which may be implemented as electrical, magnetic, auditory, visual, tactile, or another stimulus, and/or combinations.

The stimulator is preferably feedback controlled. The feedback may relate to the brainwave pattern of the recipient, and/or context or ancillary biometric basis. For example, if the second subject (recipient) begins to awaken from sleep, which differs from the first subject (donor) sleep pattern, then the stimulator may resynchronize based on this finding. That is, the stimulator control will enter a mode corresponding to the actual state of the recipient, and seek to guide the recipient to the desired state from a current state, using the available range and set of stimulation parameters. The feedback may also be used to tune the stimulator, to minimize error from a predicted or desired state of the recipient subject based on the prior and current stimulation.

The control for the stimulator is preferably adaptive and may employ a genetic algorithm to improve performance over time. For example, if there are multiple first subjects (donors), the second subject (recipient) may be matched with those donors from whose brainwave signals (or algorithmically modified versions thereof) the predicted response in the recipient is best, and distinguished from those donors from whose brainwave signals the predicted response in the recipient subject poorly corresponds. Similarly, if the donors have brainwave patterns determined over a range of time and context and stored in a database, the selection of alternates from the database may be optimized to ensure best correspondence of the recipient subject to the desired response.

It is noted that a resynthesizer-based stimulator is not required, if a signal pattern from a donor is available that properly corresponds to the recipient and permits a sufficiently low error between the desired response and the actual response. For example, if a donor and a recipient are the same subject at different times, a large database may be unnecessary, and the stimulation signal may be a minimally processed recording of the same subject at an earlier time. Likewise, in some cases, a deviation is tolerable, and an exemplar signal may be emitted, with relatively slow periodic correction. For example, a sleep signal may be derived from a single subject and replayed with a periodicity of 90 minutes or 180 minutes, such as a light or sound signal, which may be useful in a dormitory setting, where individual feedback is unavailable or unhelpful.

In some cases, it is useful to provide a stimulator and feedback-based controller on the donor. This will better match the conditions of the donor and recipient, and further allow determination of not only the brainwave pattern of the donor but also responsivity of the donor to the feedback. One difference between the donors and the recipients is that in the donor, the natural sleep pattern is sought to be maintained and not interrupted. Thus, the adaptive multi-subject database may include data records from all subject, whether selected ab initio as a useful exemplar or not. Therefore, the issue is whether a predictable and useful response can be induced in the recipient from the database record and, if so, that record may be employed. If the record would produce an unpredictable result or a non-useful result, the use of that record should be avoided. The predictability and usefulness of the responses may be determined by a genetic algorithm or other parameter-space searching technology.

Extending the sleep signal illumination example, an illuminator (e.g., red LED lightbulb) may have an intensity modulated based on a donors' brainwave pattern. The illuminator may have a flash memory module with tens or hundreds of different brainwave patterns available. The illuminator may further include a sensor, such as a camera or non-imaging optical or infrared sensor, and speech control, similar to Amazon Alexa. The illuminator may also include an associated speaker, to play synchronized sounds or music. When a sleep cycle is commenced, the illuminator begins displaying (and playing and associated audio) the brainwave pattern as a program, seeking to induce a predetermined sleep pattern. The sensors may be used to determine whether the recipient is in the predicted sleep state based on the program. If the recipient has a sleep state that deviates from the program, then the program may be reset to a portion that corresponds to the actual state of the recipient or reset to a guiding state that seeks to guide the sleep state of the recipient back to the desired program. If the target subject cannot be efficiently synchronized or guided, then the illuminator may adopt a different source subject brainwave pattern. In this case, no electrical stimulation or electrical feedback is employed, and the entire operation may be non-contact.

Figures 16, 17:
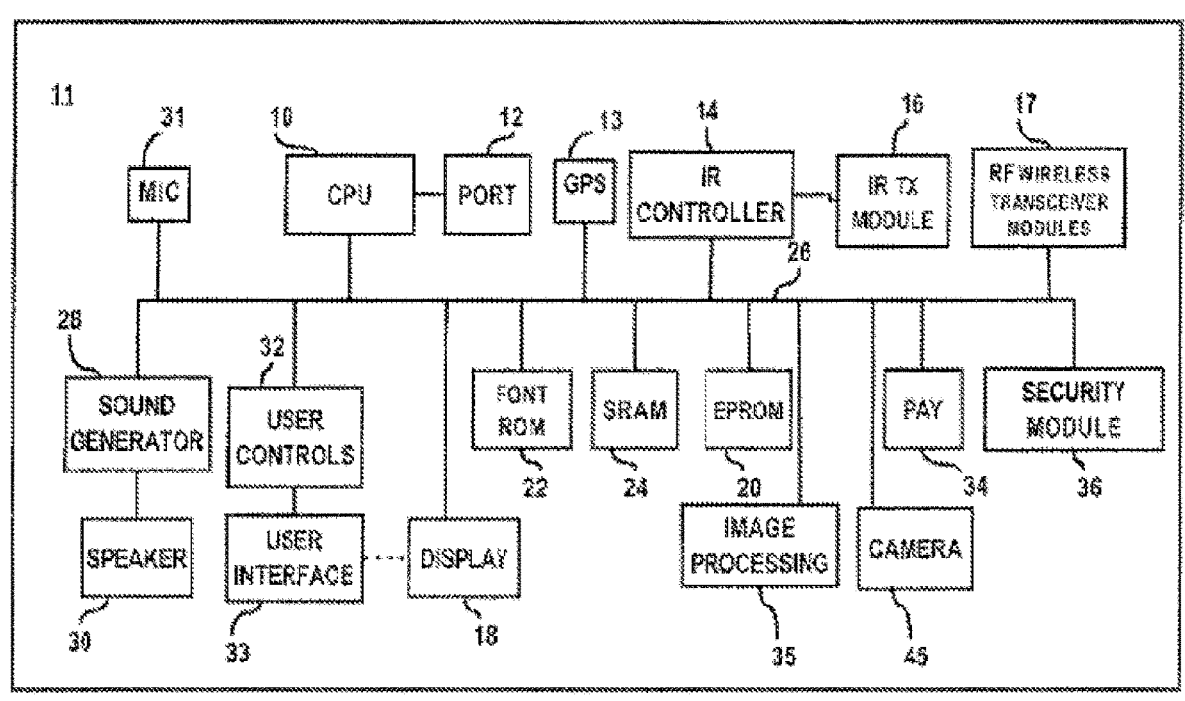
FIG. 16 shows a schematic representation of a smartphone for executing apps.
FIG. 17 shows a hypnogram of a healthy adult.

FIG. 16 shows a representation of a mobile device 11. The mobile device is shown in a familiar "smartphone" form factor. Data can be transferred to and from the mobile device 11 via wireless data communications. In general, the mobile device 11 can include a touch-sensitive display screen 18, a speaker 30, a microphone 31, and one or more control buttons 32 for controlling some operations of device 11. The device 11 depicted in FIG. 1(a) can be a device, such as, for example, a smartphone capable of communicating with a wireless local area network, and so forth. In this respect, the mobile device 11 can be implemented with touch screen capabilities associated with the display screen 18. Display screen 18 can be configured to display data including video and text and icons 33 operable as soft buttons providing options and action by the mobile device 11 when selected by a user. The mobile device 11 can be capable of carrying out a variety of functionalities. For example, microprocessor shown as CPU 10 of the mobile device 11 can function as the main controller operating under the control of operating clocks supplied from a clock oscillator. CPU 10 can be configured as, for example, a microprocessor. Such a microprocessor can be configured to facilitate the operations of and communicate by the electronic wireless hand-held multimedia device 11. External pins of CPU 10 can be coupled to an internal bus 26 so that it can be interconnected to respective components. The mobile device 11 can also be configured to include memories such as, for example, SRAM 24 which can be provided as a writeable memory that does not require a refresh operation and can be generally utilized as a working area of CPU 10, SRAM (Static RAM) is generally a form of semiconductor memory (RAM) based on a logic circuit known as a flip-flop, which retains information as long as there is enough power to run the device. Font ROM 22 can be configured as a read only memory for storing character images (e.g., icons and font) displayable on a display 18, which can be implemented as, for example, a touch-sensitive display screen. Example types of displays that can be utilized in accordance with display 18 include, for example, a TFT active matrix display, an illuminated LCD (Liquid Crystal Display), or other small-scaled displays being developed or available in the art in compact form. CPU 10 can be utilized to drive display 18 utilizing, among other media, font images from Font ROM 22 and images transmitted as data through wireless unit 17 and processed by image-processing unit 35. EPROM 20 can be configured as a read-only memory that is generally erasable under certain conditions and can be utilized for permanently storing control codes for operating respective hardware components and security data, such as a serial number. A camera capable of capturing video and pictures can be provided and can also work in conjunction with the image processing unit 35.

IR controller 14, when provided, can be generally configured as a dedicated controller for processing infrared codes transmitted/received by an IR transceiver module 16 and for capturing the same as computer data. Wireless unit 17 can be generally configured as a dedicated controller and transceiver module for processing all wireless data transmitted from and to a wireless communications network. It can be appreciated that other variations for wireless transceiver module 17 can also be provided, such as standardized Bluetooth, NFC, Zigbee, etc., and proprietary RF protocols that may be developed for specialized applications.

Port 12 can be connected to CPU 10 and can be temporarily attached, for example, to a docking station to transmit information to and from the mobile device 11 to other devices, such as personal computers. In light of the present invention, port 12 can also be connected to external probes and external sensors for monitoring or providing data. Port 12 can also be configured, for example to link with a battery charger, data communication device, and can permit network devices, a personal computer, or other computing devices to communicate with mobile device 11.

User controls 32 can permit a user to enter data to mobile device 11 and/or initiate particular processing operations via CPU 10. A user interface 33 can be linked to user controls 32 to permit a user to access and manipulate electronic wireless hand held multimedia device 11 for a particular purpose, such as, for example, viewing video images on display 18. User interface 33 can be implemented as a touch screen manipulated user interface, as indicated by the dashed lines linking display 18 with user interface 33. User interface 33 can be configured to accept user input into the mobile device 11. In addition, CPU 10 can cause a sound generator 28 to generate sounds of predetermined frequencies from a speaker 30. Speaker 30 can be utilized to produce music and other audio information associated with video data transmitted to mobile device 11 from an outside source.

A GPS (Global Positioning System) module 13 can be included in the mobile device and can be connected to bus 26. GPS module 13 can be configured to provide location information for the mobile device 11 and can operate with mapping software and resources to provide navigable directions on the display screen 18 to the user, which can be referred to as GPS mapping. The CPU 10 can execute "apps", which are downloadable programs that provide a user interface, and access to various application programming interface (API) calls made available through the operating system, but are generally limited to executing in a low privilege mode and without direct hardware or driver level access. The aps may be downloaded from the Internet, or an on-line service (e.g., iTunes store, Google Play) or through a wireless transceiver.

FIG. 17 shows a hypnogram of a healthy adult. As shown, the sleep cycle progresses non-monotonically through a series of stages.

Figure 18:
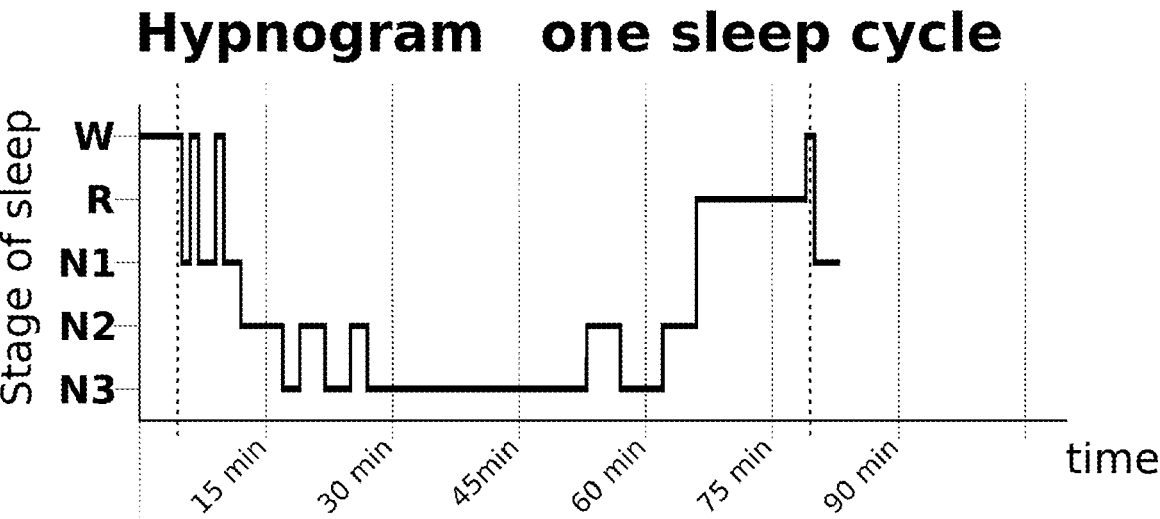
FIG. 18 shows a hypnogram of a healthy adult.

FIG. 18 shows a hypnogram of a healthy adult. As shown, one sleep cycle lasting approximately 90 min is comprised of several sleep stages, including REM sleep (R), first non-REM stage (N1), second non-REM stage (N2), and third non-REM stage (N3), also known as slow-wave sleep, having different duration and periodicity. The waking stage is indicated on the hypnogram as W.

Figure 19:
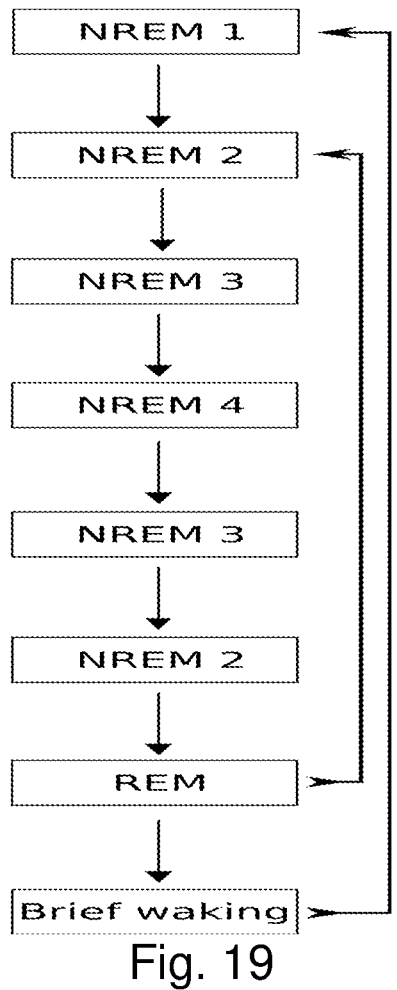
FIG. 19 shows a sequence of sleep stages in a healthy adult.

FIG. 19 shows a flowchart indicating the sequence of sleep stages.

Figures 20A, 20B, 20C, 21A:
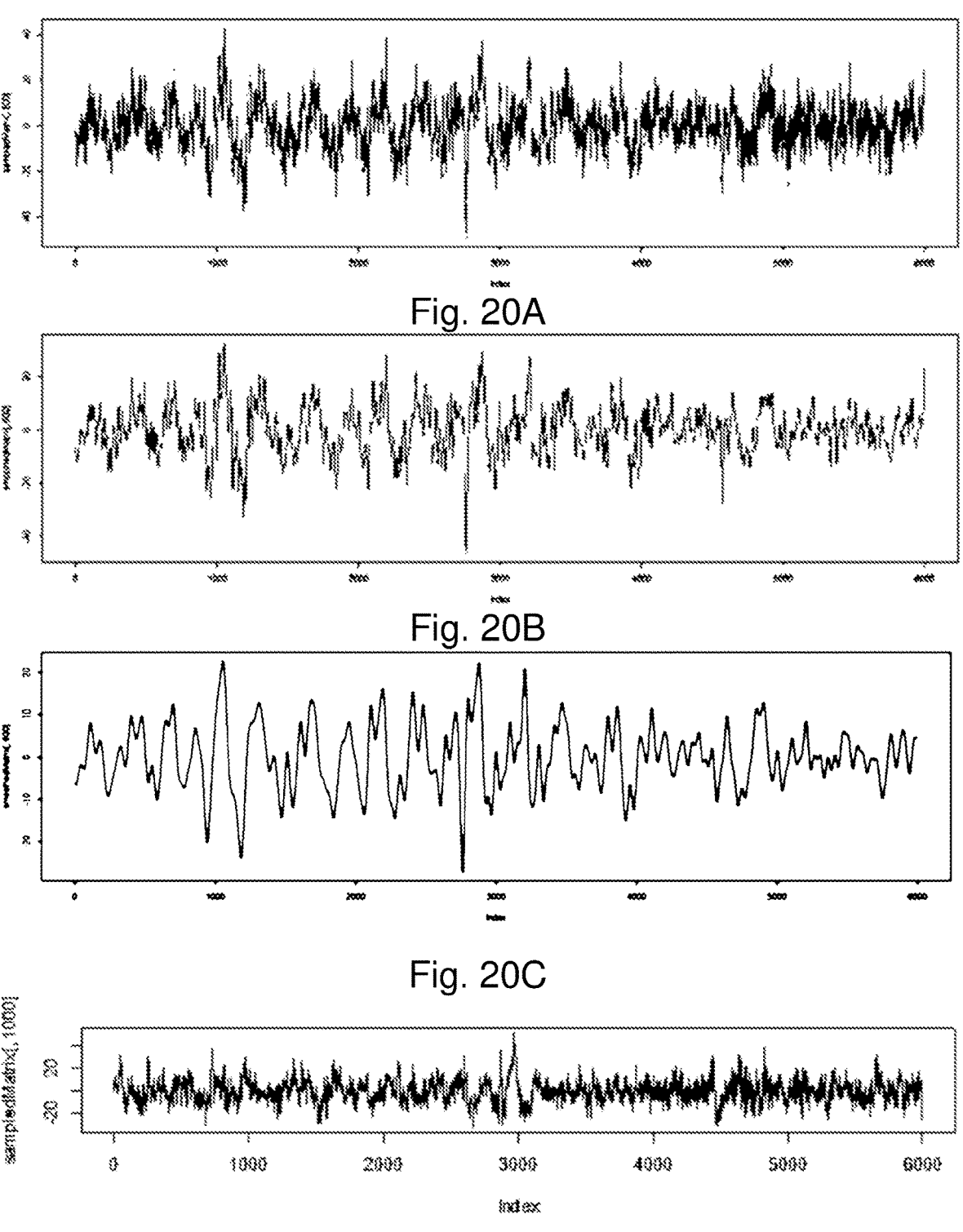
FIG. 20A shows an original EEG recording of a REM phase in a 34 years old female.
FIG. 20B shows an EEG recording of a REM phase in a 34 years old female reconstructed with 64 SSA groups.
FIG. 20C shows an EEG recording of a REM phase in a 34 years old female reconstructed with 16 SSA groups.
FIGS. 21A and 21B show an EEG for a 30 years old female in sleep stage R.

FIGS. 20A-20C show a sample of the REM stage of sleep in a 34 year-old female under different filtering. This sample is obtained from the database of Sleep EEG recordings described in B Kemp, AH Zwinderman, B Tuk, HAC Kamphuisen, JJL Oberye. Analysis of a sleep-dependent neuronal feedback loop: the slow-wave microcontinuity of the EEG. IEEE-BME 47 (9): 1185-1194 (2000) has been used. For each sleep/wake state of each subjects, 12 60-seconds samples have been obtained (totaling up to 72 samples per subject, totaling 4898 samples). Only one channel (Fpz-Cz) haa been considered. The samples have been cleaned from noise/non-stationary component using singular spectrum analysis, see Singular Spectrum Analysis with R. Springer. 2018 Authors: Golyandina, Nina, Korobeynikov, Anton, Zhigljavsky, Anatoly, generally following approach of Neurosci Methods. 2016 Nov. 1; 273:96-106. doi: 10.1016/j.jneumeth.2016.08.008. Epub 2016 Aug. 12; Improving time-frequency domain sleep EEG classification via singular spectrum analysis. Mahvash Mohammadi, Kouchaki, Ghavami, Sanei. Data analysis showed that the use of just 16 SSA components is sufficient to preserve waveform spectrum of the EEG recordings, whereas 64 SSA components is enough to very precisely match the shape as well. Restoration with the use of 64 components has been used to generate "filtered" EEG samples.

FIG. 20A shows the original, FIG. 20B shows sample reconstructed with 64 SSA groups, and FIG. 20C shows the sample reconstructed with 16 SSA groups, for a sample of REM phase of 34-year female.

Figures 21B, 22, 23A, 23B, 24A:
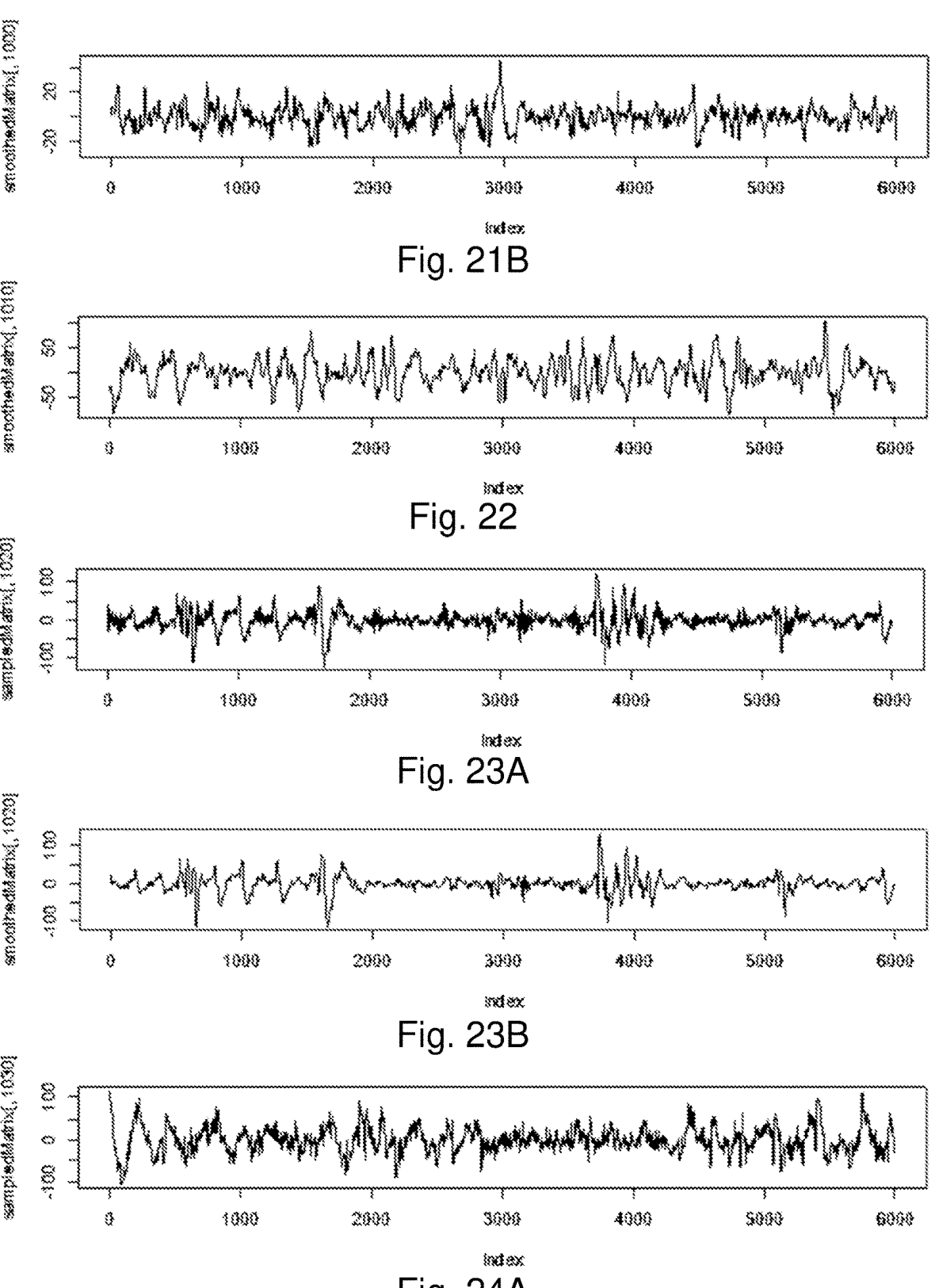
FIG. 22 show an EEG for a 30 years old female in sleep stage 3.
FIGS. 23A and 23B show an EEG for a 30 years old female in sleep stage 3.
FIGS. 24A and 24B show an EEG for a 25 years old female in sleep stage W.

FIGS. 21A and 21B show an EEG for a 30 years old female in sleep stage R.

FIG. 22 show an EEG for a 30 years old female in sleep stage 3.

FIGS. 23A and 23B show an EEG for a 30 years old female in sleep stage 3.

Figures 24B, 25A, 25B, 26A, 26B:
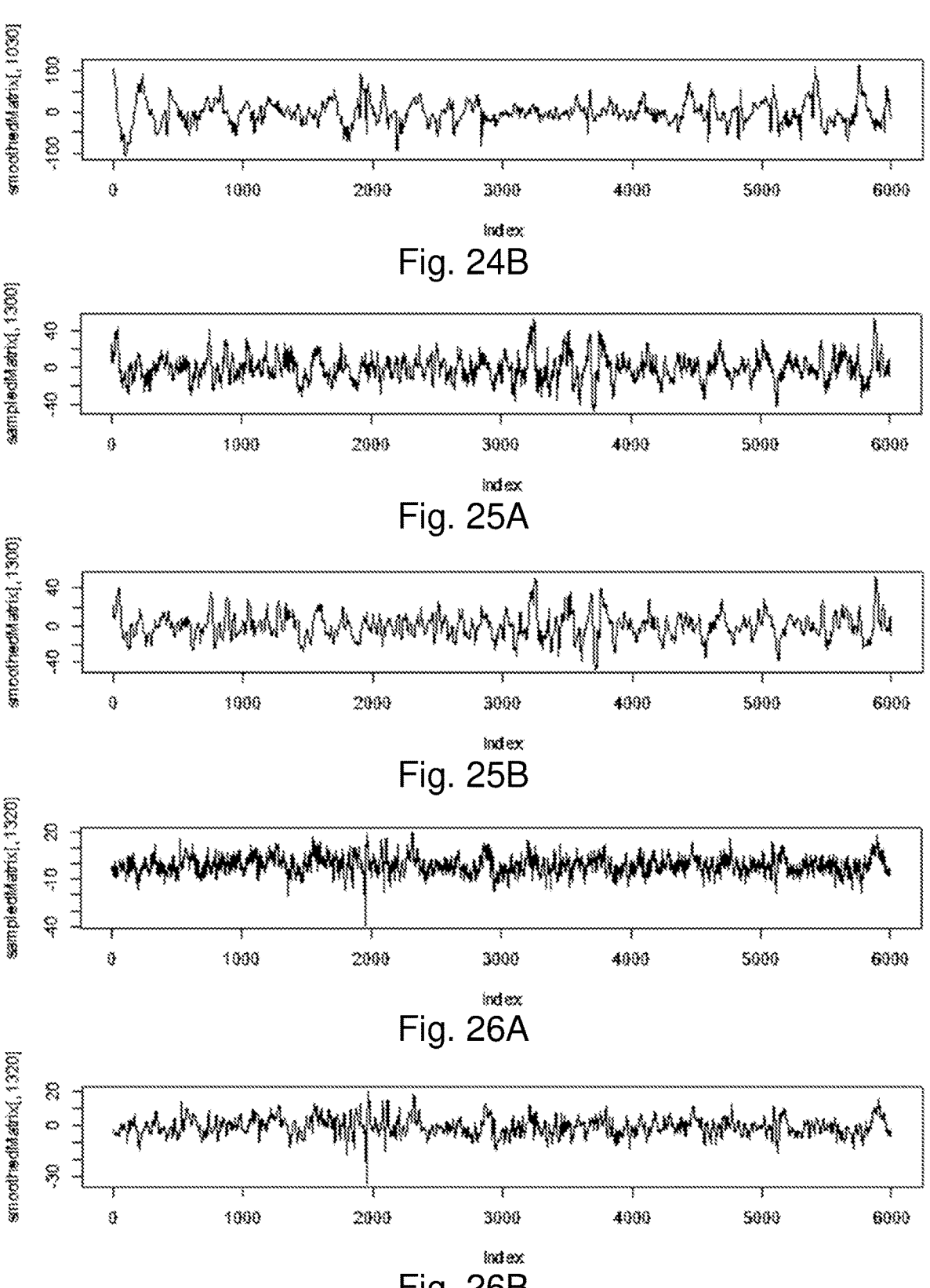
FIGS. 25A and 25B show an EEG for a 25 years old male in sleep stage 2.
FIGS. 26A and 26B show an EEG for a 25 years old male in sleep stage 1.

FIGS. 24A and 24B show an EEG for a 25 years old female in sleep stage W.

FIGS. 25A and 25B show an EEG for a 25 years old male in sleep stage 2.

FIGS. 26A and 26B show an EEG for a 25 years old male in sleep stage 1.

FIGS. 27A and 27B show an EEG for a 25 years old male in sleep stage W.

See Reference List 19

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

Other devices, apparatus, systems, methods, features, and advantages of the invention will be or will become apparent to one with skill in the art upon examination of the following figures and detailed description. It is intended that all such additional systems, methods, features, and advantages be included within this description, be within the scope of the invention, and be protected by the accompanying claims.

In this description, several preferred embodiments were discussed. Persons skilled in the art will, undoubtedly, have other ideas as to how the systems and methods described herein may be used. It is understood that this broad invention is not limited to the embodiments discussed herein. Rather, the invention is limited only by the following claims.

The aspects of the invention are intended to be separable and may be implemented in combination, sub-combination, and with various permutations of embodiments. Therefore, the various disclosure herein, including that which is represented by acknowledged prior art, may be combined, sub-combined and permuted in accordance with the teachings hereof, without departing from the spirit and scope of the invention. All references and information sources cited herein are expressly incorporated herein by reference in their entirety. The reference lists referred to hereinabove are provided in Table 1.

TABLE 1

Reference List 1
U.S. Pat. Nos. and Pub. application Nos. 5,474,082; 5,692,517; 5,813,993; 5,840,040; 6,171,239; 6,349,231; 6,539,263; 7,035,685; 7,120,486; 7,162,295; 7,392,079; 7,449,290; 7,460,903; 7,539,543; 7,546,158; 7,555,344; 7,580,742; 7,676,263; 7,706,871; 7,835,787; 7,865,235; 7,865,244; 7,890,176; 7,894,903; 7,945,316; 8,005,766; 8,027,730; 8,036,736; 8,041,418; 8,041,419; 8,068,911; 8,069,125; 8,108,038; 8,108,046; 8,112,148; 8,112,153; 8,150,523; 8,150,796; 8,155,736; 8,170,637; 8,177,732; 8,190,249; 8,195,593; 8,209,009; 8,209,019; 8,214,035; 8,271,075; 8,271,411; 8,280,515; 8,290,563; 8,298,140; 8,301,218; 8,356,004; 8,391,966; 8,463,371; 8,483,816; 8,485,979; 8,498,708; 8,527,035; 8,532,756; 8,543,199; 8,545,420; 8,552,860; 8,615,479; 8,688,208; 8,690,748; 8,725,264; 8,725,669; 8,731,650; 8,744,562; 8,753,296; 8,761,868; 8,766,819; 8,788,030; 8,805,489; 8,805,516; 8,816,861; 8,827,912; 8,843,202; 8,849,368; 8,849,727; 8,862,217; 8,862,219; 8,862,581; 8,868,039; 8,914,100; 8,923,958; 8,938,289; 9,025,800; 9,037,224; 9,084,549; 9,095,266; 9,095,713; 9,125,788; 9,131,864; 9,149,719; 9,179,854; 9,191,764; 9,210,517; 9,211,077; 9,211,078; 9,248,288; 9,326,720; 9,327,069; 9,339,495; 9,352,145; 9,357,938; 9,357,941; 9,367,131; 9,367,288; 9,389,685; 9,405,366; 9,414,776; 9,418,368; 9,439,593; 9,445,730;

TABLE 1-continued 9,445,739; 9,446,028; 9,451,883; 9,462,433; 9,468,541; 9,480,845;
9,486,332; 9,495,684; 9,503,772; 9,507,974; 9,511,877; 9,531,708;
9,532,748; 9,538,934; 9,554,484; 9,557,957; 9,563,273; 9,592,383;
9,665,824; 9,672,760; 9,694,155; 9,704,205; 9,717,440; 9,763,613;
9,764,109; 9,775,554; 9,805,381; 9,814,426; 9,824,607; 9,854,987;
9,858,540; 9,864,431; 9,867,546; 9,883,396; 9,886,493; 9,886,729;
9,892,435; 9,895,077; 9,905,239; 9,911,165; 9,927,872; 9,943,698;
9,946,344; 9,955,902; 9,955,905; 9,968,297; 9,983,670; 9,996,154;
9,996,983; 10,039,682; 10,042,993; 10,052,066; 10,080,506; 10,111,603;
10,113,913; 10,120,413; 10,126,816; 10,136,856; 10,165,949; 10,166,091;
10,182,736; 10,192,173; 10,195,455; 10,198,505; 10,203,751; 10,212,593;
10,223,633; 10,234,942; 10,258,291; 10,258,798; 10,261,947; 10,265,527;
10,271,087; 10,275,027; 10,303,258; 10,303,971; 10,314,508; 10,319,471;
20020077534; 20030097159; 20030139683; 20050017870;
20050043774; 20050085744; 20050131311; 20050137493;
20050216071; 20050228451; 20050240253; 20050283053;
20060064140; 20060135877; 20060135881; 20060136006;
20060161218; 20060178709; 20060195144; 20060206165;
20060217781; 20060224067; 20060241718; 20060247728;
20070038264; 20070043401; 20070179558; 20070185697;
20070238939; 20070239054; 20070239060; 20070239230;
20070250119; 20070260147; 20070260286; 20070260289;
20070265536; 20070265677; 20080009772; 20080021341;
20080027346; 20080027347; 20080027348; 20080027515;
20080033490; 20080033502; 20080039904; 20080097235;
20080183314; 20080208072; 20080228239; 20080234598;
20080235164; 20090216288; 20090221928; 20090265298;
20090270944; 20090306741; 20090312808; 20090312817;
20090319001; 20090326404; 20090326604; 20100004500;
20100030287; 20100042011; 20100069739; 20100069993;
20100094154; 20100125219; 20100228695; 20100241449;
20100268057; 20100268108; 20100274577; 20100274578;
20100280338; 20100280403; 20100293002; 20100305962;
20100305963; 20100312579; 20110028827; 20110035231;
20110046491; 20110087082; 20110105913; 20110144522;
20110166430; 20110238685; 20110251511; 20110270095;
20110289030; 20110298706; 20110307030; 20110307079;
20110319785; 20120021394; 20120059273; 20120078820;
20120100514; 20120101402; 20120108997; 20120112909;
20120150545; 20120177233; 20120191000; 20120203079;
20120203725; 20120221075; 20120226185; 20120245474;
20120296569; 20120330869; 20130023951; 20130035734;
20130096394; 20130127708; 20130130799; 20130138011;
20130184558; 20130211238; 20130279726; 20130289385;
20140012111; 20140018694; 20140032466; 20140058189;
20140058528; 20140106710; 20140107464; 20140114165;
20140188311; 20140194758; 20140228701; 20140257047;
20140288667; 20140303511; 20140316230; 20140330404;
20150038812; 20150071600; 20150073294; 20150091791;
20140333529; 20140335489; 20140347265; 20140369557;
20150142082; 20150174362; 20150182753; 20150196800;
20150105111; 20150105837; 20150126892; 20150141773;
20150199010; 20150235134; 20150257700; 20150290453;
20150290454; 20150313496; 20150313903; 20150323787;
20160008620; 20160022167; 20160038469; 20160051161;
20160051162; 20160055236; 20160066838; 20160073916;
20150347734; 20150351655; 20150352085; 20150367133;
20160077547; 20160078366; 20160082319; 20160103487;
20160119726; 20160120432; 20160120474; 20160164813;
20160170996; 20160170998; 20160171514; 20160196758;
20160206871; 20160210552; 20160224803; 20160228418;
20160228640; 20160232625; 20160235351; 20160239084;
20160275536; 20160299568; 20160300252; 20160302711;
20160306844; 20160317077; 20160324478; 20160345901;
20160360970; 20160360992; 20160361534; 20160363483;
20160364586; 20160370774; 20170020434; 20170031440;
20170035344; 20170042474; 20170043167; 20170056642;
20170065379; 20170071495; 20170078883; 20170080256;
20170086729; 20170087367; 20170095157; 20170095383;
20170095670; 20170103668; 20170112671; 20170120043;
20170135597; 20170139484; 20170156674; 20170164878;
20170178001; 20170185149; 20170185150; 20170188947;
20170202476; 20170215757; 20170238831; 20170262943;
20170270636; 20170304587; 20170304623; 20170311832;
20170311837; 20170316707; 20170337834; 20170347906;
20170367651; 20180012009; 20180014741; 20180025368;
20180042513; 20180081430; 20180089531; 20180092557;
20180092566; 20180093092; 20180103867; 20180103917;
20180146879; 20180166157; 20180168905; 20180169411;
20180169412; 20180190376; 20180192936; 20180196511;

20180197636; 20180214768; 20180228423; 20180234847;
20180246570; 20180279939; 20180289318; 20180292902;
20180303370; 20180303805; 20180310851; 20180310855;
20180317794; 20180328917; 20180333587; 20180341848;
20180343219; 20190029528; 20190029587; 20190033914;
20190033968; 20190046119; 20190056438; 20190059771;
20190073029; 20190073605; 20190082990; 20190082991;
20190083212; 20190099104; 20190101985; 20190107888;
20190110726; 20190113973; 20190146580; 20190159675;
20190159715; and 20190167179.
"Brain-to-brain interface lets rats share information via
internet". The Guardian. 1 Mar. 2013.
"Emotiv Homepage". Emotiv.com. Retrieved 29 Dec.
2009.
"Fiscal Year 2010 Budget Estimates. Defense Advanced Research
Projects Agency" (PDF). darpa.mil. May 2009.
"How To Hack Toy EEGs". Frontiernerds.com. Retrieved 19
Dec. 2016.
"LIFESUIT Updates & News - They Shall Walk".
Theyshallwalk.org. Retrieved 19 Dec. 2016.
"Mind Games". The Economist. 23 Mar. 2007.
"necomimi" selected "TIME MAGAZINE/The 50 best invention of
the year". Neurowear.com. Retrieved on 29 May 2012.
"Nervous System Hookup Leads to Telepathic Hand-Holding".
10 Jun. 2015.
"nia Game Controller Product Page". OCZ Technology Group.
Retrieved 30 Jan. 2013.
"Reconstructing visual experiences from brain activity evoked
by natural movies (Project page)". The Gallant Lab at UC Berkeley.
Retrieved 25 Sep. 2011.
"Roadmap - BNCI Horizon 2020". bnci-horizon-2020.eu.
Retrieved 5 May 2019.
"SmartphoneBCI". Retrieved 5 Jun. 2018.
"Sony patent neural interface". Archived from the original on 7
Apr. 2012.
"SSVEP_keyboard". Retrieved 5 Apr. 2017.
"The Annual BCI Research Award 2014 - The Winners".
Biosignal.at. 15 Jun. 2011.
"The Bionic Connection - DiscoverMagazine.com".
"The OpenEEG Project". Openeeg.sourceforge.net. Retrieved 19
Dec. 2016.
"Thought-guided helicopter takes off". bbc.co.uk. 5 Jun. 2013.
www.bbci.de/competition/iv/
Abdulkader, Sarah N.; Atia, Ayman; Mostafa, Mostafa-Sami M.
(July 2015). "Brain computer interfacing: Applications and
challenges". Egyptian Informatics Journal. 16 (2): 213-230.
doi: 10.1016/j.eij.2015.06.002. ISSN 1110-8665.
Alex Blainey controls a cheap consumer robot arm using the
EPOC headset via a serial relay port at YouTube.com
Ali, Yahia H.; Pandarinath, Chethan (24 Apr. 2019). "Brain
implants that let you speak your mind". Nature. 568 (7753): 466.
doi: 10.1038/d41586-019-01181-y.
Alizadeh-Taheri, Babak (1994). "Active Micromachined Scalp
Electrode Array for Eeg Signal Recording". PhD Thesis: 82.
Bibcode: 1994PhDT.82A.
Allison B. Z.; Wolpaw E. W.; Wolpaw J. R. (2007). "Brain
computer interface systems: Progress and prospects". British Review
of Medical Devices. 4 (4): 463-474. doi: 10.1586/17434440.4.4.463.
PMID 17605682.
Allison, B. Z., Dunne, S., Leeb, R., Millan, J., and Nijholt, A.
(2013). Towards Practical Brain-Computer Interfaces: Bridging the
Gap from Research to Real-World Applications. Springer Verlag,
Berlin Heidelberg. ISBN 978-3-642-29746-5.
Ang, Kai Keng; Chin, Zheng Yang; Wang, Chuanchu; Guan,
Cuntai; Zhang, Haihong (1 Jan. 2012). "Filter bank common
spatial pattern algorithm on BCI competition IV Datasets 2a and 2b".
Neuroprosthetics. 6: 39. doi: 10.3389/fnins.2012.00039. PMC
3314883. PMID 22479236.
Attiah, Mark A.; Farah, Martha J. (15 May 2014). "Minds,
motherboards, and money: futurism and realism in the neuroethics of
BCI technologies". Frontiers in Systems Neuroscience. 8 (86): 86.
doi: 10.3389/fnsys.2014.00086. PMC 4030132. PMID 24860445.
Baum, Michele (6 Sep. 2008). "Monkey Uses Brain Power
to Feed Itself With Robotic Arm". Pitt Chronicle. Archived from the
original on 10 Sep. 2009.
Bin, Guangyu; Gao, Xiaorong; Yan, Zheng; Hong, Bo; Gao,
Shangkai (1 Jul. 2009). "An online multi-channel SSVEP-based brain-
computer interface using a canonical correlation analysis method".
Journal of Neural Engineering. 6 (4): 046002. doi: 10.1088/1741-
2560/6/4/046002. PMID 19494422.

TABLE 1-continued

Bland, Eric (13 Oct. 2008). "Army Developing'synthetic telepathy'". Discovery News.

Blau, A (August 2011). "5". Applied Biomedical Engineering. Applied Biomedical Engineering. InTech. pp. 84-122. doi: 10.5772/23186. ISBN 9789533072562.

Boly M, Massimini M, Garrido MI, Gosseries O, Noirhomme Q, Laureys S, Soddu A (2012). "Brain connectivity in disorders of consciousness". Brain Connectivity. 2 (1): 1-10. doi: 10.1089/brain.2011.0049. PMID 22512333.

Boppart, S A (1992). "A flexible perforated microelectrode array for extended neural recording". IEEE Transactions on Biomedical Engineering. 39 (1): 37-42. doi: 10.1109/10.108125. PMID 1572679.

'Brain' in a dish flies flight simulator, CNN, 4 Nov. 2004

Brains-on with NeuroSky and Square Enix's Judecca mind-control game. Engadget.com (9 Oct. 2008).

Brunner, Clemens; Birbaumer, Niels; Blankertz, Benjamin; Guger, Christoph; Kübler, Andrea; Mattia, Donatella; Millán, José del R; Miralles, Felip; Nijholt, Anton; Opisso, Eloy; Ramsey, Nick; Salomon, Patric; Müller-Putz, Gernot R (2015). "BNCI Horizon 2020: towards a roadmap for the BCI community". Brain-Computer Interfaces. 2: 1-10. doi: 10.1080/2326263X.2015.1008956. hdl: 1874/350349.

Caltech Scientists Devise First Neurochip, Caltech, 26 Oct. 1997

Carmena, J M; Lebedev, M A; Crist, R E; O'Doherty, J E; Santucci, DM; Dimitrov, DF; Patil, PG; Henriquez, CS; Nicolelis, MA (2003). "Learning to control a brain-machine interface for reaching and grasping by primates". PLoS Biology. 1 (2): E42. doi: 10.1371/journal.pbio.0000042. PMC 261882. PMID 14624244.

Chang, Edward F.; Chartier, Josh; Anumanchipalli, Gopala K. (24 Apr. 2019). "Speech synthesis from neural decoding of spoken sentences". Nature. 568 (7753): 493-498. doi: 10.1038/s41586-019-1119-1. ISSN 1476-4687.

Chatelle, Camille; Chennu, Srivas; Noirhomme, Quentin; Cruse, Damian; Owen, Adrian M.; Laureys, Steven (2012). "Brain-computer interfacing in disorders of consciousness". Brain Injury. 26 (12): 1510-22. doi: 10.3109/02699052.2012.698362. PMID 22759199.

Chevalier, Guillaume. "Random Thoughts on Brain-Computer Interfaces, Productivity, and Privacy". Guillaume Chevalier's Blog. Retrieved 21 Apr. 2019.

Clausen, Jens (2009). "Man, machine and in between". Nature. 457 (7233): 1080-1081. Bibcode: 2009Natur.457.1080C. doi: 10.1038/4571080a. PMID 19242454.

Collinger, Jennifer L.; et al. (2013). "High-performance neuroprosthetic control by an individual with tetraplegia". The Lancet. 381 (9866): 557-564. doi: 10.1016/S0140-6736(12)61816-9. PMC 3641862. PMID 23253623.

Coming to a brain near you. Archived 10 Sep. 2006 at the Wayback Machine, Wired News, 22 Oct. 2004

Coyle, Damien; Marshall, David; Wilson, Shane; Callaghan, Michael (2013). "Games, Gameplay, and BCI: The State of the Art". IEEE Transactions on Computational Intelligence and AI in Games. 5 (2): 83. doi: 10.1109/TCIAIG.2013.2263555.

Do, An H; Wang, Po T; King, Christine E; Chun, Sophia N; Nenadic, Zoran (2013). "Brain-computer interface controlled robotic gait orthosis". Journal of NeuroEngineering and Rehabilitation. 10 (1): 111. doi: 10.1186/1743-0003-10-111. ISSN 1743-0003. PMC 3907014. PMID 24321081.

Doud, A J; Lucas, John P.; Pisansky, Marc T.; He, Bin (2011). Gribble, Paul L (ed.). "Continuous Three-Dimensional Control of a Virtual Helicopter Using a Motor Imagery Based Brain-Computer Interface". PLoS ONE. 6 (10): e26322. Bibcode: 2011PLoSO . . . 626322D. doi: 10.1371/journal.pone.0026322. PMC 3202533. PMID 22046274.

Drummond, Katie (14 May 2009). "Pentagon Preps Soldier Telepathy Push". Wired Magazine.

Edlinger, G., Allison, B. Z., and Guger, C. (2015). "How many people could use a BCI system?" pp. 33-66 in Clinical Systems Neuroscience, Kansaku, K., Cohen, L., and Birbaumer, N. (eds.) Springer Verlag Japan: Tokyo. ISBN 978-4-431-55037-2.

Fetz, E. E. (1969). "Operant Conditioning of Cortical Unit Activity". Science. 163 (3870): 955-8. Bibcode: 1969Sci . . . 163 . . . 955F. doi: 10.1126/science.163.3870.955. PMID 4974291.

Gallegos-Ayala, G; Furdea, A; Takano, K; Ruf, C A; Flor, H; Birbaumer, N (27 May 2014). "Brain communication in a completely locked-in patient using bedside near-infrared spectroscopy". Neurology. 82 (21): 1930-2. doi: 10.1212/WNL.0000000000000449. PMC 4049706. PMID 24789862.

Georgopoulos, A.; Lurito, J.; Petrides, M; Schwartz, A.; Massey, J. (1989). "Mental rotation of the neuronal population vector". Science. 243 (4888): 234-6. Bibcode: 1989Sci . . . 243 . . . 234G. doi: 10.1126/science.2911737. PMID 2911737.

TABLE 1-continued

Gibson, Raechelle M.; Fernã+hd i+l Ndez-Espejo, Davinia; Gonzalez-Lara, Laura E.; Kwan, Benjamin Y.; Lee, Donald H.; Owen, Adrian M.; Cruse, Damian (2014). "Multiple tasks and neuroimaging modalities increase the likelihood of detecting covert awareness in patients with disorders of consciousness". Frontiers in Human Neuroscience. 8: 950. doi: 10.3389/fnhum.2014.00950. PMC 4244609. PMID 25505400.

Gorman, James (28 Feb. 2013). "One Rat Thinks, and Another Reacts". New York Times.

Guger, C., Allison, B. Z., and Edlinger, G. (2013). Brain-Computer Interface Research: A State-of-the-Art Summary. Springer Verlag, Berlin Heidelberg.

Guger, C., Allison, B. Z., and Vaughan, T. M. (2014). The BCI Award 2013: A State-of-the-Art Summary 3. Springer Verlag, Berlin Heidelberg.

Guger, C., Allison, B. Z., Leuthardt, E. C., and Edlinger, G. (2014). The BCI Award 2012: A State-of-the-Art Summary 2. Springer Verlag, Berlin Heidelberg.

Gulati, Tanuj; Won, Seok Joon; Ramanathan, Dhakshin S.; Wong, Chelsea C.; Bodepudi, Anitha; Swanson, Raymond A.; Ganguly, Karunesh (2015). "Robust Neuroprosthetic Control from the Stroke Perilesional Cortex". The Journal of Neuroscience. 35 (22): 8653-8661. doi: 10.1523/JNEUROSCI.5007-14.2015. PMID 26041930.

Haider, Ali; Fazel-Rezai, Reza (2017). Event-Related Potentials and Evoked Potentials. InTech. doi: 10.5772/intechopen.69309. ISBN 978-953-51-3639-2.

Haselager, Pim; Vlek, Rutger; Hill, Jeremy; Nijboer, Femke (2009). "A note on ethical aspects of BCI". Neural Networks. 22 (9): 1352-1357. doi: 10.1016/j.neunet.2009.06.046. PMID 19616405.

Hochberg, L. R.; Bacher, D.; Jarosiewicz, B.; Masse, N. Y.; Simeral, J. D.; Vogel, J.; Haddadin, S.; Liu, J.; Cash, S. S.; Van Der Smagt, P.; Donoghue, J. P. (2012). "Reach and grasp by people with tetraplegia using a neurally controlled robotic arm". Nature. 485 (7398): 372-5. Bibcode: 2012Natur.485 . . . 372H. doi: 10.1038/nature11076. PMC 3640850. PMID 22596161.

Höhne, J; Holz, E; Staiger-Sälzer, P; Müller, K R; Kübler, A; Tangermann, M (2014). "Motor imagery for severely motor-impaired patients: evidence for brain-computer interfacing as superior control solution". PLOS ONE. 9 (8): e104854. Bibcode: 2014PLoSO . . . 9j4854H. doi: 10.1371/journal.pone.0104854. PMC 4146550. PMID 25162231.

www.gnu.org/philosophy/free-software-even-more-important.html. Missing or empty | title = (help)

www.gnu.org/philosophy/who-does-that-server-really-serve.html. Missing or empty | title = (help)

Huber, D; Petreanu, L; Ghitani, N; Ranade, S; Hromádka, T; Mainen, Z; Svoboda, K (2008). "Sparse optical microstimulation in barrel cortex drives learned behaviour in freely moving mice". Nature. 451 (7174): 61-4. Bibcode: 2008Natur.451 . . . 61H. doi: 10.1038/nature06445. PMC 3425380. PMID 18094685.

J. Vidal (1977). "Real-Time Detection of Brain Events in EEG" (PDF). IEEE Proceedings. 65 (5): 633-641. doi: 10.1109/PROC.1977.10542.

Just short of telepathy: can you interact with the outside world if you can't even blink an eye?, Psychology Today, May-June 2003

Kennedy, Pagan (18 Sep. 2011). "The Cyborg in Us All". New York Times.

Kennedy, P R; Bakay, R A (1998). "Restoration of neural output from a paralyzed patient by a direct brain connection". NeuroReport. 9 (8): 1707-11. doi: 10.1097/00001756-199806010-00007. PMID 9665587.

Kim, D H (2010). "Dissolvable films of silk fibroin for ultrathin, conformal bio-integrated electronics". Nature Materials. 9 (6): 511-517. Bibcode: 2010NatMa . . . 9 . . . 511K. doi: 10.1038/nmat2745. PMC 3034223. PMID 20400953.

Kim, D H (2012). "Flexible and stretchable electronics for bio-integrated devices". Annual Review of Biomedical Engineering. 14: 113-128. doi: 10.1146/annurev-bioeng-071811-150018. PMID 22524391.

Krucoff, Max O.; Rahimpour, Shervin; Slutzky, Marc W.; Edgerton, V. Reggie; Turner, Dennis A. (1 Jan. 2016). "Enhancing Nervous System Recovery through Neurobiologics, Neural Interface Training, and Neurorehabilitation". Neuroprosthetics. 10: 584. doi: 10.3389/fnins.2016.00584. PMC 5186786. PMID 28082858.

L. Bozinovska, G. Stojanov, M. Sestakov, S. Bozinovski: CNV pattern recognition: step toward a cognitive wave observation, In L. Torres, E. Masgrau, E. Lagunas (eds.) Signal Processing V: Theories and Applications, Proc. EUSIPCO-90: Fifth European Signal Processing Conference, Elsevier, p. 1659-1662, Barcelona, 1990

L. Bozinovska, S. Bozinovski, G. Stojanov, Electroexpectogram: experimental design and algorithms, In Proc IEEE International TABLE 1-continued Biomedical Engineering Days, p. 55-60, Istanbul, 1992
Lebedev, M. A.; Carmena, J M; O'Doherty, J E; Zacksenhouse, M;
Henriquez, C S; Principe, J C; Nicolelis, MA (2005). "Cortical Ensemble
Adaptation to Represent Velocity of an Artificial Actuator Controlled
by a Brain-Machine Interface". Journal of Neuroscience. 25 (19):
4681-93. doi: 10.1523/JNEUROSCI.4088-04.2005. PMID 15888644.
Lebedev, M A; Nicolelis, M A (2006). Brain-machine interfaces:
past, present and future" (PDF). Trends in Neurosciences. 29 (9): 536-
46. doi: 10.1016/j.tins.2006.07.004. PMID 16859758. [permanent
dead link]
Leigh R. Hochberg; Mijail D. Serruya; Friehs; Mukand; Saleh;
Caplan; Branner; Chen; Penn; Donoghue (13 Jul. 2006). Gerhard M.
Friehs, Jon A. Mukand, Maryam Saleh, Abraham H. Caplan, Almut
Branner, David Chen, Richard D. Penn and John P. Donoghue.
"Neuronal ensemble control of prosthetic devices by a human with
tetraplegia". Nature. 442 (7099): 164-171.
Bibcode: 2006Natur.442.. 164H. doi: 10.1038/nature04970. PMID
16838014.
Levine, S P; Huggins, J E; Bement, S L; Kushwaha, R K; Schuh, LA;
Rohde, MM; Passaro, EA; Ross, DA; Elisevich, KV; et al. (2000). "A
direct brain interface based on event-related potentials". IEEE
Transactions on Rehabilitation Engineering. 8 (2): 180-5.
doi: 10.1109/86.847809. PMID 10896180.
Li, Shan (8 Aug. 2010). "Mind reading is on the market". Los
Angeles Times.
Lin, Chin-Teng; Ko, Li-Wei; Chang, Che-Jui; Wang, Yu-Te; Chung,
Chia-Hsin; Yang, Fu-Shu; Duann, Jeng-Ren; Jung, Tzyy-Ping; Chiou,
Jin-Chern (2009), "Wearable and Wireless Brain-Computer Interface
and Its Applications", Foundations of Augmented Cognition.
Neuroergonomics and Operational Neuroscience, Springer Berlin
Heidelberg, pp. 741-748, doi: 10.1007/978-3-642-02812-0_84, ISBN
9783642028113
Lin, Yuan-Pin; Wang, Yijun; Jung, Tzyy-Ping (2013). A mobile
SSVEP-based brain-computer interface for freely moving humans: the
robustness of canonical correlation analysis to motion artifacts.
Conference Proceedings: . . . Annual International Conference of the
IEEE Engineering in Medicine and Biology Society. IEEE Engineering in
Medicine and Biology Society. Annual Conference. 2013. pp. 1350-
1353. doi: 10.1109/EMBC.2013.6609759. ISBN 978-1-4577-0216-7.
ISSN 1557-170X. PMID 24109946.
Mathôt, Sebastiaan; Melmi, Jean-Baptiste; Van Der Linden, Lotje;
Van Der Stigchel, Stefan (2016). "The Mind-Writing Pupil: A Human-
Computer Interface Based on Decoding of Covert Attention through
Pupillometry". PLoS ONE. 11 (2): e0148805.
Bibcode: 2016PLoSO . . . 1148805M. doi: 10.1371/journal.pone.0148805.
PMC 4743834. PMID 26848745.
Mazzatenta, A.; Giugliano, M.; Campidelli, S.; Gambazzi, L.;
Businaro, L.; Markram, H.; Prato, M.; Ballerini, L. (2007). "Interfacing
Neurons with Carbon Nanotubes: Electrical Signal Transfer and
Synaptic Stimulation in Cultured Brain Circuits". Journal of
Neuroscience. 27 (26): 6931-6. doi: 10.1523/JNEUROSCI.1051-
07.2007. PMID 17596441.
Miguel Nicolelis et al. (2001) Duke neurobiologist has developed
system that allows monkeys to control robot arms via brain signals
Archived 19 Dec. 2008 at the Wayback Machine
Miyawaki, Yoichi; Uchida, Hajime; Yamashita, Okito; Sato, Masa-
aki; Morito, Yusuke; Tanabe, Hiroki C.; Sadato, Norihiro; Kamitani,
Yukiyasu (2008). "Visual Image Reconstruction from Human Brain
Activity using a Combination of Multiscale Local Image Decoders".
Neuron. 60 (5): 915-29. doi: 10.1016/j.neuron.2008.11.004. PMID
19081384.
Monge-Pereira, Esther; Ibañez-Pereda, Jaime; Alguacil-Diego,
Isabel M.; Serrano, Jose I.; Spottorno-Rubio, Maria P.; Molina-Rueda,
Francisco (2017). "Use of Electroencephalography Brain-Computer
Interface Systems as a Rehabilitative Approach for Upper Limb
Function After a Stroke: A Systematic Review". PM&R. 9 (9): 918-932.
doi: 10.1016/j.pmrj.2017.04.016. PMID 28512066.
Mrachacz-Kersting, N.; Voigt, M.; Stevenson, A. J. T.;
Aliakbaryhosseinabadi, S.; Jiang, N.; Dremstrup, K.; Farina, D. (2017).
"The effect of type of afferent feedback timed with motor imagery on
the induction of cortical plasticity". Brain Research. 1674: 91-100.
doi: 10.1016/j.brainres.2017.08.025. PMID 28859916.
Musallam, S.; Corneil, BD; Greger, B; Scherberger, H; Andersen,
RA (2004). "Cognitive Control Signals for Neural Prosthetics". Science.
305 (5681): 258-62. Bibcode: 2004Sci . . . 305 . . . 258M.
doi: 10.1126/science.1097938. PMID 15247483.
Naumann, J. Search for Paradise: A Patient's Account of the
Artificial Vision Experiment (2012), Xlibris Corporation, ISBN 1-479-
7092-04

New games powered by brain waves. Physorg.com (10 Jan.
2009).
Nicolelis Miguel A. L; Lebedev Mikhail A (2009). "Principles of
Neural Ensemble Physiology Underlying the Operation of Brain-
Machine Interfaces". Nature Reviews Neuroscience. 10 (7): 530-540.
doi: 10.1038/nrn2653. PMID 19543222.
Nicolelis, Miguel A. L.; Wessberg, Johan; Stambaugh, Christopher
R.; Kralik, Jerald D.; Beck, Pamela D.; Laubach, Mark; Chapin, John K.;
Kim, Jung; Biggs, S. James; et al. (2000). "Real-time prediction of
hand trajectory by ensembles of cortical neurons in primates".
Nature. 408 (6810): 361-5. doi: 10.1038/35042582. PMID 11099043.
NIH Publication No. 11-4798 (1 Mar. 2011). "Cochlear
Implants". National Institute on Deafness and Other Communication
Disorders.
Nijboer, Femke; Clausen, Jens; Allison, Brendan Z; Haselager,
Pim (2011). "Stakeholders' opinions on ethical issues related to
brain-computer interfacing". Neuroethics. 6 (3): 541-578.
doi: 10.1007/s12152-011-9132-6. PMC 3825606. PMID 24273623.
Nishimoto, Shinji; Vu, An T.; Naselaris, Thomas; Benjamini,
Yuval; Yu, Bin; Gallant, Jack L. (2011). "Reconstructing Visual
Experiences from Brain Activity Evoked by Natural Movies". Current
Biology. 21 (19): 1641-1646. doi: 10.1016/j.cub.2011.08.031. PMC
3326357. PMID 21945275.
nurun.com. "Mr. Jen Naumann's high-tech paradise lost".
Thewhig.com. Retrieved 19 Dec. 2016.
O'Doherty, J E; Lebedev, M A; Ifft, P J; Zhuang, K Z; Shokur, S;
Bleuler, H; Nicolelis, MA (2011). "Active tactile exploration using a
brain-machine-brain interface". Nature. 479 (7372): 228-231.
Bibcode: 2011 Natur.479 . . . 228O. doi: 10.1038/nature10489. PMC
3236080. PMID 21976021.
Pais-Vieira, Miguel; Lebedev, Mikhail; Kunicki, Carolina; Wang,
Jing; Nicolelis, Miguel A. L. (28 Feb. 2013). "A Brain-to-Brain
Interface for Real-Time Sharing of Sensorimotor Information".
Scientific Reports. 3: 1319. Bibcode: 2013NatSR . . . 3E1319P.
doi: 10.1038/srep01319. PMC 3584574. PMID 23448946.
Pei, X. (2011). "Decoding Vowels and Consonants in Spoken and
Imagined Words Using Electrocorticographic Signals in Humans". J
Neural Eng 046028th ser. 8.4. PMID 21750369. Justin Williams, a
biomedical engineer at the university, has already transformed the
ECoG implant into a micro device that can be installed with a
minimum of fuss. It has been tested in animals for a long period of
time - the micro ECoG stays in place and doesn't seem to negatively
affect the immune system.
Peplow, Mark (2004). "Mental ping-pong could aid
paraplegics". News@nature. doi: 10.1038/news040823-18.
Pfurtscheller, G.; Müller, G. R.; Pfurtscheller, J. R.; Gerner, H. J.
R.; Rupp, R. D. (2003). "'Thought' - control of functional electrical
stimulation to restore hand grasp in a patient with tetraplegia".
Neuroscience Letters. 351 (1): 33-36. doi: 10.1016/S0304-
3940(03)00947-9. PMID 14550907.
Pitt team to build on brain-controlled arm Archived 4 Jul. 2007
at the Wayback Machine, Pittsburgh Tribune Review, 5 Sep.
2006.
Polikov, Vadim S., Patrick A. Tresco, and William M. Reichert
(2005). "Response of brain tissue to chronically implanted neural
electrodes". Journal of Neuroscience Methods. 148 (1): 1-18.
doi: 10.1016/j.jneumeth.2005.08.015. PMID 16198003.
Qin, L; Ding, Lei; He, Bin (2004). "Motor imagery classification
by means of source analysis for brain-computer interface
applications". Journal of Neural Engineering. 1 (3): 135-141.
Bibcode: 2004JNEng . . . 1 . . . 135Q. doi: 10.1088/1741-2560/1/3/002.
PMC 1945182. PMID 15876632.
Rabaey, J. M. (September 2011). "Brain-machine interfaces as
the new frontier in extreme miniaturization". 2011 Proceedings of
the European Solid-State Device Research Conference (ESSDERC): 19-
24. doi: 10.1109/essderc.2011.6044240. ISBN 978-1-4577-0707-0.
Radzik, Iwona; Miziak, Barbara; Dudka, Jaroslaw; Chrościńska-
Krawczyk, Magdalena; Czuczwar, Stanisław J. (2015). "Prospects of
epileptogenesis prevention". Pharmacological Reports. 67 (3): 663-8.
doi: 10.1016/j.pharep.2015.01.016. PMID 25933984.
Ramsey, Nick F.; Chaudhary, Ujwal; Xia, Bin; Silvoni, Stefano;
Cohen, Leonardo G.; Birbaumer, Niels (2017). "Brain-Computer
Interface-Based Communication in the Completely Locked-In State".
PLOS Biology. 15 (1): e1002593. doi: 10.1371/journal.pbio.1002593.
ISSN 1545-7885. PMC 5283652. PMID 28141803.
Ranganatha Sitaram, Andrea Caria, Ralf Veit, Tilman Gaber,
Giuseppina Rota, Andrea Kuebler and Niels Birbaumer(2007) "FMRI
Brain-Computer Interface: A Tool for Neuroscientific Research and
Treatment[permanent dead link]"
Remsik, Alexander; Young, Brittany; Vermilyea, Rebecca;

TABLE 1-continued

Kiekhoefer, Laura; Abrams, Jessica; Elmore, Samantha Evander;
Schultz, Paige; Nair, Veena; Edwards, Dorothy (3 May 2016). "A
review of the progression and future implications of brain-computer
interface therapies for restoration of distal upper extremity motor
function after stroke". Expert Review of Medical Devices. 13 (5): 445-
454. doi: 10.1080/17434440.2016.1174572. ISSN 1743-4440. PMC
5131699. PMID 27112213.
Riccio, A.; Pichiorri, F.; Schettini, F.; Toppi, J.; Risetti, M.;
Formisano, R.; Molinari, M.; Astolfi, L.; Cincotti, F. (2016). Brain-
Computer Interfaces: Lab Experiments to Real-World Applications.
Progress in Brain Research. 228. pp. 357-387.
doi: 10.1016/bs.pbr.2016.04.018. ISBN 9780128042168. PMID
27590975.
Risetti, Monica; Formisano, Rita; Toppi, Jlenia; Quitadamo, Lucia
R.; Bianchi, Luigi; Astolfi, Laura; Cincotti, Febo; Mattia, Donatella
(2013). "On ERPs detection in disorders of consciousness
rehabilitation". Frontiers in Human Neuroscience. 7: 775.
doi: 10.3389/fnhum.2013.00775. PMC 3834290. PMID 24312041.
Ritaccio, Anthony; Brunner, Peter; Gunduz, Aysegul; Hermes,
Dora; Hirsch, Lawrence J.; Jacobs, Joshua; Kamada, Kyousuke;
Sejnowski, Terrence; Worrell, Gregory; Schalk, Gerwin (2014).
Kastner, Sabine; Knight, Robert T.; Lesser, Ronald P.; Miller, Kai;
"Proceedings of the Fifth International Workshop on Advances in
Electrocorticography." Epilepsy & Behavior. 41: 183-192.
doi: 10.1016/j.yebeh.2014.09.015. PMC 4268064. PMID 25461213.
S. Bozinovski, M. Sestakov, L. Bozinovska: Using EEG alpha
rhythm to control a mobile robot, In G. Harris, C. Walker (eds.) Proc.
IEEE Annual Conference of Medical and Biological Society, p. 1515-
1516, New Orleans, 1988
S. Bozinovski: Mobile robot trajectory control: From fixed rails
to direct bioelectric control, In O. Kaynak (ed.) Proc. IEEE Workshop
on Intelligent Motion Control, p. 63-67, Istanbul, 1990
Sabathiel, Nikolaus; Irimia, Danut C.; Allison, Brendan Z.; Guger,
Christoph; Edlinger, Günter (17 Jul. 2016). Paired Associative
Stimulation with Brain-Computer Interfaces: A New Paradigm for
Stroke Rehabilitation. Foundations of Augmented Cognition:
Neuroergonomics and Operational Neuroscience. Lecture Notes in
Computer Science. pp. 261-272. doi: 10.1007/978-3-319-39955-
3_25. ISBN 9783319399546.
Santucci, David M.; Kralik, Jerald D.; Lebedev, Mikhail A.;
Nicolelis, Miguel A. L. (2005). "Frontal and parietal cortical ensembles
predict single-trial muscle activity during reaching movements in
primates". European Journal of Neuroscience. 22 (6): 1529-40.
doi: 10.1111/j.1460-9568.2005.04320.x. PMID 16190906.
Schalk, G; Miller, K J; Anderson, N R; Wilson, J A; Smyth, M D;
Ojemann, J G; Moran, D W; Wolpaw, J R; Leuthardt, E C (2008). "Two-
dimensional movement control using electrocorticographic signals in
humans". Journal of Neural Engineering.
Schmidt, E M; McIntosh, J S; Durelli, L; Bak, M J (1978). "Fine
control of operantly conditioned firing patterns of cortical neurons".
Experimental Neurology. 61 (2): 349-69. doi: 10.1016/0014-
4886(78)90252-2. PMID 101388.
Serruya M D, Donoghue J P. (2003) Chapter III: Design Principles
of a Neuromotor Prosthetic Device in Neuroprosthetics: Theory and
Practice, ed. Kenneth W. Horch, Gurpreet S. Dhillon. Imperial College
Press.
Serruya, M D; Hatsopoulos, N G; Paninski, L; Fellows, M R;
Donoghue, JP (2002). "Instant neural control of a movement signal".
Nature. 416 (6877): 141-2. Bibcode: 2002Natur.416 . . . 141S.
doi: 10.1038/416141a. PMID 11894084.
Snider, Mike (7 Jan. 2009). "Toy trains 'Star Wars' fans to
use The Force". USA Today.
Stanley, G B; Li, F F; Dan, Y (1999). "Reconstruction of natural
scenes from ensemble responses in the lateral geniculate nucleus"
(PDF). Journal of Neuroscience. 19 (18): 8036-42.
doi: 10.1523/JNEUROSCI.19-18-08036.1999. PMID 10479703.
Subject with Paraplegia Operates BCI-controlled RoGO (4x) at
YouTube.com
Symeonidou, Evangelia-Regkina; D Nordin, Andrew; Hairston, W
David; Ferris, Daniel (3 Apr. 2018). "Effects of Cable Sway, Electrode
Surface Area, and Electrode Mass on Electroencephalography Signal
Quality during Motion". Sensors (Basel, Switzerland). 18 (4): 1073.
doi: 10.3390/s18041073. PMC 5948545. PMID 29614020.
Taheri, B; Knight, R; Smith, R (1994). "A dry electrode for EEG
recording☆". Electroencephalography and Clinical Neurophysiology.
90 (5): 376-83. doi: 10.1016/0013-4694(94)90053-1. PMID 7514984.
Tamburrini, Guglielmo (2009). "Brain to Computer
Communication: Ethical Perspectives on Interaction Models".
Neuroethics. 2 (3): 137-149. doi: 10.1007/s12152-009-9040-1.
Taylor, D. M.; Tillery, SI; Schwartz, AB (2002). "Direct Cortical TABLE 1-continued Control of 3D Neuroprosthetic Devices". Science. 296 (5574): 1829-
32. Bibcode: 2002Sci . . . 296.1829T. CiteSeerX 10.1.1.1027.4335.
doi: 10.1126/science.1070291. PMID 12052948.
Teenager moves video icons just by imagination, press release,
Washington University in St Louis, 9 Oct. 2006
The Next BrainiacsWired Magazine, August 2001.
To operate robot only with brain, ATR and Honda develop BMI
base technology, Tech-on, 26 May 2006
Tuller, David (1 Nov. 2004) Dr. William Dobelle, Artificial
Vision Pioneer, Dies at 62. New York Times
Urban, Tim. "Neuralink and the Brain's Magical Future". Wait
But Why. Retrieved 21 Apr. 2019.
Várkuti, Bálint; Guan, Cuntai; Pan, Yaozhang; Phua, Kok Soon;
Ang, Kai Keng; Kuah, Christopher Wee Keong; Chua, Karen; Ang, Beng
Ti; Birbaumer, Niels (29 May 2012). "Resting State Changes in
Functional Connectivity Correlate With Movement Recovery for BCI
and Robot-Assisted Upper-Extremity Training After Stroke".
Neurorehabilitation and Neural Repair. 27 (1): 53-62.
doi: 10.1177/1545968312445910. PMID 22645108.
Velliste, M; Perel, S; Spalding, M C; Whitford, A S; Schwartz, AB
(2008). "Cortical control of a prosthetic arm for self-feeding". Nature.
453 (7198): 1098-101. Bibcode: 2008Natur.453.1098V.
doi: 10.1038/nature06996. PMID 18509337.
Vidal, J J (1973). "Toward direct brain-computer
communication". Annual Review of Biophysics and Bioengineering. 2
(1): 157-80. doi: 10.1146/annurev.bb.02.060173.001105. PMID
4583653.
Video on YouTube
Vision quest, Wired Magazine, September 2002
Volker Straebel; Wilm Thoben (2014). "Alvin Lucier's music for
solo performer: experimental music beyond sonification". Organised
Sound. 19 (1): 17-29. doi: 10.1017/S135577181300037X.
Wang, Yijun; Wang, Ruiping; Gao, Xiaorong; Hong, Bo; Gao,
Shangkai (June 2006). "A practical VEP-based brain-computer
interface". IEEE Transactions on Neural Systems and Rehabilitation
Engineering. 14 (2): 234-239. doi: 10.1109/TNSRE.2006.875576. ISSN
1534-4320. PMID 16792302.
Wang, Yu-Te; Wang, Yijun; Cheng, Chung-Kuan; Jung, Tzyy-Ping
(2013). Developing stimulus presentation on mobile devices for a
truly portable SSVEP-based BCI. Conference Proceedings: . . . Annual
International Conference of the IEEE Engineering in Medicine and
Biology Society. IEEE Engineering in Medicine and Biology Society.
Annual Conference. 2013. pp. 5271-5274.
doi: 10.1109/EMBC.2013.6610738. ISBN 978-1-4577-0216-7. ISSN
1557-170X. PMID 24110925.
Wang, Yu-Te; Wang, Yijun; Jung, Tzyy-Ping (April 2011). "A cell-
phone-based brain-computer interface for communication in daily
life". Journal of Neural Engineering. 8 (2): 025018.
doi: 10.1088/1741-2560/8/2/025018. ISSN 1741-2552. PMID
21436517.
Warneke, B.; Last, M.; Liebowitz, B.; Pister, K. S. J. (January
2001). "Smart Dust: communicating with a cubic-millimeter
computer". Computer. 34 (1): 44-51. doi: 10.1109/2.895117. ISSN
0018-9162.
Warwick, K, Gasson, M, Hutt, B, Goodhew, I, Kyberd, P,
Schulzrinne, H and Wu, X: "Thought Communication and Control: A
First Step using Radiotelegraphy", IEE Proceedings on
Communications, 151(3), pp.185-189, 2004
Warwick, K.; Gasson, M.; Hutt, B.; Goodhew, I.; Kyberd, P.;
Andrews, B.; Teddy, P.; Shad, A. (2003). "The Application of Implant
Technology for Cybernetic Systems". Archives of Neurology. 60 (10):
1369-73. doi: 10.1001/archneur.60.10.1369. PMID 14568806.
Wolpaw J. R .; Birbaumer N.; McFarland D. J.; Pfurtscheller G.;
Vaughan T. M. (2002). "Brain-computer interfaces for communication
and control". Clinical Neurophysiology. 113 (6): 767-791.
doi: 10.1016/s1388-2457(02)00057-3. PMC 3188401.
Wolpaw, J. R. and Wolpaw, E. W. (2012). "Brain-Computer
Interfaces: Something New Under the Sun". In: Brain-Computer
Interfaces: Principles and Practice, Wolpaw, J. R. and Wolpaw (eds.),
E. W. Oxford University Press.
Yam, Philip (22 Sep. 2011). "Breakthrough Could Enable
Others to Watch Your Dreams and Memories". Scientific American.
Yanagisawa, Takafumi (2011). "Electrocorticographic Control of
Prosthetic Arm in Paralyzed Patients". American Neurological
Association. doi: 10.1002/ana.22613. ECoG- Based BCI has advantage
in signal and durability that are absolutely necessary for clinical
application
Yasmin Anwar (22 Sep. 2011). "Scientists use brain
imaging to reveal the movies in our mind". UC Berkeley News Center.
Young, Brittany Mei; Nigogosyan, Zack; Remsik, Alexander;

TABLE 1-continued

Walton, Léo M.; Song, Jie; Nair, Veena A.; Grogan, Scott W.; Tyler, Mitchell E.; Edwards, Dorothy Farrar (2014). "Changes in functional connectivity correlate with behavioral gains in stroke patients after therapy using a brain-computer interface device". Frontiers in Neuroengineering. 7: 25. doi: 10.3389/fneng.2014.00025. ISSN 1662-6443. PMC 4086321. PMID 25071547.

Yuan, H; Liu, Tao; Szarkowski, Rebecca; Rios, Cristina; Ashe, James; He, Bin (2010). "Negative covariation between task-related responses in alpha/beta-band activity and BOLD in human sensorimotor cortex: an EEG and fMRI study of motor imagery and movements". NeuroImage. 49 (3): 2596-2606. doi: 10.1016/j.neuroimage.2009.10.028. PMC 2818527. PMID 19850134.

Zander, Thorsten 0; Kothe, Christian (2011). "Towards passive brain-computer interfaces: applying brain-computer interface technology to human-machine systems in general". Journal of Neural Engineering. 8 (2): 025005. Bibcode: 2011JNEng . . . 8b5005Z. doi: 10.1088/1741-2560/8/2/025005. PMID 21436512.

Reference List 2

Abeles M, Local Cortical Circuits (1982) New York: Springer-Verlag.

Braitenberg V and Schuz A (1991) Anatomy of the Cortex. Statistics and Geometry. New York: Springer-Verlag.

Ebersole J S (1997) Defining epileptogenic foci: past, present, future. J. Clin. Neurophysiology 14: 470-483.

Edelman G M and Tononi G (2000) A Universe of Consciousness, New York: Basic Books.

Freeman W J (1975) Mass Action in the Nervous System, New York: Academic Press.

Gevins A S and Cutillo B A (1995) Neuroelectric measures of mind. In: P L Nunez (Au), Neocortical Dynamics and Human EEG Rhythms. NY: Oxford U. Press, pp. 304-338.

Gevins A S, Le J, Martin N, Brickett P, Desmond J, and Reutter B (1994) High resolution EEG: 124-channel recording, spatial enhancement, and MRI integration methods. Electroencephalography and Clin. Neurophysiology 90: 337-358.

Gevins A S, Smith M E, McEvoy L and Yu D (1997) High-resolution mapping of cortical activation related to working memory: effects of task difficulty, type of processing, and practice. Cerebral Cortex 7: 374-385.

Haken H (1983) Synergetics: An Introduction, 3rd Edition, Springer-Verlag.

Haken H (1999) What can synergetics contribute to the understanding of brain functioning? In: Analysis of Neurophysiological Brain Functioning, C Uhl (Ed), Berlin: Springer-Verlag, pp 7-40.

Ingber L (1995) Statistical mechanics of multiple scales of neocortical interactions. In: P L Nunez (Au), Neocortical Dynamics and Human EEG Rhythms. NY: Oxford U. Press, 628-681.

Izhikevich E M (1999) Weakly connected quasi-periodic oscillators, FM interactions, and multiplexing in the brain, SIAM J. Applied Mathematics 59: 2193-2223.

Jirsa V K and Haken H (1997) A derivation of a macroscopic field theory of the brain from the quasi-microscopic neural dynamics. Physica D 99: 503-526.

Jirsa V K and Kelso JAS (2000) Spatiotemporal pattern formation in continuous systems with heterogeneous connection topologies. Physical Review E 62: 8462-8465.

Katznelson RD (1981) Normal modes of the brain: Neuroanatomical basis and a physiological theoretical model. In P L Nunez (Au), Electric Fields of the Brain: The Neurophysics of EEG, 1st Edition, NY: Oxford U. Press, pp 401-442.

Klimesch W (1996) Memory processes, brain oscillations and EEG synchronization. International J. Psychophysiology 24: 61-100.

Law SK, Nunez PL and Wijesinghe RS (1993) High resolution EEG using spline generated surface Laplacians on spherical and ellipsoidal surfaces. IEEE Transactions on Biomedical Engineering 40: 145-153.

Liley DTJ, Cadusch PJ and Dafilis MP (2002) A spatially continuous mean field theory of electrocortical activity network. Computation in Neural Systems 13: 67-113.

Malmuvino J and Plonsey R (1995) Bioelectromagetism. NY: Oxford U. Press.

Niedermeyer E and Lopes da Silva FH (Eds) (2005) Electroencephalography. Basic Principals, Clin. Applications, and Related Fields. 5th Edition. London: Williams and Wilkins.

Nunez PL (1989) Generation of human EEG by a combination of long and short range neocortical interactions. Brain Topography 1: 199-215.

Nunez PL (1995) Neocortical Dynamics and Human EEG Rhythms. NY: Oxford U. Press.

Nunez PL (2000) Toward a large-scale quantitative description of neocortical dynamic function and EEG (Target article), Behavioral and Brain Sciences 23: 371-398.

Nunez PL (2000) Neocortical dynamic theory should be as simple as possible, but not simpler (Response to 18 commentaries on target article), Behavioral and Brain Sciences 23: 415-437.

Nunez PL (2002) EEG. In V S Ramachandran (Ed) Encyclopedia of the Human Brain, La Jolla: Academic Press, 169-179.

Nunez PL and Silberstein RB (2001) On the relationship of synaptic activity to macroscopic measurements: Does co-registration of EEG with fMRI make sense? Brain Topog. 13: 79-96.

Nunez PL and Srinivasan R (2006) Electric Fields of the Brain: The Neurophysics of EEG, 2nd Edition, NY: Oxford U. Press.

Nunez PL and Srinivasan R (2006) A theoretical basis for standing and traveling brain waves measured with human EEG with implications for an integrated consciousness. Clin. Neurophysiology 117: 2424-2435.

Nunez PL, Srinivasan R, Westdorp A F, Wijesinghe R S, Tucker DM, Silberstein RB, and Cadusch PJ (1997) EEG coherency I: Statistics, and interpretation at multiple scales. Electroencephalography and reference electrode, volume conduction, Laplacians, cortical imaging, Clin. Neurophysiology 103: 516-527.

Nunez PL. Wingeier BM and Silberstein RB (2001) Spatial-temporal structures of human alpha rhythms: theory, micro-current sources, multiscale measurements, and global binding of local networks, Human Brain Mapping 13: 125-164.

Nuwer M (1997) Assessment of digital EEG, quantitative EEG, and EEG brain mapping: report of the American Academy of Neurology and the American Clin. Neurophysiology Society. Neurology 49: 277-292.

Penfield W and Jasper HD (1954) Epilepsy and the Functional Anatomy of the Human Brain. London: Little, Brown and Co.

Robinson PA, Rennie CJ, Rowe DL and O'Conner SC (2004) Estimation of multiscale neurophysiologic parameters by electroencephalographic means. Human Brain Mapping 23: 53-72.

Scott AC (1995) Stairway to the Mind. New York: Springer-Verlag.

Silberstein RB, Danieli F and Nunez PL (2003) Fronto-parietal evoked potential synchronization is increased during mental rotation, NeuroReport 14: 67-71.

Silberstein RB, Song J, Nunez PL and Park W (2004) Dynamic sculpting of brain functional connectivity is correlated with performance, Brain Topography 16: 240-254.

Srinivasan R and Petrovic S (2006) MEG phase follows conscious perception during binocular rivalry induced by visual stream segregation. Cerebral Cortex, 16: 597-608.

Srinivasan R, Nunez PL and Silberstein RB (1998) Spatial filtering and neocortical dynamics: estimates of EEG coherence. IEEE Trans. on Biomedical Engineering, 45: 814-825.

Srinivasan R, Russell DP, Edelman GM, and Tononi G (1999) Frequency tagging competing stimuli in binocular rivalry reveals increased synchronization of neuromagnetic responses during conscious perception. J. Neuroscience 19: 5435-5448.

Uhl C (Ed) (1999) Analysis of Neurophysiological Brain Functioning. Berlin: Springer-Verlag, Wingeier BM, Nunez PL and Silberstein RB (2001) Spherical harmonic decomposition applied to spatial-temporal analysis of human high-density electroencephalogram. Physical Review E 64: 051916-1 to 9.

en.wikipedia.org/wiki/Electroencephalography

Reference List 3

U.S. Pat. Nos. and Pub. application Nos. 4,862,359; 5,027,817; 5,198,977; 5,230,346; 5,269,315; 5,309,923; 5,325,862; 5,331,970; 5,845,639; 6,042,548; 6,080,164; 6,088,611; 6,097,980; 6,144,872; 5,546,943; 5,568,816; 5,662,109; 5,724,987; 5,797,853; 5,840,040; 6,161,031; 6,171,239; 6,240,308; 6,241,686; 6,280,393; 6,309,361; 6,319,205; 6,322,515; 6,356,781; 6,370,414; 6,377,833; 6,385,479; 6,390,979; 6,402,689; 6,419,629; 6,466,816; 6,490,472; 6,526,297; 6,527,715; 6,530,884; 6,547,746; 6,551,243; 6,553,252; 6,622,036; 6,644,976; 6,648,880; 6,663,571; 6,684,098; 6,697,660; 6,728,564; 6,740,032; 6,743,167; 6,773,400; 6,907,280; 6,947,790; 6,950,698; 6,963,770; 6,963,771; 6,996,261; 7,010,340; 7,011,814; 7,022,083; 7,092,748; 7,104,947; 7,105,824; 7,120,486; 7,130,673; 7,171,252; 7,177,675; 7,231,245; 7,254,500; 7,283,861; 7,286,871; 7,338,455; 7,346,395; 7,378,056; 7,461,045; 7,489,964; 7,490,085; 7,499,745; 7,510,699; 7,539,528; 7,547,284; 7,565,193; 7,567,693; 7,577,472; 7,613,502; 7,627,370; 7,647,098; 7,653,433; 7,697,979; 7,729,755; 7,754,190; 7,756,568; 7,766,827; 7,769,431; 7,778,692; 7,787,937; 7,899,524; 7,904,139; 7,904,144; 7,933,645; 7,962,204; 7,983,740; 7,787,946; 7,794,403; 7,831,305; 7,840,250; 7,856,264; 7,860,552; 7,986,991; 8,000,773; 8,000,793; 8,002,553; 8,014,847; 8,036,434;

TABLE 1-continued 8,065,360; 8,069,125; 8,086,296; 8,121,694; 8,190,248; 8,190,264;
8,197,437; 8,224,433; 8,233,682; 8,233,965; 8,236,038; 8,262,714;
8,280,514; 8,295,914; 8,306,607; 8,306,610; 8,313,441; 8,326,433;
8,337,404; 8,346,331; 8,346,342; 8,356,004; 8,358,818; 8,364,271;
8,380,289; 8,380,290; 8,380,314; 8,391,942; 8,391,956; 8,423,125;
8,425,583; 8,429,225; 8,445,851; 8,457,746; 8,467,878; 8,473,024;
8,498,708; 8,509,879; 8,527,035; 8,532,756; 8,538,513; 8,543,189;
8,554,325; 8,562,951; 8,571,629; 8,586,932; 8,591,419; 8,606,349;
8,606,356; 8,615,479; 8,626,264; 8,626,301; 8,632,750; 8,644,910;
8,655,817; 8,657,756; 8,666,478; 8,679,009; 8,684,926; 8,690,748;
8,696,722; 8,706,205; 8,706,241; 8,706,518; 8,712,512; 8,717,430;
8,725,669; 8,738,395; 8,761,869; 8,761,889; 8,768,022; 8,805,516;
8,814,923; 8,831,731; 8,834,546; 8,838,227; 8,849,392; 8,849,632;
8,852,103; 8,855,773; 8,858,440; 8,868,174; 8,888,702; 8,915,741;
8,918,162; 8,938,289; 8,938,290; 8,951,189; 8,951,192; 8,956,277;
8,965,513; 8,977,362; 8,989,836; 8,998,828; 9,005,126; 9,020,576;
9,022,936; 9,026,217; 9,026,218; 9,028,412; 9,033,884; 9,037,224;
9,042,201; 9,050,470; 9,067,052; 9,072,905; 9,084,896; 9,089,400;
9,089,683; 9,092,556; 9,095,266; 9,101,276; 9,107,595; 9,116,835;
9,133,024; 9,144,392; 9,149,255; 9,155,521; 9,167,970; 9,167,976;
9,167,977; 9,167,978; 9,171,366; 9,173,609; 9,179,850; 9,179,854;
9,179,858; 9,179,875; 9,192,300; 9,198,637; 9,198,707; 9,204,835;
9,211,077; 9,211,212; 9,213,074; 9,242,067; 9,247,890; 9,247,924;
9,248,288; 9,254,097; 9,254,383; 9,268,014; 9,268,015; 9,271,651;
9,271,674; 9,282,930; 9,289,143; 9,302,110; 9,308,372; 9,320,449;
9,322,895; 9,326,742; 9,332,939; 9,336,611; 9,339,227; 9,357,941;
9,367,131; 9,370,309; 9,375,145; 9,375,564; 9,387,320; 9,395,425;
9,402,558; 9,403,038; 9,414,029; 9,436,989; 9,440,064; 9,463,327;
9,470,728; 9,471,978; 9,474,852; 9,486,632; 9,492,313; 9,560,967;
9,579,048; 9,592,409; 9,597,493; 9,597,494; 9,615,789; 9,616,166;
9,655,573; 9,655,669; 9,662,049; 9,662,492; 9,669,185; 9,675,292;
9,682,232; 9,687,187; 9,707,396; 9,713,433; 9,713,444;
20010020127; 20010021800; 20010051774; 20020005784;
20020016552; 20020017994; 20020042563; 20020058867;
20020099273; 20020099295; 20020103428; 20020103429;
20020128638; 20030001098; 20030009096; 20030013981;
20030032870; 20030040660; 20030068605; 20030074032;
20030093004; 20030093005; 20030120140; 20030128801;
20030135128; 20030153818; 20030163027; 20030163028;
20030181821; 20030187359; 20030204135; 20030225335;
20030236458; 20040030585; 20040059241; 20040072133;
20040077960; 20040092809; 20040096395; 20040097802;
20040116798; 20040122787; 20040122790; 20040144925;
20040204656; 20050004489; 20050007091; 20050027284;
20050033122; 20050033154; 20050033379; 20050079474;
20050079636; 20050106713; 20050107654; 20050119547;
20050131311; 20050136002; 20050159670; 20050159671;
20050182456; 20050192514; 20050222639; 20050283053;
20060004422; 20060015034; 20060018525; 20060036152;
20060036153; 20060051814; 20060052706; 20060058683;
20060074290; 20060074298; 20060078183; 20060084858;
20060100526; 20060111644; 20060116556; 20060122481;
20060129324; 20060173510; 20060189866; 20060241373;
20060241382; 20070005115; 20070007454; 20070008172;
20070015985; 20070032737; 20070055145; 20070100251;
20070138886; 20070179534; 20070184507; 20070191704;
20070191727; 20070203401; 20070239059; 20070250138;
20070255135; 20070293760; 20070299370; 20080001600;
20080021332; 20080021340; 20080033297; 20080039698;
20080039737; 20080042067; 20080058664; 20080091118;
20080097197; 20080123927; 20080125669; 20080128626;
20080154126; 20080167571; 20080221441; 20080230702;
20080230705; 20080249430; 20080255949; 20080275340;
20080306365; 20080311549; 20090012387; 20090018407;
20090018431; 20090018462; 20090024050; 20090048507;
20090054788; 20090054800; 20090054958; 20090062676;
20090078875; 20090082829; 20090099627; 20090112117;
20090112273; 20090112277; 20090112278; 20090112279;
20090112280; 20090118622; 20090131995; 20090137923;
20090156907; 20090156955; 20090157323; 20090157481;
20090157482; 20090157625; 20090157662; 20090157751;
20090157813; 20090163777; 20090164131; 20090164132;
20090171164; 20090172540; 20090177050; 20090179642;
20090191131; 20090209845; 20090216091; 20090220429;
20090221928; 20090221930; 20090246138; 20090264785;
20090267758; 20090270694; 20090287271; 20090287272;
20090287273; 20090287274; 20090287467; 20090292180;
20090292713; 20090292724; 20090299169; 20090304582;
20090306531; 20090306534; 20090318773; 20090318794;
20100021378; 20100030073; 20100036233; 20100036453;

TABLE 1-continued

20100041962; 20100042011; 20100049276; 20100069739;
20100069777; 20100076274; 20100082506; 20100087719;
20100094154; 20100094155; 20100099975; 20100106043;
20100113959; 20100114193; 20100114237; 20100130869;
20100143256; 20100163027; 20100163028; 20100163035;
20100168525; 20100168529; 20100168602; 20100189318;
20100191095; 20100191124; 20100204748; 20100248275;
20100249573; 20100261993; 20100298735; 20100324441;
20110004115; 20110004412; 20110009777; 20110015515;
20110015539; 20110028859; 20110034821; 20110046491;
20110054345; 20110054562; 20110077503; 20110092800;
20110092882; 20110112394; 20110112426; 20110119212;
20110125048; 20110125238; 20110129129; 20110144521;
20110160543; 20110160607; 20110160608; 20110161011;
20110178359; 20110178441; 20110178442; 20110207988;
20110208094; 20110213200; 20110218405; 20110230738;
20110257517; 20110263962; 20110263968; 20110270074;
20110270914; 20110275927; 20110295143; 20110295166;
20110301448; 20110306845; 20110306846; 20110307029;
20110313268; 20110313487; 20120004561; 20120021394;
20120022343; 20120022884; 20120035765; 20120046531;
20120046971; 20120053449; 20120053483; 20120078327;
20120083700; 20120108998; 20120130228; 20120130229;
20120149042; 20120150545; 20120163689; 20120165899;
20120165904; 20120197163; 20120215114; 20120219507;
20120226091; 20120226185; 20120232327; 20120232433;
20120245493; 20120253219; 20120253434; 20120265267;
20120271148; 20120271151; 20120271376; 20120283502;
20120283864; 20120296241; 20120296253; 20120296569;
20120302867; 20120310107; 20120310298; 20120316793;
20130012804; 20130063434; 20130066350; 20130066391;
20130066394; 20130072780; 20130079621; 20130085678;
20130096441; 20130096454; 20130102897; 20130109996;
20130110616; 20130116561; 20130131755; 20130138177;
20130172716; 20130178693; 20130184728; 20130188854;
20130204085; 20130211238; 20130226261; 20130231580;
20130238063; 20130245422; 20130245424; 20130245486;
20130261506; 20130274586; 20130281879; 20130281890;
20130289386; 20130304153; 20140000630; 20140005518;
20140031703; 20140057232; 20140058241; 20140058292;
20140066763; 20140081115; 20140088377; 20140094719;
20140094720; 20140111335; 20140114207; 20140119621;
20140128763; 20140135642; 20140148657; 20140151563;
20140155952; 20140163328; 20140163368; 20140163409;
20140171749; 20140171757; 20140171819; 20140180088;
20140180092; 20140180093; 20140180094; 20140180095;
20140180096; 20140180097; 20140180099; 20140180100;
20140180112; 20140180113; 20140180176; 20140180177;
20140193336; 20140194726; 20140200414; 20140211593;
20140228649; 20140228702; 20140243614; 20140243652;
20140243714; 20140249360; 20140249445; 20140257073;
20140270438; 20140275807; 20140275851; 20140275891;
20140276013; 20140276014; 20140276187; 20140276702;
20140279746; 20140296646; 20140296655; 20140303425;
20140303486; 20140316248; 20140323849; 20140330268;
20140330394; 20140335489; 20140336489; 20140340084;
20140343397; 20140357962; 20140364721; 20140371573;
20140378830; 20140383941; 20150011866; 20150011877;
20150018665; 20150018905; 20150024356; 20150025408;
20150025422; 20150025610; 20150029087; 20150033245;
20150033258; 20150033259; 20150033262; 20150033266;
20150035959; 20150038812; 20150038822; 20150038869;
20150039066; 20150073237; 20150080753; 20150088120;
20150119658; 20150119689; 20150119698; 20150140528;
20150141529; 20150141773; 20150150473; 20150151142;
20150157266; 20150165239; 20150174418; 20150182417;
20150196800; 20150201879; 20150208994; 20150219732;
20150223721; 20150227702; 20150230744; 20150246238;
20150247921; 20150257700; 20150290420; 20150297106;
20150297893; 20150305799; 20150305800; 20150305801;
20150306340; 20150313540; 20150317796; 20150320591;
20150327813; 20150335281; 20150335294; 20150339363;
20150343242; 20150359431; 20150360039; 20160001065;
20160001096; 20160001098; 20160008620; 20160008632;
20160051289; 20160022165; 20160022167; 20160022168;
20160022206; 20160027342; 20160029946; 20160029965;
20160038049; 20160038559; 20160048659; 20160051161;
20160051162; 20160058354; 20160058392; 20160066828;
20160066838; 20160081613; 20160100769; 20160120480;
20160128864; 20160143541; 20160143574; 20160151018;

20160151628; 20160157828; 20160158553; 20160166219;
20160184599; 20160196393; 20160199241; 20160203597;
20160206380; 20160206871; 20160206877; 20160213276;
20160235324; 20160235980; 20160235983; 20160239966;
20160239968; 20160245670; 20160245766; 20160270723;
20160278687; 20160287118; 20160287436; 20160296746;
20160302720; 20160303397; 20160303402; 20160320210;
20160339243; 20160341684; 20160361534; 20160366462;
20160371721; 20170021161; 20170027539; 20170032098;
20170039706; 20170042474; 20170043167; 20170065349;
20170079538; 20170080320; 20170085855; 20170086729;
20170086763; 20170087367; 20170091418; 20170112403;
20170112427; 20170112446; 20170112577; 20170147578;
20170151435; 20170160360; 20170164861; 20170164862;
20170164893; 20170164894; 20170172527; 20170173262;
20170185714; 20170188862; 20170188866; 20170188868;
20170188869; 20170188932; 20170189691; 20170196501; and
20170202633.

Allen, Philip B., et al. High-temperature superconductivity.
Springer Science & Business Media, 2012;
Fausti, Daniele, et al. "Light-induced superconductivity in a
stripe-ordered cuprate." Science 331.6014 (2011): 189-191;
Inoue, Mitsuteru, et al. "Investigating the use of magnonic
crystals as extremely sensitive magnetic field sensors at room
temperature." Applied Physics Letters 98.13 (2011): 132511;
Kaiser, Stefan, et al. "Optically induced coherent transport far
above Tc in underdoped YBa2 Cu306+ δ." Physical Review B 89.18
(2014): 184516;
Malik, M. A., and B. A. Malik. "High Temperature
Superconductivity: Materials, Mechanism and Applications."
Bulgarian J. Physics 41.4 (2014).
Mankowsky, Roman, et al. "Nonlinear lattice dynamics as a
basis for enhanced superconductivity in YBa2Cu3O6. 5." arXiv
preprint arXiv: 1405.2266 (2014);
Mcfetridge, Grant. "Room temperature superconductor." U.S.
Pub. application No. 20020006875.
Mitrano, Matteo, et al. "Possible light-induced
superconductivity in K3C60 at high temperature." Nature 530.7591
(2016): 461-464;
Mourachkine, Andrei. Room-temperature superconductivity.
Cambridge Int Science Publishing, 2004;
Narlikar, Anant V., ed. High Temperature Superconductivity 2.
Springer Science & Business Media, 2013;
Pickett, Warren E. "Design for a room-temperature
superconductor." J. superconductivity and novel magnetism 19.3
(2006): 291-297;
Sleight, Arthur W. "Room temperature superconductors."
Accounts of chemical research 28.3 (1995): 103-108.
Hämäläinen, Matti; Hari, Riitta; Ilmoniemi, Risto J.; Knuutila,
Jukka; Lounasmaa, Olli V. (1993). "Magnetoencephalography-theory,
instrumentation, and applications to noninvasive studies of the
working human brain". Reviews of Modern Physics. 65 (2): 413-497.
ISSN 0034-6861. doi: 10.1103/RevModPhys.65.413.
Reference List 4
U.S. Pat. Nos. and Pub. application Nos. 5,293,187; 5,422,689;
5,447,166; 5,491,492; 5,546,943; 5,622,168; 5,649,061; 5,720,619;
5,740,812; 5,983,129; 6,050,962; 6,092,058; 6,149,586; 6,325,475;
6,377,833; 6,394,963; 6,428,490; 6,482,165; 6,503,085; 6,520,921;
6,522,906; 6,527,730; 6,556,695; 6,565,518; 6,652,458; 6,652,470;
6,701,173; 6,726,624; 6,743,182; 6,746,409; 6,758,813; 6,843,774;
6,896,655; 6,996,261; 7,037,260; 7,070,571; 7,107,090; 7,120,486;
7,212,851; 7,215,994; 7,260,430; 7,269,455; 7,280,870; 7,392,079;
7,407,485; 7,463,142; 7,478,108; 7,488,294; 7,515,054; 7,567,693;
7,647,097; 7,740,592; 7,751,877; 7,831,305; 7,856,264; 7,881,780;
7,970,734; 7,972,278; 7,974,787; 7,991,461; 8,012,107; 8,032,486;
8,033,996; 8,060,194; 8,095,209; 8,209,224; 8,239,030; 8,262,714;
8,320,649; 8,358,818; 8,376,965; 8,380,316; 8,386,312; 8,386,313;
8,392,250; 8,392,253; 8,392,254; 8,392,255; 8,437,844; 8,464,288;
8,475,371; 8,483,816; 8,494,905; 8,517,912; 8,533,042; 8,545,420;
8,560,041; 8,655,428; 8,672,852; 8,682,687; 8,684,742; 8,694,157;
8,706,241; 8,706,518; 8,738,395; 8,753,296; 8,762,202; 8,764,673;
8,768,022; 8,788,030; 8,790,255; 8,790,297; 8,821,376; 8,838,247;
8,864,310; 8,872,640; 8,888,723; 8,915,871; 8,938,289; 8,938,301;
8,942,813; 8,955,010; 8,955,974; 8,958,882; 8,964,298; 8,971,936;
8,989,835; 8,992,230; 8,998,828; 9,004,687; 9,060,671; 9,101,279;
9,135,221; 9,142,145; 9,165,472; 9,173,582; 9,179,855; 9,208,558;
9,215,978; 9,232,984; 9,241,665; 9,242,067; 9,254,099; 9,271,660;
9,275,191; 9,282,927; 9,292,858; 9,292,920; 9,320,450; 9,326,705;
9,330,206; 9,357,941; 9,396,669; 9,398,873; 9,414,780; 9,414,907;
9,424,761; 9,445,739; 9,445,763; 9,451,303; 9,451,899; 9,454,646;

9,462,977; 9,468,541; 9,483,117; 9,492,120; 9,504,420; 9,504,788;
9,526,419; 9,541,383; 9,545,221; 9,545,222; 9,545,225; 9,560,967;
9,560,984; 9,563,740; 9,582,072; 9,596,224; 9,615,746; 9,622,702;
9,622,703; 9,626,756; 9,629,568; 9,642,699; 9,649,030; 9,651,368;
9,655,573; 9,668,694; 9,672,302; 9,672,617; 9,682,232; 9,693,734;
9,694,155; 9,704,205; 9,706,910; 9,710,788; RE44408; RE45766;
20020024450; 20020103428; 20020103429; 20020112732;
20020128540; 20030028081; 20030028121; 20030070685;
20030083596; 20030100844; 20030120172; 20030149351;
20030158496; 20030158497; 20030171658; 20040019257;
20040024287; 20040068172; 20040092809; 20040101146;
20050019734; 20050025704; 20050038354; 20050113713;
20040116784; 20040143170; 20040267152; 20050010091;
20050124851; 20050148828; 20050228785; 20050240253;
20050245796; 20050267343; 20050267344; 20050283053;
20060020184; 20060061544; 20060078183; 20060087746;
20060102171; 20060129277; 20060161218; 20060189866;
20060200013; 20060241718; 20060252978; 20060252979;
20070050715; 20070179534; 20070191704; 20070238934;
20070273611; 20070282228; 20070299371; 20080004550;
20080009772; 20080058668; 20080081963; 20080119763;
20080123927; 20080132383; 20080228239; 20080234113;
20080234601; 20080242521; 20080255949; 20090018419;
20090058660; 20090062698; 20090076406; 20090099474;
20090112523; 20090221928; 20090267758; 20090270687;
20090270688; 20090270692; 20090270693; 20090270694;
20090270786; 20090281400; 20090287108; 20090297000;
20090299169; 20090311655; 20090312808; 20090312817;
20090318794; 20090326604; 20100004977; 20100010289;
20100010366; 20100041949; 20100069739; 20100069780;
20100163027; 20100163028; 20100163035; 20100165593;
20100168525; 20100168529; 20100168602; 20100268055;
20100293115; 20110004412; 20110009777; 20110015515;
20110015539; 20110043759; 20110054272; 20110077548;
20110092882; 20110105859; 20110130643; 20110172500;
20110218456; 20110256520; 20110270074; 20110301488;
20110307079; 20120004579; 20120021394; 20120036004;
20120071771; 20120108909; 20120108995; 20120136274;
20120150545; 20120203130; 20120262558; 20120271377;
20120310106; 20130012804; 20130046715; 20130063434;
20130063550; 20130080127; 20130120246; 20130127980;
20130185144; 20130189663; 20130204085; 20130211238;
20130226464; 20130242262; 20130245424; 20130281759;
20130289360; 20130293844; 20130308099; 20130318546;
20140058528; 20140155714; 20140171757; 20140200432;
20140214335; 20140221866; 20140243608; 20140243614;
20140243652; 20140276130; 20140276944; 20140288614;
20140296750; 20140300532; 20140303508; 20140304773;
20140313303; 20140315169; 20140316191; 20140316192;
20140316235; 20140316248; 20140323899; 20140335489;
20140343408; 20140347491; 20140350353; 20140350431;
20140364721; 20140378810; 20150002815; 20150003698;
20150003699; 20150005640; 20150005644; 20150006186;
20150012111; 20150039869; 20150045606; 20150051663;
20150099946; 20150112409; 20150120007; 20150124220;
20150126845; 20150126873; 20150133812; 20150141773;
20150145676; 20150154889; 20150174362; 20150196800;
20150213191; 20150223731; 20150234477; 20150235088;
20150235370; 20150235441; 20150235447; 20150241705;
20150241959; 20150242575; 20150242943; 20150243100;
20150243105; 20150243106; 20150247723; 20150247975;
20150247976; 20150248169; 20150248170; 20150248787;
20150248788; 20150248789; 20150248791; 20150248792;
20150248793; 20150290453; 20150290454; 20150305685;
20150306340; 20150309563; 20150313496; 20150313539;
20150324692; 20150325151; 20150335288; 20150339363;
20150351690; 20150356497; 20150366504; 20150366656;
20150366659; 20150369864; 20150370320; 20160000354;
20160004298; 20160005320; 20160007915; 20160008620;
20160012749; 20160015289; 20160022167; 20160022206;
20160029946; 20160029965; 20160038069; 20160051187;
20160051793; 20160066838; 20160073886; 20160077547;
20160078780; 20160106950; 20160112684; 20160120436;
20160143582; 20160166219; 20160167672; 20160176053;
20160180054; 20160198950; 20160199577; 20160202755;
20160216760; 20160220439; 20160228640; 20160232625;
20160232811; 20160235323; 20160239084; 20160248994;
20160249826; 20160256108; 20160267809; 20160270656;
20160287157; 20160302711; 20160306942; 20160313798;
20160317060; 20160317383; 20160324478; 20160324580;

20160334866; 20160338644; 20160338825; 20160339300;
20160345901; 20160357256; 20160360970; 20160363483;
20170000324; 20170000325; 20170000326; 20170000329;
20170000330; 20170000331; 20170000332; 20170000333;
20170000334; 20170000335; 20170000337; 20170000340;
20170000341; 20170000342; 20170000343; 20170000345;
20170000454; 20170000683; 20170001032; 20170006931;
20170007111; 20170007115; 20170007116; 20170007122;
20170007123; 20170007165; 20170007182; 20170007450;
20170007799; 20170007843; 20170010469; 20170010470;
20170017083; 20170020447; 20170020454; 20170020627;
20170027467; 20170027651; 20170027812; 20170031440;
20170032098; 20170035344; 20170043160; 20170055900;
20170060298; 20170061034; 20170071523; 20170071537;
20170071546; 20170071551; 20170080320; 20170086729;
20170095157; 20170099479; 20170100540; 20170103440;
20170112427; 20170112671; 20170113046; 20170113056;
20170119994; 20170135597; 20170135633; 20170136264;
20170136265; 20170143249; 20170143442; 20170148340;
20170156662; 20170162072; 20170164876; 20170164878;
20170168568; 20170173262; 20170173326; 20170177023;
20170188947; 20170202633; 20170209043; 20170209094; and
20170209737.
Reference List 5
U.S. Pat. Nos. and Pub. application Nos. 3,951,134; 4,437,064;
4,591,787; 4,613,817; 4,689,559; 4,693,000; 4,700,135; 4,733,180;
4,736,751; 4,749,946; 4,753,246; 4,761,611; 4 771,239; 4,801,882;
4,862,359; 4,913,152; 4,937,525; 4,940,058; 4,947,480; 4,949,725;
4,951,674; 4,974,602; 4,982,157; 4,983,912; 4,996,479; 5,008,622;
5,012,190; 5,020,538; 5,061,680; 5,092,835; 5,095,270; 5,126,315;
5,158,932; 5,159,703; 5,159,928; 5,166,614; 5,187,327; 5,198,977;
5,213,338; 5,241,967; 5,243,281; 5,243,517; 5,263,488; 5,265,611;
5,269,325; 5,282,474; 5,283,523; 5,291,888; 5,303,705; 5,307,807;
5,309,095; 5,311,129; 5,323,777; 5,325,862; 5,326,745; 5,339,811;
5,417,211; 5,418,512; 5,442,289; 5,447,154; 5,458,142; 5,469,057;
5,476,438; 5,496,798; 5,513,649; 5,515,301; 5,552,375; 5,579,241;
5,594,849; 5,600,243; 5,601,081; 5,617,856; 5,626,145; 5,656,937;
5,671,740; 5,682,889; 5,701,909; 5,706,402; 5,706,811; 5,729,046;
5,743,854; 5,743,860; 5,752,514; 5,752,911; 5,755,227; 5,761,332;
5,762,611; 5,767,043; 5,771,261; 5,771,893; 5,771,894; 5,797,853;
5,813,993; 5,815,413; 5,842,986; 5,857,978; 5,885,976; 5,921,245;
5,938,598; 5,938,688; 5,970,499; 6,002,254; 6,011,991; 6,023,161;
6,066,084; 6,069,369; 6,080,164; 6,099,319; 6,144,872; 6,154,026;
6,155,966; 6,167,298; 6,167,311; 6,195,576; 6,230,037; 6,239,145;
6,263,189; 6,290,638; 6,354,087; 6,356,079; 6,370,414; 6,374,131;
6,385,479; 6,418,344; 6,442,948; 6,470,220; 6,488,617; 6,516,246;
6,526,415; 6,529,759; 6,538,436; 6,539,245; 6,539,263; 6,544,170;
6,547,746; 6,557,558; 6,587,729; 6,591,132; 6,609,030; 6,611,698;
6,648,822; 6,658,287; 6,665,552; 6,665,553; 6,665,562; 6,684,098;
6,687,525; 6,695,761; 6,697,660; 6,708,051; 6,708,064; 6,708,184;
6,725,080; 6,735,460; 6,774,929; 6,785,409; 6,795,724; 6,804,661;
6,815,949; 6,853,186; 6,856,830; 6,873,872; 6,876,196; 6,885,192;
6,907,280; 6,926,921; 6,947,790; 6,978,179; 6,980,863; 6,983,184;
6,983,264; 6,996,261; 7,022,083; 7,023,206; 7,024,247; 7,035,646;
7,038,450; 7,039,266; 7,039,547; 7,053,610; 7,062,391; 7,092,748;
7,105,824; 7,116,102; 7,120,486; 7,130,675; 7,145,333; 7,171,339;
7,176,680; 7,177,675; 7,183,381; 7,186,209; 7,187,169; 7,190,826;
7,193,413; 7,196,514; 7,197,352; 7,199,708; 7,209,787; 7,218,104;
7,222,964; 7,224,282; 7,228,178; 7,231,254; 7,242,984; 7,254,500;
7,258,659; 7,269,516; 7,277,758; 7,280,861; 7,286,871; 7,313,442;
7,324,851; 7,334,892; 7,338,171; 7,340,125; 7,340,289; 7,346,395;
7,353,064; 7,353,065; 7,369,896; 7,371,365; 7,376,459; 7,394,246;
7,400,984; 7,403,809; 7,403,820; 7,409,321; 7,418,290; 7,420,033;
7,437,196; 7,440,789; 7,453,263; 7,454,387; 7,457,653; 7,461,045;
7,462,155; 7,463,024; 7,466,132; 7,468,350; 7,482,298; 7,489,964;
7,502,720; 7,539,528; 7,539,543; 7,553,810; 7,565,200; 7,565,809;
7,567,693; 7,570,054; 7,573,264; 7,573,268; 7,580,798; 7,603,174;
7,608,579; 7,613,502; 7,613,519; 7,613,520; 7,620,456; 7,623,927;
7,623,928; 7,625,340; 7,627,370; 7,647,098; 7,649,351; 7,653,433;
7,672,707; 7,676,263; 7,678,767; 7,697,979; 7,706,871; 7,715,894;
7,720,519; 7,729,740; 7,729,773; 7,733,973; 7,734,340; 7,737,687;
7,742,820; 7,746,979; 7,747,325; 7,747,326; 7,747,551; 7,756,564;
7,763,588; 7,769,424; 7,771,341; 7,792,575; 7,800,493; 7,801,591;
7,801,686; 7,831,305; 7,834,627; 7,835,787; 7,840,039; 7,840,248;
7,840,250; 7,853,329; 7,856,264; 7,860,552; 7,873,411; 7,881,760;
7,881,770; 7,882,135; 7,891,814; 7,892,764; 7,894,903; 7,895,033;
7,904,139; 7,904,507; 7,908,009; 7,912,530; 7,917,221; 7,917,225;
7,929,693; 7,930,035; 7,932,225; 7,933,727; 7,937,152; 7,945,304;
7,962,204; 7,974,787; 7,986,991; 7,988,969; 8,000,767; 8,000,794;
8,001,179; 8,005,894; 8,010,178; 8,014,870; 8,027,730; 8,029,553;

8,032,209; 8,036,736; 8,055,591; 8,059,879; 8,065,360; 8,069,125;
8,073,631; 8,082,215; 8,083,786; 8,086,563; 8,116,874; 8,116,877;
8,121,694; 8,121,695; 8,150,523; 8,150,796; 8,155,726; 8,160,273;
8,185,382; 8,190,248; 8,190,264; 8,195,593; 8,209,224; 8,212,556;
8,222,378; 8,224,433; 8,229,540; 8,239,029; 8,244,552; 8,244,553;
8,248,069; 8,249,316; 8,270,814; 8,280,514; 8,285,351; 8,290,596;
8,295,934; 8,301,222; 8,301,257; 8,303,636; 8,304,246; 8,305,078;
8,308,646; 8,315,703; 8,334,690; 8,335,715; 8,335,716; 8,337,404;
8,343,066; 8,346,331; 8,350,804; 8,354,438; 8,356,004; 8,364,271;
8,374,412; 8,374,696; 8,380,314; 8,380,316; 8,380,658; 8,386,312;
8,386,313; 8,388,530; 8,392,250; 8,392,251; 8,392,253; 8,392,254;
8,392,255; 8,396,545; 8,396,546; 8,396,744; 8,401,655; 8,406,838;
8,406,848; 8,412,337; 8,423,144; 8,423,297; 8,429,225; 8,431,537;
8,433,388; 8,433,414; 8,433,418; 8,439,845; 8,444,571; 8,445,021;
8,447,407; 8,456,164; 8,457,730; 8,463,374; 8,463,378; 8,463,386;
8,463,387; 8,464,288; 8,467,878; 8,473,345; 8,483,795; 8,484,081;
8,487,760; 8,492,336; 8,494,610; 8,494,857; 8,494,905; 8,498,697;
8,509,904; 8,519,705; 8,527,029; 8,527,035; 8,529,463; 8,532,756;
8,532,757; 8,533,042; 8,538,513; 8,538,536; 8,543,199; 8,548,786;
8,548,852; 8,553,956; 8,554,325; 8,559,645; 8,562,540; 8,562,548;
8,565,606; 8,568,231; 8,571,629; 8,574,279; 8,586,019; 8,587,304;
8,588,933; 8,591,419; 8,593,141; 8,600,493; 8,600,696; 8,603,790;
8,606,592; 8,612,005; 8,613,695; 8,613,905; 8,614,254; 8,614,873;
8,615,293; 8,615,479; 8,615,664; 8,618,799; 8,626,264; 8,628,328;
8,635,105; 8,648,017; 8,652,189; 8,655,428; 8,655,437; 8,655,817;
8,658,149; 8,660,649; 8,666,099; 8,679,009; 8,682,441; 8,690,748;
8,693,765; 8,700,167; 8,703,114; 8,706,205; 8,706,206; 8,706,241;
8,706,518; 8,712,512; 8,716,447; 8,721,695; 8,725,243; 8,725,668;
8,725,669; 8,725,796; 8,731,650; 8,733,290; 8,738,395; 8,762,065;
8,762,202; 8,768,427; 8,768,447; 8,781,197; 8,781,597; 8,786,624;
8,798,717; 8,814,923; 8,815,582; 8,825,167; 8,838,225; 8,838,247;
8,845,545; 8,849,390; 8,849,392; 8,855,775; 8,858,440; 8,868,173;
8,874,439; 8,888,702; 8,893,120; 8,903,494; 8,907,668; 8,914,119;
8,918,176; 8,922,376; 8,933,696; 8,934,965; 8,938,289; 8,948,849;
8,951,189; 8,951,192; 8,954,293; 8,955,010; 8,961,187; 8,974,365;
8,977,024; 8,977,110; 8,977,362; 8,993,623; 9,002,458; 9,014,811;
9,015,087; 9,020,576; 9,026,194; 9,026,218; 9,026,372; 9,031,658;
9,034,055; 9,034,923; 9,037,224; 9,042,074; 9,042,201; 9,042,988;
9,044,188; 9,053,516; 9,063,183; 9,064,036; 9,069,031; 9,072,482;
9,074,976; 9,079,940; 9,081,890; 9,095,266; 9,095,303; 9,095,618;
9,101,263; 9,101,276; 9,102,717; 9,113,801; 9,113,803; 9,116,201;
9,125,581; 9,125,788; 9,138,156; 9,142,185; 9,155,373; 9,161,715;
9,167,979; 9,173,609; 9,179,854; 9,179,875; 9,183,351; 9,192,300;
9,198,621; 9,198,707; 9,204,835; 9,211,076; 9,211,077; 9,213,074;
9,229,080; 9,230,539; 9,233,244; 9,238,150; 9,241,665; 9,242,067;
9,247,890; 9,247,911; 9,248,003; 9,248,288; 9,249,200; 9,249,234;
9,251,566; 9,254,097; 9,254,383; 9,259,482; 9,259,591; 9,261,573;
9,265,943; 9,265,965; 9,271,679; 9,280,784; 9,283,279; 9,284,353;
9,285,249; 9,289,595; 9,302,069; 9,309,296; 9,320,900; 9,329,758;
9,331,841; 9,332,939; 9,333,334; 9,336,535; 9,336,611; 9,339,227;
9,345,609; 9,351,651; 9,357,240; 9,357,298; 9,357,970; 9,358,393;
9,359,449; 9,364,462; 9,365,628; 9,367,738; 9,368,018; 9,370,309;
9,370,667; 9,375,573; 9,377,348; 9,377,515; 9,381,352; 9,383,208;
9,392,955; 9,394,347; 9,395,425; 9,396,669; 9,401,033; 9,402,558;
9,403,038; 9,405,366; 9,410,885; 9,411,033; 9,412,233; 9,415,222;
9,418,368; 9,421,373; 9,427,474; 9,438,650; 9,440,070; 9,445,730;
9,446,238; 9,448,289; 9,451,734; 9,451,899; 9,458,208; 9,460,400;
9,462,733; 9,463,327; 9,464,133; 9,471,978; 9,474,852; 9,480,845;
9,480,854; 9,483,117; 9,486,381; 9,486,389; 9,486,618; 9,486,632;
9,492,114; 9,495,684; 9,497,017; 9,498,134; 9,498,634; 9,500,722;
9,505,817; 9,517,031; 9,517,222; 9,519,981; 9,521,958; 9,534,044;
9,538,635; 9,539,118; 9,556,487; 9,558,558; 9,560,458; 9,560,967;
9,560,984; 9,560,986; 9,563,950; 9,568,564; 9,572,996; 9,579,035;
9,579,048; 9,582,925; 9,584,928; 9,588,203; 9,588,490; 9,592,384;
9,600,138; 9,604,073; 9,612,295; 9,618,591; 9,622,660; 9,622,675;
9,630,008; 9,642,553; 9,642,554; 9,643,019; 9,646,248; 9,649,501;
9,655,573; 9,659,186; 9,664,856; 9,665,824; 9,665,987; 9,675,292;
9,681,814; 9,682,232; 9,684,051; 9,685,600; 9,687,562; 9,694,178;
9,694,197; 9,713,428; 9,713,433; 9,713,444; 9,713,712; D627476;
RE44097; RE46209; 20010009975; 20020103428; 20020103429;
20020158631; 20020173714; 20030004429; 20030013981;
20030018277; 20030081818; 20030093004; 20030097159;
20030105408; 20030158495; 20030199749; 20040019370;
20040034299; 20040092809; 20040127803; 20040186542;
20040193037; 20040210127; 20040210156; 20040263162;
20050015205; 20050033154; 20050043774; 20050059874;
20050216071; 20050256378; 20050283053; 20060074822;
20060078183; 20060100526; 20060135880; 20060225437;
20070005391; 20070036355; 20070038067; 20070043392;
20070049844; 20070083128; 20070100251; 20070165915;

TABLE 1-continued

20070167723; 20070191704; 20070197930; 20070239059;
20080001600; 20080021340; 20080091118; 20080167571;
20080249430; 20080304731; 20090018432; 20090082688;
20090099783; 20090149736; 20090179642; 20090216288;
20090299169; 20090312624; 20090318794; 20090319001;
20090319004; 20100010366; 20100030097; 20100049482;
20100056276; 20100069739; 20100092934; 20100094155;
20100113959; 20100131034; 20100174533; 20100197610;
20100219820; 20110015515; 20110015539; 20110046491;
20110082360; 20110110868; 20110150253; 20110182501;
20110217240; 20110218453; 20110270074; 20110301448;
20120021394; 20120143104; 20120150262; 20120191542;
20120232376; 20120249274; 20120253168; 20120271148;
20130012804; 20130013667; 20130066394; 20130072780;
20130096453; 20130150702; 20130165766; 20130211238;
20130245424; 20130251641; 20130255586; 20130304472;
20140005518; 20140058241; 20140062472; 20140077612;
20140101084; 20140121565; 20140135873; 20140142448;
20140155730; 20140159862; 20140206981; 20140243647;
20140243652; 20140245191; 20140249445; 20140249447;
20140271483; 20140275891; 20140276013; 20140276014;
20140276187; 20140276702; 20140277582; 20140279746;
20140296733; 20140297397; 20140300532; 20140303424;
20140303425; 20140303511; 20140316248; 20140323899;
20140328487; 20140330093; 20140330394; 20140330580;
20140335489; 20140336489; 20140336547; 20140343397;
20140343882; 20140348183; 20140350380; 20140354278;
20140357507; 20140357932; 20140357935; 20140358067;
20140364721; 20140370479; 20140371573; 20140371611;
20140378815; 20140378830; 20150005840; 20150005841;
20150008916; 20150011877; 20150017115; 20150018665;
20150018702; 20150018705; 20150018706; 20150019266;
20150025422; 20150025917; 20150026446; 20150030220;
20150033363; 20150044138; 20150065838; 20150065845;
20150069846; 20150072394; 20150073237; 20150073249;
20150080695; 20150080703; 20150080753; 20150080985;
20150088024; 20150088224; 20150091730; 20150091791;
20150096564; 20150099962; 20150105844; 20150112403;
20150119658; 20150119689; 20150119698; 20150119745;
20150123653; 20150133811; 20150133812; 20150133830;
20150140528; 20150141529; 20150141773; 20150148619;
20150150473; 20150150475; 20150151142; 20150154721;
20150154764; 20150157271; 20150161738; 20150174403;
20150174418; 20150178631; 20150178978; 20150182417;
20150186923; 20150192532; 20150196800; 20150201879;
20150202330; 20150206051; 20150206174; 20150212168;
20150213012; 20150213019; 20150213020; 20150215412;
20150216762; 20150219729; 20150219732; 20150220830;
20150223721; 20150226813; 20150227702; 20150230719;
20150230744; 20150231330; 20150231395; 20150231405;
20150238104; 20150248615; 20150253391; 20150257700;
20150264492; 20150272461; 20150272465; 20150283393;
20150289813; 20150289929; 20150293004; 20150294074;
20150297108; 20150297139; 20150297444; 20150297719;
20150304048; 20150305799; 20150305800; 20150305801;
20150306057; 20150306390; 20150309582; 20150313496;
20150313971; 20150315554; 20150317447; 20150320591;
20150324544; 20150324692; 20150327813; 20150328330;
20150335281; 20150335294; 20150335876; 20150335877;
20150343242; 20150359431; 20150360039; 20150366503;
20150370325; 20150374250; 20160000383; 20160005235;
20160008489; 20160008598; 20160008620; 20160008632;
20160012011; 20160012583; 20160015673; 20160019434;
20160019693; 20160022165; 20160022168; 20160022207;
20160022981; 20160023016; 20160029958; 20160029959;
20160029998; 20160030666; 20160030834; 20160038049;
20160038559; 20160038770; 20160048659; 20160048948;
20160048965; 20160051161; 20160051162; 20160055236;
20160058322; 20160063207; 20160063883; 20160066838;
20160070436; 20160073916; 20160073947; 20160081577;
20160081793; 20160082180; 20160082319; 20160084925;
20160086622; 20160095838; 20160097824; 20160100769;
20160103487; 20160103963; 20160109851; 20160113587;
20160116472; 20160116553; 20160120432; 20160120436;
20160120480; 20160121074; 20160128589; 20160128632;
20160129249; 20160131723; 20160135748; 20160139215;
20160140975; 20160143540; 20160143541; 20160148077;
20160148400; 20160151628; 20160157742; 20160157777;
20160157828; 20160158553; 20160162652; 20160164813;
20160166207; 20160166219; 20160168137; 20160170996;

TABLE 1-continued

20160170998; 20160171514; 20160174862; 20160174867;
20160175557; 20160175607; 20160184599; 20160198968;
20160206871; 20160206877; 20160210872; 20160213276;
20160219345; 20160220163; 20160220821; 20160222073;
20160223622; 20160223627; 20160224803; 20160235324;
20160238673; 20160239966; 20160239968; 20160240212;
20160240765; 20160242665; 20160242670; 20160250473;
20160256130; 20160257957; 20160262680; 20160275536;
20160278653; 20160278662; 20160278687; 20160278736;
20160279267; 20160287117; 20160287308; 20160287334;
20160287895; 20160299568; 20160300252; 20160300352;
20160302711; 20160302720; 20160303396; 20160303402;
20160306844; 20160313408; 20160313417; 20160313418;
20160321742; 20160324677; 20160324942; 20160334475;
20160360970; 20160361532; 20160361534; 20160371387;
20170000422; 20170014080; 20170020454; 20170021158;
20170021161; 20170027517; 20170032527; 20170039591;
20170039706; 20170041699; 20170042474; 20170042476;
20170042827; 20170043166; 20170043167; 20170045601;
20170052170; 20170053082; 20170053088; 20170053461;
20170053665; 20170056363; 20170056467; 20170056655;
20170065199; 20170065349; 20170065379; 20170065816;
20170066806; 20170079538; 20170079543; 20170080050;
20170080256; 20170085547; 20170085855; 20170086729;
20170087367; 20170091418; 20170095174; 20170100051;
20170105647; 20170107575; 20170108926; 20170119270;
20170119271; 20170120043; 20170131293; 20170133576;
20170133577; 20170135640; 20170140124; 20170143986;
20170146615; 20170146801; 20170147578; 20170148213;
20170148592; 20170150925; 20170151435; 20170151436;
20170154167; 20170156674; 20170165481; 20170168121;
20170168568; 20170172446; 20170173391; 20170178001;
20170178340; 20170180558; 20170181252; 20170182176;
20170188932; 20170189691; 20170190765; 20170196519;
20170197081; 20170198017; 20170199251; 20170202476;
20170202518; 20170206654; 20170209044; 20170209062;
20170209225; 20170209389; and 20170212188.
Reference List 6
en.wikipedia.org/wiki/Brainwave_entrainment;
U.S. Pat. Nos. and Pub. application Nos. 5,070,399; 5,306,228;
5,409,445; 6,656,137; 7,749,155; 7,819,794; 7,988,613; 8,088,057;
8,167,784; 8,213,670; 8,267,851; 8,298,078; 8,517,909; 8,517,912;
8,579,793; 8,579,795; 8,597,171; 8,636,640; 8,638,950; 8,668,496;
8,852,073; 8,932,218; 8,968,176; 9,330,523; 9,357,941; 9,459,597;
9,480,812; 9,563,273; 9,609,453; 9,640,167; 9,707,372;
20050153268; 20050182287; 20060106434; 20060206174;
20060281543; 20070066403; 20080039677; 20080304691;
20100010289; 20100010844; 20100028841; 20100056854;
20100076253; 20100130812; 20100222640; 20100286747;
20100298624; 20110298706; 20110319482; 20120003615;
20120053394; 20120150545; 20130030241; 20130072292;
20130131537; 20130172663; 20130184516; 20130203019;
20130234823; 20130338738; 20140088341; 20140107401;
20140114242; 20140154647; 20140174277; 20140275741;
20140309484; 20140371516; 20150142082; 20150283019;
20150296288; 20150313496; 20150313949; 20160008568;
20160019434; 20160055842; 20160205489; 20160235980;
20160239084; 20160234501; 20170034638; 20170061760;
20170087330; 20170094385; 20170095157; 20170099713;
20170135597; and 20170149945.
Carter, J., and H. Russell. "A pilot investigation of auditory and
visual entrainment of brain wave activity in learning disabled boys."
Texas Researcher 4.1 (1993): 65-75;
Casciaro, Francesco, et al. "Alpha-rhythm stimulation using
brain entrainment enhances heart rate variability in subjects with
reduced HRV." World J. Neuroscience 3.04 (2013): 213;
Helfrich, Randolph F., et al. "Entrainment of brain oscillations
by transcranial alternating current stimulation." Current Biology
24.3 (2014): 333-339;
Huang, Tina L., and Christine Charyton. "A comprehensive
review of the psychological effects of brainwave entrainment."
Alternative therapies in health and medicine 14.5 (2008): 38;
Joyce, Michael, and Dave Siever. "Audio-visual entrainment
program as a treatment for behavior disorders in a school setting." J.
Neurotherapy 4.2 (2000): 9-25;
Keitel, Christian, Cliodhna Quigley, and Philipp Ruhnau.
"Stimulus-driven brain oscillations in the alpha range: entrainment of
intrinsic rhythms or frequency-following response?" J. Neuroscience
34.31 (2014): 10137-10140;

Lakatos, Peter, et al. "Entrainment of neuronal oscillations as a
mechanism of attentional selection." Science 320.5872 (2008): 110-
113;
Mori, Toshio, and Shoichi Kai. "Noise-induced entrainment and
stochastic resonance in human brainwaves." Physical review letters
88.21 (2002): 218101;
Padmanabhan, R., A. J. Hildreth, and D. Laws. "A prospective,
randomised, controlled study examining binaural beat audio and
pre-operative anxiety in patients undergoing general anaesthesia for
day case surgery." Anaesthesia 60.9 (2005): 874-877;
Schalles, Matt D., and Jaime A. Pineda. "Musical sequence
learning and EEG correlates of audiomotor processing." Behavioural
neurology 2015 (2015).
www.hindawi.com/journals/bn/2015/638202/
Thaut, Michael H., David A. Peterson, and Gerald C. McIntosh.
"Temporal entrainment of cognitive functions." Annals of the New
York Academy of Sciences 1060.1 (2005): 243-254.
Thut, Gregor, Philippe G. Schyns, and Joachim Gross.
"Entrainment of perceptually relevant brain oscillations by non-
invasive rhythmic stimulation of the human brain." Frontiers in
Psychology 2 (2011);
Trost, W., Frühholz, S., Schön, D., Labbé, C., Pichon, S.,
Grandjean, D., & Vuilleumier, P. (2014). Getting the beat:
entrainment of brain activity by musical rhythm and pleasantness.
NeuroImage, 103, 55-64;
Will, Udo, and Eric Berg. "Brain wave synchronization and
entrainment to periodic acoustic stimuli." Neuroscience letters 424.1
(2007): 55-60;
Zhuang, Tianbao, Hong Zhao, and Zheng Tang. "A study of
brainwave entrainment based on EEG brain dynamics." Computer
and information science 2.2 (2009): 80.
Reference List 7
Spencer K M, Nestor P G, Perlmutter R, et al. Neural synchrony
indexes disordered perception and cognition in schizophrenia. Proc
Natl Acad Sci USA. 2004; 101: 17288-17293;
Hoogenboom N, Schoffelen J M, Oostenveld R, Parkes L M, Fries P.
Localizing human visual gamma-band activity in frequency, time and
space. Neuroimage. 2006; 29: 764-773;
Le Van Quyen M, Foucher J, Lachaux J, et al. Comparison of
Hilbert transform and wavelet methods for the analysis of neuronal
synchrony. J Neurosci Methods. 2001; 111: 83-98,
Lachaux JP, Rodriguez E, Martinerie J, Varela FJ. Measuring
phase synchrony in brain signals. Hum Brain Mapp. 1999; 8: 194-208,
Rodriguez E, George N, Lachaux JP, Martinerie J, Renault B,
Varela FJ. Perception's shadow: long-distance synchronization of
human brain activity. Nature. 1999; 397: 430-433.,
Canolty RT, Edwards E, Dalal SS, et al. High gamma power is
phase-locked to theta oscillations in human neocortex. Science. 2006;
313: 1626-1628.
James W (1884.) What is an emotion? Mind 9: 188-205; Lacey
JI, Bateman DE, Vanlehn R (1953) Autonomic response specificity; an
experimental study. Psychosom Med 15: 8-21;
Levenson RW, Heider K, Ekman P, Friesen WV (1992) Emotion
and Autonomic Nervous-System Activity in the Minangkabau of West
Sumatra. J Pers Soc Psychol 62: 972-988.
Some studies have indicated that the physiological correlates of
emotions are likely to be found in the central nervous system (CNS).
See, for example:
Buck R (1999) The biological affects: A typology. Psychological
Review 106: 301-336; Izard CE (2007) Basic Emotions, Natural Kinds,
Emotion Schemas, and a New Paradigm. Perspect Psychol Sci 2: 260-
280;
Panksepp J (2007) Neurologizing the Psychology of Affects How
Appraisal-Based Constructivism and Basic Emotion Theory Can
Coexist. Perspect Psychol Sci 2: 281-296.
Reference List 8
Abeln, Vera, et al. "Brainwave entrainment for better sleep and
post-sleep state of young elite soccer players-A pilot study." European
J. Sport science 14.5 (2014): 393-402;
Acton, George. "Methods for independent entrainment of visual
field zones." U.S. Pat. No. 9,629,976. 25 Apr. 2017;
Albouy, Philippe, et al. "Selective entrainment of theta
oscillations in the dorsal stream causally enhances auditory working
memory performance." Neuron 94.1 (2017): 193-206.
Amengual, J., et al. "P018 Local entrainment and distribution
across cerebral networks of natural oscillations elicited in implanted
epilepsy patients by intracranial stimulation: Paving the way to
develop causal connectomics of the healthy human brain." Clin.
Neurophysiology 128.3 (2017): e18;

Argento, Emanuele, et al. "Augmented Cognition via Brainwave
Entrainment in Virtual Reality: An Open, Integrated Brain
Augmentation in a Neuroscience System Approach." Augmented
Human Research 2.1 (2017): 3;
Bello, Nicholas P. "Altering Cognitive and Brain States Through
Cortical Entrainment." (2014); Costa-Faidella, Jordi, Elyse S.
Sussman, and Carles Escera. "Selective entrainment of brain
oscillations drives auditory perceptual organization." NeuroImage
(2017);
Börgers, Christoph. "Entrainment by Excitatory Input Pulses."
An Introduction to Modeling Neuronal Dynamics. Springer
International Publishing, 2017. 183-192;
Calderone, Daniel ]., et al. "Entrainment of neural oscillations as
a modifiable substrate of attention." Trends in cognitive sciences 18.6
(2014): 300-309;
Chang, Daniel Wonchul. "Method and system for brain
entertainment." U.S. Pat. No. 8,636,640. 28 Jan. 2014;
Colzato, Lorenza S., Amengual, Julià L., et al. "Local
entrainment of oscillatory activity induced by direct brain stimulation
in humans." Scientific Reports 7 (2017);
Conte, Elio, et al. "A Fast Fourier Transform analysis of time
series data of heart rate variability during alfa-rhythm stimulation in
brain entrainment." NeuroQuantology 11.3 (2013);
Dikker, Suzanne, et al. "Brain-to-brain synchrony tracks real-
world dynamic group interactions in the classroom." Current Biology
27.9 (2017): 1375-1380;
Ding, Nai, and Jonathan Z. Simon. "Cortical entrainment to
continuous speech: functional roles and interpretations." Frontiers in
human neuroscience 8 (2014);
Doherty, Cormac. "A comparison of alpha brainwave
entrainment, with and without musical accompaniment." (2014);
Falk, Simone, Cosima Lanzilotti, and Daniele Schön. "Tuning
neural phase entrainment to speech." J. Cognitive Neuroscience
(2017);
Gao, Junling, et al. "Entrainment of chaotic activities in brain
and heart during MBSR mindfulness training." Neuroscience letters
616 (2016): 218-223;
Gooding-Williams, Gerard, Hongfang Wang, and Klaus Kessler.
"THETA-Rhythm Makes the World Go Round: Dissociative Effects of
TMS Theta Versus Alpha Entrainment of Right pTPJ on Embodied
Perspective Transformations." Brain Topography (2017): 1-4;
Hanslmayr, Simon, Jonas Matuschek, and Marie-Christin Fellner.
"Entrainment of prefrontal beta oscillations induces an endogenous
echo and impairs memory formation." Current Biology 24.8 (2014):
904-909;
Heideman, Simone G., Erik S. te Woerd, and Peter Praamstra.
"Rhythmic entrainment of slow brain activity preceding leg
movements." Clin. Neurophysiology 126.2 (2015): 348-355;
Henry, Molly J., et al. "Aging affects the balance of neural
entrainment and top-down neural modulation in the listening brain."
Nature Communications 8 (2017): ncomms15801;
Horr, Ninja K., Maria Wimber, and Massimiliano Di Luca.
"Perceived time and temporal structure: Neural entrainment to
isochronous stimulation increases duration estimates." Neuroimage
132 (2016): 148-156;
Irwin, Rosie. "Entraining Brain Oscillations to Influence Facial
Perception." (2015);
Kalyan, Ritu, and Bipan Kaushal. "Binaural Entrainment and Its
Effects on Memory." (2016);
Keitel, Anne, et al. "Auditory cortical delta-entrainment
interacts with oscillatory power in multiple fronto-parietal
networks." NeuroImage 147 (2017): 32-42;
Koelsch, Stefan. "Music-evoked emotions: principles, brain
correlates, and implications for therapy." Annals of the New York
Academy of Sciences1337.1 (2015): 193-201;
Kösem, Anne, et al. "Neural entrainment reflects temporal
predictions guiding speech comprehension." the Eighth Annual
Meeting of the Society for the Neurobiology of Language (SNL 2016).
2016;
Lee, Daniel Keewoong, Dongyeup Daniel Synn, and Daniel
Chesong Lee. "Intelligent earplug system." U.S. patent application
No. 15/106,989;
Lefournour, Joseph, Ramaswamy Palaniappan, and Ian V.
McLoughlin. "Inter-hemispheric and spectral power analyses of
binaural beat effects on the brain." Matters 2.9 (2016):
e201607000001;
Mai, Guangting, James W. Minett, and William S-Y. Wang.
"Delta, theta, beta, and gamma brain oscillations index levels of
auditory sentence processing." Neuroimage 133(2016): 516-528;
Marconi, Pier Luigi, et al. "The phase amplitude coupling to TABLE 1-continued assess brain network system integration." Medical Measurements and
Applications (MeMeA), 2016 IEEE International Symposium on. IEEE,
2016;
McLaren, Elgin-Skye, and Alissa N. Antle. "Exploring and
Evaluating Sound for Helping Children Self-Regulate with a Brain-
Computer Application." Proceedings of the 2017 Conference on
Interaction Design and Children. ACM, 2017;
Moisa, Marius, et al. "Brain network mechanisms underlying
motor enhancement by transcranial entrainment of gamma
oscillations." J. Neuroscience 36.47 (2016): 12053-12065;
Molinaro, Nicola, et al. "Out-of-synchrony speech entrainment
in developmental dyslexia." Human brain mapping 37.8 (2016):
2767-2783;
Moseley, Ralph. "Immersive brain entrainment in virtual worlds:
actualizing meditative states." Emerging Trends and Advanced
Technologies for Computational Intelligence. Springer International
Publishing, 2016. 315-346;
Neuling, Toralf, et al. "Friends, not foes:
magnetoencephalography as a tool to uncover brain dynamics during
transcranial alternating current stimulation." Neuroimage 118
(2015): 406-413;
Notbohm, Annika, Jürgen Kurths, and Christoph S. Herrmann.
"Modification of brain oscillations via rhythmic light stimulation
provides evidence for entrainment but not for superposition of event-
related responses." Frontiers in human neuroscience 10 (2016);
Nozaradan, S., et al. "P943: Neural entrainment to musical
rhythms in the human auditory cortex, as revealed by intracerebral
recordings." Clin. Neurophysiology 125 (2014): S299;
Palaniappan, Ramaswamy, et al. "Improving the feature
stability and classification performance of bimodal brain and heart
biometrics." Advances in Signal Processing and Intelligent
Recognition Systems. Springer, Cham, 2016. 175-186;
Palaniappan, Ramaswamy, Somnuk Phon-Amnuaisuk, and
Chikkannan Eswaran. "On the binaural brain entrainment indicating
lower heart rate variability." Int. J. Cardiol 190 (2015): 262-263;
Papagiannakis, G., et al. A virtual reality brainwave
entrainment method for human augmentation applications.
Technical Report, FORTH-ICS/TR-458, 2015;
Park, Hyojin, et al. "Frontal top-down signals increase coupling
of auditory low-frequency oscillations to continuous speech in human
listeners." Current Biology 25.12 (2015): 1649-1653;
Pérez, Alejandro, Manuel Carreiras, and Jon Andoni Duñabeitia.
"Brain-to-brain entrainment: EEG interbrain synchronization while
speaking and listening." Scientific Reports 7 (2017);
Riecke, Lars, Alexander T. Sack, and Charles E. Schroeder.
"Endogenous delta/theta sound-brain phase entrainment accelerates
the buildup of auditory streaming." Current Biology 25.24 (2015):
3196-3201;
Spaak, Eelke, Floris P. de Lange, and Ole Jensen. "Local
entrainment of alpha oscillations by visual stimuli causes cyclic
modulation of perception." J. Neuroscience 34.10(2014): 3536-3544;
Thaut, Michael H. "The discovery of human auditory-motor
entrainment and its role in the development of neurologic music
therapy." Progress in brain research 217 (2015): 253-266;
Thaut, Michael H., Gerald C. McIntosh, and Volker Hoemberg.
"Neurobiological foundations of neurologic music therapy: rhythmic
entrainment and the motor system." Frontiers in psychology 5
(2014);
Thut, G. "T030 Guiding TMS by EEG/MEG to interact with
oscillatory brain activity and associated functions." Clin.
Neurophysiology 128.3 (2017): e9;
Treviño, Guadalupe Villarreal, et al. "The Effect of Audio Visual
Entrainment on Pre-Attentive Dysfunctional Processing to Stressful
Events in Anxious Individuals." Open J. Medical Psychology 3.05
(2014): 364;
Tsai, Shu-Hui, and Yue-Der Lin. "Autonomie feedback with brain
entrainment." Awareness Science and Technology and Ubi-Media
Computing (iCAST-UMEDIA), 2013 International Joint Conference on.
IEEE, 2013;
Vossen, Alexandra, Joachim Gross, and Gregor Thut. "Alpha
power increase after transcranial alternating current stimulation at
alpha frequency (α-tACS) reflects plastic changes rather than
entrainment." Brain Stimulation 8.3 (2015): 499-508;
Witkowski, Matthias, et al. "Mapping entrained brain
oscillations during transcranial alternating current stimulation
(tACS)." Neuroimage 140 (2016): 89-98;
Zlotnik, Anatoly, Raphael Nagao, and Istvàn Z. Kiss Jr-Shin Li.
"Phase-selective entrainment of nonlinear oscillator ensembles."
Nature Communications 7 (2016).

TABLE 1-continued

Reference List 9
en.wikipedia.org/wiki/Beat_(acoustics)#Binaural_beats.
Oster, G (October 1973). "Auditory beats in the brain".
Scientific American. 229 (4): 94-102. See:
Lane, J. D., Kasian, S. J., Owens, J. E., & Marsh, G. R. (1998).
Binaural auditory beats affect vigilance performance and mood.
Physiology & behavior, 63(2), 249-252;
Foster, D. S. (1990). EEG and subjective correlates of alpha
frequency binaural beats stimulation combined with alpha
biofeedback (Doctoral dissertation, Memphis State University);
Kasprzak, C. (2011). Influence of binaural beats on EEG signal.
Acta Physica Polonica A, 119(6A), 986-990;
Pratt, H., Starr, A., Michalewski, H. J., Dimitrijevic, A., Bleich, N.,
& Mittelman, N. (2009). Cortical evoked potentials to an auditory
illusion: binaural beats. Clinical Neurophysiology, 120(8), 1514-1524;
Pratt, H., Starr, A., Michalewski, H. J., Dimitrijevic, A., Bleich, N.,
& Mittelman, N. (2010). A comparison of auditory evoked potentials
to acoustic beats and to binaural beats. Hearing research, 262(1), 34-
44;
Padmanabhan, R., Hildreth, A. J., & Laws, D. (2005). A
prospective, randomised, controlled study examining binaural beat
audio and pre-operative anxiety in patients undergoing general
anaesthesia for day case surgery. Anaesthesia, 60(9), 874-877;
Reedijk, S. A., Bolders, A., & Hommel, B. (2013). The impact of
binaural beats on creativity. Frontiers in human neuroscience, 7;
Atwater, F. H. (2001). Binaural beats and the regulation of
arousal levels. Proceedings of the TANS, 11;
Hink, R. F., Kodera, K., Yamada, O., Kaga, K., & Suzuki, J. (1980).
Binaural interaction of a beating frequency-following response.
Audiology, 19(1), 36-43;
Gao, X., Cao, H., Ming, D., Qi, H., Wang, X., Wang, X., & Zhou, P.
(2014). Analysis of EEG activity in response to binaural beats with
different frequencies. International Journal of Psychophysiology,
94(3), 399-406;
Sung, H. C., Lee, W. L., Li, H. M., Lin, C. Y., Wu, Y. Z., Wang, J. J.,
& Li, T. L. (2017). Familiar Music Listening with Binaural Beats for
Older People with Depressive Symptoms in Retirement Homes.
Neuropsychiatry, 7(4);
Colzato, L. S., Barone, H., Sellaro, R., & Hommel, B. (2017). More
attentional focusing through binaural beats: evidence from the
global-local task. Psychological research, 81(1), 271-277;
Mortazavi, S. M. J., Zahraei-Moghadam, S. M., Masoumi, S.,
Rafati, A., Haghani, M., Mortazavi, S. A. R., & Zehtabian, M. (2017).
Short Term Exposure to Binaural Beats Adversely Affects Learning and
Memory in Rats. Journal of Biomedical Physics and Engineering.
Brain Entrainment Frequency Following Response (or FFR). See,
"Stimulating the Brain with Light and Sound," Transparent
Corporation, Neuroprogrammer ™ 3,
www.transparentcorp.com/products/np/entrainment.php.
Reference List 10
www.livingflow.net/isochronic-tones-work/;
Schulze, H. H. (1989). The perception of temporal deviations in
isochronic patterns. Attention, Perception, & Psychophysics, 45(4),
291-296;
Oster, G. (1973). Auditory beats in the brain. Scientific
American, 229(4), 94-102;
Huang, T. L., & Charyton, C. (2008). A comprehensive review of
the psychological effects of brainwave entrainment. Alternative
therapies in health and medicine, 14(5), 38;
Conte, E., Conte, S., Santacroce, N., Federici, A., Todarello, O.,
Orsucci, F., . . . & Laterza, V. (2013). A Fast Fourier Transform analysis
of time series data of heart rate variability during alfa-rhythm
stimulation in brain entrainment. NeuroQuantology, 11(3);
Doherty, C. (2014). A comparison of alpha brainwave
entrainment, with and without musical accompaniment;
Moseley, R. (2015, July). Inducing targeted brain states utilizing
merged reality systems. In Science and Information Conference (SAI),
2015 (pp. 657-663). IEEE.
Reference List 11
U.S. Pat. Nos. and Pub. applications Nos. 4,407,299; 4,408,616;
4,421,122; 4,493,327; 4,550,736; 4,557,270; 4,579,125; 4,583,190;
4,585,011; 4,610,259; 4,649,482; 4,705,049; 4,736,307; 4,744,029;
4,776,345; 4,792,145; 4,794,533; 4,846,190; 4,862,359; 4,883,067;
4,907,597; 4,924,875; 4,940,058; 5,010,891; 5,020,540; 5,029,082;
5,083,571; 5,092,341; 5,105,354; 5,109,862; 5,218,530; 5,230,344;
5,230,346; 5,233,517; 5,241,967; 5,243,517; 5,269,315; 5,280,791;
5,287,859; 5,309,917; 5,309,923; 5,320,109; 5,339,811; 5,339,826;
5,377,100; 5,406,956; 5,406,957; 5,443,073; 5,447,166; 5,458,117;
5,474,082; 5,555,889; 5,611,350; 5,619,995; 5,632,272; 5,643,325;
5,678,561; 5,685,313; 5,692,517; 5,694,939; 5,699,808; 5,752,521;

TABLE 1-continued 5,755,739; 5,771,261; 5,771,897; 5,794,623; 5,795,304; 5,797,840;
5,810,737; 5,813,993; 5,827,195; 5,840,040; 5,846,189; 5,846,208;
5,853,005; 5,871,517; 5,884,626; 5,899,867; 5,916,171; 5,995,868;
6,002,952; 6,011,990; 6,016,444; 6,021,345; 6,032,072; 6,044,292;
6,050,940; 6,052,619; 6,067,462; 6,067,467; 6,070,098; 6,071,246;
6,081,735; 6,097,980; 6,097,981; 6,115,631; 6,117,075; 6,129,681;
6,155,993; 6,157,850; 6,157,857; 6,171,258; 6,195,576; 6,196,972;
6,224,549; 6,236,872; 6,287,328; 6,292,688; 6,293,904; 6,305,943;
6,306,077; 6,309,342; 6,315,736; 6,317,627; 6,325,761; 6,331,164;
6,338,713; 6,343,229; 6,358,201; 6,366,813; 6,370,423; 6,375,614;
6,377,833; 6,385,486; 6,394,963; 6,402,520; 6,475,163; 6,482,165;
6,493,577; 6,496,724; 6,511,424; 6,520,905; 6,520,921; 6,524,249;
6,527,730; 6,529,773; 6,544,170; 6,546,378; 6,547,736; 6,547,746;
6,549,804; 6,556,861; 6,565,518; 6,574,573; 6,594,524; 6,602,202;
6,616,611; 6,622,036; 6,625,485; 6,626,676; 6,650,917; 6,652,470;
6,654,632; 6,658,287; 6,678,548; 6,687,525; 6,699,194; 6,709,399;
6,726,624; 6,731,975; 6,735,467; 6,743,182; 6,745,060; 6,745,156;
6,746,409; 6,751,499; 6,768,920; 6,798,898; 6,801,803; 6,804,661;
6,816,744; 6,819,956; 6,826,426; 6,843,774; 6,865,494; 6,875,174;
6,882,881; 6,886,964; 6,915,241; 6,928,354; 6,931,274; 6,931,275;
6,981,947; 6,985,769; 6,988,056; 6,993,380; 7,011,410; 7,014,613;
7,016,722; 7,037,260; 7,043,293; 7,054,454; 7,089,927; 7,092,748;
7,099,714; 7,104,963; 7,105,824; 7,123,955; 7,128,713; 7,130,691;
7,146,218; 7,150,710; 7,150,715; 7,150,718; 7,163,512; 7,164,941;
7,177,675; 7,190,995; 7,207,948; 7,209,788; 7,215,986; 7,225,013;
7,228,169; 7,228,171; 7,231,245; 7,254,433; 7,254,439; 7,254,500;
7,267,652; 7,269,456; 7,286,871; 7,288,066; 7,297,110; 7,299,088;
7,324,845; 7,328,053; 7,333,619; 7,333,851; 7,343,198; 7,367,949;
7,373,198; 7,376,453; 7,381,185; 7,383,070; 7,392,079; 7,395,292;
7,396,333; 7,399,282; 7,403,814; 7,403,815; 7,418,290; 7,429,247;
7,450,986; 7,454,240; 7,462,151; 7,468,040; 7,469,697; 7,471,971;
7,471,978; 7,489,958; 7,489,964; 7,491,173; 7,496,393; 7,499,741;
7,499,745; 7,509,154; 7,509,161; 7,509,163; 7,510,531; 7,530,955;
7,537,568; 7,539,532; 7,539,533; 7,547,284; 7,558,622; 7,559,903;
7,570,991; 7,572,225; 7,574,007; 7,574,254; 7,593,767; 7,594,122;
7,596,535; 7,603,168; 7,604,603; 7,610,094; 7,623,912; 7,623,928;
7,625,340; 7,630,757; 7,640,055; 7,643,655; 7,647,098; 7,654,948;
7,668,525; 7,668,591; 7,672,717; 7,676,263; 7,678,061; 7,684,856;
7,697,979; 7,702,502; 7,706,871; 7,706,992; 7,711,417; 7,715,910;
7,720,530; 7,727,161; 7,729,753; 7,733,224; 7,734,334; 7,747,325;
7,751,878; 7,754,190; 7,757,690; 7,758,503; 7,764,987; 7,771,364;
7,774,052; 7,774,064; 7,778,693; 7,787,946; 7,794,406; 7,801,592;
7,801,593; 7,803,118; 7,803,119; 7,809,433; 7,811,279; 7,819,812;
7,831,302; 7,853,329; 7,860,561; 7,865,234; 7,865,235; 7,878,965;
7,879,043; 7,887,493; 7,894,890; 7,896,807; 7,899,525; 7,904,144;
7,907,994; 7,909,771; 7,918,779; 7,920,914; 7,930,035; 7,938,782;
7,938,785; 7,941,209; 7,942,824; 7,944,551; 7,962,204; 7,974,696;
7,983,741; 7,983,757; 7,986,991; 7,993,279; 7,996,075; 8,002,553;
8,005,534; 8,005,624; 8,010,347; 8,019,400; 8,019,410; 8,024,032;
8,025,404; 8,032,209; 8,033,996; 8,036,728; 8,036,736; 8,041,136;
8,046,041; 8,046,042; 8,065,011; 8,066,637; 8,066,647; 8,068,904;
8,073,534; 8,075,499; 8,079,953; 8,082,031; 8,086,294; 8,089,283;
8,095,210; 8,103,333; 8,108,036; 8,108,039; 8,114,021; 8,121,673;
8,126,528; 8,128,572; 8,131,354; 8,133,172; 8,137,269; 8,137,270;
8,145,310; 8,152,732; 8,155,736; 8,160,689; 8,172,766; 8,177,726;
8,177,727; 8,180,420; 8,180,601; 8,185,207; 8,187,201; 8,190,227;
8,190,249; 8,190,251; 8,197,395; 8,197,437; 8,200,319; 8,204,583;
8,211,035; 8,214,007; 8,224,433; 8,236,005; 8,239,014; 8,241,213;
8,244,340; 8,244,475; 8,249,698; 8,271,077; 8,280,502; 8,280,503;
8,280,514; 8,285,368; 8,290,575; 8,295,914; 8,296,108; 8,298,140;
8,301,232; 8,301,233; 8,306,610; 8,311,622; 8,314,707; 8,315,970;
8,320,649; 8,323,188; 8,323,189; 8,323,204; 8,328,718; 8,332,017;
8,332,024; 8,335,561; 8,337,404; 8,340,752; 8,340,753; 8,343,026;
8,346,342; 8,346,349; 8,352,023; 8,353,837; 8,354,881; 8,356,594;
8,359,080; 8,364,226; 8,364,254; 8,364,255; 8,369,940; 8,374,690;
8,374,703; 8,380,296; 8,382,667; 8,386,244; 8,391,966; 8,396,546;
8,396,557; 8,401,624; 8,401,626; 8,403,848; 8,425,415; 8,425,583;
8,428,696; 8,437,843; 8,437,844; 8,442,626; 8,449,471; 8,452,544;
8,454,555; 8,461,988; 8,463,007; 8,463,349; 8,463,370; 8,465,408;
8,467,877; 8,473,024; 8,473,044; 8,473,306; 8,475,354; 8,475,368;
8,475,387; 8,478,389; 8,478,394; 8,478,402; 8,480,554; 8,484,270;
8,494,829; 8,498,697; 8,500,282; 8,500,636; 8,509,885; 8,509,904;
8,512,221; 8,512,240; 8,515,535; 8,519,853; 8,521,284; 8,525,673;
8,525,687; 8,527,435; 8,531,291; 8,538,512; 8,538,514; 8,538,705;
8,542,900; 8,543,199; 8,543,219; 8,545,416; 8,545,436; 8,554,311;
8,554,325; 8,560,034; 8,560,073; 8,562,525; 8,562,526; 8,562,527;
8,562,951; 8,568,329; 8,571,642; 8,585,568; 8,588,933; 8,591,419;
8,591,498; 8,597,193; 8,600,502; 8,606,351; 8,606,356; 8,606,360;
8,620,419; 8,628,480; 8,630,699; 8,632,465; 8,632,750; 8,641,632;
8,644,914; 8,644,921; 8,647,278; 8,649,866; 8,652,038; 8,655,817;

TABLE 1-continued 8,657,756; 8,660,799; 8,666,467; 8,670,603; 8,672,852; 8,680,991;
8,684,900; 8,684,922; 8,684,926; 8,688,209; 8,690,748; 8,693,756;
8,694,087; 8,694,089; 8,694,107; 8,700,137; 8,700,141; 8,700,142;
8,706,205; 8,706,206; 8,706,207; 8,708,903; 8,712,507; 8,712,513;
8,725,238; 8,725,243; 8,725,311; 8,725,669; 8,727,978; 8,728,001;
8,738,121; 8,744,563; 8,747,313; 8,747,336; 8,750,971; 8,750,974;
8,750,992; 8,755,854; 8,755,856; 8,755,868; 8,755,869; 8,755,871;
8,761,866; 8,761,869; 8,764,651; 8,764,652; 8,764,653; 8,768,447;
8,771,194; 8,775,340; 8,781,193; 8,781,563; 8,781,595; 8,781,597;
8,784,322; 8,786,624; 8,790,255; 8,790,272; 8,792,974; 8,798,735;
8,798,736; 8,801,620; 8,821,408; 8,825,149; 8,825,428; 8,827,917;
8,831,705; 8,838,226; 8,838,227; 8,843,199; 8,843,210; 8,849,390;
8,849,392; 8,849,681; 8,852,100; 8,852,103; 8,855,758; 8,858,440;
8,858,449; 8,862,196; 8,862,210; 8,862,581; 8,868,148; 8,868,163;
8,868,172; 8,868,174; 8,868,175; 8,870,737; 8,880,207; 8,880,576;
8,886,299; 8,888,672; 8,888,673; 8,888,702; 8,888,708; 8,898,037;
8,902,070; 8,903,483; 8,914,100; 8,915,741; 8,915,871; 8,918,162;
8,918,178; 8,922,788; 8,923,958; 8,924,235; 8,932,227; 8,938,301;
8,942,777; 8,948,834; 8,948,860; 8,954,146; 8,958,882; 8,961,386;
8,965,492; 8,968,195; 8,977,362; 8,983,591; 8,983,628; 8,983,629;
8,986,207; 8,989,835; 8,989,836; 8,996,112; 9,008,367; 9,008,754;
9,008,771; 9,014,216; 9,014,453; 9,014,819; 9,015,057; 9,020,576;
9,020,585; 9,020,789; 9,022,936; 9,026,202; 9,028,405; 9,028,412;
9,033,884; 9,037,224; 9,037,225; 9,037,530; 9,042,952; 9,042,958;
9,044,188; 9,055,871; 9,058,473; 9,060,671; 9,060,683; 9,060,695;
9,060,722; 9,060,746; 9,072,482; 9,078,577; 9,084,584; 9,089,310;
9,089,400; 9,095,266; 9,095,268; 9,100,758; 9,107,586; 9,107,595;
9,113,777; 9,113,801; 9,113,830; 9,116,835; 9,119,551; 9,119,583;
9,119,597; 9,119,598; 9,125,574; 9,131,864; 9,135,221; 9,138,183;
9,149,214; 9,149,226; 9,149,255; 9,149,577; 9,155,484; 9,155,487;
9,155,521; 9,165,472; 9,173,582; 9,173,610; 9,179,854; 9,179,876;
9,183,351 RE34015; RE38476; RE38749; RE46189; 20010049480;
20010051774; 20020035338; 20020055675; 20020059159;
20020077536; 20020082513; 20020085174; 20020091319;
20020091335; 20020099295; 20020099306; 20020103512;
20020107454; 20020112732; 20020117176; 20020128544;
20020138013; 20020151771; 20020177882; 20020182574;
20020183644; 20020193670; 20030001098; 20030009078;
20030023183; 20030028121; 20030032888; 20030035301;
20030036689; 20030046018; 20030055355; 20030070685;
20030093004; 20030093129; 20030100844; 20030120172;
20030130709; 20030135128; 20030139681; 20030144601;
20030149678; 20030158466; 20030158496; 20030158587;
20030160622; 20030167019; 20030171658; 20030171685;
20030176804; 20030181821; 20030185408; 20030195429;
20030216654; 20030225340; 20030229291; 20030236458;
20040002635; 20040006265; 20040006376; 20040010203;
20040039268; 20040059203; 20040059241; 20040064020;
20040064066; 20040068164; 20040068199; 20040073098;
20040073129; 20040077967; 20040079372; 20040082862;
20040082876; 20040097802; 20040116784; 20040116791;
20040116798; 20040116825; 20040117098; 20040143170;
20040144925; 20040152995; 20040158300; 20040167418;
20040181162; 20040193068; 20040199482; 20040204636;
20040204637; 20040204659; 20040210146; 20040220494;
20040220782; 20040225179; 20040230105; 20040243017;
20040254493; 20040260169; 20050007091; 20050010116;
20050018858; 20050025704; 20050033154; 20050033174;
20050038354; 20050043774; 20050075568; 20050080349;
20050080828; 20050085744; 20050096517; 20050113713;
20050119586; 20050124848; 20050124863; 20050135102;
20050137494; 20050148893; 20050148894; 20050148895;
20050149123; 20050182456; 20050197590; 20050209517;
20050216071; 20050251055; 20050256385; 20050256418;
20050267362; 20050273017; 20050277813; 20050277912;
20060004298; 20060009704; 20060015034; 20060041201;
20060047187; 20060047216; 20060047324; 20060058590;
20060074334; 20060082727; 20060084877; 20060089541;
20060089549; 20060094968; 20060100530; 20060102171;
20060111644; 20060116556; 20060135880; 20060149144;
20060153396; 20060155206; 20060155207; 20060161071;
20060161075; 20060161218; 20060167370; 20060167722;
20060173364; 20060184059; 20060189880; 20060189882;
20060200016; 20060200034; 20060200035; 20060204532;
20060206033; 20060217609; 20060233390; 20060235315;
20060235324; 20060241562; 20060241718; 20060251303;
20060258896; 20060258950; 20060265022; 20060276695;
20070007454; 20070016095; 20070016264; 20070021673;
20070021675; 20070032733; 20070032737; 20070038382;
20070060830; 20070060831; 20070066914; 20070083128;

TABLE 1-continued

20070093721; 20070100246; 20070100251; 20070100666;
20070129647; 20070135724; 20070135728; 20070142862;
20070142873; 20070149860; 20070161919; 20070162086;
20070167694; 20070167853; 20070167858; 20070167991;
20070173733; 20070179396; 20070191688; 20070191691;
20070191697; 20070197930; 20070203448; 20070208212;
20070208269; 20070213786; 20070225581; 20070225674;
20070225932; 20070249918; 20070249952; 20070255135;
20070260151; 20070265508; 20070265533; 20070273504;
20070276270; 20070276278; 20070276279; 20070276609;
20070291832; 20080001600; 20080001735; 20080004514;
20080004904; 20080009685; 20080009772; 20080013747;
20080021332; 20080021336; 20080021340; 20080021342;
20080033266; 20080036752; 20080045823; 20080045844;
20080051669; 20080051858; 20080058668; 20080074307;
20080077010; 20080077015; 20080082018; 20080097197;
20080119716; 20080119747; 20080119900; 20080125669;
20080139953; 20080140403; 20080154111; 20080167535;
20080167540; 20080167569; 20080177195; 20080177196;
20080177197; 20080188765; 20080195166; 20080200831;
20080208072; 20080208073; 20080214902; 20080221400;
20080221472; 20080221969; 20080228100; 20080242521;
20080243014; 20080243017; 20080243021; 20080249430;
20080255469; 20080257349; 20080260212; 20080262367;
20080262371; 20080275327; 20080294019; 20080294063;
20080319326; 20080319505; 20090005675; 20090009284;
20090018429; 20090024007; 20090030476; 20090043221;
20090048530; 20090054788; 20090062660; 20090062670;
20090062676; 20090062679; 20090062680; 20090062696;
20090076339; 20090076399; 20090076400; 20090076407;
20090082689; 20090082690; 20090083071; 20090088658;
20090094305; 20090112281; 20090118636; 20090124869;
20090124921; 20090124922; 20090124923; 20090137915;
20090137923; 20090149148; 20090156954; 20090156956;
20090157662; 20090171232; 20090171240; 20090177090;
20090177108; 20090179642; 20090182211; 20090192394;
20090198144; 20090198145; 20090204015; 20090209835;
20090216091; 20090216146; 20090227876; 20090227877;
20090227882; 20090227889; 20090240119; 20090247893;
20090247894; 20090264785; 20090264952; 20090275853;
20090287107; 20090292180; 20090297000; 20090306534;
20090312663; 20090312664; 20090312808; 20090312817;
20090316925; 20090318779; 20090323049; 20090326353;
20100010364; 20100023089; 20100030073; 20100036211;
20100036276; 20100041962; 20100042011; 20100043795;
20100049069; 20100049075; 20100049482; 20100065939;
20100069762; 20100069775; 20100076333; 20100076338;
20100079292; 20100087900; 20100094103; 20100094152;
20100094155; 20100099954; 20100106044; 20100114813;
20100130869; 20100137728; 20100137937; 20100143256;
20100152621; 20100160737; 20100174161; 20100179447;
20100185113; 20100191124; 20100191139; 20100191305;
20100195770; 20100198098; 20100198101; 20100204614;
20100204748; 20100204750; 20100217100; 20100217146;
20100217348; 20100222694; 20100224188; 20100234705;
20100234752; 20100234753; 20100245093; 20100249627;
20100249635; 20100258126; 20100261977; 20100262377;
20100268055; 20100280403; 20100286549; 20100286747;
20100292752; 20100293115; 20100298735; 20100303101;
20100312188; 20100318025; 20100324441; 20100331649;
20100331715; 20110004115; 20110009715; 20110009729;
20110009752; 20110015501; 20110015536; 20110028802;
20110028859; 20110034822; 20110038515; 20110040202;
20110046473; 20110054279; 20110054345; 20110066005;
20110066041; 20110066042; 20110066053; 20110077538;
20110082381; 20110087125; 20110092834; 20110092839;
20110098583; 20110105859; 20110105915; 20110105938;
20110106206; 20110112379; 20110112381; 20110112426;
20110112427; 20110115624; 20110118536; 20110118618;
20110118619; 20110119212; 20110125046; 20110125048;
20110125238; 20110130675; 20110144520; 20110152710;
20110160607; 20110160608; 20110160795; 20110162645;
20110178441; 20110178581; 20110181422; 20110184650;
20110190600; 20110196693; 20110208539; 20110218453;
20110218950; 20110224569; 20110224570; 20110224602;
20110245709; 20110251583; 20110251985; 20110257517;
20110263995; 20110270117; 20110270579; 20110282234;
20110288424; 20110288431; 20110295142; 20110295143;
20110295338; 20110301436; 20110301439; 20110301441;
20110301448; 20110301486; 20110301487; 20110307029;

TABLE 1-continued

20110307079; 20110313308; 20110313760; 20110319724;
20120004561; 20120004564; 20120004749; 20120010536;
20120016218; 20120016252; 20120022336; 20120022350;
20120022351; 20120022365; 20120022384; 20120022392;
20120022844; 20120029320; 20120029378; 20120029379;
20120035431; 20120035433; 20120035765; 20120041330;
20120046711; 20120053433; 20120053491; 20120059273;
20120065536; 20120078115; 20120083700; 20120083701;
20120088987; 20120088992; 20120089004; 20120092156;
20120092157; 20120095352; 20120095357; 20120100514;
20120101387; 20120101401; 20120101402; 20120101430;
20120108999; 20120116235; 20120123232; 20120123290;
20120125337; 20120136242; 20120136605; 20120143074;
20120143075; 20120149997; 20120150545; 20120157963;
20120159656; 20120165624; 20120165631; 20120172682;
20120172689; 20120172743; 20120191000; 20120197092;
20120197153; 20120203087; 20120203130; 20120203131;
20120203133; 20120203725; 20120209126; 20120209136;
20120209139; 20120220843; 20120220889; 20120221310;
20120226334; 20120238890; 20120242501; 20120245464;
20120245481; 20120253141; 20120253219; 20120253249;
20120265080; 20120271190; 20120277545; 20120277548;
20120277816; 20120296182; 20120296569; 20120302842;
20120302845; 20120302856; 20120302894; 20120310100;
20120310105; 20120321759; 20120323132; 20120330109;
20130006124; 20130009783; 20130011819; 20130012786;
20130012787; 20130012788; 20130012789; 20130012790;
20130012802; 20130012830; 20130013327; 20130023783;
20130030257; 20130035579; 20130039498; 20130041235;
20130046151; 20130046193; 20130046715; 20130060110;
20130060125; 20130066392; 20130066394; 20130066395;
20130069780; 20130070929; 20130072807; 20130076885;
20130079796; 20130079621; 20130079647; 20130079656;
20130079657; 20130080127; 20130080489; 20130095459;
20130096391; 20130096393; 20130096394; 20130096408;
20130096441; 20130096839; 20130096840; 20130102833;
20130102897; 20130109995; 20130109996; 20130116520;
20130116561; 20130116588; 20130118494; 20130123584;
20130127708; 20130130799; 20130137936; 20130137938;
20130138002; 20130144106; 20130144107; 20130144108;
20130144183; 20130150650; 20130150651; 20130150659;
20130159041; 20130165812; 20130172686; 20130172691;
20130172716; 20130172763; 20130172767; 20130172772;
20130172774; 20130178718; 20130182860; 20130184552;
20130184558; 20130184603; 20130188854; 20130190577;
20130190642; 20130197321; 20130197322; 20130197328;
20130197339; 20130204150; 20130211224; 20130211276;
20130211291; 20130217982; 20130218043; 20130218053;
20130218233; 20130221961; 20130225940; 20130225992;
20130232314; 20130231580; 20130231947; 20130238049;
20130238050; 20130238063; 20130245422; 20130245486;
20130245711; 20130245712; 20130266163; 20130267760;
20130267866; 20130267928; 20130274580; 20130274625;
20130275159; 20130281811; 20130282339; 20130289401;
20130289413; 20130289417; 20130289424; 20130289433;
20130295016; 20130300573; 20130303828; 20130303934;
20130304153; 20130310660; 20130310909; 20130324880;
20130338449; 20130338459; 20130344465; 20130345522;
20130345523; 20140005988; 20140012061; 20140012110;
20140012133; 20140012153; 20140018792; 20140019165;
20140023999; 20140025396; 20140025397; 20140038147;
20140046208; 20140051044; 20140051960; 20140051961;
20140055203; 20140055284; 20140058241; 20140066739;
20140066763; 20140070958; 20140072127; 20140072130;
20140073863; 20140073864; 20140073866; 20140073870;
20140073875; 20140073876; 20140073877; 20140073878;
20140073898; 20140073948; 20140073949; 20140073951;
20140073953; 20140073954; 20140073955; 20140073956;
20140073960; 20140073961; 20140073963; 20140073965;
20140073966; 20140073967; 20140073968; 20140073974;
20140073975; 20140074060; 20140074179; 20140074180;
20140077946; 20140081114; 20140081115; 20140094720;
20140098981; 20140100467; 20140104059; 20140105436;
20140107464; 20140107519; 20140107525; 20140114165;
20140114205; 20140121446; 20140121476; 20140121554;
20140128762; 20140128764; 20140135879; 20140136585;
20140140567; 20140143064; 20140148723; 20140152673;
20140155706; 20140155714; 20140155730; 20140156000;
20140163328; 20140163330; 20140163331; 20140163332;
20140163333; 20140163335; 20140163336; 20140163337;

TABLE 1-continued

20140163385; 20140163409; 20140163425; 20140163897;
20140171820; 20140175261; 20140176944; 20140179980;
20140180088; 20140180092; 20140180093; 20140180094;
20140180095; 20140180096; 20140180097; 20140180099;
20140180100; 20140180112; 20140180113; 20140180145;
20140180153; 20140180160; 20140180161; 20140180176;
20140180177; 20140180597; 20140187994; 20140188006;
20140188770; 20140194702; 20140194758; 20140194759;
20140194768; 20140194769; 20140194780; 20140194793;
20140203797; 20140213937; 20140214330; 20140228651;
20140228702; 20140232516; 20140235965; 20140236039;
20140236077; 20140237073; 20140243614; 20140243621;
20140243628; 20140243694; 20140249429; 20140257073;
20140257147; 20140266696; 20140266787; 20140275886;
20140275889; 20140275891; 20140276013; 20140276014;
20140276090; 20140276123; 20140276130; 20140276181;
20140276183; 20140279746; 20140288381; 20140288614;
20140288953; 20140289172; 20140296724; 20140303453;
20140303454; 20140303508; 20140309943; 20140313303;
20140316217; 20140316221; 20140316230; 20140316235;
20140316278; 20140323900; 20140324118; 20140330102;
20140330157; 20140330159; 20140330334; 20140330404;
20140336473; 20140347491; 20140350431; 20140350436;
20140358025; 20140364721; 20140364746; 20140369537;
20140371544; 20140371599; 20140378809; 20140378810;
20140379620; 20150003698; 20150003699; 20150005592;
20150005594; 20150005640; 20150005644; 20150005660;
20150005680; 20150006186; 20150016618; 20150018758;
20150025351; 20150025422; 20150032017; 20150038804;
20150038869; 20150039110; 20150042477; 20150045686;
20150051663; 20150057512; 20150065839; 20150073237;
20150073306; 20150080671; 20150080746; 20150087931;
20150088024; 20150092949; 20150093729; 20150099941;
20150099962; 20150103360; 20150105631; 20150105641;
20150105837; 20150112222; 20150112409; 20150119652;
20150119743; 20150119746; 20150126821; 20150126845;
20150126848; 20150126873; 20150134264; 20150137988;
20150141529; 20150141789; 20150141794; 20150153477;
20150157235; 20150157266; 20150164349; 20150164362;
20150164375; 20150164404; 20150181840; 20150182417;
20150190070; 20150190085; 20150190636; 20150190637;
20150196213; 20150199010; 20150201879; 20150202447;
20150203822; 20150208940; 20150208975; 20150213191;
20150216436; 20150216468; 20150217082; 20150220486;
20150223743; 20150227702; 20150230750; 20150231408;
20150238106; 20150238112; 20150238137; 20150245800;
20150247921; 20150250393; 20150250401; 20150250415;
20150257645; 20150257673; 20150257674; 20150257700;
20150257712; 20150265164; 20150269825; 20150272465;
20150282730; 20150282755; 20150282760; 20150290420;
20150290453; 20150290454; 20150297106; 20150297141;
20150304101; 20150305685; 20150309563; 20150313496;
20150313535; 20150327813; 20150327837; 20150335292;
20150342478; 20150342493; 20150351655; 20150351701;
20150359441; 20150359450; 20150359452; 20150359467;
20150359486; 20150359492; 20150366497; 20150366504;
20150366516; 20150366518; 20150374285; 20150374292;
20150374300; 20150380009; 20160000348; 20160000354;
20160007915; 20160007918; 20160012749; 20160015281;
20160015289; 20160022141; 20160022156; 20160022164;
20160022167; 20160022206; 20160027293; 20160029917;
20160029918; 20160029946; 20160029950; 20160029965;
20160030702; 20160038037; 20160038038; 20160038049;
20160038091; 20160045150; 20160045756; 20160051161;
20160051162; 20160051187; 20160051195; 20160055415;
20160058301; 20160066788; 20160067494; 20160073886;
20160074661; 20160081577; 20160081616; 20160087603;
20160089031; 20160100769; 20160101260; 20160106331;
20160106344; 20160112022; 20160112684; 20160113539;
20160113545; 20160113567; 20160113587; 20160119726;
20160120433; 20160120434; 20160120464; 20160120480;
20160128596; 20160132654; 20160135691; 20160135727;
20160135754; 20160140834; 20160143554; 20160143560;
20160143594; 20160148531; 20160150988; 20160151014;
20160151018; 20160151628; 20160157742; 20160157828;
20160162652; 20160165852; 20160165853; 20160166169;
20160166197; 20160166199; 20160166208; 20160174099;
20160174863; 20160178392; 20160183828; 20160183861;
20160191517; 20160192841; 20160192842; 20160192847;
20160192879; 20160196758; 20160198963; 20160198966;

TABLE 1-continued

20160202755; 20160206877; 20160206880; 20160213276;
20160213314; 20160220133; 20160220134; 20160220136;
20160220166; 20160220836; 20160220837; 20160224757;
20160228019; 20160228029; 20160228059; 20160228705;
20160232811; 20160235324; 20160235351; 20160235352;
20160239084; 20160242659; 20160242690; 20160242699;
20160248434; 20160249841; 20160256063; 20160256112;
20160256118; 20160259905; 20160262664; 20160262685;
20160262695; 20160262703; 20160278651; 20160278697;
20160278713; 20160282941; 20160287120; 20160287157;
20160287162; 20160287166; 20160287871; 20160296157;
20160302683; 20160302704; 20160302709; 20160302720;
20160302737; 20160303402; 20160310031; 20160310070;
20160317056; 20160324465; 20160331264; 20160338634;
20160338644; 20160338798; 20160346542; 20160354003;
20160354027; 20160360965; 20160360970; 20160361021;
20160361041; 20160367204; 20160374581; 20160374618;
20170000404; 20170001016; 20170007165; 20170007173;
20170014037; 20170014083; 20170020434; 20170020447;
20170027467; 20170032098; 20170035392; 20170042430;
20170042469; 20170042475; 20170053513; 20170055839;
20170055898; 20170055913; 20170065199; 20170065218;
20170065229; 20170071495; 20170071523; 20170071529;
20170071532; 20170071537; 20170071546; 20170071551;
20170071552; 20170079538; 20170079596; 20170086672;
20170086695; 20170091567; 20170095721; 20170105647;
20170112379; 20170112427; 20170120066; 20170127946;
20170132816; 20170135597; 20170135604; 20170135626;
20170135629; 20170135631; 20170135633; 20170143231;
20170143249; 20170143255; 20170143257; 20170143259;
20170143266; 20170143267; 20170143268; 20170143273;
20170143280; 20170143282; 20170143960; 20170143963;
20170146386; 20170146387; 20170146390; 20170146391;
20170147754; 20170148240; 20170150896; 20170150916;
20170156593; 20170156606; 20170156655; 20170164878;
20170164901; 20170172414; 20170172501; 20170172520;
20170173262; 20170177023; 20170181693; 20170185149;
20170188865; 20170188872; 20170188947; 20170188992;
20170189691; 20170196497; 20170202474; 20170202518;
20170203154; 20170209053; and 20170209083.

Reference List 12

U.S. Pat. Nos. and Pub. application Nos. 6,196,972; 6,338,713;
6,442,421; 6,507,754; 6,524,249; 6,547,736; 6,616,611; 6,816,744;
6,865,494; 6,915,241; 6,936,012; 6,996,261; 7,043,293; 7,054,454;
7,079,977; 7,128,713; 7,146,211; 7,149,572; 7,164,941; 7,209,788;
7,254,439; 7,280,867; 7,282,030; 7,321,837; 7,330,032; 7,333,619;
7,381,185; 7,537,568; 7,559,903; 7,565,193; 7,567,693; 7,604,603;
7,624,293; 7,640,055; 7,715,919; 7,725,174; 7,729,755; 7,751,878;
7,778,693; 7,794,406; 7,797,040; 7,801,592; 7,803,118; 7,803,119;
7,879,043; 7,896,807; 7,899,524; 7,917,206; 7,933,646; 7,937,138;
7,976,465; 8,014,847; 8,033,996; 8,073,534; 8,095,210; 8,137,269;
8,137,270; 8,175,696; 8,177,724; 8,177,726; 8,180,601; 8,187,181;
8,197,437; 8,233,965; 8,236,005; 8,244,341; 8,248,069; 8,249,698;
8,280,514; 8,295,914; 8,326,433; 8,335,664; 8,346,342; 8,355,768;
8,386,312; 8,386,313; 8,392,250; 8,392,253; 8,392,254; 8,392,255;
8,396,542; 8,406,841; 8,406,862; 8,412,655; 8,428,703; 8,428,704;
8,463,374; 8,464,288; 8,475,387; 8,483,815; 8,494,610; 8,494,829;
8,494,905; 8,498,499; 8,509,881; 8,533,042; 8,548,786; 8,571,629;
8,579,786; 8,591,419; 8,606,360; 8,628,480; 8,655,428; 8,666,478;
8,682,422; 8,706,183; 8,706,205; 8,718,747; 8,725,238; 8,738,136;
8,747,382; 8,755,877; 8,761,869; 8,762,202; 8,768,449; 8,781,796;
8,790,255; 8,790,272; 8,821,408; 8,825,149; 8,831,731; 8,843,210;
8,849,392; 8,849,632; 8,855,773; 8,858,440; 8,862,210; 8,862,581;
8,903,479; 8,918,178; 8,934,965; 8,951,190; 8,954,139; 8,955,010;
8,958,868; 8,983,628; 8,983,629; 8,989,835; 9,020,789; 9,026,217;
9,031,644; 9,050,470; 9,060,671; 9,070,492; 9,072,832; 9,072,905;
9,078,584; 9,084,896; 9,095,295; 9,101,276; 9,107,595; 9,116,835;
9,125,574; 9,149,719; 9,155,487; 9,192,309; 9,198,621; 9,204,835;
9,211,417; 9,215,978; 9,232,910; 9,232,984; 9,238,142; 9,242,067;
9,247,911; 9,248,286; 9,254,383; 9,277,871; 9,277,873; 9,282,934;
9,289,603; 9,302,110; 9,307,944; 9,308,372; 9,320,450; 9,336,535;
9,357,941; 9,375,151; 9,375,171; 9,375,571; 9,403,038; 9,415,219;
9,427,581; 9,443,141; 9,451,886; 9,454,646; 9,462,956; 9,462,975;
9,468,541; 9,471,978; 9,480,402; 9,492,084; 9,504,410; 9,522,278;
9,533,113; 9,545,285; 9,560,984; 9,563,740; 9,615,749; 9,616,166;
9,622,672; 9,622,676; 9,622,702; 9,622,703; 9,623,240; 9,636,019;
9,649,036; 9,659,229; 9,668,694; 9,681,814; 9,681,820; 9,682,232;
9,713,428; 20020035338; 20020091319; 20020095099;
20020103428; 20020103429; 20020193670; 20030032889;
20030046018; 20030093129; 20030160622; 20030185408;

TABLE 1-continued

20030216654; 20040039268; 20040049484; 20040092809;
20040133119; 20040133120; 20040133390; 20040138536;
20040138580; 20040138711; 20040152958; 20040158119;
20050010091; 20050018858; 20050033174; 20050075568;
20050085744; 20050119547; 20050148893; 20050148894;
20050148895; 20050154290; 20050167588; 20050240087;
20050245796; 20050267343; 20050267344; 20050283053;
20050283090; 20060020184; 20060036152; 20060036153;
20060074290; 20060078183; 20060135879; 20060153396;
20060155495; 20060161384; 20060173364; 20060200013;
20060217816; 20060233390; 20060281980; 20070016095;
20070066915; 20070100278; 20070179395; 20070179734;
20070191704; 20070209669; 20070225932; 20070255122;
20070255135; 20070260151; 20070265508; 20070287896;
20080021345; 20080033508; 20080064934; 20080074307;
20080077015; 20080091118; 20080097197; 20080119716;
20080177196; 20080221401; 20080221441; 20080243014;
20080243017; 20080255949; 20080262367; 20090005667;
20090033333; 20090036791; 20090054801; 20090062676;
20090177144; 20090220425; 20090221930; 20090270758;
20090281448; 20090287271; 20090287272; 20090287273;
20090287467; 20090299169; 20090306534; 20090312646;
20090318794; 20090322331; 20100030073; 20100036211;
20100049276; 20100068751; 20100069739; 20100094152;
20100099975; 20100106041; 20100198000; 20100204604;
20100204748; 20100249638; 20100280372; 20100331976;
20110004115; 20110015515; 20110015539; 20110040713;
20110066041; 20110066042; 20110074396; 20110077538;
20110092834; 20110092839; 20110098583; 20110160543;
20110172725; 20110178441; 20110184305; 20110191350;
20110218950; 20110257519; 20110270074; 20110282230;
20110288431; 20110295143; 20110301441; 20110313268;
20110313487; 20120004518; 20120004561; 20120021394;
20120022343; 20120029378; 20120041279; 20120046535;
20120053473; 20120053476; 20120053478; 20120053479;
20120083708; 20120108918; 20120108997; 20120143038;
20120145152; 20120150545; 20120157804; 20120159656;
20120172682; 20120184826; 20120197153; 20120209139;
20120253261; 20120265267; 20120271151; 20120271376;
20120289869; 20120310105; 20120321759; 20130012804;
20130041235; 20130060125; 20130066392; 20130066395;
20130072775; 20130079621; 20130102897; 20130116520;
20130123607; 20130127708; 20130131438; 20130131461;
20130165804; 20130167360; 20130172716; 20130172772;
20130178733; 20130184597; 20130204122; 20130211238;
20130223709; 20130226261; 20130237874; 20130238049;
20130238050; 20130245416; 20130245424; 20130245485;
20130245486; 20130245711; 20130245712; 20130261490;
20130274562; 20130289364; 20130295016; 20130310422;
20130310909; 20130317380; 20130338518; 20130338803;
20140039279; 20140057232; 20140058218; 20140058528;
20140074179; 20140074180; 20140094710; 20140094720;
20140107521; 20140142654; 20140148657; 20140148716;
20140148726; 20140180153; 20140180160; 20140187901;
20140228702; 20140243647; 20140243714; 20140257128;
20140275807; 20140276130; 20140276187; 20140303454;
20140303508; 20140309614; 20140316217; 20140316248;
20140324118; 20140330334; 20140330335; 20140330336;
20140330404; 20140335489; 20140350634; 20140350864;
20150005646; 20150005660; 20150011907; 20150018665;
20150018699; 20150018702; 20150025422; 20150038869;
20150073294; 20150073306; 20150073505; 20150080671;
20150080695; 20150099962; 20150126821; 20150151142;
20150164431; 20150190070; 20150190636; 20150190637;
20150196213; 20150196249; 20150213191; 20150216439;
20150245800; 20150248470; 20150248615; 20150272652;
20150297106; 20150297893; 20150305686; 20150313498;
20150366482; 20150379370; 20160000348; 20160007899;
20160022167; 20160022168; 20160022207; 20160027423;
20160029965; 20160038042; 20160038043; 20160045128;
20160051812; 20160058304; 20160066838; 20160107309;
20160113587; 20160120428; 20160120432; 20160120437;
20160120457; 20160128596; 20160128597; 20160135754;
20160143594; 20160144175; 20160151628; 20160157742;
20160157828; 20160174863; 20160174907; 20160176053;
20160183881; 20160184029; 20160198973; 20160206380;
20160213261; 20160213317; 20160220850; 20160228028;
20160228702; 20160235324; 20160239966; 20160239968;
20160242645; 20160242665; 20160242669; 20160242690;
20160249841; 20160250355; 20160256063; 20160256105;

TABLE 1-continued

20160262664; 20160278653; 20160278713; 20160287117;
20160287162; 20160287169; 20160287869; 20160303402;
20160331264; 20160331307; 20160345895; 20160345911;
20160346542; 20160361041; 20160361546; 20160367186;
20160367198; 20170031440; 20170031441; 20170039706;
20170042444; 20170045601; 20170071521; 20170079588;
20170079589; 20170091418; 20170113046; 20170120041;
20170128015; 20170135594; 20170135626; 20170136240;
20170165020; 20170172446; 20170173326; 20170188870;
20170188905; 20170188916; 20170188922; and 20170196519.
Reference List 13
U.S. Pat. Nos. and Pub. application Nos. 5,273,038; 5,503,149;
6,240,308; 6,272,370; 6,298,259; 6,370,414; 6,385,479; 6,490,472;
6,556,695; 6,697,660; 6,801,648; 6,907,280; 6,996,261; 7,092,748;
7,254,500; 7,338,455; 7,346,382; 7,490,085; 7,497,828; 7,539,528;
7,565,193; 7,567,693; 7,577,472; 7,597,665; 7,627,370; 7,680,526;
7,729,755; 7,809,434; 7,840,257; 7,860,548; 7,872,235; 7,899,524;
7,904,134; 7,904,139; 7,907,998; 7,983,740; 7,983,741; 8,000,773;
8,014,847; 8,069,125; 8,233,682; 8,233,965; 8,235,907; 8,248,069;
8,356,004; 8,379,952; 8,406,838; 8,423,125; 8,445,851; 8,553,956;
8,586,932; 8,606,349; 8,615,479; 8,644,910; 8,679,009; 8,696,722;
8,712,512; 8,718,747; 8,761,866; 8,781,557; 8,814,923; 8,821,376;
8,834,546; 8,852,103; 8,870,737; 8,936,630; 8,951,189; 8,951,192;
8,958,882; 8,983,155; 9,005,126; 9,020,586; 9,022,936; 9,028,412;
9,033,884; 9,042,958; 9,078,584; 9,101,279; 9,135,400; 9,144,392;
9,149,255; 9,155,521; 9,167,970; 9,179,854; 9,179,858; 9,198,637;
9,204,835; 9,208,558; 9,211,077; 9,213,076; 9,235,685; 9,242,067;
9,247,924; 9,268,014; 9,268,015; 9,271,651; 9,271,674; 9,275,191;
9,292,920; 9,307,925; 9,322,895; 9,326,742; 9,330,206; 9,368,265;
9,395,425; 9,402,558; 9,414,776; 9,436,989; 9,451,883; 9,451,899;
9,468,541; 9,471,978; 9,480,402; 9,480,425; 9,486,168; 9,592,389;
9,615,789; 9,626,756; 9,672,302; 9,672,617; 9,682,232;
20020033454; 20020035317; 20020037095; 20020042563;
20020058867; 20020103428; 20020103429; 20030018277;
20030093004; 20030128801; 20040082862; 20040092809;
20040096395; 20040116791; 20040116798; 20040122787;
20040122790; 20040166536; 20040215082; 20050007091;
20050020918; 20050033154; 20050079636; 20050119547;
20050154290; 20050222639; 20050240253; 20050283053;
20060036152; 20060036153; 20060052706; 20060058683;
20060074290; 20060078183; 20060084858; 20060149160;
20060161218; 20060241382; 20060241718; 20070191704;
20070239059; 20080001600; 20080009772; 20080033291;
20080039737; 20080042067; 20080097235; 20080097785;
20080128626; 20080154126; 20080221441; 20080228077;
20080228239; 20080230702; 20080230705; 20080249430;
20080262327; 20080275340; 20090012387; 20090018407;
20090022825; 20090024050; 20090062660; 20090078875;
20090118610; 20090156907; 20090156955; 20090157323;
20090157481; 20090157482; 20090157625; 20090157751;
20090157813; 20090163777; 20090164131; 20090164132;
20090171164; 20090172540; 20090179642; 20090209831;
20090221930; 20090246138; 20090299169; 20090304582;
20090306532; 20090306534; 20090312808; 20090312817;
20090318773; 20090318794; 20090322331; 20090326604;
20100021378; 20100036233; 20100041949; 20100042011;
20100049482; 20100069739; 20100069777; 20100082506;
20100113959; 20100249573; 20110001515; 20110015539;
20110028827; 20110077503; 20110118536; 20110125077;
20110125078; 20110129129; 20110160543; 20110161011;
20110172509; 20110172553; 20110178359; 20110190846;
20110218405; 20110224571; 20110230738; 20110257519;
20110263962; 20110263968; 20110270074; 20110288400;
20110301448; 20110306845; 20110306846; 20110313274;
20120021394; 20120022343; 20120035433; 20120053483;
20120163689; 20120165904; 20120215114; 20120219195;
20120219507; 20120245474; 20120253261; 20120253434;
20120289854; 20120310107; 20120316793; 20130012804;
20130060125; 20130063550; 20130085678; 20130096408;
20130110616; 20130116561; 20130123607; 20130131438;
20130131461; 20130178693; 20130178733; 20130184558;
20130211238; 20130221961; 20130245424; 20130274586;
20130289385; 20130289386; 20130303934; 20140058528;
20140066763; 20140119621; 20140151563; 20140155730;
20140163368; 20140171757; 20140180088; 20140180092;
20140180093; 20140180094; 20140180095; 20140180096;
20140180097; 20140180099; 20140180100; 20140180112;
20140180113; 20140180176; 20140180177; 20140184550;
20140193336; 20140200414; 20140243614; 20140257047;
20140275807; 20140303486; 20140315169; 20140316248;

TABLE 1-continued

20140323849; 20140335489; 20140343397; 20140343399;
20140343408; 20140364721; 20140378830; 20150011866;
20150038812; 20150051663; 20150099959; 20150112409;
20150119658; 20150119689; 20150148700; 20150150473;
20150196800; 20150200046; 20150219732; 20150223905;
20150227702; 20150247921; 20150248615; 20150253410;
20150289779; 20150290453; 20150290454; 20150313540;
20150317796; 20150324692; 20150366482; 20150375006;
20160005320; 20160027342; 20160029965; 20160051161;
20160051162; 20160055304; 20160058304; 20160058392;
20160066838; 20160103487; 20160120437; 20160120457;
20160143541; 20160157742; 20160184029; 20160196393;
20160228702; 20160231401; 20160239966; 20160239968;
20160260216; 20160267809; 20160270723; 20160302720;
20160303397; 20160317077; 20160345911; 20170027539;
20170039706; 20170045601; 20170061034; 20170085855;
20170091418; 20170112403; 20170113046; 20170120041;
20170160360; 20170164861; 20170169714; 20170172527; and
20170202475.
Reference List 14
U.S. Pat. Nos. and Pub. application Nos. 8,406,890; 8,509,879;
8,542,916; 8,852,103; 8,934,986; 9,022,936; 9,028,412; 9,031,653;
9,033,884; 9,037,530; 9,055,974; 9,149,255; 9,155,521; 9,198,637;
9,247,924; 9,268,014; 9,268,015; 9,367,131; 9,4147,80; 9,420,970;
9,430,615; 9,442,525; 9,444,998; 9,445,763; 9,462,956; 9,474,481;
9,489,854; 9,504,420; 9,510,790; 9,519,981; 9,526,906; 9,538,948;
9,585,581; 9,622,672; 9,641,665; 9,652,626; 9,684,335; 9,687,187;
9,693,684; 9,693,724; 9,706,963; 9,712,736; 20090118622;
20100098289; 20110066041; 20110066042; 20110098583;
20110301441; 20120130204; 20120265271; 20120321759;
20130060158; 20130113816; 20130131438; 20130184786;
20140031889; 20140031903; 20140039975; 20140114889;
20140226131; 20140279341; 20140296733; 20140303424;
20140313303; 20140315169; 20140316235; 20140364721;
20140378810; 20150003698; 20150003699; 20150005640;
20150005644; 20150006186; 20150029087; 20150033245;
20150033258; 20150033259; 20150033262; 20150033266;
20150081226; 20150088093; 20150093729; 20150105701;
20150112899; 20150126845; 20150150122; 20150190062;
20150190070; 20150190077; 20150190094; 20150192776;
20150196213; 20150196800; 20150199010; 20150241916;
20150242608; 20150272496; 20150272510; 20150282705;
20150282749; 20150289217; 20150297109; 20150305689;
20150335295; 20150351655; 20150366482; 20160027342;
20160029896; 20160058366; 20160058376; 20160058673;
20160060926; 20160065724; 20160065840; 20160077547;
20160081625; 20160103487; 20160104006; 20160109959;
20160113517; 20160120048; 20160120428; 20160120457;
20160125228; 20160157773; 20160157828; 20160183812;
20160191517; 20160193499; 20160196185; 20160196635;
20160206241; 20160213317; 20160228064; 20160235341;
20160235359; 20160249857; 20160249864; 20160256086;
20160262680; 20160262685; 20160270656; 20160278672;
20160282113; 20160287142; 20160306942; 20160310071;
20160317056; 20160324445; 20160324457; 20160342241;
20160360100; 20160361027; 20160366462; 20160367138;
20160367195; 20160374616; 20160378608; 20160378965;
20170000324; 20170000325; 20170000326; 20170000329;
20170000334; 20170000335; 20170000337; 20170000340;
20170000341; 20170000342; 20170000343; 20170000345;
20170000330; 20170000331; 20170000332; 20170000333;
20170000454; 20170000683; 20170001032; 20170007111;
20170010469; 20170010470; 20170017362; 20170017083;
20170020627; 20170027521; 20170028563; 20170031440;
20170007115; 20170007116; 20170007122; 20170007123;
20170007182; 20170007450; 20170007799; 20170007843;
20170035200; 20170035306; 20170035317; 20170040699;
20170042485; 20170046052; 20170065349; 20170086695;
20170086727; 20170090475; 20170103440; 20170112446;
20170113056; 20170128006; 20170143249; 20170143442;
20170156593; 20170156606; 20170164893; 20170171441;
20170172499; 20170173262; 20170185714; 20170188933;
20170196503; 20170205259; 20170206913; and 20170214786.
U.S. Pat. No. and Pub. application Nos. 9,443,141; 20110218950;
20150248167; 20150248764; 20150248765; 20150310862;
20150331929; 20150338915; 20160026913; 20160062459;
20160085302; 20160125572; 20160247064; 20160274660;
20170053665; 20170069306; 20170173262; and 20170206691.
Amari, S., Natural gradient works efficiently in learning, Neural
Computation 10: 251-276, 1998.

TABLE 1-continued

Amari S., Cichocki, A. & Yang, H. H., A new learning algorithm for
blind signal separation. In: Advances in Neural Information
Processing Systems 8, MIT Press, 1996.
Bandettini PA, Wong EC, Hinks RS, Tikofsky RS, Hyde JS, Time
course EPI of human brain function during task activation. Magn
Reson Med 25: 390-7, 1992.
Bell A. J. & Sejnowski T. J. An information-maximization
approach to blind separation and blind deconvolution. Neural
Comput 7: 1129-59, 1995.
Bell, A. J. & Sejnowski, T. J., Learning the higher-order structure
of a natural sound, Network: Computation in Neural Systems 7,
1996b.
Bench CJ, Frith CD, Grasby PM, Friston KJ, Paulesu E, Frackowiak
RS, Dolan RJ, Investigations of the functional anatomy of attention
using the Stroop test. Neuropsychologia 31: 907-22, 1993.
Boynton GM, Engel SA, Glover GH, Heeger DJ, Linear systems
analysis of functional magnetic resonance imaging in human V1. J
Neurosci 16: 4207-21., 1996.
Bringer, Julien, Hervé Chabanne, and Bruno Kindarji. "Error-
tolerant searchable encryption." In Communications, 2009. ICC'09.
IEEE International Conference on, pp. 1-6. IEEE, 2009.
Buckner, R. L., Bandettini, P. A., O'Craven, K M, Savoy, R. L.,
Petersen, S. E., Raichle, M. E. & Rosen, B. R., Proc Natl Acad Sci U S A
93, 14878-83, 1996.
Cardoso, J-F. & Laheld, B., Equivalent adaptive source
separation, IEEE Trans. Signal Proc., in press.
Chapman, R. M. & Mccrary, J. W., EP component identification
and measurement by principal components analysis. Brain Lang. 27,
288-301, 1995.
Cichocki A., Unbehauen R., & Rummert E., Robust learning
algorithm for blind separation of signals, Electronics Letters 30,
1386-1387, 1994.
Comon P, Independent component analysis, A new concept?
Signal Processing 36: 11-20, 1994.
Cover, T. M. & Thomas, J. A., Elements of Information Theory John
Wiley, 1991.
Cox, R. W., AFNI: software for analysis and visualization of
functional magnetic resonance neuroimages. Comput Biomed Res
29: 162-73, 1996.
Cox, R. W. & Hyde J. S. Software tools for analysis and
visualization of fMRI data, NMR in Biomedicine, in press.
Dale, A. M. & Sereno, M. I., Improved localization of cortical
activity by combining EEG and MEG with MRI cortical surface
reconstruction - a linear approach. J. Cogn. Neurosci. 5: 162-176,
1993.
Friston K. J., Modes or models: A critique on independent
component analysis for fMRI. Trends in Cognitive Sciences, in press.
Friston K. J., Commentary and opinion: II. Statistical parametric
mapping: ontology and current issues. J Cereb Blood Flow Metab
15: 361-70, 1995.
Friston K. J., Statistical Parametric Mapping and Other Analyses
of Functional Imaging Data. In: A. W. Toga, J. C. Mazziotta eds., Brain
Mapping, The Methods. San Diego: Academic Press, 1996: 363-396,
1995.
Friston KJ, Frith CD, Liddle PF, Frackowiak RS, Functional
connectivity: the principal-component analysis of large (PET) data
sets. J Cereb Blood Flow Metab 13: 5-14, 1993.
Friston KJ, Holmes AP, Worsley KJ, Poline JP, Frith CD, and
Frackowiak R. S. J., Statistical Parametric Maps in Functional
Imaging: A General Linear Approach, Human Brain Mapping 2: 189-
210, 1995.
Friston KJ, Williams S, Howard R, Frackowiak RS and Turner R,
Movement-related effects in fMRI time-series. Magn Reson Med
35: 346-55, 1996.
Galambos, R. and S. Makeig, "Dynamic changes in steady-state
potentials," in: Dynamics of Sensory and Cognitive Processing of the
Brain, ed. E. Basar Springer, pp. 178-199, 1987.
Galambos, R., S. Makeig, and P. Talmachoff, A 40 Hz auditory
potential recorded from the human scalp, Proc Natl Acad Sci USA
78(4): 2643-2647, 1981.
Galil, Zvi, Stuart Haber, and Moti Yung. "Cryptographic
computation: Secure fault-tolerant protocols and the public-key
model." In Conference on the Theory and Application of
Cryptographic Techniques, pp. 135-155. Springer, Berlin, Heidelberg,
1987.
George JS, Aine CJ, Mosher JC, Schmidt DM, Ranken DM, Schlitt
HA, Wood CC, Lewine JD, Sanders JA, Belliveau JW. Mapping
function in the human brain with magnetoencephalography, anatomical
magnetic resonance imaging, and functional magnetic resonance
imaging. J Clin Neurophysiol 12: 406-31, 1995.

TABLE 1-continued

Ives, J. R., Warach S, Schmitt F, Edelman RR and Schomer DL.
Monitoring the patient's EEG during echo planar MRI,
Electroencephalogr Clin Neurophysiol, 87: 417-420, 1993.
Jackson, J. E., A User's Guide to Principal Components. New
York: John Wiley & Sons, Inc., 1991.
Jokeit, H. and Makeig, S., Different event-related patterns of
gamma-band power in brainwaves of fast- and slow-reacting
subjects, Proc. Nat. Acad. Sci USA 91: 6339-6343, 1994.
Juels, Ari, and Madhu Sudan. "A fuzzy vault scheme." Designs,
Codes and Cryptography 38, no. 2 (2006): 237-257.
Jueptner, M., K. M. Stephan, C. D. Frith, D. J. Brooks, R. S J.
Frackowiak & R. E. Passingham, Anatomy of Motor Learning. I.
Frontal Cortex and Attention. J. Neurophysiology 77: 1313-1324,
1977.
Jung, T-P., Humphries, C., Lee, T-W., Makeig, S., Mckeown, M.,
Iragui, V. and Sejnowski, T. J., "Extended ICA removes artifacts from
electroencephalographic recordings," In: Advances in Neural
Information Processing Systems 10: MIT Press, Cambridge, MA, in
press.
Jung, T-P., Humphries, C., Lee, T-W., Mckeown, M. J., Iragui, V.,
Makeig, S. & Sejnowski, T. J., Removing electroencephalographic
artifacts by blind source separation, submitted-a.
Jung, T-P., S. Makeig, M. Stensmo & T. Sejnowski, Estimating
Alertness from the EEG Power Spectrum, IEEE Transactions on
Biomedical Engineering, 44(1), 60-69, 1997.
Jung, T-P., Makeig, S., Westerfield, M., Townsend, J., Courchesne,
E. and Sejnowski, T. J., Analysis and visualization of single-trial event-
related potentials, submitted-b.
Jutten, C. & Herault, J., Blind separation of sources, part I: an
adaptive algorithm based on neuromimetic architecture. Signal
Processing 24, 1-10, 1991.
Karhumen, J., Oja, E., Wang, L., Vigario, R. & Joutsenalo, J., A
class of neural networks for independent component analysis, IEEE
Trans. Neural Networks, in press.
Kwong K. K., Functional magnetic resonance imaging with echo
planar imaging. Magn Reson Q 11: 1-20, 1995.
Kwong K. K., Belliveau J W, Chesler DA, Goldberg IE, Weisskoff
RM, Poncelet BP, Kennedy DN, Hoppel BE, Cohen MS, Turner R, et
al., Dynamic magnetic resonance imaging of human brain activity during
primary sensory stimulation. Proc Natl Acad Sci USA 89: 5675-9, 1992.
Lee, T.-W., Girolami, M., and Sejnowski, T. J., Independent
component analysis using an extended infomax algorithm for mixed
Sub-gaussian and Super-gaussian sources, Neural Computation,
submitted for publication.
Lewicki, Michael S., and Sejnowski, Terence J., Learning
nonlinear overcomplete representations for efficient coding, Eds. M.
Kearns, M. Jordan, and S. Solla, Advances in Neural Information
Processing Systems 10, in press.
Linsker, R., Local synaptic learning rules suffice to maximise
mutual information in a linear network. Neural Computation 4, 691-
702, 1992.
Liu A K, Belliveau JW, Dale AM. Spatiotemporal imaging of
human brain activity using functional MRI-constrained
magnetoencephalography data: Monte Carlo simulations. Proc Natl
Acad Sci USA 95: 8945-50, 1998
Manoach D S, Schlaug G, Siewert B, Darby DG, Bly BM, Benfield
A, Edelman RR, Warach S, Prefrontal cortex fMRI signal changes are
correlated with working memory load. Neuroreport 8: 545-9, 1997.
Mccarthy, G., Luby, M., Gore, J. and Goldman-Rakic, P.,
Infrequent events transiently activate human prefrontal and parietal
cortex as measured by functional MRI. J. Neurophysiology 77: 1630-
1634, 1997.
Mckeown, M., Makeig, S., Brown, G., Jung, T-P., Kindermann, S.,
Bell, Iragui, V. and Sejnowski, T. J., Blind separation of functional
magnetic resonance imaging (fMRI) data, Human Brain Mapping,
6: 160,18, 1998a.
Mckeown, M. J., Humphries, C., Achermann, P., Borbely, A. A. and
Sejnowski, T. J.,
A new method for detecting state changes in the EEG:
exploratory application to sleep data. J. Sleep Res. 7 suppl. 1: 48-56,
1998b.
Mckeown, M. J., Tzyy-Ping Jung, Scott Makeig, Greg Brown,
Sandra S. Kindermann, Te-Won Lee and Terrence J. Sejnowski,
Spatially independent activity patterns in functional magnetic
resonance imaging data during the Stroop color-naming task, Proc.
Natl. Acad. Sci USA, 95: 803-810, 1998c.
Mckeown, M. J. and Sejnowski, T. J., Independent component
analysis of fMRI data: examining the assumptions. Human Brain
Mapping 6: 368-372, 1998d.

Makeig, S. Auditory event-related dynamics of the EEG spectrum
and effects of exposure to tones, Electroencephalogr Clin
Neurophysiol, 86: 283-293, 1993.
Makeig, S. Toolbox for independent component analysis of
psychophysiological data, www.cnl.salk.edu/~scott/ica.html, 1997.
Makeig, S. and Galambos, R., The CERP: Event-related
perturbations in steady-state responses, in: Brain Dynamics Progress
and Perspectives, (pp. 375-400), ed. E. Basar and T. H. Bullock, 1989.
Makeig, S. and Inlow, M., Lapses in alertness: coherence of
fluctuations in performance and the EEG spectrum,
Electroencephalogr clin Neurophysiol, 86: 23-35, 1993.
Makeig, S. and Jung, T-P., Changes in alertness are a principal
component of variance in the EEG spectrum, NeuroReport 7: 213-216,
1995.
Makeig, S. and T-P. Jung, Tonic, phasic, and transient EEG
correlates of auditory awareness during drowsiness, Cognitive Brain
Research 4: 15-25, 1996.
Makeig, S., Bell, A. J., Jung, T-P. and Sejnowski, T. J.,
"Independent component analysis of electroencephalographic data,"
In: D. Touretzky, M. Mozer and M. Hasselmo (Eds). Advances in Neural
Information Processing Systems 8: 145-151 MIT Press, Cambridge, MA,
1996.
Makeig, S., Jung, T-P, and Sejnowski, T. J., "Using feedforward
neural networks to monitor alertness from changes in EEG correlation
and coherence," In: D. Touretzky, M. Mozer & M. Hasselmo(Eds).
Advances in Neural Information Processing Systems 8: 931-937 MIT
Press, Cambridge, MA, 1996.
Makeig, S., T-P. Jung, D. Ghahremani, A. J. Bell & T. J. Sejnowski,
Blind separation of auditory event-related brain responses into
independent components. Proc. Natl. Acad. Sci. USA, 94: 10979-
10984, 1997.
Makeig, S., Westerfield, M., Jung, T-P., Covington, J., Townsend,
J., Sejnowski, T. J. and Courchesne, E., Independent components of the
late positive event-related potential in a visual spatial attention task,
submitted.
Mitra P P, Ogawa S, Hu X, Ugurbil K, The nature of
spatiotemporal changes in cerebral hemodynamics as manifested in
functional magnetic resonance imaging. Magn Reson Med.37: 511-8,
1997.
Nobre A C, Sebestyen GN, Gitelman DR, Mesulam MM,
Frackowiak RS, Frith CD, Functional localization of the system for
visuospatial attention using positron emission tomography. Brain
120: 515-33, 1997.
Nunez, P. L., Electric Fields of the Brain. New York: Oxford, 1981.
Ogawa S, Tank DW, Menon R, Ellermann JM, Kim SG, Merkle H,
Ugurbil K, Intrinsic signal changes accompanying sensory stimulation:
functional brain mapping with magnetic resonance imaging. Proc
Natl Acad Sci USA 89: 5951-5, 1992.
Pearlmutter, B. and Parra, L. C. Maximum likelihood blind
source separation: a context-sensitive generalization of ICA. In: M. C.
Mozer, M. I. Jordan and T. Petsche (Eds.), Adv. in Neural Information
Processing Systems 9: 613-619 MIT Press, Cambridge, MA, 1996.
Sakai K, Hikosaka O, Miyauchi S, Takino R, Sasaki Y, Putz B.
Transition of brain activation from frontal to parietal areas in
visuomotor sequence learning. J Neurosci 18: 1827-40, 1998.
Sahai, Amit, and Brent Waters. "Fuzzy identity-based
encryption." In Annual International Conference on the Theory and
Applications of Cryptographic Techniques, pp. 457-473. Springer,
Berlin, Heidelberg, 2005.
Scherg, M. & Von Cramon, D., Evoked dipole source potentials of
the human auditory cortex. Electroencephalogr. Clin. Neurophysiol.
65: 344-601, 1986.
Tallon-Baudry, C., Bertrand, O., Delpuech, C., & Pernier, J.,
Stimulus Specificity of Phase-Locked and Non-Phase-Locked 40 Hz
Visual Responses in Human. J. Neurosci. 16: 4240-4249, 1996.
Thaker, Darshan D., Diana Franklin, John Oliver, Susmit Biswas,
Derek Lockhart, Tzvetan Metodi, and Frederic T. Chong.
"Characterization of error-tolerant applications when protecting
control data." In Workload Characterization, 2006 IEEE International
Symposium on, pp. 142-149. IEEE, 2006.
Tulving E, Markowitsch HJ, Craik FE, Habib R, Houle S, Novelty
and familiarity activations in PET studies of memory encoding and
retrieval. Cereb Cortex 6: 71-9, 1996.
Warach, S., J. R. Ives, G. Schaug, M. R. Patel, D. G. Darby, V.
Thangaraj, R. R. Edelman and D. L. Schomer, EEG-triggered echo-
planar functional MRI in epilepsy, Neurology 47: 89-93, 1996.
Reference List 15
Amenta P., D'Ambra L. (1994) Analisi non Simmetrica delle
Corrispondenze Multiple con Vincoli Lineari. Atti S.I.S. XXXVII
Sanremo, Aprile 1994.

137

TABLE 1-continued

Amenta P., D'Ambra L. (1996) L'Analisi in Componenti Principali in rapporto ad un sottospazio di riferimento con informazioni esterne, Quaderni del D.M.Q.T.E., Universita di Pescara, n. 18.

Amenta P., D'Ambra L. (1999) Generalized Constrained Principal Component Analysis. Atti Riunione Scientifica del Gruppo di Classificazione dell'IFCS su "Classificazione e Analisi dei Dati", Roma.

D'Ambra L., Lauro N. C. (1982) Analisi in componenti principali in rapporto ad un sottospazio di riferimento, Rivista di Statistica Applicata, n. 1, vol. 15.

D'Ambra L., Sabatier R., Amenta P. (1998) Analisi fattoriale delle matrici a tre vie: sintesienuovi approcci, (invited lecture) Atti XXXIX Riunione SIS.

Huon de Kermadec F., Durand J. F., Sabatier R. (1996) Comparaison de méthodes de régression pour l'étude des liens entre données hédoniques, in 3$^{rd}$ Sensometrics Meeting, E.N.T.I.A.A., Nantes.

Huon de Kermadec F., Durand J. F., Sabatier R. (1997) Comparison between linear and nonlinear PLS methods to explain overall liking from sensory characteristics, Food Quality and Preference, 8, n. 5/6.

Kiers H. A. L. (1991) Hierarchical relations among three way methods Psychometrika, 56.

Kvalheim O. M. (1988) A partial least squares approach to interpretative analysis of multivariate analysis, Chemometrics and Intelligent Laboratory System, 3.

MacFie H. J. H, Thomson D. M. H. (1988) Preference mapping and multidimensional scaling methods, in: Sensory Analysis of Foods. Elsevier Applied Science, London.

Sabatier R. (1993) Critéres et contraintes pour l'ordination simultanée de K tableaux, Biométrie et Environement, Masson, 332.

Schlich P. (1995) Preference mapping: relating consumer preferences to sensory or instrumental measurements, in: Bioflavour, INRA, Dijon.

Wold S., Geladi P., Esbensen K., Ohman J. (1987) Multi-way principal components and PLS-analysis, J. of Chemometrics, vol.1. Reference List 16

Albert, Jacobo, Sara López-Martin, José Antonio Hinojosa, and Luis Carretié. "Spatiotemporal characterization of response inhibition." Neuroimage 76 (2013): 272-281.

Arzouan Y, Goldstein A, Faust M. Brainwaves are stethoscopes: ERP correlates of novel metaphor comprehension. Brain Res 2007; 1160: 69-81.

Arzouan Y, Goldstein A, Faust M. Dynamics of hemispheric activity during metaphor comprehension: electrophysiological measures. NeuroImage 2007; 36: 222-231.

Arzy, Shahar, Yossi Arzouan, Esther Adi-Japha, Sorin Solomon, and Olaf Blanke. "The 'intrinsic' system in the human cortex and self-projection: a data driven analysis." Neuroreport 21, no. 8 (2010): 569-574.

Bao, Xuecai, Jinli Wang, and Jianfeng Hu. "Method of individual identification based on electroencephalogram analysis." In New Trends in Information and Service Science, 2009. NISS'09. International Conference on, pp. 390-393. IEEE, 2009.

Bhattacharya, Joydeep. "Complexity analysis of spontaneous EEG." Acta neurobiologiae experimentalis 60, no. 4 (2000): 495-502.

Chapman R M, Mccrary J W. EP component identification and measurement by principal components analysis. Brain and cognition 1995; 27: 288-310.

Clementz, Brett A., Stefanie K. Barber, and Jacqueline R. Dzau. "Knowledge of stimulus repetition affects the magnitude and spatial distribution of low-frequency event-related brain potentials." Audiology and Neurotology 7, no. 5 (2002): 303-314.

Dien J, Frishkoff G A, Cerbone A, Tucker D M. Parametric analysis of event-related potentials in semantic comprehension: evidence for parallel brain mechanisms. Brain research 2003; 15: 137-153.

Dien J, Frishkoff G A. Principal components analysis of event-related potential datasets. In: Handy T (ed). Event-Related Potentials: A Methods Handbook. Cambridge, Mass MIT Press; 2004.

Elbert, T. "IIIrd Congress of the Spanish Society of Psychophysiology." Journal of Psychophysiology 17 (2003): 39-53.

Groppe, David M., Scott Makeig, Marta Kutas, and S. Diego. "Independent component analysis of event-related potentials." Cognitive science online 6, no. 1 (2008): 1-44.

Have, Mid-Ventrolateral Prefrontal Cortex. "Heschl's Gyrus, Posterior Superior Temporal Gyrus." ] Neurophysiol 97 (2007): 2075-2082.

Hinojosa, J. A., J. Albert, S. López-Martin, and L. Carretié. "Temporospatial analysis of explicit and implicit processing of negative content during word comprehension." Brain and cognition 87 (2014): 109-121.

138

TABLE 1-continued

Jarchi, Delaram, Saeid Sanei, Jose C. Principe, and Bahador Makkiabadi. "A new spatiotemporal filtering method for single-trial estimation of correlated ERP subcomponents." IEEE Transactions on Biomedical Engineering 58, no. 1 (2011): 132-143.

John, Erwin Roy. "A field theory of consciousness." Consciousness and cognition 10, no. 2 (2001): 184-213.

Johnson, Mark H., Michelle de Haan, Andrew Oliver, Warwick Smith, Haralambos Hatzakis, Leslie A. Tucker, and Gergely Csibra. "Recording and analyzing high-density event-related potentials with infants using the Geodesic Sensor Net." Developmental Neuropsychology 19, no. 3 (2001): 295-323.

Jung, Tzyy-Ping, and Scott Makeig. "Mining Electroencephalographic Data Using Independent Component Analysis." EEG Journal (2003).

Kashyap, Rajan. "Improved localization of neural sources and dynamical causal modelling of latency-corrected event related brain potentials and applications to face recognition and priming." (2015).

Klawohn, Julia, Anja Riesel, Rosa Grützmann, Norbert Kathmann, and Tanja Endrass. "Performance monitoring in obsessive-compulsive disorder: A temporo-spatial principal component analysis." Cognitive, Affective, & Behavioral Neuroscience 14, no. 3 (2014): 983-995.

Lister, Jennifer J., Nathan D. Maxfield, and Gabriel J. Pitt. "Cortical evoked response to gaps in noise: within-channel and across-channel conditions." Ear and hearing 28, no. 6 (2007): 862.

Maess, Burkhard, Angela D. Friederici, Markus Damian, Antje S. Meyer, and Willem J M Levelt. "Semantic category interference in overt picture naming: Sharpening current density localization by PCA." Journal of cognitive neuroscience 14, no. 3 (2002): 455-462.

Makeig, Scott, Marissa Westerfield, Jeanne Townsend, Tzyy-Ping Jung, Eric Courchesne, and Terrence J. Sejnowski. "Functionally independent components of early event-related potentials in a visual spatial attention task." Philosophical Transactions of the Royal Society B: Biological Sciences 354, no. 1387 (1999): 1135-1144.

Matsuda, Izumi, Hiroshi Nittono, Akihisa Hirota, Tokihiro Ogawa, and Noriyoshi Takasawa. "Event-related brain potentials during the standard autonomic-based concealed information test." International Journal of Psychophysiology 74, no. 1 (2009): 58-68.

Mazaheri, Ali, and Terence W. Picton. "EEG spectral dynamics during discrimination of auditory and visual targets." Cognitive Brain Research 24, no. 1 (2005): 81-96.

Pirmoradi, Mona, Boutheina Jemel, Anne Gallagher, Julie Tremblay, Fabien D'Hondt, Dang Khoa Nguyen, Renée Béland, and Maryse Lassonde. "Verbal memory and verbal fluency tasks used for language localization and lateralization during magnetoencephalography." Epilepsy research 119 (2016): 1-9.

Potts GF, Dien J, Hartry-Speiser AL, McDougal LM, Tucker DM. Dense sensor array topography of the event-related potential to task-relevant auditory stimuli. Electroencephalography and clinical neurophysiology 1998; 106: 444-456.

Rosler F, Manzey D. Principal components and varimax-rotated components in event-related potential research: some remarks on their interpretation. Biological psychology 1981; 13: 3-26.

Ruchkin DS, McCalley MG, Glaser EM. Event related potentials and time estimation. Psychophysiology 1977; 14: 451-455.

Schroder, Hans S., James E. Glazer, Ken P. Bennett, Tim P. Moran, and Jason S. Moser. "Suppression of error-preceding brain activity explains exaggerated error monitoring in females with worry." Biological psychology 122 (2017): 33-41.

Spencer KM, Dien J, Donchin E. Spatiotemporal analysis of the late ERP responses to deviant stimuli. Psychophysiology 2001; 38: 343-358.

Squires KC, Squires NK, Hillyard SA. Decision-related cortical potentials during an auditory signal detection task with cued observation intervals. Journal of experimental psychology 1975; 1: 268-279.

van Boxtel A, Boelhouwer AJ, Bos AR. Optimal EMG signal bandwidth and interelectrode distance for the recording of acoustic, electrocutaneous, and photic blink reflexes. Psychophysiology 1998; 35: 690-697.

Veen, Vincent van, and Cameron S. Carter. "The timing of action-monitoring processes in the anterior cingulate cortex." Journal of cognitive neuroscience 14, no. 4 (2002): 593-602.

Wackermann, Jiri. "Towards a quantitative characterisation of functional states of the brain: from the non-linear methodology to the global linear description." International Journal of Psychophysiology 34, no. 1 (1999): 65-80.

Reference List 17 en.wikipedia.org/wiki/Electrooculography
www.sleepassociation.org/about-sleep/stages-of-sleep/;

TABLE 1-continued

TABLE 1-continued

U.S. Pat. Nos. and patent application Nos. 4,561,448; 4,585,011; 4,595,017; 4,618,230; 4,626,090; 4,678,640; 4,815,839; 4,818,095; 4,836,219; 4,838,681; 4,863,259; 4,889,422; 4,988,183; 4,993,825; 5,002,385; 5,070,883; 5,094,521; 5,137,345; 5,204,703; 5,293,187; 5,360,971; 5,422,689; 5,491,492; 5,513,649; 5,517,021; 5,570,698; 5,574,473; 5,621,424; 5,649,061; 5,726,916; 5,823,190; 5,851,193; 5,920,375; 5,933,210; 5,942,954; 6,033,073; 6,070,098; 6,091,334; 6,171,258; 6,231,187; 6,346,887; 6,511,424; 6,545,650; 6,710,051; 6,842,670; 7,248,928; 7,403,124; 7,448,751; 7,488,294; 7,515,054; 7,520,614; 7,554,549; 7,599,735; 7,639,146; 7,665,845; 7,682,024; 7,731,360; 7,753,523; 7,764,283; 7,783,332; 7,833,966; 7,835,498; 7,866,818; 7,872,635; 7,918,807; 7,967,439; 7,996,076; 8,021,299; 8,032,842; 8,085,902; 8,162,479; 8,192,376; 8,202,840; 8,203,530; 8,259,169; 8,265,743; 8,290,208; 8,318,485; 8,345,191; 8,357,101; 8,386,313; 8,392,253; 8,392,254; 8,392,255; 8,400,313; 8,405,610; 8,419,654; 8,430,510; 8,434,868; 8,449,116; 8,466,875; 8,477,425; 8,482,859; 8,488,246; 8,525,788; 8,533,042; 8,570,176; 8,600,502; 8,602,555; 8,635,105; 8,670,833; 8,717,292; 8,721,341; 8,764,193; 8,830,164; 8,878,782; 8,932,199; 8,939,579; 8,998,828; 9,013,264; 9,101,296; 9,107,616; 9,107,622; 9,128,281; 9,134,534; 9,167,356; 9,198,571; 9,211,411; 9,213,185; 9,213,406; 9,247,870; 9,286,515; 9,301,675; 9,370,302; 9,456,740; 9,480,429; 9,492,432; 9,510,752; 9,596,986; 9,618,759; 9,626,561; 9,632,585; 9,723,981; 9,724,357; 9,730,583; 9,785,242; 9,788,714; 9,829,971; 9,835,864; 9,841,812; 9,861,307; 9,889,271; 9,898,082; 9,921,663; 9,955,895; 9,965,860; 9,993,517; 9,996,151; 10,016,156; 10,039,445; 10,052,057; 10,073,519; 10,086,268; 10,109,056; 10,149,884; 10,149,958; 10,168,772; 10,168,793; 10,191,558; 10,198,068; 10,292,613; 20020077534; 20040013609; 20040070729; 20040102843; 20040143170; 20040163648; 20040181168; 20040220704; 20040227699; 20050043652; 20050099601; 20050110950; 20050195165; 20060061544; 20060071934; 20070015976; 20070017534; 20070040691; 20070078077; 20060077064; 20060253003; 20060255956; 20070010748; 20070121068; 20070132841; 20070146368; 20070255164; 20070273611; 20080049186; 20080049187; 20080074618; 20080181452; 20080188777; 20080252850; 20080253519; 20080262373; 20080273084; 20080278685; 20080309855; 20080319430; 20090018419; 20090024449; 20090025023; 20090036755; 20090036756; 20090058660; 20090062629; 20090062680; 20090062681; 20090063255; 20090063256; 20090214485; 20090289895; 20090292223; 20090295738; 20090299209; 20090312665; 20090327068; 20090328089; 20100036290; 20100045932; 20100081707; 20100100001; 20100165093; 20100177929; 20100201621; 20100204608; 20100249636; 20100262377; 20100283972; 20110009777; 20110026678; 20110039790; 20110046502; 20110046510; 20110060423; 20110077548; 20110096294; 20110137372; 20110170066; 20110170067; 20110178784; 20110227813; 20110295086; 20110298702; 20110310238; 20120053508; 20120075168; 20120081666; 20120127426; 20120194781; 20120200601; 20120212398; 20120212399; 20120212400; 20120229248; 20120235887; 20120236030; 20120245437; 20120256833; 20120323229; 20130033677; 20130137642; 20130278631; 20140024598; 20140055746; 20140078049; 20140081117; 20140198936; 20140204025; 20140249801; 20140303428; 20140313488; 20140320808; 20140320817; 20140323455; 20140327881; 20140362346; 20150016674; 20150035745; 20150054731; 20150065813; 20150092983; 20150126845; 20150177529; 20150213012; 20152223683; 20150261003; 20150265679; 20150324568; 20150335240; 20160005176; 20160007849; 20160029883; 20160074749; 20160140887; 20160147301; 20160150955; 20160193442; 20160250189; 20160256086; 20160262608; 20160270656; 20160317834; 20160367619; 20160374594; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000454; 20170000683; 20170001032; 20170003741; 20170003742; 20170006217; 20170007111; 20170007115; 20170007116; 20170007122; 20170007123; 20170007182; 20170007450; 20170007799; 20170007843; 20170010469; 20170010470; 20170017083; 20170020388; 20170020434; 20170035317; 20170042418; 20170049395; 20170055868; 20170102767; 20170115742; 20170150897; 20170150898; 20170216393; 20170252583319; 20170276956; 20170308172; 20170312622; 20170329401; 20170333729; 20170347947; 20170347948; 20170354327; 20170360360; 20170371421; 20180004287; 20180027176; 20180032103; 20180046248; 20180088678; 20180095532; 20180098908; 20180103917; 20180125356; 20180125405; 20180125406; 20180177393; 20180184002; 20180184964; 20180196512; 20180214020; 20180232507; 20180271362; 20180279902; 20180279960; 20180284886; 20180299953; 20180341328; 20180368722; 20190004325; 20190011612; 20190026871; 20190060602; 20190073044; 20190077409; 20190079580; 20190099076; 20190099467; 20190117062; 20190130777; 20190151337; and 20190158717.
en.wikipedia.org/wiki/Electromyography
U.S. Pat. Nos. and application Nos. 4,934,378; 5,570,698; 5,707,652; 6,117,092; 6,164,278; 6,270,466; 6,497,658; 6,665,560; 6,669,627; 6,681,774; 7,654,948; 7,678,041; 8,204,597; 8,244,340; 8,290,596;

8,309,530; 8,398,538; 8,512,221; 8,628,462; 8,812,098; 9,072,870; 9,095,268; 9,211,411; 9,492,630; 9,662,045; 9,706,957; 9,821,162; 9,872,968; 9,936,916; 10,064,578; 10,111,615; 10,130,788; 10,156,888; 10,165,977; 10,231,650; 10,299,210; 20010031930; 20030069516; 20030150465; 20040225179; 20040249237; 20050154426; 20060145457; 20080154111; 20080300449; 20090105785; 20090192556; 20090264789; 20100010385; 20100087701; 20100094103; 20100196396; 20110015467; 20110015495; 20120053508; 20120277548; 20120277618; 20120302842; 20140316191; 20140316192; 20150092050; 20150148621; 20150223731; 20150257697; 20150265207; 20150306391; 20150359482; 20160162016; 20160212708; 20160226542; 20170000970; 20170041205; 20170113057; 20170193831; 20170304587; 20170311878; 20170319109; 20170319815; 20170347948; 20170360363; 20170368348; 20180056026; 20180068581; 20180092600; 20180110991; 20180140249; 20180146916; 20180177451; 20180242902; 20180250494; 20180256094; 20180311462; 20180368755; 20190103034; 20190126033; and 20190143073.
Reference List 18
U.S. Pat. Nos. 3,565,059; 3,735,753; 3,957,036; 4,375,219; 4,638,807; 4,967,038; 4,972,492; 5,273,037; 5,313,952; 5,479,934; 6,076,003; 6,154,699; 6,574,513; 6,640,122; 7,103,398; 7,773,767; 7,885,419; 8,055,722; 8,128,422; 8,155,736; 8,160,287; 8,170,637; 8,209,224; 8,270,814; 8,271,075; 8,284,233; 8,290,563; 8,301,218; 8,335,715; 8,335,716; 8,386,261; 8,386,312; 8,386,313; 8,391,966; 8,392,250; 8,392,251; 8,392,253; 8,392,254; 8,392,255; 8,396,529; 8,396,744; 8,417,185; 8,438,659; 8,442,626; 8,464,288; 8,473,345; 8,494,610; 8,494,905; 8,533,042; 8,548,555; 8,548,558; 8,634,892; 8,635,105; 8,655,428; 8,655,437; 8,659,397; 8,676,230; 8,679,013; 8,696,113; 8,706,518; 8,733,927; 8,733,928; 8,738,395; 8,755,879; 8,780,512; 8,781,570; 8,798,736; 8,812,075; 8,816,861; 8,821,397; 8,868,039; 8,868,216; 8,897,859; 8,898,344; 8,983,591; 8,988,350; 8,989,835; 9,014,061; 9,031,631; 9,032,110; 9,042,201; 9,058,200; 9,086,884; 9,104,467; 9,104,969; 9,129,478; 9,146,618; 9,171,131; 9,179,855; 9,186,105; 9,210,517; 9,213,403; 9,224,309; 9,239,615; 9,258,301; 9,259,180; 9,268,905; 9,292,858; 9,320,450; 9,330,497; 9,354,445; 9,357,240; 9,357,941; 9,367,131; 9,377,869; 9,392,956; 9,405,366; 9,408,575; 9,408,997; 9,412,233; 9,414,780; 9,426,582; 9,432,777; 9,436,279; 9,439,593; 9,439,595; 9,439,596; 9,439,736; 9,445,763; 9,445,768; 9,451,303; 9,451,406; 9,454,646; 9,454,777; 9,462,433; 9,477,290; 9,477,317; 9,477,701; 9,482,606; 9,497,530; 9,504,420; 9,507,974; 9,516,430; 9,521,976; 9,531,708; 9,532,748; 9,557,957; 9,560,984; 9,563,927; 9,569,986; 9,577,992; 9,579,060; 9,585,581; 9,590,986; 9,594,500; 9,599,492; 9,615,746; 9,619,613; 9,622,703; 9,636,063; 9,658,473; 9,692,756; 9,693,734; 9,700,261; 9,704,205; 9,706,237; 9,722,472; 9,723,422; 9,729,252; 9,736,603; 9,737,231; 9,740,285; 9,763,613; 9,775,545; 9,779,575; 9,781,521; 9,782,122; 9,794,672; 9,795,324; 9,800,717; 9,805,339; 9,805,381; 9,808,156; 9,811,154; 9,814,426; 9,818,150; 9,820,120; 9,830,576; 9,830,577; 9,832,353; 9,833,142; 9,833,185; 9,836,896; 9,836,931; 9,842,299; 9,844,344; 9,853,976; 9,857,590; 9,858,745; 9,865,093; 9,883,396; 9,886,981; 9,888,090; 9,898,793; 9,900,669; 9,904,891; 9,904,892; 9,905,239; 9,910,298; 9,916,010; 9,936,250; 9,949,640; 9,953,650; 9,955,902; 9,962,082; 9,962,083; 9,978,095; 9,983,670; 9,990,727; 9,993,190; 9,993,386; 9,994,228; D613267; D626949; D643013S1; D6434001; D671523; D717956; D743039; D747495; D809474; 10,009,644; 10,019,060; 10,026,138; 10,029,067; 10,031,580; 10,042,038; 10,042,993; 10,052,023; 10,052,452; 10,058,285; 10,068,373; 10,075,896; 10,079,788; 10,089,074; 10,095,191; 10,108,783; 10,110,805; 10,113,913; 10,123,133; 10,123,134; 10,126,816; 10,130,278; 10,130,279; 10,130,766; 10,136,856; 10,136,862; 10,137,363; 10,143,415; 10,149,161; 10,152,957; 10,154,333; 10,154,815; 10,162,707; 10,166,091; 10,168,704; 10,169,712; 10,173,059; 10,176,894; 10,180,339; 10,185,147; 10,186,014; 10,188,307; 10,191,545; 10,198,505; 10,206,625; 10,209,779; 10,212,593; 10,213,156; 10,219,736; 10,223,710; 10,226,209; 10,227,063; 10,231,673; 10,234,942; 10,244,033; 10,254,785; 10,257,177; 10,257,555; 10,258,243; 10,258,291; 10,261,947; 10,262,356; 10,264,990; 10,271,087; 10,279,192; 10,285,634; 10,290,225; 10,291,977; 10,293,177; 10,300,240; 10,303,258; 10,303,988; 10,307,085; 10,307,104; 10,307,611; 20040073129; 20050215916; 20060094974; 20080177197; 20090112077; 20090156925; 20090214060; 20090281408; 20100068146; 20100090835; 20100094097; 20100163027; 20100163028; 20100163035; 20100168525; 20100168529; 20100168602; 20100201780; 20100234752; 20110004089; 20110040202; 20110162879; 20110224503; 20110313308; 20120029379; 20120046569; 20120108999; 20120136274; 20120150545; 20120176302; 20120190959; 20120197092; 20120220889; 20120245450; 20120250197; 20120295589; 20120296476; 20120330178; 20130012830; 20130035578; 20130039509; 20130041243;

TABLE 1-continued

20130044055; 20130046206; 20130066183; 20130066184;
20130096440; 20130096575; 20130127708; 20130130799;
20130177883; 20130179087; 20130197401; 20130208234;
20130211226; 20130211276; 20130237867; 20130242262;
20130260361; 20130278492; 20130338738; 20130343584;
20130343585; 20130345524; 20140012152; 20140020089;
20140058219; 20140073969; 20140096210; 20140098981;
20140099623; 20140106710; 20140107520; 20140108842;
20140114165; 20140114207; 20140121017; 20140146987;
20140148715; 20140160250; 20140164056; 20140179986;
20140195221; 20140210709; 20140211593; 20140221779;
20140221855; 20140223462; 20140228653; 20140257833;
20140277292; 20140278786; 20140282772; 20140304122;
20140307878; 20140313303; 20140316230; 20140316235;
20140321682; 20140330334; 20140336473; 20140342818;
20140368601; 20140369537; 20140378810; 20150000025;
20150003698; 20150003699; 20150005640; 20150005644;
20150006186; 20150012426; 20150016664; 20150033056;
20150038869; 20150040139; 20150045007; 20150073294;
20150073907; 20150091791; 20150094914; 20150105111;
20150112153; 20150121474; 20150123984; 20150126281;
20150131159; 20150135309; 20150142082; 20150150753;
20150157255; 20150162802; 20150185482; 20150185506;
20150190085; 20150199010; 20150213722; 20150227193;
20150227844; 20150235134; 20150242120; 20150248651;
20150250401; 20150250415; 20150256956; 20150257104;
20150257674; 20150264028; 20150268483; 20150272508;
20150277560; 20150278980; 20150289065; 20150293592;
20150297106; 20150297109; 20150302543; 20150305686;
20150323986; 20150338917; 20150343242; 20150347734;
20150350794; 20150350820; 20150351655; 20150366518;
20160005229; 20160005320; 20160015289; 20160022167;
20160022206; 20160029947; 20160029965; 20160042123;
20160044460; 20160045150; 20160054568; 20160054569;
20160055236; 20160062596; 20160063611; 20160065557;
20160070334; 20160071390; 20160078657; 20160081623;
20160103322; 20160109954; 20160117829; 20160119726;
20160128629; 20160132189; 20160133052; 20160142407;
20160144173; 20160150582; 20160156575; 20160156682;
20160157777; 20160164949; 20160166208; 20160167672;
20160170996; 20160170998; 20160171514; 20160191269;
20160192166; 20160196635; 20160196758; 20160213354;
20160219000; 20160224803; 20160232625; 20160235324;
20160235983; 20160259905; 20160262704; 20160265952;
20160267809; 20160269999; 20160296157; 20160299568;
20160300252; 20160302711; 20160306844; 20160310698;
20160310838; 20160316288; 20160317056; 20160320930;
20160324478; 20160331925; 20160339300; 20160342644;
20160344569; 20160349841; 20160358091; 20160358092;
20160360990; 20160361062; 20160364586; 20160367138;
20160374594; 20160378608; 20160381621; 20170000404;
20170007165; 20170007173; 20170010647; 20170010677;
20170011210; 20170020434; 20170039045; 20170042439;
20170048626; 20170049524; 20170064434; 20170065218;
20170065379; 20170068920; 20170068921; 20170071495;
20170071523; 20170071532; 20170071537; 20170071546;
20170071551; 20170078883; 20170080332; 20170086695;
20170087453; 20170091532; 20170093848; 20170095157;
20170095199; 20170103668; 20170112671; 20170119994;
20170127975; 20170133009; 20170139484; 20170142656;
20170143249; 20170157435; 20170160703; 20170162072;
20170164293; 20170164878; 20170169176; 20170169295;
20170171441; 20170172445; 20170175280; 20170177023;
20170180882; 20170185762; 20170189640; 20170193314;
20170213311; 20170215011; 20170215757; 20170221121;
20170221463; 20170243023; 20170244702; 20170245145;
20170249009; 20170251945; 20170258390; 20170259167;
20170262943; 20170265807; 20170272699; 20170272842;
20170281001; 20170293846; 20170300654; 20170309152;
20170311023; 20170311097; 20170311832; 20170323073;
20170331563; 20170332964; 20170337834; 20170347181;
20170352233; 20170367606; 20170367610; 20170367651;
20180000255; 20180005442; 20180011676; 20180011689;
20180014130; 20180025368; 20180027347; 20180042523;
20180047216; 20180070823; 20180075364; 20180081439;
20180098710; 20180103859; 20180110960; 20180113509;
20180115808; 20180116543; 20180125386; 20180133431;
20180133504; 20180133507; 20180139518; 20180150762;
20180154104; 20180157336; 20180158133; 20180160982;
20180165593; 20180173220; 20180182161; 20180184964;

20180189678; 20180193589; 20180196511; 20180214028;
20180217666; 20180220957; 20180221620; 20180234847;
20180236202; 20180246570; 20180250494; 20180263562;
20180275747; 20180276833; 20180278984; 20180279960;
20180289310; 20180296112; 20180301061; 20180317795;
20180321700; 20180321898; 20180324516; 20180333585;
20180338068; 20180344969; 20180348764; 20180364810;
20180368717; 20180368722; 20180369847; 20180373272;
20190001039; 20190008992; 20190012758; 20190013960;
20190020610; 20190029587; 20190029595; 20190033968;
20190034164; 20190043154; 20190053731; 20190053756;
20190053766; 20190070386; 20190083212; 20190086919;
20190097430; 20190108191; 20190110726; 20190113973;
20190117933; 20190133445; 20190142349; 20190167370;
20190174237; 20190174238; AU667199; AU729772; CN102458242A;
CN104605844A; EP0483698; EP1090583; EP1776922; JP4582509;
JP4699694; JP4801839; JP4829231; KR100895297; RU2563433; and
WO2015143031.
Reference List 19
U.S. Pat. Nos. and Pub. patent application Nos. 10,264,019;
10,204,251; 10,131,322; 10,129,325; 10,075,581; 10,074,224;
10,037,636; 9,980,114; 9,968,780; 9,930,155; 9,923,764; 9,922,053;
9,866,706; 9,860,273; 9,843,917; 9,813,887; 9,807,582; 9,783,162;
9,781,554; 9,760,236; 9,756,096; 9,713,013; 9,706,382; 9,706,060;
9,678,810; 9,635,605; 9,596,584; 9,595,059; 9,563,998; 9,548,050;
9,538,062; 9,432,501; 9,402,099; 9,401,977; 9,400,805; 9,399,126;
9,391,988; 9,357,329; 9,354,778; 9,324,234; 9,317,457; 9,311,640;
9,292,895; 9,240,021; 9,223,893; 9,218,530; 9,202,360; 9,183,580;
9,160,796; 9,152,582; 9,098,437; 9,071,649; 9,063,798; 9,026,709;
8,972,295; 8,898,443; 8,798,598; 8,774,784; 8,762,852; 8,751,670;
8,726,294; 8,699,747; 8,669,864; 8,630,633; 8,620,021; 8,606,923;
8,494,507; 8,441,356; 20190130750; 20190130353; 20190121682;
20190005854; 20190037067; 20190020554; 20180352326;
20180260801; 20180234479; 20180219729; 20180157379;
20180113669; 20180108192; 20180108191; 20180034855;
20180009417; 20170346851; 20170345239; 20170344991;
20170330248; 20170300998; 20170255981; 20170243203;
20170201619; 20170174180; 20170132861; 20170104928;
20170104787; 20170083312; 20170076520; 20170032584;
20170011178; 20160337857; 20160323431; 20160307380;
20160271475; 20160142252; 20160062807; 20160014224;
20150363986; 20150358526; 20150358316; 20150351698;
20150351695; 20150287403; 20150256593; 20150227922;
20150212830; 20150205482; 20150195482; 20150178388;
20150163345; 20150138089; 20150079949; 20150072728;
20150058611; 20140369550; 20140369550; 20140279541;
20140279475; 20140274078; 20140274056; 20140273947;
20140273940; 20140273939; 20140273937; 20140273935;
20140273934; 20140273924; 20140269443; 20140269442;
20140269441; 20140258110; 20140244514; 20140222612;
20140201256; 20140161412; 20140122255; 20140089462;
20140089202; 20140073298; 20140067557; 20140059566;
20130340775; 20130326333; 20130325567; 20130311329;
20130295898; 20130260727; 20130259297; 20130174047;
20130167159; 20130150121; 20130097630; 20130094702;
20120303548; 20120300972; 20120284012; 20120210233;
20120154633; 20120134548; 20120116559; 20120089906;
20120084792; 20120084791; 20120084542; 20120084481;
20120084480; 20120066393; 20120023243; and 20110319056.

What is claimed is:

1. A system for facilitating sleep, comprising:

a database comprising a plurality of database records, each database record being associated with a respective human sleep stage of a plurality of human sleep stages, and each database record defining a brain electrical activity waveform associated with the respective human sleep stage;

a neurostimulator configured to stimulate a sleeping human subject with a sensory stimulus adapted to achieve brain entrainment of the sleeping human subject, and alter a human sleep stage of the sleeping human subject; and at least one automated processor, configured to:
determine a current human sleep stage of the sleeping human subject;

monitor a progress of the sleeping human subject through a sleep cycle comprising a defined sequence of sleep stages based on current human sleep stage;

modify the progress of the sleeping human subject through the sleep cycle comprising the defined sequence of human sleep stages dependent on a deviation of the current human sleep stage of the sleeping human subject from the sleep cycle comprising the defined sequence of stages, to a portion of the sequence of sleep stages corresponding to the current sleep stage within the defined sequence of sleep stages;

define a stimulation pattern of the sensory stimulus for the sleeping human subject, dependent on the current human sleep stage, the progress of the sleeping human through the sleep cycle comprising the defined sequence of human sleep stages, and at least one database record of the database; and control the neurostimulator to deliver the sensory stimulus based on at least the defined stimulation pattern for the sleeping human subject.

2. The system according to claim 1, wherein the stimulation pattern comprises at least two concurrent modulated signals.

3. The system according to claim 2, wherein the at least two concurrent modulated signals comprise at least two different audio signals, together configured to generate binaural beats.

4. The system according to claim 1, wherein the plurality of database records are derived from brain electrical activity measurements acquired during at least one human sleep cycle.

5. The system according to claim 1, wherein the at least one automated processor is further configured to define a new database record of the database by monitoring electroencephalographic signals from a sleeping human over a sleep cycle.

6. The system according to claim 1, further comprising a memory configured to store instructions of a sleep app, configured to be executed by the at least one automated processor, the sleep app being downloadable and upgradable from a remote server.

7. The system according to claim 6, further comprising a user interface configured to control an adaptively defined sequence of the human sleep stages, and the deviation of the current human sleep stage of the sleeping human subject from the sleep cycle comprising the defined sequence of stages comprises an awakening.

8. The system according to claim 1, wherein the at least one automated processor is configured to phase synchronize the defined stimulation pattern with a brain electrical activity of the sleeping human subject detected with an electroencephalographic sensor.

9. The system according to claim 1, wherein the neurostimulator comprises a multimodal sensory stimulator.

10. The system according to claim 1, wherein the neurostimulator comprises a visual stimulator and an audio stimulator.

11. The system according to claim 1, wherein each defined brain electrical activity waveform is derived from at least one recording of brainwaves of at least one sleeping human, processed using a statistical decision analysis.

12. The system according to claim 1, wherein the neurostimulator comprises at least one light emitting diode disposed in a sleep mask configured to be illuminated proximate to the sleeping human subject's eyes.

13. The system according to claim 1, further comprising at least one sensor configured to determine at least an eye movement, and the at least one automated processor is configured to determine the current sleep stage of the sleeping human subject based on an output of the at least one sensor.

14. The system according to claim 1, further comprising providing at least one electroencephalographic sensor, and the at least one automated processor is configured to determine the current sleep stage of the sleeping human subject based on an output of the at least one electroencephalographic sensor.

15. A system for facilitating sleep, comprising:

a database configured to store a plurality of database records associated with respective human sleep stages, each database record defining a brain electrical activity waveform associated with a respective human sleep stage of a plurality of different sleep stages;

a sensor configured to determine a current human sleep stage of a sleeping human subject;

at least one automated processor configured to:

monitor a current sleep stage and a progress of the sleeping human subject through a defined sequence of the plurality of different sleep stages;

determine a deviation between the current sleep stage and an expected current sleep stage according to the defined sequence of the plurality of different sleep stages;

modify the progress of the sleeping human subject through the defined sequence of the plurality of different sleep stages dependent on at least the determined deviation, to a respective sleep stage within the defined sequence of the plurality of different sleep stages corresponding to the current sleep stage; and define a stimulation pattern for the sleeping human subject, dependent on the current sleep stage, the progress of the sleeping human subject through the defined sequence of the plurality of different sleep stages, and at least one database record of the database corresponding to a next sleep stage in the defined sequence of the plurality of different sleep stages; and a neurostimulator configured to stimulate a sleeping human subject with a sensory stimulus, dependent on at least the defined stimulation pattern for the sleeping human subject, the sensory stimulus being configured to achieve brain entrainment of the sleeping human subject.

16. The system according to claim 15, wherein the stimulation pattern comprises at least two concurrent modulated audio signals together configured to generate binaural beats.

17. The system according to claim 15, further comprising time synchronizing the defined stimulation pattern with a brain electrical activity of the sleeping human subject detected using an electroencephalographic sensor.

18. The system according to claim 15, wherein the sensor is configured to determine at least a movement of the sleeping human subject, and wherein the current sleep stage of the sleeping human subject is determined based on the at least one sensor.

19. A system to facilitate sleep in a sleeping human subject, comprising:

a user device having at least one programmable processor and a sleep app executable on the at least one programmable processor, the sleep app including:

instructions for determining a current sleep stage of the sleeping human subject;

instructions for selecting a record in a database storing a plurality of records in dependence on at least the current sleep stage, each record of the database defining a respective waveform derived from brainwaves of at least one sleeping human donor, instructions for monitoring a progress of the sleeping human subject through a defined sequence of sleep stages based on current human sleep stage; and instructions for modifying the progress of the sleeping human subject through the sequence of sleep stages dependent on a deviation of the sleeping human subject from the sleep cycle comprising the defined sequence of stages, to a portion of the sequence of sleep stages corresponding to the current sleep stage within the defined sequence of sleep stages; and instructions for stimulating the sleeping human subject with at least one stimulus modulated with the waveform defined in the selected record, wherein the selected waveform is configured to entrain the brain of the sleeping subject facilitating sleep in the sleeping human subject.

20. The system of claim 19, wherein each record of the database defines a subset of a set of components of the respective waveform, the subset selectively corresponding to respective sleep stages, derived from recordings of brainwaves of at least one sleeping human donor, the components being extracted from the recordings of brainwaves of at least one sleeping human donor using at least one of a principal component analysis (PCA), a correspondence analysis (CA), a factor analysis, a K-means clustering, a non-negative matrix factorization (NMF), a sparse PCA, a non-linear PCA, a robust PCA, an independent component analysis (ICA), a network component analysis, and a singular spectral analysis.

\* \* \* \* \*